United States Patent
Xu et al.

(10) Patent No.: US 12,286,637 B2
(45) Date of Patent: *Apr. 29, 2025

(54) COMPOSITIONS AND METHODS FOR PRODUCING TOBACCO PLANTS AND PRODUCTS HAVING REDUCED OR ELIMINATED SUCKERS

(71) Applicant: ALTRIA CLIENT SERVICES LLC, Richmond, VA (US)

(72) Inventors: Dongmei Xu, Glen Allen, VA (US); Jesse Frederick, Richmond, VA (US); Chengalrayan Kudithipudi, Midlothian, VA (US); Yanxin Shen, Glen Allen, VA (US); James Strickland, Richmond, VA (US); Jaemo Yang, Richmond, VA (US)

(73) Assignee: ALTRIA CLIENT SERVICES LLC, Richmond, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/537,046

(22) Filed: Dec. 12, 2023

(65) Prior Publication Data

US 2024/0102038 A1    Mar. 28, 2024

Related U.S. Application Data

(63) Continuation of application No. 17/406,829, filed on Aug. 19, 2021, now Pat. No. 11,879,130, which is a
(Continued)

(51) Int. Cl.
   *C12N 15/82*       (2006.01)
   *C07K 14/415*      (2006.01)

(52) U.S. Cl.
   CPC ........ *C12N 15/8265* (2013.01); *C07K 14/415* (2013.01); *C12N 15/8213* (2013.01);
(Continued)

(58) Field of Classification Search
   None
   See application file for complete search history.

(56) References Cited

U.S. PATENT DOCUMENTS

| 4,516,590 A | 5/1985 | Teng |
| 4,528,993 A | 7/1985 | Sensabaugh, Jr. et al. |

(Continued)

FOREIGN PATENT DOCUMENTS

| CN | 1824774 A | 8/2006 |
| CN | 101981192 A | 2/2011 |

(Continued)

OTHER PUBLICATIONS

Akaba et al., "Production of Homo- and Hetero-Dimeric Isozymes from Two Aldehyde Oxidase Genes of *Arabidopsis thaliana*," *Journal of Biochemistry*, 126:395-401 (1999).
(Continued)

*Primary Examiner* — Matthew R Keogh
*Assistant Examiner* — Rebecca Stephens
(74) *Attorney, Agent, or Firm* — Arnold & Porter Kaye Scholer LLP

(57) ABSTRACT

The present disclosure provides the identification of genes involved in sucker growth in tobacco. Also provided are promoters that are preferentially active in tobacco axillary buds. Also provided are modified tobacco plants comprising reduced or no sucker growth. Also provided are methods and compositions for producing modified tobacco plants comprising reduced or no sucker growth.

20 Claims, 35 Drawing Sheets

Specification includes a Sequence Listing.

Related U.S. Application Data continuation of application No. 16/124,941, filed on Sep. 7, 2018, now Pat. No. 11,104,912.

(60) Provisional application No. 62/556,804, filed on Sep. 11, 2017.

(52) U.S. Cl.
CPC ..... *C12N 15/8218* (2013.01); *C12N 15/8225* (2013.01); *C12N 15/8229* (2013.01); *C12N 15/8261* (2013.01); *C12N 15/8262* (2013.01); *C12N 15/8294* (2013.01); *C12N 2310/20* (2017.05)

(56) References Cited

U.S. PATENT DOCUMENTS

| | | | |
|---|---|---|---|
| 4,660,577 | A | 4/1987 | Sensabaugh et al. |
| 4,732,856 | A | 3/1988 | Federoff |
| 4,762,785 | A | 8/1988 | Comai |
| 4,848,373 | A | 7/1989 | Lenkey |
| 4,945,050 | A | 7/1990 | Sanford et al. |
| 4,987,907 | A | 1/1991 | Townsend |
| 5,004,863 | A | 4/1991 | Umbeck |
| 5,013,658 | A | 5/1991 | Dooner et al. |
| 5,104,310 | A | 4/1992 | Saltin |
| 5,141,131 | A | 8/1992 | Miller, Jr. et al. |
| 5,149,645 | A | 9/1992 | Hoekema et al. |
| 5,159,135 | A | 10/1992 | Umbeck |
| 5,177,010 | A | 1/1993 | Goldman et al. |
| 5,231,019 | A | 7/1993 | Paszkowski et al. |
| 5,316,931 | A | 5/1994 | Donson et al. |
| 5,372,149 | A | 12/1994 | Roth et al. |
| 5,463,174 | A | 10/1995 | Moloney et al. |
| 5,464,763 | A | 11/1995 | Schilperoort et al. |
| 5,469,976 | A | 11/1995 | Burchell |
| 5,491,081 | A | 2/1996 | Webb |
| 5,563,055 | A | 10/1996 | Townsend et al. |
| 5,565,350 | A | 10/1996 | Kmiec |
| 5,589,367 | A | 12/1996 | Donson et al. |
| 5,659,026 | A | 8/1997 | Baszczynski et al. |
| 5,689,035 | A | 11/1997 | Webb |
| 5,731,181 | A | 3/1998 | Kmiec |
| 5,756,325 | A | 5/1998 | Kmiec |
| 5,760,012 | A | 6/1998 | Kmiec et al. |
| 5,789,156 | A | 8/1998 | Bujard et al. |
| 5,795,972 | A | 8/1998 | Kmiec |
| 5,814,618 | A | 9/1998 | Bujard et al. |
| 5,866,785 | A | 2/1999 | Donson et al. |
| 5,871,984 | A | 2/1999 | Kmiec |
| 5,879,918 | A | 3/1999 | Tomes et al. |
| 5,886,244 | A | 3/1999 | Tomes et al. |
| 5,889,190 | A | 3/1999 | Donson et al. |
| 5,889,191 | A | 3/1999 | Turpen |
| 5,932,782 | A | 8/1999 | Bidney |
| 5,981,840 | A | 11/1999 | Zhao et al. |
| 6,072,050 | A | 6/2000 | Bowen et al. |
| 6,073,342 | A | 6/2000 | Asai et al. |
| 8,124,851 | B2 | 2/2012 | Dewey et al. |
| 8,319,011 | B2 | 11/2012 | Xu et al. |
| 9,187,759 | B2 | 11/2015 | Dewey et al. |
| 9,228,194 | B2 | 1/2016 | Dewey et al. |
| 9,228,195 | B2 | 1/2016 | Dewey et al. |
| 9,247,706 | B2 | 2/2016 | Dewey et al. |
| 10,435,700 | B2 | 10/2019 | Kudithipudi et al. |
| 10,731,173 | B2 | 8/2020 | Xu et al. |
| 11,104,912 | B2 * | 8/2021 | Xu .................... C12N 15/8261 |
| 11,879,130 | B2 * | 1/2024 | Xu .................... C12N 15/8262 |
| 2004/0118422 | A1 | 6/2004 | Lundin et al. |
| 2005/0178398 | A1 | 8/2005 | Breslin et al. |
| 2006/0191548 | A1 | 8/2006 | Strickland et al. |
| 2006/0200878 | A1 | 9/2006 | Lutfiyya et al. |
| 2006/0230470 | A1 | 10/2006 | Higo et al. |
| 2016/0281100 | A1 | 9/2016 | Kudithipudi et al. |
| 2016/0374387 | A1 | 12/2016 | Adams et al. |
| 2017/0260535 | A1 | 9/2017 | Xu et al. |
| 2019/0360279 | A1 | 11/2019 | Trowbridge et al. |

FOREIGN PATENT DOCUMENTS

| | | | |
|---|---|---|---|
| CN | 102217650 | A | 10/2011 |
| CN | 102823449 | A | 12/2012 |
| CN | 102919283 | A | 2/2013 |
| CN | 103190397 | A | 7/2013 |
| CN | 107250355 | A | 10/2017 |
| CN | 107267528 | A | 10/2017 |
| CN | 108271341 | A | 7/2018 |
| CN | 109715810 | A | 5/2019 |
| CN | 113652416 | A | 11/2021 |
| CN | 114981440 | A | 8/2022 |
| EP | 0845933 | A2 | 6/1998 |
| FR | 1228274 | A | 8/1960 |
| FR | 2122503 | A1 | 9/1972 |
| JP | WO2003/004649 | | 7/2005 |
| JP | 2007-289042 | A | 11/2007 |
| WO | WO 91/00009 | A1 | 1/1991 |
| WO | WO 98/49350 | A1 | 11/1998 |
| WO | WO 99/07865 | A1 | 2/1999 |
| WO | WO 99/25921 | A1 | 5/1999 |
| WO | WO 2003/004649 | | 1/2003 |
| WO | WO 2004/041006 | A1 | 5/2004 |
| WO | WO 2008/133643 | A2 | 11/2008 |
| WO | WO 2009/027824 | A1 | 3/2009 |
| WO | WO 2011/027315 | A1 | 3/2011 |
| WO | WO 2016/057515 | A2 | 4/2016 |
| WO | WO 2016/210303 | A1 | 12/2016 |
| WO | WO 2017/156535 | A1 | 9/2017 |
| WO | WO 2021/113337 | A1 | 6/2021 |

OTHER PUBLICATIONS

Allen et al., "Evolution of microRNA genes by inverted duplication of target gene sequences in *Arabidopsis thaliana*," *Nature Genetics*, 36(12):1282-1290 (2004).

Allen et al., "microRNA-Directed Phasing during Trans-Acting siRNA Biogenesis in Plants," *Cell*, 121:207-221 (2005).

Altschul et al., "Basic Local Alignment Search Tool," *Journal of Molecular Biology*, 215:403-410 (1990).

Altschul et al., "Gapped BLAST and PSI-BLAST: a new generation of protein database search programs," *Nucleic Acids Research*, 25(17):3389-3402 (1997).

Amaya et al., "Expression of CENTRORADIALIS(CEN) and CEN-like Genes in Tobacco Reveals a Conserved Mechanism Controlling Plase Change in Diverse Species," *The Plant Cell*, 11:1405-1417 (1999).

Avci et al., "Cysteine proteases XCP1 and XCP2 aid microautolysis within the intact central vacuole during xylogenesis in *Arabidopsis* roots," *The Plant Journal*, 56:303-315 (2008).

Axtell et al., "A Two-Hit Trigger for siRNA Biogenesis in Plants," *Cell*, 127:L565-577 (2006).

Bartel, D.P., "MicroRNAs: Genomics, Biogenesis, mechanism, and Function," *Cell*, 116:281-297 (2004).

Beetham et al., "A tool for functional plant genomics: Chimeric RNA/DNA oligonucleotides case in vivo gene-specific mutations," *Proc. Natl. Acad. Sci. USA*, 96:8774-8778 (1999).

Bender et al., "*Pseudomonas syringae* Phytotoxins: Mode of Action, Regulation, and Biosynthesis by Peptide and Polyketide Synthetases," *Microbiology and Molecular Biology Reviews*, 63:266-292 (1999).

Bowman et al., "Revised North Carolina grade index for flue-cured tobacco," *Tobacco Science*, 32:39-40 (1988).

Canevascini et al., "Tissue-Specific Expression and Promoter Analysis of the Tobacco Itp1 Gene," *Plant Physiology*, 112:513-524 (1996).

Cermak et al., "Efficient design and assembly of custom TALEN and other TAL effector-based constructs for DNA targeting," *Nucleic Acids Research*, 39(12):e82 (2011).

Chapters 4B and 4C of Tobacco, Production, Chemistry and Technology, Davis & Nielsen, eds., Blackwell Publishing, pp. 70-103, (1999) (Oxford, UK).

(56) References Cited

OTHER PUBLICATIONS

Chatfield et al., "The hormonal regulation of axillary bud growth in *Arabidopsis*," *The Plant Journal*, 24(2):159-169 (2000).
Chen et al., "Molecular Cloning and Expression Analysis of BRANCHED1-Like Gene in Common Tobacco," *Journal of Plant Genetic Resources*, vol. 16, Issue 6, pp. 1321-1329, (Dec. 2015) (English abstract) available online at https://www.zwyczy.cn/zwyczyxben/article/abstract/20141023002?st=article_issue.
Cheng et al., "Auxin Synthesized by the YUCCA Flavin Monoxygenases Is essential for Embryogenesis and Leaf Formation in *Arabidopsis*," *The Plant Cell*, 19:2430-2439 (2007).
Chinese Search Report issued in corresponding Chinese Patent Application No. 2018800586156, dated Feb. 17, 2023 with English translation (9 pages).
Christensen et al., "Maize polyubiquitin genes: structure, thermal perturbation of expression and transcript splicing, and promoter activity following transfer to protoplasts by electroporation," *Plant Molecular Biology*, 18:675-589 (1992).
Christensen et al., "Sequence analysis and transcriptional regulation by heat shock of plyubiquitin transcripts from maize," *Plant Molecular Biology*, 12:619-632 (1989).
Christou et al., "Stable Transformation of Soybean Callus by DNA-Coated Gold Particles," *Plant Physiology*, 87:671-674 (1988).
Crone et al., "The differential expression of a heat shock promoter in floral and reproductive tissues," *Plant, Cell and Enviroment*, 24:869-874 (2001).
Crossway et al., "Micromanipulation Techniques in Plant Biotechnology," *BioTechniques*, 4(4):320-334 (1986).
D'Halluin et al., "Transgenic Maize Plants by Tissue Electroporation," *The Plant Cell*, 4:1495-1505 (1992).
Devarenne et al., "Adi3 is Pdk1-interacting AGC kinase that negatively regulates plant cell death," *The EMBO Journal*, 25:255-265 (2006).
De Jong et al., "Chemical-induced apoptotic cell death in tomato cells: involvement of caspase-like proteases," *Planta*, 211(5):656-662 (2000).
De Wet et al., "Exogenous gene transfer in maize (*Zea mays*) using DNA-treated pollen," in *The Experimental Manipulation of Ovule Tissues*, Chapter 16, Chapman et al. (eds.), Longman, New York, pp. 197-209 (1985).
Doyle et al., "TAL Effector-Nucleotide Targeter (TALE-NT) 2.0: tools for TAL effector design and target prediction," *Nucleic Acids Research*, 40:W117-W122 (2012).
Dugas et al., "MicroRNA regulation of gene expression in plants," *Current Opinion in Plant Biology*, 7:512-520 (2004).
Escamez et al., "Programmes of cell death and autolysis in tracheary elements: when a suicidal cell arranges its own corpse removal," *Journal of Experimental Botany*, 65(5)1313-1321 (2014).
Estruch et al., "Transgenic plants: An emerging approach to pest control," *Nature Biotechnology*, 15:137-141 (1997).
Fedoroff et al., "Cloning of the bronze locus in maize by a simple and generalizable procedure using the transposable controlling element Activator (Ac)," *Proc. Natl. Acad. Sci. USA*, 81:3825-3829 (1984).
Finer et al., "Transformation of Soybean via Particle Bombardment of Embryogenic Suspension Culture Tissue," *In Vitro Cell. Dev. Biol.*, 27P:175-182 (1991).
Fisher et al., "Topping, Managing Suckers, and Using Ethephon," in *Flue-Cured Tobacco Information*, Chapter 7, North Carolina State University, pp. 96-117 (2016).
Franco-Zorrilla et al., "Target mimicry provides a new mechanism for regulation of microRNA activity," *Nature Genetics*, 39(8):1033-1037 (2007).
Gälweiler et al., "Regulation of Polar Auxin Transport by AtPIN1 in *Arabidopsis* Vasulcar Tissue," *Science*, 282:2226-2230 (1998).
Gao et al., "NgBRC1 suppresses axillary branching in tobacco after decapitation," *Genetics and Molecular Research*, 15(4), whole document (2016).
Gatz et al., "Regulation of a modified CaMV 35S promoter by the Tn10-encoded Tet repressor in transgenic tobacco," *Mol Gen Genet*, 227:229-237 (1991).
Goldman et al., "Female sterile tobacco plants are produced by stigma-specific cell ablation," *The EMBO Journal*, 13(13):2976-2984 (1994).
González-Grandío et al., "BRANCHED1 Promotes Axillary Bud Dormancy in Response to Shade in *Arabidopsis*," *The Plant Cell*, 25:834-850 (2013).
Greb et al., "Molecular analysis of the LATERAL SUPPRESSOR gene in *Arabidopsis* reveals a conserved control mechanism for axillary meristem formation," *Gene & Development*, 17:1175-1187 (2003).
Griffiths-Jones et al., "Rfam: an RNA family database," *Nucleic Acids Research*, 31(1):439-441 (2003).
Guevara-García et al., "Tissue-specific and wound-inducible pattern of expression of the mannopine synthase promoter is determined by the interaction between positive and negative cis-regulatory elements," *The Plant Journal*, 4(3):495-505 (1993).
Hansen et al., "Wound-inucible and organ-specific expression of $ORF_{13}$ from *Agrobacterium rhizogenes* 8196 T-DNA in transgenic tobacco plants," *Molecular and General Genetics*, 254(3):337-343 (1997).
Hartley, R.W., "Barnase and barstar: two small proteins to fold and fit," *Trends in Biochemical Sciences*, 14(11):450-454 (1989).
Hildering et al., "Chimeric Structure of the Tomato Plant After Seed Treatment With EMS and X-rays," The Use of Induced Mutations in Plant Breeding (Supplement to Radiation Botany), vol. 5, Pergamon Press Ltd., pp. 317-320, with cover page (1965) (London, UK).
Hoekema et al., "A binary plant vector strategy based on separation of vir- and T-region of the *Agrobacterium tumefaciens* Ti-plasmid," *Nature*, 303:179-180 (1983).
Horsch et al., "A Simple and General Method for Transferring Genes into Plants," *Science*, 227(4691):1229-1231 (1985).
International Search Report and Written Opinion mailed Nov. 22, 2018, in PCT/US2018/049959.
Jones-Rhoades et al., "Computational Identification of Plant MicroRNAs and Their Targets, Including a Stress-Induced MiRNA," *Molecular Cell*, 14:787-799 (2004).
Kaeppler et al., "Silicon carbide fiber-mediated DNA delivery into plant cells," *Plant Cell Reports*, 9:415-418 (1990).
Kaeppler et al., "Silicon carbide fiber-mediated stable transformation of plant cells," Theor. Appl. Genet., 84:560-566 (1992).
Katoh et al., "Specific residues at every third position of siRNA shape its efficient RNAi activity," *Nucleic Acids Research*, 35(4):e27 (2007).
Kawamata et al., "Temporal and Spatial Pattern of Expression of the Pea Phenylalanine Ammonia-Lyase Gene1 Promoter in Transgenic Tobacco," *Plant Cell Physiology*, 38(7)792-803 (1997).
Keller et al., "*Arabidopsis* Regulator of Axillary MERISTEMS1 Controls oa Leaf Axil Stem Cell Niche and Modulates Vegetative Development," *The Plant Cell*, 18:598-611 (2006).
Khvorova et al., "Functional siRNAs and miRNAs Exhibit Strand Bias," *Cell*, 115:209-216 (2003).
Kim, V.N., "MicroRNA Biogenesis: Coordinated Cropping and Dicing," *Mol. Cell. Bio.*, 6:379-385 (2005).
Lam, E., "Analysis of Tissue-Specific Elements in the CaMV $_{35}$S Promoted," *Results and Problems in Cell Differentiation: Plant Promoters and Transcription Factors*, 20:181-196 (1994).
Last et al., "pEmu: an improved promoter for gene expression in cereal cells," *Theor Appl Genet*, 81:581-588 (1991).
Long et al., "A member of the Knotted class of homeodomain proteins encoded by the STM gene of *Arabidopsis*," *Nature*, 379:66-69 (1996).
Matsuoka et al., "Tissue-specific light-regulated expression directed by the promoter of a $C_4$ gene, maize pyruvate, orthophosphate dikinase, in a $C_3$ plant rice," *Proc. Natl. Acad. Sci. USA*, 90:9586-9590 (1993).
Mayo et al., "Genetic transformation of tobacco NT1 cells with *Agrobacterium tumefaciens*," *Nature Protocols*, 1(3):1105-1111 (2006).
McCabe et al., "Stable Transformation of Soybean (*Glycine max*) by Particle Acceleration," *BioTechnology*, 6:923-926 (1998).

(56) References Cited

OTHER PUBLICATIONS

McCallum et al., "Targeted screening for induced mutations," *Nature Biotechnology*, 18:455-457 (2000).

McNellis et al., "Glucocorticoid-inducible expression of a bacterial avirulence gene in transgenic *Arabidopsis* induces hypersensitive cell death," *The Plant Journal*, 14(2):247-257 (1998).

Miller "Memorandum: Proposed Burley Tobacco Grade Index," Legacy Tobacco Document Library, The University of Tennessee Agricultural Experiment Station (Bates Document #523267826-523267833) (Jul. 1988) (Knoxville, USA).

Miller et al., "A Grade Index for Type 22 and 23 Fire-Cured Tobacco," *Tobacco International*, 192:55-57 (1990).

Miller, R.D., Memorandum on the Proposed Burley Tobacco Grade Index, Legacy Tobacco Document Library (Bates Document #523267826-523267833, Jul. 1, 1988.

Murchison et al., "miRNAs on the move: miRNA biogenesis and the RNAi machinery," *Current Opinion in Cell Biology*, 16(3):223-229 (2004).

Neu et al., "*Arabidopsis* amidase 1, a member of the amidase signature familey," *FEBS Journal*, 274:3440-3451 (2007).

Odell et al., "Identification of DNA sequences required for activity of the cauliflower mosaic virus 35S promoter," *Nature*, 313:810-812 (1985).

Official Standard Grades for Burley Tobacco (U.S. Type 31 and Foreign Type 93), effective Nov. 5, 1990 (55 F.R. 40645).

Official Standard Grades for Flue-Cured Tobacco (U.S. Types 11, 12, 13, 14, and Foreign Type 92), effective Mar. 27, 1989 (54 F.R. 7925).

Official Standard Grades for Pennsylvania Seedleaf Tobacco (U.S. Type 41), effective Jan. 8, 1965 (29 F.R. 16854).

Official Standard Grades for Ohio Cigar-Leaf Tobacco (U.S. Types 42, 43, and 44), effective Dec. 8, 1963 (28 F.R. 11719 and 28 F.R. 11926).

Official Standard Grades for Wisconsin Cigar-Binder Tobacco (U.S. Types 54 and 55), effective Nov. 20, 1969 (34 F.R. 17061).

Official Standard Grades for Georgia and Florida Shade-Grown Cigar-Wrapper Tobacco (U.S. Type 62), Effective Apr. 1971.

Orozco et al., "Localization of light-inducible and tissue-specific regions of the spinach ribulose bisphosphate carboxylase/oxygenase (rubisco) activase promoter in transgenic tobacco plants," *Plant Molecular Biology*, 23(6):1129-1138 (1993).

Ortiz-Morea et al., "Global analysis of the sugarcane microtransciptome reveals a unique composition of small RNAs associated with axillary bud outgrowth," *Journal of Experimental Botany*, 64(8):2307-2320 (2013).

Parizotto et al., "In vivo investigation of the transcription, processing, endonucleolytic activity, and functional relevance of the spatial distribution of a plant miRNA," *Genes & Development*, 18:2237-2242 (2004).

Paszkowski et al., "Direct gene transfer to plants," *The EMBO Journal*, 3(12):2717-2722 (1984).

Porta et al., "Use of Viral Replicons for the Expression of Genes in Plants," *Molecular Biotechnology*, 5:209-221 (1996).

Reynolds et al., "Rational siRNA design for RNA interference," *Nature Biotechnology*, 22:326-330 (2004).

Rhoades et al., "Prediction of Plant MicroRNA Targets," *Cell*, 110:513-520 (2002).

Riggs et al., "Stable transformation of tobacco by electroporation: Evidence for plasmid concatenation," *Proc. Natl. Acad. Sci. USA*, 83:5602-5606 (1986).

Rinehart et al., "Tissue-Specific and Developmental Regulation of Cotton Gene FbL2A," *Plant Physiology*, 112:1331-1341 (1996).

Rinne et al., "Axillary buds are dwarfed shoots that tightly regulate GA pathway and GA-inducible 1,3-β-glucanase genes during branching in hybrid aspen." *J Exp Bot.* 67(21), pp. 5975-5991 (Nov. 2016) available online: doi: 10.1093/jxb/erw352. Epub Oct. 3, 2016. PMID: 27697786; PMCID: PMC510014.

Russell et al., "Tissue-specific expression in transgenic maize of four endosperm promoters from maize and rice," *Transgenic Research*, 6(2):157-168 (1997).

Schena et al., "A steroid-inducible gene expression system for plant cells," *Proc. Natl. Acad. Sci. USA*, 88:10421-10425 (1991).

Shillito et al., "Direct Gene Transfer to Protoplasts of Dicotyledonous and Monocotyledonous Plants by a Number of Methods, Including Electroporation," *Methods in Enzymology*, 153:313-336 (1987).

Singh et al., "Cytological characterization of transgenic soybean," *Theor. Appl. Genet.*, 96:319-324 (1998).

Smith, W.D., "Seedling Production," in *Tobacco, Production, Chemistry and Technology*, Chapters 4B and 4C, Davis & Nielsen (eds.), Blackwell Publishing, Oxford, pp. 70-103.

Stepanova et al., "TAA1-Mediated Auxin Biosynthesis Is Essential for Hormone Crosstalk and Plant Development," *Cell*, 133:177-191 (2008).

Stirnberg et al., "MAX1 and MAX2 control shoot lateral braching in *Arabidopsis*," *Development*, 129:1131-1141 (2002).

Sun et al., "Inhibition of tobacco axillary bud differentiation by silencing CUP-Shaped Cotyledon 3," *African Journal of Biotechnology*, 11(16), whole document (2000).

Sun et al., "Cotton GhBRC1 regulates branching, flowering, and growth by integrating multiple hormone pathways," The Crop Journal, vol. 10; pp. 75-87 (2022) (available online Mar. 2021) ( Amsterdam, Netherlands).

Sunkar et al., "Novel and Stress-Regulated MicroRNAs and Other Small RNAs from *Arabidopsis*," *The Plant Cell*, 16:2001-2019 (2004).

Tadege et al., "STENOFOLIA Regulates Blade Outgrowth and Leaf Vasular Patterning in *Medicago truncatula* and *Nicotiana sylvestris*," *The Plant Cell*, 23(6):2125-2142 (2011).

Tanaka et al., "Studies on Biological Effects of Ion Beams on Lethality, Molecular Nature of Mutation, Mutation Rate, and Spectrum of Mutation Phenotype for Mutation Breeding in Higher Plants," *J. Radiat. Res.*, 51:223-233 (2010).

Tanaka-Ueguchi et al., "Over-expression of a tobacco homeobox gene, NTH15, decreases the expression of a gibberellin biosynthetic gene encoding GA 20-oxidase," *The Plant Journal*, 15(3):391-400 (1998).

Tomes et al., "Direct DNA Trasfer into Intact Plant Cells via Microprojectile Bombardment," in Plant Cell, Tissue and Organ Culture, Chapter 16, Fundamental Methods edition, Gamborg and Phillips (eds.), Springer-Verlag, Berlin (1995).

Trobacher et al., "Induction of a ricinosomal-protease and programmed cell death in tomato endosperm by gibberellic acid," *Planta*, 237(3):665-679 (2013).

Tso "Seed to Smoke," Chapter 1 in Davis and Nielsen (ed.), Tobacco: Production, Chemistry and Technology, Blackwell Science Publishing, pp. 1-31 with cover page (Oxford, UK).

Van Camp et al., "Tissue-Specific Activity of Two Manganese Superoxide Dismutase Promoters in Transgenic Tobacco," *Plant Physiology*, 112:525-535 (1996).

Velten et al., "Isolation of a dual plant promoter fragment from the Ti plasmid of *Agrobacterium tumefaciens*," *The EMBO Journal*, 3(12):2723-2730 (1984).

Verkerk, K., "Chimerism of the tomato plant after seed irradiation," *Neth. J. Agric. Sci.*, 19:197-203 (1971).

Wang et al., "MicroRNA171c-Targeted SCL6-II, SCL6-III, and SCL6-IV Genes Regulate Shoot Branching in *Arabidopsis*," *Molecular Plant*, 3(5):794-806 (2010).

Watanabe et al., "*Arabidopsis* metacaspase 2d is a positive mediator of cell death induced during biotic and abiotic stresses," *The Plant Journal*, 66:969-982 (2011).

Weising et al., "Foreign Genes in Plants: Transfer, Structure, Expression, and Applications," *Annu. Rev. Genet.*, 22:421-477 (1988).

Wernsman et al., "Tobacco," in Cultivar Development. Crop Sciences., Chapter 17, W.H. Fehr (ed.), MacMillan Publishing Co., Inc., New York, NY, pp. 669-698 (1987).

Yadav et al., "WUSCHEL protein movement mediates stem cell homeostasis in the *Arabidopsis* shoot apex," *Genes & Development*, 25:2025-2030 (2011).

Yamada et al., "The Transport Inhibitor Response2 Gene Is Required for Auxin Synthesis and Diverse Aspects of Plant Development," *Plant Physiology*, 151:168-179 (2009).

(56) References Cited

OTHER PUBLICATIONS

Yamamoto et al., "The Promoter of a Pine Phtosynthetic Gene Allows Expression of a beta-Glucuronidase Reporter Gene in Transgenic Rice Plants in a Light-Independent but Tissue-Specific Manner," *Plant Cell Physiology*, 35(5):773-778 (1994).

Yamamoto et al., "Light-responsive elements of the tobacco PSI-D gene are located both upstream and within the transcribed region," *The Plant Journal*, 12(2):255-265 (1997).

Zeng et al., "Both Natural and Designed Micro RNAs Can Inhibit the Expression of Cognate mRNAs When Expressed in Human Cells," *Molecular Cell*, 9:1327-1333 (2002).

Zhang et al., "Transcription Activator-Like Effector Nucleases Enable Efficient Plant Genome Engineering," *Plant Physiology*, 161:20-27 (2013).

\* cited by examiner

FIGURE 5
Figure 5A
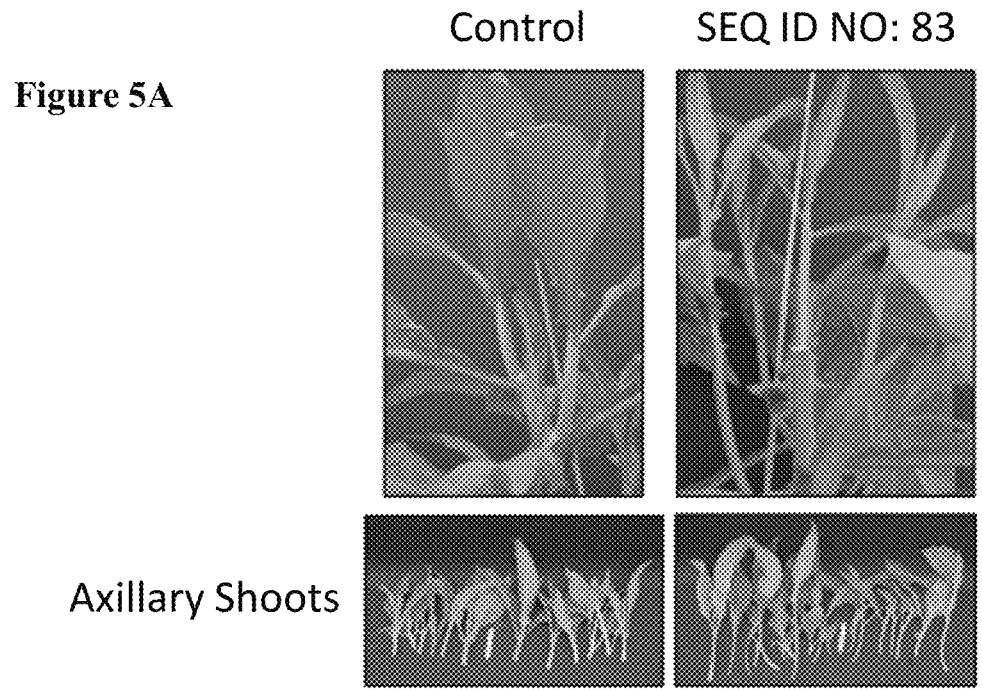
Figure 5B
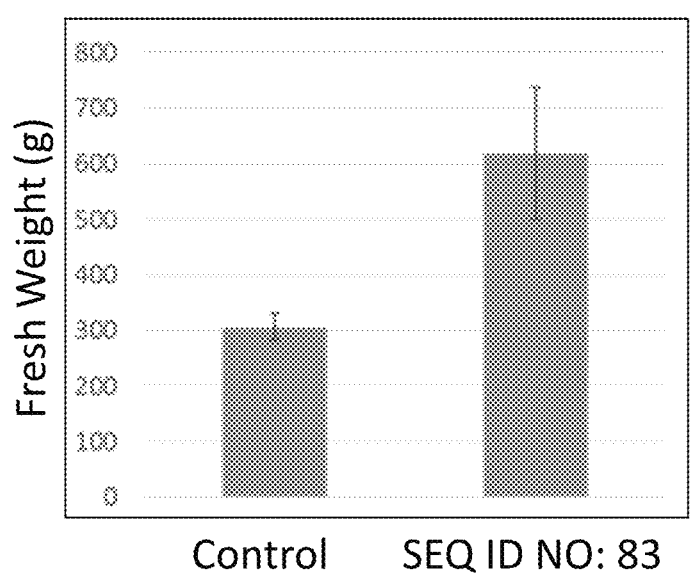

Seedling

Seedling SAM

SAM | Axillary Buds 0 hours | 0 hours | 3 days | 5 days | 7 days 0 hours 7 days 10 days

FIGURE 14
Figure 14A
SAM and Axillary Buds
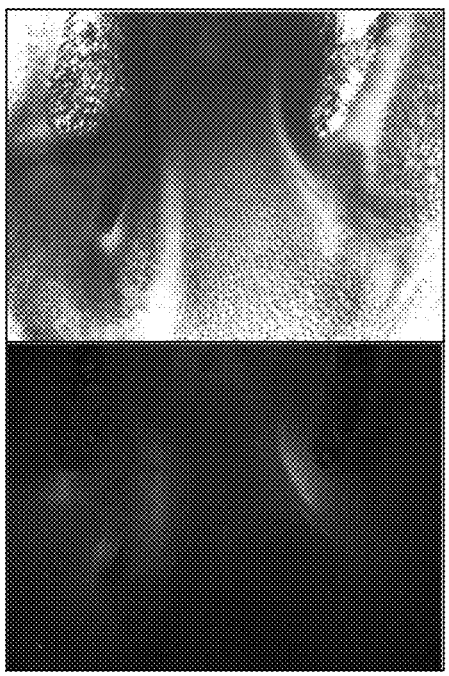
Axillary Bud
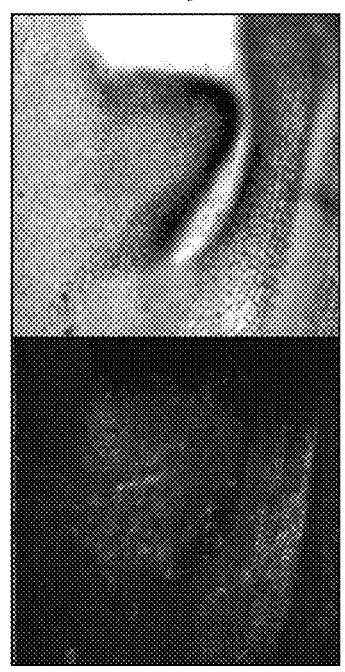
Figure 14B
SAM and Axillary Buds
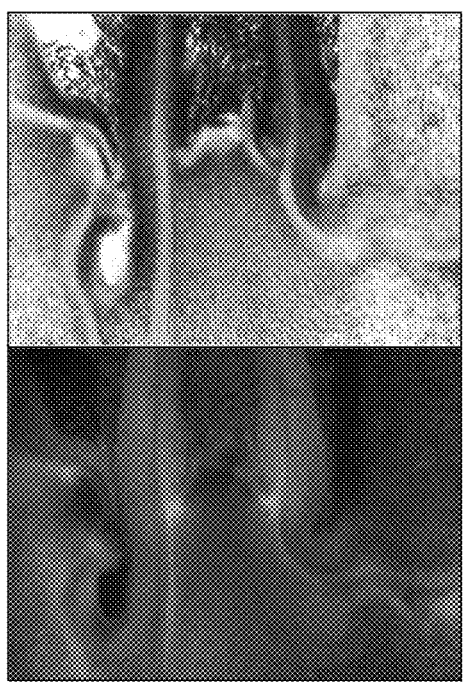
Axillary Bud
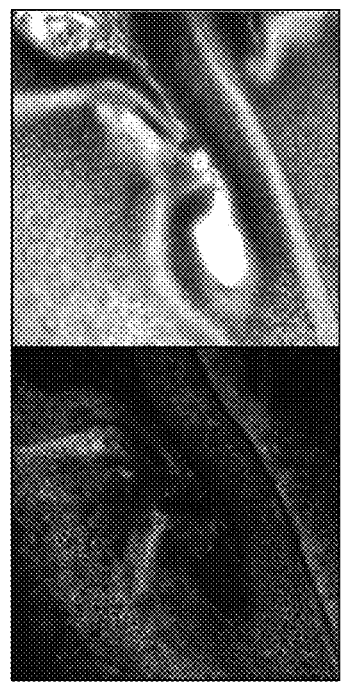

Control

SEQ ID NO: 117 (promoter) driving SEQ ID NO: 59

Positive Control (SEQ ID NO: 79)

Negative Control (Empty vector)

SEQ ID NO: 203

SEQ ID NO: 208

SEQ ID NO: 209

SEQ ID NO: 210

SEQ ID NO: 216

SEQ ID NO: 228

SEQ ID NO: 230

SEQ ID NO: 232

Floral Organs

Early developing capsules

Later stages of capsule development

FIGURE 22
FIGURE 22B
Line 1
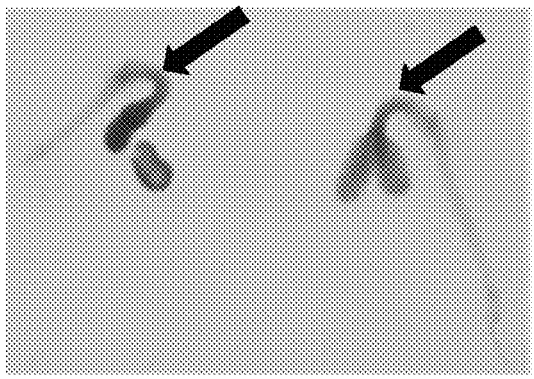
Line 2
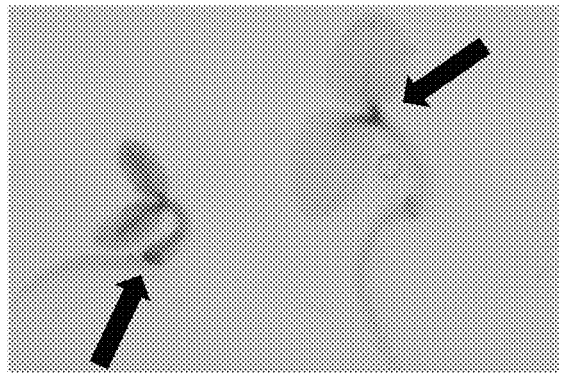

FIGURE 23
FIGURE 23B
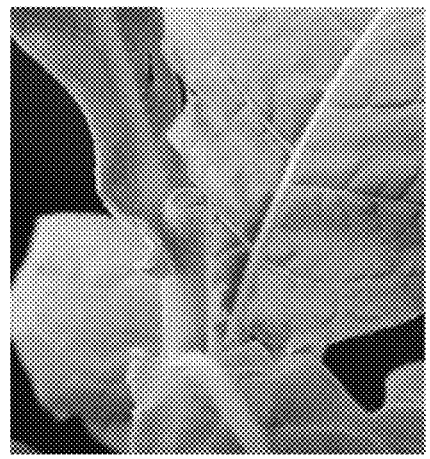
P15-5kb:BA
P15-5kb:BA
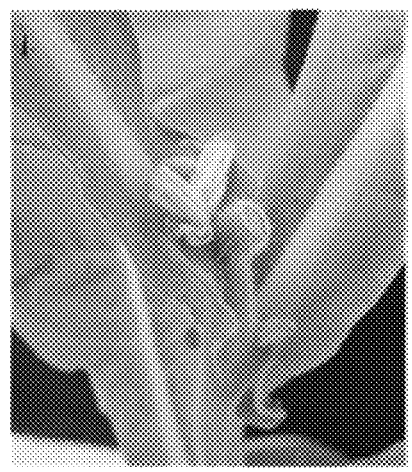
P15-5kb:BA
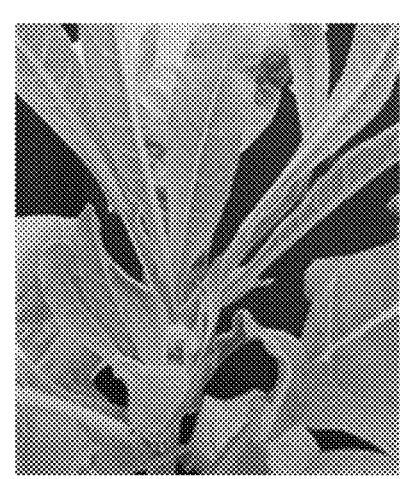
Wildtype Seed Seed Mature SAM Floral Buds 2 day seedling 9 day seedling Ungerminated Seed Ungerminated Seed 1-day post germination seed 3-day post germination seed Control Line 1

Line 2

Line 3

RAX1 Knockout

RAX2 Knockout

COMPOSITIONS AND METHODS FOR PRODUCING TOBACCO PLANTS AND PRODUCTS HAVING REDUCED OR ELIMINATED SUCKERS

CROSS-REFERENCE TO RELATED APPLICATION

This application is a continuation of U.S. patent application Ser. No. 17/406,829, filed Aug. 19, 2021, which is a continuation of U.S. patent application Ser. No. 16/124,941, filed Sep. 7, 2018, now U.S. Pat. No. 11,104,912, issued Aug. 31, 2021, which claims the benefit of U.S. Provisional Application No. 62/556,804, filed Sep. 11, 2017, all of which are incorporated by reference in its entireties herein.

INCORPORATION OF SEQUENCE LISTING

A sequence listing contained in the file named "P34549US03_SL.xml" which is 618,780 bytes (measured in MS-Windows®) and created on Dec. 12, 2023 is filed electronically herewith and incorporated by reference in its entirety.

FIELD

The present disclosure identifies axillary bud-specific promoters and genes involved in sucker growth. Also provided are methods and compositions related to reducing or eliminating suckers in tobacco plants, their development via breeding or transgenic approaches, and production of tobacco products from those tobacco plants.

BACKGROUND

Tobacco is a plant species that exhibits exceptionally strong apical dominance. Molecular signals from the shoot apical meristem (SAM) mediate a hormonal signal that effectively inhibits axillary bud growth. Upon removal of the SAM (also known as "topping"), physiological and molecular changes occur, enabling the growth of new shoots (or "suckers") from axillary meristems (buds). Sucker growth results in loss of yield and leaf quality. Suckers have been controlled by manual removal and through the application of chemicals. Maleic hydrazide and flumetralin are routinely used on topped plants to inhibit axillary bud growth ("suckering"). However, labor and chemical agents to control suckers are very expensive. Control of suckering in tobacco through conventional breeding, mutation breeding, and transgenic approaches have been a major objective for several decades but, to date, successful inhibition or elimination of suckering has not been achieved through these approaches. Therefore, development of tobacco traits with limited or no suckering would result in a reduction of the use of chemical agents and would reduce costs and labor associated with tobacco production.

SUMMARY

In one aspect, the present disclosure provides a modified tobacco plant comprising no or reduced suckering compared to a control tobacco plant of the same variety when grown under comparable conditions.

In one aspect, the present disclosure provides a modified tobacco plant, where the modified tobacco plant exhibits: inhibited or eliminated axillary meristem growth; inhibited or eliminated axillary meristem maintenance; or a combination thereof compared to a control tobacco plant of the same variety when grown under comparable conditions.

In one aspect, the present disclosure provides a plant or seed comprising a recombinant polynucleotide, where the recombinant polynucleotide comprises a promoter that is functional in an L1 layer, an L2 layer, an L3 region, a rib zone, a central zone, a peripheral zone, or any combination thereof, which is operably linked to a structural nucleic acid molecule comprising a nucleic acid sequence, where the nucleic acid sequence encodes a polypeptide having at least 70% sequence identity to a polypeptide selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 161-185, 187, 189, 191, 193, 195, 197, 199, 201, 203, 206, 208, 210, 212, 214, 216, 218, 220, 222, 224, 229, 231, 233, 235, 237, 239, 241, 243, 245, 247, 249, 251, 253, and 255.

In one aspect, the present disclosure provides a recombinant DNA construct comprising a promoter that is functional in an L1 layer, an L2 layer, an L3 region, a rib zone, a central zone, a peripheral zone, or a combination thereof; and a heterologous and operably linked nucleic acid sequence, where the nucleic acid sequence encodes a non-coding RNA or a polypeptide.

In one aspect, the present disclosure provides a method of reducing or eliminating topping-induced suckering in a tobacco plant, where the method comprises transforming a tobacco plant with a recombinant DNA construct comprising a promoter functional in an L1 layer, an L2 layer, an L3 region, a rib zone, a central zone, a peripheral zone, or a combination thereof.

In one aspect, the present disclosure provides a method comprising transforming a tobacco plant with a recombinant DNA construct comprising a heterologous promoter that is functional in an L1 layer, an L2 layer, an L3 region, a rib zone, a central zone, a peripheral zone, or a combination thereof, and is operably linked to a polynucleotide that is transcribed into an RNA molecule that suppresses the level of an endogenous gene, and where the endogenous gene promotes or is required for axillary meristem growth, axillary meristem maintenance, or both.

In one aspect, the present disclosure provides a method for producing a tobacco plant comprising crossing at least one tobacco plant of a first tobacco variety with at least one tobacco plant of a second tobacco variety, where the at least one tobacco plant of the first tobacco variety exhibits no or reduced topping-induced suckering compared to a control tobacco plant of the same variety grown under comparable conditions; and selecting for progeny tobacco plants that exhibit no or reduced topping-induced suckering compared to a control tobacco plant of the same cross grown under comparable conditions.

In one aspect, the present disclosure provides a tobacco plant, or part thereof, comprising a heterologous promoter operably linked to a polynucleotide encoding a polypeptide having at least 70% sequence identity to a polypeptide selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 161-185, 187, 189, 191, 193, 195, 197, 199, 201, 203, 206, 208, 210, 212, 214, 216, 218, 220, 222, 224, 229, 231, 233, 235, 237, 239, 241, 243, 245, 247, 249, 251, 253, and 255.

In one aspect, the present disclosure provides a recombinant DNA construct comprising a heterologous promoter operably linked to a polynucleotide encoding a polypeptide having at least 70% sequence identity to a polypeptide selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 161-185, 187, 189, 191, 193, 195, 197, 199, 201, 203, 206, 208, 210, 212, 214, 216, 218, 220, 222, 224, 229, 231, 233, 235, 237, 239, 241, 243, 245, 247, 249, 251, 253, and 255.

In one aspect, the present disclosure provides a method of growing a modified tobacco plant comprising planting a modified tobacco seed comprising a heterologous promoter that is operably linked to a polynucleotide encoding a polypeptide having at least 70% sequence identity to a polypeptide selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 161-185, 187, 189, 191, 193, 195, 197, 199, 201, 203, 206, 208, 210, 212, 214, 216, 218, 220, 222, 224,229, 231, 233, 235, 237, 239, 241, 243, 245, 247,249, 251, 253, and 255; and growing the modified tobacco plant from the seed.

In one aspect, the present disclosure provides a method for controlling topping-induced suckering in a plant comprising transforming the plant with a recombinant DNA construct, where the recombinant DNA construct comprises a promoter that is operably linked to a polynucleotide encoding a polypeptide having at least 70% sequence identity to a polypeptide selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 161-185, 187, 189, 191, 193, 195, 197, 199, 201, 203, 206, 208, 210, 212, 214, 216, 218, 220, 222, 224, 229, 231, 233, 235, 237, 239, 241, 243, 245, 247, 249, 251, 253, and 255.

In one aspect, the present disclosure provides a tobacco plant, or part thereof, comprising a heterologous promoter operably linked to a polynucleotide that encodes a non-coding RNA molecule, where the non-coding RNA molecule is capable of binding to an RNA encoding a polypeptide having at least 70% sequence identity to a polypeptide selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 70, 72, 74, 76, 78, 161-185, 187, 189, 191, 197, 199, 224, 229, 231, 233, 235, 237, 239, 241, 243, 245, 247, 249, 251, 253, and 255, and where the non-coding RNA molecule suppresses the expression of the polypeptide.

In one aspect, the present disclosure provides a recombinant DNA construct comprising a heterologous axillary meristem-specific promoter operably linked to a polynucleotide that encodes a non-coding RNA molecule, where the non-coding RNA molecule is capable of binding to an RNA encoding a polypeptide having at least 70% sequence identity to a polypeptide selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 70, 72, 74, 76, 78, 161-185, 187, 189, 191, 197, 199, 224, 229, 231, 233, 235, 237, 239, 241, 243, 245, 247, 249, 251, 253, and 255, and where the non-coding RNA molecule suppresses the expression of the polypeptide.

In one aspect, the present disclosure provides a method of growing a modified tobacco plant comprising planting a modified tobacco seed comprising a recombinant DNA construct comprising a heterologous promoter that is functional in an L1 layer, an L2 layer, an L3 region, a rib zone, a central zone, a peripheral zone, or a combination thereof, and is operably linked to a polynucleotide that encodes a non-coding RNA molecule, where the non-coding RNA molecule is capable of binding to an RNA encoding a polypeptide having at least 70% sequence identity to a polypeptide selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 70, 72, 74, 76, 78, 161-185, 187, 189, 191, 197, 199, 224, 229, 231, 233, 235, 237, 239, 241, 243, 245, 247, 249, 251, 253, and 255, and where the non-coding RNA molecule suppresses the expression of the polypeptide; and growing the modified tobacco plant from the seed.

In one aspect, the present disclosure provides a method for controlling topping-induced suckering in a plant comprising transforming the plant with a recombinant DNA construct, where the recombinant DNA construct comprises a heterologous promoter that is functional in an L1 layer, an L2 layer, an L3 region, a rib zone, a central zone, a peripheral zone, or a combination thereof, and where the promoter is operably linked to a polynucleotide that encodes a non-coding RNA molecule, where the non-coding RNA molecule is capable of binding to an RNA encoding a polypeptide having at least 70% sequence identity to a polypeptide selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 70, 72, 74, 76, 78, 161-185, 187, 189, 191, 197, 199, 224, 229, 231, 233, 235, 237, 239, 241, 243, 245, 247, 249, 251, 253, and 255, and where the non-coding RNA molecule suppresses the expression of the polypeptide.

In one aspect, the present disclosure provides a bacterial cell comprising a recombinant DNA construct provided herein.

In one aspect, the present disclosure provides a plant genome comprising a recombinant DNA construct provided herein.

In one aspect, the present disclosure provides a method for manufacturing a modified seed comprising introducing a recombinant DNA construct provided herein into a plant cell; screening a population of plant cells for the recombinant DNA construct; selecting one or more plant cells from the population, generating one or more modified plants from the one or more plant cells; and collecting one or more modified seeds from the one or more modified plants.

In one aspect, the present disclosure provides a method of producing a modified tobacco plant to reduce or eliminate suckering, where the method comprises introducing one or more mutations in one or more tobacco genome loci.

In one aspect, the present disclosure provides a method of producing a modified tobacco plant to reduce or eliminate suckering, where the method comprises introducing one or more mutations in one or more tobacco genome loci, and where tobacco products are made from the modified tobacco plants.

In one aspect, the present disclosure provides a plant or seed comprising a recombinant polynucleotide, where the recombinant polynucleotide comprises a promoter that is functional in an L1 layer, an L2 layer, an L3 region, a rib zone, a central zone, a peripheral zone, or any combination thereof, which is operably linked to a structural nucleic acid molecule comprising a nucleic acid sequence, where the nucleic acid sequence encodes an auxin biosynthesis protein or an auxin transport protein.

In one aspect, the present disclosure provides a recombinant DNA construct comprising a promoter that is functional in an L1 layer, an L2 layer, an L3 region, a rib zone, a central zone, a peripheral zone, or any combination thereof; and a heterologous and operably linked nucleic acid sequence, where the nucleic acid sequence encodes an auxin biosynthesis protein or an auxin transport protein.

In one aspect, the present disclosure provides a recombinant DNA construct comprising a heterologous axillary meristem-specific promoter operably linked to a polynucleotide that encodes an auxin biosynthesis protein or an auxin transport protein.

In one aspect, the present disclosure provides a tobacco plant, or part thereof, comprising a heterologous promoter having at least 90% sequence identity to a polynucleotide selected from the group consisting of SEQ ID NOs: 113-118, 148-160, 204, and fragments thereof operably linked to a polynucleotide encoding an auxin biosynthesis protein or an auxin transport protein.

In one aspect, the present disclosure provides a method for controlling topping-induced suckers in a plant comprising transforming said plant with a recombinant DNA construct, where the recombinant DNA construct comprises a promoter that is operably linked to a polynucleotide encoding an auxin biosynthesis protein or an auxin transport protein.

BRIEF DESCRIPTION OF THE SEQUENCES

SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83-160, 186, 188, 190, 192, 194, 196, 198, 200, 202, 204, 205, 207, 209, 211, 213, 215, 217, 219, 221, 223, 225-228, 230, 232, 234, 236, 238, 240, 242, 244, 246, 248, 250, 252, and 254 are nucleic acid sequences. SEQ ID NOs: 83-101 are RNAi constructs. SEQ ID NOs: 113-118, 148-160, and 204 are promoter or regulatory nucleic acid sequences. SEQ ID NOs: 119-122 are sequences used in TALEN mutagenesis.

SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 161-185, 187, 189, 191, 193, 195, 197, 199, 201, 203, 206, 208, 210, 212, 214, 216, 218, 220, 222, 224, 229, 231, 233, 235, 237, 239, 241, 243, 245, 247, 249, 251, 253, and 255 are polypeptide sequences. Additional descriptions of the SEQ ID NOs provided herein can be found in Table 1.

TABLE 1

Description of sequences

| SEQ ID NO | Sequence Type | Sequence Description | NCBI Accession Number of the Top Hit of A BLAST Search |
|---|---|---|---|
| 1 | Nucleic Acid | Transcription factor CYCLOIDEA-like | XM_009609861.1 |
| 2 | Peptide | Transcription factor CYCLOIDEA-like | |
| 3 | Nucleic Acid | Flower-specific gamma-thionin | P32026.1 |
| 4 | Peptide | Flower-specific gamma-thionin | |
| 5 | Nucleic Acid | Polyphenoloxidase | XP_006347083.1 |
| 6 | Peptide | Polyphenoloxidase | |
| 7 | Nucleic Acid | UDP-glucose:glucosyltransferase | BAG80546.1 |
| 8 | Peptide | UDP-glucose:glucosyltransferase | |
| 9 | Nucleic Acid | Tumor-related protein | BAA05479.1 |
| 10 | Peptide | Tumor-related protein | |
| 11 | Nucleic Acid | Hypothetical protein | CAN66732.1 |
| 12 | Peptide | Hypothetical protein | |
| 13 | Nucleic Acid | TCP1 protein-like gene | FJ194953.1 |
| 14 | Peptide | TCP1 protein-like gene | |
| 15 | Nucleic Acid | Chlorophyllase-2 | EYU43828.1 |
| 16 | Peptide | Chlorophyllase-2 | |
| 17 | Nucleic Acid | AP2/ERF domain-containing transcription factor | XP_006363442.1 |
| 18 | Peptide | AP2/ERF domain-containing transcription factor | |
| 19 | Nucleic Acid | Putative miraculin | XP_006360306.1 |
| 20 | Peptide | Putative miraculin | |
| 21 | Nucleic Acid | Oleosin | XP_004236249.1 |
| 22 | Peptide | Oleosin | |
| 23 | Nucleic Acid | ACC synthase | XP_006356827.1 |
| 24 | Peptide | ACC synthase | |
| 25 | Nucleic Acid | LOB domain-containing protein 18-like | XP_007052037.1 |
| 26 | Peptide | LOB domain-containing protein 18-like | |
| 27 | Nucleic Acid | Vicilin-like antimicrobial peptides cupin super family | XP_006363154.1 |
| 28 | Peptide | Vicilin-like antimicrobial peptides cupin super family | |
| 29 | Nucleic Acid | Abscisic acid insensitive | XP_006341248.1 |

TABLE 1-continued

Description of sequences

| SEQ ID NO | Sequence Type | Sequence Description | NCBI Accession Number of the Top Hit of A BLAST Search |
|---|---|---|---|
| 30 | Peptide | Abscisic acid insensitive | |
| 31 | Nucleic Acid | Seipin-like | XP_004237589.1 |
| 32 | Peptide | Seipin-like | |
| 33 | Nucleic Acid | Transcription factor CYCLOIDEA-like | XM_009618194.1 |
| 34 | Peptide | Transcription factor CYCLOIDEA-like | |
| 35 | Nucleic Acid | Transcription factor DICHOTOMA-like | XM_009593876.1 |
| 36 | Peptide | Transcription factor DICHOTOMA-like | |
| 37 | Nucleic Acid | Transcription factor CYCLOIDEA-like | XM_009764845.1 |
| 38 | Peptide | Transcription factor CYCLOIDEA-like | |
| 39 | Nucleic Acid | RING-H2 finger protein ATL11-like | XP_004251547.1 |
| 40 | Peptide | RING-H2 finger protein ATL11-like | |
| 41 | Nucleic Acid | Homeobox-leucine zipper protein ATHB-40-like | XP_004232382.1 |
| 42 | Peptide | Homeobox-leucine zipper protein ATHB-40- like | |
| 43 | Nucleic Acid | Uncharacterized protein- LOC102586855 isoform X1 | XP_006357617.1 |
| 44 | Peptide | Uncharacterized protein- LOC102586855 isoform X1 | |
| 45 | Nucleic Acid | Unknown | CAN63006.1 |
| 46 | Peptide | Unknown | |
| 47 | Nucleic Acid | MADS affecting flowering 5-like isoform X1/X2 | XP_006366525.1 |
| 48 | Peptide | MADS affecting flowering 5-like isoform X1/X2 | |
| 49 | Nucleic Acid | Nuclear transcription factor Y subunit | XP_006351227.1 |
| 50 | Peptide | Nuclear transcription factor Y subunit | |
| 51 | Nucleic Acid | Nuclear transcription factor Y subunit A-7-like | XP_006351229.1 |
| 52 | Peptide | Nuclear transcription factor Y subunit A-7-like | |
| 53 | Nucleic Acid | Transcription factor CYCLOIDEA-like | XM_009767637.1 |
| 54 | Peptide | Transcription factor CYCLOIDEA-like | |
| 55 | Nucleic Acid | *Arabidopsis* cytokinin oxidase | NM_129714.3 |
| 56 | Peptide | *Arabidopsis* cytokinin oxidase | |
| 57 | Nucleic Acid | *Nicotiana tabacum* cytokinin oxidase | XM_009611148.1 |
| 58 | Peptide | *Nicotiana tabacum* cytokinin oxidase | |
| 59 | Nucleic Acid | *Nicotiana tabacum* cytokinin oxidase | XM_009632505.1 |
| 60 | Peptide | *Nicotiana tabacum* cytokinin oxidase | |
| 61 | Nucleic Acid | *Nicotiana tabacum* Isopentenyl transferase gene (IPT-g120126) | XM_009784416.1 |
| 62 | Peptide | *Nicotiana tabacum* Isopentenyl transferase gene (IPT-g120126) | |
| 63 | Nucleic Acid | *Nicotiana tabacum* WUSCHEL (WUS-g151887) | XM_009589135.1 |
| 64 | Peptide | *Nicotiana tabacum* WUSCHEL (WUS-g151887) | |
| 65 | Nucleic Acid | *Nicotiana tabacum* WUSCHEL (WUS-g135280) | XM_009793912.1 |
| 66 | Peptide | *Nicotiana tabacum* WUSCHEL (WUS-g135280) | |
| 67 | Nucleic Acid | *Arabidopsis thaliana* CLAVATA3 (CLV3) | NM_001124926.1 |
| 68 | Peptide | *Arabidopsis thaliana* CLAVATA3 (CLV3) | |
| 69 | Nucleic Acid | *Nicotiana tabacum* CLAVATA3 (Scaffold00010610) | XM_009628563.1 |
| 70 | Peptide | *Nicotiana tabacum* CLAVATA3 (Scaffold00010610) | |
| 71 | Nucleic Acid | *Nicotiana tabacum* LATERAL SUPPRESSOR (g56830) | XM_009619761.1 |
| 72 | Peptide | *Nicotiana tabacum* LATERAL SUPPRESSOR (g56830) | |
| 73 | Nucleic Acid | *Nicotiana tabacum* LATERAL SUPPRESSOR (scafflod0004261) | XM_009766770.1 |

TABLE 1-continued

Description of sequences

| SEQ ID NO | Sequence Type | Sequence Description | NCBI Accession Number of the Top Hit of A BLAST Search |
|---|---|---|---|
| 74 | Peptide | *Nicotiana tabacum* LATERAL SUPPRESSOR (scafflod0004261) | |
| 75 | Nucleic Acid | *Nicotiana tabacum* REGULATOR OF AXILLARY MERISTEMS (RAX-scaffold0000950) | XM_009802273.1 |
| 76 | Peptide | *Nicotiana tabacum* REGULATOR OF AXILLARY MERISTEMS (RAX-scaffold0000950) | |
| 77 | Nucleic Acid | *Nicotiana tabacum* REGULATOR OF AXILLARY MERISTEMS (RAX-scaffold00001904) | XM_009602411.1 |
| 78 | Peptide | *Nicotiana tabacum* REGULATOR OF AXILLARY MERISTEMS (RAX-scaffold00001904) | |
| 79 | Nucleic Acid | *Bacillus amyloliquefaciens* extracellular ribonuclease (Barnase) | CP009748.1 |
| 80 | Peptide | *Bacillus amyloliquefaciens* extracellular ribonuclease (Barnase) | |
| 81 | Nucleic Acid | *Arabidopsis thaliana* BRANCHED1 | NM_001125184.1 |
| 82 | Peptide | *Arabidopsis thaliana* BRANCHED1 | |
| 83 | Nucleic Acid | RNAi_1 (targeting SEQ ID NO: 1) | |
| 84 | Nucleic Acid | RNAi_2 (targeting SEQ ID NO: 3) | |
| 85 | Nucleic Acid | RNAi_5 (targeting SEQ ID NO: 9) | |
| 86 | Nucleic Acid | RNAi_7 (targeting SEQ ID NO: 13) | |
| 87 | Nucleic Acid | RNAi_8 (targeting SEQ ID NO: 15) | |
| 88 | Nucleic Acid | RNAi_9 (targeting SEQ ID NO: 17) | |
| 89 | Nucleic Acid | RNAi_10 (targeting SEQ ID NO: 19) | |
| 90 | Nucleic Acid | RNAi_12 (targeting SEQ ID NO: 21) | |
| 91 | Nucleic Acid | RNAi_14 (targeting SEQ ID NO: 25) | |
| 92 | Nucleic Acid | RNAi_15 (targeting SEQ ID NO: 27) | |
| 93 | Nucleic Acid | RNAi_16 (targeting SEQ ID NO: 29) | |
| 94 | Nucleic Acid | RNAi_17 (targeting SEQ ID NO: 31) | |
| 95 | Nucleic Acid | RNAi_18 (targeting SEQ ID NO: 35) | |
| 96 | Nucleic Acid | RNAi_26 (targeting SEQ ID NO: 49) | |
| 97 | Nucleic Acid | RNAi_61 (targeting SEQ ID NO: 61) | |
| 98 | Nucleic Acid | RNAi_63 and 65 (targeting SEQ ID NO: 63 and 65) | |
| 99 | Nucleic Acid | RNAi_71 and 73 (targeting SEQ ID NO: 71 and 73) | |
| 100 | Nucleic Acid | RNAi_75 and 77 (targeting SEQ ID NO: 75 and 77) | |
| 101 | Nucleic Acid | RNAi_CET-26-6 (targeting SEQ ID NO: 11, 49, 108, 109 and 110) | |
| 102 | Nucleic Acid | RNAi_45-2-7-TDNA-145337-RI (targeting SEQ ID NO: 39) | |
| 103 | Nucleic Acid | RNAi_45-2-7-TDNA-348CDS-RI (targeting SEQ ID NO: 41) | |
| 104 | Nucleic Acid | RNAi_45-2-7-TDNA-131180CDS-RI (targeting SEQ ID NO: 43) | |
| 105 | Nucleic Acid | RNAi_45-2-7-TDNA-22266-RI (targeting SEQ ID NO: 45) | |
| 106 | Nucleic Acid | RNAi_45-2-7-TDNA-53803/75660-RI (targeting SEQ ID NO: 49) | |
| 107 | Nucleic Acid | RNAi_45-2-7-TDNA-21860-RI (targeting SEQ ID NO: 47) | |
| 108 | Nucleic Acid | CEN-like protein 2 (CET2) g114109 | AF145260.1 |
| 109 | Nucleic Acid | CEN-like protein 2 (CET2) g2420 | XM_009596199.1 |

TABLE 1-continued

Description of sequences

| SEQ ID NO | Sequence Type | Sequence Description | NCBI Accession Number of the Top Hit of A BLAST Search |
|---|---|---|---|
| 110 | Nucleic Acid | CEN-like protein 2 (CET2) Scaffold0003597 CDS | XM_009787775.1 |
| 111 | Nucleic Acid | Transformation cassette | |
| 112 | Nucleic Acid | *Agrobacterium* transformation vector p45-2-7 | |
| 113 | Nucleic Acid | A promoter sequence of a gene encoding SEQ ID NO: 2 (Gene 1) | |
| 114 | Nucleic Acid | A promoter sequence of a gene encoding SEQ ID NO: 8 (Gene 4) | |
| 115 | Nucleic Acid | A promoter sequence of a gene encoding SEQ ID NO: 14 (Gene 7) | |
| 116 | Nucleic Acid | promoter of SEQ ID NO: 275 (Gene 11) | |
| 117 | Nucleic Acid | A promoter sequence of a gene encoding SEQ ID NO: 28 (Gene 15) | |
| 118 | Nucleic Acid | A promoter sequence of a gene encoding SEQ ID NO: 4 (Gene 2) | |
| 119 | Nucleic Acid | Sequence for TALEN donor, which targets a gene encoding SEQ ID NO: 1 | |
| 120 | Nucleic Acid | Sequence for TALEN binding sites, which targets a gene encoding SEQ ID NO: 1 | |
| 121 | Nucleic Acid | Sequence for TALEN, include promoter NO: 118, NO: 113 which targets a gene encoding SEQ ID NO: 13 | |
| 122 | Nucleic Acid | Sequence for TALEN biding sites, which targets a gene encoding SEQ ID NO: 13 | |
| 123 | Nucleic Acid | *Nicotiana tabacum* T2 Rnase | XP_009794914.1 |
| 124 | Nucleic Acid | *Nicotiana tabacum* T2 Rnase | XP_009766067.1 |
| 125 | Nucleic Acid | *Nicotiana tabacum* P1 Rnase | XP_009597823.1 |
| 126 | Nucleic Acid | *Nicotiana tabacum* Rnase | XP_009775662.1 |
| 127 | Nucleic Acid | *Nicotiana tabacum* T2 Rnase | XM_009794797.1 |
| 128 | Nucleic Acid | *Nicotiana tabacum* T2 Rnase | XM_009627900.1 |
| 129 | Nucleic Acid | *Nicotiana tabacum* T2 Rnase | JQ041907.1 |
| 130 | Nucleic Acid | *Nicotiana tabacum* T2 Rnase | XM_009795594.1 |
| 131 | Nucleic Acid | *Nicotiana tabacum* T2 Rnase | XM_009795502.1 |
| 132 | Nucleic Acid | *Nicotiana tabacum* 12 Rnase | XM_009606804.1 |
| 133 | Nucleic Acid | *Nicotiana tabacum* 12 Rnase | XM_009794798.1 |
| 134 | Nucleic Acid | *Nicotiana tabacum* 12 Rnase | AB034638.1 |
| 135 | Nucleic Acid | *Nicotiana tabacum* 12 Rnase | XM_009784762.1 |
| 136 | Nucleic Acid | *Nicotiana tabacum* 12 Rnase | XM_009798107.1 |
| 137 | Nucleic Acid | VPE14 | XM_009773063.1 |
| 138 | Nucleic Acid | VPE15 | XM_009594104.1 |
| 139 | Nucleic Acid | VPE16 | XM_009784979.1 |
| 140 | Nucleic Acid | VPE17 | XM_009765910.1 |
| 141 | Nucleic Acid | VPE4 | XM_009623321.1 |
| 142 | Nucleic Acid | VPE6 | XM_009764257.1 |
| 143 | Nucleic Acid | VPE7 | AB075949.1 |
| 144 | Nucleic Acid | *Nicotiana tabacum* Proteinase | XM_009801188.1 |
| 145 | Nucleic Acid | *Nicotiana tabacum* Proteinase | XM_009792063.1 |
| 146 | Nucleic Acid | *Nicotiana tabacum* Proteinase | XM_009779330.1 |

TABLE 1-continued

Description of sequences

| SEQ ID NO | Sequence Type | Sequence Description | NCBI Accession Number of the Top Hit of A BLAST Search |
|---|---|---|---|
| 147 | Nucleic Acid | *Nicotiana tabacum* Proteinase | XM_009764284.1 |
| 148 | Nucleic Acid | Thionin 5' upstream regulatory sequence | |
| 149 | Nucleic Acid | *Nicotiana tabacum* Lateral Suppressor1 (LAS1) 5' upstream regulatory sequence | |
| 150 | Nucleic Acid | *Nicotiana tabacum* LAS1 3' downstream regulatory sequence | |
| 151 | Nucleic Acid | *Nicotiana tabacum* LAS2 5' upstream regulatory sequence | |
| 152 | Nucleic Acid | *Nicotiana tabacum* LAS2 3' downstream regulatory sequence | |
| 153 | Nucleic Acid | *Nicotiana tabacum* Regulator of Axillary Meristems1 (RAX1) 5' upstream regulatory sequence | |
| 154 | Nucleic Acid | *Nicotiana tabacum* RAX1 3' downstream regulatory sequence | |
| 155 | Nucleic Acid | *Nicotiana tabacum* RAX2 5' upstream regulatory sequence | |
| 156 | Nucleic Acid | *Nicotiana tabacum* RAX2 3' downstream regulatory sequence | |
| 157 | Nucleic Acid | SEQ ID NO: 27 5' upstream regulatory sequence | |
| 158 | Nucleic Acid | SEQ ID NO: 27 3' downstream regulatory sequence | |
| 159 | Nucleic Acid | SEQ ID NO: 27 homolog 5' upstream regulatory sequence | |
| 160 | Nucleic Acid | SEQ ID NO: 27 homolog 3' downstream regulatory sequence | |
| 161 | Peptide | *Nicotiana tabacum* T2 Rnase encoded by SEQ ID NO: 123 | |
| 162 | Peptide | *Nicotiana tabacum* T2 Rnase encoded by SEQ ID NO: 124 | |
| 163 | Peptide | *Nicotiana tabacum* P1 Rnase encoded by SEQ ID NO: 125 | |
| 164 | Peptide | *Nicotiana tabacum* Rnase encoded by SEQ ID NO: 126 | |
| 165 | Peptide | *Nicotiana tabacum* T2 Rnase encoded by SEQ ID NO: 127 | |
| 166 | Peptide | *Nicotiana tabacum* T2 Rnase encoded by SEQ ID NO: 128 | |
| 167 | Peptide | *Nicotiana tabacum* T2 Rnase encoded by SEQ ID NO: 129 | |
| 168 | Peptide | *Nicotiana tabacum* T2 Rnase encoded by SEQ ID NO: 130 | |
| 169 | Peptide | *Nicotiana tabacum* T2 Rnase encoded by SEQ ID NO: 131 | |
| 170 | Peptide | *Nicotiana tabacum* T2 Rnase encoded by SEQ ID NO: 132 | |
| 171 | Peptide | *Nicotiana tabacum* T2 Rnase encoded by SEQ ID NO: 133 | |
| 172 | Peptide | *Nicotiana tabacum* T2 Rnase encoded by SEQ ID NO: 134 | |
| 173 | Peptide | *Nicotiana tabacum* T2 Rnase encoded by SEQ ID NO: 135 | |
| 174 | Peptide | *Nicotiana tabacum* T2 Rnase encoded by SEQ ID NO: 136 | |
| 175 | Peptide | VPE14 encoded by SEQ ID NO: 137 | |
| 176 | Peptide | VPE15 encoded by SEQ ID NO: 138 | |
| 177 | Peptide | VPE16 encoded by SEQ ID NO: 139 | |
| 178 | Peptide | VPE17 encoded by SEQ ID NO: 140 | |
| 179 | Peptide | VPE4 encoded by SEQ ID NO: 141 | |
| 180 | Peptide | VPE6 encoded by SEQ ID NO: 142 | |
| 181 | Peptide | VPE7 encoded by SEQ ID NO: 143 | |
| 182 | Peptide | *Nicotiana tabacum* Proteinase encoded by SEQ ID NO: 144 | |
| 183 | Peptide | *Nicotiana tabacum* Proteinase encoded by SEQ ID NO: 145 | |
| 184 | Peptide | *Nicotiana tabacum* Proteinase encoded by SEQ ID NO: 146 | |
| 185 | Peptide | *Nicotiana tabacum* Proteinase encoded by SEQ ID NO: 147 | |
| 186 | Nucleic Acid | C12866 (Gene 11) | XP_006467846.1 |

TABLE 1-continued

Description of sequences

| SEQ ID NO | Sequence Type | Sequence Description | NCBI Accession Number of the Top Hit of A BLAST Search |
|---|---|---|---|
| 187 | Peptide | C12866 (Gene 11) | |
| 188 | Nucleic Acid | *Nicotiana tabacum* STM homolog (NTH15) | AB004785 |
| 189 | Peptide | *Nicotiana tabacum* STM homolog (NTH15) | |
| 190 | Nucleic Acid | *Nicotiana tabacum* (Grassy Tillers1) GT1 homolog | |
| 191 | Peptide | *Nicotiana tabacum* (Grassy Tillers1) GT1 homolog | |
| 192 | Nucleic Acid | *Arabidopsis thaliana* More Axillary Branching1 (MAX1) | AK316903.1 |
| 193 | Peptide | *Arabidopsis thaliana* More Axillary Branching1 (MAX1) | |
| 194 | Nucleic Acid | *Arabidopsis thaliana* MAX2 | AAK97303.1 |
| 195 | Peptide | *Arabidopsis thaliana* MAX2 | |
| 196 | Nucleic Acid | *Nicotiana tabacum* MAX1 homolog | XM_009801023.1 |
| 197 | Peptide | *Nicotiana tabacum* MAX1 homolog | |
| 198 | Nucleic Acid | *Nicotiana tabacum* MAX2 homolog | XM_009625596.1 |
| 199 | Peptide | *Nicotiana tabacum* MAX2 homolog | |
| 200 | Nucleic Acid | *Arabidopsis thaliana* Lateral Suppressor (LAS) | BT026519.1 |
| 201 | Peptide | *Arabidopsis thaliana* Lateral Suppressor (LAS) | |
| 202 | Nucleic Acid | *Arabidopsis thaliana* Regulator of Axillary Meristems (RAX) | AY519628.1 |
| 203 | Peptide | *Arabidopsis thaliana* Regulator of Axillary Meristems (RAX) | |
| 204 | Nucleic Acid | Regulatory region of *Solanum lycopersicum* homolog of SEQ ID NO: 28 | |
| 205 | Nucleic Acid | *Solanum lycopersicum* homolog of SEQ ID NO: 28 | HG975514.1 |
| 206 | Peptide | *Solanum lycopersicum* homolog of SEQ ID NO: 28 | |
| 207 | Nucleic Acid | *Arabidopsis thaliana* ALCATRAZ | |
| 208 | Peptide | *Arabidopsis thaliana* ALCATRAZ | |
| 209 | Nucleic Acid | *Arabidopsis thaliana* VND6 | |
| 210 | Peptide | *Arabidopsis thaliana* VND6 | |
| 211 | Nucleic Acid | *Arabidopsis thaliana* VND7 | |
| 212 | Peptide | *Arabidopsis thaliana* VND7 | |
| 213 | Nucleic Acid | *Solanum lycopersicum* Adi3 | |
| 214 | Peptide | *Solanum lycopersicum* Adi3 | |
| 215 | Nucleic Acid | *Arabidopsis thaliana* XCP1 | |
| 216 | Peptide | *Arabidopsis thaliana* XCP1 | |
| 217 | Nucleic Acid | *Arabidopsis thaliana* XCP2 | |
| 218 | Peptide | *Arabidopsis thaliana* XCP2 | |
| 219 | Nucleic Acid | *Arabidopsis thaliana* Metacaspase 2d (ATMC4) | |
| 220 | Peptide | *Arabidopsis thaliana* Metacaspase 2d (ATMC4) | |
| 221 | Nucleic Acid | *Arabidopsis thaliana* disease resistance protein RPS5 | |
| 222 | Peptide | *Arabidopsis thaliana* disease resistance protein RPS5 | |
| 223 | Nucleic Acid | *Nicotiana tabacum* TMV resistance N gene | |
| 224 | Peptide | *Nicotiana tabacum* TMV resistance N gene | |
| 225 | Nucleic Acid | *Saccharum* spp. mature miRNA159 | |
| 226 | Nucleic Acid | *Nicotiana tabacum* precursor miRNA159 | |
| 227 | Nucleic Acid | *Nicotiana tabacum* mature miRNA159 | |
| 228 | Nucleic Acid | *Nicotiana* NAC089 | |

TABLE 1-continued

Description of sequences

| SEQ ID NO | Sequence Type | Sequence Description | NCBI Accession Number of the Top Hit of A BLAST Search |
|---|---|---|---|
| 229 | Peptide | *Nicotiana* NAC089 | |
| 230 | Nucleic Acid | *Nicotiana* BAG6 | |
| 231 | Peptide | *Nicotiana* BAG6 | |
| 232 | Nucleic Acid | *Nicotiana* mitogen-activated protein kinase kinase 2 (NtMEK2) | |
| 233 | Peptide | *Nicotiana* mitogen-activated protein kinase kinase 2 (NtMEK2) | |
| 234 | Nucleic Acid | *Arabidopsis thaliana* Flavin monooxygenase (YUCCA1) | |
| 235 | Peptide | *Arabidopsis thaliana* Flavin monooxygenase (YUCCA1) | |
| 236 | Nucleic Acid | *Arabidopsis thaliana* Pin-formed1 (PIN1) | |
| 237 | Peptide | *Arabidopsis thaliana* Pin-formed1 (PIN1) | |
| 238 | Nucleic Acid | *Arabidopsis thaliana* Tryptophan aminotransferase1/Transport inhibitor response2 (TAA1/TIR2) | |
| 239 | Peptide | *Arabidopsis thaliana* Tryptophan aminotransferase1/Transport inhibitor response2 (TAA1/TIR2) | |
| 240 | Nucleic Acid | *Arabidopsis thaliana* Aldehyde oxidase1 (AAO1) | |
| 241 | Peptide | *Arabidopsis thaliana* Aldehyde oxidase1 (AAO1) | |
| 242 | Nucleic Acid | *Arabidopsis thaliana* Indole-3-acetamide hydrolase1 (AMI1) | |
| 243 | Peptide | *Arabidopsis thaliana* Indole-3-acetamide hydrolase1 (AMI1) | |
| 244 | Nucleic Acid | *Nicotiana* Flavin monooxygenase (NtYUCCA-like1) | |
| 245 | Peptide | *Nicotiana* Flavin monooxygenase (NtYUCCA-like1) | |
| 246 | Nucleic Acid | *Nicotiana* Flavin monooxygenase (NtYUCCA-like2) | |
| 247 | Peptide | *Nicotiana* Flavin monooxygenase (NtYUCCA-like2) | |
| 248 | Nucleic Acid | *Nicotiana* Pin-formed1-like (NtPIN1-like) | |
| 249 | Peptide | *Nicotiana* Pin-formed1-like (NtPIN1-like) | |
| 250 | Nucleic Acid | *Nicotiana* Tryptophan aminotransferase1/Transport inhibitor response2-like (NtTAA1/TIR2-like) | |
| 251 | Peptide | *Nicotiana* Tryptophan aminotransferase1/Transport inhibitor response2-like (NtTAA1/TIR2-like) | |
| 252 | Nucleic Acid | *Nicotiana* Aldehyde oxidase1-like (NtAAO1-like) | |
| 253 | Peptide | *Nicotiana* Aldehyde oxidase1-like (NtAAO1-like) | |
| 254 | Nucleic Acid | *Nicotiana* Indole-3-acetamide hydrolase1-like (NtAMI1-like) | |
| 255 | Peptide | *Nicotiana* Indole-3-acetamide hydrolase1-like (NtAMI1-like) | |
| 256 | Peptide | 6× Histidine tag | |

BRIEF DESCRIPTION OF THE DRAWINGS

FIG. 5 shows the growth of axillary shoots in control tobacco plants and modified tobacco plants that express SEQ ID NO: 83, an RNAi construct that targets SEQ ID NO: 1 for inhibition. FIG. 5A shows photographs of representative control and modified tobacco plants, as well as all of the axillary shoots from one plant two weeks after topping. FIG.

5B is a graph displaying the total fresh weight of axillary shoots from control and modified plants two weeks after topping. Modified plants exhibit increased axillary shoot mass compared to control plants.

Figure 6:
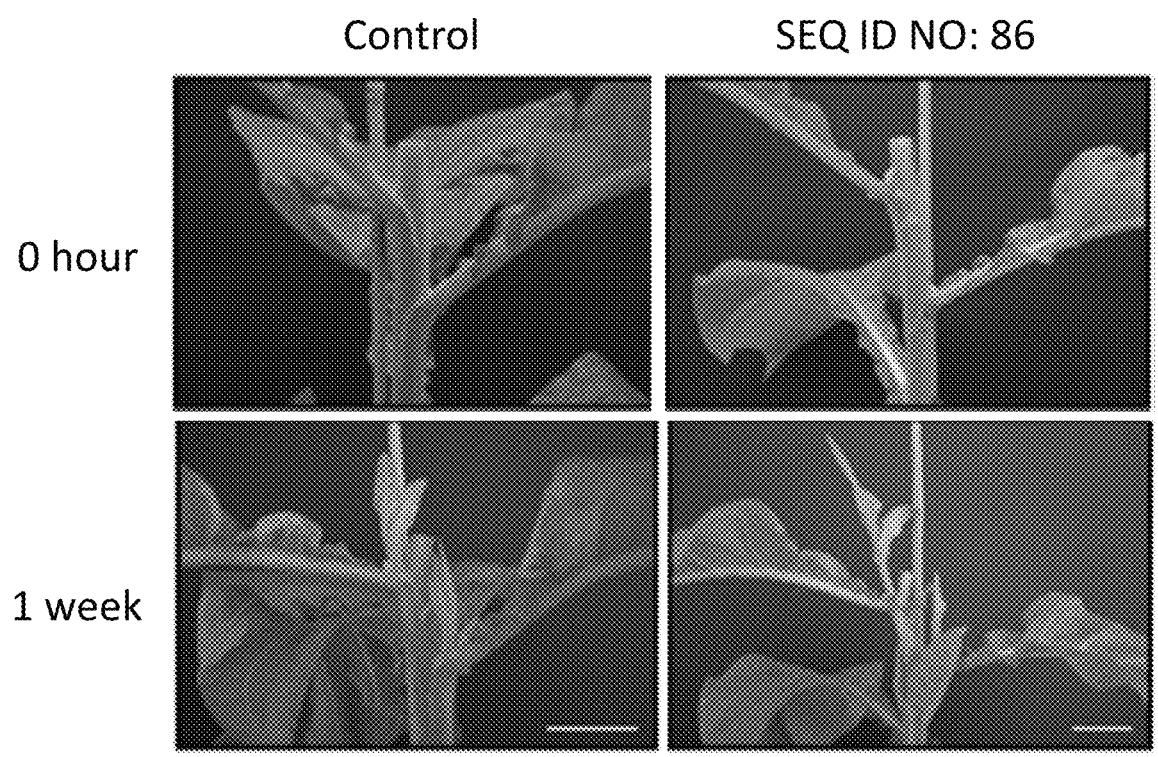

FIG. 6 shows photographs of control tobacco plants and modified tobacco plants that express SEQ ID NO: 86, an RNAi construct that targets SEQ ID NO: 13 for inhibition. Plants are shown at the time of topping (0 hour) and one week after topping. Modified plants exhibit enhanced suckering compared to control plants.

Figure 7:
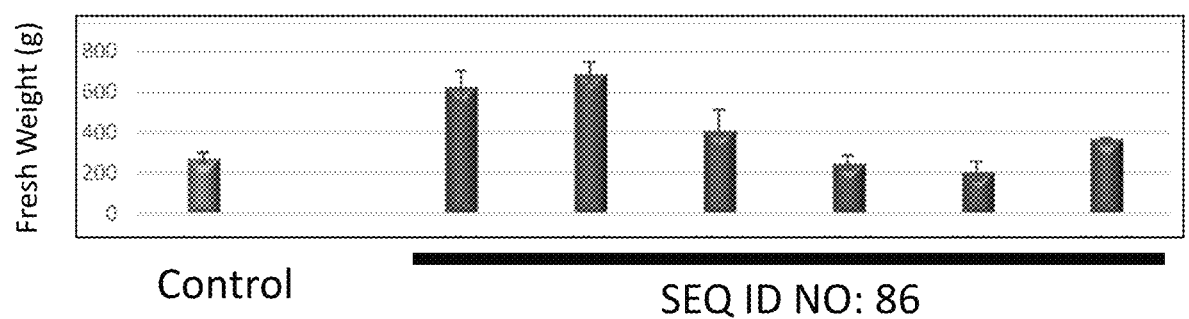

FIG. 7 is a graph displaying the total fresh weight of axillary shoots from control plants and modified tobacco plants that express SEQ ID NO: 86, an RNAi construct that targets SEQ ID NO: 13 for inhibition, two weeks after topping. Data from six independent modified tobacco lines are shown. Modified plants exhibit increased sucker mass compared to control plants.

Figure 8:
Figure 8:

FIG. 8 shows photographs of modified tobacco plants that express SEQ ID NO: 95, an RNAi construct that targets SEQ ID NO: 35 for inhibition. Modified tobacco plants exhibit sucker outgrowth prior to topping. Arrows point to suckers.

Figure 9:
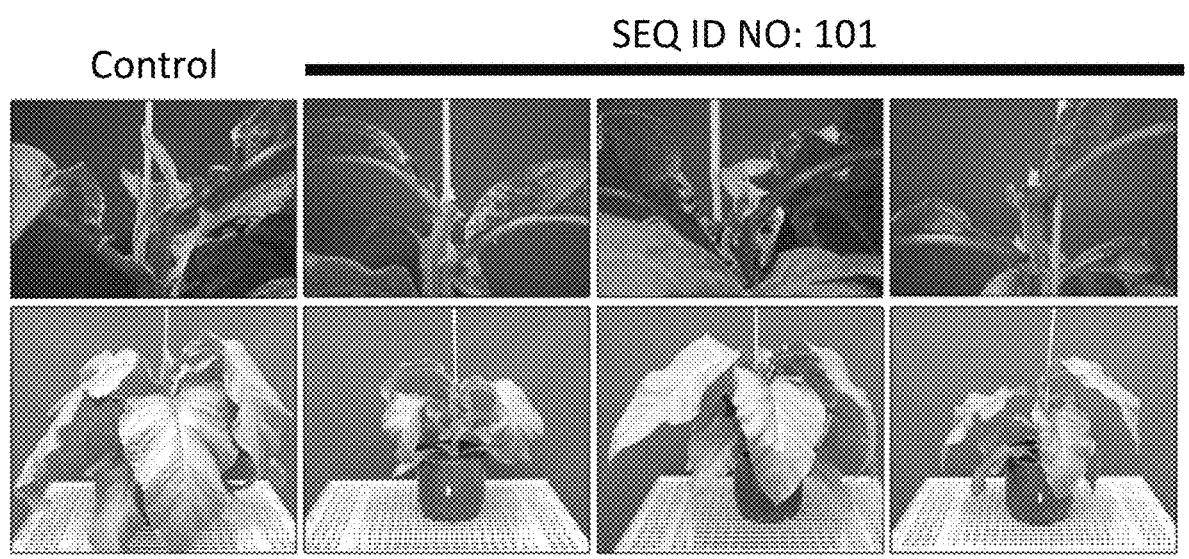

FIG. 9 shows photographs of control tobacco plants and three independent lines of modified tobacco plants that express SEQ ID NO: 101, an RNAi construct that targets tobacco CENTRORADIALIS (SEQ ID NOs: 108-110). Photographs show the apex of a plant (top panel) or an entire plant (lower panel) one week after topping. Sucker growth is reduced in modified plants.

Figure 10:
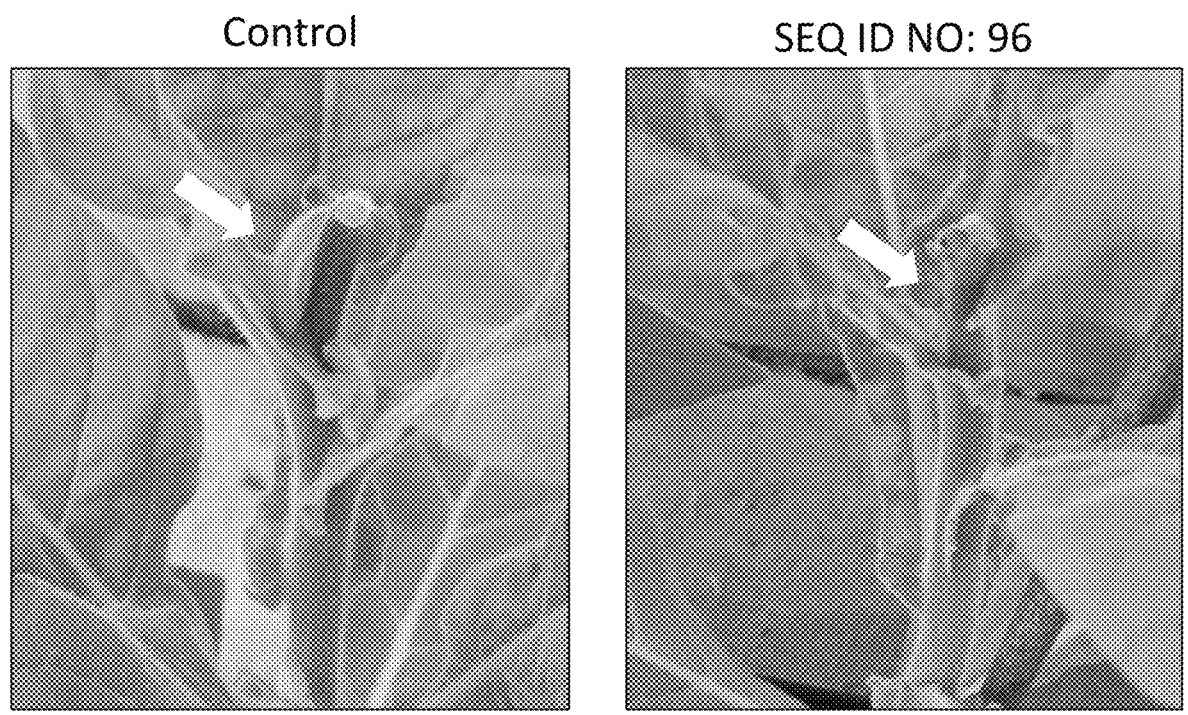

FIG. 10 shows photographs of a control tobacco plant and a modified tobacco plant that expresses SEQ ID NO: 96, an RNAi construct that targets SEQ ID NO: 49 for inhibition. Modified tobacco plants exhibit reduced sucker growth (arrows) compared to control tobacco plants.

Figure 11:
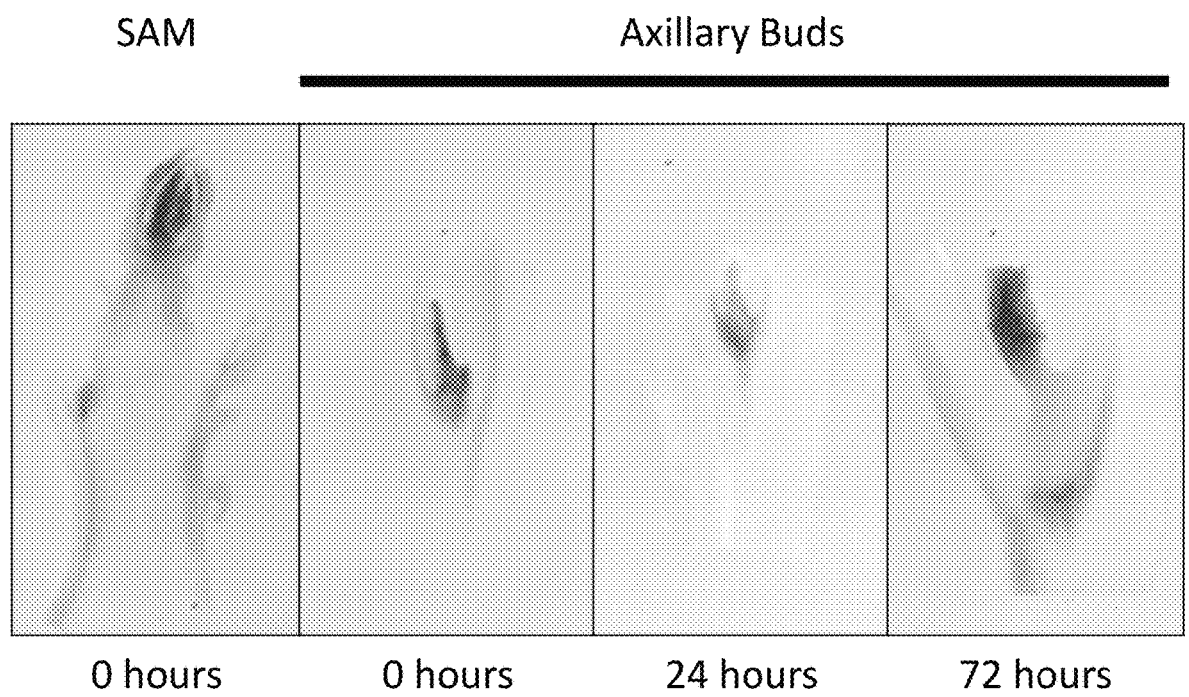

FIG. 11 shows the expression pattern of Promoter P1 (SEQ ID NO: 113) fused to β-glucuronidase (GUS) in a tobacco shoot apical meristem (SAM) at the time of topping (0 hours) and in an axillary bud at 0 hours, 24 hours after topping, and 72 hours after topping. Dark areas of GUS accumulation demonstrate where Promoter P1 is active. Promoter P1 is functional in both shoot apical and axillary buds.

Figure 12:
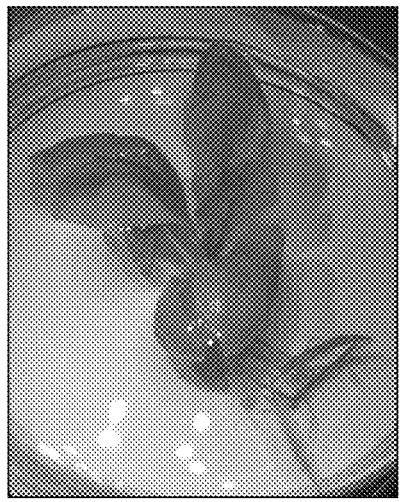
Figure 12:
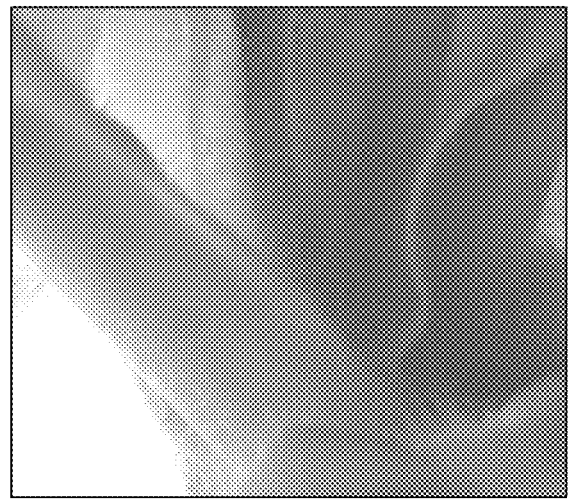
Figure 12:
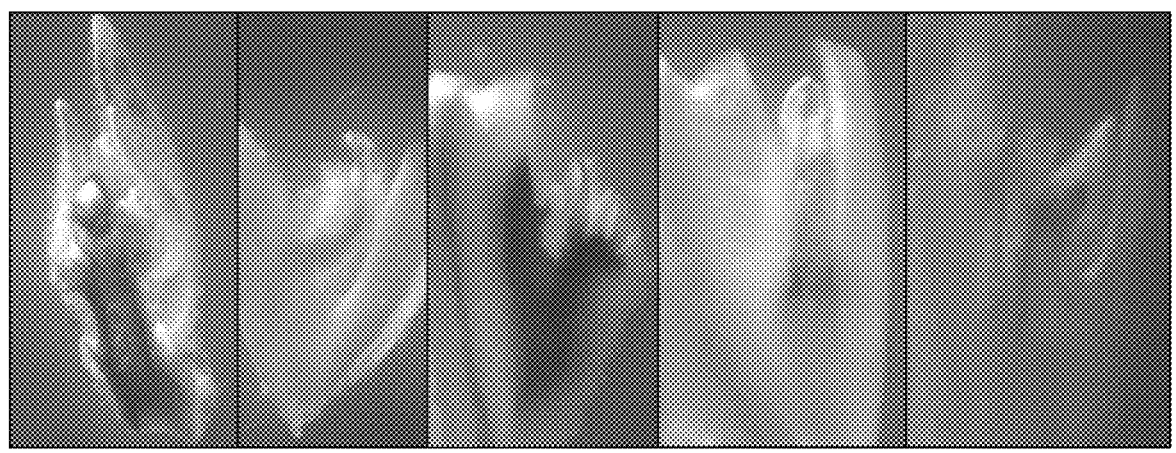

FIG. 12 shows the expression pattern of Promoter P11 (SEQ ID NO: 116) fused to β-glucuronidase (GUS) in a tobacco seedling; a tobacco seedling shoot apical meristem (SAM); a mature SAM at the time of topping (0 hours); and an axillary bud at the time of topping, 3 days after topping, 5 days after topping, and 7 days after topping. Dark areas of GUS accumulation demonstrate where Promoter P11 is active. Promoter P11 is weakly active in axillary buds prior to topping and has higher activity in axillary buds 3 days after topping. Activity of Promoter P11 decreases by 5 and 7 days after topping. Promoter P11 is also active in the SAM prior to topping. No GUS staining is detected in seedlings.

Figures 13, 13A:
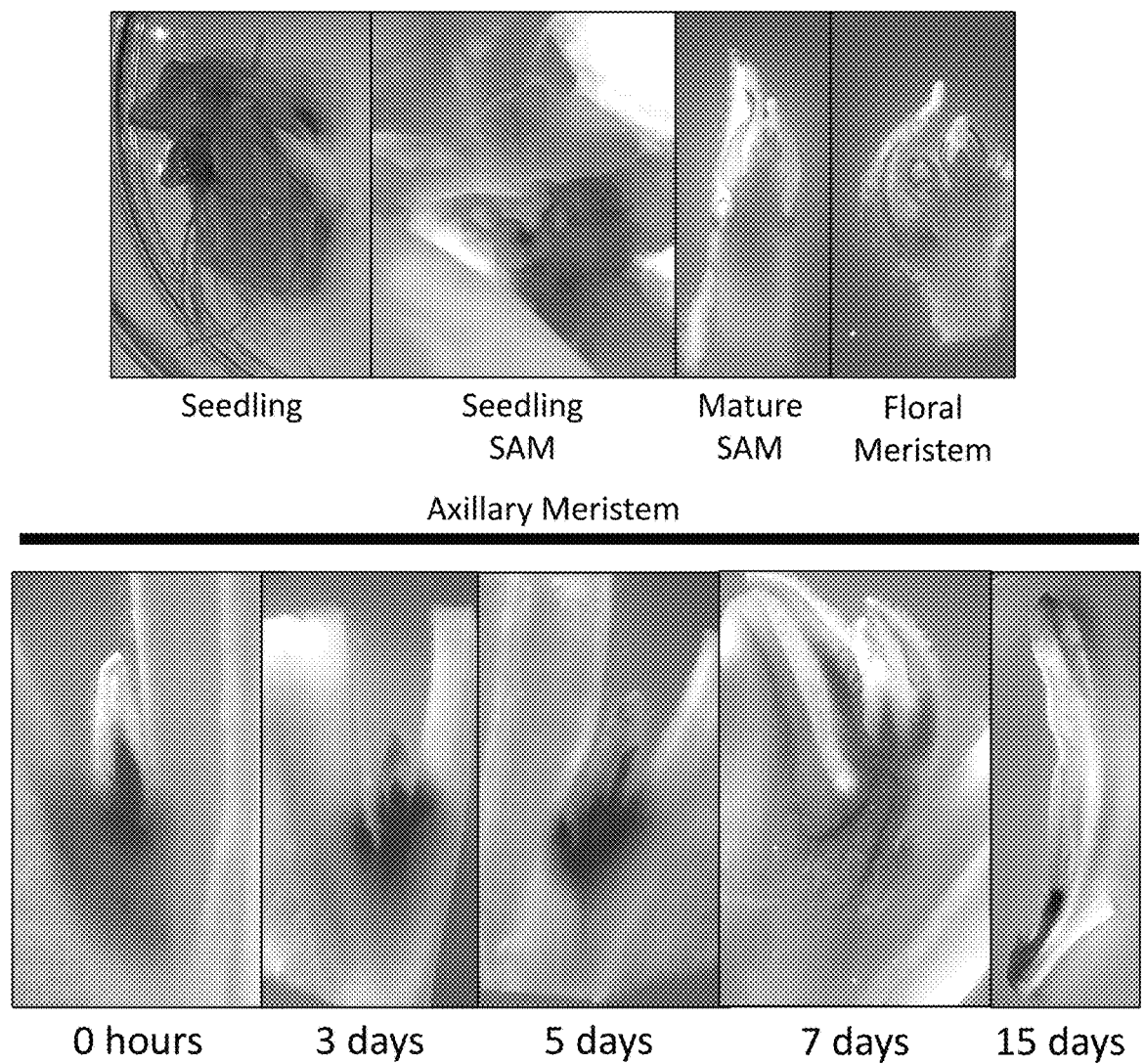
Figures 13, 13B:
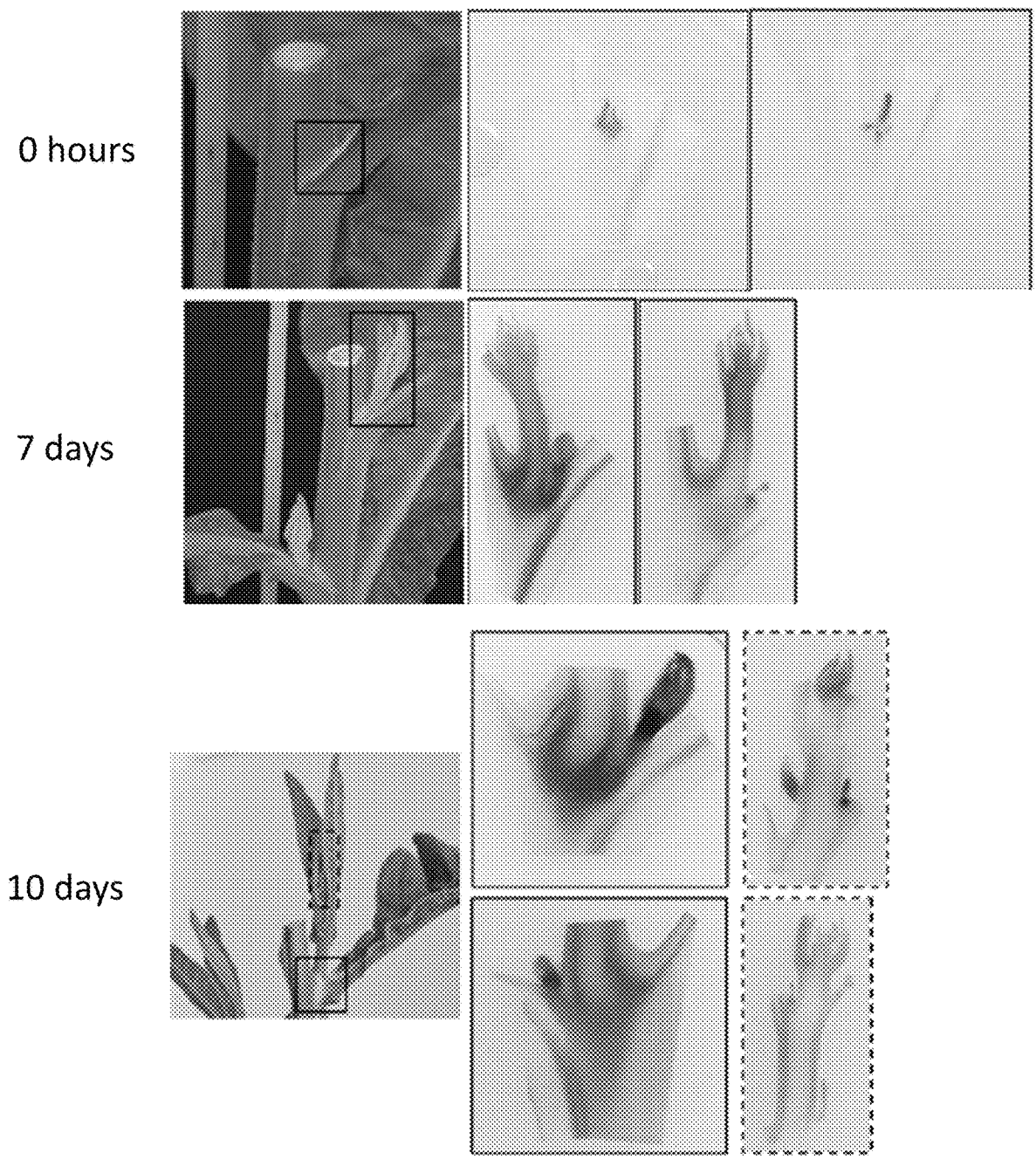
Figures 13, 13C:
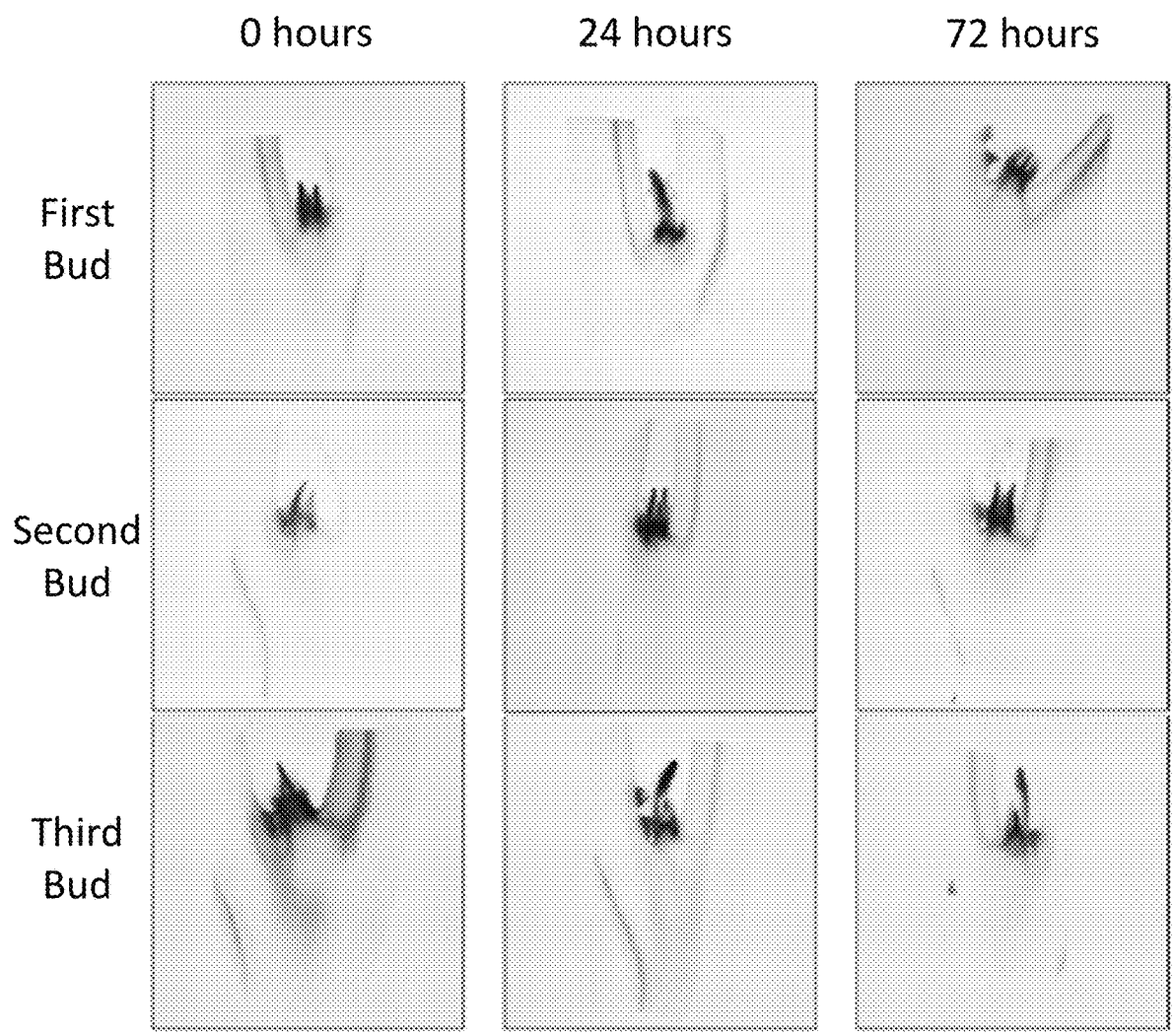

FIG. 13 shows the expression pattern of Promoter P15 (SEQ ID NO: 117) fused to β-glucuronidase (GUS) in tobacco. Dark areas of GUS accumulation demonstrate where Promoter P15 is active. FIG. 13A shows Promoter P15 activity in a tobacco seedling; a tobacco seedling shoot apical meristem (SAM); a mature SAM at the time of topping (0 hours); and an axillary bud at the time of topping, 3 days after topping, 5 days after topping, 7 days after topping, and 15 days after topping. Promoter P15 is not active in seedlings. Promoter P15 is active at the base of the SAM, but it is not active in floral meristems. Promoter P15 exhibits strong activity in axillary buds prior to topping, and the activity is maintained for at least 15 days after topping. FIG. 13B further demonstrates the axillary bud specificity of Promoter P15. FIG. 13B shows GUS expression driven by Promoter P15 at the time of topping (0 hours), 7 days after topping, and 10 days after topping. At each time point, exemplary GUS staining of axillary buds from two independent modified tobacco lines is shown. FIG. 13C displays GUS staining in multiple axillary buds from individual plants at the time of topping (0 hours), 24 hours after topping, and 72 hours after topping.

FIG. 14 shows microscopy photographs displaying the activity of axillary bud-specific promoters fused to green fluorescent protein (GFP). FIG. 14A shows results of a Promoter P15 (SEQ ID NO: 117)::GFP fusion in a shoot apical meristem (SAM) and axillary bud (left panel) and in an axillary bud (right panel). Promoter P15 activity is restricted to axillary buds. FIG. 14B shows results of a Promoter P1 (SEQ ID NO: 113)::GFP fusion in a shoot apical meristem (SAM) and axillary bud (left panel) and in an axillary bud (right panel).

Figure 15:
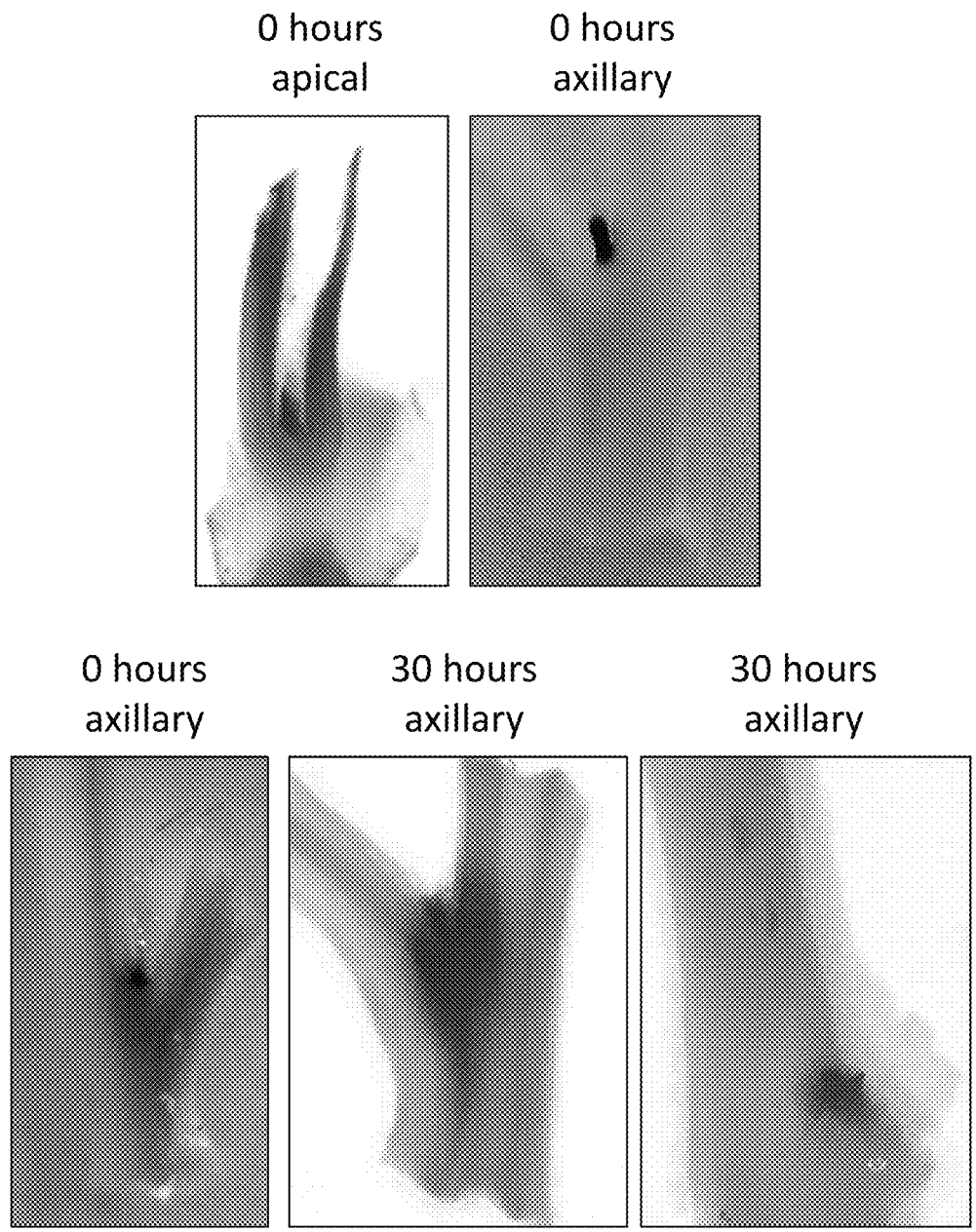

FIG. 15 shows the expression pattern of an axillary bud Thionin promoter (pABTh, SEQ ID NO: 118) fused to β-glucuronidase (GUS) in tobacco apical and axillary meristems at the time of topping (0 hours) and 30 hours after topping. Dark areas of GUS accumulation demonstrate where Promoter P15 is active.

Figure 16:
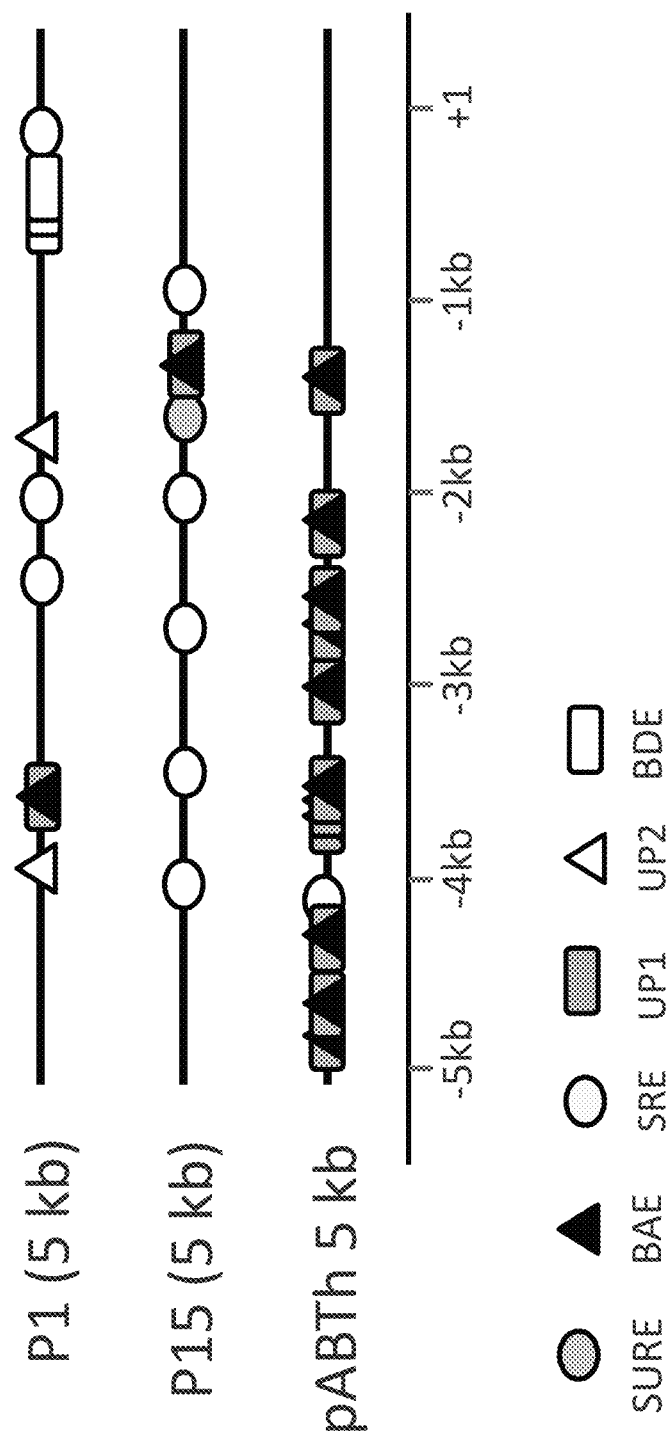

FIG. 16 shows the locations of cis-regulatory elements in Promoter P1 (SEQ ID NO: 113), Promoter P15 (SEQ ID NO: 117), and Promoter pABTh (SEQ ID NO: 118). +1 designates the transcriptional start site.

Figure 17:
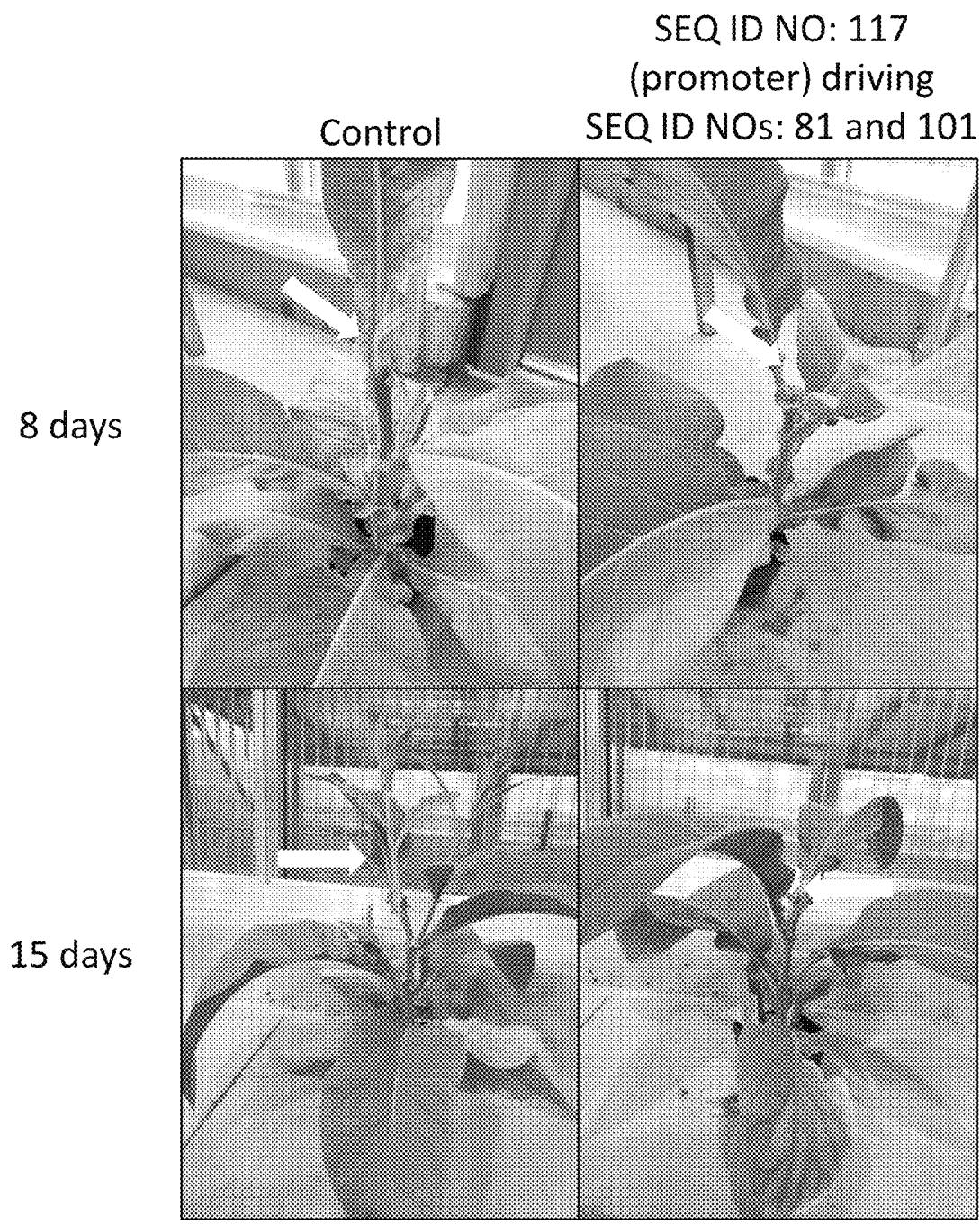

FIG. 17 shows photographs of control tobacco plants and modified tobacco plants that express SEQ ID NO: 81, which encodes *Arabidopsis thaliana* BRANCHED1 and inhibits sucker growth, and SEQ ID NO: 101, an RNAi construct that targets tobacco CENTRORADIALIS and reduces sucker growth, driven by axillary bud-specific Promoter P15 (SEQ ID NO: 117). Plants are shown 8 days after topping and 15 days after topping. Modified plants exhibit reduced sucker growth (arrows) compared to control plants.

Figure 18:
Figure 18:
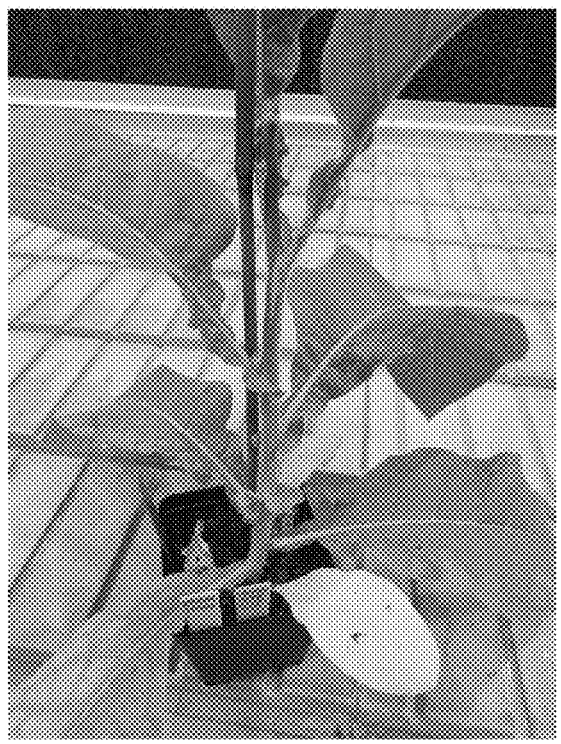
Figure 18:
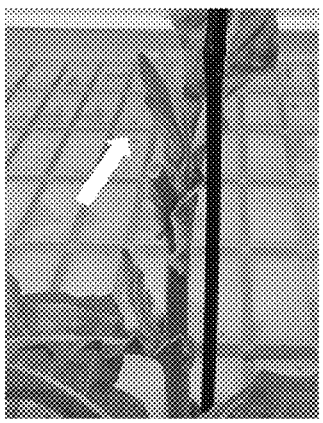
Figure 18:

FIG. 18 shows photographs of control plants and a modified tobacco plant that expresses SEQ ID NO: 59 (*Nicotiana tabacum* cytokinin oxidase 13) under the control of Promoter P15 (SEQ ID NO: 117) eight days after topping. Modified plants exhibit reduced sucker growth (arrows) compared to control plants.

Figure 19:
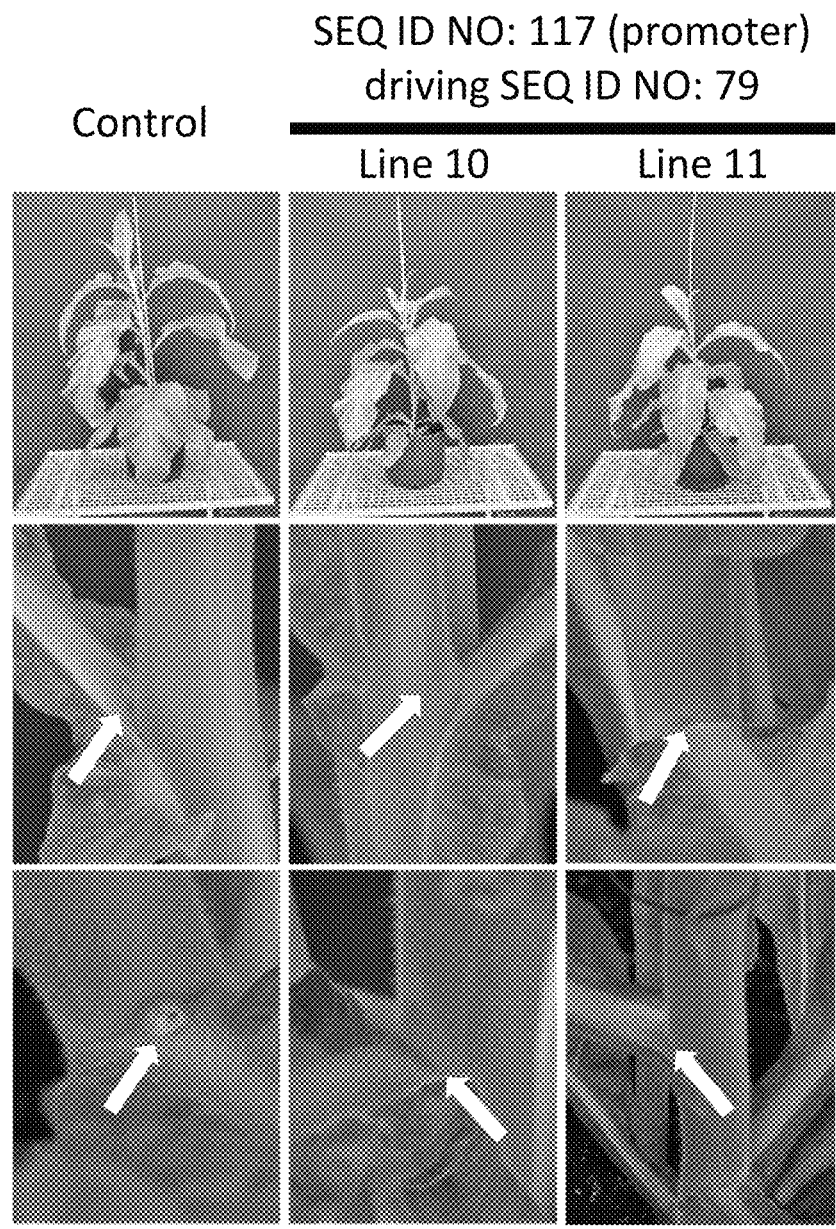

FIG. 19 shows photographs of control plants and two independent lines of modified tobacco plants that express SEQ ID NO: 79 (Barnase) under the control of Promoter P15 (SEQ ID NO: 117). Modified plants exhibit reduced sucker growth (arrows) compared to control plants. No axillary meristem primordia are observed before topping the modified plants.

Figures 20, 20A:
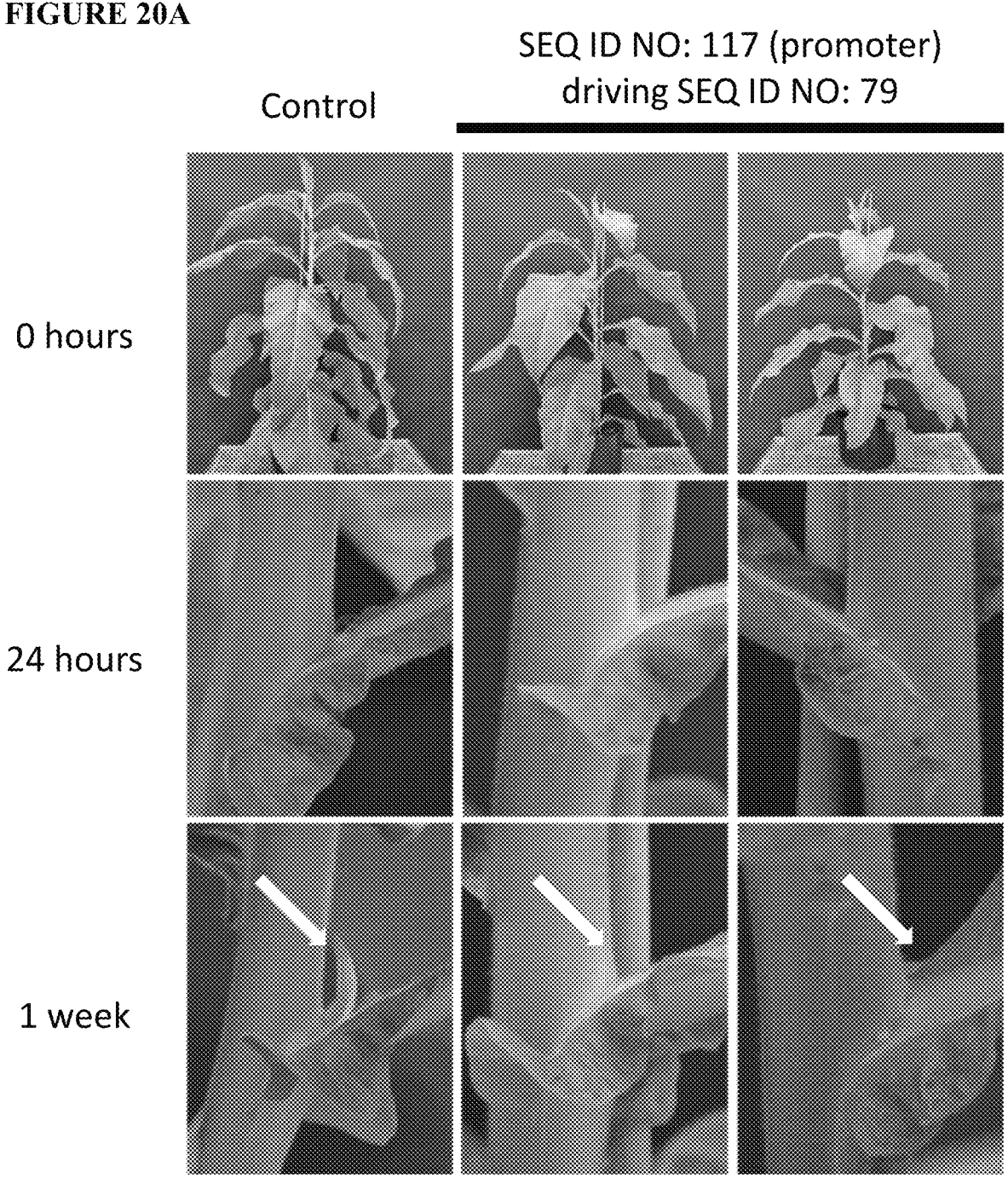
Figures 20, 20B:
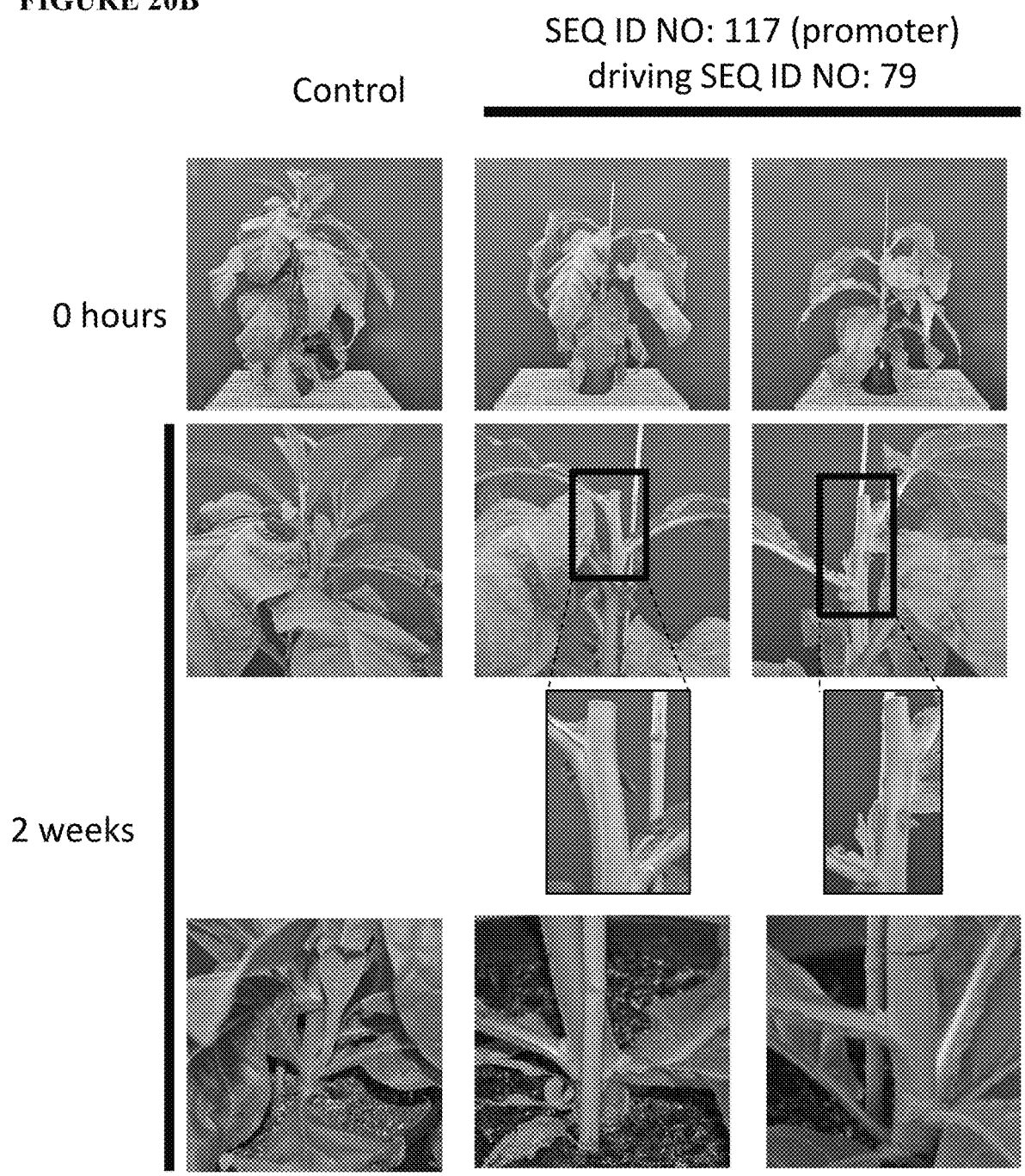
Figures 20, 20C:
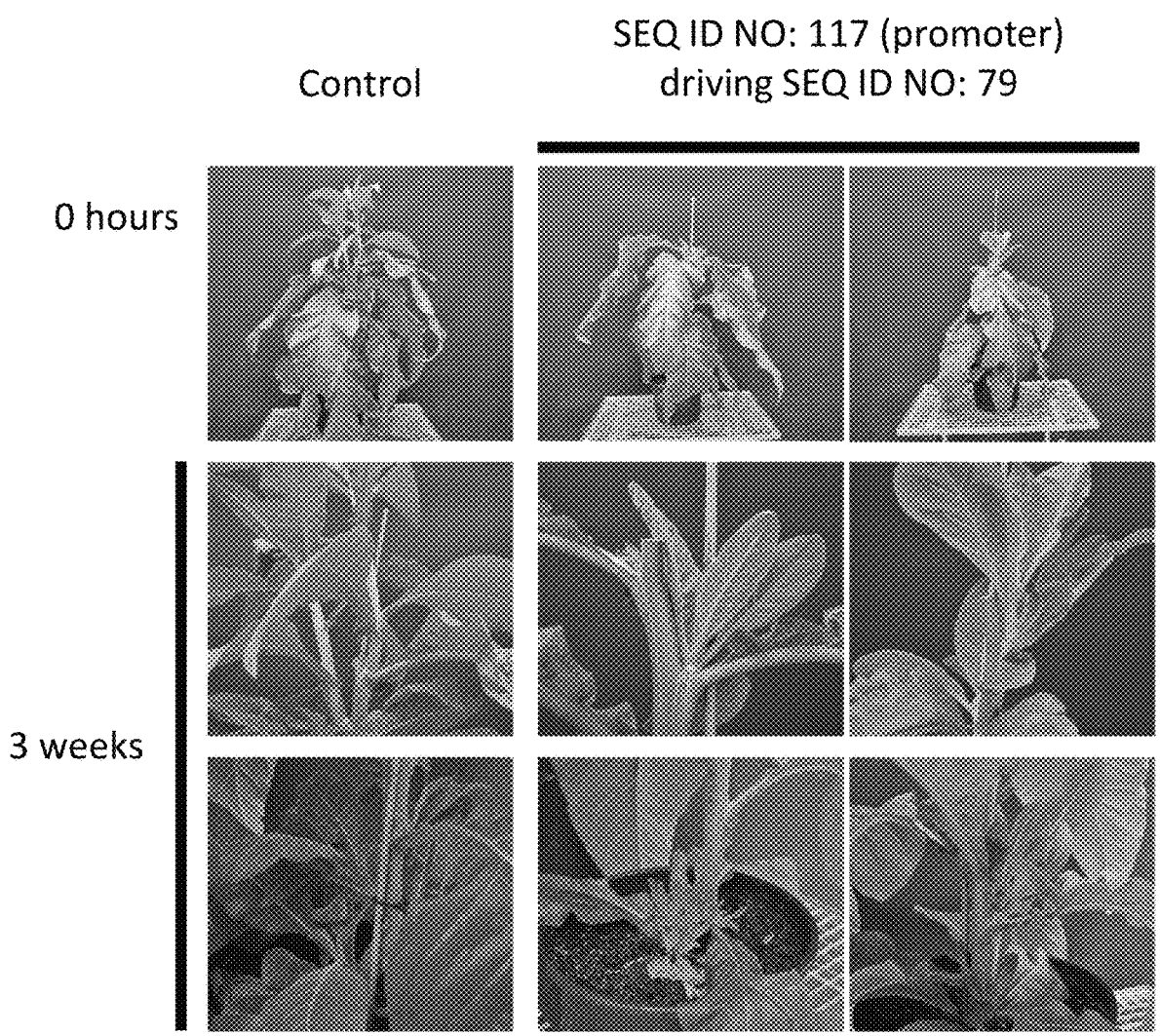

FIG. 20 shows photographs of control plants and two independent lines of modified tobacco plants that express SEQ ID NO: 79 (Barnase) under the control of Promoter P15 (SEQ ID NO: 117). Modified plants exhibit reduced sucker growth (arrows) compared to control plants one week after topping (FIG. 20A), two weeks after topping (FIG. 20B), and three weeks after topping (FIG. 20C).

Figure 21:
Figure 21:
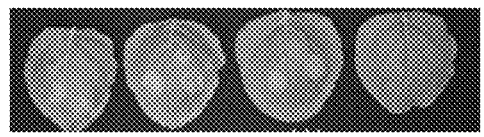
Figure 21:
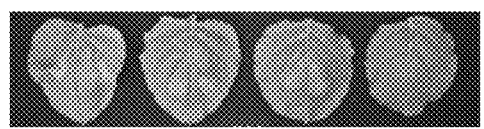
Figure 21:
Figure 21:
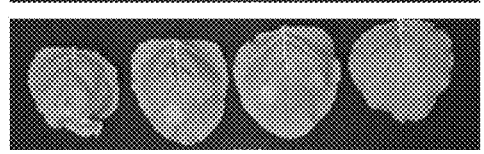
Figure 21:
Figure 21:
Figure 21:
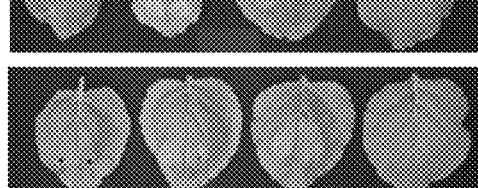
Figure 21:
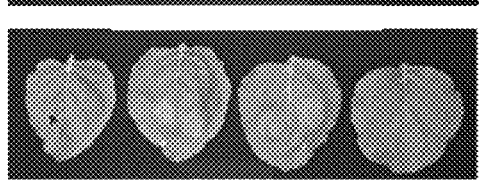
Figure 21:

FIG. 21 shows photographs of tobacco leaves subjected to agroinfiltration as described in Example 15. A vector expressing SEQ ID NO: 79 (Barnase) is used as a positive control, and an vector lacking an insert (empty vector) is used as a negative control. Genes of interest are examined ability to induce cellular death in a tobacco leaf according to Example 15. For example, SEQ ID NO: 232 causes cellular death when expressed in a tobacco leaf.

Figures 22, 22A:
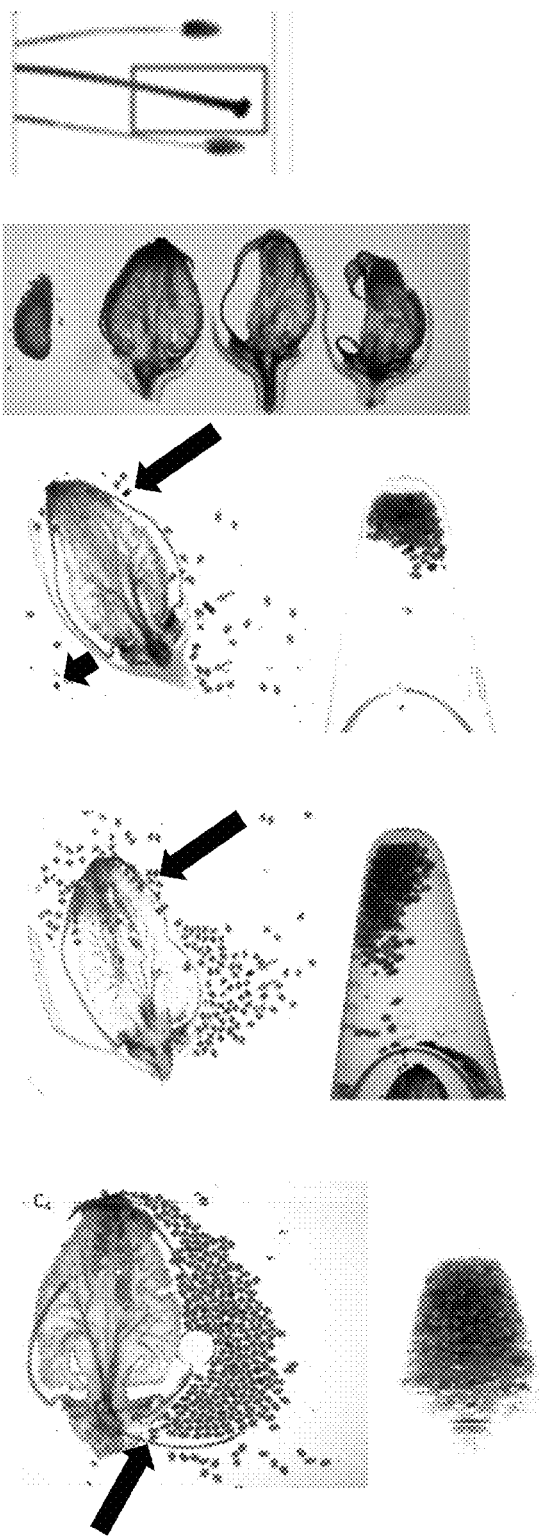

FIG. 22 shows the expression pattern of Promoter P15 (SEQ ID NO: 117) fused to β-glucuronidase (GUS) in tobacco. Dark areas of GUS accumulation demonstrate where Promoter P15 is active. FIG. 22A shows the accumulation of GUS in floral organs (the stigma is enclosed in a gray box), early developing seed capsules, and later stages of seed capsule development. Black arrows point to positive GUS staining. FIG. 22B shows the accumulation of GUS in tobacco seedlings of two independent modified tobacco lines. Black arrows point to positive GUS staining.

Figures 23, 23A:
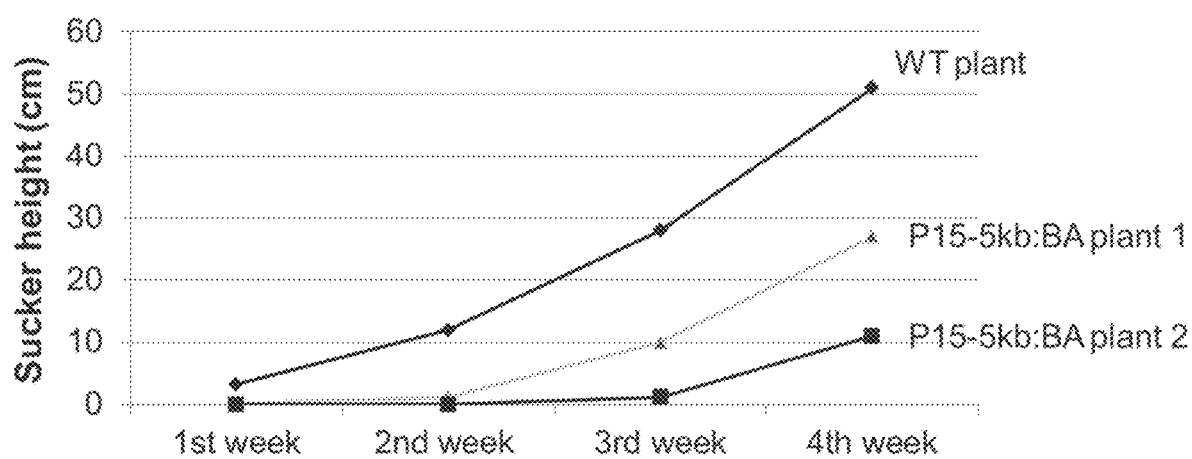

FIG. 23 shows the phenotypic effects of expressing Barnase (BA; SEQ ID NO: 79) under the control of Promoter P15-5 kb (SEQ ID NO: 157). FIG. 23A shows a line graph demonstrating that sucker height is reduced in modified plants as compared to a wildtype (WT) control plant. FIG. 23B shows photographs of sucker outgrowth in modified (P15-5 kb:BA) and wildtype tobacco plants.

Figure 24:
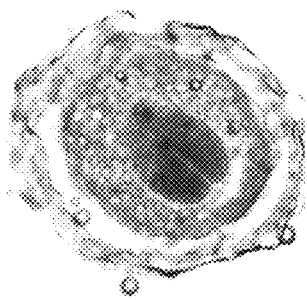
Figure 24:
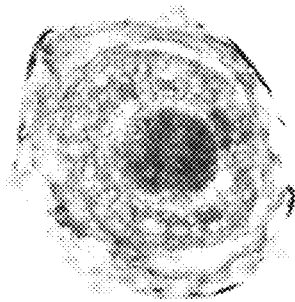
Figure 24:
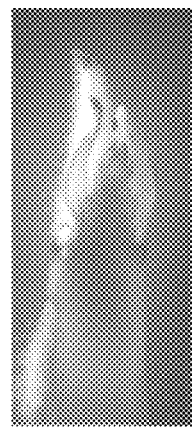
Figure 24:
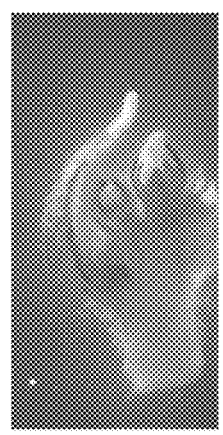
Figure 24:
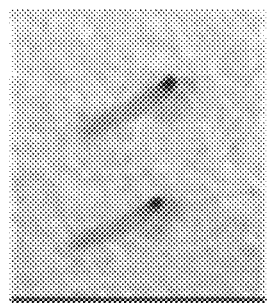
Figure 24:
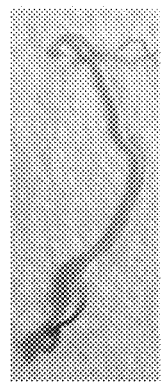

FIG. 24 shows the expression pattern of Promoter P15-5 kb (SEQ ID NO: 157) fused to β-glucuronidase (GUS) in tobacco. Dark areas of GUS accumulation demonstrate where Promoter P15 is active. Promoter P15-5 kb is active in seed, mature shoot apical meristems (SAM), floral buds, 2-day old seedlings, and 9-day old seedlings.

Figure 25:
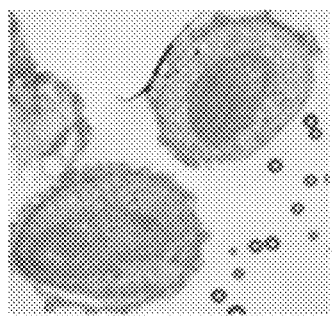
Figure 25:
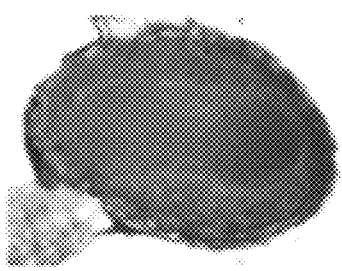
Figure 25:
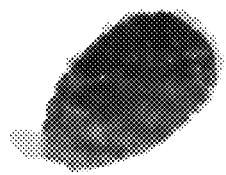
Figure 25:

FIG. 25 shows the expression pattern of Promoter PAB Thionin-5 kb (SEQ ID NO: 148) fused to β-glucuronidase (GUS) in tobacco. Dark areas of GUS accumulation demonstrate where Promoter P15 is active. Promoter PAB Thionin-5 kb is not active in ungerminated seeds, 1-day post-germination seeds, or 3-day post germination seeds.

Figure 26:
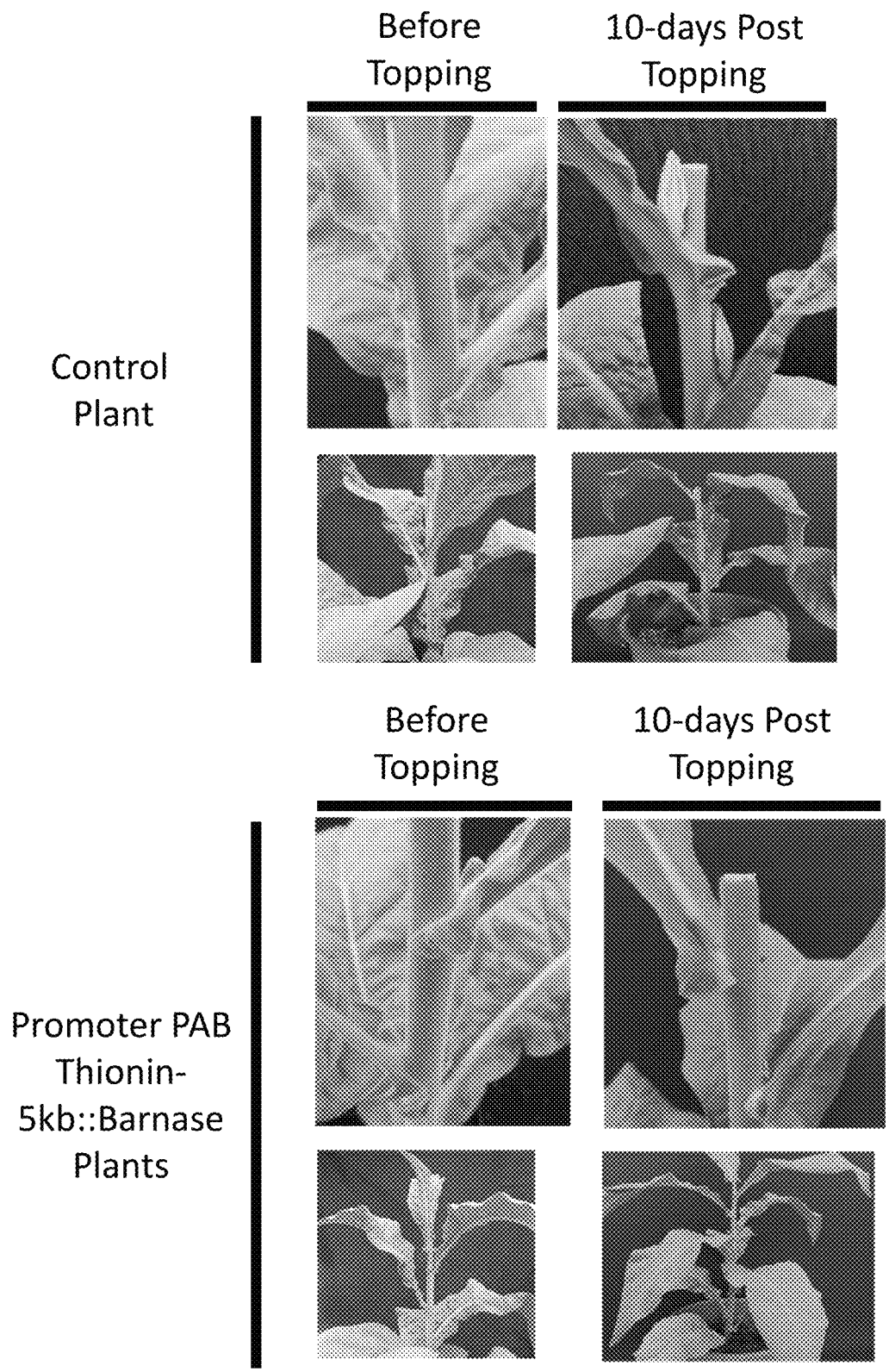

FIG. 26 shows photographs of tobacco plants expressing Barnase (SEQ ID NO: 79) under the control of Promoter PAB Thionin-5 kb (SEQ ID NO: 148) and control plants that lack the Promoter PAB Thionin-5 kb::Barnase construct. Sucker outgrowth is inhibited in the Promoter PAB Thionin-5 kb::Barnase plants as compared to the control plants.

Figure 27:
Figure 27:
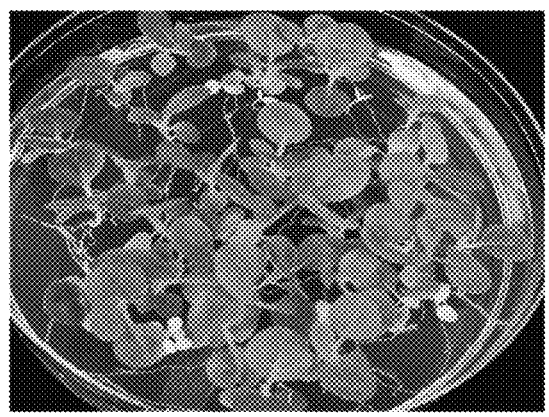
Figure 27:
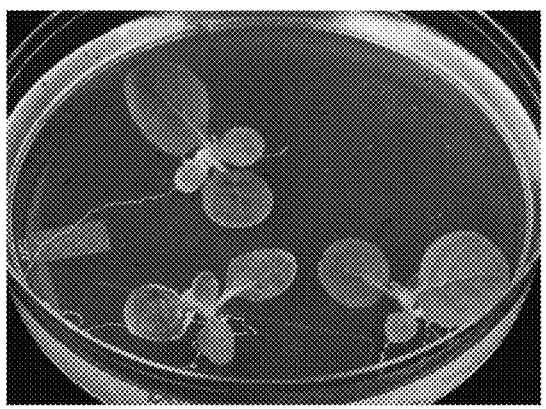
Figure 27:
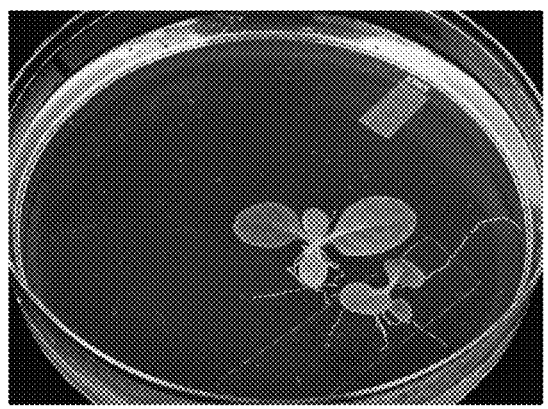

FIG. 27 shows photographs demonstrating the germination of three independent lines of Promoter PAB Thionin-5 kb::Barnase T1 generation tobacco plants and a control tobacco line lacking the Promoter PAB Thionin-5 kb::Barnase construct.

Figure 28:
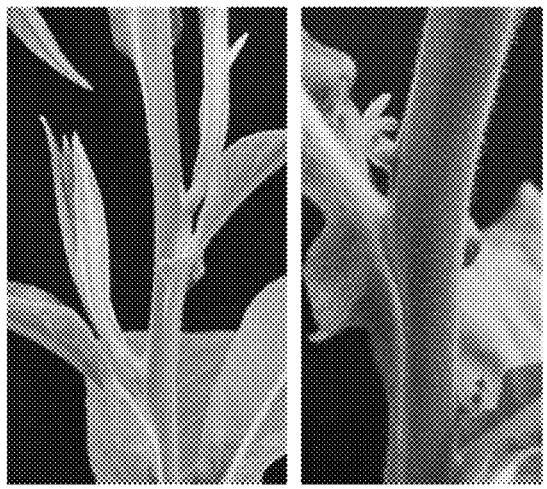
Figure 28:
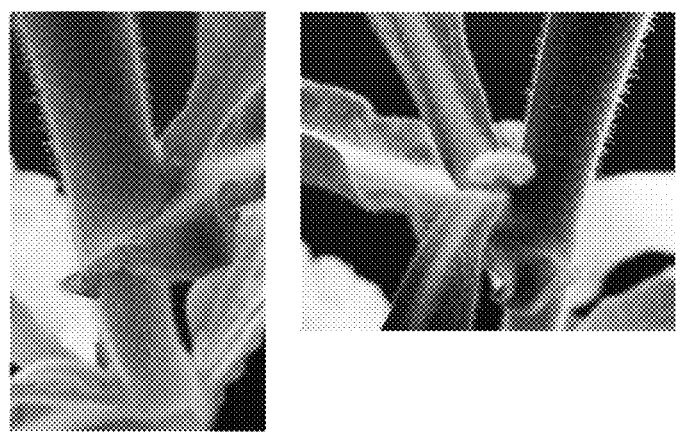

FIG. 28 shows photographs of RAX1 (SEQ ID NO: 75) and RAX2 (SEQ ID NO: 77) knockout tobacco plants. Sucker outgrowth is delayed and/or mislocalized.

DETAILED DESCRIPTION

Unless defined otherwise, technical and scientific terms used herein have the same meaning as commonly understood by one of ordinary skill in the art. One skilled in the art will recognize many methods can be used in the practice of the present disclosure. Indeed, the present disclosure is in no way limited to the methods and materials described. For purposes of the present disclosure, the following terms are defined below.

Any references cited herein, including, e.g., all patents, published patent applications, and non-patent publications, are incorporated by reference in their entirety.

As used herein, the singular form "a," "an," and "the" include plural references unless the context clearly dictates otherwise. For example, the term "a compound" or "at least one compound" may include a plurality of compounds, including mixtures thereof.

The term "about" is used herein to mean approximately, roughly, around, or in the region of. When the term "about" is used in conjunction with a numerical range, it modifies that range by extending the boundaries above and below the numerical values set forth.

As used herein, a tobacco plant can be from any plant from the *Nicotiana tabacum* genus including, but not limited to *Nicotiana tabacum tabacum*; *Nicotiana tabacum amplexicaulis* PI 271989; *Nicotiana tabacum benthamiana* PI 555478; *Nicotiana tabacum bigelovii* PI 555485; *Nicotiana tabacum debneyi*; *Nicotiana tabacum excelsior* PI 224063; *Nicotiana tabacum glutinosa* PI 555507; *Nicotiana tabacum goodspeedii* PI 241012; *Nicotiana tabacum gossei* PI 230953; *Nicotiana tabacum hesperis* PI 271991; *Nicotiana tabacum knightiana* PI 555527; *Nicotiana tabacum maritima* PI 555535; *Nicotiana tabacum megalosiphon* PI 555536; *Nicotiana tabacum nudicaulis* PI 555540; *Nicotiana tabacum paniculata* PI 555545; *Nicotiana tabacum plumbaginifolia* PI 555548; *Nicotiana tabacum repanda* PI 555552; *Nicotiana tabacum rustica*; *Nicotiana tabacum suaveolens* PI 230960; *Nicotiana tabacum sylvestris* PI 555569; *Nicotiana tabacum tomentosa* PI 266379; *Nicotiana tabacum tomentosiformis*; and *Nicotiana tabacum trigonophylla* PI 555572.

In one aspect, this disclosure provides methods and compositions related to modified tobacco plants, seeds, plant components, plant cells, and products made from modified tobacco plants, seeds, plant parts, and plant cells. In one aspect, a modified seed provided herein gives rise to a modified plant provided herein. In one aspect, a modified plant, seed, plant component, plant cell, or plant genome provided herein comprises a recombinant DNA construct provided herein. In another aspect, cured tobacco material or tobacco products provided herein comprise modified tobacco plants, plant components, plant cells, or plant genomes provided herein.

As used herein, "modified" refers to plants, seeds, plant components, plant cells, and plant genomes that have been subjected to mutagenesis, genome editing, genetic transformation, or a combination thereof.

In one aspect, modified tobacco plants provided herein exhibit no or reduced suckering compared to control tobacco plants of the same variety when grown under comparable conditions. In one aspect, modified tobacco plants provided herein exhibit no or reduced topping-induced suckering compared to control tobacco plants of the same variety when grown under comparable conditions. Also provided herein are methods of producing modified tobacco plants that exhibit no or reduced suckering compared to control tobacco plants of the same variety when grown under comparable conditions. In one aspect, methods provided herein produce modified tobacco plants that exhibit no or reduced topping-induced suckering compared to control tobacco plants of the same variety when grown under comparable conditions.

As used herein, "cisgenesis" or "cisgenic" refers to genetic modification of a plant, plant cell, or plant genome in which all components (e.g., promoter, donor nucleic acid, selection gene) have only plant origins (i.e., no non-plant origin components are used). In one aspect, a modified plant, plant cell, or plant genome provided herein is cisgenic. Cisgenic plants, plant cells, and plant genomes provided herein can lead to ready-to-use tobacco lines. In another aspect, a modified tobacco plant provided herein comprises no non-tobacco genetic material or sequences.

As used herein, "suckering" refers to the development and/or growth of axillary (or lateral) buds ("suckers") from axillary meristems that grow between a leaf and the stalk. An axillary bud is an embryonic shoot that comprises an axillary meristem, surrounding leaf tissue, and surrounding stem tissue. In one aspect, suckering is induced by topping a plant.

As used herein, "topping" refers to the removal of the stalk apex, including the SAM, flowers, and up to several adjacent leaves, when a plant is near maturity. Topping a tobacco plant results in the loss of apical dominance. Prior to topping, suckering is largely kept dormant by hormonal signals emanating from the SAM; topping removes the hormonal signals and can allow the outgrowth of suckers ("topping-induced suckering"). Provided suckering is sufficiently controlled, topping increases yield, increases value-per-acre, and results in desirable modifications to physical and chemical properties of tobacco leaves.

As used herein, "comparable growth conditions" refers to similar environmental conditions and/or agronomic practices for growing and making meaningful comparisons between two or more plant genotypes so that neither environmental conditions nor agronomic practices would contribute to, or explain, any differences observed between the two or more plant genotypes. Environmental conditions include, for example, light, temperature, water, humidity, and nutrition (e.g., nitrogen and phosphorus). Agronomic practices include, for example, seeding, clipping, undercutting, transplanting, topping, and suckering. See Chapters 4B and 4C of Tobacco, Production, Chemistry and Technology, Davis & Nielsen, eds., Blackwell Publishing, Oxford (1999), pp. 70-103.

As used herein, "reduced topping-induced suckering" refers to a reduction in the number of suckers; a reduction in the size of suckers (e.g., biomass), and/or a reduction of the impact suckers have on agronomic performance (e.g., yield, quality and overall productivity of the plant) compared to a control plant when grown under comparable conditions. As used herein, a "reduction" in the number of suckers, the size of suckers, and/or the impact suckers have on agronomic performance refers to a statistically significant reduction. As used herein, "statistically significant" refers to a p-value of less than 0.05, a p-value of less than 0.025, a p-value of less than 0.01, or a p-value of less than 0.001 when using an appropriate measure of statistical significance (e.g., a one-tailed two sample t-test).

The present disclosure provides modified tobacco plants with desirable or enhanced properties, e.g., inhibited or reduced sucker growth prior to or after topping. In one aspect, a modified plant provided herein comprises fewer total suckers, smaller suckers, or both compared to a control plant lacking such modification when grown under comparable conditions. In one aspect, smaller suckers of a modified plant provided herein comprise reduced mass, reduced length, reduced diameter, or a combination thereof compared to suckers of a control plant grown under comparable conditions. The diameter of a sucker is measured at the base of the sucker where it adjoins the main stem of the plant.

In one aspect, the mass of suckers of a modified tobacco plant provided herein is at least 10%, at least 15%, at least 20%, at least 25%, at least 30%, at least 35%, at least 40%, at least 45%, at least 50%, at least 60%, at least 70%, at least 80%, at least 90%, or at least 95% reduced compared to the mass of suckers of an unmodified control tobacco plant grown under comparable conditions. In one aspect, the mass of suckers of a modified tobacco plant provided herein is reduced by 1%-25%, 1%-50%, 1%-75%, 1%-100%, 5%-25%, 5%-50%, 5%-75%, 5%-100%, 10%-25%, 10%-50%, 10%-75%, 10%-100%, 25%-50%, 25%-75%, 25%-100%, 50%-75%, or 50%-100% as compared to the mass of suckers of an unmodified control tobacco plant grown under comparable conditions. In another aspect, the length of suckers of a modified tobacco plant provided herein is at least 10%, at least 15%, at least 20%, at least 25%, at least 30%, at least 35%, at least 40%, at least 45%, at least 50%, at least 60%, at least 70%, at least 80%, at least 90%, or at least 95% reduced compared to the length of suckers of an unmodified control tobacco plant grown under comparable conditions. In one aspect, the length of suckers of a modified tobacco plant provided herein is reduced by 1%-25%, 1%-50%, 1%-75%, 1%-100%, 5%-25%, 5%-50%, 5%-75%, 5%-100%, 10%-25%, 10%-50%, 10%-75%, 10%-100%, 25%-50%, 25%-75%, 25%-100%, 50%-75%, or 50%-100% as compared to the length of suckers of an unmodified control tobacco plant grown under comparable conditions. In one aspect, the diameter of suckers of a modified tobacco plant provided herein is at least 10%, at least 15%, at least 20%, at least 25%, at least 30%, at least 35%, at least 40%, at least 45%, at least 50%, at least 60%, at least 70%, at least 80%, at least 90%, or at least 95% reduced compared to the diameter of suckers of an unmodified control tobacco plant grown under comparable conditions. In one aspect, the diameter of suckers of a modified tobacco plant provided herein is reduced by 1%-25%, 1%-50%, 1%-75%, 1%-100%, 5%-25%, 5%-50%, 5%-75%, 5%-100%, 10%-25%, 10%-50%, 10%-75%, 10%-100%, 25%-50%, 25%-75%, 25%-100%, 50%-75%, or 50%-100% as compared to the diameter of suckers of an unmodified control tobacco plant grown under comparable conditions.

In another aspect, a modified tobacco plant provided herein comprises at least 1, at least 2, at least 3, at least 4, at least 5, at least 6, at least 7, at least 8, at least 9, at least 10, at least 15, at least 20, at least 30, at least 40, at least 50, or at least 60 fewer total suckers compared to an unmodified control tobacco plant grown under comparable conditions. In another aspect, a modified tobacco plant provided herein comprises at least 10%, at least 15%, at least 20%, at least 25%, at least 30%, at least 35%, at least 40%, at least 45%, at least 50%, at least 60%, at least 70%, at least 80%, at least 90%, or at least 95% fewer suckers compared to an unmodified control tobacco plant grown under comparable conditions. In one aspect, the number of suckers of a modified tobacco plant provided herein is reduced by 1%-25%, 1%-50%, 1%-75%, 1%-100%, 5%-25%, 5%-50%, 5%-75%, 5%-100%, 10%-25%, 10%-50%, 10%-75%, 10%-100%, 25%-50%, 25%-75%, 25%-100%, 50%-75%, or 50%-100% as compared to the number of suckers of an unmodified control tobacco plant grown under comparable conditions.

Shoot apical and axillary meristems have two main functions: to maintain themselves as a group of pluripotent cells, and to generate lateral above-ground organs of the plant (e.g., stems, leaves, flowers). If a meristem fails to maintain itself, for any reason, it will eventually exhaust its pluripotent cells and cease giving rise to additional organs. In one aspect, a modified tobacco plant provided herein exhibits inhibited or eliminated axillary meristem growth; inhibited or eliminated axillary meristem maintenance; or a combination thereof compared to a control tobacco plant of the same variety when grown under comparable conditions.

As used herein, the term "similar" refers to within 10%. For example, if a control plant has a height of 100 centimeters, "similar" plant heights would range from 90 centimeters to 110 centimeters.

In one aspect, a modified tobacco plant provided herein has similar or higher leaf yield compared to a control tobacco plant when grown under comparable conditions. In an aspect, leaf yield is selected from the group consisting of fresh yield, dry yield, and cured yield. In one aspect, a modified tobacco plant provided herein produces a leaf yield mass within about 50%, within about 45%, within about 40%, within about 35%, within about 30%, within about 25%, within about 20%, within about 15%, within about 10%, within about 5%, within about 4%, within about 3%, within about 2%, within about 1%, or within about 0.5% compared to a control tobacco plant when grown under comparable conditions. In another aspect, a modified tobacco plant provided herein produces a leaf yield mass at least 0.25%, 0.5%, 1%, 2.5%, 5%, 10%, 15%, 20%, 25%, 30%, 40%, 50%, 60%, 70%, 80%, 90%, 100%, or more than 100% higher compared to a control tobacco plant when grown under comparable conditions. In another aspect, a modified tobacco plant provided herein produces a leaf yield mass 0.25%-100%, 0.5%-100%, 1%-100%, 2.5%-100%, 5%-100%, 10%-100%, 15%-100%, 20%-100%, 25%-100%, 30%-100%, 40%-100%, 50%-100%, 60%-100%, 70%-100%, 80%-100%, 90%-100%, 100%-200%, 100%-175%, 100%-150%, 100%-125%, 0.25%-50%, 0.5%-50%, 1%-50%, 2.5%-50%, 5%-50%, 10%-50%, 15%-50%, 20%-50%, 25%-50%, 30%-50%, 40%-50%, 50%-200%, 50%-175%, 50%-150%, 50%-125%, 0.25%-25%, 0.5%-25%, 1%-25%, 2.5%-25%, 5%-25%, 10%-25%, 15%-25%, 20%-25%, 25%-200%, 25%-175%, 25%-150%, or 25%-125% higher compared to a control tobacco plant when grown under comparable conditions. In an aspect, a modified tobacco plant provided herein produces a number of leaves within 75%, within 60%, within 50%, within 45%, within 40%, within 35%, within 30%, within 25%, within 20%, within 15%, within 10%, within 5%, within 4%, within 3%, within 2%, within 1%, or within 0.5% the number of leaves produced by an unmodified control tobacco plant grown under comparable conditions.

In one aspect, a modified tobacco plant provided herein has a similar or comparable plant height compared to a control tobacco plant when grown under comparable conditions. In one aspect, a modified tobacco plant provided herein comprises a height within about 50%, within about 45%, within about 40%, within about 35%, within about 30%, within about 25%, within about 20%, within about 15%, within about 10%, within about 5%, within about 4%, within about 3%, within about 2%, within about 1%, or within about 0.5% compared to a control tobacco plants when grown under comparable conditions. In another aspect, a modified tobacco plant provided herein comprises a height 0.25%, 0.5%, 1%, 2.5%, 5%, 10%, 15%, 20%, 25%, 30%, 40%, 50%, 60%, 70%, 80%, 90%, 100%, or more than 100% taller compared to a control tobacco plant when grown under comparable conditions. In another aspect, a modified tobacco plant comprises a height 0.25%-100%, 0.5%-100%, 1%-100%, 2.5%-100%, 5%-100%, 10%-100%, 15%-100%, 20%-100%, 25%-100%, 30%-100%, 40%-100%, 50%-100%, 60%-100%, 70%-100%, 80%-100%, 90%-100%, 100%-200%, 100%-175%, 100%-150%, 100%-125%, 0.25%-50%, 0.5%-50%, 1%-50%, 2.5%-50%, 5%-50%, 10%-50%, 15%-50%, 20%-50%, 25%-50%, 30%-50%, 40%-50%, 50%-200%, 50%-175%, 50%-150%, 50%-125%, 0.25%-25%, 0.5%-25%, 1%-25%, 2.5%-25%, 5%-25%, 10%-25%, 15%-25%, 20%-25%, 25%-200%, 25%-175%, 25%-150%, or 25%-125% taller compared to a control tobacco plant when grown under comparable conditions.

In one aspect, a modified tobacco plant provided herein produces leaves that have a similar or higher USDA grade index value compared to a control tobacco plant when grown under comparable conditions. In one aspect, a modified tobacco plant provided herein produces leaves with a USDA grade index value within about 50%, within about 45%, within about 40%, within about 35%, within about 30%, within about 25%, within about 20%, within about 15%, within about 10%, within about 5%, within about 4%, within about 3%, within about 2%, within about 1%, or within about 0.5% compared to a control tobacco plant when grown under comparable conditions. In one aspect, a modified tobacco plant provided herein is capable of producing leaves having a USDA grade index value of 55 or more, 60 or more, 65 or more, 70 or more, 75 or more, 80 or more, 85 or more, 90 or more, or 95 or more. In one aspect, a modified tobacco plant provided herein produces leaves with a USDA grade index value at least 1, 2, 3, 4, 5, 6, 7, 8, 9, 10, 12, 13, 14, 15, 16, 17, 18, 19, 20, 21, 22, 23, 24, 25, 26, 27, 28, 29, 30, 35, 40, 45, 50, or more than 50 units higher compared to a control tobacco plant when grown under comparable conditions. In one aspect, a modified tobacco plant provided herein produces leaves with a USDA grade index value 1-50, 1-45, 1-40, 1-35, 1-30, 1-29, 1-28, 1-27, 1-26, 1-25, 1-24, 1-23, 1-22, 1-21, 1-20, 1-19, 1-18, 1-17, 1-16, 1-15, 1-14, 1-13, 1-12, 1-11, 1-10, 1-9, 1-8, 1-7, 1-6, 1-5, 1-4, 1-3, 1-2, 2-50, 2-45, 2-40, 2-35, 2-30, 2-29, 2-28, 2-27, 2-26, 2-25, 2-24, 2-23, 2-22, 2-21, 2-20, 2-19, 2-18, 2-17, 2-16, 2-15, 2-14, 2-13, 2-12, 2-11, 2-10, 2-9, 2-8, 2-7, 2-6, 2-5, 2-4, 2-3, 3-50, 3-45, 3-40, 3-35, 3-30, 3-29, 3-28, 3-27, 3-26, 3-25, 3-24, 3-23, 3-22, 3-21, 3-20, 3-19, 3-18, 3-17, 3-16, 3-15, 3-14, 3-13, 3-12, 3-11, 3-10, 3-9, 3-8, 3-7, 3-6, 3-5, 3-4, 4-50, 4-45, 4-40, 4-35, 4-30, 4-29, 4-28, 4-27, 4-26, 4-25, 4-24, 4-23, 4-22, 4-21, 4-20, 4-19, 4-18, 4-17, 4-16, 4-15, 4-14, 4-13, 4-12, 4-11, 4-10, 4-9, 4-8, 4-7, 4-6, 4-5, 5-50, 5-45, 5-40, 5-35, 5-30, 5-29, 5-28, 5-27, 5-26, 5-25, 5-24, 5-23, 5-22, 5-21, 5-20, 5-19, 5-18, 5-17, 5-16, 5-15, 5-14, 5-13, 5-12, 5-11, 5-10, 5-9, 5-8, 5-7, 5-6, 10-50, 10-40, 10-30, 10-20, 20-50, 20-30, 20-40, or 20-30 units higher compared to a control tobacco plant when grown under comparable conditions.

Tobacco grades are evaluated based on factors including, but not limited to, the leaf stalk position, leaf size, leaf color, leaf uniformity and integrity, ripeness, texture, elasticity, sheen (related with the intensity and the depth of coloration of the leaf as well as the shine), hygroscopicity (the faculty of the tobacco leaves to absorb and to retain the ambient moisture), and green nuance or cast. Leaf grade can be determined, for example, using an Official Standard Grade published by the Agricultural Marketing Service of the US Department of Agriculture (7 U.S.C. § 511). See, e.g., Official Standard Grades for Burley Tobacco (U.S. Type 31 and Foreign Type 93), effective Nov. 5, 1990 (55 F.R. 40645); Official Standard Grades for Flue-Cured Tobacco (U.S. Types 11, 12, 13, 14 and Foreign Type 92), effective Mar. 27, 1989 (54 F.R. 7925); Official Standard Grades for Pennsylvania Seedleaf Tobacco (U.S. Type 41), effective Jan. 8, 1965 (29 F.R. 16854); Official Standard Grades for Ohio Cigar-Leaf Tobacco (U.S. Types 42, 43, and 44), effective Dec. 8, 1963 (28 F.R. 11719 and 28 F.R. 11926); Official Standard Grades for Wisconsin Cigar-Binder Tobacco (U.S. Types 54 and 55), effective Nov. 20, 1969 (34 F.R. 17061); Official Standard Grades for Wisconsin Cigar-Binder Tobacco (U.S. Types 54 and 55), effective Nov. 20, 1969 (34 F.R. 17061); Official Standard Grades for Georgia and Florida Shade-Grown Cigar-Wrapper Tobacco (U.S. Type 62), Effective April 1971. A USDA grade index value can be determined according to an industry accepted grade index. See, e.g., Bowman et al, *Tobacco Science,* 32:39-40 (1988); Legacy Tobacco Document Library (Bates Document #523267826-523267833, Jul. 1, 1988, Memorandum on the Proposed Burley Tobacco Grade Index); and Miller et al., 1990, *Tobacco Intern.,* 192:55-57 (all foregoing references are incorporated by inference in their entirety). Alternatively, leaf grade can be determined via hyper-spectral imaging. See e.g., WO 2011/027315 (published on Mar. 10, 2011, and incorporated by inference in its entirety).

In one aspect, a modified plant provided herein requires reduced management for controlling suckering compared to a control plant when grown under comparable conditions. As used herein, "management" refers to manually removing suckers, application of chemicals (e.g., maleic hydrazide, flumetralin) to inhibit or remove suckers, or both. In one aspect, a modified plant provided herein requires reduced frequency of manual sucker removal, reduced frequency of chemical application, reduced quantities of chemical application, or a combination thereof, compared to a control plant grown under comparable conditions. See, for example, Fisher et al. "Topping, Managing Suckers, and Using Ethephon," pages 96-117 In: 2016 Flue-Cured Tobacco Information, North Carolina State University, which is herein incorporated by reference in its entirety. In one aspect, a modified plant provided herein requires manual removal of suckers 10%, 20%, 30%, 40%, 50%, 60%, 70%, 75%, 80%, 85%, 90%, or 95% as frequently as a control plant when grown under comparable conditions. In one aspect, a modified plant provided herein requires manual removal of suckers less than 10%, less than 20%, less than 30%, less than 40%, less than 50%, less than 60%, less than 70%, less than 75%, less than 80%, less than 85%, less than 90%, or less than 95% as frequently as a control plant when grown under comparable conditions. In one aspect, a modified plant provided herein requires manual removal of suckers 10%-95%, 20%-95%, 30%-95%, 40%-95%, 50%-95%, 60%-95%, 70%-95%, 80%-95%, 85%-95%, 90%-95%, 10%-50%, 20%-50%, 30%-50%, 40%-50%, 10%-20%, 10%-30%, 10%-40%, 10%-50%, 10%-60%, 10%-70%, 10%-80%, 10%-85%, or 10%-90% as frequently as a control plant when grown under comparable conditions. In one aspect, a modified plant provided herein requires chemical application to control suckering 10%, 20%, 30%, 40%, 50%, 60%, 70%, 75%, 80%, 85%, 90%, or 95% as frequently as a control plant when grown under comparable conditions. In one aspect, a modified plant provided herein requires chemical application to control suckering less than 10%, less than 20%, less than 30%, less than 40%, less than 50%, less than 60%, less than 70%, less than 75%, less than 80%, less than 85%, less than 90%, or less than 95% as frequently as a control plant when grown under comparable conditions. In one aspect, a modified plant provided herein requires chemical application to control suckering 10%-95%, 20%-95%, 30%-95%, 40%-95%, 50%-95%, 60%-95%, 70%-95%, 80%-95%, 85%-95%, 90%-95%, 10%-50%, 20%-50%, 30%-50%, 40%-50%, 10%-20%, 10%-30%, 10%-40%, 10%-50%, 10%-60%, 10%-70%, 10%-80%, 10%-85%, or 10%-90% as frequently as a control plant when grown under comparable conditions. In one aspect, a modified plant provided herein requires a chemical spray volume of 10%, 20%, 30%, 40%, 50%, 60%, 70%, 75%, 80%, 85%, 90%, or 95% of the volume used to control suckering of a control plant when grown under comparable conditions. In one aspect, a modified plant provided herein requires a chemical spray volume of less than 10%, less than 20%, less than 30%, less than 40%, less than 50%, less than 60%, less than 70%, less than 75%, less than 80%, less than 85%, less than 90%, or less than 95% of the volume used to control suckering of a control plant when grown under comparable conditions. In one aspect, a modified plant provided herein requires a chemical spray volume 10%-95%, 20%-95%, 30%-95%, 40%-95%, 50%-95%, 60%-95%, 70%-95%, 80%-95%, 85%-95%, 90%-95%, 10%-50%, 20%-50%, 30%-50%, 40%-50%, 10%-20%, 10%-30%, 10%-40%, 10%-50%, 10%-60%, 10%-70%, 10%-80%, 10%-85%, 10%-90% less than a control plant when grown under comparable conditions.

Unless specified otherwise, measurements of sucker length, sucker mass, number of suckers, leaf yield, or leaf grade index values mentioned herein for a tobacco plant, variety, cultivar, or line refer to average measurements, including, for example, an average of multiple leaves (e.g., 2, 3, 4, 5, 6, 7, 8, 9, 10, 11, 12, 13, 14, 15, 16, 17, 18, 19, or 20 or more leaves) of a single plant or an average measurement from a population of tobacco plants from a single variety, cultivar, or line. A population of tobacco plants or a collection of tobacco leaves for determining an average measurement (e.g., fresh weight or leaf grading) can be of any size, for example, 5, 10, 15, 20, 25, 30, 35, 40, or 50. Industry-accepted standard protocols are followed for determining average measurements or grade index values.

In one aspect, a modified plant or leaf has a similar leaf chemistry profile compared to a control plant when grown under comparable conditions. Without being limiting, a leaf chemistry profile can comprise the amount of alkaloids (e.g., nicotine, nornicotine, anabasine, anatabine), malic acid, and reducing sugars (e.g., dextrose), or a combination thereof in a tobacco plant or tobacco leaf. In one aspect, a modified plant or leaf provided herein comprises a total alkaloids level within about 50%, within about 45%, within about 40%, within about 35%, within about 30%, within about 25%, within about 20%, within about 15%, within about 10%, within about 5%, within about 4%, within about 3%, within about 2%, within about 1%, or within about 0.5% of the total alkaloids level of a control plant when grown under comparable conditions. In one aspect, a modified plant or leaf provided herein comprises a nicotine level within about 50%, within about 45%, within about 40%, within about 35%, within about 30%, within about 25%, within about 20%, within about 15%, within about 10%, within about 5%, within about 4%, within about 3%, within about 2%, within about 1%, or within about 0.5% of the nicotine level of a control plant when grown under comparable conditions. In one aspect, a modified plant or leaf provided herein comprises a nornicotine level within about 50%, within about 45%, within about 40%, within about 35%, within about 30%, within about 25%, within about 20%, within about 15%, within about 10%, within about 5%, within about 4%, within about 3%, within about 2%, within about 1%, or within about 0.5% of the nornicotine level of a control plant when grown under comparable conditions. In one aspect, a modified plant or leaf provided herein comprises an anabasine level within about 50%, within about 45%, within about 40%, within about 35%, within about 30%, within about 25%, within about 20%, within about 15%, within about 10%, within about 5%, within about 4%, within about 3%, within about 2%, within about 1%, or within about 0.5% of the anabasine level of a control plant when grown under comparable conditions. In one aspect, a modified plant or leaf provided herein comprises an anatabine level within about 50%, within about 45%, within about 40%, within about 35%, within about 30%, within about 25%, within about 20%, within about 15%, within about 10%, within about 5%, within about 4%, within about 3%, within about 2%, within about 1%, or within about 0.5% of the anatabine level of a control plant when grown under comparable conditions. In one aspect, a modified plant or leaf provided herein comprises a malic acid level within about 50%, within about 45%, within about 40%, within about 35%, within about 30%, within about 25%, within about 20%, within about 15%, within about 10%, within about 5%, within about 4%, within about 3%, within about 2%, within about 1%, or within about 0.5% of the malic acid level of a control plant when grown under comparable conditions. In one aspect, a modified plant or leaf provided herein comprises a reducing sugars level within about 50%, within about 45%, within about 40%, within about 35%, within about 30%, within about 25%, within about 20%, within about 15%, within about 10%, within about 5%, within about 4%, within about 3%, within about 2%, within about 1%, or within about 0.5% of the reducing sugars level of a control plant when grown under comparable conditions. In one aspect, a modified plant or leaf provided herein comprises a dextrose level within about 50%, within about 45%, within about 40%, within about 35%, within about 30%, within about 25%, within about 20%, within about 15%, within about 10%, within about 5%, within about 4%, within about 3%, within about 2%, within about 1%, or within about 0.5% of the dextrose level of a control plant when grown under comparable conditions.

In one aspect, a modified plant or leaf provided herein comprises no or reduced suckers compared to a control plant and further comprises a nicotine level at least 50%, at least 60%, at least 70%, at least 80%, at least 85%, at least 90%, at least 91%, at least 92%, at least 93%, at least 94%, at least 95%, at least 96%, at least 97%, at least 98%, at least 99%, at least 99.5%, or at least 99.9% lower than the nicotine level of a control plant when grown under comparable conditions.

In one aspect, a plant component provided herein includes, but is not limited to, a leaf, a stem, a root, a seed, a flower, pollen, an anther, an ovule, a pedicel, a fruit, a meristem, a cotyledon, a hypocotyl, a pod, an embryo, endosperm, an explant, a callus, a tissue culture, a shoot, a cell, and a protoplast. In further aspects, this disclosure provides tobacco plant cells, tissues, and organs that are not reproductive material and do not mediate the natural reproduction of the plant. In another aspect, this disclosure also provides tobacco plant cells, tissues, and organs that are reproductive material and mediate the natural reproduction of the plant. In another aspect, this disclosure provides tobacco plant cells, tissues, and organs that cannot maintain themselves via photosynthesis. In another aspect, this disclosure provides somatic tobacco plant cells. Somatic cells, contrary to germline cells, do not mediate plant reproduction.

Provided cells, tissues and organs can be from seed, fruit, leaf, cotyledon, hypocotyl, meristem, embryos, endosperm, root, shoot, stem, pod, flower, inflorescence, stalk, pedicel, style, stigma, receptacle, petal, sepal, pollen, anther, filament, ovary, ovule, pericarp, phloem, and vascular tissue. In another aspect, this disclosure provides a tobacco plant chloroplast. In a further aspect, this disclosure provides an epidermal cell, a stomata cell, a leaf hair (trichome), a root hair, or a storage root. In another aspect, this disclosure provides a tobacco protoplast.

Skilled artisans understand that tobacco plants naturally reproduce via seeds, not via asexual reproduction or vegetative propagation. In one aspect, this disclosure provides tobacco endosperm. In another aspect, this disclosure provides a tobacco endosperm cell. In a further aspect, this disclosure provides a male or female sterile tobacco plant, which cannot reproduce without human intervention.

In one aspect, a modified plant, seed, plant part, or plant cell provided herein comprises one or more non-naturally occurring mutations. In one aspect, a mutation provided herein suppresses suckering in a plant. In another aspect, a mutation provided herein suppresses topping-induced suckering in a plant. In still another aspect, a mutation provided herein suppresses suckering in a plant prior to topping. Types of mutations provided herein include, for example, substitutions (point mutations), deletions, insertions, duplications, and inversions. Such mutations are desirably present in the coding region of a gene; however, mutations in a promoter or other regulatory region, an intron, an intron-exon boundary, or an untranslated region of a gene may also be desirable.

In one aspect, methods provided herein are capable of producing a tobacco plant with reduced suckering using mutagenesis. Mutagenesis methods include, without limitation, chemical mutagenesis, for example, treatment of seeds with ethyl methylsulfate (EMS) (Hildering and Verkerk, In, The use of induced mutations in plant breeding. Pergamon Press, pp. 317-320, 1965); or UV-irradiation, X-rays, electron beams, ion beams (e.g., carbon ion beam, helium ion beam, neon ion beam), and fast neutron irradiation (see, for example, Verkerk, *Neth. J. Agric. Sci.* 19:197-203, 1971; Poehlman, Breeding Field Crops, Van Nostrand Reinhold, New York (3.sup.rd ed.), 1987; and Tanaka, *J. Radiat. Res.* 51:223-233, 2010); transposon tagging (Fedoroff et al., 1984; U.S. Pat. Nos. 4,732,856 and 5,013,658); and T-DNA insertion methodologies (Hoekema et al., 1983; U.S. Pat. No. 5,149,645). EMS-induced mutagenesis consists of chemically inducing random point mutations over the length of a genome. Fast neutron mutagenesis consists of exposing seeds to neutron bombardment which causes large deletions through double stranded DNA breakage. Transposon tagging comprises inserting a transposon within an endogenous gene to reduce or eliminate expression of the gene.

In addition, a fast and automatable method for screening for chemically induced mutations, TILLING (Targeting Induced Local Lesions In Genomes), using denaturing HPLC or selective endonuclease digestion of selected PCR products is also applicable to the present disclosure. See, McCallum et al. (2000) *Nat. Biotechnol.* 18:455-457. Mutations that impact gene expression or that interfere with the function of genes provided herein can be determined using methods that are well known in the art. Insertional mutations in gene exons usually result in null-mutants. Mutations in conserved residues can be particularly effective in inhibiting the function of a protein. In an aspect, a mutation provided herein is a null, or knockout, mutation.

The screening and selection of mutagenized tobacco plants can be through any methodologies known to those having ordinary skill in the art. Examples of screening and selection methodologies include, but are not limited to, Southern analysis, PCR amplification for detection of a polynucleotide, Northern blots, RNase protection, primer-extension, RT-PCR amplification for detecting RNA transcripts, Sanger sequencing, Next Generation sequencing technologies (e.g., Illumina, PacBio, Ion Torrent, 454) enzymatic assays for detecting enzyme or ribozyme activity of polypeptides and polynucleotides, and protein gel electrophoresis, Western blots, immunoprecipitation, and enzyme-linked immunoassays to detect polypeptides. Other techniques such as in situ hybridization, enzyme staining, and immunostaining also can be used to detect the presence or expression of polypeptides and/or polynucleotides. Methods for performing all of the referenced techniques are known.

In one aspect, a polynucleotide provided herein comprises at least 1, at least 2, at least 3, at least 4, at least 5, at least 6, at least 7, at least 8, at least 9, at least 10, or more than 10 mutations compared to a naturally existing polynucleotide. In another aspect, a mutation provided herein is positioned within a polynucleotide selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83-160, 186, 188, 190, 192, 194, 196, 198, 200, 202, 204, 205, 207, 209, 211, 213, 215, 217, 219, 221, 223, 225-228, 230, 232, 234, 236, 238, 240, 242, 244, 246, 248, 250, 252, and 254. In one aspect, a mutation provided herein is positioned within a polynucleotide encoding a polypeptide selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 161-185, 187, 189, 191, 193, 195, 197, 199, 201, 203, 206, 208, 210, 212, 214, 216, 218, 220, 222, 224, 229, 231, 233, 235, 237, 239, 241, 243, 245, 247, 249, 251, 253, and 255.

In one aspect, a plant genome provided herein is mutated (edited) by a nuclease selected from the group consisting of a meganuclease, a zinc-finger nuclease (ZFN), a transcription activator-like effector nuclease (TALEN), a CRISPR/Cas9 nuclease, or a CRISPR/Cpf1 nuclease. In another aspect, a plant genome provided herein is mutated by a CRISPR/CasX or a CRISPR/CasY nuclease. In a further aspect, a plant genome provided herein is mutated by a CRISPR/Csm1 nuclease. As used herein, "editing" or "genome editing" refers to targeted mutagenesis of at least 1, at least 2, at least 3, at least 4, at least 5, at least 6, at least 7, at least 8, at least 9, or at least 10 nucleotides of an endogenous plant genome nucleic acid sequence, or removal or replacement of an endogenous plant genome nucleic acid sequence. In one aspect, an edited nucleic acid sequence provided herein has at least 99.9%, at least 99.5%, at least 99%, at least 98%, at least 97%, at least 96%, at least 95%, at least 94%, at least 93%, at least 92%, at least 91%, at least 90%, at least 85%, at least 80%, or at least 75% sequence identity with an endogenous nucleic acid sequence. In one aspect, an edited nucleic acid sequence provided herein has at least 99.9%, at least 99.5%, at least 99%, at least 98%, at least 97%, at least 96%, at least 95%, at least 94%, at least 93%, at least 92%, at least 91%, at least 90%, at least 85%, at least 80%, or at least 75% sequence identity with a polynucleotide selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83-160, 186, 188, 190, 192, 194, 196, 198, 200, 202, 204, 205, 207, 209, 211, 213, 215, 217, 219, 221, 223, 225-228, 230, 232, 234, 236, 238, 240, 242, 244, 246, 248, 250, 252, 254, and fragments thereof. In another aspect, an edited nucleic acid sequence provided herein has at least 99.9%, at least 99.5%, at least 99%, at least 98%, at least 97%, at least 96%, at least 95%, at least 94%, at least 93%, at least 92%, at least 91%, at least 90%, at least 85%, at least 80%, or at least 75% sequence identity with a polynucleotide encoding a polypeptide selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 161-185, 187, 189, 191, 193, 195, 197, 199, 201, 203, 206, 208, 210, 212, 214, 216, 218, 220, 222, 224, 229, 231, 233, 235, 237, 239, 241, 243, 245, 247, 249, 251, 253, and 255.

In one aspect, a nuclease provided herein is used to edit a plant genomic locus encoding a sequence having at least 70%, at least 75%, at least 80%, at least 85%, at least 90%, at least 95%, at least 96%, at least 97%, at least 98%, at least 99% or 100% sequence identity to a polynucleotide selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83-160, 186, 188, 190, 192, 194, 196, 198, 200, 202, 204, 205, 207, 209, 211, 213, 215, 217, 219, 221, 223, 225-228, 230, 232, 234, 236, 238, 240, 242, 244, 246, 248, 250, 252, 254, and fragments thereof.

In another aspect, a nuclease provided herein is used to edit a plant genomic locus encoding a polypeptide having at least 70%, at least 75%, at least 80%, at least 85%, at least 90%, at least 95%, at least 96%, at least 97%, at least 98%, at least 99% or 100% sequence identity to a polypeptide selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 161-185, 187, 189, 191, 193, 195, 197, 199, 201, 203, 206, 208, 210, 212, 214, 216, 218, 220, 222, 224, 229, 231, 233, 235, 237, 239, 241, 243, 245, 247,249, 251, 253, and 255. In another aspect, a nuclease provided herein is used to edit a plant genome locus encoding a polypeptide having at least 70%, at least 75%, at least 80%, at least 85%, at least 90%, at least 95%, at least 96%, at least 97%, at least 98%, at least 99% or 100% sequence similarity to a polypeptide selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 161-185, 187, 189, 191, 193, 195, 197, 199, 201, 203, 206, 208, 210, 212, 214, 216, 218, 220, 222, 224, 229, 231, 233, 235, 237, 239, 241, 243, 245, 247, 249,251, 253, and 255.

Meganucleases, ZFNs, TALENs, CRISPR/Cas9, and CRISPR/Cpf1 induce a double-strand DNA break at a target site of a genomic sequence that is then repaired by the natural processes of homologous recombination (HR) or non-homologous end-joining (NHEJ). Sequence modifications then occur at the cleaved sites, which can include deletions or insertions that result in gene disruption in the case of NHEJ, or integration of donor nucleic acid sequences by HR. In one aspect, a methods provided herein comprises editing a plant genome with a nuclease provided herein to mutate at least 1, at least 2, at least 3, at least 4, at least 5, at least 6, at least 7, at least 8, at least 9, at least 10, or more than 10 nucleotides in the plant genome via HR with a donor polynucleotide. In one aspect, a mutation provided herein is caused by genome editing using a nuclease. In another aspect, a mutation provided herein is caused by non-homologous end-joining or homologous recombination.

Meganucleases, which are commonly identified in microbes, are unique enzymes with high activity and long recognition sequences (>14 bp) resulting in site-specific digestion of target DNA. Engineered versions of naturally occurring meganucleases typically have extended DNA recognition sequences (for example, 14 to 40 bp).

In one aspect, a meganuclease provided herein edits a polynucleotide having at least 70%, at least 75%, at least 80%, at least 85%, at least 90%, at least 95%, at least 96%, at least 97%, at least 98%, at least 99% or 100% sequence identity to a polynucleotide selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83-160, 186, 188, 190, 192, 194, 196, 198, 200, 202, 204, 205, 207, 209, 211, 213, 215, 217, 219, 221, 223, 225-228, 230, 232, 234, 236, 238, 240, 242, 244, 246, 248, 250, 252, 254, and fragments thereof. In another aspect, a meganuclease provided herein edits a polynucleotide encoding a polypeptide having at least 70%, at least 75%, at least 80%, at least 85%, at least 90%, at least 95%, at least 96%, at least 97%, at least 98%, at least 99% or 100% sequence identity to a polypeptide selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 161-185, 187, 189, 191, 193, 195, 197, 199, 201, 203, 206, 208, 210, 212, 214, 216, 218, 220, 222, 224, 229, 231, 233, 235, 237, 239, 241, 243, 245, 247, 249, 251, 253, and 255. In another aspect, a meganuclease provided herein edits a polynucleotide encoding a polypeptide having at least 70%, at least 75%, at least 80%, at least 85%, at least 90%, at least 95%, at least 96%, at least 97%, at least 98%, at least 99% or 100% sequence similarity to a polypeptide selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 161-185, 187, 189, 191, 193, 195, 197, 199, 201, 203, 206, 208, 210, 212, 214, 216, 218, 220, 222, 224, 229, 231, 233, 235, 237, 239, 241, 243, 245, 247, 249, 251, 253, and 255.

The engineering of meganucleases can be more challenging than that of ZFNs and TALENs because the DNA recognition and cleavage functions of meganucleases are intertwined in a single domain. Specialized methods of mutagenesis and high-throughput screening have been used to create novel meganuclease variants that recognize unique sequences and possess improved nuclease activity.

ZFNs are synthetic proteins consisting of an engineered zinc finger DNA-binding domain fused to the cleavage domain of the FokI restriction endonuclease. ZFNs can be designed to cleave almost any long stretch of double-stranded DNA for modification of the zinc finger DNA-binding domain. ZFNs form dimers from monomers composed of a non-specific DNA cleavage domain of FokI endonuclease fused to a zinc finger array engineered to bind a target DNA sequence.

The DNA-binding domain of a ZFN is typically composed of 3-4 zinc-finger arrays. The amino acids at positions −1, +2, +3, and +6 relative to the start of the zinc finger ∞-helix, which contribute to site-specific binding to the target DNA, can be changed and customized to fit specific target sequences. The other amino acids form the consensus backbone to generate ZFNs with different sequence specificities. Rules for selecting target sequences for ZFNs are known in the art.

The FokI nuclease domain requires dimerization to cleave DNA and therefore two ZFNs with their C-terminal regions are needed to bind opposite DNA strands of the cleavage site (separated by 5-7 bp). The ZFN monomer can cute the target site if the two-ZF-binding sites are palindromic. The term ZFN, as used herein, is broad and includes a monomeric ZFN that can cleave double stranded DNA without assistance from another ZFN. The term ZFN is also used to refer to one or both members of a pair of ZFNs that are engineered to work together to cleave DNA at the same site.

Without being limited by any scientific theory, because the DNA-binding specificities of zinc finger domains can in principle be re-engineered using one of various methods, customized ZFNs can theoretically be constructed to target nearly any gene sequence. Publicly available methods for engineering zinc finger domains include Context-dependent Assembly (CoDA), Oligomerized Pool Engineering (OPEN), and Modular Assembly.

In one aspect, a ZFN provided herein edits a polynucleotide having at least 70%, at least 75%, at least 80%, at least 85%, at least 90%, at least 95%, at least 96%, at least 97%, at least 98%, at least 99% or 100% sequence identity to a polynucleotide selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83-160, 186, 188, 190, 192, 194, 196, 198, 200, 202, 204, 205, 207, 209, 211, 213, 215, 217, 219, 221, 223, 225-228, 230, 232, 234, 236, 238, 240, 242, 244, 246, 248, 250, 252, 254, and fragments thereof. In another aspect, a ZFN provided herein edits a polynucleotide encoding a polypeptide having at least 70%, at least 75%, at least 80%, at least 85%, at least 90%, at least 95%, at least 96%, at least 97%, at least 98%, at least 99% or 100% sequence identity to a polypeptide selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 161-185, 187, 189, 191, 193, 195, 197, 199, 201, 203, 206, 208, 210, 212, 214, 216, 218, 220, 222, 224, 229, 231, 233, 235, 237, 239, 241, 243, 245, 247, 249, 251, 253, and 255. In another aspect, a ZFN provided herein edits a polynucleotide encoding a polypeptide having at least 70%, at least 75%, at least 80%, at least 85%, at least 90%, at least 95%, at least 96%, at least 97%, at least 98%, at least 99% or 100% sequence similarity to a polypeptide selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 161-185, 187, 189, 191, 193, 195, 197, 199, 201, 203, 206, 208, 210, 212, 214, 216, 218, 220, 222, 224, 229, 231, 233, 235, 237, 239, 241, 243, 245, 247, 249, 251, 253, and 255.

TALENs are artificial restriction enzymes generated by fusing the transcription activator-like effector (TALE) DNA binding domain to a FokI nuclease domain. When each member of a TALEN pair binds to the DNA sites flanking a target site, the FokI monomers dimerize and cause a double-stranded DNA break at the target site.

The term TALEN, as used herein, is broad and includes a monomeric TALEN that can cleave double stranded DNA without assistance from another TALEN. The term TALEN is also used to refer to one or both members of a pair of TALENs that work together to cleave DNA at the same site.

Transcription activator-like effectors (TALEs) can be engineered to bind practically any DNA sequence. TALE proteins are DNA-binding domains derived from various plant bacterial pathogens of the genus *Xanthomonas*. The X pathogens secrete TALEs into the host plant cell during infection. The TALE moves to the nucleus, where it recognizes and binds to a specific DNA sequence in the promoter region of a specific DNA sequence in the promoter region of a specific gene in the host genome. TALE has a central DNA-binding domain composed of 13-28 repeat monomers of 33-34 amino acids. The amino acids of each monomer are highly conserved, except for hypervariable amino acid residues at positions 12 and 13. The two variable amino acids are called repeat-variable diresidues (RVDs). The amino acid pairs NI, NG, HD, and NN of RVDs preferentially recognize adenine, thymine, cytosine, and guanine/adenine, respectively, and modulation of RVDs can recognize consecutive DNA bases. This simple relationship between amino acid sequence and DNA recognition has allowed for the engineering of specific DNA binding domains by selecting a combination of repeat segments containing the appropriate RVDs.

Besides the wild-type FokI cleavage domain, variants of the FokI cleavage domain with mutations have been designed to improve cleavage specificity and cleavage activity. The FokI domain functions as a dimer, requiring two constructs with unique DNA binding domains for sites in the target genome with proper orientation and spacing. Both the number of amino acid residues between the TALEN DNA binding domain and the FokI cleavage domain and the number of bases between the two individual TALEN binding sites are parameters for achieving high levels of activity.

The relationship between amino acid sequence and DNA recognition of the TALE binding domain allows for designable proteins. Software programs such as DNA Works can be used to design TALE constructs. Other methods of designing TALE constructs are known to those of skill in the art. See Doyle et al., *Nucleic Acids Research* (2012) 40: W117-122; Cermak et al., *Nucleic Acids Research* (2011). 39:e82; and tale-nt.cac.cornell.edu/about.

In one aspect, a TALEN provided herein edits a polynucleotide having at least 70%, at least 75%, at least 80%, at least 85%, at least 90%, at least 95%, at least 96%, at least 97%, at least 98%, at least 99% or 100% sequence identity to a polynucleotide selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83-160, 186, 188, 190, 192, 194, 196, 198, 200, 202, 204, 205, 207, 209, 211, 213, 215, 217, 219, 221, 223, 225-228, 230, 232, 234, 236, 238, 240, 242, 244, 246, 248, 250, 252, 254, and fragments thereof. In another aspect, a TALEN provided herein edits a polynucleotide encoding a polypeptide having at least 70%, at least 75%, at least 80%, at least 85%, at least 90%, at least 95%, at least 96%, at least 97%, at least 98%, at least 99% or 100% sequence identity to a polypeptide selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 161-185, 187, 189, 191, 193, 195, 197, 199, 201, 203, 206, 208, 210, 212, 214, 216, 218, 220, 222, 224, 229, 231, 233, 235, 237, 239, 241, 243, 245, 247, 249, 251, 253, and 255. In another aspect, a TALEN provided herein edits a polynucleotide encoding a polypeptide having at least 70%, at least 75%, at least 80%, at least 85%, at least 90%, at least 95%, at least 96%, at least 97%, at least 98%, at least 99% or 100% sequence similarity to a polypeptide selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 161-185, 187, 189, 191, 193, 195, 197, 199, 201, 203, 206, 208, 210, 212, 214, 216, 218, 220, 222, 224, 229, 231, 233, 235, 237, 239, 241, 243, 245, 247, 249, 251, 253, and 255.

A CRISPR/Cas9 system or a CRISPR/Cpf1 system are alternatives to the FokI-based methods ZFN and TALEN. The CRISPR systems are based on RNA-guided engineered nucleases that use complementary base pairing to recognize DNA sequences at target sites.

CRISPR/Cas9 systems are part of the adaptive immune system of bacteria and archaea, protecting them against invading nucleic acids such as viruses by cleaving the foreign DNA in a sequence-dependent manner. The immunity is acquired by the integration of short fragments of the invading DNA known as spacers between two adjacent repeats at the proximal end of a CRISPR locus. The CRISPR arrays, including the spacers, are transcribed during subsequent encounters with invasive DNA and are processed into small interfering CRISPR RNAs (crRNAs) approximately 40 nt in length, which combine with the trans-activating CRISPR RNA (tracrRNA) to activate and guide the Cas9 nuclease. This cleaves homologous double-stranded DNA sequences known as protospacers in the invading DNA. A prerequisite for cleavage is the presence of a conserved protospacer-adjacent motif (PAM) downstream of the target DNA, which usually has the sequence 5-NGG-3 but less frequently NAG. Specificity is provided by the so-called "seed sequence" approximately 12 bases upstream of the PAM, which must match between the RNA and target DNA. Cpf1 acts in a similar manner to Cas9, but Cpf1 does not require a tracrRNA.

In one aspect, an engineered guide RNA provided herein guides a Cas9 or Cpf1 nuclease to a polynucleotide having at least 70%, at least 75%, at least 80%, at least 85%, at least 90%, at least 95%, at least 96%, at least 97%, at least 98%, at least 99% or 100% sequence identity to a polynucleotide selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83-160, 186, 188, 190, 192, 194, 196, 198, 200, 202, 204, 205, 207, 209, 211, 213, 215, 217, 219, 221, 223, 225-228, 230, 232, 234, 236, 238, 240, 242, 244, 246, 248, 250, 252, 254, and fragments thereof. In another aspect, an engineered guide RNA provided herein guides a Cas9 or Cpf1 nuclease to a polynucleotide encoding a polypeptide having at least 70%, at least 75%, at least 80%, at least 85%, at least 90%, at least 95%, at least 96%, at least 97%, at least 98%, at least 99% or 100% sequence identity to a polypeptide selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 161-185, 187, 189, 191, 193, 195, 197, 199, 201, 203, 206, 208, 210, 212, 214, 216, 218, 220, 222, 224, 229, 231, 233, 235, 237, 239, 241, 243, 245, 247, 249, 251, 253, and 255. In another aspect, an engineered guide RNA provided herein guides a Cas9 or Cpf1 nuclease to a polynucleotide encoding a polypeptide having at least 70%, at least 75%, at least 80%, at least 85%, at least 90%, at least 95%, at least 96%, at least 97%, at least 98%, at least 99% or 100% sequence similarity to a polypeptide selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 161-185, 187, 189, 191, 193, 195, 197, 199, 201, 203, 206, 208, 210, 212, 214, 216, 218, 220, 222, 224, 229, 231, 233, 235, 237, 239, 241, 243, 245, 247,249, 251, 253, and 255.

In one aspect, a Cas9 or a Cpf1 nuclease provided herein cleaves a polynucleotide having at least 70%, at least 75%, at least 80%, at least 85%, at least 90%, at least 95%, at least 96%, at least 97%, at least 98%, at least 99% or 100% sequence identity to a polynucleotide selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83-160, 186, 188, 190, 192, 194, 196, 198, 200, 202, 204, 205, 207, 209, 211, 213, 215, 217, 219, 221, 223, 225-228, 230, 232, 234, 236, 238, 240, 242, 244, 246, 248, 250, 252, 254, and fragments thereof. In another aspect, a Cas9 or a Cpf1 nuclease provided herein cleaves a polynucleotide encoding a polypeptide having at least 70%, at least 75%, at least 80%, at least 85%, at least 90%, at least 95%, at least 96%, at least 97%, at least 98%, at least 99% or 100% sequence identity to a polypeptide selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 161-185, 187, 189, 191, 193, 195, 197, 199, 201, 203, 206, 208, 210, 212, 214, 216, 218, 220, 222, 224, 229, 231, 233, 235, 237, 239, 241, 243, 245, 247, 249, 251, 253, and 255. In another aspect, a Cas9 or a Cpf1 nuclease provided herein cleaves a polynucleotide encoding a polypeptide having at least 70%, at least 75%, at least 80%, at least 85%, at least 90%, at least 95%, at least 96%, at least 97%, at least 98%, at least 99% or 100% sequence similarity to a polypeptide selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 161-185, 187, 189, 191, 193, 195, 197, 199, 201, 203, 206, 208, 210, 212, 214, 216, 218, 220, 222, 224, 229, 231, 233, 235, 237, 239, 241, 243, 245, 247, 249, 251, 253, and 255.

In one aspect, a mutagenesis system provided herein (e.g., chemical mutagenesis, irradiation mutagenesis, transposon mutagenesis, *Agrobacterium*-mediated transformation, a meganuclease, a ZFN, a TALEN, a CRISPR/Cas9 system, a CRISPR/Cpf1 system), or a combination of mutagenesis systems provided herein, is used in a method to introduce one or more mutations to a tobacco gene that is natively expressed in at least one tobacco axillary meristem cell.

In still another aspect, a modified tobacco plant provided herein further comprises one or more mutations in one or more loci encoding a nicotine demethylase (e.g., CYP82E4, CYP82E5, CYP82E10) that confer reduced amounts of nornicotine (See U.S. Pat. Nos. 8,319,011; 8,124,851; 9,187,759; 9,228,194; 9,228,195; 9,247,706) compared to control plant lacking one or more mutations in one or more loci encoding a nicotine demethylase. In another aspect, a tobacco plant provided herein further comprises one or more mutations in a Nic1 locus, a Nic2 locus, or both, which confer reduced amounts of nicotine compared to a control plant lacking one or more mutations in a Nic1 locus, a Nic2 locus, or both.

In one aspect, recombinant DNA constructs or expression cassettes provided herein comprise a promoter selected from the group consisting of a constitutive promoter, an inducible promoter, and a tissue-preferred promoter (for example, without being limiting, a leaf-specific promoter, a root-specific promoter, or a meristem-specific promoter).

In one aspect, a promoter provided herein is an axillary bud-specific promoter. In one aspect, a promoter provided herein is an axillary meristem-specific promoter. In one aspect, an axillary meristem-specific promoter provided herein is functional or preferentially functional in an L1 layer, an L2 layer, an L3 layer, or a combination thereof. Dicot shoot apical and axillary meristems comprise three distinct cell layers: the L1 layer (outermost layer), the L2 layer (middle layer), and the L3 layer (innermost layer). The L1 and L2 layers make up the tunica, and they divide anticlinally (the division plane is perpendicular to the surface of the meristem). The L3 layer, or corpus, divides in all directions. The L1 layer eventually gives rise to epidermal tissue; the L2 layer gives rise to ground tissue (e.g., parenchyma, collenchyma, sclerenchyma); and the L3 layer typically gives rise to vascular tissue (e.g., xylem, phloem)

Shoot apical and axillary meristems can also be divided into three zones: a central zone, a peripheral zone, and a rib zone. Cells from the central zone, comprising parts of the L1, L2, and L3 layers at the peak of the meristem, serve to organize and maintain the meristem; the central zone comprises pluripotent stem cells. The peripheral zone surrounds the central zone and will form organs (e.g., leaf primordia, flower primordia) and undergo morphogenesis; this zone comprises high mitotic activity. The rib zone, or rib meristem, is positioned below the central zone; the rib zone gives rise to stem and vasculature tissue. In one aspect, an axillary meristem-specific promoter provided herein is functional or preferentially functional in a central zone, a peripheral zone, a rib zone, or a combination thereof.

In one aspect, an axillary bud-specific promoter comprises a polynucleotide sequence having at least 60%, at least 70%, at least 75%, at least 80%, at least 85%, at least 90%, at least 95%, at least 96%, at least 97%, at least 98%, at least 99% or 100% sequence identity to a polynucleotide selected from the group consisting of SEQ ID NOs: 113-118, 148-160, 204 and fragments thereof. In another aspect, an axillary meristem-specific promoter comprises a polynucleotide sequence having at least 60%, at least 70%, at least 75%, at least 80%, at least 85%, at least 90%, at least 95%, at least 96%, at least 97%, at least 98%, at least 99% or 100% sequence identity to a polynucleotide selected from the group consisting of SEQ ID NOs: 113-118, 148-160, 204 and fragments thereof. In still another aspect, a promoter active in an L1 layer, an L2 layer, an L3 layer, or a combination thereof comprises a polynucleotide sequence selected from the group consisting of SEQ ID NOs: 113-118, 148-160, 204 and a fragment thereof. In another aspect, a promoter active in a central zone, a peripheral zone, a rib zone, or a combination thereof comprises a polynucleotide sequence selected from the group consisting of SEQ ID NOs: 113-118, 148-160, 204 and a fragment thereof. In one aspect, a promoter fragment provided herein has a length of at least 50, at least 75, at least 100, at least 200, at least 300, at least 400, at least 500, at least 600, at least 700, at least 800, at least 900, at least 1000, at least 1250, at least 1500, at least 1750, at least 2000, at least 2500, at least 3000, at least 3500, at least 4000, at least 4500, or at least 4999 nucleotides. In another aspect, a promoter fragment provided herein has a length of between 50 and 200, between 100 and 200, between 100 and 300, between 100 and 400, between 100 and 500, between 100 and 600, between 100 and 700, between 100 and 800, 100 and 900, between 100 and 1000, between 100 and 2000, between 200 and 300, between 200 and 400, between 200 and 500, between 200 and 600, between 200 and 700, between 200 and 800, between 200 and 900, between 200 and 1000, between 200 and 2000, between 200 and 2500, between 200 and 3000, between 500 and 1000, between 500 and 1500, between 500 and 2000, between 500 and 2500, between 500 and 3000, between 1000 and 2000, between 1000 and 3000, between 1500 and 2000, between 1500 and 2500, between 1500 and 3000, between 2000 and 3000 nucleotides, between 100 and 3500, between 100 and 4000, between 100 and 4500, between 100 and 4999, between 500 and 3500, between 500 and 4000, between 500 and 4500, between 500 and 4999, between 1000 and 3500, between 1000 and 4000, between 1000 and 4500, between 1000 and 4999, between 2000 and 3500, between 2000 and 4000, between 2000 and 4500, between 2000 and 4999, between 3000 and 3500, between 3000 and 4000, between 3000 and 4500, between 3000 and 4999, between 3500 and 4000, between 3500 and 4500, between 3500 and 4999, between 4000 and 4500, between 4000 and 4999, or between 4500 and 4999 nucleotides.

In one aspect, a recombinant DNA construct of the present disclosure comprises a polynucleotide selected from the group consisting of SEQ ID NOs: 113-118, 148-160, 204 and a fragment thereof operably linked to a polynucleotide encoding a polypeptide having at least 70%, at least 75%, at least 80%, at least 85%, at least 90%, at least 95%, at least 96%, at least 97%, at least 98%, at least 99% or 100% sequence identity to a polypeptide selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 161-185, 187, 189, 191, 193, 195, 197, 199, 201, 203, 206, 208, 210, 212, 214, 216, 218, 220, 222, 224, 229, 231, 233, 235, 237, 239, 241, 243, 245, 247, 249, 251, 253, and 255.

In one aspect, a recombinant DNA construct of the present disclosure comprises a polynucleotide selected from the group consisting of SEQ ID NOs: 113-118, 148-160, 204 and a fragment thereof operably linked to a polynucleotide encoding a polypeptide having at least 70%, at least 75%, at least 80%, at least 85%, at least 90%, at least 95%, at least 96%, at least 97%, at least 98%, at least 99% or 100% sequence similarity to a polypeptide selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 161-185, 187, 189, 191, 193, 195, 197, 199, 201, 203, 206, 208, 210, 212, 214, 216, 218, 220, 222, 224, 229, 231, 233, 235, 237, 239, 241, 243, 245, 247, 249, 251, 253, and 255.

In one aspect, a recombinant DNA construct of the present disclosure comprises a polynucleotide selected from the group consisting of SEQ ID NOs: 113-118, 148-160, 204 and a fragment thereof operably linked to a polynucleotide having at least 60%, at least 65%, at least 70%, at least 75%, at least 80%, at least 85%, at least 90%, at least 95%, at least 96%, at least 97%, at least 98%, at least 99% or 100% identity to a polynucleotide selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83-160, 186, 188, 190, 192, 194, 196, 198, 200, 202, 204, 205, 207, 209, 211, 213, 215, 217, 219, 221, 223, and 225-228, 230, 232, 234, 236, 238, 240, 242, 244, 246, 248, 250, 252, 254, and fragments thereof.

In one aspect, a tobacco plant, or part thereof, of the present disclosure comprises a heterologous promoter having at least 90% sequence identity to a polynucleotide selected from the group consisting of SEQ ID NOs: 113-118, 148-160, 204, and fragments thereof operably linked to a polynucleotide encoding an auxin biosynthesis protein or an auxin transport protein.

Exemplary constitutive promoters include the core promoter of the Rsyn7 promoter and other constitutive promoters disclosed in U.S. Pat. No. 6,072,050; the core CaMV 35S promoter (Odell et al. (1985) Nature 313:810-812); ubiquitin (Christensen et al. (1989) Plant Mol. Biol. 12:619-632 and Christensen et al. (1992) Plant Mol. Biol. 18:675-689); pEMU (Last et al. (1991) Theor. Appl. Genet. 81:581-588); MAS (Velten et al. (1984) EMBO J 3:2723-2730); ALS promoter (U.S. Pat. No. 5,659,026), and the like.

Exemplary chemical-inducible promoters include the tobacco PR-1a promoter, which is activated by salicylic acid. Other chemical-inducible promoters of interest include steroid-responsive promoters (see, for example, the glucocorticoid-inducible promoter in Schena et al. (1991) Proc. Natl. Acad. Sci. USA 88:10421-10425 and McNellis et al. (1998) Plant J. 14(2):247-257) and tetracycline-inducible promoters (see, for example, Gatz et al. (1991) Mol. Gen. Genet. 227:229-237, and U.S. Pat. Nos. 5,814,618 and 5,789,156). Additional exemplary promoters that can be used herein are those responsible for heat-regulated gene expression, light-regulated gene expression (for example, the pea rbcS-3A; the maize rbcS promoter; the chlorophyll a/b-binding protein gene found in pea; or the Arabssu promoter), hormone-regulated gene expression (for example, the abscisic acid (ABA) responsive sequences from the Em gene of wheat; the ABA-inducible HVA1 and HVA22, and rd29A promoters of barley and *Arabidopsis*; and wound-induced gene expression (for example, of wun1), organ specific gene expression (for example, of the tuber-specific storage protein gene; the 23-kDa zein gene from maize described by; or the French bean (β-phaseolin gene), or pathogen-inducible promoters (for example, the PR-1, prp-1, or (β-1,3 glucanase promoters, the fungal-inducible wirla promoter of wheat, and the nematode-inducible promoters, TobRB7-5A and Hmg-1, of tobacco arid parsley, respectively).

Additional exemplary tissue-preferred promoters include those disclosed in Yamamoto et al. (1997) Plant J. 12(2): 255-265; Kawamata et al. (1997) Plant Cell Physiol. 38(7): 792-803; Hansen et al. (1997) Mol. Gen. Genet. 254(3):337-343; Russell et al. (1997) Transgenic Res. 6(2):157-168; Rinehart et al. (1996) Plant Physiol. 112(3):1331-1341; Van Camp et al. (1996) Plant Physiol. 112(2):525-535; Canevascini et al. (1996) Plant Physiol. 112(2):513-524; Yamamoto et al. (1994) Plant Cell Physiol. 35(5):773-778; Lam (1994) Results Probl. Cell Differ. 20:181-196; Orozco et al. (1993) Plant Mol. Biol. 23(6):1129-1138; Matsuoka et al. (1993) Proc Natl. Acad. Sci. USA 90(20):9586-9590; and Guevara-Garcia et al. (1993) Plant J. 4(3):495-505.

As used herein, "operably linked" refers to a functional linkage between two or more elements. For example, an operable linkage between a polynucleotide of interest and a regulatory sequence (e.g., a promoter) is a functional link that allows for expression of the polynucleotide of interest. Operably linked elements may be contiguous or non-contiguous. In one aspect, a promoter provided herein is operably linked to a polynucleotide selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83-160, 186, 188, 190, 192, 194, 196, 198, 200, 202, 204, 205, 207, 209, 211, 213, 215, 217, 219, 221, 223, 225-228, 230, 232, 234, 236, 238, 240, 242, 244, 246, 248, 250, 252, 254, and fragments thereof. In another aspect, a promoter provided herein is operably linked to a polynucleotide encoding a polypeptide selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 161-185, 187, 189, 191, 193, 195, 197, 199, 201, 203, 206, 208, 210, 212, 214, 216, 218, 220, 222, 224, 229, 231, 233, 235, 237, 239, 241, 243, 245, 247, 249, 251, 253, and 255.

As used herein, "heterologous" refers to a sequence that originates from a foreign species, or, if from the same species, is substantially modified from its native form in composition and/or genomic locus by deliberate human intervention. The term also is applicable to nucleic acid constructs, also referred to herein as "polynucleotide constructs" or "nucleotide constructs." In this manner, a "heterologous" nucleic acid construct is intended to mean a construct that originates from a foreign species, or, if from the same species, is substantially modified from its native form in composition and/or genomic locus by deliberate human intervention. Heterologous nucleic acid constructs include, but are not limited to, recombinant nucleotide constructs that have been introduced into a plant or plant part thereof, for example, via transformation methods or subsequent breeding of a transgenic plant with another plant of interest.

In one aspect, a modified plant, seed, plant component, plant cell, or plant genome provided herein comprises a heterologous promoter operably linked to a polynucleotide encoding a polypeptide having at least 40%, at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to a polypeptide selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 161-185, 187, 189, 191, 193, 195, 197, 199, 201, 203, 206, 208, 210, 212, 214, 216, 218, 220, 222, 224, 229, 231, 233, 235, 237, 239, 241, 243, 245, 247, 249, 251, 253, and 255. In another aspect, a recombinant DNA construct provided herein comprises a heterologous promoter operably linked to a polynucleotide encoding a polypeptide having at least 40%, at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to a polypeptide selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 161-185, 187, 189, 191, 193, 195, 197, 199, 201, 203, 206, 208, 210, 212, 214, 216, 218, 220, 222, 224, 229, 231, 233, 235, 237, 239, 241, 243, 245, 247, 249, 251, 253, and 255.

Enhancer elements are regions of DNA that can be bound by proteins to activate RNA transcription. In one aspect, a promoter sequence provided herein is operably linked to an enhancer element. In another aspect, a polynucleotide selected from the group consisting of SEQ ID NOs: 113-118, 148-160, 204, and a fragment thereof is operably linked to an enhancer element. In one aspect, an enhancer element provided herein is at least 10, at least 25, at least 50, at least 75, at least 100, at least 150, at least 200, at least 250, at least 300, at least 350, at least 400, at least 450, at least 500, at least 550, at least 600, at least 650, at least 700, at least 750, at least 800, at least 850, at least 900, at least 950, at least 1000, at least 1100, at least 1200, at least 1300, at least 1400, at least 1500, at least 1750, at least 2000, at least 2500, at least 3000, at least 3500, at least 4000, at least 4500, or at least 5000 nucleotides in length. In one aspect, an enhancer element provided herein is a CsVMV promoter.

Many gene promoters contain cis-regulatory elements that function to regulate gene transcription. Cis-regulatory elements often function by serving as binding sites for transcription factors. In one aspect, a promoter provided herein comprises at least 1, at least 2, at least 3, at least 4, at least 5, or at least 6 cis regulatory elements selected from the group consisting of a bud dormancy element (BDE), an axillary bud growth UP1 element, an axillary bud growth UP2 element, a sucrose responsive element (SRE), a sugar repressive element (SURE), and a bud activation or TCP-binding element (BAE). In another aspect, a recombinant nucleotide provided herein comprises a promoter, where the promoter comprises at least 1, at least 2, at least 3, at least 4, at least 5, or at least 6 cis elements selected from the group consisting of a bud dormancy element (BDE), an axillary bud growth UP1 element, an axillary bud growth UP2 element, a sucrose responsive element (SURE), a sugar repressive element (SRE), and a bud activation or TCP-binding element (BAE).

In one aspect, a promoter provided herein comprises at least 1, at least 2, at least 3, at least 4, at least 5, or at least 6 cis-regulatory elements within 1, 3, 5, 10, 15, 20, 25, 30, 35, 40, 45, 50, 75, 100, 200, 300, 400, 500, 600, 700, 800, 900, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900, 5000, 7500, or 10,000 nucleotides of a transcriptional start site. In another aspect, a promoter provided herein comprises at least 1, at least 2, at least 3, at least 4, at least 5, or at least 6 cis-regulatory elements within 1-10,000, 1-7500, 1-5000, 1-4900, 1-4800, 1-4700, 1-4600, 1-4500, 1-4400, 1-4300, 1-4200, 1-4100, 1-4000, 1-3900, 1-3800, 1-3700, 1-3600, 1-3500, 1-3400, 1-3300, 1-3200, 1-3100, 1-3000, 1-2900, 1-2800, 1-2700, 1-2600, 1-2500, 1-2400, 1-2300, 1-2200, 1-2100, 1-2000, 1-1900, 1-1800, 1-1700, 1-1600, 1-1500, 1-1400, 1-1300, 1-1200, 1-1100, 1-1000, 1-900, 1-800, 1-700, 1-600, 1-500, 1-400, 1-300, 1-200, 1-100, 1-75, 1-50, 1-45, 1-40, 1-35, 1-30, 1-25, 1-20, 1-15, 5-10,000, 5-7500, 5-5000, 5-4900, 5-4800, 5-4700, 5-4600, 5-4500, 5-4400, 5-4300, 5-4200, 5-4100, 5-4000, 5-3900, 5-3800, 5-3700, 5-3600, 5-3500, 5-3400, 5-3300, 5-3200, 5-3100, 5-3000, 5-2900, 5-2800, 5-2700, 5-2600, 5-2500, 5-2400, 5-2300, 5-2200, 5-2100, 5-2000, 5-1900, 5-1800, 5-1700, 5-1600, 5-1500, 5-1400, 5-1300, 5-1200, 5-1100, 5-1000, 5-900, 5-800, 5-700, 5-600, 5-500, 5-400, 5-300, 5-200, 5-100, 5-75, 5-50, 5-45, 5-40, 5-35, 5-30, 5-25, 5-20, 20-10,000, 20-7500, 20-5000, 20-4900, 20-4800, 20-4700, 20-4600, 20-4500, 20-4400, 20-4300, 20-4200, 20-4100, 20-4000, 20-3900, 20-3800, 20-3700, 20-3600, 20-3500, 20-3400, 20-3300, 20-3200, 20-3100, 20-3000, 20-2900, 20-2800, 20-2700, 20-2600, 20-2500, 20-2400, 20-2300, 20-2200, 20-2100, 20-2000, 20-1900, 20-1800, 20-1700, 20-1600, 20-1500, 20-1400, 20-1300, 20-1200, 20-1100, 20-1000, 20-900, 20-800, 20-700, 20-600, 20-500, 20-400, 20-300, 20-200, 20-100, 20-75, 20-50, 20-45, 20-40, 20-35, 20-30, 20-25, 50-10,000, 50-7500, 50-5000, 50-4900, 50-4800, 50-4700, 50-4600, 50-4500, 50-4400, 50-4300, 50-4200, 50-4100, 50-4000, 50-3900, 50-3800, 50-3700, 50-3600, 50-3500, 50-3400, 50-3300, 50-3200, 50-3100, 50-3000, 50-2900, 50-2800, 50-2700, 50-2600, 50-2500, 50-2400, 50-2300, 50-2200, 50-2100, 50-2000, 50-1900, 50-1800, 50-1700, 50-1600, 50-1500, 50-1400, 50-1300, 50-1200, 50-1100, 50-1000, 50-900, 50-800, 50-700, 50-600, 50-500, 50-400, 50-300, 50-200, 50-100, 50-75, 100-10,000, 100-7500, 100-5000, 100-4900, 100-4800, 100-4700, 100-4600, 100-4500, 100-4400, 100-4300, 100-4200, 100-4100, 100-4000, 100-3900, 100-3800, 100-3700, 100-3600, 100-3500, 100-3400, 100-3300, 100-3200, 100-3100, 100-3000, 100-2900, 100-2800, 100-2700, 100-2600, 100-2500, 100-2400, 100-2300, 100-2200, 100-2100, 100-2000, 100-1900, 100-1800, 100-1700, 100-1600, 100-1500, 100-1400, 100-1300, 100-1200, 100-1100, 100-1000, 100-900, 100-800, 100-700, 100-600, 100-500, 100-400, 100-300, 100-200, 500-10,000, 500-7500, 500-5000, 500-4900, 500-4800, 500-4700, 500-4600, 500-4500, 500-4400, 500-4300, 500-4200, 500-4100, 500-4000, 500-3900, 500-3800, 500-3700, 500-3600, 500-3500, 500-3400, 500-3300, 500-3200, 500-3100, 500-3000, 500-2900, 500-2800, 500-2700, 500-2600, 500-2500, 500-2400, 500-2300, 500-2200, 500-2100, 500-2000, 500-1900, 500-1800, 500-1700, 500-1600, 500-1500, 500-1400, 500-1300, 500-1200, 500-1100, 500-1000, 500-900, 500-800, 500-700, or 500-600 nucleotides of a transcriptional start site.

In one aspect, a promoter provided herein is functional in an axillary bud cell and comprises at least 1, at least 2, at least 3, at least 4, at least 5, or at least 6 cis-regulatory elements selected from the group consisting of a bud dormancy element (BDE), an axillary bud growth UP1 element, an axillary bud growth UP2 element, a sucrose responsive element (SURE), a sugar repressive element (SRE), and a bud activation or TCP-binding element (BAE).

Also provided herein are the transformation of tobacco plants with recombinant constructs or expression cassettes described herein using any suitable transformation methods known in the art. Methods for introducing polynucleotide sequences into tobacco plants are known in the art and include, but are not limited to, stable transformation methods, transient transformation methods, and virus-mediated methods. "Stable transformation" refers to transformation where the nucleotide construct of interest introduced into a plant integrates into a genome of the plant and is capable of being inherited by the progeny thereof. "Transient transformation" is intended to mean that a sequence is introduced into the plant and is only temporally expressed or is only transiently present in the plant.

In one aspect, methods and compositions provided herein comprise the introduction of one or more polynucleotides into one or more plant cells. In one aspect, a plant genome provided herein is modified to include an introduced polynucleotide or recombinant DNA construct. As used herein, "plant genome" refers to a nuclear genome, a mitochondrial genome, or a plastid (e.g., chloroplast) genome of a plant cell. In another aspect, a polynucleotide provided herein is integrated into an artificial chromosome. In one aspect, an artificial chromosome comprising a polynucleotide provided herein is integrated into a plant cell.

In one aspect, a modified plant, seed, plant component, plant cell, or plant genome provided herein comprises one or more transgenes. In one aspect, a transgene provided herein suppresses suckering in a plant. In another aspect, a transgene provided herein suppresses topping-induced suckering in a plant. In still another aspect, a transgene provided herein suppresses suckering in a plant prior to topping. As used herein, a "transgene" refers to a polynucleotide that has been transferred into a genome by any method known in the art. In one aspect, a transgene is an exogenous polynucleotide. In one aspect, a transgene is an endogenous polynucleotide that is integrated into a new genomic locus where it is not normally found.

In one aspect, transgenes provided herein comprise a recombinant DNA construct. In one aspect, recombinant DNA constructs or expression cassettes provided herein can comprise a selectable marker gene for the selection of transgenic cells. Selectable marker genes include, but are not limited to, genes encoding antibiotic resistance, such as those encoding neomycin phosphotransferase II (NEO) and hygromycin phosphotransferase (HPT), as well as genes conferring resistance to herbicidal compounds, such as glufosinate ammonium, bromoxynil, imidazolinones, triazolopyrimidines, sulfonylurea (e.g., chlorsulfuron and sulfometuron methyl), and 2,4-dichlorophenoxyacetate (2,4-D). Additional selectable markers include phenotypic markers such as β-galactosidase and fluorescent proteins such as green fluorescent protein (GFP).

In one aspect, methods and compositions provided herein comprise a vector. As used herein, the terms "vector" or "plasmid" are used interchangeably and refer to a circular, double-stranded DNA molecule that is physically separate from chromosomal DNA. In one aspect, a plasmid or vector used herein is capable of replication in vivo. A "transformation vector," as used herein, is a plasmid that is capable of transforming a plant cell. In an aspect, a plasmid provided herein is a bacterial plasmid. In another aspect, a plasmid provided herein is an *Agrobacterium* Ti plasmid or derived from an *Agrobacterium* Ti plasmid.

In one aspect, a plasmid or vector provided herein is a recombinant vector. As used herein, the term "recombinant vector" refers to a vector formed by laboratory methods of genetic recombination, such as molecular cloning. In another aspect, a plasmid provided herein is a synthetic plasmid. As used herein, a "synthetic plasmid" is an artificially created plasmid that is capable of the same functions (e.g., replication) as a natural plasmid (e.g., Ti plasmid). Without being limited, one skilled in the art can create a synthetic plasmid de novo via synthesizing a plasmid by individual nucleotides, or by splicing together nucleic acid molecules from different pre-existing plasmids.

Vectors are commercially available or can be produced by recombinant DNA techniques routine in the art. In one aspect, a vector provided herein comprises all or part of SEQ ID NO: 112. A vector containing a nucleic acid can have expression elements operably linked to such a nucleic acid, and further can include sequences such as those encoding a selectable marker (e.g., an antibiotic resistance gene). A vector containing a nucleic acid can encode a chimeric or fusion polypeptide (i.e., a polypeptide operatively linked to a heterologous polypeptide, which can be at either the N-terminus or C-terminus of the polypeptide). Representative heterologous polypeptides are those that can be used in purification of the encoded polypeptide (e.g., 6×His tag (SEQ ID NO: 256), glutathione S-transferase (GST)).

Suitable methods of introducing polynucleotides (e.g., transgenes, recombinant vectors, recombinant DNA constructs, expression constructs) into plant cells of the present disclosure include microinjection (Crossway et al. (1986) *Biotechniques* 4:320-334), electroporation (Shillito et al. (1987) *Meth. Enzymol.* 153:313-336; Riggs et al. (1986) *Proc. Natl. Acad. Sci. USA* 83:5602-5606), *Agrobacterium*-mediated transformation (U.S. Pat. Nos. 5,104,310, 5,149,645, 5,177,010, 5,231,019, 5,463,174, 5,464,763, 5,469,976, 4,762,785, 5,004,863, 5,159,135, 5,563,055, and 5,981,840), direct gene transfer (Paszkowski et al. (1984) *EMBO J.* 3:2717-2722), and ballistic particle acceleration (see, for example, U.S. Pat. Nos. 4,945,050, 5,141,131, 5,886,244, 5,879,918, and 5,932,782; Tomes et al. (1995) in *Plant Cell, Tissue, and Organ Culture Fundamental Methods*, ed. Gamborg and Phillips (Springer-Verlag, Berlin); McCabe et al. (1988) *Biotechnology* 6:923-926). Also see Weissinger et al. (1988) *Ann. Rev. Genet.* 22:421-477; Christou et al. (1988) *Plant Physiol.* 87:671-674 (soybean); McCabe et al. (1988) *Bio/Technology* 6:923-926 (soybean); Finer and McMullen (1991) *In Vitro Cell Dev. Biol.* 27P: 175-182 (soybean); Singh et al. (1998) *Theor. Appl. Genet.* 96:319-324 (soybean); De Wet et al. (1985) in *The Experimental Manipulation of Ovule Tissues*, ed. Chapman et al. (Longman, N.Y.), pp. 197-209 (pollen); Kaeppler et al. (1990) *Plant Cell Reports* 9:415-418 and Kaeppler et al. (1992) *Theor. Appl. Genet.* 84:560-566 (whisker-mediated transformation); D'Halluin et al. (1992) *Plant Cell* 4:1495-1505 (electroporation). In one aspect, a bacterial cell provided herein comprises a recombinant DNA construct or recombinant vector provided herein.

In another aspect, recombinant constructs or expression cassettes provided herein may be introduced into plants by contacting plants with a virus or viral nucleic acids. Generally, such methods involve incorporating an expression cassette of the present disclosure within a viral DNA or RNA molecule. It is recognized that promoters for use in the expression cassettes provided herein also encompass promoters utilized for transcription by viral RNA polymerases. Methods for introducing polynucleotides into plants and expressing a protein encoded therein, involving viral DNA or RNA molecules, are known in the art. See, for example, U.S. Pat. Nos. 5,889,191, 5,889,190, 5,866,785, 5,589,367, 5,316,931, and Porta et al. (1996) *Molecular Biotechnology* 5:209-221.

Any plant tissue that can be subsequently propagated using clonal methods, whether by organogenesis or embryogenesis, may be transformed with a recombinant construct or an expression cassette provided herein. By "organogenesis" in intended the process by which shoots and roots are developed sequentially from meristematic centers. By "embryogenesis" is intended the process by which shoots and roots develop together in a concerted fashion (not sequentially), whether from somatic cells or gametes. Exemplary tissues that are suitable for various transformation protocols described herein include, but are not limited to, callus tissue, existing meristematic tissue (e.g., apical meristems, axillary buds, and root meristems) and induced meristem tissue (e.g., cotyledon meristem and hypocotyl meristem), hypocotyls, cotyledons, leaf disks, pollen, embryos, and the like.

In one aspect, this disclosure provides a plant or seed comprising a recombinant polynucleotide, where the recombinant polynucleotide comprises a promoter that is functional in an L1 layer, an L2 layer, an L3 region, a rib zone, a central zone, a peripheral zone, or any combination thereof, which is operably linked to a structural nucleic acid molecule comprising a nucleic acid sequence, where the nucleic acid sequence encodes a polypeptide having at least 40%, at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to a polypeptide selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 161-185, 187, 189, 191, 193, 195, 197, 199, 201, 203, 206, 208, 210, 212, 214, 216, 218, 220, 222, 224, 229, 231, 233, 235, 237, 239, 241, 243, 245, 247, 249, 251, 253, and 255.

In one aspect, an auxin biosynthesis protein or an auxin transport protein is selected from the group consisting of SEQ ID NOs: 235, 237, 239, 241, 243, 245, 247, 249, 251, 253, and 255. In another aspect, an auxin biosynthesis protein or an auxin transport protein comprises at least 40%, at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to a polypeptide selected from the group consisting of SEQ ID NOs: 235, 237, 239, 241, 243, 245, 247, 249, 251, 253, and 255. In another aspect, an auxin biosynthesis protein or an auxin transport protein comprises at least 40%, at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence similarity to a polypeptide selected from the group consisting of SEQ ID NOs: 235, 237, 239, 241, 243, 245, 247, 249, 251, 253, and 255. In one aspect, an auxin biosynthesis protein or an auxin transport protein is encoded by a nucleic acid sequence, where the nucleic acid sequence encodes a polypeptide having at least 40%, at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to a polypeptide elected from the group consisting of SEQ ID NOs: 235, 237, 239, 241, 243, 245, 247, 249, 251, 253, and 255.

In one aspect, an auxin biosynthesis protein or an auxin transport protein is encoded by a polynucleotide selected from the group consisting of SEQ ID NOs: 234, 236, 238, 240, 242, 244, 246, 248, 250, 252, and 254. In one aspect, an auxin biosynthesis protein or an auxin transport protein is encoded by a polynucleotide having at least 40%, at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identity to a polynucleotide selected from the group consisting of SEQ ID NOs: 234, 236, 238, 240, 242, 244, 246, 248, 250, 252, and 254.

In one aspect, this disclosure provides a plant or seed comprising a recombinant polynucleotide, where the recombinant polynucleotide comprises a promoter that is functional in an L1 layer, an L2 layer, an L3 region, a rib zone, a central zone, a peripheral zone, or a combination thereof, which is operably linked to a structural nucleic acid molecule comprising a nucleic acid sequence, where the nucleic acid sequence encodes an auxin biosynthesis protein or an auxin transport protein.

In another aspect, this disclosure provides a recombinant DNA construct comprising a promoter that is functional in an L1 layer, an L2 layer, an L3 region, a rib zone, a central zone, a peripheral zone, or a combination thereof; and a heterologous and operably linked nucleic acid sequence, where the nucleic acid sequence encodes a non-coding RNA or a polypeptide. In another aspect, this disclosure provides a recombinant DNA construct comprising a promoter that is functional in an L1 later, an L2 layer, an L3 region, a rib zone, a central zone, a peripheral zone, or a combination thereof; and a heterologous and operably linked nucleic acid sequence, where the nucleic acid sequence encodes an auxin biosynthesis protein or an auxin transport protein.

In one aspect, this disclosure provides a recombinant DNA construct comprising a heterologous axillary meristem-specific promoter operably linked to a polynucleotide that encodes an auxin biosynthesis protein or an auxin transport protein.

In one aspect, this disclosure provides a method of reducing or eliminating topping-induced suckering in a tobacco plant comprising transforming a tobacco plant with a recombinant DNA construct comprising a promoter expressing in an L1 layer, an L2 layer, an L3 region, a rib zone, a central zone, a peripheral zone, or a combination thereof. In another aspect, this disclosure provides a method comprising transforming a tobacco plant with a recombinant DNA construct comprising a heterologous promoter that is functional in an L1 layer, an L2 layer, an L3 region, a rib zone, a central zone, a peripheral zone, or a combination thereof, and is operably linked to a polynucleotide that is transcribed into an RNA molecule that suppresses the level of an endogenous gene, and where the endogenous gene promotes or is required for axillary meristem growth, axillary meristem maintenance, or both.

In one aspect, this disclosure provides a method for controlling topping-induced suckering in a plant comprising transforming the plant with a recombinant DNA construct, where the recombinant DNA construct comprises a promoter that is operably linked to a polynucleotide encoding a polypeptide having at least 40%, at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to a polypeptide selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 161-185, 187, 189, 191, 193, 195, 197, 199, 201, 203, 206, 208, 210, 212, 214, 216, 218, 220, 222, 224, 229, 231, 233, 235, 237, 239, 241, 243, 245, 247,249, 251, 253, and 255.

In one aspect, this disclosure provides a method for controlling topping-induced suckers in a plant comprising transforming said plant with a recombinant DNA construct, wherein said recombinant DNA construct comprises a promoter that is operably linked to a polynucleotide encoding an auxin biosynthesis protein or an auxin transport protein.

It is understood that any modified tobacco plant of the present disclosure can further comprise additional agronomically desirable traits, for example, by transformation with a genetic construct or transgene using a technique known in the art. Without limitation, an example of a desired trait is herbicide resistance, pest resistance, disease resistance, high yield, high grade index value, curability, curing quality, mechanical harvestability, holding ability, leaf quality, height, plant maturation (e.g., early maturing, early to medium maturing, medium maturing, medium to late maturing, or late maturing), stalk size (e.g., a small, medium, or a large stalk), or leaf number per plant (e.g., a small (e.g., 5-10 leaves), medium (e.g., 11-15 leaves), or large (e.g., 16-21) number of leaves), or any combination. In one aspect, reduced suckering tobacco plants or seeds provided herein comprise one or more transgenes expressing one or more insecticidal proteins, such as, for example, a crystal protein of *Bacillus thuringiensis* or a vegetative insecticidal protein from *Bacillus cereus*, such as VIP3 (see, for example, Estruch et al. (1997) *Nat. Biotechnol.* 15:137). In another aspect, tobacco plants provided herein further comprise an introgressed trait conferring resistance to brown stem rot (U.S. Pat. No. 5,689,035) or resistance to cyst nematodes (U.S. Pat. No. 5,491,081).

The level and/or activity of polypeptides provided herein may be modulated by employing a polynucleotide that is not capable of directing, in a transformed plant, the expression of a protein or an RNA. For example, the polynucleotides of the invention may be used to design polynucleotide constructs that can be employed in methods for altering or mutating a genomic nucleotide sequence in an organism. Such polynucleotide constructs include, but are not limited to, RNA:DNA vectors, RNA:DNA mutational vectors, RNA:DNA repair vectors, mixed-duplex oligonucleotides, self-complementary RNA:DNA oligonucleotides and recombinogenic oligonucleobases. Such nucleotide constructs and methods of use are known in the art. See, U.S. Pat. Nos. 5,565,350; 5,731,181; 5,756,325; 5,760,012; 5,795,972 and 5,871,984; each of which is incorporated herein by reference as if set forth in its entirety. See also, International Patent Application Publication Nos. WO 98/149350, WO 99/107865 and WO 99/125921; and Beetham et al. (1999) Proc. Natl. Acad. Sci. USA 96:8774-8778; each of which is incorporated herein by reference as if set forth in its entirety.

The present disclosure provides compositions and methods for inhibiting the expression or function of one or more polypeptides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 161-185, 187, 189, 191, 193, 195, 197, 199, 201, 203, 206, 208, 210, 212, 214, 216, 218, 220, 222, 224, 229, 231, 233, 235, 237, 239, 241, 243, 245, 247, 249, 251, 253, and 255 in a plant, particularly plants of the *Nicotiana tabacum* genus, including tobacco plants of various commercial varieties.

In one aspect, inhibition of the expression of one or more polypeptides provided herein may be obtained by RNA interference (RNAi) by expression of a polynucleotide provided herein. In one aspect, RNAi comprises expressing a non-coding RNA. As used herein, a "non-coding RNA" is selected from the group consisting of a microRNA (miRNA), a small interfering RNA (siRNA), a trans-acting siRNA (ta-siRNA), a transfer RNA (tRNA), a ribosomal RNA (rRNA), an intron, a hairpin RNA (hpRNA), and an intron-containing hairpin RNA (ihpRNA). In one aspect, a single non-coding RNA provided herein inhibits the expression of at least 1, at least 2, at least 3, at least 4, at least 5, at least 6, at least 7, at least 8, at least 9, at least 10, or more than 10 polypeptides. In one aspect, a non-coding RNA provided herein is stably transformed into a plant genome. In another aspect, a non-coding RNA provided herein is transiently transformed into a plant genome.

In one aspect, this disclosure provides RNA molecules useful for inhibiting the expression or function or one or more polypeptides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 161-185, 187, 189, 191, 193, 195, 197, 199, 201, 203, 206, 208, 210, 212, 214, 216, 218, 220, 222, 224, 229, 231, 233, 235, 237, 239, 241, 243, 245, 247, 249, 251, 253, and 255. In one aspect, an RNA molecule provided herein is a non-coding RNA.

In another aspect, the recombinant DNA construct encodes a double stranded RNA. Also provided are modified tobacco plants or part thereof, cured tobacco material, or tobacco products comprising these recombinant DNA constructs. In one aspect, these transgenic plants, cured tobacco material, or tobacco products comprise reduced suckering compared to a control tobacco plant without the recombinant DNA construct. Further provided are methods of reducing sucker growth of a tobacco plant, the method comprising transforming a tobacco plant with any of these recombinant DNA constructs.

In one aspect, a tobacco plant or part thereof provided herein comprises a heterologous promoter operably linked to a polynucleotide that encodes a non-coding RNA molecule, where the non-coding RNA molecule is capable of binding to an RNA encoding a polypeptide having at least 40%, at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to a polypeptide selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 161-185, 187, 189, 191, 193, 195, 197, 199, 224, 229, 231, 233, 245, 247, 249, 251, 253, and 255, and where the non-coding RNA molecule suppresses the expression of the polypeptide.

As used herein, the terms "suppress," "inhibit," "inhibition," and "inhibiting" are defined as any method known in the art or described herein that decreases the expression or function of a gene product of interest (e.g., an mRNA, a protein, a non-coding RNA). "Inhibition" can be in the context of a comparison between two plants, for example, a modified plant versus a control plant. Alternatively, inhibition of expression or function of a target gene product can be in the context of a comparison between plant cells, organelles, organs, tissues, or plant components within the same plant or between different plants, and includes comparisons between developmental or temporal stages within the same plant or plant component or between plants or plant components. "Inhibition" includes any relative decrement of function or production of a gene product of interest, up to and including complete elimination of function or production of that gene product. The term "inhibition" encompasses any method or composition that down-regulates translation and/or transcription of the target gene product or functional activity of the target gene product.

The term "inhibitory sequence" encompasses any polynucleotide or polypeptide sequence capable of inhibiting the expression or function of a gene in a plant, such as full-length polynucleotide or polypeptide sequences, truncated polynucleotide or polypeptide sequences, fragments of polynucleotide or polypeptide sequences, variants of polynucleotide or polypeptide sequences, sense-oriented nucleotide sequences, antisense-oriented nucleotide sequences, the complement of a sense- or antisense-oriented nucleotide sequence, inverted regions of nucleotide sequences, hairpins of nucleotide sequences, double-stranded nucleotide sequences, single-stranded nucleotide sequences, combinations thereof, and the like. The term "polynucleotide sequence" includes sequences of RNA, DNA, chemically modified nucleic acids, nucleic acid analogs, combinations thereof, and the like.

Inhibitory sequences are designated herein by the name of the target gene product. Thus, as a non-limiting example, an "NTH15 inhibitory sequence" refers to an inhibitory sequence that is capable of inhibiting the expression of an NTH15 locus in a plant, for example, at the level of transcription and/or translation, or which is capable of inhibiting the function of a gene product. When the phrase "capable of inhibiting" is used in the context of a polynucleotide inhibitory sequence, it is intended to mean that the inhibitory sequence itself exerts the inhibitory effect; or, where the inhibitory sequence encodes an inhibitory nucleotide molecule (for example, hairpin RNA, miRNA, or double-stranded RNA polynucleotides), or encodes an inhibitory polypeptide (e.g., a polypeptide that inhibits expression or function of the target gene product), following its transcription (for example, in the case of an inhibitory sequence encoding a hairpin RNA, miRNA, or double-stranded RNA polynucleotide) or its transcription and translation (in the case of an inhibitory sequence encoding an inhibitory polypeptide), the transcribed or translated product, respectively, exerts the inhibitory effect on the target gene product (e.g., inhibits expression or function of the target gene product).

An inhibitory sequence provided herein can be a sequence triggering gene silencing via any silencing pathway or mechanism known in the art, including, but not limited to, sense suppression/co-suppression, antisense suppression, double-stranded RNA (dsRNA) interference, hairpin RNA interference and intron-containing hairpin RNA interference, amplicon-mediated interference, ribozymes, small interfering RNA, artificial or synthetic microRNA, and artificial trans-acting siRNA. An inhibitory sequence may range from at least about 20 nucleotides, at least about 50 nucleotides, at least about 70 nucleotides, at least about 100 nucleotides, at least about 150 nucleotides, at least about 200 nucleotides, at least about 250 nucleotides, at least about 300 nucleotides, at least about 350 nucleotides, at least about 400 nucleotides, and up to the full-length polynucleotide encoding the proteins of the present disclosure, depending upon the desired outcome. In one aspect, an inhibitory sequence can be a fragment of between about 50 and about 400 nucleotides, between about 70 and about 350 nucleotides, between about 90 and about 325 nucleotides, between about 90 and about 300 nucleotides, between about 90 and about 275 nucleotides, between about 100 and about 400 nucleotides, between about 100 and about 350 nucleotides, between about 100 and about 325 nucleotides, between about 100 and about 300 nucleotides, between about 125 and about 300 nucleotides, or between about 125 and about 275 nucleotides in length.

In one aspect, the present disclosure provides a recombinant DNA construct comprising a promoter that is functional in a tobacco cell and operably linked to a polynucleotide that encodes an RNA molecule capable of binding to an RNA encoding a polypeptide having an amino acid sequence at least 60%, at least 70%, at least 75%, at least 80%, at least 85%, at least 90%, at least 95%, at least 96%, at least 97%, at least 98%, at least 99%, or 100% identical to an amino acid sequence selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 70, 72, 74, 76, 78, 161-185, 187, 189, 191, 197, 199, 224, 229, 231, 233, 235, 237, 239, 241, 243, 245, 247, 249, 251, 253, 255, and fragments thereof. In one aspect, the present disclosure provides a recombinant DNA construct comprising a promoter that is functional in a tobacco cell and operably linked to a polynucleotide having at least 60%, at least 70%, at least 75%, at least 80%, at least 85%, at least 90%, at least 95%, at least 96%, at least 97%, at least 98%, at least 99%, or 100% identical to a polynucleotide selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83-160, 186, 188, 190, 192, 194, 196, 198, 200, 202, 204, 205, 207, 209, 211, 213, 215, 217, 219, 221, 223, 225-228, 230, 232, 234, 236, 238, 240, 242, 244, 246, 248, 250, 252, 254, and fragments thereof.

In one aspect, the present disclosure provides a recombinant DNA construct comprising a promoter that is functional in a tobacco cell and operably linked to a polynucleotide that encodes an RNA molecule capable of binding to an RNA encoding a polypeptide having an amino acid sequence at least 60%, at least 70%, at least 75%, at least 80%, at least 85%, at least 90%, at least 95%, at least 96%, at least 97%, at least 98%, at least 99%, or 100% identical to an amino acid sequence selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 70, 72, 74, 76, 78, 161-185, 187, 189, 191, 197, 199, 224, 229, 231, 233, 235, 237, 239, 241, 243, 245, 247, 249, 251, 253, 255, and fragments thereof, and where the RNA molecule suppresses the expression of the polypeptide. In one aspect, the present disclosure provides a recombinant DNA construct comprising a promoter that is functional in a tobacco cell and operably linked to a polynucleotide having at least 60%, at least 70%, at least 75%, at least 80%, at least 85%, at least 90%, at least 95%, at least 96%, at least 97%, at least 98%, at least 99%, or 100% identical to a polynucleotide selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83-160, 186, 188, 190, 192, 194, 196, 198, 200, 202, 204, 205, 207, 209, 211, 213, 215, 217, 219, 221, 223, 225-228, 230, 232, 234, 236, 238, 240, 242, 244, 246, 248, 250, 252, 254, and fragments thereof, and where the RNA molecule suppresses the expression of the polynucleotide.

In one aspect, this disclosure provides a recombinant DNA construct comprising a heterologous axillary meristem-specific promoter operably linked to a polynucleotide that encodes a non-coding RNA molecule, where the non-coding RNA molecule is capable of binding to an RNA encoding a polypeptide having at least 40%, at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to a polypeptide selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 70, 72, 74, 76, 78, 161-185, 187, 189, 191, 197, 199, 224, 229, 231, 233, 245, 247, 249, 251, 253, and 255, and where the non-coding RNA molecule suppresses the expression of the polypeptide.

In one aspect, this disclosure provides a method for controlling topping-induced suckering in a plant comprising transforming the plant with a recombinant DNA construct, where the recombinant DNA construct comprises a heterologous promoter that is functional in an L1 layer, an L2 layer, an L3 region, a rib zone, a central zone, a peripheral zone, or a combination thereof, and where the promoter is operably linked to a polynucleotide that encodes a non-coding RNA molecule, where the non-coding RNA molecule is capable of binding to an RNA encoding a polypeptide having at least 40%, at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to a polypeptide selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 70, 72, 74, 76, 78, 161-185, 187, 189, 191, 197, 199, 224, 229, 231, 233, 245, 247, 249, 251, 253, and 255, and where the non-coding RNA molecule suppresses the expression of the polypeptide.

MicroRNAs (miRNAs) are non-protein coding RNAs, generally of between about 19 to about 25 nucleotides (commonly about 20-24 nucleotides in plants), that guide cleavage in trans of target transcripts, negatively regulating the expression of genes involved in various regulation and development pathways (Bartel (2004) Cell, 116:281-297). In some cases, miRNAs serve to guide in-phase processing of siRNA primary transcripts (see Allen et al. (2005) Cell, 121:207-221).

Many microRNA genes (MIR genes) have been identified and made publicly available in a database ("miRBase", available on line at microrna.sanger.ac.uk/sequences; also see Griffiths-Jones et al. (2003) Nucleic Acids Res., 31:439-441). MIR genes have been reported to occur in intergenic regions, both isolated and in clusters in the genome, but can also be located entirely or partially within introns of other genes (both protein-coding and non-protein-coding). For a recent review of miRNA biogenesis, see Kim (2005) Nature Rev. Mol. Cell. Biol., 6:376-385. Transcription of MIR genes can be, at least in some cases, under promotional control of a MIR gene's own promoter. The primary transcript, termed a "pri-miRNA", can be quite large (several kilobases) and can be polycistronic, containing one or more pre-miRNAs (fold-back structures containing a stem-loop arrangement that is processed to the mature miRNA) as well as the usual 5' "cap" and polyadenylated tail of an mRNA. See, for example, FIG. 1 in Kim (2005) Nature Rev. Mol. Cell. Biol., 6:376-385.

Maturation of a mature miRNA from its corresponding precursors (pri-miRNAs and pre-miRNAs) differs significantly between animals and plants. For example, in plant cells, microRNA precursor molecules are believed to be largely processed to the mature miRNA entirely in the nucleus, whereas in animal cells, the pri-miRNA transcript is processed in the nucleus by the animal-specific enzyme Drosha, followed by export of the pre-miRNA to the cytoplasm where it is further processed to the mature miRNA. Mature miRNAs in plants are typically 21 nucleotides in length. For a recent review of miRNA biogenesis in both plants and animals, see Kim (2005) Nature Rev. Mol. Cell. Biol., 6:376-385. Additional reviews on miRNA biogenesis and function are found, for example, in Bartel (2004) Cell, 116:281-297; Murchison and Hannon (2004) Curr. Opin. Cell Biol., 16:223-229; and Dugas and Bartel (2004) Curr. Opin. Plant Biol., 7:512-520.

Transgenic expression of miRNAs (whether a naturally occurring sequence or an artificial sequence) can be employed to regulate expression of the miRNA's target gene or genes. Inclusion of a miRNA recognition site in a transgenically expressed transcript is also useful in regulating expression of the transcript; see, for example, Parizotto et al. (2004) Genes Dev., 18:2237-2242. Recognition sites of miRNAs have been validated in all regions of an mRNA, including the 5' untranslated region, coding region, and 3' untranslated region, indicating that the position of the miRNA target site relative to the coding sequence may not necessarily affect suppression (see, e.g., Jones-Rhoades and Bartel (2004). Mol. Cell, 14:787-799, Rhoades et al. (2002) Cell, 110:513-520, Allen et al. (2004) Nat. Genet., 36:1282-1290, Sunkar and Zhu (2004) Plant Cell, 16:2001-2019). Because miRNAs are important regulatory elements in eukaryotes, transgenic suppression of miRNAs is useful for manipulating biological pathways and responses. Finally, promoters of MIR genes can have very specific expression patterns (e.g., cell-specific, tissue-specific, temporally specific, or inducible), and thus are useful in recombinant constructs to induce such specific transcription of a DNA sequence to which they are operably linked. Various utilities of miRNAs, their precursors, their recognition sites, and their promoters are described in detail in U.S. Patent Application Publication 2006/0200878 A1, incorporated by reference herein. Non-limiting examples of these utilities include: (1) the expression of a native miRNA or miRNA precursor sequence to suppress a target gene; (2) the expression of an artificial miRNA or miRNA precursor sequence to suppress a target gene; (3) expression of a transgene with a miRNA recognition site, where the transgene is suppressed when the mature miRNA is expressed; (4) expression of a transgene driven by a miRNA promoter.

Designing an artificial miRNA sequence can be as simple as substituting sequence that is complementary to the intended target for nucleotides in the miRNA stem region of the miRNA precursor, as demonstrated by Zeng et al. (2002) Mol. Cell, 9:1327-1333. One non-limiting example of a general method for determining nucleotide changes in the native miRNA sequence to produce the engineered miRNA precursor includes the following steps: (a) Selecting a unique target sequence of at least 18 nucleotides specific to the target gene, e.g., by using sequence alignment tools such as BLAST (see, for example, Altschul et al. (1990) J. Mol. Biol., 215:403-410; Altschul et al. (1997) Nucleic Acids Res., 25:3389-3402), for example, of both tobacco cDNA and genomic DNA databases, to identify target transcript orthologues and any potential matches to unrelated genes, thereby avoiding unintentional silencing of non-target sequences; (b) Analyzing the target gene for undesirable sequences (e.g., matches to sequences from non-target species), and score each potential 19-mer segment for GC content, Reynolds score (see Reynolds et al. (2004) Nature Biotechnol., 22:326-330), and functional asymmetry characterized by a negative difference in free energy (".DELTA..DELTA.G" or "ΔΔG") (see Khvorova et al. (2003) Cell, 115:209-216). Preferably 19-mers are selected that have all or most of the following characteristics: (1) a Reynolds score>4, (2) a GC content between about 40% to about 60%, (3) a negative ΔΔG, (4) a terminal adenosine, (5) lack of a consecutive run of 4 or more of the same nucleotide; (6) a location near the 3' terminus of the target gene; (7) minimal differences from the miRNA precursor transcript. Positions at every third nucleotide in an siRNA have been reported to be especially important in influencing RNAi efficacy and an algorithm, "siExplorer" is publicly available at rna.chem.t.u-tokyo.ac.jp/siexplorer.htm (see Katoh and Suzuki (2007) Nucleic Acids Res., 10.1093/nar/gk11120); (c) Determining the reverse complement of the selected 19-mers to use in making a modified mature miRNA. The additional nucleotide at position 20 is preferably matched to the selected target sequence, and the nucleotide at position 21 is preferably chosen to either be unpaired to prevent spreading of silencing on the target transcript or paired to the target sequence to promote spreading of silencing on the target transcript; and (d) transforming the artificial miRNA into a plant.

In one aspect, an artificial miRNA provided herein is complementary to a polynucleotide having at least 40%, at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to a polynucleotide selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 69, 71, 73, 75, 77, 83-160, 186, 188, 190, 196, 198, 223, 225-228, 230, 232, 234, 236, 238, 240, 242, 244, 246, 248, 250, 252, 254, and fragments thereof. In another aspect, an artificial miRNA provided herein is complementary to a polynucleotide encoding a polypeptide having at least 40%, at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to a polypeptide selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 70, 72, 74, 76, 78, 161-185, 189, 191, 197, 199, 224, 229, 231, 233, 235, 237, 239, 241, 243, 245, 247, 249, 251, 253, 255. In yet another aspect, an artificial miRNA provided herein is complementary to a polynucleotide encoding a polypeptide having at least 40%, at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence similarity to a polypeptide selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 70, 72, 74, 76, 78, 161-185, 189, 191, 197, 199, 224, 229, 231, 233, 235, 237, 239, 241, 243, 245, 247, 249, 251, 253, 255.

In one aspect, an artificial miRNA provided herein reduces or eliminates RNA transcription or protein translation of a target gene.

In one aspect, a miRNA or an artificial miRNA provided herein is under the control of a tissue specific promoter. In another aspect, a miRNA or an artificial miRNA provided herein is under the control of a promoter selected from the group consisting of SEQ ID NOs: 113-118, 148-160, 204, and a fragment thereof. In one aspect, a modified plant provided herein comprises an artificial miRNA under the control of a heterologous promoter selected from the group consisting of SEQ ID NOs: 113-118, 148-160, 204, and a fragment thereof.

Plant microRNAs regulate their target genes by recognizing and binding to a near-perfectly complementary sequence (miRNA recognition site) in the target transcript, followed by cleavage of the transcript by RNase III enzymes such as Argonaute 1. In plants, certain mismatches between a given miRNA recognition site and the corresponding mature miRNA are not tolerated, particularly mismatched nucleotides at positions 10 and 11 of the mature miRNA. Positions within the mature miRNA are given in the 5' to 3' direction. Perfect complementarity between a given miRNA recognition site and the corresponding mature miRNA is usually required at positions 10 and 11 of the mature miRNA. See, for example, Franco-Zorrilla et al. (2007) Nature Genetics, 39:1033-1037; and Axtell et al. (2006) Cell, 127:565-577.

This characteristic of plant miRNAs is exploited to arrive at rules for predicting a "microRNA decoy sequence", i.e., a sequence that can be recognized and bound by an endogenous mature miRNA resulting in base-pairing between the miRNA decoy sequence and the endogenous mature miRNA, thereby forming a cleavage-resistant RNA duplex that is not cleaved because of the presence of mismatches between the miRNA decoy sequence and the mature miRNA. Mismatches include canonical mismatches (e. g., G-A, C-U, C-A) as well as G::U wobble pairs and indels (nucleotide insertions or deletions). In general, these rules define (1) mismatches that are required, and (2) mismatches that are permitted but not required.

Required mismatches include: (a) at least 1 mismatch between the miRNA decoy sequence and the endogenous mature miRNA at positions 9, 10, or 11 of the endogenous mature miRNA, or alternatively, (b) 1, 2, 3, 4, or 5 insertions (i. e., extra nucleotides) at a position in the miRNA decoy sequence corresponding to positions 9, 10, or 11 of the endogenous mature miRNA.

Mismatches that are permitted, but not required, include: (a) 0, 1, or 2 mismatches between the miRNA decoy sequence and the endogenous mature miRNA at positions 1, 2, 3, 4, 5, 6, 7, 8, and 9 of the endogenous mature miRNA, and (b) 0, 1, 2, or 3 mismatches between the miRNA decoy sequence and the endogenous mature miRNA at positions 12 through the last position of the endogenous mature miRNA (i. e., at position 21 of a 21-nucleotide mature miRNA), where each of the mismatches at positions 12 through the last position of the endogenous mature miRNA is adjacent to at least one complementary base-pair (i. e., so that there is not more than 2 contiguous mismatches at positions 12 through the last position of the endogenous mature miRNA).

A miRNA decoy sequence can be of any length as long as it is recognized and bound by an endogenous mature miRNA to form a cleavage-resistant RNA duplex. In one aspect, a miRNA decoy sequence includes between about 18 to about 36 nucleotides. In another aspect, a microRNA decoy provided herein is a small RNA molecule of at least 15, at least 16, at least 17, at least 18, at least 19, at least 20, at least 21, at least 22, at least 23, at least 24, at least 25, at least 26, at least 27, at least 28, at least 29, at least 30, or more than 30 nucleotides that is capable of binding to a mature miRNA. See, for example, WO 2008/133643, which is herein incorporated by reference in its entirety.

In one aspect, an endogenous miRNA is regulated by a miRNA decoy provided herein. A microRNA decoy provided herein is capable of preventing a complementary mature miRNA from binding its native target gene, thereby increasing expression of the target gene.

In another aspect, a recombinant DNA construct provided herein comprises at least 1, at least 2, at least 3, at least 4, at least 5, at least 6, at least 7, at least 8, at least 9, at least 10, or more than 10 miRNA decoys. In one aspect, a miRNA decoy provided herein is under the control of a regulatory sequence selected from the group consisting of SEQ ID NOs: 113-118, 148-160, 204, and a fragment thereof.

In another aspect, an endogenous miRNA target is edited with a site-specific nuclease provided herein to mutate at least one miRNA binding site, thereby rendering the endogenous miRNA target resistant to miRNA-mediated degradation. As used herein, a "miRNA target" refers to a contiguous stretch of at least 18, at least 19, at least 20, at least 21, at least 22, at least 23, at least 24, at least 25, at least 26, at least 27, at least 28, at least 29, at least 30, or more than 30 nucleotides having at least 75%, at least 80%, at least 85%, at least 88%, at least 90%, at least 91%, at least 92%, at least 93%, at least 94%, at least 95%, at least 96%, at least 97%, at least 98%, at least 99% or 100% identity to a mature miRNA. In one aspect, a miRNA target is capable of being hybridized by a mature miRNA, and then cleaved by a mature miRNA/Argonaute RNA-induced silencing complex, under typical cellular conditions.

Also provided herein is cured tobacco material made from tobacco plants or plant components provided herein. "Curing" is the aging process that reduces moisture and brings about the destruction of chlorophyll giving tobacco leaves a golden color and by which starch is converted to sugar. Cured tobacco therefore has a higher reducing sugar content and a lower starch content compared to harvested green leaf. In one aspect, tobacco plants or plant components provided herein can be cured using conventional means, e.g., flue-cured, barn-cured, fire-cured, air-cured or sun-cured. See, for example, Tso (1999, Chapter 1 in Tobacco, Production, Chemistry and Technology, Davis & Nielsen, eds., Blackwell Publishing, Oxford) for a description of different types of curing methods. Cured tobacco is usually aged in a wooden drum (e.g., a hogshead) or cardboard cartons in compressed conditions for several years (e.g., two to five years), at a moisture content ranging from 10% to about 25%. See, U.S. Pat. Nos. 4,516,590 and 5,372,149. Cured and aged tobacco then can be further processed. Further processing includes conditioning the tobacco under vacuum with or without the introduction of steam at various temperatures, pasteurization, and fermentation. Fermentation typically is characterized by high initial moisture content, heat generation, and a 10 to 20% loss of dry weight. See, for example, U.S. Pat. Nos. 4,528,993, 4,660,577, 4,848,373, 5,372,149; U.S. Publication No. 2005/0178398; and Tso (1999, Chapter 1 in Tobacco, Production, Chemistry and Technology, Davis & Nielsen, eds., Blackwell Publishing, Oxford). Cured, aged, and fermented tobacco can be further processed (e.g., cut, shredded, expanded, or blended). See, for example, U.S. Pat. Nos. 4,528,993; 4,660,577; and 4,987,907. In one aspect, the cured tobacco material of the present disclosure is flue-cured, sun-cured, air-cured, or fire-cured.

Tobacco material obtained from modified tobacco lines, varieties or hybrids of the present disclosure can be used to make tobacco products. As used herein, "tobacco product" is defined as any product made or derived from tobacco that is intended for human use or consumption. In an aspect, a tobacco product provided herein comprises cured components from a modified tobacco plant provided herein. In another aspect, a tobacco product provided herein comprises cured tobacco leaves from a modified tobacco plant provided herein.

Tobacco products provided herein include, without limitation, cigarette products (e.g., cigarettes, bidi cigarettes, kreteks), cigar products (e.g., cigars, cigar wrapping tobacco, cigarillos), pipe tobacco products, products derived from tobacco, tobacco-derived nicotine products, smokeless tobacco products (e.g., moist snuff, dry snuff, chewing tobacco, moist smokeless tobacco, fine cut chewing tobacco, long cut chewing tobacco, pouched chewing tobacco), films, chewables (e.g., gum), lozenges, dissolving strips, tabs, tablets, shaped parts, gels, consumable units, insoluble matrices, hollow shapes, reconstituted tobacco, expanded tobacco, and the like. See, for example, U.S. Patent Publication No. US 2006/0191548.

As used herein, "cigarette" refers a tobacco product having a "rod" and "filler". The cigarette "rod" includes the cigarette paper, filter, plug wrap (used to contain filtration materials), tipping paper that holds the cigarette paper (including the filler) to the filter, and all glues that hold these components together. The "filler" includes (1) all tobaccos, including but not limited to reconstituted and expanded tobacco, (2) non-tobacco substitutes (including but not limited to herbs, non-tobacco plant materials and other spices that may accompany tobaccos rolled within the cigarette paper), (3) casings, (4) flavorings, and (5) all other additives (that are mixed into tobaccos and substitutes and rolled into the cigarette).

In one aspect, this disclosure provides nicotine derived from and a method of producing nicotine from a modified tobacco plant provided herein for use in a product.

In one aspect, a method provided herein comprises preparing a tobacco product using a cured tobacco leaf from a modified tobacco plant provided herein.

As used herein, "reconstituted tobacco" refers to a part of tobacco filler made from tobacco dust and other tobacco scrap material, processed into sheet form and cut into strips to resemble tobacco. In addition to the cost savings, reconstituted tobacco is very important for its contribution to cigarette taste from processing flavor development using reactions between ammonia and sugars.

As used herein, "expanded tobacco" refers to a part of tobacco filler which is processed through expansion of suitable gases so that the tobacco is "puffed" resulting in reduced density and greater filling capacity. It reduces the weight of tobacco used in cigarettes.

Tobacco products derived from plants of the present disclosure also include cigarettes and other smoking articles, particularly those smoking articles including filter elements, where the rod of smokeable material includes cured tobacco within a tobacco blend. In an aspect, a tobacco product of the present disclosure is selected from the group consisting of a cigarillo, a non-ventilated recess filter cigarette, a vented recess filter cigarette, a bidi cigarette, a cigar, snuff, pipe tobacco, cigar tobacco, cigarette tobacco, chewing tobacco, leaf tobacco, hookah tobacco, shredded tobacco, and cut tobacco. In another aspect, a tobacco product of the present disclosure is a smokeless tobacco product. Smokeless tobacco products are not combusted and include, but not limited to, chewing tobacco, moist smokeless tobacco, snus, and dry snuff. Chewing tobacco is coarsely divided tobacco leaf that is typically packaged in a large pouch-like package and used in a plug or twist. Moist smokeless tobacco is a moist, more finely divided tobacco that is provided in loose form or in pouch form and is typically packaged in round cans and used as a pinch or in a pouch placed between an adult tobacco consumer's cheek and gum. Snus is a heat treated smokeless tobacco. Dry snuff is finely ground tobacco that is placed in the mouth or used nasally. In a further aspect, a tobacco product of the present disclosure is selected from the group consisting of loose leaf chewing tobacco, plug chewing tobacco, moist snuff, and nasal snuff. In yet another aspect, a tobacco product of the present disclosure is selected from the group consisting of an electronically heated cigarette, an e-cigarette, an electronic vaporing device.

The present disclosure further provides a method manufacturing a tobacco product comprising tobacco material from tobacco plants provided herein. In one aspect, methods provided herein comprise conditioning aged tobacco material made from tobacco plants provided herein to increase its moisture content from between about 12.5% and about 13.5% to about 21%, blending the conditioned tobacco material to produce a desirable blend. In one aspect, the method of manufacturing a tobacco product provided herein further comprises casing or flavoring the blend. Generally, during the casing process, casing or sauce materials are added to blends to enhance their quality by balancing the chemical composition and to develop certain desired flavor characteristics. Further details for the casing process can be found in *Tobacco Production, Chemistry and Technology*, Edited by L. Davis and M. Nielsen, Blackwell Science, 1999.

Tobacco material provided herein can be also processed using methods including, but not limited to, heat treatment (e.g., cooking, toasting), flavoring, enzyme treatment, expansion and/or curing. Both fermented and non-fermented tobaccos can be processed using these techniques. Examples of suitable processed tobaccos include dark air-cured, dark fire cured, burley, flue cured, and cigar filler or wrapper, as well as the products from the whole leaf stemming operation. In one aspect, tobacco fibers include up to 70% dark tobacco on a fresh weight basis. For example, tobacco can be conditioned by heating, sweating and/or pasteurizing steps as described in U.S. Publication Nos. 2004/0118422 or 2005/0178398.

Tobacco material provided herein can be subject to fermentation. Fermenting typically is characterized by high initial moisture content, heat generation, and a 10 to 20% loss of dry weight. See, e.g., U.S. Pat. Nos. 4,528,993; 4,660,577; 4,848,373; and 5,372,149. In addition to modifying the aroma of the leaf, fermentation can change either or both the color and texture of a leaf. Also during the fermentation process, evolution gases can be produced, oxygen can be taken up, the pH can change, and the amount of water retained can change. See, for example, U.S. Publication No. 2005/0178398 and Tso (1999, Chapter 1 in Tobacco, Production, Chemistry and Technology, Davis & Nielsen, eds., Blackwell Publishing, Oxford). Cured, or cured and fermented tobacco can be further processed (e.g., cut, expanded, blended, milled or comminuted) prior to incorporation into the oral product. The tobacco, in some cases, is long cut fermented cured moist tobacco having an oven volatiles content of between 48 and 50 weight percent prior to mixing with a copolymer and, optionally, flavorants and other additives.

In one aspect, tobacco material provided herein can be processed to a desired size. In certain aspects, tobacco fibers can be processed to have an average fiber size of less than 200 micrometers. In one aspect, tobacco fibers are between 75 and 125 micrometers. In another aspect, tobacco fibers are processed to have a size of 75 micrometers or less. In one aspect, tobacco fibers include long cut tobacco, which can be cut or shredded into widths of about 10 cuts/inch up to about 110 cuts/inch and lengths of about 0.1 inches up to about 1 inch. Double cut tobacco fibers can have a range of particle sizes such that about 70% of the double cut tobacco fibers falls between the mesh sizes of −20 mesh and 80 mesh.

Tobacco material provided herein can be processed to have a total oven volatiles content of about 10% by weight or greater; about 20% by weight or greater; about 40% by weight or greater; about 15% by weight to about 25% by weight; about 20% by weight to about 30% by weight; about 30% by weight to about 50% by weight; about 45% by weight to about 65% by weight; or about 50% by weight to about 60% by weight. Those of skill in the art will appreciate that "moist" tobacco typically refers to tobacco that has an oven volatiles content of between about 40% by weight and about 60% by weight (e.g., about 45% by weight to about 55% by weight, or about 50% by weight). As used herein, "oven volatiles" are determined by calculating the percentage of weight loss for a sample after drying the sample in a pre-warmed forced draft oven at 110° C. for 3.25 hours. An oral product can have a different overall oven volatiles content than the oven volatiles content of the tobacco fibers used to make the oral product. The processing steps described herein can reduce or increase the oven volatiles content.

In one aspect, tobacco plants, seeds, plant components, plant cells, and plant genomes provided herein are from a tobacco type selected from the group consisting of flue-cured tobacco, sun-cured tobacco, air-cured tobacco, dark air-cured tobacco, and dark fire-cured tobacco. In another aspect, tobacco plants, seeds, plant components, plant cells, and plant genomes provided herein are from a tobacco type selected from the group consisting of Burley tobacco, Maryland tobacco, bright tobacco, Virginia tobacco, Oriental tobacco, Turkish tobacco, and Galpão tobacco. In one aspect, a tobacco plants or seed provided herein is a hybrid plants or seed. As used herein, a "hybrid" is created by crossing two plants from different varieties or species, such that the progeny comprises genetic material from each parent. Skilled artisans recognize that higher order hybrids can be generated as well. For example, a first hybrid can be made by crossing Variety C with Variety D to create a C×D hybrid, and a second hybrid can be made by crossing Variety E with Variety F to create an E×F hybrid. The first and second hybrids can be further crossed to create the higher order hybrid (C×D)×(E×F) comprising genetic information from all four parent varieties.

Flue-cured tobaccos (also called Virginia of bright tobaccos) amount to approximately 40% of world tobacco production. Flue-cured tobaccos are often also referred to as "bright tobacco" because of the golden-yellow to deep-orange color it reaches during curing. Flue-cured tobaccos have a light, bright aroma and taste. Flue-cured tobaccos are generally high in sugar and low in oils. Major flue-cured tobacco growing countries are Argentina, Brazil, China, India, Tanzania and the U.S. In one aspect, modified tobacco plants or seeds provided herein are in a flue-cured tobacco background selected from the group consisting of CC 13, CC 27, CC 33, CC35, CC 37, CC 65, CC 67, CC 700, GF 318, GL 338, GL 368, GL 939, K 346, K 399, K326, NC 102, NC 196, NC 291, NC 297, NC 299, NC 471, NC 55, NC 606, NC 71, NC 72, NC 92, PVH 1118, PVH 1452, PVH 2110, SPEIGHT 168, SPEIGHT 220, SPEIGHT 225, SPEIGHT 227, SPEIGHT 236, and any variety essentially derived from any one of the foregoing varieties. In another aspect, modified tobacco plants or seeds provided herein are in a flue-cured tobacco background selected from the group consisting of Coker 48, Coker 176, Coker 371-Gold, Coker 319, Coker 347, GL 939, K 149, K326, K 340, K 346, K 358, K 394, K 399, K 730, NC 27NF, NC 37NF, NC 55, NC 60, NC 71, NC 72, NC 82, NC 95, NC 297, NC 606, NC 729, NC 2326, McNair 373, McNair 944, Ox 207, Ox 414 NF, Reams 126, Reams 713, Reams 744, RG 8, RG 11, RG 13, RG 17, RG 22, RG 81, RG H4, RG H51, Speight H-20, Speight G-28, Speight G-58, Speight G-70, Speight G-108, Speight G-111, Speight G-117, Speight 168, Speight 179, Speight NF-3, Va 116, Va 182, and any variety essentially derived from any one of the foregoing varieties. See WO 2004/041006 A1. In further aspects, modified tobacco plants, seeds, hybrids, varieties, or lines provided herein are in any flue cured background selected from the group consisting of K326, K346, and NC196.

Air-cured tobaccos include Burley, Maryland, and dark tobaccos. The common factor is that curing is primarily without artificial sources of heat and humidity. Burley tobaccos are light to dark brown in color, high in oil, and low in sugar. Burley tobaccos are air-cured in barns. Major Burley growing countries are Argentina, Brazil, Italy, Malawi, and the U.S. Maryland tobaccos are extremely fluffy, have good burning properties, low nicotine and a neutral aroma. Major Maryland growing countries include the U.S. and Italy. In one aspect, modified tobacco plants or seeds provided herein are in a Burley tobacco background selected from the group consisting of Clay 402, Clay 403, Clay 502, Ky 14, Ky 907, Ky 910, Ky 8959, NC 2, NC 3, NC 4, NC 5, NC 2000, TN 86, TN 90, TN 97, R 610, R 630, R 711, R 712, NCBH 129, HB4488PLC, PD 7319LC, Bu 21×Ky 10, HB04P, Ky 14×L 8, Kt 200, Newton 98, Pedigo 561, Pf561 and Va 509. In further aspects, modified tobacco plants, seeds, hybrids, varieties, or lines provided herein are in any Burley background selected from the group consisting of TN 90, KT 209, KT 206, KT212, and HB 4488. In another aspect, modified tobacco plants or seeds provided herein are in a Maryland tobacco background selected from the group consisting of Md 10, Md 40, Md 201, Md 609, Md 872 and Md 341.

Dark air-cured tobaccos are distinguished from other types primarily by its curing process which gives dark air-cured tobacco its medium- to dark-brown color and distinct aroma. Dark air-cured tobaccos are mainly used in the production of chewing tobacco and snuff. In one aspect, modified tobacco plants or seeds provided herein are in a dark air-cured tobacco background selected from the group consisting of Sumatra, Jatim, Dominican Cubano, Besuki, One sucker, Green River, Virginia sun-cured, and Paraguan Passado.

Dark fire-cured tobaccos are generally cured with low-burning wood fires on the floors of closed curing barns. Dark fire-cured tobaccos are used for making pipe blends, cigarettes, chewing tobacco, snuff and strong-tasting cigars. Major growing regions for dark fire-cured tobaccos are Tennessee, Kentucky, and Virginia, USA. In one aspect, modified tobacco plants or seeds provided herein are in a dark fire-cured tobacco background selected from the group consisting of Narrow Leaf Madole, Improved Madole, Tom Rosson Madole, Newton's VH Madole, Little Crittenden, Green Wood, Little Wood, Small Stalk Black Mammoth, DT 508, DT 518, DT 592, KY 171, DF 911, DF 485, TN D94, TN D950, VA 309, and VA 359.

Oriental tobaccos are also referred to as Greek, aroma and Turkish tobaccos due to the fact that they are typically grown in eastern Mediterranean regions such as Turkey, Greece, Bulgaria, Macedonia, Syria, Lebanon, Italy, and Romania. The small plant and leaf size, characteristic of today's Oriental varieties, as well as its unique aroma properties are a result of the plant's adaptation to the poor soil and stressful climatic conditions in which it develop over many past centuries. In one aspect, modified tobacco plants or seeds provided herein are in an Oriental tobacco background selected from the group consisting of Izmir, Katerini, Samsun, Basma and Krumovgrad, Trabzon, Thesalian, Tasova, Sinop, Izmit, Hendek, Edirne, Semdinli, Adiyanman, Yayladag, Iskenderun, Duzce, Macedonian, Mavra, Prilep, Bafra, Bursa, Bucak, Bitlis, Balikesir, and any variety essentially derived from any one of the foregoing varieties.

In one aspect, modified tobacco plants, seeds, hybrids, varieties, or lines provided herein are essentially derived from or in the genetic background of BU 64, CC 101, CC 200, CC 13, CC 27, CC 33, CC 35, CC 37, CC 65, CC 67, CC 301, CC 400, CC 500, CC 600, CC 700, CC 800, CC 900, CC 1063, Coker 176, Coker 319, Coker 371 Gold, Coker 48, CU 263, DF911, Galpão, GL 26H, GL 338, GL 350, GL 395, GL 600, GL 737, GL 939, GL 973, GF 157, GF 318, RJR 901, HB 04P, K 149, K 326, K 346, K 358, K394, K 399, K 730, NC 196, NC 37NF, NC 471, NC 55, NC 92, NC2326, NC 95, NC 925, PVH 1118, PVH 1452, PVH 2110, PVH 2254, PVH 2275, VA 116, VA 119, KDH 959, KT 200, KT204LC, KY 10, KY 14, KY 160, KY 17, KY 171, KY 907, KY 907LC, KTY14×L8 LC, Little Crittenden, McNair 373, McNair 944, male sterile KY 14×L8, Narrow Leaf Madole, MS KY171, Narrow Leaf Madole (phph), MS Narrow Leaf Madole, MS TND950, PD 7302LC, PD 7305LC, PD 7309LC, PD 7312LC, PD 7318LC, PD 7319LC, MSTKS 2002, TKF 2002, TKF 6400, TKF 4028, TKF 4024, KT206LC, KT209LC, KT210LC, KT212LC, NC 100, NC 102, NC 2000, NC 291, NC 297, NC 299, NC 3, NC 4, NC 5, NC 6, NC7, NC 606, NC 71, NC 72, NC 810, NC BH 129, NC 2002, Neal Smith Madole, OXFORD 207, 'Perique', PVH03, PVH9, PVH19, PVH50, PVH51, R 610, R 630, R 7-11, R 7-12, RG 17, RG 81, RG H51, RGH 4, RGH 51, RS 1410, Speight 168, Speight 172, Speight 179, Speight 210, Speight 220, Speight 225, Speight 227, Speight 234, Speight G-28, Speight G-70, Speight H-6, Speight H20, Speight NF3, TI 1406, TI 1269, TN 86, TN86LC, TN 90, TN90LC, TN 97, TN97LC, TN D94, TN D950, a TR (Tom Rosson) Madole, VA 309, VA 359, or any commercial tobacco variety according to standard tobacco breeding techniques known in the art.

All foregoing mentioned specific varieties of dark air-cured, Burley, Maryland, dark fire-cured, or Oriental type are only listed for exemplary purposes. Any additional dark air-cured, Burley, Maryland, dark fire-cured, Oriental varieties are also contemplated in the present application.

Also provided herein are populations of tobacco plants described herein. In one aspect, a population of tobacco plants provided herein has a planting density of between about 5,000 and about 8000, between about 5,000 and about 7,600, between about 5,000 and about 7,200, between about 5,000 and about 6,800, between about 5,000 and about 6,400, between about 5,000 and about 6,000, between about 5,000 and about 5,600, between about 5,000 and about 5,200, between about 5,200 and about 8,000, between about 5,600 and about 8,000, between about 6,000 and about 8,000, between about 6,400 and about 8,000, between about 6,800 and about 8,000, between about 7,200 and about 8,000, or between about 7,600 and about 8,000 plants per acre. In another aspect, a population of tobacco plants provided herein is in a soil type with low to medium fertility.

Also provided herein are containers of seeds from tobacco plants described herein. A container of tobacco seeds of the present disclosure may contain any number, weight, or volume of seeds. For example, a container can contain at least, or greater than, about 100, at least, or greater than, about 200, at least, or greater than, about 300, at least, or greater than, about 400, at least, or greater than, about 500, at least, or greater than, about 600, at least, or greater than, about 700, at least, or greater than, about 800, at least, or greater than, about 900, at least, or greater than, about 1000, at least, or greater than, about 1500, at least, or greater than, about 2000, at least, or greater than, about 2500, at least, or greater than, about 3000, at least, or greater than, about 3500, at least, or greater than, or about 4000 or more seeds. Alternatively, the container can contain at least, or greater than, about 1 ounce, at least, or greater than, about 5 ounces, at least, or greater than, about 10 ounces, at least, or greater than, about 1 pound, at least, or greater than, about 2 pounds, at least, or greater than, about 3 pounds, at least, or greater than, about 4 pounds, at least, or greater than, about 5 pounds or more seeds. Containers of tobacco seeds may be any container available in the art. By way of non-limiting example, a container may be a box, a bag, a packet, a pouch, a tape roll, a tube, or a bottle.

The present disclosure also provides methods for breeding tobacco lines, cultivars, or varieties comprising reduced or eliminated suckering. Breeding can be carried out via any known procedures. DNA fingerprinting, SNP mapping, haplotype mapping or similar technologies may be used in a marker-assisted selection (MAS) breeding program to transfer or breed a desirable trait or allele into a tobacco plant. For example, a breeder can create segregating populations in an $F_2$ or backcross generation using $F_1$ hybrid plants provided herein or further crossing the $F_1$ hybrid plants with other donor plants with an agronomically desirable genotype. Plants in the $F_2$ or backcross generations can be screened for a desired agronomic trait or a desirable chemical profile using one of the techniques known in the art or listed herein. Depending on the expected inheritance pattern or the MAS technology used, self-pollination of selected plants before each cycle of backcrossing to aid identification of the desired individual plants can be performed. Backcrossing or other breeding procedure can be repeated until the desired phenotype of the recurrent parent is recovered. In one aspect, a recurrent parent in the present disclosure can be a flue-cured variety, a Burley variety, a dark air-cured variety, a dark fire-cured variety, or an Oriental variety. In another aspect, a recurrent parent can be a modified tobacco plant, line, or variety. Other breeding techniques can be found, for example, in Wernsman, E. A., and Rufty, R. C. 1987. Chapter Seventeen. Tobacco. Pages 669-698 In: Cultivar Development. Crop Species. W. H. Fehr (ed.), MacMillan Publishing Go., Inc., New York, N.Y., incorporated herein by reference in their entirety.

Results of a plant breeding program using modified tobacco plants described herein includes useful lines, cultivars, varieties, progeny, inbreds, and hybrids of the present disclosure. As used herein, the term "variety" refers to a population of plants that share constant characteristics which separate them from other plants of the same species. A variety is often, although not always, sold commercially. While possessing one or more distinctive traits, a variety is further characterized by a very small overall variation between individuals within that variety. A "pure line" variety may be created by several generations of self-pollination and selection, or vegetative propagation from a single parent using tissue or cell culture techniques. A variety can be essentially derived from another line or variety. As defined by the International Convention for the Protection of New Varieties of Plants (Dec. 2, 1961, as revised at Geneva on Nov. 10, 1972; on Oct. 23, 1978; and on Mar. 19, 1991), a variety is "essentially derived" from an initial variety if: a) it is predominantly derived from the initial variety, or from a variety that is predominantly derived from the initial variety, while retaining the expression of the essential characteristics that result from the genotype or combination of genotypes of the initial variety; b) it is clearly distinguishable from the initial variety; and c) except for the differences which result from the act of derivation, it conforms to the initial variety in the expression of the essential characteristics that result from the genotype or combination of genotypes of the initial variety. Essentially derived varieties can be obtained, for example, by the selection of a natural or induced mutant, a somaclonal variant, a variant individual from plants of the initial variety, backcrossing, or transformation. A first tobacco variety and a second tobacco variety from which the first variety is essentially derived, are considered as having essentially identical genetic background. A "line" as distinguished from a variety most often denotes a group of plants used non-commercially, for example in plant research. A line typically displays little overall variation between individuals for one or more traits of interest, although there may be some variation between individuals for other traits.

In one aspect, the present disclosure provides a method of producing a tobacco plant comprising crossing at least one tobacco plant of a first tobacco variety with at least one tobacco plant of a second tobacco variety, where the at least one tobacco plant of the first tobacco variety exhibits no or reduced topping-induced suckering compared to a control tobacco plant of the same variety grown under comparable conditions; and selecting for progeny tobacco plants that exhibit no or reduced topping-induced suckering compared to a control tobacco plant of the same cross grown under comparable conditions. In one aspect, a first tobacco variety provided herein comprises modified tobacco plants. In another aspect, a second tobacco variety provided herein comprises modified tobacco plants. In one aspect, a first or second tobacco variety is male sterile. In another aspect, a first or second tobacco variety is cytoplasmically male sterile. In another aspect, a first or second tobacco variety is female sterile. In one aspect, a first or second tobacco variety is an elite variety. In another aspect, a first or second tobacco variety is a hybrid.

In one aspect, the present disclosure provides a method of introgressing one or more transgenes into a tobacco variety, the method comprising: (a) crossing a first tobacco variety comprising one or more transgenes with a second tobacco variety without the one or more transgenes to produce one or more progeny tobacco plants; (b) genotyping the one or more progeny tobacco plants for the one or more transgenes; and (c) selecting a progeny tobacco plant comprising the one or more transgenes. In another aspect, these methods further comprise backcrossing the selected progeny tobacco plant with the second tobacco variety. In further aspects, these methods further comprise: (d) crossing the selected progeny plant with itself or with the second tobacco variety to produce one or more further progeny tobacco plants; and (e) selecting a further progeny tobacco plant comprising the one or more transgenes. In one aspect, the second tobacco variety is an elite variety.

In one aspect, the present disclosure provides a method of introgressing one or more mutations into a tobacco variety, the method comprising: (a) crossing a first tobacco variety comprising one or more mutations with a second tobacco variety without the one or more mutations to produce one or more progeny tobacco plants; (b) genotyping the one or more progeny tobacco plants for the one or more mutations; and (c) selecting a progeny tobacco plant comprising the one or more mutations. In another aspect, these methods further comprise backcrossing the selected progeny tobacco plant with the second tobacco variety. In further aspects, these methods further comprise: (d) crossing the selected progeny plant with itself or with the second tobacco variety to produce one or more further progeny tobacco plants; and (e) selecting a further progeny tobacco plant comprising the one or more mutations. In one aspect, the second tobacco variety is an elite variety.

In one aspect, the present disclosure provides a method of growing a population of modified tobacco plants comprising no or reduced suckering, where the method comprises planting a population of tobacco seeds comprising one or more mutations, one or more transgenes, or both, where the one or more modified tobacco plants exhibit no or reduced suckering compared to control tobacco plants of the same variety when grown under comparable conditions.

In one aspect, the present disclosure provides a method of growing a modified tobacco plant comprising planting a modified tobacco seed comprising a heterologous promoter that is operably linked to a polynucleotide encoding a polypeptide having at least 40%, at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to a polypeptide selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 161-185, 187, 189, 191, 193, 195, 197, 199, 201, 203, 206, 208, 210, 212, 214, 216, 218, 220, 222, 224, 229, 231, 233, 235, 237, 239, 241, 243, 245, 247, 249, 251, 253, 255; and growing the modified tobacco plant from the seed. In another aspect, this disclosure provides a method of growing a modified tobacco plant comprising planting a modified tobacco seed comprising a recombinant DNA construct comprising a heterologous promoter that is functional in an L1 layer, an L2 layer, an L3 region, a rib zone, a central zone, a peripheral zone, or a combination thereof, and is operably linked to a polynucleotide that encodes a non-coding RNA molecule, where the non-coding RNA molecule is capable of binding to an RNA encoding a polypeptide having at least 40%, at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to a polypeptide selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 70, 72, 74, 76, 78, 161-185, 187, 189, 191, 197, 199, 224, 229, 231, 233, 235, 237, 239, 241, 243, 245, 247, 249, 251, 253, 255, and where the non-coding RNA molecule suppresses the expression of the polypeptide; and growing the modified tobacco plant the the seed. In an aspect, growing comprises germinating a seed. In another aspect, growing comprises placing a seedling in soil, agar, agar-based media, or a hydroponics system. In another aspect, growing comprises providing a seed or plant with water, light (e.g., artificial light, sunlight), fertilizer, a rooting media, or a combination thereof. In an aspect, growing can take place indoors (e.g., a greenhouse) or outdoors (e.g., a field). In one aspect, growing comprises placing a seed or a plant in a container.

In one aspect, this disclosure provides a method for manufacturing a modified seed, comprising introducing a recombinant DNA construct provided herein into a plant cell; screening a population of plant cells for the recombinant DNA construct; selecting one or more plant cells from the population; generating one or more modified plants from the one or more plant cells; and collecting one or more modified seeds from the one or more modified plants.

As used herein, "locus" is a chromosome region where a polymorphic nucleic acid, trait determinant, gene, or marker is located. The loci of this disclosure comprise one or more polymorphisms in a population; e.g., alternative alleles are present in some individuals. As used herein, "allele" refers to an alternative nucleic acid sequence at a particular locus. The length of an allele can be as small as 1 nucleotide base, but is typically larger. For example, a first allele can occur on one chromosome, while a second allele occurs on a second homologous chromosome, e.g., as occurs for different chromosomes of a heterozygous individual, or between different homozygous or heterozygous individuals in a population. As used herein, a chromosome in a diploid plant is "hemizygous" when only one copy of a locus is present. For example, an inserted transgene is hemizygous when it only inserts into one sister chromosome (i.e., the second sister chromosome does not contain the inserted transgene).

In one aspect, a modified plant, seed, plant component, plant cell, or plant genome is homozygous for a transgene provided herein. In another aspect, a modified plant, seed, plant component, plant cell, or plant genome is heterozygous for a transgene provided herein. In one aspect, a modified plant, seed, plant component, plant cell, or plant genome is hemizygous for a transgene provided herein. In one aspect, a modified plant, seed, plant component, plant cell, or plant genome is homozygous for a mutation provided herein. In another aspect, a modified plant, seed, plant component, plant cell, or plant genome is heterozygous for a mutation provided herein. In one aspect, a modified plant, seed, plant component, plant cell, or plant genome is hemizygous for a mutation provided herein.

As used herein, "introgression" or "introgress" refers to the transmission of a desired allele of a genetic locus from one genetic background to another.

As used herein, "crossed" or "cross" means to produce progeny via fertilization (e.g. cells, seeds or plants) and includes crosses between different plants (sexual) and self-fertilization (selfing).

As used herein, "backcross" and "backcrossing" refer to the process whereby a progeny plant is repeatedly crossed back to one of its parents. In a backcrossing scheme, the "donor" parent refers to the parental plant with the desired gene or locus to be introgressed. The "recipient" parent (used one or more times) or "recurrent" parent (used two or more times) refers to the parental plant into which the gene or locus is being introgressed. The initial cross gives rise to the $F_1$ generation. The term "BC1" refers to the second use of the recurrent parent, "BC2" refers to the third use of the recurrent parent, and so on. In one aspect, a backcross is performed repeatedly, with a progeny individual of each successive backcross generation being itself backcrossed to the same parental genotype.

As used herein, "elite variety" means any variety that has resulted from breeding and selection for superior agronomic performance.

As used herein, "selecting" or "selection" in the context of breeding refer to the act of picking or choosing desired individuals, normally from a population, based on certain pre-determined criteria.

In one aspect, tobacco plants provided herein are hybrid plants. Hybrids can be produced by preventing self-pollination of female parent plants (e.g., seed parents) of a first variety, permitting pollen from male parent plants of a second variety to fertilize the female parent plants, and allowing F₁ hybrid seeds to form on the female plants. Self-pollination of female plants can be prevented by emasculating the flowers at an early stage of flower development. Alternatively, pollen formation can be prevented on the female parent plants using a form of male sterility. For example, male sterility can be produced by male sterility (MS), or transgenic male sterility where a transgene inhibits microsporogenesis and/or pollen formation, or self-incompatibility. Female parent plants containing MS are particularly useful. In aspects in which the female parent plants are MS, pollen may be harvested from male fertile plants and applied manually to the stigmas of MS female parent plants, and the resulting F₁ seed is harvested. Additionally, female sterile plants can also be used to prevent self-fertilization.

Plants can be used to form single-cross tobacco F₁ hybrids. Pollen from a male parent plant is manually transferred to an emasculated female parent plant or a female parent plant that is male sterile to form F₁ seed. Alternatively, three-way crosses can be carried out where a single-cross F₁ hybrid is used as a female parent and is crossed with a different male parent. As another alternative, double-cross hybrids can be created where the F₁ progeny of two different single-crosses are themselves crossed. Self-incompatibility can be used to particular advantage to prevent self-pollination of female parents when forming a double-cross hybrid.

In one aspect, a tobacco variety provided herein is male sterile. In another aspect, a tobacco variety provided herein is cytoplasmic male sterile (CMS). Male sterile tobacco plants may be produced by any method known in the art. Methods of producing male sterile tobacco are described in Wernsman, E. A., and Rufty, R. C. 1987. Chapter Seventeen. Tobacco. Pages 669-698 In: Cultivar Development. Crop Species. W. H. Fehr (ed.), MacMillan Publishing Go., Inc., New York, N.Y. 761 pp. In another aspect, a tobacco variety provided herein is female sterile. As a non-limiting example, female sterile plants can be made by mutating the STIG1 gene. See, for example, Goldman et al. 1994, *EMBO Journal* 13:2976-2984.

As used herein, the term "sequence identity" or "identity" in the context of two polynucleotide or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity."

The use of the term "polynucleotide" is not intended to limit the present disclosure to polynucleotides comprising DNA. Those of ordinary skill in the art will recognize that polynucleotides and nucleic acid molecules can comprise ribonucleotides and combinations of ribonucleotides and deoxyribonucleotides. Such deoxyribonucleotides and ribonucleotides include both naturally occurring molecules and synthetic analogues. The polynucleotides of the present disclosure also encompass all forms of sequences including, but not limited to, single-stranded forms, double-stranded forms, hairpins, stem-and-loop structures, and the like.

As used herein, the term "polypeptide" refers to a chain of at least two covalently linked amino acids.

The present disclosure provides recombinant, purified, isolated, or processed nucleic acids and polypeptides. In one aspect, the present disclosure provides a nucleic acid molecule comprising at least about 40%, about 45%, about 50%, about 55%, about 60%, about 65%, about 70%, about 75%, about 80%, about 85%, about 90%, about 91%, about 92%, about 93%, about 94%, about 95%, about 96%, about 97%, about 98%, about 99%, or about 100% identity to a sequence selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83-160, 186, 188, 190, 192, 194, 196, 198, 200, 202, 204, 205, 207, 209, 211, 213, 215, 217, 219, 221, 223, 225-228, 230, 232, 234, 236, 238, 240, 242, 244, 246, 248, 250, 252, 254, and fragments thereof. In one aspect, the present disclosure provides a nucleic acid molecule comprising at least 18, at least 19, at least 20, at least 21, at least 22, at least 23, at least 24, at least 25, at least 26, at least 27, at least 28, at least 29, at least 30, or more than 30 contiguous nucleotides identical to a polynucleotide selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83-160, 186, 188, 190, 192, 194, 196, 198, 200, 202, 204, 205, 207, 209, 211, 213, 215, 217, 219, 221, 223, 225-228, 230, 232, 234, 236, 238, 240, 242, 244, 246, 248, 250, 252, and 254.

In another aspect, the present disclosure provides a polynucleotide encoding a polypeptide comprising at least about 40%, at least about 45%, at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, about 98%, at least about 99%, or about 100% sequence identity to a polypeptide sequence selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 161-185, 187, 189, 191, 193, 195, 197, 199, 201, 203, 206, 208, 210, 212, 214, 216, 218, 220, 222, 224, 229, 231, 233, 235, 237, 239, 241, 243, 245, 247, 249, 251, 253, and 255. In another aspect, the present disclosure provides a polynucleotide encoding a polypeptide comprising at least about 40%, at least about 45%, at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or about 100% similarity to a polypeptide sequence selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 161-185, 187, 189, 191, 193, 195, 197, 199, 201, 203, 206, 208, 210, 212, 214, 216, 218, 220, 222, 224, 229, 231, 233, 235, 237, 239, 241, 243, 245, 247, 249, 251, 253, and 255.

In one aspect, the present disclosure provides a polypeptide comprising at least about 40%, at least about 45%, at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or about 100% identity to an amino acid sequence selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 161-185, 187, 189, 191, 193, 195, 197, 199, 201, 203, 206, 208, 210, 212, 214, 216, 218, 220, 222, 224, 229, 231, 233, 235, 237, 239, 241, 243, 245, 247, 249, 251, 253, and 255. In one aspect, the present disclosure provides a polypeptide comprising at least about 40%, at least about 45%, at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or about 100% similarity to an amino acid sequence selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 161-185, 187, 189, 191, 193, 195, 197, 199, 201, 203, 206, 208, 210, 212, 214, 216, 218, 220, 222, 224, 229, 231, 233, 235, 237, 239, 241, 243, 245, 247, 249, 251, 253, and 255. In one aspect, the present disclosure provides a polypeptide comprising at least 10, at least 11, at least 12, at least 13, at least 14, at least 15, at least 16, at least 17, at least 18, at least 19, at least 20, at least 21, at least 22, at least 23, at least 24, at least 25, at least 30, at least 40, at least 50, or more than 50 contiguous amino acid residues identical to an amino acid sequence in a polypeptide selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 161-185, 187, 189, 191, 193, 195, 197, 199, 201, 203, 206, 208, 210, 212, 214, 216, 218, 220, 222, 224, 229, 231, 233, 235, 237, 239, 241, 243, 245, 247, 249, 251, 253, and 255.

In another aspect, the present disclosure provides a biologically active variant of a protein having an amino acid sequence selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 161-185, 187, 189, 191, 193, 195, 197, 199, 201, 203, 206, 208, 210, 212, 214, 216, 218, 220, 222, 224, 229, 231, 233, 235, 237, 239, 241, 243, 245, 247, 249, 251, 253, and 255. A biologically active variant of a protein of the present disclosure may differ from that protein by as few as 1-15 amino acid residues, as few as 10, as few as 9, as few as 8, as few as 7, as few as 6, as few as 5, as few as 4, as few as 3, as few as 2, or as few as 1 amino acid residue. Also provided herein are orthologous genes or proteins of genes or proteins selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 161-185, 187, 189, 191, 193, 195, 197, 199, 201, 203, 206, 208, 210, 212, 214, 216, 218, 220, 222, 224, 229, 231, 233, 235, 237, 239, 241, 243, 245, 247, 249, 251, 253, and 255. "Orthologs" are genes derived from a common ancestral gene and which are found in different species as a result of speciation. Orthologs may share at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or greater sequence identity or similarity at the nucleotide sequence and/or the amino acid sequence level. Functions of orthologs are often highly conserved among species.

Nucleic acid molecules, polypeptides, or proteins provided herein can be isolated or substantially purified. An "isolated" or "purified" nucleic acid molecule, polypeptide, protein, or biologically active portion thereof, is substantially or essentially free from components that normally accompany or interact with the polynucleotide or protein as found in its naturally occurring environment. For example, an isolated or purified polynucleotide or protein is substantially free of other cellular material, or culture medium when produced by recombinant techniques, or substantially free of chemical precursors or other chemicals when chemically synthesized. In one aspect, an isolated polynucleotide provided herein can contain less than about 5000 nucleotides, less than about 4000 nucleotides, less than about 3000 nucleotides, less than about 2000 nucleotides, less than about 1000 nucleotides, less than about 500 nucleotides, or less than about 100 nucleotides of nucleic acid sequence that naturally flank the polynucleotide in genomic DNA of the cell from which the polynucleotide is derived. In one aspect, an isolated polynucleotide provided herein can contain 100-5000, 500-5000, 1000-5000, 2000-5000, 3000-5000, 4000-5000, 1-500, 1-1000, 1-2000, 1-3000, 1-4000, 1-5000, 100-500, 100-1000, 100-2000, 100-3000, or 100-4000 nucleotides of nucleic acid sequence that naturally flank the polynucleotide in genomic DNA of the cell from which the polynucleotide is derived. In another aspect, an isolated polypeptide provided herein is substantially free of cellular material in preparations having less than about 30%, less than about 20%, less than about 10%, less than about 5%, or less than about 1% (by dry weight) of chemical precursors or non-protein-of-interest chemicals. Fragments of the disclosed polynucleotides and polypeptides encoded thereby are also encompassed by the present invention. Fragments of a polynucleotide may encode polypeptide fragments that retain the biological activity of the native polypeptide. Alternatively, fragments of a polynucleotide that are useful as hybridization probes or PCR primers using methods known in the art generally do not encode fragment polypeptides retaining biological activity. Fragments of a polynucleotide provided herein can range from at least about 20 nucleotides, about 50 nucleotides, about 70 nucleotides, about 100 nucleotides, about 150 nucleotides, about 200 nucleotides, about 250 nucleotides, about 300 nucleotides, and up to the full-length polynucleotide encoding the polypeptides of the invention, depending on the desired outcome.

Nucleic acids can be isolated using techniques routine in the art. For example, nucleic acids can be isolated using any method including, without limitation, recombinant nucleic acid technology, and/or the polymerase chain reaction (PCR). General PCR techniques are described, for example in PCR Primer: A Laboratory Manual, Dieffenbach & Dveksler, Eds., Cold Spring Harbor Laboratory Press, 1995. Recombinant nucleic acid techniques include, for example, restriction enzyme digestion and ligation, which can be used to isolate a nucleic acid. Isolated nucleic acids also can be chemically synthesized, either as a single nucleic acid molecule or as a series of oligonucleotides. Polypeptides can be purified from natural sources (e.g., a biological sample) by known methods such as DEAE ion exchange, gel filtration, and hydroxyapatite chromatography. A polypeptide also can be purified, for example, by expressing a nucleic acid in an expression vector. In addition, a purified polypeptide can be obtained by chemical synthesis. The extent of purity of a polypeptide can be measured using any appropriate method, e.g., column chromatography, polyacrylamide gel electrophoresis, or HPLC analysis.

In one aspect, this disclosure provides methods of detecting recombinant nucleic acids and polypeptides in plant cells. Without being limiting, nucleic acids also can be detected using hybridization. Hybridization between nucleic acids is discussed in detail in Sambrook et al. (1989, Molecular Cloning: A Laboratory Manual, 2nd Ed., Cold Spring Harbor Laboratory Press, Cold Spring Harbor, NY).

Polypeptides can be detected using antibodies. Techniques for detecting polypeptides using antibodies include enzyme linked immunosorbent assays (ELISAs), Western blots, immunoprecipitations and immunofluorescence. An antibody provided herein can be a polyclonal antibody or a monoclonal antibody. An antibody having specific binding affinity for a polypeptide provided herein can be generated using methods well known in the art. An antibody provided herein can be attached to a solid support such as a microtiter plate using methods known in the art.

Detection (e.g., of an amplification product, of a hybridization complex, of a polypeptide) can be accomplished using detectable labels. The term "label" is intended to encompass the use of direct labels as well as indirect labels. Detectable labels include enzymes, prosthetic groups, fluorescent materials, luminescent materials, bioluminescent materials, and radioactive materials.

The following exemplary, non-limiting embodiments are envisioned:

1. A modified tobacco plant comprising no or reduced suckers compared to a control tobacco plant of the same variety when grown under comparable conditions.
2. The modified tobacco plant of embodiment 1, wherein said suckers is topping-induced suckers.
3. The modified tobacco plant of embodiment 1, wherein said modified tobacco plant comprises one or more mutations.
4. The modified tobacco plant of embodiment 1, wherein said modified tobacco plant comprises one or more transgenes.
5. The modified tobacco plant of embodiment 3, wherein said one or more mutations suppress suckers.
6. The modified tobacco plant of embodiment 4, wherein said one or more transgenes suppress suckers.
7. The modified tobacco plant of embodiment 3, wherein said one or more mutations suppress topping-induced suckers.
8. The modified tobacco plant of embodiment 4, wherein said one or more transgenes suppress topping-induced suckers.
9. The modified tobacco plant of embodiment 3, wherein said one or more mutations suppress suckers prior to topping.
10. The modified tobacco plant of embodiment 4, wherein said one or more transgenes suppress suckers prior to topping.
11. The modified tobacco plant of embodiment 3, wherein said one or more mutations are selected from the group consisting of an insertion, a deletion, an inversion, a substitution, and a combination thereof.
12. The modified tobacco plant of embodiment 4, wherein said one or more transgenes comprise an axillary meristem-specific promoter.
13. The modified tobacco plant of embodiment 12, wherein said axillary meristem-specific promoter is functional or preferentially functional in an L1 layer, an L2 layer, an L3 region, or a combination thereof.
14. The modified tobacco plant of embodiment 12, wherein said axillary meristem-specific promoter is functional or preferentially functional in a central zone, a peripheral zone, a rib zone, or a combination thereof of an axillary meristem.
15. The modified tobacco plant of embodiment 11, wherein said one or more mutations is introduced via a system selected from the group consisting of chemical mutagenesis, irradiation mutagenesis, transposon mutagenesis, *Agrobacterium*-mediated transformation, a meganuclease, a zinc-finger nuclease (ZFN), a transcription activator-like effector nuclease (TALEN), a clustered regularly-interspaced short palindromic repeats (CRISPR)/Cas9 system, a CRISPR/Cpf1 system, and a combination thereof.
16. The modified tobacco plant of embodiment 11, wherein said one or more mutations are in a gene encoding a polypeptide having at least 70% sequence identity to a polypeptide selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 58, 60, 62, 68, 70, 72, 74, 76, 78, 80, 82, 161-185, 187, 189, 191, 193, 195, 197, 199, 201, 203, 206, 208, 210, 212, 214, 216, 218, 220, 222, 224, 229, 231, 233, 235, 237, 239, 241, 243, 245, 247, 249, 251, 253, 255.
17. The modified tobacco plant of embodiment 3 or 4, wherein said modified tobacco plant has a similar or higher leaf yield compared to said control tobacco plant when grown under comparable conditions.
18. The modified tobacco plant of embodiment 17, wherein said higher leaf yield is at least 0.5%, 1%, 2.5%, 5%, 10%, 15%, or at least 20% higher.
19. The modified tobacco plant of embodiment 3 or 4, wherein said modified tobacco plant has a similar plant height compared to said control tobacco plant when grown under comparable conditions.
20. The modified tobacco plant of embodiment 19, wherein said similar plant height is within 1%, 5%, 10%, 20%, or 25%.
21. The modified tobacco plant of embodiment 3 or 4, wherein said modified tobacco plant has a similar cured leaf chemistry profile compared to said control tobacco plant when grown under comparable conditions.
22. The modified tobacco plant of embodiment 3 or 4, wherein said modified tobacco plant produces cured leaves that have a similar or higher USDA grade index value compared to cured leaves from said control tobacco plant when grown under comparable conditions.
23. The modified tobacco plant of embodiment 1, wherein said reduced topping-induced suckers comprises fewer total suckers, smaller suckers, or both when compared to topping-induced suckers of a control tobacco plant when grown under comparable conditions.
24. The modified tobacco plant of embodiment 23, wherein said smaller suckers comprise reduced mass, reduced length, or both when compared to topping-induced suckers of a control tobacco plant when grown under comparable conditions.
25. The modified tobacco plant of embodiment 3 or 4, wherein said modified tobacco plant requires reduced management for controlling suckers compared to a control tobacco plant when grown under comparable conditions.

26. The modified tobacco plant of embodiment 25, wherein said reduced management comprises reduced manual removal frequency to control suckers, reduced chemical application frequency to control suckers, reduced quantities of chemical application to control suckers, or any combination thereof compared to a control tobacco plant when grown under comparable conditions.

27. The modified tobacco plant of embodiment 26, wherein said reduced manual removal frequency to control suckers comprises less than 10%, less than 20%, less than 30%, less than 40%, less than 50%, less than 60%, less than 70%, less than 75%, less than 80%, less than 85%, less than 90%, or less than 95% as frequently as a control plant when grown under comparable conditions.

28. The modified tobacco plant of embodiment 3 or 4, wherein said modified tobacco plant is homozygous for said one or more transgenes or said one or more mutations.

29. The modified tobacco plant of embodiment 3 or 4, wherein said modified tobacco plant is hemizygous for said one or more transgenes or said one or more mutations.

30. The modified tobacco plant of embodiment 3 or 4, wherein said modified tobacco plant is heterozygous for said one or more transgenes or said one or more mutations.

31. The modified tobacco plant of embodiment 1, wherein said plant is selected from the group consisting of a flue-cured variety, a bright variety, a Burley variety, a Virginia variety, a Maryland variety, a dark variety, an Oriental variety, and a Turkish variety.

32. The modified tobacco plant of embodiment 1, wherein said tobacco plant is selected from the group consisting a BU 64 plant, a CC 101 plant, a CC 200 plant, a CC 13 plant, a CC 27 plant, a CC 33 plant, a CC 35 plant, a CC 37 plant, a CC 65 plant, a CC 67 plant, a CC 301 plant, a CC 400 plant, a CC 500 plant, CC 600 plant, a CC 700 plant, a CC 800 plant, a CC 900 plant, a CC 1063 plant, a Coker 176 plant, a Coker 319 plant, a Coker 371 Gold plant, a Coker 48 plant, a CU 263 plant, a DF911 plant, a Galpão plant, a GL 26H plant, a GL 338 plant, a GL 350 plant, a GL 395 plant, a GL 600 plant, a GL 737 plant, a GL 939 plant, a GL 973 plant, a GF 157 plant, a GF 318 plant, an RJR 901 plant, an HB 04P plant, a K 149 plant, a K 326 plant, a K 346 plant, a K 358 plant, a K394 plant, a K 399 plant, a K 730 plant, an NC 196 plant, an NC 37NF plant, an NC 471 plant, an NC 55 plant, an NC 92 plant, an NC2326 plant, an NC 95 plant, an NC 925 plant, a PVH 1118 plant, a PVH 1452 plant, a PVH 2110 plant, a PVH 2254 plant, a PVH 2275 plant, a VA 116 plant, a VA 119 plant, a KDH 959 plant, a KT 200 plant, a KT204LC plant, a KY 10 plant, a KY 14 plant, a KY 160 plant, a KY 17 plant, a KY 171 plant, a KY 907 plant, a KY 907LC plant, a KTY14×L8 LC plant, a Little Crittenden plant, a McNair 373 plant, a McNair 944 plant, a male sterile KY 14×L8 plant, a Narrow Leaf Madole plant, a MS KY171 plant, a Narrow Leaf Madole (phph) plant, a MS Narrow Leaf Madole plant, a MS TND950 plant, a PD 7302LC plant, a PD 7305LC plant, a PD 7309LC plant, a PD 7312LC plant, a PD 7318LC plant, a PD 7319LC plant, a MSTKS 2002 plant, a TKF 2002 plant, a TKF 6400 plant, a TKF 4028 plant, a TKF 4024 plant, a KT206LC plant, a KT209LC plant, a KT210LC plant, a KT212LC plant, an NC 100 plant, an NC 102 plant, an NC 2000 plant, an NC 291 plant, an NC 297 plant, an NC 299 plant, an NC 3 plant, an NC 4 plant, an NC 5 plant, an NC 6 plant, an NC7 plant, an NC 606 plant, an NC 71 plant, an NC 72 plant, an NC 810 plant, an NC BH 129 plant, an NC 2002 plant, a Neal Smith Madole plant, an OXFORD 207 plant, a 'Perique' plant, a PVH03 plant, a PVH09 plant, a PVH19 plant, a PVH50 plant, a PVH51 plant, an R 610 plant, an R 630 plant, an R 7-11 plant, an R 7-12 plant, an RG 17 plant, an RG 81 plant, an RG H51 plant, an RGH 4 plant, an RGH 51 plant, an RS 1410 plant, a Speight 168 plant, a Speight 172 plant, a Speight 179 plant, a Speight 210 plant, a Speight 220 plant, a Speight 225 plant, a Speight 227 plant, a Speight 234 plant, a Speight G-28 plant, a Speight G-70 plant, a Speight H-6 plant, a Speight H20 plant, a Speight NF3 plant, a TI 1406 plant, a TI 1269 plant, a TN 86 plant, a TN86LC plant, a TN 90 plant, a TN90LC plant, a TN 97 plant, a TN97LC plant, a TN D94 plant, a TN D950 plant, a TR (Tom Rosson) Madole plant, a VA 309 plant, and a VA 359 plant.

33. The modified tobacco plant of embodiment 1, wherein said modified tobacco plant is a hybrid.

34. The modified tobacco plant of embodiment 1, wherein said modified tobacco plant is male sterile or cytoplasmically male sterile (CMS).

35. The modified tobacco plant of embodiment 1, wherein said modified tobacco plant is female sterile.

36. A tobacco leaf of the modified tobacco plant of embodiment 1.

37. The tobacco leaf of embodiment 35, wherein said tobacco leaf is a cured tobacco leaf.

38. The tobacco leaf of embodiment 36, wherein said cured tobacco leaf is air-cured, fire-cured, sun-cured, or flue-cured.

39. A tobacco product comprising cured tobacco material from the modified tobacco plant of embodiment 1.

40. The tobacco product of embodiment 39, wherein said tobacco product is selected from the group consisting of a cigarette, a kretek, a bidi cigarette, a cigar, a cigarillo, a non-ventilated cigarette, a vented recess filter cigarette, pipe tobacco, snuff, chewing tobacco, moist smokeless tobacco, fine cut chewing tobacco, long cut chewing tobacco, pouched chewing tobacco product, gum, a tablet, a lozenge, and a dissolving strip.

41. A seed giving rise to the modified tobacco plant of embodiment 1.

42. A method comprising preparing a tobacco product using a cured tobacco leaf from the modified tobacco plant of embodiment 1.

43. A modified tobacco plant, wherein said modified tobacco plant exhibits:
    a. inhibited or eliminated axillary meristem growth;
    b. inhibited or eliminated axillary meristem maintenance; or
    c. a combination thereof
    compared to a control tobacco plant of the same variety when grown under comparable conditions.

44. A plant or seed comprising a recombinant polynucleotide, wherein said recombinant polynucleotide comprises:
    a. a promoter that is functional in an L1 layer, an L2 layer, an L3 region, a rib zone, a central zone, a peripheral zone, or any combination thereof, which is operably linked to
    b. a structural nucleic acid molecule comprising a nucleic acid sequence, wherein said nucleic acid sequence encodes a polypeptide having at least 70% sequence identity to a polypeptide selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 58, 60, 62, 68, 70, 72, 74, 76, 78, 80, 82, 161-185, 189, 191, 193, 195, 197, 199, 201, 203, 206, 208, 210, 212, 214, 216, 218, 220, 222, 224, 229, 231, 233, 235, 237, 239, 241, 243, 245, 247, 249, 251, 253, 255.

45. The plant or seed of embodiment 43, wherein said promoter comprises a nucleic acid sequence having at least 90% sequence identity to a polynucleotide selected from the group consisting of SEQ ID NOs: 113-118, 148-160, 204 and fragments thereof.

46. The plant or seed of embodiment 43, wherein said plant or seed is a tobacco plant or seed.

47. A recombinant DNA construct comprising:
   a. a promoter that is functional in an L1 layer, an L2 layer, an L3 region, a rib zone, a central zone, a peripheral zone, or a combination thereof; and
   b. a heterologous and operably linked nucleic acid sequence, wherein said nucleic acid sequence encodes a non-coding RNA or a polypeptide.

48. The recombinant DNA construct of embodiment 46, wherein said promoter comprises a nucleic acid sequence having at least 90% sequence identity to a polynucleotide selected from the group consisting of SEQ ID NOs: 113-118, 148-160, 204 and fragments thereof.

49. A method of reducing or eliminating topping-induced suckers in a tobacco plant, said method comprising transforming a tobacco plant with a recombinant DNA construct comprising a promoter functional in an L1 layer, an L2 layer, an L3 region, a rib zone, a central zone, a peripheral zone, or a combination thereof.

50. The method of embodiment 48, wherein said promoter comprises a nucleic acid sequence having at least 90% sequence identity to a polynucleotide selected from the group consisting of SEQ ID NOs: 113-118, 148-160, 204 and fragments thereof.

51. A method comprising transforming a tobacco plant with a recombinant DNA construct comprising a heterologous promoter that is functional in an L1 layer, an L2 layer, an L3 region, a rib zone, a central zone, a peripheral zone, or a combination thereof, and is operably linked to a polynucleotide that is transcribed into an RNA molecule that suppresses the level of an endogenous gene, and wherein said endogenous gene promotes or is required for axillary meristem growth, axillary meristem maintenance, or both.

52. A method for producing a tobacco plant comprising:
   a. crossing at least one tobacco plant of a first tobacco variety with at least one tobacco plant of a second tobacco variety, wherein said at least one tobacco plant of said first tobacco variety exhibits no or reduced topping-induced suckers compared to a control tobacco plant of the same variety grown under comparable conditions; and
   b. selecting for progeny tobacco plants that exhibit no or reduced topping-induced suckers compared to a control tobacco plant of the same cross grown under comparable conditions.

53. A tobacco plant, or part thereof, comprising a heterologous promoter operably linked to a polynucleotide encoding a polypeptide having at least 70% sequence identity to a polypeptide selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 68, 70, 72, 74, 76, 78, 80, 82, 161-185, 189, 191, 193, 195, 197, 199, 201, 203, 206, 208, 210, 212, 214, 216, 218, 220, 222, 224, 229, 231, 233, 235, 237, 239, 241, 243, 245, 247, 249, 251, 253, 255.

54. The tobacco plant, or part thereof, of embodiment 52, wherein said promoter comprises a nucleic acid molecule having at least 90% sequence identity to a polynucleotide selected from the group consisting of SEQ ID NOs: 113-118, 148-160, 204 and fragments thereof.

55. The tobacco plant, or part thereof, of embodiment 52, wherein said polynucleotide has at least 90% sequence identity to a polynucleotide selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 67, 69, 71, 73, 75, 77, 79, 81, 83-160, 186, 188, 190, 192, 194, 196, 198, 200, 202, 204, 205, 207, 209, 211, 213, 215, 217, 219, 221, 223, 228, 230, 232, 234, 236, 238, 240, 242, 244, 246, 248, 250, 252, and 254.

56. The tobacco plant, or part thereof, of embodiment 52, wherein said polypeptide comprises at least 15 contiguous amino acid residues identical to said polypeptide selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 68, 70, 72, 74, 76, 78, 80, 82, 161-185, 189, 191, 193, 195, 197, 199, 201, 203, 206, 208, 210, 212, 214, 216, 218, 220, 222, 224, 229, 231, 233, 235, 237, 239, 241, 243, 245, 247, 249, 251, 253, 255.

57. A recombinant DNA construct comprising a heterologous promoter operably linked to a polynucleotide encoding a polypeptide having at least 70% sequence identity to a polypeptide selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 58, 60, 62, 68, 70, 72, 74, 76, 78, 80, 82, 161-185, 189, 191, 193, 195, 197, 199, 201, 203, 206, 208, 210, 212, 214, 216, 218, 220, 222, 224, 229, 231, 233, 235, 237, 239, 241, 243, 245, 247, 249, 251, 253, 255.

58. A method of growing a modified tobacco plant comprising planting a modified tobacco seed comprising a heterologous promoter that is operably linked to a polynucleotide encoding a polypeptide having at least 70% sequence identity to a polypeptide selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 58, 60, 62, 68, 70, 72, 74, 76, 78, 80, 82, 161-185, 189, 191, 193, 195, 197, 199, 201, 203, 206, 208, 210, 212, 214, 216, 218, 220, 222, 224, 229, 231, 233, 235, 237, 239, 241, 243, 245, 247, 249, 251, 253, 255; and growing said modified tobacco plant from said seed.

59. A method for controlling topping-induced suckers in a plant comprising transforming said plant with a recombinant DNA construct, wherein said recombinant DNA construct comprises a promoter that is operably linked to a polynucleotide encoding a polypeptide having at least 70% sequence identity to a polypeptide selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 58, 60, 62, 68, 70, 72, 74, 76, 78, 80, 82, 161-185, 187, 189, 191, 193, 195, 197, 199, 201, 203, 206, 208, 210, 212, 214, 216, 218, 220, 222, 224, 229, 231, 233, 235, 237, 239, 241, 243, 245, 247, 249, 251, 253, 255.

60. A tobacco plant, or part thereof, comprising a heterologous promoter operably linked to a polynucleotide that encodes a non-coding RNA molecule, wherein said non-coding RNA molecule is capable of binding to an RNA encoding a polypeptide having at least 70% sequence identity to a polypeptide selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 70, 72, 74, 76, 78, 161-185, 187, 189, 191, 197, 199, 224, 229, 231, 233, 235, 237, 239, 241, 243, 245, 247, 249, 251, 253, 255, and wherein said non-coding RNA molecule suppresses the expression of said polypeptide.

61. The tobacco plant, or part thereof, of embodiment 59, wherein said promoter comprises a nucleic acid sequence having at least 90% sequence identity to a polynucleotide selected from the group consisting of SEQ ID NOs: 113-118, 148-160, 204 and fragments thereof.

62. The tobacco plant, or part thereof, of embodiment 59, wherein said polynucleotide has at least 90% sequence identity to a polynucleotide selected from the group consisting of SEQ ID NOs: 83-101.

63. The tobacco plant, or part thereof, of embodiment 59, wherein said polynucleotide comprises at least 18, 19, 20, 21, 22, 23, 24, 25, 26, 27, 28, 29, 30, or more than 30 contiguous nucleotides identical to a polynucleotide selected from the group consisting of SEQ ID NOs: 83-101.

64. A recombinant DNA construct comprising a heterologous axillary meristem-specific promoter operably linked to a polynucleotide that encodes a non-coding RNA molecule, wherein said non-coding RNA molecule is capable of binding to an RNA encoding a polypeptide having at least 70% sequence identity to a polypeptide selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 70, 72, 74, 76, 78, 161-185, 187, 189, 191, 197, 199, 224, 229, 231, 233, 235, 237, 239, 241, 243, 245, 247, 249, 251, 253, 255, and wherein said non-coding RNA molecule suppresses the expression of said polypeptide.

65. A method of growing a modified tobacco plant comprising planting a modified tobacco seed comprising a recombinant DNA construct comprising a heterologous promoter that is functional in an L1 layer, an L2 layer, an L3 region, a rib zone, a central zone, a peripheral zone, or a combination thereof, and is operably linked to a polynucleotide that encodes a non-coding RNA molecule, wherein said non-coding RNA molecule is capable of binding to an RNA encoding a polypeptide having at least 70% sequence identity to a polypeptide selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 70, 72, 74, 76, 78, 161-185, 187, 189, 191, 197, 199, 224, 229, 231, 233, 235, 237, 239, 241, 243, 245, 247, 249, 251, 253, 255, and wherein said non-coding RNA molecule suppresses the expression of said polypeptide; and growing said modified tobacco plant from said seed.

66. A method for controlling topping-induced suckers in a plant comprising transforming said plant with a recombinant DNA construct, wherein said recombinant DNA construct comprises a heterologous promoter that is functional in an L1 layer, an L2 layer, an L3 region, a rib zone, a central zone, a peripheral zone, or a combination thereof, and wherein said promoter is operably linked to a polynucleotide that encodes a non-coding RNA molecule, wherein said non-coding RNA molecule is capable of binding to an RNA encoding a polypeptide having at least 70% sequence identity to a polypeptide selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 70, 72, 74, 76, 78, 161-185, 187, 189, 191, 197, 199, 224, 229, 231, 233, 235, 237, 239, 241, 243, 245, 247, 249, 251, 253, 255, and wherein said non-coding RNA molecule suppresses the expression of said polypeptide.

67. A bacterial cell comprising the recombinant DNA construct of any one of embodiments 46, 56, or 63.

68. A plant genome comprising the recombinant DNA construct of any one of embodiments 46, 56, or 63.

69. A method for manufacturing a modified seed, said method comprising:
    a. introducing the recombinant DNA construct from any one of embodiments 46, 56, or 63 into a plant cell;
    b. screening a population of plant cells for said recombinant DNA construct;
    c. selecting one or more plant cells from said population;
    d. generating one or more modified plants from said one or more plant cells; and
    e. collecting one or more modified seeds from said one or more modified plants.

70. A method of producing a modified tobacco plant to reduce or eliminate suckers, said method comprising introducing one or more mutations in one or more tobacco genome loci.

71. The method of embodiment 69, wherein said one or more mutations are introduced via a system selected from the group consisting of chemical mutagenesis, irradiation mutagenesis, transposon mutagenesis, *Agrobacterium*-mediated transformation, a meganuclease, a ZFN, a TALEN, a CRISPR/Cas9 system, a CRISPR/Cpf1 system, and a combination thereof.

72. A recombinant DNA construct comprising:
    a. a promoter that is functional in an L1 layer, an L2 layer, an L3 region, a rib zone, a central zone, a peripheral zone, or a combination thereof; and
    b. a heterologous and operably linked to an artificial microRNA, wherein said artificial miRNA has at least 70% identity to an RNA encoding a polypeptide having at least 70% sequence identity to a polypeptide selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 70, 72, 74, 76, 78, 161-185, 187, 189, 191, 197, 199, 224, 229, 231, 233, 235, 237, 239, 241, 243, 245, 247, 249, 251, 253, 255, and wherein said artificial microRNA suppresses the expression of said polypeptide.

73. A plant or seed comprising a recombinant polynucleotide, wherein said recombinant polynucleotide comprises:
    a. a promoter that is functional in an L1 layer, an L2 layer, an L3 region, a rib zone, a central zone, a peripheral zone, or any combination thereof, which is operably linked to b. a structural nucleic acid molecule comprising a nucleic acid sequence, wherein said nucleic acid sequence encodes an auxin biosynthesis protein or an auxin transport protein.

74. A recombinant DNA construct comprising:
   a. a promoter that is functional in an L1 layer, an L2 layer, an L3 region, a rib zone, a central zone, a peripheral zone, or any combination thereof; and
   b. a heterologous and operably linked nucleic acid sequence, wherein said nucleic acid sequence encodes an auxin biosynthesis protein or an auxin transport protein.

75. A recombinant DNA construct comprising a heterologous axillary meristem-specific promoter operably linked to a polynucleotide that encodes an auxin biosynthesis protein or an auxin transport protein.

76. The recombinant DNA construct of embodiment 74, wherein said auxin biosynthesis protein or auxin transport protein is encoded by a polynucleotide encoding a polypeptide having at least 70% sequence identity to a polypeptide selected from the group consisting of SEQ ID NOs: 235, 237, 239, 241, 243, 245, 247, 249, 251, 253, and 255.

77. A tobacco plant, or part thereof, comprising a heterologous promoter having at least 90% sequence identity to a polynucleotide selected from the group consisting of SEQ ID NOs: 113-118, 148-160, 204, and fragments thereof operably linked to a polynucleotide encoding an auxin biosynthesis protein or an auxin transport protein.

78. The tobacco plant, or part thereof, of embodiment 76, wherein said auxin biosynthesis protein or auxin transport protein is encoded by a polynucleotide encoding a polypeptide having at least 70% sequence identity to a polypeptide selected from the group consisting of SEQ ID NOs: 235, 237, 239, 241, 243, 245, 247, 249, 251, 253, and 255.

79. A method for controlling topping-induced suckers in a plant comprising transforming said plant with a recombinant DNA construct, wherein said recombinant DNA construct comprises a promoter that is operably linked to a polynucleotide encoding an auxin biosynthesis protein or an auxin transport protein.

80. The method of embodiment 78, wherein said auxin biosynthesis protein or auxin transport protein is encoded by a polynucleotide encoding a polypeptide having at least 70% sequence identity to a polypeptide selected from the group consisting of SEQ ID NOs: 235, 237, 239, 241, 243, 245, 247, 249, 251, 253, and 255.

81. The modified tobacco plant of embodiment 23, wherein said fewer total suckers comprises at least 10%, at least 15%, at least 20%, at least 25%, at least 30%, at least 35%, at least 40%, at least 45%, at least 50%, at least 60%, at least 70%, at least 80%, at least 90%, or at least 95% fewer total suckers compared to an unmodified control tobacco plant grown under comparable conditions.

82. The modified tobacco plant of embodiment 24, wherein said reduced mass comprises at least 10%, at least 15%, at least 20%, at least 25%, at least 30%, at least 35%, at least 40%, at least 45%, at least 50%, at least 60%, at least 70%, at least 80%, at least 90%, or at least 95% reduced mass compared to the mass of suckers of an unmodified control tobacco plant grown under comparable conditions.

83. The modified tobacco plant of embodiment 24, wherein said reduced length comprises at least 10%, at least 15%, at least 20%, at least 25%, at least 30%, at least 35%, at least 40%, at least 45%, at least 50%, at least 60%, at least 70%, at least 80%, at least 90%, or at least 95% reduced length compared to the length of suckers of an unmodified control tobacco plant grown under comparable conditions.

84. A modified tobacco plant comprising no or reduced suckers compared to a control tobacco plant of the same variety when grown under comparable conditions, wherein said modified tobacco plant comprises a transgene encoding a polypeptide at least 90% identical or similar to the amino acid sequence of SEQ ID NO: 79 operably linked to a promoter comprising a nucleic acid sequence at least 90% identical to a sequence selected from the group consisting of SEQ ID NOs: 148 and 157.

85. The modified tobacco plant of embodiment 84, wherein nucleic acid sequence is at least 95% identical to a sequence selected from the group consisting of SEQ ID NOs: 148 and 157.

86. The modified tobacco plant of embodiment 84, wherein nucleic acid sequence is 100% identical to a sequence selected from the group consisting of SEQ ID NOs: 148 and 157.

87. The modified tobacco plant of any one of embodiments 84-86, wherein said reduced suckers comprises at least 10% fewer suckers.

88. The modified tobacco plant of any one of embodiments 84-87, wherein said reduced suckers comprises reduced mass, reduced length, or both.

89. The modified tobacco plant of any one of embodiments 84-88, wherein said modified tobacco plant requires reduced management for controlling suckers compared to a control tobacco plant when grown under comparable conditions.

90. The modified tobacco plant of embodiment 89, wherein said reduced management comprises reduced manual removal frequency to control suckers, reduced chemical application frequency to control suckers, reduced quantities of chemical application to control suckers, or any combination thereof.

91. The modified tobacco plant of any one of embodiments 84-90, wherein said suckers are topping-induced suckers.

92. The modified tobacco plant of embodiment 91, wherein said reduced topping-induced suckers comprises fewer total suckers, smaller suckers, or both when compared to topping-induced suckers of a control tobacco plant when grown under comparable conditions.

93. A tobacco leaf of the modified tobacco plant of any one of embodiments 84-92.

94. A tobacco product comprising cured tobacco material from the modified tobacco plant of any one of embodiments 84-92.

95. The tobacco product of embodiment 94, wherein said tobacco product is selected from the group consisting of a cigarette, a kretek, a bidi cigarette, a cigar, a cigarillo, a non-ventilated cigarette, a vented recess filter cigarette, pipe tobacco, snuff, chewing tobacco, moist smokeless tobacco, fine cut chewing tobacco, long cut chewing tobacco, pouched chewing tobacco product, gum, a tablet, a lozenge, and a dissolving strip.

96. A modified tobacco plant comprising a non-naturally occurring mutation positioned in a nucleic acid molecule encoding a polypeptide having the amino acid sequence of SEQ ID NO: 78.
97. The modified tobacco plant of embodiment 96, wherein said nucleic acid molecule comprises SEQ ID NO: 77.
98. The modified tobacco plant of embodiment 96 or 97, wherein said modified tobacco plant comprises no or reduced suckers as compared to a control tobacco plant of the same variety when grown under comparable conditions.
99. The modified tobacco plant of any one of embodiments 96-98, wherein said modified tobacco plant exhibits delayed axillary bud outgrowth as compared to a control tobacco plant of the same variety when grown under comparable conditions.
100. The modified tobacco plant of any one of embodiments 96-99, wherein said mutation is a null mutation.
101. A method of generating a modified tobacco plant comprising:
  a. editing a nucleic acid molecule encoding a polypeptide having the amino acid sequence of SEQ ID NO: 78 in a tobacco cell;
  b. regenerating a modified tobacco plant from said tobacco cell, wherein said tobacco plant comprises no or reduced suckers compared to a control tobacco plant of the same variety when grown under comparable conditions.
102. The method of embodiment 101, wherein said editing comprises the use of a nuclease selected from the group consisting of a meganuclease, a zinc-finger nuclease, a transcription activator-like nuclease, a CRISPR/Cas9 nuclease, a CRISPR/Cpf1 nuclease, a CRISPR/CasX nuclease, a CRISPR/CasY nuclease, and a CRISPR/Csm1 nuclease.
103. The method of embodiment 101 or 102, wherein said modified tobacco plant comprises an edited nucleic acid molecule at least 99% identical or complementary to SEQ ID NO: 77.

Having now generally described the disclosure, the same will be more readily understood through reference to the following examples that are provided by way of illustration, and are not intended to be limiting of the present disclosure, unless specified.

EXAMPLES

Example 1. Identification of Topping-Inducible Genes

RNA samples from 4 week old TN90 tobacco plants are obtained from 10 tissue types (axillary buds before topping; axillary buds 2 hours after topping; axillary buds 6 hours after topping; axillary buds 24 hours after topping; axillary buds 72 hours after topping; roots before topping; roots 24 hours after topping; roots 72 hours after topping; young leaf at the time of topping; and shoot apical meristem). The resulting RNA samples (three independently collected samples for each tissue type) are used as starting material for Illumina 1×100 bp sequencing.

Illumina reads are mapped and used to identify a list of candidate genes exhibiting high axillary bud expression. Expression of candidate genes is confirmed using RT-PCR. See U.S. patent application Ser. No. 14/875,928, filed on Oct. 6, 2015, published on Sep. 29, 2016 as US 2016/0281100, which is herein incorporated by reference in its entirety. After confirming candidate genes are differentially expressed in axillary buds, full-length candidate genes are cloned using gene specific primers designed from predicted full-length cDNA sequences (Table 2A). Normalized Illumina read counts for selected loci are provided in Table 2B.

TABLE 2A

Selected full-length candidate tobacco genes exhibiting differential expression in axillary buds

| SEQ ID NO (DNA/peptide) | Coding Sequence | Polynucleotide Length (nucleotides) | Polypeptide Length (amino acids) | Annotation |
|---|---|---|---|---|
| 1/2 | Full length confirmed | 987 | 328 | Transcription factor CYCLOIDEA-like |
| 3/4 | Full length confirmed | 318 | 105 | Flower-specific gamma-thionin |
| 5/6 | Full length confirmed | 1797 | 598 | Polyphenoloxidase |
| 7/8 | Full length confirmed | 1392 | 463 | UDP-glucose:glucosyltransferase |
| 9/10 | Full length confirmed | 405 | 134 | Tumor-related protein |
| 11/12 | Full length confirmed | 630 | 209 | Hypothetical protein |
| 13/14 | Full length confirmed | 1143 | 380 | TCP1 protein-like gene |
| 15/16 | Full length confirmed | 915 | 304 | Chlorophyllase-2 |
| 17/18 | Full length confirmed | 1353 | 450 | AP2/ERF domain-containing transcription factor |
| 19/20 | Full length confirmed | 732 | 243 | Putative miraculin |
| 186/187 | Pseudo gene | 2340 | 87 | (E,E)-geranyllinalool synthase |
| 21/22 | Full length confirmed | 471 | 156 | Oleosin |
| 23/24 | Full length confirmed | 1437 | 478 | ACC synthase |

TABLE 2A-continued

Selected full-length candidate tobacco genes exhibiting differential expression in axillary buds

| SEQ ID NO (DNA/peptide) | Coding Sequence | Polynucleotide Length (nucleotides) | Polypeptide Length (amino acids) | Annotation |
|---|---|---|---|---|
| 25/26 | Full length confirmed | 645 | 214 | LOB domain-containing protein 18-like |
| 27/28 | Full length confirmed | 2205 | 734 | Vicilin-like antimicrobial peptides cupin super family |
| 29/30 | Full length confirmed | 1302 | 433 | Abscisic acid insensitive |
| 31/32 | Full length confirmed | 1266 | 421 | Seipin-like |
| 33/34 | Full length confirmed | 597 | 198 | Transcription factor CYCLOIDEA-like |
| 35/36 | Full length confirmed | 1038 | 345 | Transcription factor DICHOTOMA-like |
| 37/38 | Full length confirmed | 1014 | 337 | Transcription factor CYCLOIDEA-like |

TABLE 2B

Normalized Illumina read counts for selected candidate genes.

| SEQ NO ID (DNA/Peptide) | Axillary Buds Before Topping | Axillary Buds After Topping | | | | Roots Before Topping | Roots After Topping | | Shoot Apical Meristem | Young Leaf |
|---|---|---|---|---|---|---|---|---|---|---|
| | | 2 hrs | 6 hrs | 24 hrs | 72 hrs | | 24 hrs | 72 hrs | | |
| 1/2 | 1,072 | 998 | 1,346 | 663 | 652 | 7 | 9 | 11 | 180 | 47 |
| 3/4 | 1,387 | 927 | 3,527 | 44,790 | 23,270 | 108 | 90 | 128 | 8,913 | 72 |
| 5/6 | 763 | 1,132 | 1,852 | 5,559 | 2,644 | 110 | 156 | 80 | 513 | 7 |
| 9/10 | 2,342 | 2,357 | 2,992 | 3,143 | 2,190 | 38 | 28 | 27 | 26 | 103 |
| 11/12 | 47 | 29 | 54 | 18 | 17 | 1 | 0 | 0 | 23 | 1 |
| 13/14 | 128 | 131 | 187 | 69 | 54 | 0 | 1 | 1 | 13 | 0 |
| 15/16 | 124 | 308 | 1,619 | 337 | 136 | 217 | 143 | 160 | 88 | 234 |
| 17/18 | 3 | 162 | 186 | 9 | 9 | 22 | 22 | 29 | 6 | 2 |
| 19/20 | 41 | 98 | 334 | 136 | 101 | 1 | 0 | 0 | 50 | 0 |
| 186/187 | 1,479 | 1,486 | 4,216 | 16,176 | 12,228 | 46 | 36 | 33 | 2,144 | 839 |
| 21/22 | 52 | 27 | 81 | 13 | 9 | 2 | 1 | 3 | 5 | 1 |
| 23/24 | 152 | 114 | 135 | 46 | 45 | 2 | 2 | 2 | 1 | 0 |
| 25/26 | 60 | 34 | 22 | 17 | 13 | 2 | 4 | 1 | 30 | 1 |
| 29/30 | 624 | 583 | 1,279 | 300 | 215 | 14 | 9 | 18 | 71 | 9 |
| 31/32 | 176 | 121 | 253 | 95 | 70 | 7 | 1 | 1 | 69 | 27 |
| 33/34 | 268 | 279 | 410 | 231 | 207 | 1 | 1 | 1 | 22 | 11 |
| 35/36 | 193 | 241 | 366 | 117 | 123 | 2 | 2 | 2 | 13 | 1 |
| 37/38 | 394 | 353 | 505 | 207 | 204 | 2 | 2 | 1 | 34 | 2 |

Example 2. Development of Modified Plants

Figure 1:
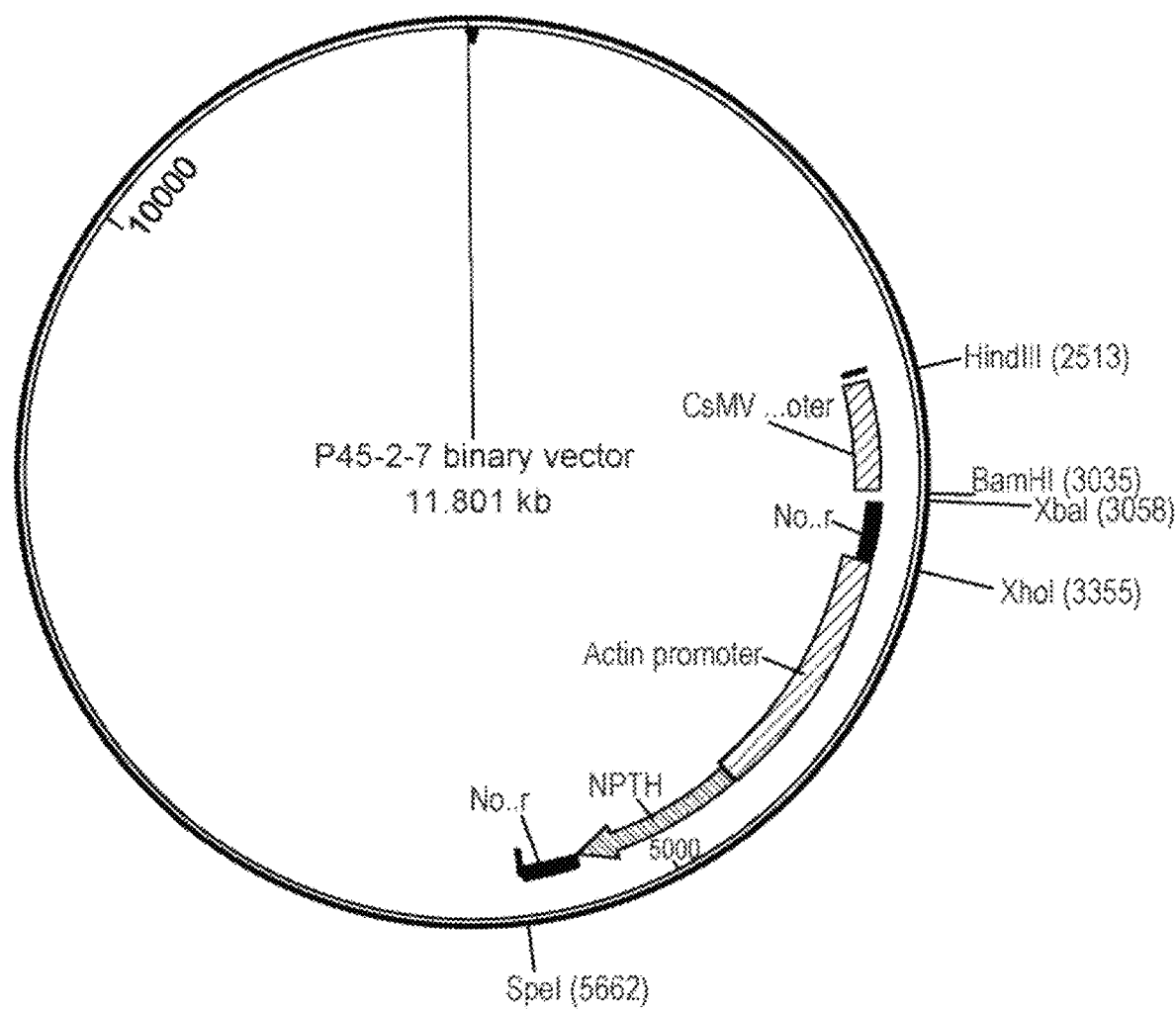
FIG. 1 is a plasmid map of binary vector p45-2-7 (SEQ ID NO: 112).

An expression vector, p45-2-7 (SEQ ID NO: 112; FIG. 1), is used as a backbone to generate multiple transformation vectors (See Examples 6-10 and 13-20). p45-2-7 contains a CsVMV promoter, a NOS terminator, and a cassette comprising a kanamycin selection marker (NPT II) operably linked to an Actin2 promoter and a NOS terminator. Nucleic acid vectors comprising transgenes of interest are introduced into tobacco leaf discs via *Agrobacterium* transformation. See, for example, Mayo et al., 2006, *Nat Protoc.* 1:1105-11 and Horsch et al., 1985, *Science* 227:1229-1231.

Narrow Leaf Madole (NLM) tobacco plants are grown in Magenta™ GA-7 boxes and leaf discs are cut and placed into Petri plates. *Agrobacterium tumefaciens* cells comprising a transformation vector are collected by centrifuging a 20 mL cell suspension in a 50 mL centrifuge tube at 3500 RPM for 10 minutes. The supernatant is removed and the *Agrobacterium tumefaciens* cell pellet is re-suspended in 40 mL liquid re-suspension medium. Tobacco leaves, avoiding the midrib, are cut into eight 0.6 cm discs with a #15 razor blade and placed upside down in a Petri plate. A thin layer of Murashige & Skoog with B5 vitamins liquid re-suspension medium is added to the Petri plate and the leaf discs are poked uniformly with a fine point needle. About 25 mL of the *Agrobacterium tumefaciens* suspension is added to the Petri plate and the leaf discs are incubated in the suspension for 10 minutes.

Leaf discs are transferred to co-cultivation Petri plates (½ MS medium) and discs are placed upside down in contact with filter paper overlaid on the co-cultivation TOM medium (MS medium with 20 g/L sucrose; 1 mg/L indole-3-acetic acid; and 2.5 mg/L 6-benzyl aminopurine (BAP)). The Petri plate is sealed with parafilm prior to incubation in dim light (60-80 mE/ms) with 18 hours on, 6 hours off photoperiods at 24 degrees Celsius for three days. After incubation, leaf discs are transferred to regeneration/selection TOM K medium Petri plates (TOM medium plus 300 mg/L kanamycin). Leaf discs are sub-cultured bi-weekly to fresh TOM K medium in dim light with 18 hours on, 6 hours off photoperiods at 24 degrees Celsius until shoots become excisable. Shoots from leaves are removed with forceps and inserted in MS basal medium with 100 mg/L kanamycin. Shoots on MS basal medium with 100 mg/L kanamycin are incubated at 24 degrees Celsius with 18 hours on, 6 hours off photoperiods with high intensity lighting (6080 mE/ms) to induce rooting.

When plantlets containing both shoots and roots grow large enough (e.g., reach approximately half the height of a Magenta™ GA-7 box), they are transferred to soil. Established seedlings are transferred to a greenhouse for further analysis and to set seed. Evaluation of suckering phenotypes is conducted by growing modified plants (T0, T1, T2, or later generations) and control plants to layby stage. Control plants are either NLM plants that have not been transformed or NLM plants that have been transformed with an empty p45-2-7 vector. Plants that have reached layby stage are manually topped (the shoot apical meristem and surrounding tissue is removed), and axillary bud growth is evaluated at specific time points after topping. Observations are typically performed at the time of topping (i.e., 0 hours), 24 hours (i.e., 1 day) after topping, 7-8 days after topping (i.e., one week), and/or 14-15 days (i.e., two weeks) after topping. Observations comprise qualitatively examining the presence or absence of axillary bud growth and overall plant appearance. Observations also comprise quantitatively measuring the fresh weight of all axillary buds at a specific time point after topping and/or measuring the length of all axillary bud outgrowths at a specific time point after topping.

Example 3. Identification of Tobacco Genes that Function in Sucker Development

Transformation vectors and modified tobacco plants are generated to over-express full-length coding sequences from tobacco genes (e.g., SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 57, 59, and 69).

Figure 2:
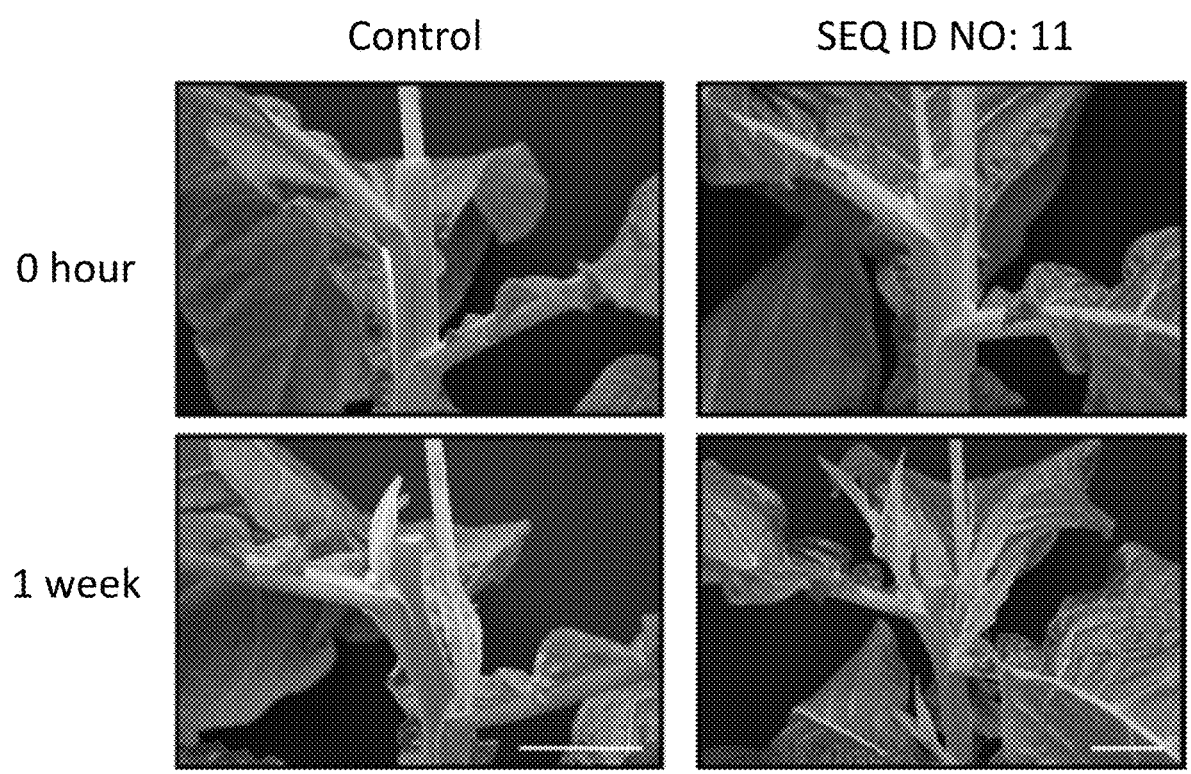
FIG. 2 shows photographs of control tobacco plants and modified tobacco plants that overexpress SEQ ID NO: 11, which encodes a product that promotes sucker growth in tobacco. Plants are shown at the time of topping (0 hour) and one week after topping. Modified plants exhibit increased sucker growth compared to control plants.

As an illustration, SEQ ID NO: 11 is incorporated into a p45-2-7 transformation vector, and modified tobacco plants are generated, according to Example 2. Modified tobacco plants (T0 generation) and control tobacco plants are grown to the layby stage, then plants are topped to remove the shoot apical meristem according to Example 2. Sucker growth is evaluated at the time of topping and one week after topping. Overexpression of SEQ ID NO:11 increases bud outgrowth in tobacco, indicating expression of SEQ ID NO: 11 promotes sucker growth (FIG. 2).

Example 4. Expression of Non-Tobacco Origin Genes that Affect Tobacco Sucker Growth Multiple genes have been identified to play a role in sucker growth in non-tobacco species. Transformation vectors and modified tobacco plants are generated to express non-tobacco origin full-length genes (e.g., SEQ ID NOs: 55, 67, 79, and 81). SEQ ID NO: 81 (encoding *Arabidopsis thaliana* BRANCHED1 (BRC1)) is incorporated into a p45-2-7 transformation vector and modified tobacco plants are generated according to Example 2. In *Arabidopsis*, BRC1 is expressed in developing buds, where it functions to arrest bud development. See, for example, González-Grandío et al., 2013, *Plant Cell* 25: 834-850, which is herein incorporated by reference in its entirety.

Figures 3, 3A:
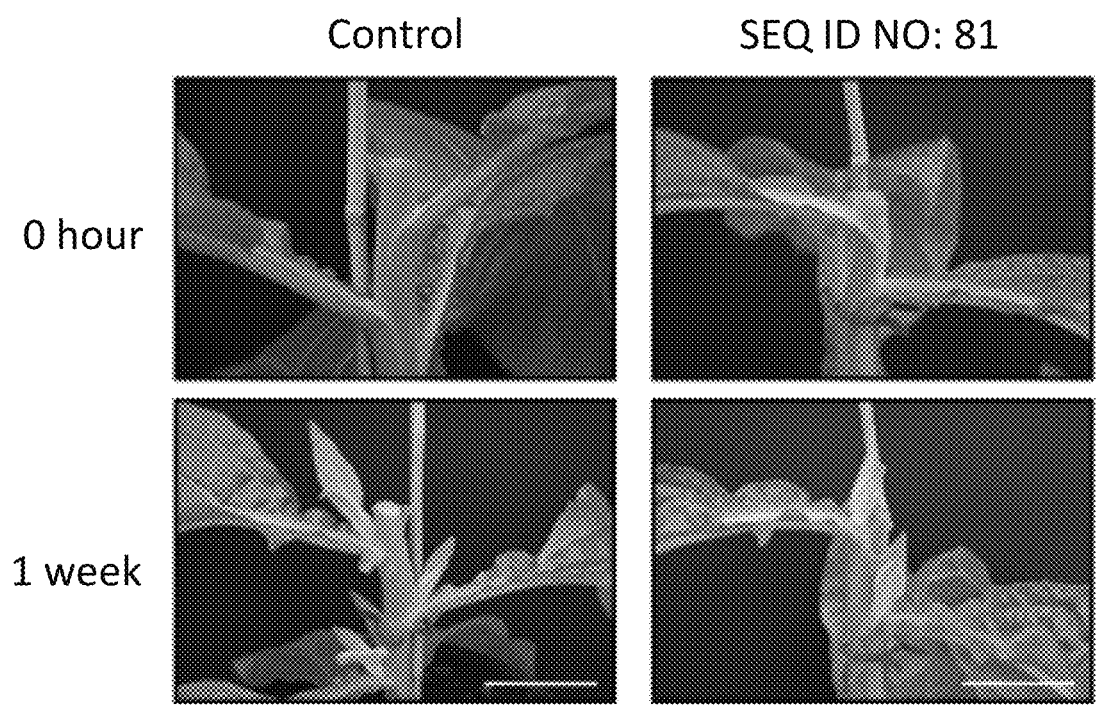
FIG. 3 shows photographs of control tobacco plants and modified tobacco plants that overexpress SEQ ID NO: 81, which encodes *Arabidopsis thaliana* BRANCHED1.
FIG. 3A shows plants at the time of topping (0 hour) and one week after topping. Modified plants exhibit decreased sucker growth compared to control plants.
Figures 3, 3B:
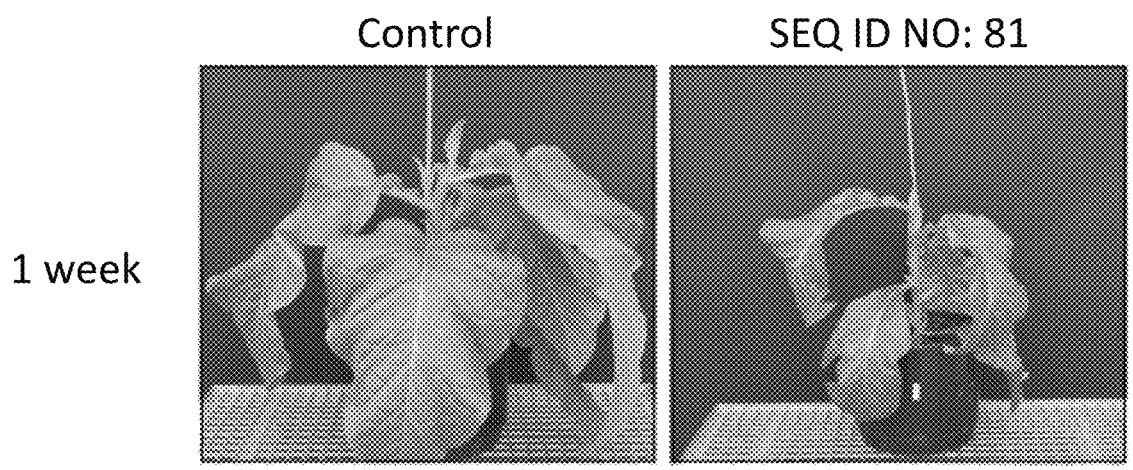
FIG. 3B shows that modified plants overexpressing SEQ ID NO: 81 exhibit stunted growth compared to control plants.

Modified tobacco plants (T0 generation) and control tobacco plants are grown to the layby stage, then plants are topped to remove the shoot apical meristem according to Example 2. Sucker growth is evaluated at the time of topping and one week after topping (FIG. 3A). Expression of SEQ ID NO: 81 in tobacco reduces bud outgrowth. These plants also exhibit stunted growth (FIG. 3B).

Example 5. Identification of Native Tobacco Genes that Inhibit Sucker Growth

Transformation vectors and modified tobacco plants are generated to use RNAi to inhibit endogenous tobacco genes (e.g., SEQ ID NOs: 83-107) and identify their role in sucker outgrowth.

Three tobacco genes (SEQ ID NOs: 1, 13, and 35) are identified as TCP-family proteins having homology to *Arabidopsis* BRC1. Transformation vectors and modified tobacco plants are generated according to Example 2; resulting modified tobacco plants are phenotypically evaluated after topping according to Example 2.

Figure 4:
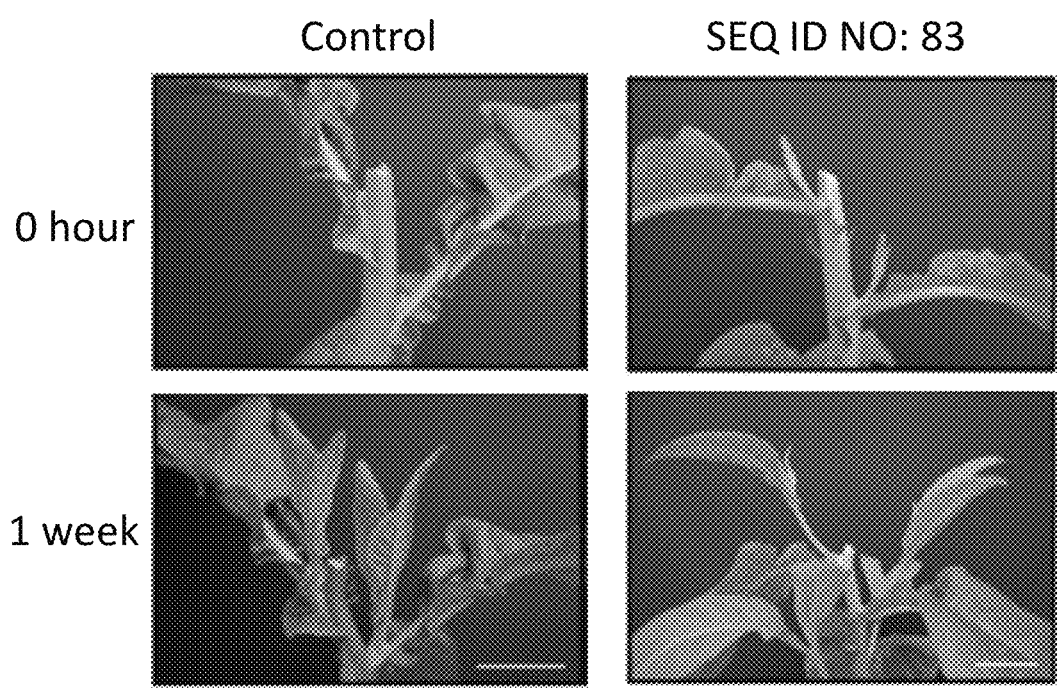
FIG. 4 shows photographs of control tobacco plants and modified tobacco plants that express SEQ ID NO: 83, an RNAi construct that targets SEQ ID NO: 1 for inhibition. Plants are shown at the time of topping (0 hour) and one week after topping. Modified plants exhibit enhanced suckering compared to control plants.

A first transformation vector comprises SEQ ID NO: 83 inserted into a p45-2-7 backbone for constitutive suppression of native SEQ ID NO: 1 via RNAi, and plants comprising this vector are hereinafter referred to as RNAi_1 plants. RNAi_1 tobacco plants (T0 generation) and control tobacco plants are grown to the layby stage, then plants are topped to remove the shoot apical meristem. Sucker growth is evaluated at the time of topping and one week after topping. Bud outgrowth is apparent in RNAi_1 plants prior to topping, and bud outgrowth increases after topping (FIG. 4). RNAi_1 T1 generation plants continue to show increased bud outgrowth (FIGS. 5A and B) at least two weeks after topping. The fresh weight of all axillary shoots two weeks after topping in T1 RNAi_1 plants averages ~600 grams; the fresh weight of all axillary shoots two weeks after topping of control plants is ~300 grams (FIG. 5B). These results indicate SEQ ID NO: 1 functions to inhibit sucker outgrowth in tobacco.

A second transformation vector comprises SEQ ID NO: 86 inserted into a p45-2-7 backbone. This second transformation vector is designed to repress native SEQ ID NO: 13 via RNAi mechanisms, and plants comprising this vector are hereinafter referred to as RNAi_7 plants. RNAi_7 tobacco plants (T0 generation) and control tobacco plants are grown to the layby stage, then plants are topped to remove the shoot apical meristem. Sucker growth is evaluated at the time of topping and one week after topping. Bud outgrowth increases in RNAi_7 plants (FIG. 6). T1 generation RNAi_7 plants continue to show increased bud outgrowth (FIG. 7) at least two weeks after topping. The fresh weight of all axillary shoots two weeks after topping in seven T1 RNAi_7 plant lines average ~600 grams, ~700 grams, ~400 grams, ~250 grams, ~200 grams, and ~375 grams; the fresh weight of all axillary shoots two weeks after topping of control plants is ~300 grams (FIG. 7). These results indicate SEQ ID NO: 13 functions to inhibit sucker outgrowth in tobacco.

A third transformation vector comprises SEQ ID NO: 95 inserted into a p45-2-7 backbone. This third transformation vector is designed to repress native SEQ ID NO: 35 via RNAi mechanisms, and plants comprising this vector are hereinafter referred to as RNAi_18 plants. RNAi_18 plants develop axillary branches at every node prior to topping (FIG. 8). These results indicate SEQ ID NO: 35 functions to inhibit sucker outgrowth in tobacco.

Example 6. Identification of Native Tobacco Genes that Promote Sucker Growth

Some tobacco genes natively function to promote sucker outgrowth. Inhibiting these genes using RNAi constructs decreases sucker outgrowth and positively identifies the genes as promoters of sucker outgrowth in tobacco. Transformation vectors designed to inhibit predicted promoters of sucker outgrowth via RNAi mechanisms are created according to Example 2; modified tobacco plants comprising the transformation vectors are created and phenotypically evaluated according to Example 2.

A transformation vector is created to comprise SEQ ID NO: 101 in a p45-2-7 backbone, which is homologous to a region of CET2, a CENTRORADIALIS (CEN)-like gene from Tobacco (SEQ ID NOs: 108-110). CET genes are not expressed in the shoot apical meristem in tobacco, although CEN is required for shoot apical meristem growth in *Antirrhinum majus*. In tobacco, expression of CEN extends the vegetative phase and delays flowering. See, for example, Amaya et al., 1999, *Plant Cell* 11:1405-1418, which is herein incorporated by reference in its entirety. Plants comprising a transformation vector comprising SEQ ID NO: 101 are hereinafter referred to as RNAi_NtCET2 plants.

RNAi_NtCET2 plants (T0 generation), and control tobacco plants are grown to the layby stage, then plants are topped to remove the shoot apical meristem. Sucker growth is evaluated at the time of topping and one week after topping. Bud outgrowth is reduced in RNAi_NtCET2 plants (FIG. 9), indicating that native NtCET2 promotes sucker outgrowth.

Another transformation vector comprises SEQ ID NO: 96, and plants comprising this vector are hereinafter referred to as RNAi_26 plants. RNAi_26 plants (T0 generation) and control tobacco plants are grown to the layby stage, then plants are topped to remove the shoot apical meristem. Sucker growth is evaluated at the time of topping and one week after topping. Bud outgrowth decreases in RNAi_26 plants (FIG. 10), indicating that SEQ ID NO: 49 natively functions to promote sucker outgrowth.

Example 7. Identification of Axillary Bud-Specific Promoters

Expression of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 67, 69, 79, 81, and 83-107 (See Examples 6-8) can be better utilized to reduce or eliminate sucker outgrowth in modified plants if the polynucleotides are expressed in a tissue-dependent manner (e.g., only in the axillary bud). The expression pattern of 28 candidate genes is analyzed, and promoters of the genes having high expression in axillary buds, but low expression in other tissues, are selected (Table 3). Expression patterns of the candidate genes are confirmed by real-time PCR analysis. Six axillary meristem-specific promoters (SEQ ID NOs: 113-118) are cloned by PCR methods from tobacco TN90 genomic DNA using gene-specific primers.

Expression patterns of candidate promoters are analyzed by transformation of tobacco with a chimeric candidate promoter::beta-glucuronidase (GUS) reporter gene within the same plasmid backbone (p45-2-7) described in Example 2. The chimeric gene is introduced via *Agrobacterium*-mediated transformation into an NLM line. GUS staining is used to identify tissue-specific promoter expression following the method of Crone et al., 2001, *Plant Cell Environ.* 24:869-874.

Briefly, tissue from young seedlings comprising a candidate promoter::GUS transformation construct is placed in cold 90% acetone on ice. When all samples are harvested, samples are placed at room temperature for 20 minutes. Samples are placed back on ice and acetone is removed from the samples. Next, staining buffer (0.2% Triton X-100; 50 mM $NaHPO_4$, pH7.2; 2 mM potassium ferrocyanide) is added to the samples. X-Gluc is added to the staining buffer to a final concentration of 2 mM. Staining buffer is removed from the samples and fresh staining buffer with X-Gluc is added. The samples are then infiltrated under vacuum, on ice, for 15 to 20 minutes. The samples are incubated at 37 degrees Celsius for 2-18 hours before the staining buffer is removed. Samples are washed through an ethanol series (i.e., 10%, 30%, 50%, 70%, 95%) in the dark for 30 minutes per wash. Finally, samples are transferred into 100% ethanol.

GUS-positive plant tissues are examined with a brightfield microscope (Leica Q500MC; Cambridge, England) at a low magnification and photographed with a digital camera. Results of experiments using three different promoters (SEQ ID NOs: 113, 116, and 117) are shown in FIGS. 11, 12, and 13, respectively. These promoter sequences can be used to drive the expression of a sequence of interest exclusively, or predominantly, within an axillary bud while limiting expression in the rest of the plant.

GUS-positive expression, indicating expression driven by SEQ ID NOs: 113, 116, and 117, is concentrated in axillary buds. Thus, SEQ ID NOs: 113, 116, and 117 are tissue-specific promoters that are active in axillary buds, but not in stem or leaf tissue (FIGS. 11, 12, and 13). The expression of GUS under the direction of SEQ ID NOs: 113 (Promoter P1, hereinafter) and 116 (Promoter P11, hereinafter) decreases after topping, which coincides with the gene expression pattern that is observed for the endogenous genes that are normally regulated by these promoters (FIGS. 11 and 12). Promoter P1 and Promoter P11 are also functional in the tobacco shoot apical meristem. (FIGS. 11 and 12).

In contrast, SEQ ID NO: 117 (Promoter P15, hereinafter) drives GUS expression in the axillary meristem prior to topping and for at least fifteen days after topping, which coincides with the gene expression pattern that is observed for the endogenous gene that is normally regulated by this promoter (FIGS. 13A-C). Promoter P15 is also functional in the base of the shoot apical meristem (FIG. 13A).

Additional candidate promoters of topping-inducible, and tissue-specific, promoters to control sucker outgrowth include SEQ ID NOs: 148-160 and 204, which represent an axillary bud-specific thionin 5' upstream regulatory sequence (SEQ ID NO: 148); a tobacco lateral suppressor 1 (LAS1) 5' upstream regulatory sequence (SEQ ID NO: 149); a LAS1 3' downstream regulatory sequence (SEQ ID NO: 150); a LAS2 5' upstream regulatory sequence (SEQ ID NO: 151); a LAS2 3' downstream regulatory sequence (SEQ ID NO: 152); a tobacco regulator of axillary meristems1 (RAX1) 5' upstream regulatory sequence (SEQ ID NO: 153); a RAX1 3' downstream regulatory sequence (SEQ ID NO: 154); a RAX2 5' upstream regulatory sequence (SEQ ID NO: 155); a RAX2 3' downstream regulatory sequence (SEQ ID NO: 156); a Promoter P15 5' region (SEQ ID NO: 157); a Promoter P15 3' downstream region, (SEQ ID NO: 158); a 5' upstream regulatory sequence of a P15 homolog (SEQ ID NO: 159); a 3' downstream regulatory sequence of a P15 homolog (SEQ ID NO: 160); and a regulatory region of a P15 homolog from tomato (*Solanum lycopersicum*) (SEQ ID NO: 204). The sequences are cloned by PCR methods from NLM genomic DNA using gene-specific primers. These regulatory sequences are tested for their tissue specificity and developmental regulation as shown for Promoters P1, P11, and P15. The regulatory sequences that exhibit axillary meristem-specific or -preferential expression are used for driving heterologous gene expression and modulating sucker growth.

TABLE 3

Selected clones for promoter analysis

| SEQ ID NO | Length of Promoter |
|---|---|
| 113 | 2248 |
| 114 | 2800 |
| 115 | 3356 |
| 116 | 3150 |
| 117 | 2964 |
| 118 | 941 |
| 148 | 5000 |
| 149 | 5000 |
| 150 | 5000 |
| 151 | 5000 |
| 152 | 5000 |
| 153 | 5000 |
| 154 | 5000 |
| 155 | 5000 |
| 156 | 5000 |
| 157 | 5000 |
| 158 | 5000 |
| 159 | 5000 |
| 160 | 5000 |
| 204 | 5000 |

TABLE 4

Axillary bud-preferred promoter cis-elements

| Cis-regulatory element Name | Cis-regulatory element Nucleotide Sequence |
|---|---|
| Bud Dormancy Element (BDE) | CACGTG |
| Axillary Bud Growth (Up1) | GGCCCAW |
| Axillary Bud Growth (Up2) | AAACCCTA |
| Sucrose Responsive Element (SURE) | AATAGAAAA |
| Sugar Repressive Element (SRE) | TTATCC |
| Bud Activation Element or TCP Binding Element (BAE) | GGCCCAT |

Example 8. Cellular Specificity of Promoter P1, Promoter P15, and Promoter PAB Thionin To analyze the expression pattern of Promoter P1 (SEQ ID NO: 113) and Promoter P15 (SEQ ID NO: 117) at the cellular level in meristem regions, vectors are produced comprising a green fluorescent protein (GFP) gene under the control of either Promoter P1 or Promoter P15 as described in Example 2. The chimeric vectors are introduced into an NLM tobacco plant via *Agrobacterium*-mediated transformation. GFP expression is observed using fluorescence microscopy. Promoter P15 is restricted to tissue within the axillary buds (FIG. 14A). Promoter P1 has a slightly broader expression pattern (FIG. 14B).

To analyze the expression pattern of a 0.9 kb long Promoter PAB Thionin (pABTh-0.9 kb, SEQ ID NO: 118) at the cellular level in meristem regions, a vector is produced comprising a GUS gene under the control of Promoter PAB Thionin as described in Example 2. The chimeric vector is introduced into an NLM tobacco plant via *Agrobacterium*-mediated transformation. GUS expression is observed in axillary bud tissue and meristem tissue (FIG. 15).

Promoters P1, P15, and PAB Thionin (pABth-5 kb, SEQ ID NO: 148) are analyzed for similar and/or unique cis-regulatory elements. Six cis-regulatory elements are identified (Table 4) upstream of the transcriptional start sites of the genes natively regulated by Promoters P1, P15, and PAB Thionin (FIG. 16). These cis-regulatory elements can have direct and/or indirect effects towards regulating sucker-specific or meristem-specific expression patterns.

Example 9. Efficacy Testing of Sucker Inhibiting Constructs

After testing of the tissue-specific expression patterns of candidate promoters using promoter::GUS fusion analysis in transgenic plants, vectors and modified plants are constructed as described in Example 2 to express target genes only in axillary buds. Exemplary constructs are shown in Table 5.

TABLE 5

Exemplary constructs for axillary bud-specific expression of a target gene.

| Construct | Promoter SEQ ID NO. | Target Gene SEQ ID NO. |
|---|---|---|
| 1 | 113 | 17 |
| 2 | 113 | 104 |
| 3 | 113 | 7 |
| 4 | 113 | 41 |
| 5 | 113 | 5 |
| 6 | 118 | 17 |
| 7 | 118 | 104 |
| 8 | 118 | 7 |
| 9 | 118 | 41 |
| 10 | 118 | 5 |
| 11 | 115 | 17 |
| 12 | 115 | 104 |
| 13 | 115 | 7 |
| 14 | 115 | 41 |
| 15 | 115 | 5 |
| 16 | 117 | 17 |
| 17 | 117 | 104 |
| 18 | 117 | 7 |
| 19 | 117 | 41 |
| 20 | 117 | 5 |

Efficacy testing for the impact of Constructs 1-20 is carried out under greenhouse and field conditions. Transgenic plants and matched wild type controls are grown to layby stage, then topped and phenotypically evaluated as described in Example 2. Field efficacy testing also determines the type and extent of sucker control chemical application needed under normal agronomical practices.

Example 10. Regulating Axillary Bud Outgrowth Via Overexpressing Genes

Sucker outgrowth can be regulated by modifying the expression of genes and/or genetic pathways that regulate branching. Some genes natively function to restrict bud outgrowth and are defined by mutants with increased branching, for example the *Arabidopsis* BRANCHED1 gene (SEQ ID NO:81) and tobacco homologs (SEQ ID NOs: 1, 13, 35, 37, and 39); and the *Arabidopsis* MORE AXILLARY BRANCHING1 (MAX1) and MAX2 genes (SEQ ID NO: 193 and 195) and tobacco homologs (SEQ ID NO: 197 and 199). See, for example, Stirnberg et al., 2002, *Development* 129: 1131-1141, which is herein incorporated by reference in its entirety.

Transformation vectors are created to overexpress proteins that restrict sucker outgrowth in tobacco. Separate transformation vectors comprising one of SEQ ID NOs: 1, 13, 35, 37, 39, and 81 are incorporated into p45-2-7 transformation vectors. Additional transformation vectors are created comprising one of SEQ ID NOs: 1, 13, 35, 37, 39, and 81 driven by the axillary bud-specific Promoter P15 (SEQ ID NO: 117). Modified tobacco plants are generated from these transformation vectors according to Example 2. Modified tobacco plants (T0 generation) and control tobacco plants are then phenotypically evaluated as described in Example 2. The modified tobacco plants exhibit reduced sucker growth compared to control tobacco plants.

Example 11. Regulating Axillary Bud Outgrowth by Suppressing Genes that Promote Sucker Growth Some genes promote axillary meristem development and are defined by mutants with decreased branching. For example, the *Arabidopsis* LAS gene (SEQ ID NO: 201), and homologs in tobacco (SEQ ID NOs: 71 and 73); and the *Arabidopsis* RAX gene (SEQ ID NO: 203), as well as tobacco homologs (SEQ ID NOs: 75 and 77). See, for example, Greb et al., 2003, *Genes & Development* 17: 1175-1187; and Keller et al., 2006, *Plant Cell* 18: 598-611, both of which are herein incorporated by reference in their entireties.

Transformation vectors comprising RNAi constructs are designed to inhibit tobacco proteins that promote sucker outgrowth. Separate transformation vectors comprise one of SEQ ID NOs: 71, 73, 75, and 77, which are incorporated into p45-2-7 transformation vectors. Additional transformation vectors are created comprising one of SEQ ID NOs: 71, 73, 75, and 77 driven by axillary bud-specific Promoter P15 (SEQ ID NO: 117). These vectors are used to generate modified tobacco plants according to Example 2. Modified tobacco plants and control tobacco plants are then phenotypically evaluated as described in Example 2. The modified tobacco plants exhibit reduced sucker growth compared to control tobacco plants.

Example 12. Regulating Sucker Growth with RNAi, Artificial miRNAs and Gene Overexpression A transformation vector is created in which Promoter P15 (SEQ ID NO: 117) drives the expression of SEQ ID NOs: 81 (BRC1) and 101 (RNAi targeting NtCET2) in a tissue-specific manner. The Promoter P15::BRC1::NtCET2 vector over-expresses BRC1 and inhibits NtCET2 in axillary buds. The transformation vector and modified tobacco plants are generated as described in Example 2.

Modified tobacco plants (T0 generation) having a Promoter P15::BRC1::NtCET2 construct and control tobacco plants are grown to the layby stage, then plants are topped to remove the shoot apical meristem. Sucker growth is evaluated at the time of topping, 8 days after topping, and 15 days after topping (FIG. 17). Expression of SEQ ID NOs: 81 and 101, driven by Promoter P15, eliminates sucker growth in tobacco.

Additional transformation vectors are created in which Promoter P15 (SEQ ID NO: 117) drives the expression of an artificial miRNA designed to reduce the transcription or translation of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 69, 71, 73, 75, 77, 123-147, 186, 188, 190, 196, and 198. The transformation vectors and modified tobacco plants are generated as described in Example 2.

Modified tobacco plants (T0 generation) having a Promoter P15::artificial miRNA construct and control tobacco plants are grown to the layby stage, then plants are topped to remove the shoot apical meristem. Modified and control tobacco plants are phenotypically evaluated according to Example 2.

Example 13. Regulating Sucker Growth Via Modifying Cytokinin Synthesis and Distribution Removing the shoot apical meristem releases axillary buds from dormancy and promotes sucker outgrowth. Auxin derived from an intact shoot apical meristem suppresses sucker outgrowth, whereas cytokinin induced by removal of the shoot apical meristem promotes sucker outgrowth.

Depletion of cytokinin in axillary bud regions by over-expressing genes involved in cytokinin catabolism with an axillary bud specific promoter is used to reduce cytokinin and inhibit axillary meristem outgrowth. For example, *Arabidopsis* cytokinin oxidase (CKX; SEQ ID NO: 55), tobacco CKXs (SEQ ID NOs: 57 and 59); and a tobacco adenosine phosphate-isopentenyltransferase gene (SEQ ID NO: 61) are tested. A transformation vector comprising SEQ ID NO: 59 driven by Promoter P15 (SEQ ID NO: 117) is created according to Example 2. Modified tobacco plants are generated using this vector, and then phenotypically evaluated, according to Example 2. The modified tobacco plants exhibit reduced sucker growth compared to control tobacco plants (FIG. 18).

Example 14. Regulating Sucker Growth Via Inhibition of Axillary Meristem Stem Cell Signaling Shoot meristems comprise stem cells that are continuously replenished through a feedback circuit involving the WUSCHEL (WUS)-CLAVATA (CLV) signaling pathway. See, for example, Yadav et al., 2011, *Genes & Development* 25:2025-2030, which is herein incorporated by reference in its entirety. Genes from this pathway include, e.g., WUS (SEQ ID NOs: 63 and 65); CLV1; CLV2; and CLV3 (SEQ ID NOs: 67 and 69). A transformation vector is created comprising SEQ ID NO: 67 driven by Promoter P15 (SEQ ID NO: 117), which causes overexpression of CLV3 in axillary buds. Modified tobacco plants are generated using this transformation vector, and phenotypically evaluated, according to Example 2. The modified tobacco plants exhibit reduced sucker growth compared to control tobacco plants.

Additional transformation vectors are created according to Example 2 to comprise either SEQ ID NO: 63 or 65 driven by Promoter P15 (SEQ ID NO: 117), which inhibit WUS via RNAi. Modified tobacco plants are generated using these transformation vectors, and then phenotypically evaluated, according to Example 2. The modified tobacco plants exhibit reduced sucker growth compared to control tobacco plants.

*Arabidopsis* SHOOT MERISTEMLESS (STM) is a KNOX protein that is essential for shoot meristem formation and maintenance. See, for example, Long et al., 1996, Nature 379:66-69, which is herein incorporated by reference in its entirety. NTH15 (SEQ ID NO: 189) is a tobacco homolog of STM that is expressed in tobacco meristems. See, for example, Tanaka-Ueguchi et al., 1998, *Plant Journal* 15:391-400, which is herein incorporated by references in its entirety. A transformation vector is created comprising an RNAi construct that targets SEQ ID NO: 188 for inhibition, driven by Promoter P15 (SEQ ID NO: 117). Modified tobacco plants are generated using these transformation vectors, and then phenotypically evaluated, according to Example 2. The modified tobacco plants exhibit reduced sucker growth compared to control tobacco plants.

Example 15. Screening for Genes to Control Suckers Using Agroinfiltration

Expression of some plant genes (without being limiting, e.g., RNases; proteases; cell cycle genes; transcription factors; kinases; caspases) can elicit a cell death response when expressed at certain times and/or cell types. Identification of such genes is desired, as they can be operably linked to an axillary bud-preferred or axillary bud-specific promoter (e.g., Promoter P15/SEQ ID NO: 117) to reduce or eliminate axillary bud growth and/or development.

Agroinfiltration is used to transiently express a tobacco genes (e.g., SEQ ID NOs: 201-222, 228, 230, and 232) in tobacco leaves. Plant genes of interest are inserted into a pBIN19 plasmid and transformed into *Agrobacterium tumefaciens* cells. The transformed bacteria are grown in a liquid culture, washed, and suspended in a buffer solution. The buffer solution containing the transformed *A. tumefaciens* cells is injected into one or more living tobacco leaves. Plant leaf phenotypes are then evaluated for presence or absence of cellular death after 5 days. An empty plasmid is used as a negative control, while a plasmid containing a Barnase gene (SEQ ID NO: 79) is used as a positive control. Plant genes inducing cell death in tobacco leaves are used for reducing axillary bud growth and/or development. See, for example, FIG. 21.

*Nicotiana thaliana* mitogen-activated protein kinase kinase 2 (NtMEK2; SEQ ID NO: 232) has been identified as being capable of inducing a cell death response in tobacco. The expression of SEQ ID NO: 232 is directed to axillary buds by driving its expression with Promoter P15 (SEQ ID NO: 117).

Separate transformation vectors are created according to Example 2 to comprise one of SEQ ID NOs: 201-222, 228, 230, and 232 driven by Promoter P15 (SEQ ID NO: 117). Modified tobacco plants are then generated with the Promoter P15::cell death gene vectors, and then phenotypically evaluated, according to Example 2. The modified tobacco plants exhibit reduced sucker growth compared to control tobacco plants.

Example 16. Regulating Sucker Growth Using RNases

The presence of some proteins at elevated levels, in cells where they are not normally expressed, or in subcellular locations where they are not normally located, can induce cell death. Axillary bud specific promoters, such as Promoter P1 (SEQ ID NO: 113) and Promoter P15 (SEQ ID NO: 117) are used to the express heterologous genes that are detrimental to an axillary bud and ultimately result in its death.

RNA-degrading enzymes, such as the bacterial RNase Barnase (SEQ ID NO: 79; and see, e.g., Hartley, 1989, *Trends in Biochemical Sciences* 14:450-454) are used to induce cellular death in the axillary bud when their expression is driven by Promoter P15 (SEQ ID NO: 117). A transformation vector is created according to Example 2 to comprise SEQ ID NO: 79 driven by Promoter P15 (SEQ ID NO: 117). Modified tobacco plants are then generated with the Promoter P15::Barnase vector according to Example 2. Modified tobacco plants (T0 generation) and control tobacco plants are grown to the layby stage, then plants are topped to remove the shoot apical meristem. Sucker growth is observed at the time of topping, 24 hours after topping, one week after topping, two weeks after topping, and three weeks after topping (FIGS. 19 and 20). Expression of SEQ ID NO: 79 driven by Promoter P15 eliminates sucker outgrowth in tobacco.

Additional transformation vectors similar to Promoter P15::Barnase are also created using endogenous tobacco RNases such as: RNase Phy3 (SEQ ID NO: 123), RNase H (SEQ ID NO: 124), RNase P (SEQ ID NO: 125), RNase III (SEQ ID NO: 126), and RNase T2 (SEQ ID NOs: 127-136) in place of Barnase (SEQ ID NO: 79). Each of these vectors is used to generate modified tobacco plants, and to then phenotypically evaluate the tobacco plants, as described in Example 2. The modified tobacco plants exhibit reduced sucker growth compared to control tobacco plants.

Example 17. Regulating Sucker Growth Using Vacuolar Processing Enzymes

Vacuolar processing enzymes (VPEs) are proteases that function in normal plant growth and development, and are also implicated in vacuole-dependent programmed cell death through their caspase-like activity. Eight out of 17 VPE proteins found in the tobacco genome comprise protease domains that contain all the residues required for caspase-like activity (SEQ ID NOs: 137-143). The expression of SEQ ID NOs: 137-143 is directed to axillary buds by driving their expression with Promoter P15 (SEQ ID NO: 117). Expression of proteins encoded by SEQ ID NOs: 137-143 can be further restricted to vacuoles within axillary bud cells by including an N-terminal vacuolar sorting signal.

Separate transformation vectors are created according to Example 2 to comprise one of SEQ ID NOs: 137-143 driven by Promoter P15 (SEQ ID NO: 117). Modified tobacco plants are then generated with the Promoter P15::VPE vectors, and then phenotypically evaluated, according to Example 2. The modified tobacco plants exhibit reduced sucker growth compared to control tobacco plants.

Example 18. Regulating Sucker Growth Using Proteases

Additional plant proteases are expressed in certain tissues to eliminate the cells responsible for axillary shoot meristem development. Proteolytic enzymes are divided into four groups based on their catalytic domain: aspartic proteases, cysteine proteases, metalloproteases, and serine proteases. All of these protease families are found in tobacco and are used to inhibit the development of axillary shoot meristems. For example, an aspartic protease (SEQ ID NO: 144), a cysteine protease (SEQ ID NO: 145), a metalloprotease (SEQ ID NO: 146), or a serine protease (SEQ ID NO: 147) are expressed with a tissue specific promoter (e.g., SEQ ID NOs: 113-118, 148-160, and 204).

Separate transformation vectors are created according to Example 2 to comprise one of SEQ ID NOs: 144-147 driven by Promoter P15 (SEQ ID NO: 117). Modified tobacco plants are then generated with a Promoter P15::protease vector, and then phenotypically evaluated, according to Example 2. The modified tobacco plants exhibit reduced sucker growth compared to control tobacco plants.

Example 19. Genome Editing Using TALEN

Transcription activator-like effector nuclease (TALEN) technology is used to modify commercial tobacco varieties such as TN90, K326 and Narrow Leaf Madole. TALENs enable genetic modification through induction of a double strand break (DSB) in a DNA target sequence. The ensuing DNA break repair by either a non-homologous end joining (NHEJ) or a homology-directed repair (HDR)-mediated pathway is exploited to introduce a desired modification (e.g., gene disruption, gene correction or gene insertion).

PEG-mediated protoplast transformation is used to introduce a TALEN and a donor DNA molecule into a plant cell. Tobacco leaves from 4-8 weeks old tobacco plants from sterile culture are cut into small pieces and transferred into a petri dish containing filter-sterilized enzyme solution containing 1.0% Cellulase onuzuka R10 and 0.5% Macerozym. The leaf strips in the petri dish are vacuum infiltrated for 30 minutes in the dark using a desiccator. After incubation, the digested leaves are resuspended by shaking at 45 R.P.M. for 230 minutes, and then filtered through a sterilized 100 μm nylon filter by collecting in a 50 mL centrifuge tube. The solution is applied to Lymphoprep and separated via centrifugation at 100×g for 10 minutes. Protoplast bands are collected using a pipette, and purified protoplasts are washed with an equal volume of W5n solution containing NaCl, $CaCl_2$, KCl, MES, and glucose, prior to additional centrifugation for 5 minutes at 2000 R.P.M. Protoplast pellets are resuspended at $2 \times 10^5$/mL in W5n solution, and left on ice for 30 minutes. Next, supernatant is removed and protoplast pellets are resuspended in filter-sterilized MMM solution containing mannitol, $MgCl_2$ and MES.

PEG transfection of tobacco protoplasts is performed according to a method described by Zhang et al. (2013, *Plant Physiology* 161:20-27) with some modifications. A 500 μL aliquot of protoplast suspension is transferred into a 10 mL culture tube and 25 μL (~10 μg) of plasmid DNA is slowly added to the protoplasts suspension. Next, 525 μL PEG solution is added to the protoplast-DNA solution and mixed by carefully tapping the tube. Tubes are incubated for 20 minutes, then 2.5 mL W5n solution is added to stop the reaction. The solution is centrifuged at 100×g for 5 minutes, and washed with protoplast culture media. PEG-treated protoplasts are resuspended in 1 mL culture media containing 0.1 mg/L NAA and 0.5 mg/L BAP, and mixed with 1 mL low-melting agar to make protoplast beads. Protoplast beads are cultured in liquid media, and calli growing from protoplast beads are transferred onto solid shooting media. When shoots are well developed, they are transferred into a Magenta™ GA-7 box for root formation. When root systems are fully developed and shoot growth resumes, plants are transplanted into soil.

Multiple TALEN approaches are used to prevent or reduce sucker growth in tobacco. Instead of randomly inserting a gene into a tobacco genome using conventional transformation methods, TALEN is used for targeted replacement of an endogenous coding sequence. In one example, a coding sequence of interest (e.g., SEQ ID NOs: 123-147) can be placed under the control of an axillary bud-specific promoter sequence (e.g., SEQ ID NOs: 113-118, 148-160, and 204), and the construct can be used with a TALEN to homologously recombine the construct into the endogenous genomic region controlled by the promoter. A TALEN donor sequence is shown in SEQ ID NO:119, and a TALEN target sequence is shown in SEQ ID NO:120.

A second example places an axillary bud-specific promoter and a coding sequence of interest under the control of a native axillary bud-specific promoter to provide two doses of promoter control. A construct including a first promoter (SEQ ID NO:118), a second promoter (SEQ ID NO:113), and a coding sequence (SEQ ID NO:13) is homologously recombined into the genomic region containing native SEQ ID NO: 118 using TALEN, thereby directing expression of the coding sequence by both promoters (SEQ ID NO:118 and 113). A TALEN donor sequence is shown in SEQ ID NO:121.

A third example uses TALEN to disrupt a target gene that promotes sucker growth and/or development. TALEN target sequences are identified for nucleic acid sequences (e.g., SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 69, 71, 73, 75, 77, 108-110, 123-147, 186, 188, 190, 196, 198) and nucleic acid sequences encoding polypeptides (e.g., SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 70, 72, 74, 76, 78, 161-185, 187, 189, 191, 197, 199). Gene-specific TALENs are designed and introduced into tobacco cells to cause deletions or insertions in an endogenous target gene. For example, potential TALEN target sites in a coding sequence (SEQ ID NO: 11) are identified, and homologous recombination sites within the coding sequence of the gene are selected. A TALEN target sequence is shown in SEQ ID NO:122 (the target sequences are underlined).

Example 20. Additional Methods of Regulating Sucker Growth Using Gene Editing Technologies Gene editing technologies such as CRISPR/Cas9, CRISPR/Cpf1, zinc-finger nucleases (ZFN), and transcription activator-like effector nucleases (TALENs) are used to replace the coding region of an axillary meristem-specific gene with a cell death/axillary shoot suppressor sequence. These gene editing technologies are also used to edit or replace an endogenous promoter sequence to drive its cognate protein expression in axillary buds. For example, an endogenous RNase promoter is edited or replaced so the RNase is only expressed in axillary buds, where it can function to reduce sucker outgrowth via the induction of cell death. Alternatively, the promoter of an axillary meristem regulator gene is mutated (edited) to eliminate regulatory region(s) required for timely expression during sucker activation and/or outgrowth, which can lead to growth defects and/or death of axillary shoots. Gene editing technologies are further used to edit or replace of an endogenous gene that natively functions in axillary buds. An endogenous gene such as NtCET2 is edited so that it no longer makes a functional protein, thereby inhibiting sucker outgrowth.

Separate CRISPR/Cas9 or CRISPR/Cpf1 guide RNAs are constructed to recognize and hybridize to the promoter sequence of each one of SEQ ID NOs: 123-147. The engineered guide RNA and a donor polynucleotide comprising Promoter P15 (SEQ ID NO: 117) are provided to a tobacco plant, allowing Promoter P15 to replace the endogenous promoter of SEQ ID NO: 123-147 and restrict expression of endogenous SEQ ID NOs: 123-147 to the axillary bud. The edited tobacco plants exhibit reduced sucker growth compared to control tobacco plants.

Example 21. Development of Novel Mutations Via Random Mutagenesis

Random mutagenesis of tobacco plants are performed using ethyl methanesulfonate (EMS) mutagenesis or fast neutron bombardment. EMS mutagenesis consists of chemically inducing random point mutations. Fast neutron mutagenesis consists of exposing seeds to neutron bombardment which causes large deletions through double stranded DNA breakage.

For EMS mutagenesis, one gram (approximately 10,000 seeds) of Tennessee 90 tobacco (TN90) seeds are washed in 0.1% Tween for fifteen minutes and then soaked in 30 mL of ddH$_2$O for two hours. One hundred fifty (150) μL of 0.5% EMS (Sigma, Catalogue No. M-0880) is then mixed into the seed/ddH$_2$O solution and incubated for 8-12 hours (rotating at 30 R.P.M.) under a hood at room temperature (RT; approximately 20° C.). The liquid then is removed from the seeds and mixed into 1 M NaOH overnight for decontamination and disposal. The seeds are then washed twice with 100 mL ddH$_2$O for 2-4 hours. The washed seeds are then suspended in 0.1% agar solution.

The EMS-treated seeds in the agar solution are evenly spread onto water-soaked Carolina's Choice Tobacco Mix (Carolina Soil Company, Kinston, NC) in flats at ~2000 seeds/flat. The flats are then covered with plastic wrap and placed in a growth chamber. Once the seedlings emerge from the soil, the plastic wrap is punctured to allow humidity to decline gradually. The plastic wrap is completely removed after two weeks. Flats are moved to a greenhouse and fertilized with NPK fertilizer. The seedlings are replugged into a float tray and grown until transplanting size. The plants are subsequently transplanted into a field. During growth, the plants self-pollinate to form M1 seeds. At the mature stage, five capsules are harvested from each plant and individual designations are given to the set of seeds from each plant. This forms the M1 population. A composite of M1 seed from each M0 plant are grown, and plants are phenotypically evaluated as described in Example 2. M1 plants exhibiting enhanced or reduced sucker growth are selected and screened for mutations using DNA sequencing and gene mapping techniques known in the art.

Example 22. Regulating Sucker Growth Using Inducible Promoters

Inducible promoters are also used to express a functional gene in a controlled manner to reduce or eliminate sucker development. These promoters are induced by either a chemical spray or at certain time points (i.e., after topping). Exemplary promoters include alcohol-regulated promoters; tetracycline-regulated promoters; steroid-regulated promoters (e.g., glucocorticoid (See, for example, Schena et al., 1991, *Proceedings of the National Academy of Sciences USA* 88:10421-10425, which is herein incorporated by reference in its entirety); human estrogen; ecdysone); and metal-regulated promoters. For example, an RNase (e.g., SEQ ID NOs: 79 and 123-136), a VPE (e.g., SEQ ID NOs: 137-143), or a protease (e.g., SEQ ID NOs: 144-147) are expressed in a tobacco plant with an inducible promoter.

In one example, a first vector containing a rat glucocorticoid receptor under the control of a constitutive CsVMV promoter and a second vector containing a sequence of interest (e.g., SEQ ID NOs: 83-101) operably linked to one or more glucocorticoid response elements are created according to Example 2. Modified tobacco plants are then generated containing both of these vectors. Dexamethasone is sprayed on the plants to induce the expression of the sequence of interest, then the plants are phenotypically evaluated. The modified tobacco plants exhibit reduced sucker growth compared to control tobacco plants.

In a second example, a first vector containing a rat glucocorticoid receptor under the control of Promoter P15 (SEQ ID NO: 117) and a second vector containing a sequence of interest (e.g., SEQ ID NOs: 79 and 123-147) operably linked to one or more glucocorticoid response elements are created according to Example 2. Modified tobacco plants are then generated containing both of these vectors. Dexamethasone is sprayed on the plants to induce the expression of the sequence of interest, then the plants are phenotypically evaluated. The modified tobacco plants exhibit reduced sucker growth compared to control tobacco plants.

Example 23. Regulating Sucker Growth Using Phytotoxins and Immune Receptors

Tobacco plants are metabolically engineered to produce one or more phytotoxins (e.g., tabtoxin; coronatine; syringomycin; syringopeptin; phaseolotoxin) or immune receptors in an axillary meristem to inhibit cell growth or cell division within the axillary shoot meristem. See, for example, Bender et al., 1999, *Microbiology and Molecular Biology Reviews* 63:266-292, which is herein incorporated by reference in its entirety. As an example, the tabA/tblA genes from *Pseudomonas syringae* required to produce tabtoxin are expressed with a tissue specific promoter (e.g., SEQ ID NOs: 113-118, 148-160, and 204).

Immune receptor genes include wide range of genes. Some examples include *Arabidopsis thaliana* disease resistance protein RPS5 (SEQ ID NO: 222) and tobacco TMV resistance N gene (SEQ ID NO: 224).

A transformation vector is created according to Example 2 to comprise SEQ ID NO: 221 driven by Promoter P15 (SEQ ID NO: 117). Modified tobacco plants are then generated with a Promoter P15::RPS5 vector, and then phenotypically evaluated, according to Example 2. The modified tobacco plants exhibit reduced sucker growth compared to control tobacco plants.

Example 24. Regulating Sucker Growth Using Programmed Cell Death-Inducing Genes The presence of some proteins at elevated levels, in cells where they are not normally expressed, or in subcellular locations where they are not normally located, can induce cell death. Axillary bud specific promoters, such as Promoter P1 (SEQ ID NO: 113) and Promoter P15 (SEQ ID NO: 117) are used to the express heterologous genes that in axillary bud cells and ultimately result in death of the axillary bud.

Programmed cell death-inducing (PCD-inducing) enzymes (e.g., transcription factors (SEQ ID NOs: 208, 210, and 212), kinases (SEQ ID NO: 214), cysteine proteases (SEQ ID NOs: 216 and 218), and caspases (SEQ ID NO: 220); see Table 6) are used to induce cellular death in the axillary bud when their expression is driven by Promoter P15 (SEQ ID NO: 117). Transformation vectors are created according to Example 2 to comprise SEQ ID NOs: 208, 210, 212, 214, 216, 218, and 220 driven by Promoter P15 (SEQ ID NO: 117). Modified tobacco plants are then generated with the Promoter P15::PCD-inducing enzyme vector according to Example 2. Modified tobacco plants (T0 generation) and control tobacco plants are grown to the layby stage, then plants are topped to remove the shoot apical meristem. Sucker growth is observed at the time of topping, 24 hours after topping, and one week after topping. Expression of PCD-inducing enzymes driven by Promoter P15 eliminates sucker outgrowth in tobacco.

TABLE 6

Programmed Cell Death (PCD)-Inducing Genes

| SEQ ID NOs (Nucleic Acid/Protein) | Gene Name | Species | Sequence Description | Sequence Source |
|---|---|---|---|---|
| 207/208 | ALCATRAZ | Arabidopsis thaliana | Transcription factor (myc/bHLH), fruit dehiscence | Current Biology 2001, 11: 1941-1922 |
| 209/210 | VND6 | Arabidopsis thaliana | Transcription factor, PCD- xylogenesis | JEB 2014, 65: 1313-1321 |
| 211/212 | VND7 | Arabidopsis thaliana | Transcription factor, PCD- xylogenesis | JEB 2014, 65: 1313-1321 |
| 213/214 | Adi3 | Solanum lycopersicum | AGC kinase, negative regulator, PCD with pathogen attack | EMBO 2006, 25: 255-265 |
| 215/216 | XCP1 | Arabidopsis thaliana | Cysteine protease, PCD-xylogenesis | Plant Journal 2008, 56: 303-315 |
| 217/218 | XCP2 | Arabidopsis thaliana | Cysteine protease, PCD-xylogenesis | Plant Journal 2008, 56: 303-315 |
|  | SlCysEP | Solanum lycopersicum | Cysteine protease, ricinosomal protease, PCD-endosperm | Planta 2013, 237: 664-679 |
| 219/220 | Metacaspase 2d (ATMC4) | Arabidopsis thaliana | Protease, PCD during biotic and abiotic stresses | Plant Journal 2011, 66: 969-982 |
|  | Caspase-like protease | Solanum lycopersicum | PCD, like apoptosis in mammalian cells | Planta 2000, 211: 656-662 |

Example 25. Regulating Sucker Growth by Regulating microRNAs miRNAs can be involved in the regulation of axillary bud development. See Ortiz-Morea et al., 2013, *Journal of Experimental Botany* 64:2307-2320; and Wang et al., 2010, *Molecular Plant* 3:794-806, which are herein incorporated by reference in their entireties. To identify miRNAs involved in tobacco sucker development, total RNA samples are extracted from axillary buds and phloem of 4 week old TN90 tobacco plants before topping and several time points after topping (e.g., 2 hours after topping, 6 hours after topping, 24 hours after topping, 72 hours after topping, 96 hours after topping). Small RNA (sRNA) are separated and purified from the total RNAs. The resulting sRNA samples (three independently collected samples for each tissue type) are processed and subjected to Illumina sequencing. The Illumina reads are mapped and used to evaluate the expression profiles of miRNAs and other small RNAs (e.g., small-interfering RNAs (siRNAs), trans-acting siRNAs). Small RNAs, including miRNAs, that exhibit differential expression in axillary buds before and after topping are identified. These sRNAs play a role in the formation or outgrowth of suckers. The identified sRNAs' precursor sequences and genomic sequences are subsequently identified.

Some tobacco sRNAs are associated with reduced sucker development and/or growth. Over-expression of these sRNAs is used to inhibit suckers. sRNAs found to be associated with reduced sucker development and/or growth are placed under the regulation of a promoter functional in an axillary bud (e.g., SEQ ID NOs: 113-118, 148-160, and 204), or a constitutive promoter (e.g., CaMV 35S) according to Example 2.

A transformation vector is created according to Example 2 to comprise sRNAs of interest driven by Promoters P1, P11, P15, or PAB Thionin (SEQ ID NO: 118). Modified tobacco plants are then generated and phenotypically evaluated according to Example 2. The modified tobacco plants exhibit reduced sucker growth compared to control tobacco plants.

miRNAs that promote sucker formation or outgrowth by repressing genes that would otherwise inhibit sucker formation or outgrowth are targeted for regulation by generating constructs comprising at least one miRNA decoy under the regulation of a promoter functional in an axillary bud (e.g., SEQ ID NOs: 113-118, 148-160, and 204), or a constitutive promoter according to Example 2.

A transformation vector is created according to Example 2 to comprise a miRNA decoy driven by Promoters P1, P11, P15, or PAB Thionin (SEQ ID NO: 118). Modified tobacco plants are then generated and phenotypically evaluated, according to Example 2. The modified tobacco plants exhibit reduced sucker growth compared to control tobacco plants.

A further transformation vector is created according to Example 2 to comprise a tobacco miR159 decoy driven by Promoter PAB Thionin (SEQ ID NO: 118). Tobacco mature miR159 (SEQ ID NO: 227) is complementary to at least SEQ ID NOs: 1, 13, and 35, which all function to inhibit sucker growth in tobacco. Preventing miR159-mediated degradation of SEQ ID NOs: 1, 13, and 35 reduces sucker growth. Modified tobacco plants are then generated with an axillary meristem promoter::miR159 decoy vector, and then phenotypically evaluated, according to Example 2. The modified tobacco plants exhibit reduced sucker growth compared to control tobacco plants.

Example 26. Regulating Sucker Growth Via Modifying Auxin Synthesis and Transport Removing the shoot apical meristem releases axillary buds from dormancy and promotes sucker outgrowth. Auxin derived from an intact shoot apical meristem suppresses sucker outgrowth. Typically, cytokinin induced by removal of the shoot apical meristem promotes axillary meristem outgrowth. Without being bound to any scientific theory, maintaining a high auxin:cytokinin ratio in and around axillary buds after removal of the shoot apical meristem can suppress axillary bud outgrowth.

Localized increases in auxin concentration in and around axillary bud regions can suppress sucker outgrowth. Genes related to auxin biosynthesis and/or transport are used to suppress axillary meristem outgrowth when their expression is driven by Promoter P15 (SEQ ID NO: 117) or other promoters functional in axillary buds (e.g., SEQ ID NOs: 113-118, 148-160, 204, and fragments thereof). A transformation vector is created according to Example 2 to comprise SEQ ID NO: 234 (YUCCA1; flavin monooxygenase) driven by Promoter P15 (SEQ ID NO: 117). Modified tobacco plants are then generated with the Promoter P15::YUCCA1 vector according to Example 2. Modified tobacco plants (T0 generation) and control tobacco plants are grown to the layby stage, then plants are topped to remove the shoot apical meristem. Sucker growth is observed at the time of topping, 24 hours after topping, one week after topping, two weeks after topping, and three weeks after topping (FIGS. 19 and 20). Expression of SEQ ID NO: 234 driven by Promoter P15 suppresses sucker outgrowth in tobacco.

Additional transformation vectors similar to Promoter P15::YUCCA1 are also created using other auxin biosynthesis and auxin transport genes from *Arabidopsis* such as: PIN-FORMED1 (PIN1; SEQ ID NO: 236); TRYPTOPHAN AMINOTRANSFERASE1|TRANSPORT INHIBITOR RESPONSE2 (TAA1/TIR2; SEQ ID NO: 238); ALDEHYDE OXIDASE1 (AAO1; SEQ ID NO: 240); and INDOLE-3-ACETAMIDE HYDROLASE1 (AMI1; SEQ ID NO: 242). In addition to Promoter P15, several promoters functional in axillary buds (e.g., SEQ ID NOs: 113-118, 148-160, 204, and fragments thereof) are used to drive the expression of auxin biosynthesis and auxin transport genes (e.g., SEQ ID NOs: 234, 236, 238, 240, and 242). Furthermore, tobacco genes homologous to *Arabidopsis* auxin biosynthesis and auxin transport genes (e.g., NtYUCCA-like, SEQ ID NOs:244 and 246; NtPIN1-like, SEQ ID NO:248; NtTAA1/NtTIR2-like, SEQ ID NO:250; NtAAO1-like, SEQ ID NO:252; and NtAMI1-like, SEQ ID NO:254) are included in separate vector constructs with Promoter P15 as well as other promoters (e.g., SEQ ID NOs: 113-118, 148, 160, 204, and fragments thereof) functional in axillary buds.

Each of these vectors is used to generate modified tobacco plants, and to then phenotypically evaluate the tobacco plants, as described in Example 2. The modified tobacco plants exhibit reduced sucker growth compared to control tobacco plants.

TABLE 7

| Auxin biosynthesis and auxin transport genes | | | | |
|---|---|---|---|---|
| SEQ ID NOs (Nucleic Acid/Protein) | Gene Name | Species | Sequence Description | Sequence Source |
| 234/235 | YUCCA1 | *Arabidopsis thaliana* | FLAVIN MONOOXYGENASE | *Plant Cell* 2007, 19: 2430-2439 |
| 236/237 | PIN1 | *Arabidopsis thaliana* | PIN-FORMED1 | *Science* 1998, 282: 2226-2230 |
| 238/239 | TAA1/TIR2 | *Arabidopsis thaliana* | TRYPTOPHAN AMINOTRANSFERASES TRANSPORT INHIBITOR RESPONSE2 | *Cell* 1998, 133: 177-191; *Plant Physiology* 2009, 151: 168-179 |
| 240/241 | AAO1 | *Arabidopsis thaliana* | ALDEHYDE OXIDASE1 | *J Biochem* 1999, 126: 395-401 |
| 242/243 | AMI1 | *Arabidopsis thaliana* | INDOLE-3-ACETAMIDE HYDROLASE | *FEBS J* 2007, 274: 3440-3451 |

Example 27. Additional Analysis of Cellular Specificity of Promoter P1, Promoter P15, and Promoter PAB Thionin Three modified tobacco lines are created according to Example 2 using a vector comprising Promoter P15 (SEQ ID NO: 117) driving the expression of Barnase (SEQ ID NO: 79). In the T0 generation, axillary structures exhibit extremely reduced outgrowth after topping. However, the T1 generation exhibits poor germination and no phenotypic analysis is performed.

Additional modified tobacco lines are created according to Example 2 using a vector comprising Promoter P15 (SEQ ID NO: 117) driving the expression of GUS. See also Example 7. GUS staining is examined in germinating seeds, seedlings, and reproductive organs of the modified tobacco lines to further determine the tissues in which Promoter P15 is active. Promoter P15 is active in germinating seeds, seedlings, developing seeds, and the stigma. See FIGS. 22A-B.

In order to determine the specificity of a longer Promoter P15, a longer, approximately 5 kb promoter is generated (Promoter P15-5 kb; SEQ ID NO: 157). Modified tobacco lines are generated according to Example 2 using Promoter P15-5 kb to drive the expression of either Barnase (SEQ ID NO: 79) or GUS. T0 plants expressing Barnase under the control of Promoter P15-5 kb exhibit strong inhibition of sucker outgrowth. See FIG. 23A-B. T0 plants expressing GUS under the control of Promoter P15-5 kb demonstrate that Promoter P15-5 kb is active in seeds and seedlings. See FIG. 24. The T1 seeds of Promoter P15-5 kb::Barnase and Promoter P15-5 kb::GUS lines have difficulty germinating.

A longer version of Promoter PAB Thionin is also generated (Promoter PAB Thionin-5 kb; SEQ ID NO: 148). Modified tobacco lines are generated according to Example 2 using Promoter PAB Thionin-5 kb to drive the expression of either Barnase (SEQ ID NO: 79) or GUS. Promoter PAB Thionin-5 kb exhibit no GUS expression in ungerminated or germinated seed. See FIG. 25. Promoter PAB Thionin-5 kb exhibits strong inhibition of sucker outgrowth after topping. See FIG. 26. Additionally, the T1 seeds of the Promoter PAB Thionin-5 kb::Barnase and Promoter PAB Thionin-5 kb::GUS lines germinate successfully. See FIG. 27.

Example 28. Knocking Out RAX1 and RAX2 Genes Using Gene Editing Technology

As transcription factors, REGULATOR OF AXILLARY MERISTEMS (RAX) play an important role in the formation of branch meristems. In tobacco, there are two RAX genes: RAX1 (SEQ ID NOs: 75 and 76) and RAX2 (SEQ ID NOs: 77 and 78).

RAX1 (SEQ ID NO: 75) and RAX2 (SEQ ID NO: 77) are knocked out in separate tobacco lines. The knockout mutant of RAX1 show the mislocalization of axillary buds in leaf axil (see FIG. 28, upper right panel), but after topping the axillary buds demonstrate normal growth characteristics and phenotype in the mislocalized position (see FIG. 28, upper panel left). However, the knockout mutant of RAX2 delays axillary bud outgrowth for approximately two weeks after topping (see FIG. 28, lower panels). Thus, both RAX1 and RAX2 are functionally related to axillary formation and axillary bud out-growth.

```
SEQUENCE LISTING

Sequence total quantity: 256
SEQ ID NO: 1            moltype = DNA  length = 987
FEATURE                 Location/Qualifiers
misc_feature            1..987
                        note = Description of Artificial Sequence: Synthetic
                        polynucleotide
source                  1..987
                        mol_type = other DNA
                        organism = synthetic construct
SEQUENCE: 1
atgtatccgc caagcaacag ctgcaactac agccccattt tcaacatccc ttctccttgt   60
atgcaatatg gagacgaact attcttccaa tattatcctg accatttcct tcaacagcaa  120
caagtgcctt tgatagaaga tcagagtgtt gacatcttag ctgattgcac tgagaatgtt  180
actaacgaag aaactgtcat caatactgat actgtaaaag ttctttatga cacaggagct  240
gttacaaaca gtcagtgttg gggaggaaat gaagaagtag aagaaggccg cgaaaacaaa  300
agaaatgaca tgagaagcac cattagtatt attcatgtac ggaaaaacaa gaaatgttcc  360
aataaagatc gacatagcaa gattaacact gctcgtggcc tcagagaccg aaggatgaga  420
ctttcccttg atgcagctcg caagtttttc agtttacaag acatgttggg gttcgataag  480
gcaagtaaaa ctgtagaatg gttgcttatc aaatcggagt ctgaaatcga agagctagcc  540
aaaggcaata aaggaggagg cattcctaaa caaagctgca gtactactaa tggaattggt  600
gcaattagta ctgcaatatc ctctatttct gagtgtgagg ttatatcagg aactgatgaa  660
tctttctcta ttacttataa aaagaagctg aaaactgcta aaggagcctc gaaaaagacg  720
gctaaaactg ctcgtagagc tgcatttgat cgtcttatta caagggaaac gaggaatcaa  780
gcaagggcta gggctagaga gagaacaaaa ataaagaaaa gcctcggtaa atccaaagag  840
aacagtgctg attactgtaa tttggtggat aattatgcag attggagtca atttagtatc  900
ttcaactatc agaaaaatgc agttggaatt tcccatgatc aggtggggttc aataattaaa  960
caacatgatt ttttaggatt tcaatag                                      987

SEQ ID NO: 2            moltype = AA  length = 328
FEATURE                 Location/Qualifiers
REGION                  1..328
                        note = Description of Artificial Sequence: Synthetic
                        polypeptide
source                  1..328
                        mol_type = protein
                        organism = synthetic construct
SEQUENCE: 2
```

```
MYPPSNSCNY SPIFNIPSPC MQYGDELFFQ YYPDHFLQQQ QVPLIEDQSV DILADCTENV   60
TNEETVINTD TVKVLYDTGA VTNSQCWGGN EEVEEGRENK RNDMRSTISI IHVRKNKKCS  120
NKDRHSKINT ARGLRDRRMR LSLDAARKFF SLQDMLGFDK ASKTVEWLLI KSESEIEELA  180
KGNKGGGIPK QSCSTTNGIG AISTAISSIS ECEVISGTDE SFSITYKKKL KTAKGASKKT  240
AKTARRAAFD RLITRETRNQ ARARARERTK IKKSLGKSKE NSADYCNLVD NYGDWSQFSI  300
FNYQKNAVGI SHDQVGSIIK QHDFLGFQ                                    328

SEQ ID NO: 3            moltype = DNA   length = 318
FEATURE                 Location/Qualifiers
misc_feature            1..318
                        note = Description of Artificial Sequence: Synthetic
                         polynucleotide
source                  1..318
                        mol_type = other DNA
                        organism = synthetic construct
SEQUENCE: 3
atggctcgct ccttgtgttt catggcattt gcagtcttgg caatgatgct ctttgttgcc   60
tatgaggttc aagctagaga atgcaaaaca gaaagcaata cattccctgg attatgcatt  120
accaaaccac catgcagaaa agcttgtatc agtgagggat ttactgatgg tcattgtagc  180
aaaatcctca aaggtgcct atgcactaag ccatgtgtgt tcgatgagaa gatgatcaaa   240
acaggagctg aaacttttgc tgaggaagca aaaactttgg ctgcagcttt gcttgaagaa  300
gagataatgg ataactaa                                               318

SEQ ID NO: 4            moltype = AA    length = 105
FEATURE                 Location/Qualifiers
REGION                  1..105
                        note = Description of Artificial Sequence: Synthetic
                         polypeptide
source                  1..105
                        mol_type = protein
                        organism = synthetic construct
SEQUENCE: 4
MARSLCFMAF AVLAMMLFVA YEVQARECKT ESNTFPGLCI TKPPCRKACI SEGFTDGHCS   60
KILRRCLCTK PCVFDEKMIK TGAETFAEEA KTLAAALLEE EIMDN                 105

SEQ ID NO: 5            moltype = DNA   length = 1797
FEATURE                 Location/Qualifiers
misc_feature            1..1797
                        note = Description of Artificial Sequence: Synthetic
                         polynucleotide
source                  1..1797
                        mol_type = other DNA
                        organism = synthetic construct
SEQUENCE: 5
atggcttctc ttcccttct caccaccaat gccatctctt catcagcttc ttctttaacc    60
accacacctc tttccaattt gcattcttct cctttcttta caaagacatc aaaagtttcc  120
actatagata agtgcagtaa ctatcgtttc caagtttcat gcaagggtac agaagatgac  180
caaaccatca acacttccaa atcttctgat tcttcaaaca ataagatcat tgatagaaga  240
aacatgctac ttggattagg aggcatttat ggtgctgcta ctcttgttgg tggtcatccc  300
tttgccttcg cggctcctgt gcccggacct gacgtttcca aatgtggtcc tgcagatttg  360
ccaccaggtc cagcaccagt caactgttgt cctccgacaa cggcgaacat catcgactc   420
caacttccac caccgtcaac cacccctccg tacacggccag cagctcattc cgccgatagt  480
gcctatatag agaaattcaa cagagctatt cagctcatga acaacttcc agataacgat   540
ccacgtagct tcaagcaaca agcaaatgtt cattgtgctt actgtgatgg agcttatgga  600
caactaggtt tcccaagttc tgaactccaa gttcattcct cttggcttt cttccctttc  660
catcgttgtt atctctactt cttcgaaaaa atcttgggaa gtttaataaa tgacccctact 720
ttcgctatcc cattttggaa ctgggatcat cctgatggca tgagacttcc ggccatgtat  780
gcgaaccgta gttcttctct cttcgatcct ctccgtgatc agaagcatca gcctccggtc  840
attgttgatc tcgacttcaa tggagcggat cctaacataa gtaacgctca acaaacttcc  900
cagaatctga caatcatgta taggcaaatg gtctctctag gaagtactcc ggcagctttc  960
ctcggagacc cttaccgtgc cggtggcaa ccgggtggtg ctgggtccct cgagaacatt  1020
ccacatggaa cggtccatgt ttggaccggt gatagaaccc aacctaattt tgaaaatatg  1080
ggagtttttt atgcagctgg tagagaccct attttctatg ctcatcattc taatattgat  1140
agattgtgga gtgtttggaa aaccctaggt ggaagcgtc aagattttac tgaccctgat  1200
ttttaaaatt cttcgttttt gttttacgat gagaaagcac aaatggtacg tattagggta  1260
cgtgactgtt tggatacaac aagacttgga tacgtttatc aaggtgtagt taatccgtgg  1320
ataaattctc gtccaagggc tagggtttca agtgctttga gtagcgtaag gaggcttgct  1380
gaagcaaaag attatttccc aacaaaactt ggccatgtga taagagtaat ggtgaaaagg  1440
ccaaataata aaagagaaa caaggaggag aaagatgcaa aagaggagtt tttagtggtt  1500
gaagggatag agctgaaaac tgatgttttt gtcaagtttg atgtgttgat taatgatgaa  1560
gatgagactg taatttcgcc gaataatgct gagtttgcag gtagtttgt gaacgtgcca   1620
catcttagtc atggtaagag tgacgagaaa cgtaagacta gttgaagtt ggctataact   1680
gagctgctgg aagatttaga tgctgaggat gatgatcatg tggtggtgac ttttgttcca  1740
aagaatggtt ctggtgctgt gaaaattgga ggtgtcaaga ttgtgcttga ggattga     1797

SEQ ID NO: 6            moltype = AA    length = 598
FEATURE                 Location/Qualifiers
REGION                  1..598
                        note = Description of Artificial Sequence: Synthetic
```

```
                        polypeptide
source                  1..598
                        mol_type = protein
                        organism = synthetic construct
SEQUENCE: 6
MASLPLLTTN AISSSASSLT TTPLSNLHSS PFFTKTSKVS TIDKCSNYRF QVSCKGTEDD    60
QTINTSKSSD SSNNKIIDRR NMLLGLGGIY GAATLVGGHP FAFAAPVPGP DVSKCGPADL   120
PPGAAPVNCC PPTTANIIDF QLPPPSTTLR TRPAAHSADS AYIEKFNRAI QLMKQLPDND   180
PRSFKQQANV HCAYCDGAYG QLGFPSSELQ VHSSWLFPPF HRCYLYFFEK ILGSLINDPT   240
FAIPFWNWDH PDGMRLPAMY ANRSSSLFDP LRDQKHQPPV IVDLDFNGAD PNISNAQQTS   300
QNLTIMYRQM VSLGSTPAAF LGDPYRAGGE PGGAGSLENI PHGTVHVWTG DRTQPNFENM   360
GVFYAAGRDP IFYAHHSNID RLWSVWKTLG GRRQDFTDPD FLNSSFLFYD EKAQMVRIRV   420
RDCLDTTRLG YVYQGVVNPW INSRPRARVS SALSSVRRLA EAKDYFPTKL GHVIRVMVKR   480
PNNKKRNKEE KDAKEEFLVV EGIELETDVF VKFDVLINDE DETVISPNNA EFAGSFVNVP   540
HLSHGKSDEK RKTKLKLAIT ELLEDLDAED DDHVVVTFVP KNGSGAVKIG GVKIVLED    598

SEQ ID NO: 7            moltype = DNA   length = 1392
FEATURE                 Location/Qualifiers
misc_feature            1..1392
                        note = Description of Artificial Sequence: Synthetic
                        polynucleotide
source                  1..1392
                        mol_type = other DNA
                        organism = synthetic construct
SEQUENCE: 7
atggtaggca aaagaaatga gcctcatgtc atatttgtac cttacccaag ccaaggtcac    60
attaaccctc ttctccaatt tgcaaaacgc ttatactcca aaggtgtaaa agcaacttta   120
gccactacta aatacacagt caagtctatt aattcaccca catttcagt tgaagcaatt   180
tctgatggat ttgacgaaag tggttttcc caagcccaaa aagcagatat atatctcaaa   240
tcattcaaag aaaatggttc aacaactcta tcagaaataa taaaaaatta cgagaattcg   300
acacatccga taagttgcat tgtttatgat tcgtttttac catgggctct tgatgtggct   360
aaaaaacatg ggatttatgg agctgcgttt tttacaaatt cagccactgt ttgtgtagtt   420
tttgctcaca ttcattataa aacattttca ttgccggcga agattgaaga aaatgagcca   480
ttgttattgc ctggattgcc tagtttgtac ccaattgtag ttcctggatt tattagggag   540
cctgaaagtt accctgctta cttagccatg aaaatgagtc aattctctaa tttgaaaat   600
gctgattggg ttttgataa ctcctttcaa gaactagaag agagatagc aagtggagtt   660
tcaaatattt ggccagcaag gttaattgga ccaatggtgc catcatccta tttagatgac   720
ataatagaag gtgacaaagg gtacggagca agtctatgga aaccacttag tgaagaatgt   780
ctcaaatggc taaaaacaaa gccaaatcaa tcagtaatct acatttcttt tggcagcagg   840
gtatcactca caccacaaca aatggaagaa atgcaaatg ctttaataga cagcaacatg   900
aatttccttt gggttgtaag agaaaccgaa aaaggcaaat tgccaaaaaa attcatagaa   960
tccacaattg gaaaagggtt aattgtgtca tggtgcaatc aattagaaat gctagcaaat  1020
caagccattg gttgttttgt gactcattgt ggatggaatt cgactcttga aggattggc  1080
cttggcgtgc caatggtggc aatgccacaa tggtctgatc aaatgacgga tgctaaattt  1140
ataggtgaga tttgggaaat tggtgtgagg cctaagttgg ataagtttgg gattgttaga  1200
agagaagagc tattgttttg tttaaaggaa gtaatgggag ggaagaggag ttatgagatt  1260
aggagaaatg ctggaaaatg gaagaacttg gctaagaaag caattagtga aggagggtagc  1320
tcggacaagt ctattaatgt atttgtgaac agtcttagtc tagcatgcca gatgaagaag  1380
tacaagaaat aa                                                     1392

SEQ ID NO: 8            moltype = AA   length = 463
FEATURE                 Location/Qualifiers
REGION                  1..463
                        note = Description of Artificial Sequence: Synthetic
                        polypeptide
source                  1..463
                        mol_type = protein
                        organism = synthetic construct
SEQUENCE: 8
MVGKRNEPHV IFVPYPSQGH INPLLQFAKR LYSKGVKATL ATTKYTVKSI NSPNISVEAI    60
SDGFDESGFS QAQKADIYLK SFKENGSTTL SEIIKNYENS THPISCIVYD SFLPWALDVA   120
KKHGIYGAAF FTNSATVCVV FAHIHYKTFS LPAKIEENEP LLLPGLPSLY PIDVPGFIRE   180
PESPAYLAM KMSQFSNLEN ADWVFDNSFQ ELEGEIASGV SNIWPARLIG PMVPSSYLDD   240
IIEGDKGYGA SLWKPLSEEC LKWLKTKPNQ SVIYISFGSM VSLTPQQMEE MANALIDSNM   300
NFLWVVRETE KGKLPKKFIE STIGKGLIVS WCNQLEMLAN QAIGCFVTHC GWNSTLEGLS   360
LGVPMVAMPQ WSDQMTDAKF IGEIWEIGVR PKLDKFGIVR REELLFCLKE VMGGKRSYEI   420
RRNAGKWKNL AKKAISEGGS SDKSINVFVN SLSLACQMKK YKK                    463

SEQ ID NO: 9            moltype = DNA   length = 405
FEATURE                 Location/Qualifiers
misc_feature            1..405
                        note = Description of Artificial Sequence: Synthetic
                        polynucleotide
source                  1..405
                        mol_type = other DNA
                        organism = synthetic construct
SEQUENCE: 9
atggcaggga aggttgagaa agtgcttgca gtagtgatgc ttgcaatgct tctgtttcg    60
gagcatttaa tggctgctaa tcatgaaatt aaaacaactg aagataactc tactattagc   120
```

```
cctttctgct tagtaaaatg tttatttgga tgtaggggt tgccacctgt acaagcatcc    180
atttgtgctg ctcaatgtta tttaaagtgc cgtgaccaag atgcggcaa tattgctgaa    240
actaagggca taattggtga gactgcatac aaccagtatg atgttggatg tgcccttggc    300
tactgctctg agttcctgtt gaattatgat gagaagaggt tcaagtgctg catggaatac    360
tgccgcgagg acaaaatgat ttgtcctgtt gaggctgcag cttga                   405

SEQ ID NO: 10            moltype = AA   length = 134
FEATURE                  Location/Qualifiers
REGION                   1..134
                         note = Description of Artificial Sequence: Synthetic
                           polypeptide
source                   1..134
                         mol_type = protein
                         organism = synthetic construct
SEQUENCE: 10
MAGKVEKVLA VVMLAMLLFS EHLMAANHEI KTTEDNSTIS PFCLVKCLFG CRGLPPVQAS    60
ICAAQCYLKC RDQDAANIAE TKGIIGETAY NQYDVGCALG YCSEFLLNYD EKRFKCCMEY   120
CREDKMICPV EAAA                                                    134

SEQ ID NO: 11            moltype = DNA   length = 630
FEATURE                  Location/Qualifiers
misc_feature             1..630
                         note = Description of Artificial Sequence: Synthetic
                           polynucleotide
source                   1..630
                         mol_type = other DNA
                         organism = synthetic construct
SEQUENCE: 11
atgaattcaa agaaaaacaa ctcaccaaga aaaaggttga aaaatatca tacaagaaaa     60
gctcctatta ttagctctta tatggacatg gctgaagcta gaagagaaat tgttcatgct   120
ttacaacttc atcgatcttc atcttcatct ccaactccgt ctattaatag cccaaagaag   180
tacacattat tgggtcaagg agttgtaagc tctcaacaat attactatta ctcaatagtg   240
gaatctatgc ctattcctga accaacatgg tctacaacgg ctccggcaat acttaatgca   300
ctgccaccgc tgccgctgcc gctgccgcca cctccgccgc tgtcttcttc ttccggtgaa   360
gttccagagt ttgaatggtg gatagggttt ttgaagtcgt tggacggcaa gaagagtgct   420
aacaatggtg aagtagtcat agaaaatat tttcctctag aagaaatgt tttgatggaa    480
aattcaaaga caggttttgg tcaattagaa catggattaa acagtgagtc tcctaatgt    540
atagataaga atgatgatcc taattaccaa tttccagatg agtggttgat tatccctaca   600
gctgatgatg attatgtact tgagctttaa                                   630

SEQ ID NO: 12            moltype = AA   length = 209
FEATURE                  Location/Qualifiers
REGION                   1..209
                         note = Description of Artificial Sequence: Synthetic
                           polypeptide
source                   1..209
                         mol_type = protein
                         organism = synthetic construct
SEQUENCE: 12
MNSKKNNSPR KRLRKYHTRK APIISSYMDM AEARREIVHA LQLHRSSSSS PTPSINSPKK    60
YTLLGQGVVS SQQYYYYSIV ESMPIPEPTW STTAPAILNA LPPLPLPLPP PPPLSSSSGE   120
VPEFEWWIGF LKSLDGKKSA NNGEVVIEKY FPLEENVLME NSKTGFGQLE HGLNSESPNC   180
IDKNDDPNYQ FPDEWLIIPT ADDDYVLEL                                    209

SEQ ID NO: 13            moltype = DNA   length = 1143
FEATURE                  Location/Qualifiers
misc_feature             1..1143
                         note = Description of Artificial Sequence: Synthetic
                           polynucleotide
source                   1..1143
                         mol_type = other DNA
                         organism = synthetic construct
SEQUENCE: 13
atgtatccgt caagcaacag ctgtaattac agcctcaata tttcctcctc aaataactta    60
tttcacattc catctccgaa ttctatgcaa tatgaacacg aacttttcca atattttcat   120
gaccatcatc tccttcaacc ccaacaacaa caacaacaac aacaactctt gactacacct   180
gatcattata tggcagcaga ttccaacaaa gacaccgtaa tcagtagtac taatcaagat   240
cctgaagaag ttgaattaca aggccgctgc aagaacaaaa aggtgacaa taagagacgt   300
gttgcttaca agaaagatag acacagcaag attaacactg ctcacggccc tagagaccga   360
agaatgagac tttctctcga tgtagctcgc aaatttttca atttgcaaga cttgcttgga   420
ttcgataagg ctagcaaaac tgtggagtgg ttgctaacaa agtccaaatg tgctgtcaat   480
gagctcgtcc aaggcataaa taagaaaat tgcgctactg ctaatattgg tgcaattagt    540
acatgctcta ctacatctga gtgtgaagtt gtatcaggaa ttgatgaatc tacaaccact   600
aatgatattc ataagcagtc aaatagaggt aaagtagggg agaagaagaa ggctaataaa   660
ctagttcgta gagctgcatt taatcctgtg gcaaaggaat caagaaagca agctagagcg   720
agggcaaggg agaaacaaaa aataaagaaa gctttttaa atattggtga tcagtctatg   780
gcggctgatg atttaaaacg attaggatgt tggagtcttt tgaaacagg tgaagaatca    840
ggtattcaag gtactaatca tcaaattgaa gaacacacca cgcaccacga ggagcctctt    900
ttggggacta atgagaatgt tgatgattgt aatttggttg ttaccggcaa ctggaaccca   960
```

```
tataccatct tcaattatca ccacagtact gaaatttctc acgaggtagg ttttacactt    1020
catttaaatc caagagtaat tcttttagag ttcaagattc tgatattttt tttggtggcg    1080
agacccttttc ttatatcaaa gcaaccttca aggtacatac aagattggat aaaccaattc   1140
tga                                                                  1143
```

| | | |
|---|---|---|
| SEQ ID NO: 14 | moltype = AA  length = 380 | |
| FEATURE | Location/Qualifiers | |
| REGION | 1..380 | |
| | note = Description of Artificial Sequence: Synthetic polypeptide | |
| source | 1..380 | |
| | mol_type = protein | |
| | organism = synthetic construct | |

```
SEQUENCE: 14
MYPSSNSCNY SLNISSSNNL FHIPSPNSMQ YEHELFQYFH DHHLLQPQQQ QQQQQLLTTP     60
DHYMAADSNK DTVISSTNQD PEEVELQGRC KNKKGDNKRR VAYKKDRHSK INTAHGPRDR    120
RMRLSLDVAR KFFNLQDLLG FDKASKTVEW LLTKSKCAVN ELVQGINKEN CATANIGAIS    180
TCSTTSECEV VSGIDESTTT NDIQKQSNRG KVGEKKKANK LVRRAAFNPV AKESRKQARA    240
RARERTKIKK SFLNIGDQSM AADDLKRLGC WSLFETGEES GIQGTNHQIE EHTTHHEEPL    300
LGTNENVDDC NLVVTGNWNP YTIFNYHHST EISHEVGFTL HLNPRVILLE FKILIFFLVA    360
RPFLISKQPS RYIQDWINQF                                                380
```

| | | |
|---|---|---|
| SEQ ID NO: 15 | moltype = DNA  length = 915 | |
| FEATURE | Location/Qualifiers | |
| misc_feature | 1..915 | |
| | note = Description of Artificial Sequence: Synthetic polynucleotide | |
| source | 1..915 | |
| | mol_type = other DNA | |
| | organism = synthetic construct | |

```
SEQUENCE: 15
atggaaaagg ttcatgagaa accgctatct ctttataatg gatcattatc tgtttttaga     60
ttaggagatt tggctgtgaa aataacaaag gtgaaaaagg gatcattaaa taatgataat    120
ctttcacccc caacttcatt gttagttgtt tcaccaatca taccaggaac ttatccagtt    180
ttactctttt ttcatggctt cgttctcaag cctatatggt acaagtctct ccttcaacat    240
atttcttccc acggctatat agttgttgct ccacagtttt ctcaaagcga agaagtgaaa    300
aaagcagcca agttacagaa atggttaagt aaagccctcg aatccgtact gccggagaaa    360
gtacagccgg atctactcca gctcgccgtc tccggccaca gcagaggtgg taaaatagca    420
tttgcactag cttttaggata tggcatcaaa tttcaagcac ttctaggaat tgatccagtt    480
gcaggttttt tctccgtccaa ccgatctgct ccaaaaattc ttaaatatat tcctcgtatt    540
ttcgatcaga cggtccctgt ggcggtgatc ggcgctggct tgtcaaacca aagtgcgaat    600
tgtatctttc caccccttcgc accaaacggt gtcaaccatt cggagttttt taacgagtcc    660
aaaccacctt gctgttattt tctggctaaa aattatgaac atactgatat gttagatgac    720
agaattgctg caattgcgag ttggatttca aagagtggga agggacccaa ggaccttatg    780
agaaaggctg ttggagggat tgttgtggct tttcttgagg ctaaattggg agagaaagtg    840
gataatctaa atgccattgt tcaagaacct ctcttgctc ccatcatcct tgacccagtc     900
atatctgtca aataa                                                     915
```

| | | |
|---|---|---|
| SEQ ID NO: 16 | moltype = AA  length = 304 | |
| FEATURE | Location/Qualifiers | |
| REGION | 1..304 | |
| | note = Description of Artificial Sequence: Synthetic polypeptide | |
| source | 1..304 | |
| | mol_type = protein | |
| | organism = synthetic construct | |

```
SEQUENCE: 16
MEKVHEKPLS LYNGSLSVFR LGDLAVKITK VKKGSLNNDN LSPPTSLLVV SPIIPGTYPV     60
LLFFHGFVLK PIWYKSLLQH ISSHGYIVVA PQVSQSEEVK KAAKVTEWLS KALESVLPEK    120
VQPDLLQLAV SGHSRGGKIA FALALGYGIK FQALLGIDPV AGFSPSNRSA PKILKYIPRI    180
FDQTVPVAVI GAGLSNQSAN CIFPPFAPNG VNHSEFFNES KPPCCYFLAK NYGHTDMLDD    240
RIAAIASWIS KSGKGPKDLM RKAVGGIVVA FLEAKLGEKV DNLNAIVQEP SLAPIILDPV    300
ISVK                                                                 304
```

| | | |
|---|---|---|
| SEQ ID NO: 17 | moltype = DNA  length = 1353 | |
| FEATURE | Location/Qualifiers | |
| misc_feature | 1..1353 | |
| | note = Description of Artificial Sequence: Synthetic polynucleotide | |
| source | 1..1353 | |
| | mol_type = other DNA | |
| | organism = synthetic construct | |

```
SEQUENCE: 17
atgtgtttgt taataaaggt ggcgaatcca ggagaatccg gcgagcatga cagaattcca     60
tcaacgggag gtgattcaga aagtacaact actaccacag aaggaggaat tccgcagcta    120
tatgaacaat acaatcaca atcacaatca tttgaagaaa tgttgcggca acaaatacaa     180
caagaaacag agtatttgat gtcttcatct gcaactccta tgtttttcacg gtatagtcag    240
acaagggaga gtgtcggcaat ggtaacggcg ttaacgcatg tggtatcagg acggagagag    300
ggagagtgga cttacaggcc ggatattagt gccggcgctg ttacgacgtc gtttgctggt    360
```

```
ggttcgagta tttattcggc gagttcgccg tcgtcttcaa gttcagggtc atgggctgga    420
cagaagagaa gacgtgatca agaagaaagt gttgctgcag agcaagttca aagggtttat    480
ggagctttg gtgaatttag aggtggagaa tcatcttcct ctgttaaaac tgaagaagct     540
tcaagcatgg tagcaccacc aaccaccacc agcactacca ccacaaccac cacggcggcg    600
caaacaccac cagaaccagc ggaaggagga ggagctgaaa aaacagggga aaggaggagg    660
agatacagag gagtaagaca aaggccatgg ggaaaatggg cagcagaaat aagagatcca    720
cacaaagcag ctagagtttg gttaggcaca tttgatacag ctgaagctgc tgctagagct    780
tatgatgaag ctgcccttag attcagagga acagagcta aactcaattt ccccgaaaat    840
gtccgcatat taccacaaca acaacagcaa caacctcaag ccacaacaag atcagccatt    900
tccagctcct ccgcagcttc acaattccca ttaatggctg cagcaacaac tccatcacca    960
tttttccaaa cttatcaacc tcagcagcag cagctgcctt ttcagagttc agaaatggtt    1020
agagattatt gggaatactc acagttactt caaaatccag agagtttca tttacaacaa    1080
cagccttcag ccttgttaga gcaaatgttg tttgcttctt catcaatggg tcttttgcaa   1140
tcacacacat tccccttctta ttcttcatct tcctcattag tcacttcctc tgcagcttca   1200
tccctgcat atccctgtt ttactctgct caacaatcac gtttctttca gcccccacaa     1260
agtactcatc aaaatcaaac tagtagcagc agctccagtt tccctgcacc attttggact   1320
agttcaaccc actacccacc ttcttctagt taa                                 1353

SEQ ID NO: 18           moltype = AA  length = 450
FEATURE                 Location/Qualifiers
REGION                  1..450
                        note = Description of Artificial Sequence: Synthetic
                         polypeptide
source                  1..450
                        mol_type = protein
                        organism = synthetic construct
SEQUENCE: 18
MCLLIKVANP GESGEHDRIP STGGDSESTT TTTEGGIPQL YEQLQSQSQS FEEMLRQQIQ   60
QETEYLMSSS ATPMFSRYSQ TREMSAMVTA LTHVVSGRRE GEWTYRPDIS AGAVTTSFAG  120
GSSIYSASSP SSSSSGSWAG QKRRRDQEES VAAEQVQRVY GAFGEFRGGE SSSSVKTEEA  180
SSMVAPPTTT STTTTTTAA QTPPEPAEGG GAEETGERRR RYRGVRQRPW GKWAAEIRDP   240
HKAARVWLGT FDTAEAAARA YDEAALRFRG NRAKLNFPEN VRILPQQQQQ QPQATTRSAI  300
SSSSAASQFP LMAAATTPSP FFQTYQPQQQ QLPFQSSEMV RDYWEYSQLL QNPGEFHLQQ  360
QPSALLEQML FASSSMGLLQ SHTFPSYSSS SSLATSSAAS SPAYPLFYSA QQSRFFQPPQ  420
STHQNQTSSS SSSFPAPFWT SSTHYPPSSS                                    450

SEQ ID NO: 19           moltype = DNA  length = 732
FEATURE                 Location/Qualifiers
misc_feature            1..732
                        note = Description of Artificial Sequence: Synthetic
                         polynucleotide
source                  1..732
                        mol_type = other DNA
                        organism = synthetic construct
SEQUENCE: 19
atggcacatt tcttctctat aaattcaacg ttagcaggaa cgaataaagc atccaaaaca    60
aatttcacat attcaactca agaaacagaa aaaccaaaat taaagatcat cttactcttg   120
tttttctcttg cattagttcc cttgtcagca atggcaactt gcaccactga tactccaaac   180
caagcactat tgagggatgt acacgatata gatggtaacc cccttcaagt aaaagccagg   240
tacttcatat ttccagttat tggcggtggt ggtgtacggc ttgctaatct tggagatcaa   300
gacgaaaacg cttgtgccac agcggtggtg ctatcacgca gtgaagttca aaaggtaaa   360
gcagtcaact tcataccta agaccccaaa catgagaaga ttgtggaggc ctcttcagta   420
aacatccagt tttatcttga ttattataag tgtgctaacc taactgtgtg gaaagtagac   480
aactacccta cacttccaag tcgctacacc ataagcacag gtgcaacgcc gggaaatccc   540
ctagagttga atagctggtt tcaaattatg tctcttggtg gctcgacgta taagatagtc   600
ttctgtccct ttggagaatg ccaaaatgtt ggcattgccg aggaaaatgg atataatcgt   660
ttggttctcg cagagaatgc aaaggccttt gttttcataa agcaaggcgg atatggaaag   720
gccgaagcat ga                                                       732

SEQ ID NO: 20           moltype = AA  length = 243
FEATURE                 Location/Qualifiers
REGION                  1..243
                        note = Description of Artificial Sequence: Synthetic
                         polypeptide
source                  1..243
                        mol_type = protein
                        organism = synthetic construct
SEQUENCE: 20
MAHFFSINST LAGTNKASKT NFTYSTQETE KPKIKIILLL FSLALVPLSA MATCTTDTPN    60
QALLRDVHDI DGNPLQVKAR YFIFPVIGGG GVRLANLGDQ DENACATAVV LSRSEVDKGK   120
AVNFIPKDPK HEKIVEASSV NIQFYLDYYK CANLTVWKVD NYPTLPSRYT ISTGATPGNP   180
LELNSWFQIM SLGGSTYKIV FCPFGECQNV GIAEENGYNR LVLAENAKAF VFIKQGGYGK   240
AEA                                                                  243

SEQ ID NO: 21           moltype = DNA  length = 471
FEATURE                 Location/Qualifiers
misc_feature            1..471
                        note = Description of Artificial Sequence: Synthetic
                         polynucleotide
```

```
source                  1..471
                        mol_type = other DNA
                        organism = synthetic construct
SEQUENCE: 21
atggctgagc aacaccagcg ccaccagcaa cagcagcagc agcagcagat gcaagtgggc    60
cacccgacgg aggcaatcaa gagccttctt cctcaaaggg gtccctctaa atcccaagtc   120
cttgctgtcg tcactctctt ccctgttggt ggggccctcc tctgccttgc tggactgacg   180
ctcgccggaa ctctgatcgg gcttgcagtc gctacgccgg ttttcttact gttcagcccg   240
gttttggtcc ccgctgccct gacaatcgcg ttggccgtca ctggattctt gacttccggc   300
gcctttggaa taacggcgct gtcgtcgctc tcgtggatca ttaactatat gaggagaatc   360
acaggtccag cagcagagca gatggagcat gcaaagcgga gggtgcagga cactgctggt   420
catatgggac agagaggtgg acagaagatt caagaaactg ctagaacttg a           471

SEQ ID NO: 22           moltype = AA length = 156
FEATURE                 Location/Qualifiers
REGION                  1..156
                        note = Description of Artificial Sequence: Synthetic
                        polypeptide
source                  1..156
                        mol_type = protein
                        organism = synthetic construct
SEQUENCE: 22
MAEQHQRHQQ QQQQQMQVG HPTEAIKSLL PQRGPSKSQV LAVVTLFPVG GALLCLAGLT    60
LAGTLIGLAV ATPVFLLFSP VLVPAALTIA LAVTGFLTSG AFGITALSSL SWIINYMRRI   120
TGPAAEQMEH AKRRVQDTAG HMGQRGGQKI QETART                             156

SEQ ID NO: 23           moltype = DNA length = 1437
FEATURE                 Location/Qualifiers
misc_feature            1..1437
                        note = Description of Artificial Sequence: Synthetic
                        polynucleotide
source                  1..1437
                        mol_type = other DNA
                        organism = synthetic construct
SEQUENCE: 23
atggatagtg ataggaggga ttgccacttg aacatgttgt ccaaaatggc tatgtgcaaa    60
tcacacgggc aagactcttc ctatttcata ggatggcaag aatatgagaa gaacccttat   120
catcccattc aaaatccttt ggtattatt cagatgggtc ttgctgagaa tcagctctca    180
ttcgatcttc ttgaatcatg gctcacaaga aaccaagatg taatccagtt tagagaaaat   240
ggaggatcta tgttcagaga cttggctctt ttccaagatt atcatggatt gcaggctttc   300
aagaacgtac tagtgtcatt catgggtgag atcagaagaa ggaaagtaaa atttgatcca   360
gagaagctag tactcacagc tggttcaact tcagcaaacg aaacccctca tattttgctta   420
gctgaacctg gagaagctct cctcttcca actccttatt atccagggtt tgatagagat   480
ctaaaatgga gaacaggggc tgaaattgta cccatacact gctacagttc aaataacttc   540
agaataactg agtctgccct tgaagatgca tatgaagaag cccaacgact taatttaaga   600
gtcaaggggta tatttatcac aaatcctcca aatccactag gacaaccat gtcacgagac   660
gaattaaaca atcttatcac ctttgccatg gccaaaaata ttcatatagt tagcgacgaa   720
atatacgctg aacagttttt cgattcgcca aaattcataa gcataatgga agctttaatt   780
gacagaaaac atgaaaaatc caaaatgtgg agtcaagttc acattgtgtc aagtctatca   840
aaagatctag gtctaccagg tttcagaatt gggatgattt attcaaacaa tgaaactctt   900
atagctgctg ctacaaaaat gtcaagtttt ggactcattt catctcaaac tcagtatcta   960
ctatctaaaa ttcttggaga taaaaaattt ataaaacgtt acattaaaga aacaagaaa   1020
ggattgaaaa agaggaggga aatgcttgtt ccgggttag agaatagtgg gattgagtgt   1080
ttgaaaagta atgctggatt attttgtttt gtggacatga gcatttgct aaattcaaac   1140
acatttgaag cagaaatgga actgtggaga aaaatactac taagtgatgt tggttttaaat  1200
gtgtctcctg gatcttcttg tcactgtagt gaacctggtt ggttaaaat tgtttttgca   1260
aatattgccg aagaaactct tgatctcgcg atgcagagga ttaatgattt tgtcagttct   1320
atgaatcttc aacggcgaca gctgatcgcg gcggcgtcgg cgtctagctc aaggaggagg   1380
acacttgcga actgggttgt taagttatct tcaggtgaag gaaaaacata tcgttaa     1437

SEQ ID NO: 24           moltype = AA length = 478
FEATURE                 Location/Qualifiers
REGION                  1..478
                        note = Description of Artificial Sequence: Synthetic
                        polypeptide
source                  1..478
                        mol_type = protein
                        organism = synthetic construct
SEQUENCE: 24
MDSDRRDCHL NMLSKMAMCK SHGQDSSYFI GWQEYEKNPY HPIQNPSGII QMGLAENQLS    60
FDLLESWLTR NQDVIQFREN GGSMFRDLAL FQDYHGLQAF KNVLVSFMGE IRRRKVKFDP   120
EKLVLTAGST SANETLIFCL AEPGEALLLP TPYYPGFDRD LKWRTGAEIV PIHCYSSNNF   180
RITESALEDA YEEAQRLNLR VKGVFITNPS NPLGTTMSRD ELNNLITFAM AKNIHIVSDE   240
IYAGTVFDSP KFISIMEALI DRKHEKSKMW SQVHIVSSLS KDLGLPGFRI GMIYSNNETL   300
IAAATKMSSF GLISSQTQYL LSKILGDKKF IKRYIKENKK GLKKRREMLV SGLENSGIEC   360
LKSNAGLFCF VDMRHLLNSN TFEAEMELWR KILLSDVGLN VSPGSSCHCS EPGWFKICFA   420
NIAEETLDLA MQRINDFVSS MNLQRRQLIA AASASSSRRR TLANWVVKLS SGEGKTYR     478

SEQ ID NO: 25           moltype = DNA length = 645
```

```
FEATURE                 Location/Qualifiers
misc_feature            1..645
                        note = Description of Artificial Sequence: Synthetic
                         polynucleotide
source                  1..645
                        mol_type = other DNA
                        organism = synthetic construct
SEQUENCE: 25
atgaacggtg gttcatgtgg tggtgctgat cgtgagtata ataacaataa caacaataat    60
gttgtaggtg gaggaggtgg cgggccttgt ggtgcatgca agtttcttag aagaaaatgt   120
gtgaggggat gcatatttgc accttatttt gattctgatc aaggcactgc tcatttcgct   180
gctgtacata aggtgtttgg tgctagcaat gcctctaaat tgctgctcag aattccagcg   240
cataaacgtc tggatgctgt cgttacactt tgctatgagg ctcttgctag agttagagac   300
cctatctatg gttgtgttgc tcacatcttt actcttcagc aacaggttgt aactttgcaa   360
gctgagttag catatgttca agcccgcctt tctaccctac cacacctacc tatgcgacaa   420
agtccaatta caccaacagg gctgcaatca tcttcagata tcttctgcac tacttcaagc   480
atatcatctt caagtaataa tatggaatat cctcaatttg acataactgc gggtttaagt   540
gattcgttcg atgaaaaaga actggagaac tttgagctcc atacattagc acgagagttg   600
gtttctagac acttacctgg agttagattt agaccttcac cataa                   645

SEQ ID NO: 26           moltype = AA  length = 214
FEATURE                 Location/Qualifiers
REGION                  1..214
                        note = Description of Artificial Sequence: Synthetic
                         polypeptide
source                  1..214
                        mol_type = protein
                        organism = synthetic construct
SEQUENCE: 26
MNGGSCGGAD REYNNNNNNN VVGGGGGGPC GACKFLRRKC VRGCIFAPYF DSDQGTAHFA    60
AVHKVFGASN ASKLLLRIPA HKRLDAVVTL CYEALARVRD PIYGCVAHIF TLQQQVVTLQ   120
AELAYVQARL STLPHLPMRQ SPITPTGLQS SSDIFCTTSS ISSSSNNMEY PQFDITAGLS   180
DSFDEKELEN FELHTLAREL VSRHLPGVRF RPSP                               214

SEQ ID NO: 27           moltype = DNA  length = 2205
FEATURE                 Location/Qualifiers
misc_feature            1..2205
                        note = Description of Artificial Sequence: Synthetic
                         polynucleotide
source                  1..2205
                        mol_type = other DNA
                        organism = synthetic construct
SEQUENCE: 27
atgtcggata aaaaatctgt ctcgacgcca tttgaatgtt gcagaatctt gtttaagttt    60
ctgctgttta tggttattat cagtaatgtg gcgatccatg taacagcttt gagtgggcga   120
gaaggaataa ccccaagtac ggaatggggt ttggggcctc tggtgaagag aggagaaaga   180
aaactagtag tttcaactga aaatgggag gtctcttcag tcagagtagc tgatggaatc   240
accggttcct atcatcttca gttcatcaca ttggagccca attccctctt ccttcctgtt   300
gttctacatg cagatatggt cttctatgtc cacactgggt cgggaaggct gacttggatg   360
gatgaaactg aacaaaagtc agtggattta agaattggag atgttttcag gttgcccttt   420
ggaactatttt tcttcataga gagcaactta gagcctgcgc gacagaaact tagagttgat   480
tccatcttta ccaattcagg ggatgatttg agagagccgt tgtccggacc acactctagc   540
atccgtgata tggttcttgg attcgatagg aaagttctcc aggcggcatt tcatgtacca   600
gaggatgtga tagatgaagt gttgaatggg acagaagtac cagccatcat acatggtgtg   660
cccaagacaa caaaaaagac cctgtgggaa atggaggctc aattcatgaa aagtcttcta   720
ggaaggggtg gtcacggttt ctttgactcc caaagcaata aaaagaagac tgaattgttc   780
aatattttca agagaaaacc agattttgag aattgcaatg gctggagcac tgtaattaca   840
cggaaaaaat tacccgcatt aaagggttcc cacattggta tttatgtagt gaacttaacc   900
aagggatcaa tgatggcgcc acactggaat ccaacgcgcaa ctgaaatagg aatagcattg   960
caaggagaag gaatggtaag ggtagtttgc tcaagcacgg aacaaagca aggatgccaa   1020
aacatgaggt ttaaggtgga agaaggagat gtatttgcag tgccaaggtt cgtcctatg   1080
gctcaaatgg ctttcaacaa caactcattt gtctttgttg gttttagtac aactacaaag   1140
agacatcatc ctcagtacct aacagggaag gcttcagtcc tccgaacact ggataggcaa   1200
atcttggcag cttcctttaa tgtgactaac acaacagtag atcggattct ggaggcacaa   1260
ggtgagtcag tcatactgga gtgtacttct tgtgctgaag aagaagtgag attaatggaa   1320
gaagaagga ggaggcaga ggaggaagaa aggagaaggg aagaagaga ggcaaggcag   1380
agggaggaag aaaggaggag ggaagaagag gaagctagaa ggaaggaaga ggaagaagca   1440
aggaaggctg aagaagaaag aagaagagaa gaggcagaag aagcaagaag acgagaaagg   1500
gaggcaacaa gggagaaaga gaacaaagg aggagacaag aagaagaagc caggagagag   1560
gaagaggagg aagccagaag gcaagaagaa gaaatcagaa ggagacaaga gaagggaaa   1620
gctaggaaga gaagagaga aggagcagct gaaggcaac aggaggaaga agctgagaga   1680
gaggcagaag aagcgaggac aagagaagag gaagaggcag ctagaaggca gcagggaa   1740
gaagcacaaa gggaggcaga ggaagcaaga aggagaggag aaagaagagc aaggaggagg   1800
gaggaacaag cgcagagga ggcggagga caagtagga agagcagcagct   1860
agaaggagac aggaacgaga ggaagcagaa agggaaagac aagcaggga gccaggagg   1920
gagggagagg aaacaaggag acatgaagaa gaagaagaag aagaaggga ggaggaa   1980
acaaggagag agagagggg agaggaggag gaggaaggag gaagaaaaga gaggaggcg   2040
gcaagagagg ccgagaaaag aaggcaagaa gaagcccaga caacaagag agcagctagg   2100
agacaggaag aagaaatgga aagaaggcat caagaagaag aaaccgagga gaggagcag   2160
```

```
ggtccttacg cacggaggaa aagaacattc cttaaaacag catga              2205
```

| SEQ ID NO: 28 | moltype = AA   length = 734 |
|---|---|
| FEATURE | Location/Qualifiers |
| REGION | 1..734 |
|  | note = Description of Artificial Sequence: Synthetic polypeptide |
| source | 1..734 |
|  | mol_type = protein |
|  | organism = synthetic construct |

```
SEQUENCE: 28
MSDKKSVSTP FECCRILFKF LLFMVIISNV AIHVTALSGR EGITPSTEWG LGPLVKRGER    60
KLVVSTENGE VSSVRVADGI TGSYHLQFIT LEPNSLFLPV VLHADMVFYV HTGSGRLTWM   120
DETEQKSVDL RIGDVFRLPF GTIFFIESNL EPARQKLRVY SIFTNSGDDL REPLSGPHSS   180
IRDMVLGFDR KVLQAAFHVP EDVIDEVLNG TEVPAIIHGV PKTTKKTLWE MEAQFMKSLL   240
GRGGHGFFDS QSNKKKTELF NIFKEKPDFE NCNGWSTVIT RKKLPALKGS HIGIYVVNLT   300
KGSMMAPHWN PTATEIGIAL QGEGMVRVVC SSTGTKQGCQ NMRFKVEEGD VFAVPRFRPM   360
AQMAFNNNSF VFVGFSTTTK RHHPQYLTGK ASVLRTLDRQ ILAASFNVTN TTMDRILEAQ   420
GESVILECTS CAEEEVRLME EERRRAEEEE RRREEEEARQ REEEERRREE EARRKEEEEA   480
RKAEEERRKR EAEEEARRREE EATREKEEQR RRQEEEARRR EEEEARRQEE EIRRRQEEGE   540
ARKREEEEAA RRQQEEEAER EAEEARTREE EEAARRQQGE EAQREAEEAR RREEEAARRR   600
EEQAQREAEE ASRREEEAAA RRRQEREEAE RERQAEEARR EGEETRRHEE EEEEEEEEEE   660
TRRGERGEEE EEGGRKEEEA AREAEKRRQE EAQRQQEAAR RQEEEMERRH QEEETEEEEQ   720
GPYARRKRTF LKTA                                                    734
```

| SEQ ID NO: 29 | moltype = DNA   length = 1302 |
|---|---|
| FEATURE | Location/Qualifiers |
| misc_feature | 1..1302 |
|  | note = Description of Artificial Sequence: Synthetic polynucleotide |
| source | 1..1302 |
|  | mol_type = other DNA |
|  | organism = synthetic construct |

```
SEQUENCE: 29
atgggcgtac cagaatcgga ggtggtgtca caaggtgagg ttgaatcacc attgcaacca    60
gatcaaaacc agcacaagaa ccatcagttc ccgtccctcg gtagacaagc atcgatctac   120
tccctcactc tcgacgaatt ccaacacacc ctatgtgaaa gtggcaagaa tttcgggtcg   180
atgaatatgg atgaattcct taacagcatt tggactgctg aagaaaacca agcccacgca   240
cacgcccatg cccatgccgc gcacgggcat gcgcacgcgc attctcatgc tcatagccaa   300
gcaccaagta caggggaagc cactagcaca ccacattttg cgataggaca gagcaatgtt   360
tcaatggaga aagctattgc caagcagcca agcttgccaa gacagggttc tcttacgctt   420
ccggaacctt gtgtcggaa aactgtggat gaagtttggt cagaaattca taagagccaa   480
aaagagcaac atcagaataa tgggggcagt gtcccggaca cgggtaattc cgctcaacgg   540
caggttacat ttggcgaaat gacacttgag gatttcttgg tcaaagcagg ggtagtacgc   600
gaacaggaga atgcccctgc acctcctcaa cagcaatcat atatgatgta tcaaaacagc   660
aacaatcccg ctatgccaa tatggctcga cctgttattg gcttaggtgg agtcacgggc   720
agcgttggag ttggcattcc tagctatcca ccacttcctc agaccggtgt tgttgaggcc   780
ccaatatacc cggtaagtat gaaaaggggt gccggattcc cacaacagcc aacggctgtt   840
tacggcggga gaatggggaa tggtggcggg gtcgggatgg gcaagtaca aggagtggcc   900
gggatggggt cgccactaag tccagtgtcg tcggatggat tatgcgttaa tcaagtcgat   960
agcgggggtc aatacgggtt ggaaatggga atgagagggg gaagaaaacg cataatgat   1020
ggtccggtag agaaagtggt ggaaaggagg caaggagaa tgatcaagaa tagagaatca  1080
gcagcaagat caagagcaag aaagcaggct tacacagtag aacttgaggc agaactgaac  1140
cagctaaaag aagagaatgc acatctgaaa caggccctgg cggagctcga gagaaaagg   1200
aaacaacagt actttgacga agggaaaatg aaagtgcaaa cgaaagcgca aaaggcgact  1260
aacaaattga gaggtatgag gaggagtttg agttgccctt ga                     1302
```

| SEQ ID NO: 30 | moltype = AA   length = 433 |
|---|---|
| FEATURE | Location/Qualifiers |
| REGION | 1..433 |
|  | note = Description of Artificial Sequence: Synthetic polypeptide |
| source | 1..433 |
|  | mol_type = protein |
|  | organism = synthetic construct |

```
SEQUENCE: 30
MGVPESEVVS QGEVESPLQP DQNQHKNHQF PSLGRQASIY SLTLDEFQHT LCESGKNFGS    60
MNMDEFLNSI WTAEENQAHA HAHAHAAHGH AHAHSHAHSQ APSTGEATST PHFAIGQSNV   120
SMEKAIAKQP SLPRQGSLTL PEPLCRKTVD EVVWSEIHKSQ KEQHQNNGGS VPDTGNSAQR   180
QVTFGEMTLE DFLVKAGVVR EQENAPAPPQ QQSYMMYQNS NNPAMANMAR PVIGLGGVTG   240
SVGVGIPSYP PLPQTGVVEA PIYPVSMKRG AGFPQQPTAV YGGRMGNGGG VGYGQVQGVA   300
GMGSPLSPVS SDGLCVNQVD SGGQYGLEMG MRGGRKRIID GPVEKVVERR QRRMIKNRES   360
AARSRARKQA YTVELEAELN QLKEENAHLK QALAELERKR KQQYFDEGKM KVQTKAQKAT   420
NKLRGMRRSL SCP                                                     433
```

| SEQ ID NO: 31 | moltype = DNA   length = 1266 |
|---|---|
| FEATURE | Location/Qualifiers |
| misc_feature | 1..1266 |
|  | note = Description of Artificial Sequence: Synthetic |

|  |  | polynucleotide |  |
| --- | --- | --- | --- |
| source |  | 1..1266 |  |
|  |  | mol_type = other DNA |  |
|  |  | organism = synthetic construct |  |

SEQUENCE: 31

```
atggaggaaa aagatgaact tgaggaagaa gaagaatatg ttgatgatga aatcaagaac   60
aatttaccag tccaaaactc atcttcaata agttggttca caaaaatgat atctttacaa  120
gtagagatct tcaccactat cttagtttcc cccattttct atatcctctc ttttgtatct  180
gacttcaact tcctccgccc tgaagaaacc gaaaagaacg tagctgtagc tgtaaatgct  240
gctgctacag taccttcaaa agtagtacat ggaagtactt tactgctcaa gaaatttggt  300
gttggaattc ttggagctgc ttatgttgga atggttttga caacgttgtt gattttgtcg  360
ggggttctgg gatttgggtt agtgagaatg tgggcggaag agcctgtggt attgagagag  420
aagctgtatt ttgattatgc agatgtttat cctaaggctg ttttttcttt tgctgaatat  480
ggtctggaga attataacca taattttatg atgttgaagc agaagaagaa ttttggtgtg  540
ccagttgggc atacaatgta tgtttctttg tttctactga tgcctgaatc tgatttcaac  600
agagatattg tgttttccag gttggttgca gaagcgttat cagccgaggg gatcataatg  660
gcaagatcaa gtcatccacg tatgttgcga ttcagaagcc tgccaatccg tctcatgcga  720
gaatttatta tgagtgtgcc cctagtactt ggacttacag ctgaaacaca aaggatgatc  780
attccaatgt taaagcataa ggaaggtatt ccaagaacga aggcaatcaa ataactatg   840
atacctcgag ctggaacgct agccctgccg cagctttatc aatcggagat catattgaag  900
tctcatcctc cttggtataa agacttggca tacaagtgga aatggacatt ctccgtctgg  960
acctctatgt atatgtatgt tacactgctc ataattctac tcaactggtg cagaccgctc 1020
gtatttccag tgatcgcaac aagctttagg acacgcgttg atgagagttt aacagtggaa 1080
gcatcagaag aaccacaaga gaaagctcga gaagaaagtg atgtgtcgga gtcggtaaga 1140
agatggcggc agagcagaag aaagaggaag gcaatgcttc aacagagtgt ctcgccagag 1200
ttcgcggatg attctgcatc aagcatttct gtgactaggg aggatacagc tgagtcaagc 1260
gagtaa                                                            1266
```

| SEQ ID NO: 32 | moltype = AA length = 421 |
| --- | --- |
| FEATURE | Location/Qualifiers |
| REGION | 1..421 |
|  | note = Description of Artificial Sequence: Synthetic polypeptide |
| source | 1..421 |
|  | mol_type = protein |
|  | organism = synthetic construct |

SEQUENCE: 32

```
MEEKDELEEE EEYVDDEIKN NLPVQNSSSI SWFTKMISLQ VEIFTTILVS PIFYILSFVS   60
DFNFLRPEET EKNVAVAVNA AATVPSKVVH GSTLLLKKFG VGILGAAYVG MVLTTLLILS  120
GVLGFGLVRM WAEEPVVLRE KLYFDYADVY PKAVFSFAEY GLENYNHNFM MLKQKKNFGV  180
PVGHTMYVSL FLLMPESDFN RDIGVFQLVA EALSAEGIIM ARSSHPRMLR FRSLPIRLMR  240
EFIMSVPLVL GLTAETQRMI IPMLKHKEGI PRTEAIKITM IPRAGTLALP QLYQSEIILK  300
SHPPWYKDLA YKWKWTFSVW TSMYMYVTLL IILLNWCRPL VFPVIATSFR TRVDESLTVE  360
ASEEPQEKAR EESDVSESVR RWRQSRRRKR AMLQQSVSPE FADDSASSIS VTREDTAESS  420
E                                                                 421
```

| SEQ ID NO: 33 | moltype = DNA length = 597 |
| --- | --- |
| FEATURE | Location/Qualifiers |
| misc_feature | 1..597 |
|  | note = Description of Artificial Sequence: Synthetic polynucleotide |
| source | 1..597 |
|  | mol_type = other DNA |
|  | organism = synthetic construct |

SEQUENCE: 33

```
atgtataact caagcaacta cagctgtaat tacaacccca tttctcatc  taatttattc    60
aacatccctt ctccttgtat gcaatatgaa cacgaacttt tcttccaata ttaccatgat  120
caacttcaac agaatcttga cgatacctta gctgagatca gtactgagac tgccattatt  180
aacacggcag attccagcaa agacgaggct ataatcagta gaaatgaact tgaacaagat  240
caggaagcgc gtaagaataa aaagggtaaa gtaagcagca acaagagagt gtctaagaaa  300
gatagacaca gcaagattaa cactgctaaa ggcccgagag accgaagaat aagactttca  360
attgatattg ctcgcaattt tttcaattta caagacatgt tgaggttcga aaggccagc   420
aaaactctgg agtggttgct tataaagtca aaatctgata tcaaggagct ctccaaaagt  480
cgaataagca aattaagatg tagtactgtt atgggtgcaa atagtgaaac ctccacttct  540
gaatgtgaag ttgtatcagg aattgatgaa ctccatcca atcaaggcaa atgctaa      597
```

| SEQ ID NO: 34 | moltype = AA length = 198 |
| --- | --- |
| FEATURE | Location/Qualifiers |
| REGION | 1..198 |
|  | note = Description of Artificial Sequence: Synthetic polypeptide |
| source | 1..198 |
|  | mol_type = protein |
|  | organism = synthetic construct |

SEQUENCE: 34

```
MYNSSNYSCN YNPIFSSNLF NIPSPCMQYE HELFFQYYHD QLQQNLDDTL AEISTETAII   60
NTADSSKDEA IISRNELEQD QEARKNKKGK VSSNKRVSKK DRHSKINTAK GPRDRRIRLS  120
IDIARNFFNL QDMLRFEKAS KTLEWLLIKS KSDIKELSKS RISKLRCSTV MGANSETSTS  180
ECEVVSGIDE SPSNQGKC                                                198
```

```
SEQ ID NO: 35          moltype = DNA  length = 1038
FEATURE                Location/Qualifiers
misc_feature           1..1038
                       note = Description of Artificial Sequence: Synthetic
                       polynucleotide
source                 1..1038
                       mol_type = other DNA
                       organism = synthetic construct
SEQUENCE: 35
atgtatccgt caagcaacat ctgtaattac aaccccaata tttcctcctc aaataactta    60
tttcacattc catctcctaa ttctatgcaa tatgaacacg aacttttcca atatttccac   120
gaccatcatc tccttcaacc ccaacaacaa caactactct tgactacacc tgatcattac   180
atggcagcag attccaacaa agataccgta atcagtagta ctattaatca actggaagt    240
cctaaagaag ttgaattaca aggcagctgc aagaacaaaa atggtgaaaa taagagagct   300
gttgcttaca agaaagatag acacagcaag attaatacag ctcacggccc tagagatcga   360
agaatgagac tttctctcga tgttgctcgc aaattttca atttgcaaga cttgcttgga    420
ttcgataagg ccagcaaaac tgtggagtgg ttgcttacca agtccaaatc tgctatcaat   480
gagctcgtcc aaagtactgc tactggtgca attagtacat cctctacgac atccgagtgt   540
gaagtgatat caggaattga tgaatctaca accactaatg atattcagaa gcagccaaat   600
agaagtaaag taggggagaa gaaaaaggct aataaactag ctcgtagagc tgcatttaat   660
cctgtggcaa aggaatcaag gaaacaagct agagcgaggg caagggagag aacaaaaata   720
aagaaaagcc ttttaaatat tggtgatcag tctatggcgg ctgatgattt aaaacgatta   780
ggatgttgga gtcctttga aacaggtgaa gaatcaggta ttcaaggcta tagtactaat    840
catcaagtag aagaccaaca cactacgaac acgaggagc atcttttggg gactaaagag    900
aatgttgatg gctgtaattt ggttgttact ggcaactgga acccatttac tatcttcaac   960
tatcaccaca atactgaaat ttctcacgag caacaattta caaacttcca gttttctggg  1020
aagttttggg aagtttag                                                1038

SEQ ID NO: 36          moltype = AA  length = 345
FEATURE                Location/Qualifiers
REGION                 1..345
                       note = Description of Artificial Sequence: Synthetic
                       polypeptide
source                 1..345
                       mol_type = protein
                       organism = synthetic construct
SEQUENCE: 36
MYPSSNICNY NPNISSSNNL FHIPSPNSMQ YEHELFQYFH DHHLLQPQQQ QLLLTTPDHY    60
MAADSNKDTV ISSTINQLEG PKEVELQGSC KNKNGENKRA VAYKKDRHSK INTAHGPRDR   120
RMRLSLDVAR KFFNLQDLLG FDKASKTVEW LLTKSKSAIN ELVQSTATGA ISTSSTTSEC   180
EVISGIDEST TTNDIQKQPN RSKVGEKKKA NKLARRAAFN PVAKESRKQA RARARERTKI   240
KKSLLNIGDQ SMAADDLKRL GCWSPFETGE ESGIQGYSTN HQVEDQHTTN HEEHLLGTKE   300
NVDGCNLVVT GNWNPFTIFN YHHNTEISHE QQFTNFQFSG KFWEV                   345

SEQ ID NO: 37          moltype = DNA  length = 1014
FEATURE                Location/Qualifiers
misc_feature           1..1014
                       note = Description of Artificial Sequence: Synthetic
                       polynucleotide
source                 1..1014
                       mol_type = other DNA
                       organism = synthetic construct
SEQUENCE: 37
atgtatccgc caagcaatag ctgcaactac agccccattt tcaacatccc ttctccttgt    60
atgcaatatg gagacgaact attcttccaa tattatcatg acgattacct tcaagagcaa   120
caagtaccgt gatagaaga tcagtgtctt gacatcttag ctgagagcac tgagactgtt   180
actaataaca agaaaccgt catcaattct gatcatagtg taaagtttta acatagaa     240
actgttacaa acagtcaggg tttgggagga aatgaagaaa aagagtaga aggccgcgaa   300
aacaaaagag atgtatatgag cggcaccatt agtatcattc atggacggaa aaacaagaaa   360
tgttcccata aagatcgaca tagcaagatt agcactgctc gtggccttag agatcgaagg   420
atgagacttt cccttgatgc agctcgcaag tttttcagtt tacaagacat gttggggttc   480
gataaggcaa gtaaaactgt agaatggttg cttaccaaat cggagtctga aatcgaagag   540
ctagctaaag gcaataaaga aggagaatcc cttcctaaac aaagctgcag tactaccaat   600
ggaattggtg caattagtac tgcaatatcc tctatttctg agtgtgaggt tatatcagga   660
actgatgaat cttcttctat tactgataaa aagaagctgg aaactgctaa aggaccgttg   720
aaaaagaagg gtaaaactgc tcgtagagct acatttgatc ctcttattac aagggaatcg   780
aggaatcaag caagggttag ggctagagag cgaacaaaac taaagaaaag ccttagtaaa   840
tccaaagcca tgactcatga gaacagtgct gatgactgta atttggttgt taattttgga   900
gattggagtc aatttagcat cttcaactat cagcaaaatg cagttggaat ttcccatgat   960
cagcagcaat ttacagactt ccaatttgt ggtaataagc tgtgggaagt ctag          1014

SEQ ID NO: 38          moltype = AA  length = 337
FEATURE                Location/Qualifiers
REGION                 1..337
                       note = Description of Artificial Sequence: Synthetic
                       polypeptide
source                 1..337
                       mol_type = protein
```

```
                         organism = synthetic construct
SEQUENCE: 38
MYPPSNSCNY SPIFNIPSPC MQYGDELFFQ YYHDDYLQEQ QVPLIEDQSL DILAESTETV    60
TNNKETVINS DHSVKVYNIE TVTNSQGLGG NEEKRVEGRE NKRDDMSGTI SIIHGRKNKK   120
CSHKDRHSKI STARGLRDRR MRLSLDAARK FFSLQDMLGF DKASKTVEWL LTKSESEIEE   180
LAKGNKEGES LPKQSCSTTN GIGAISTAIS SISECEVISG TDESSSITDK KKLETAKGPL   240
KKKGKTARRA TFDPLITRES RNQARVRARE RTKLKKSLSK SKAMTHENSA DDCNLVVNFG   300
DWSQFSIFNY QQNAVGISHD QQQFTDFQFC GNKLWEV                           337

SEQ ID NO: 39             moltype = DNA  length = 867
FEATURE                   Location/Qualifiers
misc_feature              1..867
                          note = Description of Artificial Sequence: Synthetic
                           polynucleotide
source                    1..867
                          mol_type = other DNA
                          organism = synthetic construct
SEQUENCE: 39
atgggcctct cacaatatcc agctccagca gatgcaggag tactgtgtgt gattcttgta    60
aacacagcca tatctatttc cattgtcaag gagatagtcc gatcgatcct tcacgttatt   120
ggcatccata tcgcatcatg gaagattat tcttttgaag gatcatttga atgccgcgga   180
agcccatcag agtcatacat ggaggagttt agaagccgaa cacctgcatt tcgttatgac   240
tcggtgtgta tctctaacca ccctgagcaa gaatgctctg tgtgcctgac taaattcgag   300
cctgacacag agataaaccg tctctcctgt ggccatgttt tccataagct gtgtctagag   360
aagtggctca gtattggca tgtaacttgc cctcttttgca ggaaacacat gatgcctcac   420
gagcaagagg acgatacatg tccaatgtca ttttccaatg atgttgcgcg aactctccaa   480
aatgctaccg catttatgtt ggatcctcca aaaatgcact actttttggag gatccgacat   540
gtgcctgatg acattttcgg agaatctgag caacattgct ttccagtagc caactcagag   600
agtttcgagc caactgacat gctagtgcga gtcaacgcag ggttcctgtg gtatctgcac   660
ctgaaagaac ctgcatgtgt agttggtgag cacaagcagc tgtaccttac acttgatgtc   720
tttcgcaatg ctgacggtga agaaggcgtc gaggatggta atggtgccat agttggttgt   780
ggttgttcag ccatccttca gcagattctg cagaagaaat taatagatat gaacaagaaa   840
ttctggatta actatgaggt agagtag                                       867

SEQ ID NO: 40             moltype = AA  length = 288
FEATURE                   Location/Qualifiers
REGION                    1..288
                          note = Description of Artificial Sequence: Synthetic
                           polypeptide
source                    1..288
                          mol_type = protein
                          organism = synthetic construct
SEQUENCE: 40
MGLSQYPAPA DAGVLCVILV NTAISISIVK EIVRSILHVI GIHIASWEDY SFEGSFECRG    60
SPSESYMEEF RSRTPAFRYD SVCISNHPEQ ECSVCLTKFE PDTEINRLSC GHVFHKLCLE   120
KWLKYWHVTC PLCRKHMMPH EQEDDTCPMS FSSYVARTLQ NATAFMLDPP KMHYFWRIRH   180
VPDDIFGESE QHCFPVANSE SFEPTDMLVR VNAGFLWYLH LKEPACVVGE HKQLYLTLDV   240
FRNADGEEGV EDGNGAIVGC GCSAILQQIL QKKLIDMNKK FWIDYEVE                288

SEQ ID NO: 41             moltype = DNA  length = 2562
FEATURE                   Location/Qualifiers
misc_feature              1..2562
                          note = Description of Artificial Sequence: Synthetic
                           polynucleotide
source                    1..2562
                          mol_type = other DNA
                          organism = synthetic construct
SEQUENCE: 41
atgaatcttc aggtggatga tcaaatgata ctcatttctc agtactatcc tggtatctac    60
actcaagagt taccagaaca aggggaggcg aaacaaagga ggagacgaaa gaagaacaaa   120
ggagaagcaa gtgaggttat gaggaaaaga aagcttagtg aagaacaagt gaatctgctt   180
gaacagagct ttgggaaaga gcacaaactg gagtccgaga ggaaagacaa gcttgcctct   240
gagctggggc ttgatcctag gcaagttgct gtctggtttc agaacagaag ggctagatgg   300
aagaacaaga agttggagga ggaatactct aagttgaagt ctgagcatga cactaacatt   360
gttcataatt gccgtcttga aaatgaggtt tgaagctgaa ggaacagtt gtctgaagca   420
gagaaagaga tacaaaggtt gctgatggag agatgtgatg gggttaattc gagcaatagc   480
ccaactactt catcactctc aatggaagca gccaatatgg aacctccttt tcttgggaa   540
tttggaatgg aaggatttga caatacattt tatgtgccag aaaaacactta ctctcaggga   600
ttggaatgga atggaccatt ttttgcacct cctgatatta attatgggat cattaggttc   660
cagacattac ccgaccccac tattcctggg cagtatgcga actacacatg gggtagtgaa   720
tcttatacac aattgcttca gtccgttagg cacaagctca accttctgt tcatttttat   780
gtcattcgag gcattgcact agctatgcaa atatggttgt atgagtgttg ctctaccgtc   840
aacactgata tagctacaag gatttctaat tcaatctctc gcatacttag ctggtcagct   900
agtaaggaca agatatggtt atctgcaatt gaagataaga tgatcaaacc atcatggatc   960
aagttcacca acataattga agcaccagag gagctttcaa gaatgaattt gccaaataaa  1020
gttgaataca ttcttgaaga agttgaaaca aagtccgagc atccgataga tgctccatct  1080
ccatccgttg gttcagatct tggaactttc aagaagagg ttttttgaaga actagataca  1140
gggcaggtga atgatataaa aattatggag aatgttcctg taggtgttga tttatcttcc  1200
caatttgaag gggcatttga tgaagagaat gcagagaagg aaactatgca tgtagaatct  1260
```

```
ccaaaacaga aagctacaat aagcattcca ggaaaacaaa aaaatgagga gaaggagaca   1320
aaaatacaat ctcacattca agaagagaac gttatacaac aaggagatga ttgttgtgaa   1380
gatttcagtg gtgaatcagc cgactacatt aatataggtg attcagacaa tgactctaga   1440
tctgaaaaaa gagaagtaac acttgatgat tttgagctgc cagagaactt ctcccagatt   1500
attaattctg gggggagaac ttctgttgga cctccaattt tcctcatcaa gcatccattt   1560
actggggtta ttggcgaaga tgttgatcct gacttattgg aagaattcaa taagtggtta   1620
tactttggta tcgatacagt ttcaaagagg aggaaggcgc ttattctgt aaaagataac   1680
cagcttaagc cgtggtatga ttttggagtg agaaagttg ataaaaatga gaggttttat   1740
actttggtac accccgggca agtcctcaac gatacgcaca ttgatgttat tttatactat   1800
ttgagaaaga gaggaaagta tggtcgtcaa aacaaaatat ggtttacaat cattgattgt   1860
atgttcaaca ctagaattga acaaatttat cagaggtaca tcaatactcc tgccgataag   1920
aagcttgttg ttgtcaaatc ccaagacgtc gtatcagaat acatattggg gtacagatta   1980
ctcgcaaata ttgcattgga tcaagttgat tttgtgatta tgcccataaa cattgtgaaa   2040
aaatttttatt ggttgttggt tgtgtttgac attaccgata gggttctata tgtttatgat   2100
tctatgttct cttcacgaaa tcacaacctt gttgaatttg ttgtcaacaa gtttgctgtt   2160
atgatccccc tctacttgtc atgcaccgac ttctatggca agcgtccaga catcaactac   2220
aagaacacaa aagcatacat tgaaaaatgt gttactgacc ctcttgacat tcagtggttg   2280
gtcggtgaga tactccatca aaatgaggga tcacttgact gtagtgtata cgtggctgca   2340
tttacagaat atgtcagcat ggagagcta gcagtttcaa aggaagacct ttctgatatt   2400
gatcaacatc gtagacgcta tggagcgcta ctttgggatt atgataggaa gaagcaagat   2460
actggtgcaa ttagtgagag cgaggtgact ggcagattag caagaagaaa aggtgcacca   2520
gctgtgaacg agaacacaca agtccggaag aagaagaatt ag                      2562
```

```
SEQ ID NO: 42           moltype = AA   length = 853
FEATURE                 Location/Qualifiers
REGION                  1..853
                        note = Description of Artificial Sequence: Synthetic
                        polypeptide
source                  1..853
                        mol_type = protein
                        organism = synthetic construct
SEQUENCE: 42
MNLQVDDQMI LISQYYPGIY TQELPEQGEA KQRRRRKKNK GEASEVMRKR KLSEEQVNLL   60
EQSFGKEHKL ESERKDKLAS ELGLDPRQVA VWFQNRRARW KNKKLEEEYS KLKSEHDTNI   120
VHNCRLENEV LKLKEQLSEA EKEIQRLLME RCDGVNSSNS PTTSSLSMEA ANMEPPFLGE   180
FGMEGFDNTF YVPENTYSQG LEWNGPFFAP PDIDYGIIRF QTLPDPTIPG QYANYTWGSE   240
SYTQLLQSVR HKLNPSVHFY VIRGIALAMQ IWLYECCSTV NTDIATRISN SISRILSWSA   300
SKDKIWLSAI EDRMIKPSWI KFTNIIEAPE ELSRMNLPNK VEYILEEVET KSEHPIDAPS   360
PSVGSDLGTF KKEVFEELDT GQVNDIKIME NVPVGVDLSS QFEGAFDEEN AEKETMHVES   420
PKQKATISIP GKQKNEEKET KIQSHIQEEN VIQQGDDCCE DFSGESADYI NIGDSDNDSR   480
SEKREVTLDD FELPENFSQI INSGGRTSVG PPIFLIKHPF TGVIGEDVDP DLLEEFNKWL   540
YFGIDTVSKR RKAPYSVKDN QLKPWYDFGV EKVDKNERFY TLVHPGQVLN DTHIDVILYY   600
LRKRGKYGRQ NKIWFTIIDC MFNTRIEQIY QRYINTPADK KLVVVKSQDV VSEYILGYRL   660
LANIALDQVD FVIMPINIVK KFYWLLVVFD ITDRVLYVYD SMFSSRNHNL VEFVVNKFAV   720
MIPLYLSCTD FYGKRPDINY KNTKAYIEKC VTDPLDIQWL VGEILHQNEG SLDCSVYVAA   780
FTEYVSIGEL AVSKEDLSDI DQHRRRYGAL LWDYDRKKQD TGAISESEVT GRLARRKGAP   840
AVNERTQVRK KKN                                                      853

SEQ ID NO: 43           moltype = DNA   length = 2790
FEATURE                 Location/Qualifiers
misc_feature            1..2790
                        note = Description of Artificial Sequence: Synthetic
                        polynucleotide
source                  1..2790
                        mol_type = other DNA
                        organism = synthetic construct
SEQUENCE: 43
atgatagtag taagatggtg gatgacaaca ttccaattga cagagctgtt tgtgagttgt   60
ttagttcatt tgacttacgg gctttacata ttcagcacag cagtggccgg tgatgttttcc  120
cagactctga gcgattggct tttgcaagcca aatttgaaa ctagccttaa aacagatgat   180
tcaaaaaaga ctaacactga tttgcctcct attgtgttgg ttcatggaat ctttggtttt   240
ggcaaaggga gattgggagg actttcatat ttcgctggtg cagagaaaaa ggatgaaagg   300
gttctagtac cggatttggg ttcacttact agcatttatg acagggcacg tgaattgttt   360
tattatttga aaggagggca ggttgattat ggggaggaac acagtaaggc ttgtgggcat   420
tcccaatttg gacgaattta tgaacaagga cactaccccg agtgggatga agatcatcct   480
attcattttg tgggccattc agctggagca caggttgttc gagtcttgca acagatgctg   540
gctgacaagg cattcaaagg ttacgacaac acttcagaga actgggtgtt aagcctaaca   600
tcattatctg gagcacttaa cggagacaac cgaacttact ttgatggaat gcaacctgaa   660
gatgggaagt ccttaacgcc cgtatgtttg ctccaactt gccgcattgg agtaataagt   720
tatgagtggc ttgacattcc cttgctgaag gactattaca actttggctt tgaccacttc   780
agtatgtcct ggaggaaaag tggtatccgg ggttttgttg attgccttt agggaatggc   840
ggtccatttg cttcgggaga ttggatactt ccagatctta ctatccaggg gtcaatgaag   900
ttgaacagcc acttacgtac atttccgcaa acatactact tcagctatgc taccaagcgt   960
accacaacaag taatgggtct tacagttcct ttggcgtta tagggataca tccgctacgc  1020
ttcatcagag tcctgcaaat gagccaatgg cggcatccac aagatgtttc tcctccgtac  1080
aagggctata gggatgaaga ttggtgggac aatgacggtg ctctcaacac catatctatg  1140
acgcacccac gcttgccggt tgaacacccg agtcaccttg tcgttaaaga ttctgattgt  1200
cagcccttgc aacctggcat ctggaatcat caagtttcct cttctgtgca gttgttatca  1260
ccaccattgg ctcgtaggct ttccgtgggg aaatgtgaaa gggaaatatc tgtcattctc  1320
```

-continued

```
agttatgtta cggaaagatc agctctcacc attagaaacc ccgatgaag  ccaacaacaa   1380
accaccaaga  tcctctttca  ccaccagaag  tgccgcatgcc  ttccgtctta  ctgtgaacgc   1440
ccacgtccaa  tggaatttct  gggaaggatt  tcaagaaatg  tagaaggaaa  tgatactaag   1500
gctaggattt  ctgcagctat  tttactagtt  tgcattatcc  ttcctttgct  agcctcagca   1560
tttcttgatc  atcttcctga  atttctagaa  catgattcta  gaaataaaga  tgtaacaatc   1620
cgtggtgata  ataatattgt  tcgtgccaat  gacaatgact  ttactcttcc  tcgctcacat   1680
gagaaaaaga  atgaaagatc  tttaagagaa  aagaagtcaa  agaagaagaa  gcataagaag   1740
aagaagaaca  agaagggaaa  gaaatcacac  aaagataaaa  tttttgattt  tgaccatatt   1800
tttgaggaa   accaacaaga  aggagatgaa  ttttcccctt  atttgcaacc  atttgatgtg   1860
cctcaaacaa  cagaagaaca  agaacagacc  gagaattatg  atggattacg  tgagggattt   1920
taccagaaaa  catgtcctca  agcagagaat  attataagaa  atggtctaat  cagggccttt   1980
cagaatgact  ctaccattgc  tgctgcatta  cctcgcctttc  tcttgcatga  ttgctttgtc   2040
aatggatgtg  atgggtcgat  attactagat  acaacacccg  tggtgcaag   agtggagaag   2100
ttagcaggca  caaatggtgc  tacagtcaag  ggatttgaac  tcatagacga  gatcaaagcc   2160
gagctcgaga  gacaatgccc  tggcattgtc  tcctgctctg  atatttttggc  atacttgtcg   2220
cgcgatgcct  ttgttttatc  aggcctcccc  aattacaacg  tgctaggtgg  tcgacgcgat   2280
ggcatggaat  ccaatgaagc  aaacgttgtt  ggaaacctac  cacttcctgg  cgacacagtg   2340
gatcaaatga  ttgatctttt  tcaaaagaaa  ggcctaaatt  cggaagattt  ggttgtccta   2400
attggtgcac  attcaattgg  agtagcccat  tgtttcaact  tcctttacag  attggacgaa   2460
ccagagaagg  cacaaatgtt  agatccaagg  cttgctggag  tcatgagatt  tatttgtact   2520
aaccaaatga  ataccttacc  ttttgatccc  acaacacagt  acaagatgga  ttcaattttc   2580
tacaagcaac  taatgatgaa  gaaagggttg  attgaatcgg  atcaaatact  ggctcaagat   2640
attagaacga  ggggcttggt  gcaaagtttt  ggtgatgatg  aaatgggatg  gtttgataag   2700
tttggtaagg  ctatgaataa  attgggagca  attgaagtgc  tcactggaaa  ccaaggccag   2760
atcaggagac  agtgtagagc  tgttaactga                                      2790

SEQ ID NO: 44         moltype = AA   length = 929
FEATURE               Location/Qualifiers
REGION                1..929
                      note = Description of Artificial Sequence: Synthetic
                       polypeptide
source                1..929
                      mol_type = protein
                      organism = synthetic construct
SEQUENCE: 44
MIVVRWWMTT FQLTELFVSC LVHLTYGLYI FSTAVAGDVS QTLSDWLFKP NLETSLKTDD    60
SKKTNTDLPP IVLVHGIFGF GKGRLGGLSY FAGAEKKDER VLVPDLGSLT SIYDRARELF   120
YYLKGGQVDY GEEHSKACGH SQFGRIYEQG HYPEWDEDHP IHFVGHSAGA QVVRVLQQML   180
ADKAFKGYDN TSENWVLSLT SLSGALNGTT RTYFDGMQPE DGKSLTPVCL LQLCRIGVII   240
YEWLDIPLLK DYYNFGFDHF SMSWRKSGIR GFVDCLLGNG GPFASGDWIL PDLTIQGSMK   300
LNSHLRTFPQ TYYFSYATKR TTQVMGLTVP SGVLGIHPLL FIRVLQMSQW RHPQDVSPPY   360
KGYRDEDWWD NDGALNTISM THPRLPVEHP SHLVVKDSDC QPLQPGIWNH QVSSSVQLLS   420
PPLARRLSVG KCEREISVIL SYVTERSALT IRNPDGSQQQ TTKILFHHQK CACLPSYCER   480
PRPMEFLGRI SRNVEGNDTK ARISAAILLV CIILPLLASA FLDHLPEFLE HDSRNKDVTI   540
RGDNNIVRAN DNDFTLPRSH EKKNERSLRE KKSKKKKHKK KKNKKGKKSH KDKIFDFDHI   600
FGGNQQEGDE FSPYLQPFDV PQTTEEQEQT ENYDGLREGF YQKTCPQAEN IIRNGLIRAF   660
QNDSTIAAAL PRLLLHDCFV NGCDGSILLD TTPSGARVEH LAGTNGATVK GFELIDEIKA   720
ELERQCPGIV SCSDILAYLS RDAFVLSGLP NYNVLGGRRD GMESNEANVV GNLPLPGDTV   780
DQMIDLFQKK GLNSEDLVVL IGAHSIGVAH CFNFLYRLDE PEKAQMLDPR LAGVMRFICT   840
NQMNTLPFDP TTQYKMDSIF YKQLMMKKGL IESDQILAQD IRTRGLVQKF GDDEMGWFDK   900
FGKAMNKLGA IEVLTGNQGQ IRRQCRAVN                                    929

SEQ ID NO: 45         moltype = DNA   length = 2478
FEATURE               Location/Qualifiers
misc_feature          1..2478
                      note = Description of Artificial Sequence: Synthetic
                       polynucleotide
source                1..2478
                      mol_type = other DNA
                      organism = synthetic construct
SEQUENCE: 45
gtatgtttca  gtctcacaga  gatcgttcat  cgataccaca  gccatgtgga  agcagaaaaa    60
gagagctctg  cagaagtttt  ggacaccgag  cactctaaat  atgcaagctt  catgacagtg   120
ggacaactgt  tacaaacggt  aggaaggcaa  ctcgaggaac  tgctgttga   tgatctcagt   180
gtaactgacc  ttgtccattt  ggaaaaccaa  ctgccaactg  ctctaatgca  agtcagatct   240
agcaagacgc  atttgatgat  tgaatctatc  aaaagtcttc  gtgagaagga  aaaactgctg   300
agtgaagaaa  acaaacatct  ggagaacaag  tacactccag  cttacaactt  caaatcagca   360
atggcctcta  ctatcgacct  cgaagccggc  cttcaagatg  aaaccaacaa  cttgcgcccc   420
ggggccgaa   ggctacctga  cgacggcaac  gaggctcgaa  tcgaagaacc  cgaaattcga   480
gccgaagtac  cattggatat  caattccaca  atagctctag  aagcgaatca  gcgttctgaa   540
ccggaaagaa  gcgttcaggg  cggtgctcga  cccatagccc  gagacaccta  cagcacgggg   600
gaaatcgggg  tcagcttgcg  tatgattttc  gaaatgttac  agcccaaca  agcagcgata   660
gctcagttgc  agagccgaac  tcatatgcaa  agcgggccga  actccaatcc  gcttcttcga   720
gaagtcaccc  ccagaacgga  gcccgccgta  gtgaaatcaa  aagaaaggaa  cagatcgggg   780
gctcctgaaa  ttgctaaatt  gctcgaggaa  ctcacaaaac  gagtcgaagc  caacgacaaa   840
aaagtgaaa   cgtataacgc  tagggtcgat  caaatcccgg  ggctccgcc   aatgataaaa   900
gggctcgatt  cgaaaaaatt  catacaaaag  ccttttccct  cgagcgcggc  cccaaaacca   960
atccccaaaa  aattccgtat  gcccgaaatt  cccaaatata  acggtacgac  cgatcctaac  1020
gaacatgtca  cctcctacac  atgtgccatc  aaaggcaacg  atttggagga  cgatgagatc  1080
```

```
gaatccgtgt tgttgaaaaa gttcggagag accctcgcaa agggagcaat gatctggtat   1140
cacaacttac caccaaattc cattgattct tttgccatgt tagcagattc gttcgtaaaa   1200
gcacatgctg gtgccataaa ggttgcaaca aggaaatcag acctcttcaa agtaaaacaa   1260
aggggtaacg aaatgctgag ggaattcgta tcccgatttc aaatgaacg tatggacttg    1320
ccaccggtca cagacgattg ggccgtacaa gctttcaagg acttagcaa gcgggctaagt   1380
tcgacagcat cacatcggat gaacaacggt tcagcacgtg atacggttcg gaacaaccga   1440
aggactgatc gggggcaaaa ttctcgggga cttatgagca agagcggctt tgataaaatat  1500
gccgatccta tagaagtccc tcgattatcg gagtataact tcaacattga tacatccgcc   1560
atcgtatcgg ccatcggacg catcaaagac accagatggc ctcgaccccat gcagaccgat  1620
cctgcccaaa ggaatcccaa tcaaatgtgc gaatatcatg gcacccatgg ccacagaacg   1680
gaagattgca ggcaactaag agaggaagtg gcccgcttat ttaacaaagg acaccttcgg   1740
gaatttctga gtgataggc gaagaaccat tttaggaaca aggaattcgg caagcaaaac    1800
gagccagaag aaccgcaaca cgtcattcac atgatcatcg cggcgtcga tgcccctcag    1860
ggaccgatgc ttaaacgcac taaaacatcg attgtgaggg aaaagcgatc tcgaactcaa   1920
gattatacac ccatagggac tttgtccttc agtgatgaag atacagaggg aatcatccaa   1980
ccccataacg atgcactggt aatatccgta ctcatgaata aaactaagat taagcgtgtg   2040
ttaattgatc caggtagctc ggccaatatc atcgatcga gggtcgtaga acagctccggc   2100
ctgcaagatc aggtcgtacc cgcaactctg gttctaaacg gattcaatat ggcatgtgaa   2160
accaccaaag gcgagattac cctaccgata aacgtggccg gaaccatcca ggaaacaaag   2220
tttcacgtga tcgaaggtga tatgagatat aacgcccttt tcggaaggcc gtggatccac   2280
agcatgagag ccgtaccctc gacctacac caggtcctca aattcccaac atcgggaggt   2340
gtcaaaatag tgtacggaga acaaccggcc gcaaaggaaa tgttctccgt cgaagaagca   2400
aaatcaatat cctcgtcttc gccgataaaa ggatcaggtt cagaaggaga cacaatcgga   2460
gagcagagcg ccaaatag                                                2478

SEQ ID NO: 46         moltype = AA   length = 825
FEATURE               Location/Qualifiers
REGION                1..825
                      note = Description of Artificial Sequence: Synthetic
                      polypeptide
source                1..825
                      mol_type = protein
                      organism = synthetic construct
SEQUENCE: 46
VCFSLTEIVH RYHSHVEAEK ESSAEVLDTE HSKYASFMTV GQLLQTVGRQ LEEPAVDDLS    60
VTDLVHLENQ LPTALMQVRS SKTHLMIESI KSLREKEKLL SEENKHLENK YTPAYNFKSA   120
MALPIDLEAG LQDETNNLAP GAGRLPDDGN EARIEEPEIR AEVPLDINSQ IALEANQRSE   180
PERSVQGGAR PIARDTYSTG EIGVSLRMIF EMLQAQQAAI AQLQSRTHMQ SGPNSNPLLR   240
EVTPRTEPAV VKSNEQESGT APEIAKLLEE LTKRVEANDK KVETYNARVD QIPGAPPMIK   300
GLDSKKFIQK PFPSSAAPKP IPKKFRMPEI PKYNGTTDPN EHVTSYTCAI KGNDLEDDEI   360
ESVLLKKFGE TLAKGAMIWY HNLPPNSIDS FAMLADSFVK AHAGAIKVAT RKSDLFKVKQ   420
RGNEMLREFV SRFQMERMDL PPVTDDWAVQ AFTQGLNGLS STASHRMNNG SARDTVRNNR   480
RTDRGQNSRG LMSKSGFDKY ADPIEVPRLS EYNFNIDTSA IVSAIGRIKD TRWPRPMQTD   540
PAQRNPNQMC EYHGTHGHRT EDCRQLREEV ARLFNKGHLR EFLSDRAKNH FRNKEFGKQN   600
EPEEPQHVIH MIIGGVDAPQ GPMLKRTKTS IVREKRSRTQ DYTPIGTLSF SDEDTEGIIQ   660
PHNDALVISV LMNKTKIKRV LIDPGSSANI IRSRVVEQLG LQDQVVPATL VLNGFNMACE   720
TTKGEITLPI NVAGTIQETK FHVIEGDMRY NALFGRPWIH SMRAVPSTLH QVLKFPTSGG   780
VKIVYGEQPA AKEMFSVEEA KSISSSSPIK GSGSEGDTIG EQSAK                   825

SEQ ID NO: 47         moltype = DNA   length = 1152
FEATURE               Location/Qualifiers
misc_feature          1..1152
                      note = Description of Artificial Sequence: Synthetic
                      polynucleotide
source                1..1152
                      mol_type = other DNA
                      organism = synthetic construct
SEQUENCE: 47
atgcagtctg tactctggaa cctaaggaag attgaaattc aagataaatt ctgcgatatt    60
gaaaggataa gtcctgcata cctcaacaca aatgacacgg caaagaaaat tcaagaagaa   120
atcaatggct tgcattgtaa actggaggag gctgagggat tattaagaat atttgaacca   180
gatacaaaaa aaattacatc actccatgag cttgatttgt gtgaaaaacg tcttcaggtt   240
gccttgaacc aagttaggca aagaatgaa caactctcca acaatcataa tacatcaagt   300
tatgaagata atatggagca aataaatgca ctccttcaat acatagacaa cacacaaact   360
gaggacacaa aaccctcgtt ggaggaatct ccctatgact tatggctaga gcttgaagat   420
tatagttaca caaactatat taatgacaac aacaatagtc atctctatgc tgcctcagaa   480
acatcttctc ttactcaaag ttctatgagc ctttcttctc caattattta tgatgcaata   540
tcccaaacaa gtataagtgg tgtgactaat tatcataaga agggactttt tagttcttta   600
actgatgaga atttaagca atcacaacat tcaaccagaa ccttccaac tctccacttta   660
caaacttcat tcaaatttgc caagcctgaa atgaaaactc ccacatctgc actacgccg    720
gtagcgccat atctgcatgt tgaagcaaca gcagcgtgta gccagcaacc agtttcaagt   780
gattattata aagagaacaa tgaactcgac tgcagatttc aacctaaagt tacaacgtct   840
aactatcaaa tgtcccaaaa acgtactgca gaaggaagtt ttagttcctt aactgatgaa   900
agcttaagc aatcacaatg ttcaaccagg atcttccaaa ctatcgctcc attacaaact   960
tcattctcat ttgccacgcc tgaaatgaaa actccaacct cagcattgcg gccggtggca  1020
ccatatctgc aggctgaagc agcagcatcc tctaaccagc agctaccttc taataatatt  1080
gaagaagaga accatgaaat ctcttggttt cagcctcaaa tgaaaagtc gaagtatcat   1140
catttagctt ga                                                      1152
```

```
SEQ ID NO: 48            moltype = AA  length = 383
FEATURE                  Location/Qualifiers
REGION                   1..383
                         note = Description of Artificial Sequence: Synthetic
                         polypeptide
source                   1..383
                         mol_type = protein
                         organism = synthetic construct
SEQUENCE: 48
MQSVLWNLRK IEIQDKFCDI ERISPAYLNT NDTAKKIQEE INGLHCKLEE AEGLLRIFEP    60
DTKKITSLHE LDLCEKRLQV ALNQVRQRME QLSNNHNTSS YEDNMEQINA LLQYIDNTQT   120
EDTKPSLEES PYDLWLELED YSYTNYINDN NNSHLYAASE TSSLTQSSMS LSSPIIYDAI   180
SQTSISGVTN YHKEGTFSSL TDENFKQSQH STRTFPTLTL QTSFKFAKPE METPTSALRP   240
VAPYLHVEAT AACSQQPVSS DYYKENNELD CRFQPKVTTS NYQMSQKRTA EGSFSSLTDE   300
SFKQSQCSTR IFPPIAPLQT SFSFATPEME TPTSALRPVA PYLQAEAAAS SNQQLPSNNI   360
EEENHEISWF QPQMKKSKYH HLA                                           383

SEQ ID NO: 49            moltype = DNA  length = 813
FEATURE                  Location/Qualifiers
misc_feature             1..813
                         note = Description of Artificial Sequence: Synthetic
                         polynucleotide
source                   1..813
                         mol_type = other DNA
                         organism = synthetic construct
SEQUENCE: 49
atgggaactg gtacttatgg agaagtggga cgtacaatac atcaaagatc aggaacacat    60
atacctcaaa ttctcgatcc gcctttgcta ggggatagtg attgcaagcg agaaggcaaa   120
catgtagaat ttatgcctcc aatcatgggt gaaaacttaa aagcagctaa tcaatttgaa   180
ctgatggccc cgtcaattgc attcaaatca tatcccatct cggaggtacc acaatattct   240
ggtggcaatg tggctgctgc atgtggtgaa tctttggtac atcaaaatat agaaagatca   300
gtgcataatg gtagaatgat tttgccaatt gaagtgaagg aggagcctat gtatgtaaat   360
gccaaacaat accatggaat tctaaggcga aggcaacttc gtgcaaaggc tgtgttggag   420
caaaaagtgg ttaaatctag aaaagcctta tcttcatgaa tctcggcaccg gcatgcgatg   480
agaagagcta gagatggtgg aggccgatttt ctcaacacaa aaagaagat ccaacttcgt   540
gctaataata atattaatac aactactcca gtagtaaag gcaaaggttg tgcagcctcg   600
gaagtcagtt ccatggactc tgatttctct caaaattact tgctcaattc tggacatatt   660
ggatcatcca atgctacttc tgttgaagga ttccagttcc aaggaataca taatacagat   720
aatcctcaat ggggttgtca ttatcagtgg aatctcaatg acaaccattg ctattgcatg   780
cagtcaggag cttctaatct ccaaccatt tga                                 813

SEQ ID NO: 50            moltype = AA  length = 270
FEATURE                  Location/Qualifiers
REGION                   1..270
                         note = Description of Artificial Sequence: Synthetic
                         polypeptide
source                   1..270
                         mol_type = protein
                         organism = synthetic construct
SEQUENCE: 50
MGTGTYGEVG RTIHQRSGTH IPQILDPPLL GDSDCKREGK HVEFMPPIMG ENLKAANQFE    60
LMAPSIAFKS YPYSEVPQYS GGNVAAACGE SLVHQNIERS VHNGRMILPI EVKEEPMYVN   120
AKQYHGILRR RQLRAKAVLE QKVVKSRKPY LHESRHRHAM RRARDGGGRF LNTKKKIQLP   180
ANNNINTTTP SSKGKGCAAS EVSSMDSDFS QNYLLNSGHI GSSNATSVEG FQFQGIHNTD   240
NPQLGCHYQW NLNDNHCYCM QSGASNLQPF                                    270

SEQ ID NO: 51            moltype = DNA  length = 762
FEATURE                  Location/Qualifiers
misc_feature             1..762
                         note = Description of Artificial Sequence: Synthetic
                         polynucleotide
source                   1..762
                         mol_type = other DNA
                         organism = synthetic construct
SEQUENCE: 51
atgggagctg gtgcttttgg agaagccgga cgtacaatat atcaaagtc cgatagtgat    60
tgcaagcgag atggcaaacg tgtagaattt atgcctccaa tcatgggtga aaacttaaga   120
gcagctaatc aatttgaact gatgccccc tcaattgcat tcagatcata tccctattca   180
gaagtaccac aatattctgg tggcaatgtg gctgctgcat ttggcgaatc tacggtacat   240
caaaatatag aaagatcagt gcataatggt agaatgattt tgccacttga agtgaaggag   300
gagcctatgt atgtaaatgc caaacaatac catggaattc taaggcgaag gcaactccgt   360
gcaaaggctg tgttggagca aaaggtggtc aaatctagaa agcctatctt tcatgaatct   420
cggcaccggc atgcgatgag aagagctaga gatggtggcg ccgatttct caacacaaag   480
aagaatcc aacttactac taataataat aataataatg ggaatactaa tgcaactcgt   540
agtagtaaag gcaaaggttg ttcagcctca gaagtcagtt ccatggactc ttattctgga   600
catattggat catccaatag tactgctcat gtccagggat tcagttcca aggaatacat   660
aatacagaaa atcctcaact gggttgtcat tatcagtgga atctcaatga taaccattgc   720
aattgcatgc agtcaggagc ttctaatatc caaccatttt ga                     762
```

```
SEQ ID NO: 52              moltype = AA   length = 253
FEATURE                    Location/Qualifiers
REGION                     1..253
                           note = Description of Artificial Sequence: Synthetic
                           polypeptide
source                     1..253
                           mol_type = protein
                           organism = synthetic construct
SEQUENCE: 52
MGAGAFGEAG RTIYQKSDSD CKRDGKRVEF MPPIMGENLR AANQFELMPP SIAFRSYPYS    60
EVPQYSGGNV AAAFGESTVH QNIERSVHNG RMILPLEVKE EPMYVNAKQY HGILRRRQLR   120
AKAVLEQKVV KSRKPYLHES RHRHAMRRAR DGGGRFLNTK KKIQLTTNNN NNNGNTNATP   180
SSKGKGSSAS EVSSMDSYSG HIGSSNSTAH VQGFQFQGIH NTENPQLGCH YQWNLNDNHC   240
NCMQSGASNI QPF                                                     253

SEQ ID NO: 53              moltype = DNA   length = 753
FEATURE                    Location/Qualifiers
misc_feature               1..753
                           note = Description of Artificial Sequence: Synthetic
                           polynucleotide
source                     1..753
                           mol_type = other DNA
                           organism = synthetic construct
SEQUENCE: 53
atgcaatatg aacacgaatt tttcttccaa tattaccatg atcaacttca acagaatctt    60
gatgatacct tagctgagat cagtactgag actgccatta taacacggc agattccaac   120
aaagacgacg ctttaataag tagaaatgaa cttgaacaag aggaaggatg tgagaataaa   180
aagggtaaaa taagcagcaa caagagagtg tctaagaaag atagacacag tgcaaatagt   240
gaatcctcta cttctgaatg tgaagttgta tcagaaattg atgaatctcc atctaatcat   300
aaggcaaatg ctaaaggaaa ttcttgcaac aaggagaagg agaagaagaa gaaggagaag   360
gagaaatcag ttcgtcgagc tgcattttat catccatttg caaaagaatc aaggaaacaa   420
gcaagagaga gggcaaggga gaaacaaaa ctaaagaaaa actttttgtaa atctcatcat   480
ttgaacttaa gatcttggaa tttctccgaa ggggggcgaag aatcagcggg atatattagc   540
atgaatcttc cttgtcaaga aatgcaagct gaaatagttg aagaactcac ctcccacaat   600
gagaagcagc ttttattagg gattaaagaa aacattgcta atgattgtaa tttggtggct   660
actggcaatt ggagcccaaa tgccattttc aactatcaac aaaatgctgg aattcctcat   720
gagcatcaaa ttacagacat tccgttttca tga                               753

SEQ ID NO: 54              moltype = AA   length = 250
FEATURE                    Location/Qualifiers
REGION                     1..250
                           note = Description of Artificial Sequence: Synthetic
                           polypeptide
source                     1..250
                           mol_type = protein
                           organism = synthetic construct
SEQUENCE: 54
MQYEHEFFFQ YYHDQLQQNL DDTLAEISTE TAIINTADSN KDDALISRNE LEQEEGCENK    60
KGKISSNKRV SKKDRHSANS ESSTSECEVV SEIDESPSNH KANAKGNSCN KEKEKKKKEK   120
EKSVRRAAFY HPFAKESRKQ ARERARERTK LKKNFCKSHH LNLRSWNFSE GGEESAGYIS   180
MNLPCQEMQA EIVEELTSHN EKQLLLGIKE NIANDCNLVA TGNWSPNAIF NYQQNAGIPH   240
EHQITDIPFS                                                         250

SEQ ID NO: 55              moltype = DNA   length = 1422
FEATURE                    Location/Qualifiers
misc_feature               1..1422
                           note = Description of Artificial Sequence: Synthetic
                           polynucleotide
source                     1..1422
                           mol_type = other DNA
                           organism = synthetic construct
SEQUENCE: 55
atgatgaagc atatagtaca tctgggctcc acctcaaatc ttacagtagc agctagaggc    60
catggtcact cgcttcaagg acaagctcta gctcatcaag gtgttgtcat caaaatggag   120
tcacttcgaa gtcctgatat caggatttat aaggggaagc aaccatatgt tgatgtctca   180
ggtggtgaaa tatggataaa cattctacgc gagactctaa aatacggtct ttcaccaaag   240
tcctggacag actaccttca tttgaccgtt ggaggtacac tatctaatgc tggaatcagc   300
ggtcaagcat tcaagcatgg accccaaatc aacaacgtct accagctaga gattgttaca   360
gggaaaggag aagtcgtaac ctgttctgag aagcggaatt ctgaactttt cttcagtgtt   420
cttggcgggc ttggacagtt tggcataatc acccgggcac ggatctctct tgaaccagca   480
ccgcatatgg ttaaatggat cagggtactc tactctgact tttctgcatt tcaagggac   540
caagaatatc tgatttcgaa ggagaaaact tttgattacg ttgaaggatt tgtgataatc   600
aatagaacag accttctcaa taattggcga tcgtcattca gtcccaacga ttccacacag   660
gcaagcagat tcaagtcgca tgggaaaact cttttattgc tagaagtggt caaatatttc   720
aacccagaag aagctagctc tatggatcag gaaactggca agttactttc agagttaaat   780
tatattccat ccactttgtt ttcatctgaa gtgccatata tcgagtttct ggatcgcgtg   840
catatcgcag agagaaaact aagagcaaag ggtttatggg aggttccaca tccctggctg   900
aatctcctga ttcctaagag cagcatatac caatttgcta cagaagtttt caacaacatt   960
ctcacaagca acaacaacgg tcctatcctt atttatccag tcaatcaatc caagtggaag  1020
```

```
aaacatacat ctttgataac tccaaatgaa gatatattct atctcgtagc ctttctcccc    1080
tctgcagtgc caaattcctc agggaaaaac gatctagagt acctttgaa acaaaaccaa     1140
agagttatga acttctgcgc agcagcaaac ctcaacgtga agcagtattt gccccattat    1200
gaaactcaaa aagagtggaa atcacacttt ggcaaaagat gggaaacatt tgcacagagg    1260
aaacaagcct acgaccctct agcgattcta gcacctggcc aaagaatatt ccaaaagaca    1320
acaggaaaat tatctcccat ccaactcgca aagtcaaagg caacaggaag tcctcaaagg    1380
taccattacg catcaatact gccgaaacct agaactgtat aa                      1422

SEQ ID NO: 56          moltype = AA  length = 473
FEATURE                Location/Qualifiers
REGION                 1..473
                       note = Description of Artificial Sequence: Synthetic
                       polypeptide
source                 1..473
                       mol_type = protein
                       organism = synthetic construct
SEQUENCE: 56
MMKHIVHLGS TSNLTVAARG HGHSLQGQAL AHQGVVIKME SLRSPDIRIY KGKQPYVDVS     60
GGEIWINILR ETLKYGLSPK SWTDYLHLTV GGTLSNAGIS GQAFKHGPQI NNVYQLEIVT    120
GKGEVVTCSE KRNSELFFSV LGGLGQFGII TRARISLEPA PHMVKWIRVL YSDFSAFSRD    180
QEYLISKEKT FDYVEGFVII NRTDLLNNWR SSFSPNDSTQ ASRFKSDGKT LYCLEVVKYF    240
NPEEASSMDQ ETGKLLSELN YIPSTLFSSE VPYIEFLDRV HIAERKLRAK GLWEVPHPWL    300
NLLIPKSSIY QFATEVFNNI LTSNNNGPIL IYPVNQSKWK KHTSLITPNE DIFYLVAFLP    360
SAVPNSSGKN DLEYLLKQNQ RVMNFCAAAN LNVKQYLPHY ETQKEWKSHF GKRWETFAQR    420
KQAYDPLAIL APGQRIFQKT TGKLSPIQLA KSKATGSPQR YHYASILPKP RTV           473

SEQ ID NO: 57          moltype = DNA  length = 1659
FEATURE                Location/Qualifiers
misc_feature           1..1659
                       note = Description of Artificial Sequence: Synthetic
                       polynucleotide
source                 1..1659
                       mol_type = other DNA
                       organism = synthetic construct
SEQUENCE: 57
atgaagtcac caccaactca tgtcttcttt aaacataaaa gtatgcttct taggttgctt     60
atattcatac taggcatttg ctcaataaac agaactaacc tttgttgtga ccaaccttt     120
gccaccccaa tatcttcttc ttcttctacc ccttcaagtt tttcagtgat tcaatcatca    180
ttgaaacagt taaattga agggtatttt agtttcgatca cgcggccaaa atttcgatca    240
gactttggca acagatatca cttcttgcca tcggcagttc tgtatccaaa atcagtttct    300
gatatatcat ctaccataaa acatgttttt gacatgggtg ttactacaga cctaactgtt    360
gctgctagag ccatggcca ttctttagaa ggccaagctc aagcttacca aggagtagtg    420
atcaatatgg aatcgcttcg agcgccagca atgcgtttca acacagggaa tcaagaactg    480
cctttgttg atgtctctgc aggagaactt tggataaaca tcctgcatga agtcttaaa    540
cttggattaa caccaaaatc ttggactgat atcttcacc tcaccgttgg agggactttg    600
tcgaatgccg aatcagtggt caagcattc aaacatggac cacagatcaa taatgttac    660
caacttgagg ttgtcactgg taaaggagag gtgattactt gttcagagga gaagaatgct    720
gacctgttct atggtgtatt aggaggacta ggccagtttg gtatcatcac aagggctaga    780
attgctcttg aaccagcacc taaaaaggta aagtggatca gagtgctgta ttcgatttc    840
tccacatttt cctatgatca gaacacttg atatcatccg agaactcttt tgactatata    900
gaaggattg tcattatcaa tagaacagga ttgttaaaca actggaggtc tacttttcaat    960
cctaaagatc cacttctagc caaagagttc agttctgagg aaaaagttct gtactgccta    1020
gaagttgcca aatacttcaa tccagaagag acaaccaaaa ctgatcagaa tgttgatgtt    1080
cttttatcaa agttgaatta tatccaatcg acgctgttcc aatcagaagt atcctacgtg    1140
gatttcctcg acagagttca cgtatccgag atgaaacttc aagagaaggg gttatgggat    1200
attcctcatc catggctaaa ccttctaatt ccaaagagca agattcatga ctttgcacga    1260
gaagttttg ggaagatact taccgacact agccacggtc ctatactcat ctacccagtc    1320
aacaaatcaa agtggagaaa aggaacatca gtagttacac tgaagaaaga tgttatgtat    1380
ctaatagcat ttctatcttc tgccatgcca tcttcacag gaaaggacgg cgtagaatat    1440
attctaaata agaataagaa gatactaaac ttttgcagaa aagcacatat tggaatgaaa    1500
cagtatttgc cacactacac aacgcaggaa gactggaaag gtcactttgg tccccagtgg    1560
gaaacattta aaggaggaa atctacatat gaccctttgg ctatcctagc tcctggccag    1620
agaatttta gaagagcatc aggcgttcaa caacaatga                            1659

SEQ ID NO: 58          moltype = AA  length = 552
FEATURE                Location/Qualifiers
REGION                 1..552
                       note = Description of Artificial Sequence: Synthetic
                       polypeptide
source                 1..552
                       mol_type = protein
                       organism = synthetic construct
SEQUENCE: 58
MKSPPTHVFF KHKSMLLRLL IFILGICSIN RTNLCCDQPF ATPISSSSST PSSFSVIQSS     60
LKQLNIEGYF SFKNFDHAAK DFGNRYHFLP SAVLYPKSVS DSSTIKHVF DMGVTTDLTV    120
AARGHGHSLE GQAQAYQGVV INMESLRAPA MRFHTGNQEL PFVDVSAGEL WINILHESLK    180
LGLTPKSWTD YLHLTVGGTL SNAGISGQAF KHGPQINNVY QLEVVTGKGE VITCSEEKNA    240
DLFYGVLGGL GQFGIITRAR IALEPAPKKV KWIRVLYSDF STFSYDQEHL ISSENSFDYI    300
EGFVIINRTG LLNNWRSTFN PKDPLLAKEF SSEGKVLYCL EVAKYFNPEE TTKTDQNVDV    360
```

```
LLSKLNYIQS TLFQSEVSYV DFLDRVHVSE MKLQEKGLWD IPHPWLNLLI PKSKIHDFAR  420
EVFGKILTDT SHGPILIYPV NKSKWRKGTS VVTPEEDVMY LIAFLSSAMP SSTGKDGVEY  480
ILNKNKKILN FCRKAHIGMK QYLPHYTTQE DWKGHFGPQW ETFKRRKSTY DPLAILAPGQ  540
RIFRRASGVQ QQ                                                     552

SEQ ID NO: 59           moltype = DNA   length = 1632
FEATURE                 Location/Qualifiers
misc_feature            1..1632
                        note = Description of Artificial Sequence: Synthetic
                         polynucleotide
source                  1..1632
                        mol_type = other DNA
                        organism = synthetic construct
SEQUENCE: 59
atgaaattac catcccattt tttatttaag caaaatgact tgctcctgaa attgcttata   60
ttcatactct gcagttgttc aagcaacaaa aataaactct gctgtaatta tcatcagttt  120
gccacccctg cagtttctac cccctcaagt ttctcactga attatttatc attgaaacaa  180
ttacaacttg aaggttacct taaatttgac aacttagaac atgcagccaa agactttggt  240
aatagatgcc acttccttcc attagcagtt ttgtacccaa aatcagtttc tgatatctct  300
tccactataa aacatgtctt tgaaataggt ccaaaactg atttaactgt tgctgctaga   360
ggccatggcc attctctaga aggtcaagct caagcttatc aaggagtagt gattagtatg  420
gaatcactac aaacaccagc aatgaaattc aagactggaa attgcctta tgttgatgtt  480
tctgctggag agctttggat taatatcctg aagaaaagtc ttaaacttgg gcttgcacct  540
aaatcttgga ctgattatct tcacctcaca gttggcggca ctttgtctaa tgctggaatc  600
agtggacaag ctttccgcca cggaccgcag atcaataacg tccaacaact tgaagttgtc  660
actggtaaag gagaggtgat tacttgttca gaggagcaaa atgcagactt gtttcatggt  720
gtactaggag gactggggca atttggtatt attaccagag caaggattgc tcttgaaaca  780
gcacctaaac aggtcaagtg gattagagtg ctgtattcag atttttccat attttccaat  840
gatcaagagc acttgatatc aactcaggat acatttgact atattgaagg ttttgtcact  900
atcaaccaaa ctggattatt aaataactgg aggtctgctt tcaatccctaa agatccagtt  960
ctagccagca atttcagttc tgagggtaga gttttgttct gcttagaaat tgccaaatac 1020
ttcaatccag aagtcacaga tagtattgat cagaacattg atgtgatctt atcaaagttg 1080
aattatatcc gatccacgct gttcctatca gaagtctcct acacagaatt cctcgacagg 1140
gtgcatgtct ctgagatgaa actccaagaa aatgtttctc atccatggct aaatcttcta 1200
ataccaaaaa gcaggattct tgaatttgca caacaagttt ttggcaagat tcttactgac 1260
actagcaatg gtcctttact catctaccct gtcaacaaat caaagtggag aaaaggaaca 1320
tccatggtta cccctgacga agatgttttt tatctgatcg cgttcctatc ttctgctatg 1380
tcatcttcaa caggaaacga tggactaaga catattcttg ctcagagcaa aaggatactg 1440
aactttgtg aagaaacaaa tatcggaatg aaacaattat taccaaatta caagactaag 1500
gaagagtgga aggatcactt tggtcatcaa tgggaagcat ttgctagaag gaaatctaca 1560
tatgacccct ggcaatact tgctcctggc cagagaattt tcagaagggc agaagcctgt 1620
gaacaacaat aa                                                    1632

SEQ ID NO: 60           moltype = AA   length = 543
FEATURE                 Location/Qualifiers
REGION                  1..543
                        note = Description of Artificial Sequence: Synthetic
                         polypeptide
source                  1..543
                        mol_type = protein
                        organism = synthetic construct
SEQUENCE: 60
MKLPSHFLFK QNDLLLKLLI FILCSCSSNK NKLCCNYHQF ATPAVSTPSS FSLNYLSLKQ   60
LQLEGYLKFD NLEHAAKDFG NRCHFLPLAV LYPKSVSDIS STIKHVFEIG SKTDLTVAAR  120
GHGHSLEGQA QAYQGVVISM ESLQTPAMKF KTGELPYVDV SAGELWINIL KESLKLGLAP  180
KSWTDYLHLT VGGTLSNAGI SGQAFRHGPQ INNVQQLEVV TGKGEVITCS EEQNADLFHG  240
VLGGLGQFGI ITRARIALET APKQVKWIRV LYSDFSIFSN DQEHLISTQD TFDYIEGFVT  300
INQTGLLNNW RSAFNPKDPV LASNFSSEGR VLFCLEIAKY FNPEVTDSID QNIDVILSKL  360
NYIRSTLFLS EVSYTEFLDR VHVSEMKLQE NVSHPWLNLL IPKSRILEFA QQVFGKILTD  420
TSNGPLLIYP VNKSKWRKGT SMVTPDEDVF YLIAFLSSAM SSSTGNDGLR HILAQSKRIL  480
NFCEETNIGM KQYLPNYKTK EEWKDHFGHQ WEAFARRKST YDPLAILAPG QRIFRRAEAC  540
EQQ                                                               543

SEQ ID NO: 61           moltype = DNA   length = 960
FEATURE                 Location/Qualifiers
misc_feature            1..960
                        note = Description of Artificial Sequence: Synthetic
                         polynucleotide
source                  1..960
                        mol_type = other DNA
                        organism = synthetic construct
SEQUENCE: 61
atgagaaaact cttcactaat gtgcaaacaa gtatggccaa ctttgcgaaa tttgcctcaa   60
aaggacaagg ttgtgtttgt gatgggagtc accggcgccg gaaaatcaag actgtcaata  120
gacttagcca ctcaattcag aggagaaata gtgaactccg acaaaataca agtgtacaaa  180
ggtcttgata ttgccactaa caaaatcaca caagaagaac gttgtggtgt accacaccat  240
ctcctaggcg taattgatcc ttacaaagaa ttcaccacca aaaacttctg caacatggct  300
tcacttgcag ttaactctat aaccgaccgc ggtaaacttc cgatcatcgt tggaggttcc  360
aattcgttta tcgaggcgct tgtccacgac aactctcata ttttcgtac gaggtatgat  420
```

```
tgttgtttcc tatgggtcga tgtgtccatg aacgtactaa attcattttt gtacgaacga    480
gtggacaaaa tgatggagca aggtatgact gacgaagtaa gaagcatgtt caatccaaaa    540
aacacagatt ataccaaagg catacgtaaa gcaattggcg taccagaatt cgatagttat    600
tttcgagctg aattatcaaa ttctgttgac gtggagacgc gcgagaggct actaaaagaa    660
gctattaatg aagtgaagat caataactgt atactagcaa gtaagcaact agagaaaata    720
aagagactca taaatgttaa gggatgaaaa attcaaagat tagatgcaac agaagttttt    780
aggaggaaac agaaaatgc agaggaagaa gccgaggaaa tttggaagaa tatggtgatg    840
ggacagagca taaagattgt gggtaaattt ttatgcgaaa ataatcggag caaaatggtt    900
tacagaaatg atgtgacagc cattaagaga gcagcagcgt cggccatagc tcaatattag    960
```

| | |
|---|---|
| SEQ ID NO: 62 | moltype = AA length = 319 |
| FEATURE | Location/Qualifiers |
| REGION | 1..319 |
| | note = Description of Artificial Sequence: Synthetic polypeptide |
| source | 1..319 |
| | mol_type = protein |
| | organism = synthetic construct |

SEQUENCE: 62

```
MRNSSLMCKQ VWPTLRNLPQ KDKVVFVMGV TGAGKSRLSI DLATQFRGEI VNSDKIQVYK     60
GLDIATNKIT QEERCGVPHH LLGVIDPYKE FTTKNFCNMA SLAVNSITDR GKLPIIVGGS    120
NSFIEALVHD NSHNFRTRYD CCFLWVDVSM NVLNSFLYER VDKMMEQGMT DEVRSMFNPK    180
NTDYTKGIRK AIGVPEFDSY FRAELSNSVD VETRERLLKE AINEVKINNC ILASKQLEKI    240
KRLINVKGWK IQRLDATEVF RRKQRNAEEE AEEIWKNMVM GQSIKIVGKF LCENNRSKMV    300
YRNDVTAIKR AASAIAQY                                                 319
```

| | |
|---|---|
| SEQ ID NO: 63 | moltype = DNA length = 930 |
| FEATURE | Location/Qualifiers |
| misc_feature | 1..930 |
| | note = Description of Artificial Sequence: Synthetic polynucleotide |
| source | 1..930 |
| | mol_type = other DNA |
| | organism = synthetic construct |

SEQUENCE: 63

```
atggaagctg ctcaacaaca aaaccagcag cactatcttc accaacaaca tttatcaatt     60
ggacaggtgg caaacaacat tgaagatggt gttggtggta atagcagcaa aaacaacagc    120
agcagtttca tgtgcaggca agtagtacg aggtggacac ccacaactga ccagataaga    180
attttgaagg acctttacta caacaatgga gttaggtctc caactgctga acagattcag    240
aggatctctg ctaagttaag acagtacggt aagattgaag caagaatgt gttttattgg    300
tttcagaacc ataaagctcg tgaaaggcaa aagaagaggc ttattgctgc tgctgccact    360
gataacaaca ataaatcccc catgcaaatg agaggtgttt ggagatctgc tgatgatccc    420
attcaccaca agtataacaa cactacaggt attcactgtc cttctcatgg t              480
gtactagcag ttggacagaa tggaaactat ggttatggaa ctgtagctat ggagaagagc    540
tttaggggact gttcaatatc accaggtggt aactccaacg gatcaatggg tcatcaaaac    600
attacatggg ttggagttga tccctacact tctcatcaag catacccttt tcttgaaaag    660
actaaacatt ttgatgaaac cctagacgat tatgaggaac tgcaacaaga agaagaaaat    720
taccaaagag cctctgcttt agaaactctc ccacttttc ccatgcacga agagaacatt    780
tccagtttct gcaacatcaa aatgaatct tcaggcggat tctacacaga atggtatcgt    840
tcagatgatc ataacttggc tgctgcggcc agagcttctc ttgaactcag tctcaactct    900
ttcattggca gatctcctaa ttccccttaa                                    930
```

| | |
|---|---|
| SEQ ID NO: 64 | moltype = AA length = 309 |
| FEATURE | Location/Qualifiers |
| REGION | 1..309 |
| | note = Description of Artificial Sequence: Synthetic polypeptide |
| source | 1..309 |
| | mol_type = protein |
| | organism = synthetic construct |

SEQUENCE: 64

```
MEAAQQQNQQ HYLHQQHLSI GQVANNIEDG VGGNSSKNNS SSFMCRQSST RWTPTTDQIR     60
ILKDLYYNNG VRSPTAEQIQ RISAKLRQYG KIEGKNVFYW FQNHKARERQ KKRLIAAAAT    120
DNNNIPMQM RGVWRSADDP IHHKYNNTTG IHCPSASSHG VLAVGQNGNY GYGTVAMEKS    180
FRDCSISPGG NSNGSMGHQN ITWVGVDPYT SHQAYPFLEK TKHFDETLDD YEELQQEEEN    240
YQRASALETL PLFPMHEENI SSFCNIKHES SGGFYTEWYR SDDHNLAAAA RASLELSLNS    300
FIGRSPNSP                                                           309
```

| | |
|---|---|
| SEQ ID NO: 65 | moltype = DNA length = 822 |
| FEATURE | Location/Qualifiers |
| misc_feature | 1..822 |
| | note = Description of Artificial Sequence: Synthetic polynucleotide |
| source | 1..822 |
| | mol_type = other DNA |
| | organism = synthetic construct |

SEQUENCE: 65

```
atggaagctg cccaacaaca aaaccagcag cactatcttc accaacaaca tttatcaatt     60
ggacaggtga caaacaacat tattgaagat ggtgttggtg gtaatagcag caaaaacaac    120
```

```
agcagcagtt tcatgtgcag gcaaagtagt acgaggtgga cacccacaac tgaccagata    180
agaatcttga aggatcttta ctacaacaat ggagttaggt ctccaactgc tgaacagatt    240
cagaggatct ctgctaagtt aagacagtac ggtaagattg aaggcaagaa tgtgttttat    300
tggtttcaga accataaagc tcgtgaaagg caaaagaaga ggcttattgc tgctgctgct    360
actgcagca acaataatat tcccatgcac atgagagtg tttggagatc tgctgatgat    420
cctatccacc acaagtataa caacactaca ggtattcact gtccatcagc ttcttctcat    480
ggtgtactgg ccgttggaca gaatggaaac tatggttatg aactttagc tatggaaaag    540
agctttagga ctaaacattt tgatgaaacc ctagtagacg attatgagga actgcaacaa    600
gaagaagaaa attaccaaag agcctctgct ttagaaactc tcccacttt tcccatgcat    660
gaagagaaca tctccagttt ctgcaacatc aaacatgaat cttcaggcg attctacaca    720
gaatggtacc gttcagatga tcataacttg gctgctgcgg ccagagcttc tcttgaactt    780
agtctcaact ctttcattgg cagatctcct aattcccctt aa                        822

SEQ ID NO: 66          moltype = AA   length = 273
FEATURE                Location/Qualifiers
REGION                 1..273
                       note = Description of Artificial Sequence: Synthetic
                       polypeptide
source                 1..273
                       mol_type = protein
                       organism = synthetic construct
SEQUENCE: 66
MEAAQQQNQQ HYLHQQHLSI GQVTNNIIED GVGGNSSKNN SSSFMCRQSS TRWTPTTDQI     60
RILKDLYYNN GVRSPTAEQI QRISAKLRQY GKIEGKNVFY WFQNHKARER QKKRLIAAAA    120
TDSNNNIPMH MRGVWRSADD PIHHKYNNTT GIHCPSASSH GVLAVGQNGN YGYGTLAMEK    180
SFRTKHFDET LVDDYEELQQ EEENYQRASA LETLPLFPMH EENISSFCNI KHESSGGFYT    240
EWYRSDDHNL AAAARASLEL SLNSFIGRSP NSP                                  273

SEQ ID NO: 67          moltype = DNA   length = 291
FEATURE                Location/Qualifiers
misc_feature           1..291
                       note = Description of Artificial Sequence: Synthetic
                       polynucleotide
source                 1..291
                       mol_type = other DNA
                       organism = synthetic construct
SEQUENCE: 67
atggattcga agagttttct gctactacta ctactcttct gcttcttgtt ccttcatgat     60
gcttctgatc tcactcaagc tcatgctcac gttcaaggac tttccaaccg caagatgatg    120
atgatgaaaa tggaaagtga atgggttgga gcaaatggag aagcagagaa ggcaaagacg    180
aagggtttag gactacatga agagttaagg actgttcctt cgggacctga cccgttgcac    240
catcatgtga acccaccaag acagccaaga acaactttc agctcccttg a              291

SEQ ID NO: 68          moltype = AA   length = 96
FEATURE                Location/Qualifiers
REGION                 1..96
                       note = Description of Artificial Sequence: Synthetic
                       polypeptide
source                 1..96
                       mol_type = protein
                       organism = synthetic construct
SEQUENCE: 68
MDSKSFLLLL LLFCFLFLHD ASDLTQAHAH VQGLSNRKMM MMKMESEWVG ANGEAEKAKT     60
KGLGLHEELR TVPSGPDPLH HHVNPPRQPR NNFQLP                               96

SEQ ID NO: 69          moltype = DNA   length = 396
FEATURE                Location/Qualifiers
misc_feature           1..396
                       note = Description of Artificial Sequence: Synthetic
                       polynucleotide
source                 1..396
                       mol_type = other DNA
                       organism = synthetic construct
SEQUENCE: 69
atgtgtattc catatcttga tccgtttgtt tcttactcac ttatagatca acaacttgca     60
tctactgcat ttctgttcgc ttctgaaatg actaatttca ctgccaaacg tttcaccctc    120
ttcctcttgc tgtgtgtttt ggttgtgcaa gaatctcatg ggtgcactag tagctcaaaa    180
tgcatttcac aaaaggaagt tgcttctgtg agaatactaa acagaaaggt tttaggaagc    240
cagcgggctg cttttggaaa gggcttaaat ggaaactaca atcattcagg gaagattaat    300
gacaagtttg ctgattggga gcttagggga attccagctg gtcctgatcc attgcaccac    360
aatggtgcta atccgaagaa accccggact ccataa                               396

SEQ ID NO: 70          moltype = AA   length = 131
FEATURE                Location/Qualifiers
REGION                 1..131
                       note = Description of Artificial Sequence: Synthetic
                       polypeptide
source                 1..131
                       mol_type = protein
```

```
                        organism = synthetic construct
SEQUENCE: 70
MCIPYLDPFV SYSLIDQQLA STAFLFASEM TNFTAKRFTL FLLLCVLVVQ ESHGCTSSSK    60
CISQKEVASV RILNRKVLGS QRAAFGKGLN GNYNHSGKIN DKFADWELRG IPAGPDPLHH   120
NGANPKKPRT P                                                        131

SEQ ID NO: 71           moltype = DNA  length = 1158
FEATURE                 Location/Qualifiers
misc_feature            1..1158
                        note = Description of Artificial Sequence: Synthetic
                        polynucleotide
source                  1..1158
                        mol_type = other DNA
                        organism = synthetic construct
SEQUENCE: 71
atgttaggat cctttggttc atcatctcaa tctcatgatg aagaagctga tgatcaacgg    60
cggagatgca gttccacttc ccctgcaatc caaatccggc aactactcat tagctgcgcg   120
gagttaatct cacggtccga tttctcggcg gcaaacagac tcctccaccat tttatcaact   180
aactcttccc cttttgccac taatttcttg acacctaatg catcatctaa tgttgttgaa   240
agttcaaatg attcagctct acttcagtca tcctatcttt ccctaaaacca agtgaccccct  300
tttattagat ttagtcagct aactgctaat caagcgattt tagaagctat taacgataac   360
caacaagcga tccacatcgt tgattttgat attaatcacg gtgttcaatg gccaccgtta   420
atgcaagcac tagctgatcg ttaccctcct ccaactcttc ggattaccgg tactggaaat   480
gacctcgata cccttcgtag aaccggagat cgtttagcta aatttgctca ctcttttaggc   540
cttagatttc agtttcaccc tcttttgatc accaataata atgacaatga tcatgaccct   600
tcaatcattt cttctattgt tcttctccct gatgagacat tagcaatcaa ctgtgtattt   660
tatcttcaca ggctcttaaa agaccgcgaa atgttaagga ttttttttgca taggattaaa   720
tccatgaacc ctaaagttgt aacactggcc gagagagaag caaatcataa tcacccactt   780
tttttgcaaa gatttgtgga ggctttggat tattatgcag ctgtctttga ttcattggaa   840
gcaactttgc cgccgagcag tagagagagg atgacggttg agcaagtttg gttcggaaga   900
gaaattatag atatagtagc agcagaagga gataagagaa gagaaagaca cgagagattc   960
agatcatggg aagtaatgtt gaggagctgt ggatttagca atgttgcttt aagtcctttt  1020
gcactttcac aagctaaact tctcttgaga cttcattacc cttctgaagg ataccagctt  1080
agtgtttcga gtacgagtaa ttcttttctt tgggttggc aaaatcaacc ccttttttcc    1140
atatcttctt ggcgttaa                                                 1158

SEQ ID NO: 72           moltype = AA  length = 385
FEATURE                 Location/Qualifiers
REGION                  1..385
                        note = Description of Artificial Sequence: Synthetic
                        polypeptide
source                  1..385
                        mol_type = protein
                        organism = synthetic construct
SEQUENCE: 72
MLGSFGSSSQ SHDEEADDQR RRCSSTSPAI QIRQLLISCA ELISRSDFSA ANRLLTILST    60
NSSPFATNFL TPNASSNVVE SSNDSALLQS SYLSLNQVTP FIRFSQLTAN QAILEAINDN   120
QQAIHIVDFD INHGVQWPPL MQALADRYPP PTLRITGTGN DLDTLRRTGD RLAKFAHSLG   180
LRFQFHPLLI TNNNDNDHDP SIISSIVLLP DETLAINCVF YLHRLLKDRE MLRIFLHRIK   240
SMNPKVVTLA EREANHNHPL FLQRFVEALD YYAAVFDSLE ATLPPSSRER MTVEQVWFGR   300
EIIDIVAAEG DKRRERHERF RSWEVMLRSC GFSNVALSPF ALSQAKLLLR LHYPSEGYQL   360
SVSSTSNSFF LGWQNQPLFS ISSWR                                         385

SEQ ID NO: 73           moltype = DNA  length = 1224
FEATURE                 Location/Qualifiers
misc_feature            1..1224
                        note = Description of Artificial Sequence: Synthetic
                        polynucleotide
source                  1..1224
                        mol_type = other DNA
                        organism = synthetic construct
SEQUENCE: 73
atgttaggat cctttggttc atcatctcaa tctcatgatg aagaaactga tgatcaacgg    60
cggagattca gttccacttc ccctgcaatc caaatccggc aactactcat tagctgcgcg   120
gagttaatct cgcggtccga tttctcggcc gcaaacagac tcctcaccat tttatcaact   180
aactcttccc cttttggtga ttcaactgaa agattagtcc atcagttcac tcgcgcactt   240
tctcttcgcc tcaaccgtta tatctcttca gccactaatt tcttgacacc atctaatgtt   300
gttgaaagtt caaatgattc agctctactt cagtcatcct atctttccct aaaccaagtg   360
actcctttca ttagatttag tcagctaact gctaatcaag cgattttgag agctattaac   420
gataaccaac aagcgatcca catcgttgat tttgatatta tcacggtgt tcaatggcca   480
ccgttaatgc aagcactagc tgatcgttac cctcctccaa ctcttcggat taccggtact   540
ggaaatgacc ttgataccct tcgtagaacc ggagatcgtt tagctaaatt tgctcactct   600
ttaggcctta gatttcagtt tcaccctctt ttgattacca ataataatga caatgatcat   660
gacccttcaa taatttcttc tattgttctt ctccctgatg agacattagc tatcaactgt   720
gtatttttatc ttcacaggct cttgaaagac cgcgaaaagt taaggatttt tttgcatagg   780
attaaatcca tgaaccctaa agttgtaacg ctggccgaga gagaagcaaa tcataatcac   840
ccactttttt tgcaaagatt tgtggaggct ttggattatt atgcagctgt gtttgattca   900
ttggaagcaa ctttgccacc gagcagtaga gagaggatga cagtggaaca gtttggttc    960
gggagagaaa taattgatat agtagcagca gaaggagata gagaagaga aagacacgag  1020
```

```
agattcagat catgggaagt aatgttgagg agctgtggat ttagcaatgt tgctttaagc   1080
ccttttgcac tctcacaagc taaacttctc ttgagacttc attacccatc tgaaggatac   1140
cagcttagtg tttcgagtac gagtaattct ttcttcttgg gttggcaaaa tcaaccccctt  1200
ttttccatat cttcttggcg ttaa                                          1224
```

```
SEQ ID NO: 74           moltype = AA   length = 407
FEATURE                 Location/Qualifiers
REGION                  1..407
                        note = Description of Artificial Sequence: Synthetic
                         polypeptide
source                  1..407
                        mol_type = protein
                        organism = synthetic construct
SEQUENCE: 74
MLGSFGSSSQ SHDEETDDQR RRFSSTSPAI QIRQLLISCA ELISRSDFSA ANRLLTILST    60
NSSPFGDSTE RLVHQFTRAL SLRLNRYISS ATNFLTPSNV VESSNDSALL QSSYLSLNQV   120
TPFIRFSQLT ANQAILEAIN DNQQAIHIVD FDINHGVQWP PLMQALADRY PPPTLRITGT   180
GNDLDTLRRT GDRLAKFAHS LGLRFQFHPL LITNNNDNDH DPSIISSIVL LPDETLAINC   240
VFYLHRLLKD REKLRIFLHR IKSMNPKVVT LAEREANHNH PLFLQRFVEA LDYYAAVFDS   300
LEATLPPSSR ERMTVEQVWF GREIIDIVAA EGDKRRERHE RFRSWEVMLR SCGFSNVALS   360
PFALSQAKLL LRLHYPSEGY QLSVSSTSNS FFLGWQNQPL FSISSWR                 407
```

```
SEQ ID NO: 75           moltype = DNA   length = 1014
FEATURE                 Location/Qualifiers
misc_feature            1..1014
                        note = Description of Artificial Sequence: Synthetic
                         polynucleotide
source                  1..1014
                        mol_type = other DNA
                        organism = synthetic construct
SEQUENCE: 75
atggggagag ctccatgttg tgataaagca aatgtgaaga gagggccatg gtctcctgaa    60
gaagatgcta aactcaaaga tttcattcac aaatatggaa ctggtggaaa ttggattgct   120
cttcctcaaa aagctggtct aaagagatgt gggaagagtt gtagattgag atggctaaat   180
tatttaaggc ctaacattaa acatggtgat ttttctgagg aagaagatag agttatttgc   240
accttgtatt ccaccattgg aagcaggtgg tcaataatag cagctcaatt accgggaaga   300
actgacaatg atatcaagaa ttactggaat actaagctca agaaaaaacc tatgggatta   360
atgcaatcaa ctaaccaaag aaaatcacca tatttttccag ctactaattc tcttcaaacc   420
caacccccaga taaattcaag tcttttttaga gacttatatt acaccccaaa taataggcct   480
aatattacag gcctaaatca tcagtccatt tcttctgccc accagacaaa ttttctctac   540
actaataata acatgaactt tcctaatttg ggtgctacaa ataatcaata tccttataat   600
atccaaagtc ataatttact tatgtttgga gaagcaagtt gttcttcatc agatggaagt   660
tgcagccaaa tgagttttgg taaagaaatc aagagagaaa aaattatgag taatagttta   720
caacaaggtc aaattttcaag tgttaatgct tttgaagaaa accaccagaa ttttactctt   780
gattatggca atagtagtag taattgggtg gatcaaaaac caaatgtgta ttttggtact   840
actactactc aagtacttca gtatgataat gttgaagaag ttaagcagca gctaacaagt   900
tgtaccaatg gcaacaatgg tagtactatt ggatgtaaca acaacaacag tatgttcgtg   960
ttcaatgatg agaattataa caagtcaaat gagatagaga tgttctatta ctga         1014
```

```
SEQ ID NO: 76           moltype = AA   length = 337
FEATURE                 Location/Qualifiers
REGION                  1..337
                        note = Description of Artificial Sequence: Synthetic
                         polypeptide
source                  1..337
                        mol_type = protein
                        organism = synthetic construct
SEQUENCE: 76
MGRAPCCDKA NVKRGPWSPE EDAKLKDFIH KYGTGGNWIA LPQKAGLKRC GKSCRLRWLN    60
YLRPNIKHGD FSEEEDRVIC TLYSTIGSRW SIIAAQLPGR TDNDIKNYWN TKLKKKPMGL   120
MQSTNQRKSP YFPATNSLQT QPQINSSLFR DLYYTPNNRP NITGLNHQSI SSAHQTNFLY   180
TNNNMNFPNL GATNNQYPYN IQSHNLLMFG EASCSSSDGS CSQMSFGKEI KREEIMSNSL   240
QQGQISSVNA FEENHQNFTL DYGNSSSNWV DQKPNVYFGT TTTQVLQYDN VEEVKQQLTS   300
CTNGNNGSTI GCNNNNSMFV FNDENYNKSN EIEMFYY                            337
```

```
SEQ ID NO: 77           moltype = DNA   length = 1011
FEATURE                 Location/Qualifiers
misc_feature            1..1011
                        note = Description of Artificial Sequence: Synthetic
                         polynucleotide
source                  1..1011
                        mol_type = other DNA
                        organism = synthetic construct
SEQUENCE: 77
atggggagag ctccatgttg tgataaagca aatgtgaaga gagggccatg gtctcctgaa    60
gaagatgcta aactcaaaga tttcattcac aaatatggaa ctggtggaaa ttggattgct   120
cttcccaaa aagcaggtct aaagagatgt gggaagagtt gtagattgag atggctaaat   180
tatctaaggc ctaatatcaa acatggtgat ttttcggagg aagaagatag agttatttgc   240
agcttgtatt ccaccattgg aagcaggtgg tcaataatag cagctcaatt accaggaagg   300
```

-continued

```
actgacaatg atatcaagaa ttactggaat actaaactca agaaaaagct tatgggatta   360
atgcaatcaa caaaccaaag aaaatcacca tattttccag ctactaattc tcttcaaacc   420
caaccccaga taaattcaag tcttttttaga gacttatatt acaacccaaa taataggcct  480
attattacag gcctaaatca gtccatttct tctgcccacc agccaaattt tctctacact   540
aatagtaaca tgaattttcc taatttgggt gctacaaata gtcaatatcc ttataatatt   600
caaagtcata atttacttat gtttggagaa gcaagttgtt cttcatcaga tggaagttga   660
agccaaatga gttttggcaa agaaatcaag agagaggaaa ttatgagtaa ttgtttacaa   720
caaggtcaaa tttcaagtgt taatgctttt gaagaaaatc agaatttcac tcttgattat   780
ggtaacagta gtagtaattg ggtggatcaa aaaccaaatg tgtattttgg aaatactact   840
actactactc aagtacttca gtatgatgtt gaagaagtta agcagcagct aacaagttgt   900
accaatggca acaatggcag tactattgga tgtaacaaca caacagtat  gttcgtgttc   960
aatgatgaga attataacaa gtcaaatgag atagggatgt tctattactg a           1011

SEQ ID NO: 78          moltype = AA   length = 336
FEATURE                Location/Qualifiers
REGION                 1..336
                       note = Description of Artificial Sequence: Synthetic
                        polypeptide
source                 1..336
                       mol_type = protein
                       organism = synthetic construct
SEQUENCE: 78
MGRAPCCDKA NVKRGPWSPE EDAKLKDFIH KYGTGGNWIA LPQKAGLKRC GKSCRLRWLN    60
YLRPNIKHGD FSEEEDRVIC SLYSTIGSRW SIIAAQLPGR TDNDIKNYWN TKLKKKLMGL   120
MQSTNQRKSP YFPATNSLQT QPQINSSLFR DLYYNPNNRP IITGLNQSIS SAHQPNFLYT   180
NSNMNFPNLG ATNSQYPYNI QSHNLLMFGE ASCSSSDGSC SQMSFGKEIK REEIMSNCLQ   240
QGQISSVNAF EENQNFTLDY GNSSSNWVDQ KPNVYFGNTT TTTQVLQYDV EEVKQQLTSC   300
TNGNNGSTIG CNNNNSMFVF NDENYNKSNE IGMFYY                             336

SEQ ID NO: 79          moltype = DNA   length = 495
FEATURE                Location/Qualifiers
source                 1..495
                       mol_type = unassigned DNA
                       organism = Bacillus amyloliquefaciens
SEQUENCE: 79
atgaaaagga atcagcttca catgatgaaa atgggaggta ttgctttgaa aaacgattca    60
tcgtggattt ccgtttgttt actggtgctt gtctccgcgg cggggatgct gttttcaaca   120
gctgccaaaa cggaaacatc ttctcacaag gcacacacag aagcacaggt tatcaacacg   180
tttgacgggg ttgcggatta tcttcagaca tatcataagc tacctgataa ttacattaca   240
aaatcagaag cacaagccct cggctgggtg gcatcaaaag gaaccttgc  agacgtcgct   300
ccggggaaaa gcatcggcgg agacatcttc tcaaacaggg aaggcaaact cccgggcaaa   360
agcggacgaa catggcgtga agcggatatt aactatacat caggcttcag aaattcagac   420
cggattcttt actcaagcga ctggctgatt tacaaaacaa cggaccatta tcagaccttt   480
acaaaaatca gataa                                                    495

SEQ ID NO: 80          moltype = AA   length = 164
FEATURE                Location/Qualifiers
source                 1..164
                       mol_type = protein
                       organism = Bacillus amyloliquefaciens
SEQUENCE: 80
MKRNQLHMMK MGGIALKKRL SWISVCLLVL VSAAGMLFST AAKTETSSHK AHTEAQVINT    60
FDGVADYLQT YHKLPDNYIT KSEAQALGWV ASKGNLADVA PGKSIGGDIF SNREGKLPGK   120
SGRTWREADI NYTSGFRNSD RILYSSDWLI YKTTDHYQTF TKIR                    164

SEQ ID NO: 81          moltype = DNA   length = 1290
FEATURE                Location/Qualifiers
source                 1..1290
                       mol_type = unassigned DNA
                       organism = Arabidopsis thaliana
SEQUENCE: 81
atgaacaaca acattttcag tactactacc accatcaatg acgactacat gttattccct    60
tataatgacc attattcctc acaaccattg ctcccttttta gccttcttc  ttccattaac   120
gacatcttga ttcactccac ctctaacaca tcaaacaatc atcttgacca tcatcatcaa   180
ttccaacaac cttctccttt ttctcacttc gaatttgccc cggactgcgc cctcctcacc   240
tctttccacc cagaaaacaa tggcatgatg ataaccaaa  ccatcccaaa cgacaatcat   300
catccatcac ttcactttcc cttgaacaac accattgtag aacaacccac tgagccctcg   360
gaaactataa accttataga agattcccag agaatctcaa cttctcaaga cccaaaaatg   420
aaaaaagcca agaaacccag cagaacggac aggcacagca agatcaaaac ggccaaaggg   480
acacgagatc gtaggatgag actctcgcta gatgtcgcca agagttgtt  tggcttacaa   540
gacatgcttg gatttgacaa agccagcaaa accgttgaat ggttgcttac acaagcaaaa   600
cctgagatca taaagatcgc gacaacccttt tctcaccatg gctgcttcag cagcggcgat   660
gagtctcata tccgatccat ggacacatct tctgatctat gtgaacttgc atccatgtgg   720
acggtcgacg ataggagcag caatactaac acgaccgaaa caagaggaaa caaggtcgat   780
gggagatcga tgagagggaa gagaaagagg ccagaaccgc gaacgcccat tttaaagaag   840
ttgtccaagg aggagagagc gaaagctaga gaaagagcaa agggtagaac aatggagaaa   900
atgatgatga agatgaaagg aagatcacaa ttagtgaaaa ttgtggaaga agacgctcat   960
gatcatggtg agataataaa gaataataat agaagccaag tgaatcggag ttctttttgag  1020
atgacacact gcgaagacaa gatcgaagaa ctttgcaaga acgatcgttt tgcagtttgc  1080
```

```
aacgaattta tcatgaataa gaaagatcac atttcaaatg aatcttatga cttagtcaac   1140
tacaaaccga actcatcatt cccagtgatt aaccaccatc gcagccaagg agcagctaat   1200
tccattgagc agcatcagtt tacggatctt cattactcct tcggcgcgaa accaagagac   1260
ctcatgcaca actatcaaaa catgtattga                                    1290

SEQ ID NO: 82           moltype = AA   length = 429
FEATURE                 Location/Qualifiers
source                  1..429
                        mol_type = protein
                        organism = Arabidopsis thaliana
SEQUENCE: 82
MNNNIFSTTT TINDDYMLFP YNDHYSSQPL LPFSPSSSIN DILIHSTSNT SNNHLDHHHQ    60
FQQPSPFSHF EFAPDCALLT SFHPENNGHD DNQTIPNDNH HPSLHFPLNN TIVEQPTEPS   120
ETINLIEDSQ RISTSQDPKM KKAKKPSRTD RHSKIKTAKG TRDRRMRLSL DVAKELFGLQ   180
DMLGFDKASK TVEWLLTQAK PEIIKIATTL SHHGCFSSGD ESHIRSMDTS SDLCELASMW   240
TVDDRGSNTN TTETRGNKVD GRSMRGKRKR PEPRTPILKK LSKEERAKAR ERAKGRTMEK   300
MMMKMKGRSQ LVKVVEEDAH DHGEIIKNNN RSQVNRSSFE MTHCEDKIEE LCKNDRFAVC   360
NEFIMNKKDH ISNESYDLVN YKPNSSFPVI NHHRSQGAAN SIEQHQFTDL HYSFGAKPRD   420
LMHNYQNMY                                                          429

SEQ ID NO: 83           moltype = DNA   length = 299
FEATURE                 Location/Qualifiers
misc_feature            1..299
                        note = Description of Artificial Sequence: Synthetic
                         polynucleotide
source                  1..299
                        mol_type = other DNA
                        organism = synthetic construct
SEQUENCE: 83
atgtatccgc caagcaacag ctgcaactac agccccattt tcaacatccc ttctccttgt    60
atgcaatatg gagacgaact attcttccaa tattatcctg accatttcct tcaacagcaa   120
caagtgccct tgatagaaga tcagagtgtt gacatcttag ctgattgcac tgagaatgtt   180
actaacgaag aaactgtcat caatactgat actgtaaaag ttctttatga cacaggagct   240
gttacaaaca gtcagtgttg gggaggaaat gaagaagtag aagaaggccg cgaaaacaa    299

SEQ ID NO: 84           moltype = DNA   length = 318
FEATURE                 Location/Qualifiers
misc_feature            1..318
                        note = Description of Artificial Sequence: Synthetic
                         polynucleotide
source                  1..318
                        mol_type = other DNA
                        organism = synthetic construct
SEQUENCE: 84
atggctcgct ccttgtgttt catggcattt gcagtcttgg caatgatgct ctttgttgcc    60
tatgaggtgc aagctagaga atgcaaaaca gaaagcaata cattccctgg attatgcatt   120
accaaccac catgcagaaa agcttgtatc agtgagggat ttactgatgg tcattgtagc   180
aaaatcctca gaaggtgcct atgcactaag ccatgtgtgt ttgatgagaa gatgatcaaa   240
acaggagctg aaacttttgc tgaggaagca aaaactttgg ctgcagcttt gcttgaagaa   300
gagataatgg ataactaa                                                 318

SEQ ID NO: 85           moltype = DNA   length = 300
FEATURE                 Location/Qualifiers
misc_feature            1..300
                        note = Description of Artificial Sequence: Synthetic
                         polynucleotide
source                  1..300
                        mol_type = other DNA
                        organism = synthetic construct
SEQUENCE: 85
atggcaggga aggttgagaa agtgcttgca gtagtgatgc ttgcaatgct tctgttttcg    60
gagcatttaa tggctgctaa tcatgaaatt aaaacaactg aagataactc tactattagc   120
cctttctgct tagtaaaatg tttatttgga tgtaggggt tgccacctgt acaagcatcc   180
atttgtgctg ctcaatgtta tttaaagtgc cgtgaccaag atgcggccaa tattgctgaa   240
actaagggca taattggtga gactgcatac aaccagtatg atgttggatg tgcccttggc   300

SEQ ID NO: 86           moltype = DNA   length = 300
FEATURE                 Location/Qualifiers
misc_feature            1..300
                        note = Description of Artificial Sequence: Synthetic
                         polynucleotide
source                  1..300
                        mol_type = other DNA
                        organism = synthetic construct
SEQUENCE: 86
atgtatccgt caagcaacag ctgtaattac agcctcaata tttcctcctc aaataactta    60
tttcacattc catctccgaa ttctatgcaa tatgaacacg aacttttcca atattttcat   120
gaccatcatc tccttcaacc ccaacaacaa caacaacaac aacaactctt gactacacct   180
gatcattata tggcagcaga ttccaacaaa gacaccgtaa tcagtagtac taatcaagat   240
```
cctgaagaag ttgaattaca aggccgctgc aagaacaaaa aaggtgacaa taagagacgt 300

```
SEQ ID NO: 87          moltype = DNA  length = 362
FEATURE                Location/Qualifiers
misc_feature           1..362
                       note = Description of Artificial Sequence: Synthetic
                       polynucleotide
source                 1..362
                       mol_type = other DNA
                       organism = synthetic construct
SEQUENCE: 87
```
atggaaaagg ttcatgagaa accgctatct ctttataatg gatcattatc tgtttttaga 60
ttaggagatt tggctgtgaa aataacaaag gtgaaaaagg gatcattaaa taatgataat 120
ctttcaccc caacttcatt gttagttgtt tcaccaatca taccaggaac ttatccagtt 180
ttactctttt ttcatggctt cgttctcaag cctatatggt acaagtctct ccttcaacat 240
atttcttccc acggctatat agttgttgct ccacaggttt ctcaaagcga agaagtgaaa 300
aaagcagcca aagttacaga atggttaagt aaagccctcg aatccgtact gccggagaaa 360
gt                                                                362

```
SEQ ID NO: 88          moltype = DNA  length = 300
FEATURE                Location/Qualifiers
misc_feature           1..300
                       note = Description of Artificial Sequence: Synthetic
                       polynucleotide
source                 1..300
                       mol_type = other DNA
                       organism = synthetic construct
SEQUENCE: 88
```
atgtgtttgt taataaaggt ggcgaatcca ggagaatccg gcgagcatga cagaattcca 60
tcaacgggag gtgattcaga aagtacaact actaccacag aaggaggaat tccgcagcta 120
tatgaacaat tacaatcaca atcacaatca tttgaagaaa tgttgcggca caaatacaa 180
caagaaacag agtatttgat gtcttcatct gcaactccta tgttttcacg gtatagtcag 240
acaagggaga gtgtcggcaat ggtaacggcg ttaacgcatg tggtatcagg acggagagag 300

```
SEQ ID NO: 89          moltype = DNA  length = 300
FEATURE                Location/Qualifiers
misc_feature           1..300
                       note = Description of Artificial Sequence: Synthetic
                       polynucleotide
source                 1..300
                       mol_type = other DNA
                       organism = synthetic construct
SEQUENCE: 89
```
atggcacatt tcttctctat aaattcaacg ttagcaggaa cgaataaagc atccaaaaca 60
aatttcacat attcaactca agaaacagaa aaaccaaaaa taaagatcat cttactcttg 120
tttttctcttg cattagttcc cttgtcagcg atggcaactt gcaccactga tactccaaac 180
caagcactat tgagggatgt acacgatata gatggtaacc ccttcaagt aaaagccagg 240
tacttcatat ttccagttat tggcggtggt ggtgtacggc ttgctaatct tggagatcaa 300

```
SEQ ID NO: 90          moltype = DNA  length = 348
FEATURE                Location/Qualifiers
misc_feature           1..348
                       note = Description of Artificial Sequence: Synthetic
                       polynucleotide
source                 1..348
                       mol_type = other DNA
                       organism = synthetic construct
SEQUENCE: 90
```
atggctgagc aacaccagcg ccaccagcaa cagcagcagc agcagcagat gcaagtgggc 60
cacccgacgg aggcaatcaa gagccttctt cctcaaaggg gtccctctaa atcccaagtc 120
cttgctgtcg tcactctctt ccctgttggt ggggccctcc tctgccttgc tggactgacg 180
ctcgccggaa ctctgatcgg gcttgcagtc gctacgccgg ttttcttact gttcagcccg 240
gttttggtcc ccgctgccct gacaatcgcg ttggccgtca ctggattctt gacttccggc 300
gcctttggaa taacggcgct gtcgtcgctc tcgtggatca ttaactat                348

```
SEQ ID NO: 91          moltype = DNA  length = 300
FEATURE                Location/Qualifiers
misc_feature           1..300
                       note = Description of Artificial Sequence: Synthetic
                       polynucleotide
source                 1..300
                       mol_type = other DNA
                       organism = synthetic construct
SEQUENCE: 91
```
atgaacggtg ttcatgtgg tggtgctgat cgtgagtata ataacaataa caacaataat 60
gttgtaggtg gaggaggtgg cgggccttgt ggtgcatgca gtttcttag aagaaaatgt 120
gtgaggggat gcatatttgc accttatttt gattctgatc aaggcactgc tcatttcgct 180
gctgtacata aggtgtttgg tgctagcaat gcctctaaat tgctgctcag aattccagcg 240
cataaacgtc tggatgctgt cgttacactt tgctatgagg ctcttgctag agttagagac 300

```
SEQ ID NO: 92           moltype = DNA  length = 300
FEATURE                 Location/Qualifiers
misc_feature            1..300
                        note = Description of Artificial Sequence: Synthetic
                         polynucleotide
source                  1..300
                        mol_type = other DNA
                        organism = synthetic construct
SEQUENCE: 92
atgtcggata aaaaatctgt ctcgacgcca tttgaatgtt gcagaatctt gtttaagttt   60
ctgctgttta tggttattat cagtaatgtg gcgatccatg taacagcttt gagtgggcga  120
gaaggaataa ccccaagtac ggaatggggt ttggggcctc tggtgaagag aggagaaaga  180
aaactagtag tttcaactga aaatggggag gtctcttcag tcagagtagc tgatggaatc  240
accggttcct atcatcttca gttcatcaca ttggagccca attccctctt ccttcctgtt  300

SEQ ID NO: 93           moltype = DNA  length = 293
FEATURE                 Location/Qualifiers
misc_feature            1..293
                        note = Description of Artificial Sequence: Synthetic
                         polynucleotide
source                  1..293
                        mol_type = other DNA
                        organism = synthetic construct
SEQUENCE: 93
atgggcgtac cagaatcgga ggtggtgtca caaggtgagg ttgaatcacc attgcaacca   60
gatcaaaacc agcacaagaa ccatcagttc ccgtccctcg gtagacaagc atcgatctac  120
tccctcactc tcgacgaatt ccaacacacc ctatgtgaaa gtggcaagaa tttcgggtcg  180
atgaatatgg atgaattcct aacagcattt ggactgctga agaaaaccaa gcccacgcac  240
acgcccatgc ccatgccgcg cacgggcatg cgcacgcgca ttctcatgct cat         293

SEQ ID NO: 94           moltype = DNA  length = 300
FEATURE                 Location/Qualifiers
misc_feature            1..300
                        note = Description of Artificial Sequence: Synthetic
                         polynucleotide
source                  1..300
                        mol_type = other DNA
                        organism = synthetic construct
SEQUENCE: 94
atggaggaaa aagatgaact tgaggaagaa gaagaatatg ttgatgatga atcaagaac    60
aatttaccag tccaaaactc atcttcaata agttggttca caaaaatgat atctttacaa  120
gtagagatct tcaccactat cttagtttcc cccattttct atatcctctc ttttgtatct  180
gacttcaact tcctccgccc tgaagaaacc gaaaagaacg tagctgtagc tgtaaatgct  240
gctgctacag taccttcaaa agtagtacat ggaagtactt tactgctcaa gaaatttggt  300

SEQ ID NO: 95           moltype = DNA  length = 300
FEATURE                 Location/Qualifiers
misc_feature            1..300
                        note = Description of Artificial Sequence: Synthetic
                         polynucleotide
source                  1..300
                        mol_type = other DNA
                        organism = synthetic construct
SEQUENCE: 95
atgtataact caagcaacta cagctgtaat tacaaccca ttttctcatc taatttattc    60
aacatccctt ctccttgtat gcaatatgaa cacgaacttt tcttccaata ttaccatgat  120
caacttcaac agaatcttga cgataccttA gctgagatca gtactgagac tgccattatt  180
aacacggcag attccagcaa agacgaggct ataatcagta gaaatgaact tgaacaagat  240
caggaagcgc gtaagaataa aaagggtaaa gtaagcagca caagagagt gtctaagaaa   300

SEQ ID NO: 96           moltype = DNA  length = 300
FEATURE                 Location/Qualifiers
misc_feature            1..300
                        note = Description of Artificial Sequence: Synthetic
                         polynucleotide
source                  1..300
                        mol_type = other DNA
                        organism = synthetic construct
SEQUENCE: 96
atgggaactg gtacttatgg agaagtggga cgtacaatac atcaaagatc aggaacacat   60
atacctcaaa ttctcgatcc gcctttgcta ggggatagta attgcaagcg agaaggcaaa  120
catgtagaat ttatgcctcc aatcatgggt gaaaacttaa aagcagctaa tcaatttgaa  180
ctgatggccc cgtcaattgc attcaaatca tatccctatt cggaggtacc acaatattct  240
ggtggcaatg tggctgctgc atgtggtgaa tctttggtac atcaaaatat agaaagatca  300

SEQ ID NO: 97           moltype = DNA  length = 320
FEATURE                 Location/Qualifiers
misc_feature            1..320
```

```
                        note = Description of Artificial Sequence: Synthetic
                            polynucleotide
source                  1..320
                        mol_type = other DNA
                        organism = synthetic construct
SEQUENCE: 97
aggacaaggt tgtgtttgtg atgggagtca ccggcgccgg aaaatcaaga ctgtcaatag   60
acttagccac tcaattcaga ggagaaatag tgaactccga caaaatacaa gtgtacaaag  120
gtcttgatat tgccactaac aaaatcacac aagaagaacg ttgtggtgta ccacaccatc  180
tcctaggcgt aattgatcct tacaaagaat tcaccaccaa aaacttctgc aacatggctt  240
cacttgcagt taactctata accgaccgcg gtaaacttcc gatcatcgtt ggaggttcca  300
attcgtttat cgaggcgctt                                              320

SEQ ID NO: 98           moltype = DNA  length = 297
FEATURE                 Location/Qualifiers
misc_feature            1..297
                        note = Description of Artificial Sequence: Synthetic
                            polynucleotide
source                  1..297
                        mol_type = other DNA
                        organism = synthetic construct
SEQUENCE: 98
gaagatggtg ttggtggtaa tagcagcaaa acaacagca gcagtttcat gtgcaggcaa    60
agtagtacga ggtggacacc cacaactgac cagataagaa tcttgaagga tctttactac  120
aacaatggag ttaggtctcc aactgctgaa cagattcaga ggatctctgc taagttaaga  180
cagtacggta agattgaagg caagaatgtg ttttattggt ttcagaacca taaagctcgt  240
gaaaggcaaa agaagaggct tattgctgct gctgctactg atagcaacaa taatatt     297

SEQ ID NO: 99           moltype = DNA  length = 339
FEATURE                 Location/Qualifiers
misc_feature            1..339
                        note = Description of Artificial Sequence: Synthetic
                            polynucleotide
source                  1..339
                        mol_type = other DNA
                        organism = synthetic construct
SEQUENCE: 99
tctaatgttg ttgaaagttc aaatgattca gctctacttc agtcatccta tctttcccta   60
aaccaagtga ctcctttcat tagatttagt cagctaactg ctaatcaagc gattttggaa  120
gctattaacg ataaccaaca agcgatccac atcgttgatt ttgatattaa tcacggtgtt  180
caatggccac cgttaatgca agcactagct gatcgttacc ctcctccaac tcttcggatt  240
accggtactg gaaatgacct tgatacccct cgtagaaccg gagatcgttt agctaaattt  300
gctcactctt taggccttag atttcagttt caccctctt                         339

SEQ ID NO: 100          moltype = DNA  length = 480
FEATURE                 Location/Qualifiers
misc_feature            1..480
                        note = Description of Artificial Sequence: Synthetic
                            polynucleotide
source                  1..480
                        mol_type = other DNA
                        organism = synthetic construct
SEQUENCE: 100
actgacaatg atatcaagaa ttactggaat actaagctca agaaaaaacc tatgggatta   60
atgcaatcaa ctaaccaaag aaaatcacca tattttccag ctactaattc tcttcaaacc  120
caacccccaga taaattcaag tcttttttaga gacttatatt acaccccaaa taataggcct 180
aatattacag gcctaaatca tcagtccatt tcttctgccc accagacaaa ttttctctac  240
actaatagta acatgaattt tcctaatttg ggtgctacaa atagtcaata tccttataat  300
attcaaagtc ataatttact tatgtttgga gaagcaagtt gttcttcatc agatggaagt  360
tgtagccaaa tgagttttgg caaagaaatc aagagagagg aaattatgag taattgttta  420
caacaaggtc aaatttcaag tgttaatgct tttgaagaaa atcagaattt cactcttgat  480

SEQ ID NO: 101          moltype = DNA  length = 900
FEATURE                 Location/Qualifiers
misc_feature            1..900
                        note = Description of Artificial Sequence: Synthetic
                            polynucleotide
source                  1..900
                        mol_type = other DNA
                        organism = synthetic construct
SEQUENCE: 101
atgaattcaa agaaaaacaa ctcaccaaga aaaaggttga aaaatatca tacaagaaaa    60
gctcctatta ttagctctta tatggacatg gctgaagcta gaagagaaat tgttcatgct  120
ttacaactte atcgatcttc atcttcatct ccaactcgtc ctattaatag cccaaagaag  180
tacacattat tgggtcaagg agttgtaagc tctcaacaat attactatta ctcaatagtg  240
gaatctatgc ctattcctga accaacatgg tctacaacgg ctccggcaat acttaatgca  300
atgggaactg gtacttatgg agaagtggga cgtacaacatc atcaaagatc aggaacacat  360
atacctcaaa ttctcgatcc gcctttgcta ggggatagtg attgcaagcg agaaggcaaa  420
catgtagaat ttatgcctcc aatcatgggt gaaaacttaa aagcagctaa tcaatttgaa  480
```

```
ctgatggccc cgtcaattgc attcaaatca tatccctatt cggaggtacc acaatattct    540
ggtggcaatg tggctgctgc atgtggtgaa tctttggtac atcaaaatat agaaagatca    600
atgtctgatc cccttgtgat tggtagagtg attggggaag ttgttgatta tttcactcca    660
agtgttaaga tgtctgttac ttataacagc agcaagcatg tttataatgg gcatgaactc    720
tttccttcct cagtcacctc taaacctagg gttgaagttc atggaggtga tttgagatct    780
ttctttacaa tgatcatgat agacccagat gttcctggtc ctagtgatcc atatctcagg    840
gaacacctac actggattgt cacagacatt ccaggcacta cagattgctc gtttgggaaa    900

SEQ ID NO: 102           moltype = DNA   length = 150
FEATURE                  Location/Qualifiers
misc_feature             1..150
                         note = Description of Artificial Sequence: Synthetic
                         polynucleotide
source                   1..150
                         mol_type = other DNA
                         organism = synthetic construct
SEQUENCE: 102
caccacatag attgaacgga gggaataata gtgtagcccc attgggaaac accatattta     60
tataggtaga agaaatactc cagatttaac tagaatttct actgacaaaa gatcttttac    120
actatcaatc acttaaaaga taactacagg                                     150

SEQ ID NO: 103           moltype = DNA   length = 141
FEATURE                  Location/Qualifiers
misc_feature             1..141
                         note = Description of Artificial Sequence: Synthetic
                         polynucleotide
source                   1..141
                         mol_type = other DNA
                         organism = synthetic construct
SEQUENCE: 103
cactaagctt tcttttcctc ataacctcac ttgcttctcc tttgttcttc ttcgtctcc      60
tcctttgttt cgcctcccct tgttctggta actcttgagt gtagatacca ggatagtact    120
gagaaatgag tatcatttga t                                              141

SEQ ID NO: 104           moltype = DNA   length = 150
FEATURE                  Location/Qualifiers
misc_feature             1..150
                         note = Description of Artificial Sequence: Synthetic
                         polynucleotide
source                   1..150
                         mol_type = other DNA
                         organism = synthetic construct
SEQUENCE: 104
catgaaccaa cacaatagga ggcaaatcag tgttagtctt ttttgaatca tctgttttaa     60
ggctagtttc caaatttggc ttgaaaagcc aatcgctcag agtctgggaa acatcaccgg    120
ccactgaaac agctctgtca attggaatgt                                     150

SEQ ID NO: 105           moltype = DNA   length = 165
FEATURE                  Location/Qualifiers
misc_feature             1..165
                         note = Description of Artificial Sequence: Synthetic
                         polynucleotide
source                   1..165
                         mol_type = other DNA
                         organism = synthetic construct
SEQUENCE: 105
gttatcacaa ttcacaaggg aaagttcata acatgaccac tgtcgaatca aaaagggaaa     60
gttcatatat aatacgctta ggctttgggt ttttcaaatg aagggtagag ttcttcataa    120
acgaaattcc acattgttac ttcatatttc acatattccc gaata                    165

SEQ ID NO: 106           moltype = DNA   length = 153
FEATURE                  Location/Qualifiers
misc_feature             1..153
                         note = Description of Artificial Sequence: Synthetic
                         polynucleotide
source                   1..153
                         mol_type = other DNA
                         organism = synthetic construct
SEQUENCE: 106
ttctccttat acctcctgag taccataatt tacactcatc tatgtccaat gccttacatc     60
ccacccatct aatttcctga acacaagcta cactaatctt ctaatgagcg caaaatacaa    120
cacaaaatta ttgctcgcta gtcaaagata ata                                 153

SEQ ID NO: 107           moltype = DNA   length = 180
FEATURE                  Location/Qualifiers
misc_feature             1..180
                         note = Description of Artificial Sequence: Synthetic
                         polynucleotide
source                   1..180
```

```
                        mol_type = other DNA
                        organism = synthetic construct
SEQUENCE: 107
tgggacattt gatagttaga cgttgtaact ttaggttgaa atctgcagtc gagttcattg   60
ttctctttat aataatcact tgaaactggt tgctggctac acgctgctgt tgcttcaaca  120
tgcagatatg gcgctaccgg ccgtagtgca gatgtggagt tttccatttc aggcttggca  180

SEQ ID NO: 108          moltype = DNA  length = 560
FEATURE                 Location/Qualifiers
misc_feature            1..560
                        note = Description of Artificial Sequence: Synthetic
                         polynucleotide
source                  1..560
                        mol_type = other DNA
                        organism = synthetic construct
SEQUENCE: 108
attactctta actttaaata gatttcttat atatgggttc aaaaatgtct gatccccttg   60
tgattggtag agtgattggg gaagttgttg attatttcac tccaagttgt aagatgtctg  120
ttacttataa cagcagcaag catgtttata atgggcatga actctttcct tcctcagtca  180
cctctaaacc taggttgaa gttcatggag gtgatttgag atctttcttt acaatgatca  240
tgatagaccc agatgttcct ggtcctagtg atccatatct cagggaacac ctacactgga  300
ttgtcacaga cattccaggc actacagatt gctcgtttga aaagaaata gttggctatg  360
aaatgccaag gccaaatatt ggaattcaca ggtttgtatt tctgctgttc aagcagaaga  420
agaggcaaac agtattgact gcacctctct ccagggatcg atttaatacg cgtaaattcg  480
cagaagaaaa tgagcttggg tctcctgttg cagcagtttt cttcaattgc cagagggaaa  540
ctgctgccag aaggcgttga                                              560

SEQ ID NO: 109          moltype = DNA  length = 522
FEATURE                 Location/Qualifiers
misc_feature            1..522
                        note = Description of Artificial Sequence: Synthetic
                         polynucleotide
source                  1..522
                        mol_type = other DNA
                        organism = synthetic construct
SEQUENCE: 109
atggctcaaa tgacagatcc ccttgtgatt agtagggtgg ttggagatgt tgttgattat   60
ttctctccaa gtgttaagat gtgtgttatt tataacccca gtaagcatgt ctataatggg  120
catgaactct ttccatccct tgttacctct aaacctaagg ttgaagttca tggaggtgac  180
atgagatcct tctttacact gatcatgact gaccctgatg ttcctggtcc tagcgatcca  240
tatcttaggg agcacttaca ttgggtaatt acagacattc caggcactac agattcctcg  300
tttggaaaag aagtggtggg ctatgaaatg ccaatgccta acattggaat ccataggttt  360
gtgtttctgc tcttcaagca gaagaagagg caaacagtga gcgcaccatt atccaggac  420
cgattcaata cgcggaaata cgcagaagaa aatgagcttg gctctccagt tgctgctgtt  480
ttcttcaact gccaaaggga aaccgcggcc agaaagcgtt ga                     522

SEQ ID NO: 110          moltype = DNA  length = 453
FEATURE                 Location/Qualifiers
misc_feature            1..453
                        note = Description of Artificial Sequence: Synthetic
                         polynucleotide
source                  1..453
                        mol_type = other DNA
                        organism = synthetic construct
SEQUENCE: 110
atggctcaaa tgagtacaga tccccttgtg attggcaggg tggttggaga tgttgttgat   60
tatttctccc caagtgttaa aatgtctgtt atttgtaacc ccagcaaaca tgtctataat  120
gggcatgaac tctttccatc ctctgttacc tctaaaccta aggttgaagt taacggaggt  180
gacatgacat ccttctttac attgatcatg actgaccctg atgttcctgg tcctagtgat  240
ccatatatta gggagcactt gcactgtgaa agaattaagt ggtgggctat gaaatgccaa  300
tgccaaataa aggaatccat aggttttgtgt tgtgctgtt caagcagaag aaaaggcaaa  360
cagtatgcat tatccaggga ccgattcaat accaatacag ctgctgctgt tttcttcaat  420
tgccaaaggg aaaccgcggc cagaaggcgt tga                               453

SEQ ID NO: 111          moltype = DNA  length = 3155
FEATURE                 Location/Qualifiers
misc_feature            1..3155
                        note = Description of Artificial Sequence: Synthetic
                         polynucleotide
source                  1..3155
                        mol_type = other DNA
                        organism = synthetic construct
SEQUENCE: 111
aagcttccag aaggtaatta tccaagatgt agcatcaaga atccaatgtt tacgggaaaa   60
actatggaag tattatgtga gctcagcaag aagcagatca atatgcggca catatgcaac  120
ctatgttcaa aaatgaagaa tgtacagata caagatccta tactgccaga atacgaagaa  180
gaatacgtag aaattgaaaa agaagaacca ggcgaagaaa agaatcttga agacgtaagc  240
actgacgaca caatgaaaa gaagaagata aggtcggtga ttgtgaaaga gacatagagg  300
acacatgtaa ggtggaaaat gtaagggcgg aaagtaacct tatcacaaag gaatcttatc  360
```

```
ccccactact tatcctttta tattttccg tgtcattttt gcccttgagt tttcctatat    420
aaggaaccaa gttcggcatt tgtgaaaaca agaaaaaatt tggtgtaagc tattttcttt    480
gaagtactga ggatacaact tcagagaaat ttgtaagttt gtggatcctg caggctagcg    540
tgcactctag actcgacgaa ctgacgagct cgaattccc cgatcgttca aacatttggc    600
aataaagttt cttaagattg aatcctgttg ccggtcttgc gatgattatc atataatttc    660
tgttgaatta cgttaagcat gtaataatta acatgtaatg catgacgtta tttatgagat    720
gggttttat gattagagtc ccgcaattat acatttaata cgcatagaaa acaaaatat    780
agcgcgcaaa ctatgataaa ttatcgcgcg cggtgtcatc tatgttacta gatcgggaat    840
tcctcgagca actatttta tgtatgcaag agtcagcata tgtataattg attcagaatc    900
gttttgacga gttcggatgt agtagtagcc attatttaat gtacatacta atcgtgaata    960
gtgaatatga tgaaacattg tatcttattg tataaatatc cataaacaca tcatgaaaga    1020
cactttcttt cacggtctga attaattatg atacaattct aatagaaaac gaattaaatt    1080
acgttgaatt gtatgaaatc taattgaaca agccaaccac gacgacgact aacgttgcct    1140
ggattgactc ggtttaagtt aaccactaaa aaaacggagc tgtcatgtaa cacgcggatc    1200
gagcaggtca cagtcatgaa gccatcaaag caaagaact aatccaaggg ctgagatgat    1260
taattagttt aaaaattagt taacacgagg gaaaaggctg tctgacagcc aggtcacgtt    1320
atctttacct gtggtcgaaa tgattcgtgt ctgtcgattt taattatttt tttgaaaggc    1380
cgaaaataaa gttgtaagag ataaacccgc ctatataaat tcatatattt tcctctccgc    1440
tttgaattgt ctcgttgtcc tcctcacttt catcagccgt tttgaatctc cggcgacttg    1500
acagagaaga acaaggaaga agactaagag agaaagtaag agataatcca ggagattcat    1560
tctccgtttt gaatcttcct caatctcatc ttcttccgct ctttctttcc aaggtaatag    1620
gaactttctg gatctacttt atttgctgga tctcgatctt gttttctcaa tttccttgag    1680
atctggaatt cgtttaattt ggatctgtga acctccacta aatctttgg ttttactaga    1740
atcgatctaa gttgaccgat cagttagctc gattatagct accagaattt ggcttgacct    1800
tgatggagag atccatgttc atgttacctg ggaaatgatt tgtatatgtg aattgaaatc    1860
tgaactgttg aagttagatt gaatctgaac actgtcaatg ttagattgaa tctgaacact    1920
gtttaaggtt agatgaagtt tgtgtataga ttcttcgaaa ctttaggatt tgtagtgtcg    1980
tacgttgaac agaaagctat ttctgattca atcaggggttt atttgactgt attgaactct    2040
ttttgtgtgt ttgcagctca taaaaggtac caaacaatga ttgaacaaga tggattgcac    2100
gcaggttctc cggccgcttg ggtggagagg ctattcggct atgactgggc acaacagaca    2160
atcggctgct ctgatgccgc cgtgttccgg ctgtcagcgc aggggcgccc ggttcttttt    2220
gtcaagaccg acctgtccgg tgccctgaat gaactgcagg acgaggcagc gcggctatcg    2280
tggctggcca cgacgggcgt tccttgcgca gctgtgctcg acgttgtcac tgaagcggga    2340
agggactggc tgctattggg cgaagtgccg gggcaggatc tcctgtcatc tcaccttgct    2400
cctgccgaga aagtatccat catggctgat gcaatgcggc ggctgcatac gcttgatccg    2460
gctacctgcc cattcgacca ccaagcgaaa catcgcatcg agcgagcacg tactcggatg    2520
gaagccggtc ttgtcgatca ggatgatctg gacgaagagc atcaggggct cgcgccagcc    2580
gaactgttcg ccaggctcaa ggcgcgcatg cccgacggcg aggatctcgt cgtgacccat    2640
ggcgatgcct gcttgccgaa tatcatggtg gaaaatggcc gcttttctgg attcatcgac    2700
tgtggccggc tgggtgtggc ggaccgctat caggacatag cgttggctac ccgtgatatt    2760
gctgaagagc ttggcggcga atgggctgac cgcttcctcg tgctttacgg tatcgccgct    2820
cccgattcgc agcgcatcgc cttctatcgc cttcttgacg agttcttttg agcgggactc    2880
tggcgatcgc cccgatcgtt caaacatttg gcaataaagt ttcttaagat tgaatcctgt    2940
tgccggtctt gcgatgatta tcatataatt tctgttgaat tacgttaagc atgtaataat    3000
taacatgtaa tgcatgacgt tatttatgag atgggttttt atgattagag tcccgcaatt    3060
atacatttaa tacgcgatag aaaacaaaat atagcgcgca aactaggata aattatcgcg    3120
cgcggtgtca tctatgttac tagatcggga ctagt                              3155

SEQ ID NO: 112          moltype = DNA   length = 11801
FEATURE                 Location/Qualifiers
misc_feature            1..11801
                        note = Description of Artificial Sequence: Synthetic
                        polynucleotide
source                  1..11801
                        mol_type = other DNA
                        organism = synthetic construct
SEQUENCE: 112
tgagcgtcgc aaaggcgctc ggtcttgcct tgctcgtcgg tgatgtactt caccagctcc     60
gcgaagtcgc tcttcttgat ggagcgcatg gggacgtgct tggcaatcac gcgcacccc    120
cggccgtttt agcggctaaa aaagtcatgg ctctgccctc gggcggacca cgcccatcat    180
gaccttgcca agctcgtcct gcttctcttc gatcttcgcc agcagggcga ggatcgtggc    240
atcaccgaac cgcgccgtgc gcgggtcgtc ggtgagccag agtttcagca ggccgcccag    300
gcggcccagg tcgccattga tgcgggccag ctcgcggacg tgctcatagt ccacgacgcc    360
cgtgattttg tagcccctgg cgacggccag caggtaggcc tgcccgccga    420
cgccgccttt tcctcaatcg ctcttccgttc gtctggaagg cagtacacct tgataggtgg    480
gctgcccttc ctggttggct tggtttcatc agccatccgc ttgccctcat ctgttacgcc    540
ggcggtagcc ggccagcctc gcagagcagg attcccgttg agcaccgcca ggtgcgaata    600
agggacagtg aagaaggaac acccgctcgc gggtgggcct acttcaccta tcctgcccgg    660
ctgacgccgt tggatacacc aaggaaagtc tacacgaacc ctttgcaaa atcctgtata    720
tcgtgcgaaa aaggatggat ataccgaaaa aatcgctata atgacccga agcagggtta    780
tgcagcggaa aagcgccacg cttcccgaag ggagaaaggc ggacaggtat ccggtaagcg    840
gcagggtcgg aacaggagag cgcacgaggg agcttccagg ggaaacgcc tggtatcttt    900
atagtcctgt cgggtttcgc cacctctgac ttgagcgtcg attttttgtga tgctcgtcag    960
ggggcggagc cctatggaaa aacgccagca acgcggcctt tttacggttc ctggcctttt   1020
gctggccttt tgctcacatg ttctttcctg cgttatcccc tgattctgtg gataaccgta   1080
ttaccgcctt tgagtgagct gataccgctc gccgcagccg aacgaccgag cgcagcgagt   1140
cagtgagcga ggaagcggaa gagcgccaga aggcgccag agaggccgag cgcggccgtg   1200
aggcttggac gctagggcag ggcatgaaaa agcccgtagc gggctgctac gggcgtctga   1260
cgcggtggaa aggggagggg gatgttgtct acatggctct gctgtagtga gtgggttgcg   1320
```

```
ctccggcagc ggtcctgatc aatcgtcacc ctttctcggt ccttcaacgt tcctgacaac   1380
gagcctcctt ttcgccaatc catcgacaat caccgcgagt ccctgctcga acgctgcgtc   1440
cggaccggct tcgtcaagg cgtctatcgc ggcccgcaac agcggcgaga gcggagcctg    1500
ttcaacggtg ccgccgcgct cgccggcatc gctgtcgccg gcctgctcct caagcacggc   1560
cccaacagtg aagtagctga ttgtcatcag cgcattgacg gcgtccccgg ccgaaaaacc   1620
cgcctcgcag aggaagcgaa gctgcgcgtc ggccgtttcc atctgcggtg cgcccggtcg   1680
cgtgccggca tggatgcgcg cgccatcgcg gtaggcgagc agcgcctgcc tgaagctgcg   1740
ggcattcccg atcagaaatg agcgccagtc gtcgtcggct ctcggcaccg aatgcgtatg   1800
attctccgcc agcatggctt cggccagtgc gtcgagcagg gcccgcttgt tcctgaagtg   1860
ccagtaaagc gccggctgct gaacccccaa ccgttccgcc agtttgcgtg tcgtcagacc   1920
gtctacgccg acctcgttca acaggtccag ggcggcacgg atcactgtat tcggctgcaa   1980
ctttgtcatg cttgacactt tatcactgat aaacataata tgtccaccaa cttatcagtg   2040
ataaagaatc cgcgcgttca atcggaccag cggaggctgg tccggaggcc agacgtgaaa   2100
cccaacatac ccctgatcgt aattctgagc actgtcgcgc tcgacgctgt cggcatcggc   2160
ctgattatgc cggtgctgcc gggcctcctg cgcgatctgg ttcactcgaa cgacgtcacc   2220
gcccactatg gcattctgct ggcgctgtat gcgttggtgc aatttgcctg cgcacctgtg   2280
ctgggcgcgc tgtcggatcg tttcgggcgg cggccaatct tgctcgtctc gctggccggc   2340
gccagatctg gggaaccctg tggttggcat gcacatacaa atggacgaac ggataaacct   2400
tttcacgccc ttttaaatat ccgattattc taataaacgc tcttttctct taggtttacc   2460
cgccaatata tcctgtcaaa cactgatagt ttaaactgaa ggcgggaaac gaagcttcca   2520
gaaggtaatt atccaagatg tagcatcaag aatccaatgt ttacgggaaa aactatggaa   2580
gtattatgtg agctcagcaa gaagcagatc aaatatgcggc acatatgcca cctatgttca   2640
aaaatgaaga atgtacagat acaagatcct atactgccag aatacgaaga agaatacgta   2700
gaaattgaaa agaagaacc aggcgaagaa aagaatcttg aagacgtaag cactgacgac   2760
aacaatgaaa agaagaagat aaggtcggtg attgtgaaag agacatagag gacacatgta   2820
aggtggaaaa tgtaagggcg gaaagtaacc ttatcacaaa ggaatcttat cccccactac   2880
ttatcctttt atattttcc gtgtcatttt tgcccttgag ttttcctata taaggaacca   2940
agttcggcat ttgtgaaaac aagaaaaaat ttggtgtaag ctattttctt tgaagtactg   3000
aggatacaac ttcagagaaa tttgtaagtt tgtggatcct gcaggctagc gtgcactcta   3060
gactcgacga actgacgagc tcgaaatttcc ccgatcgttc aaacatttgg caataaagtt   3120
tcttaagatt gaatcctgtt gccggtcttg cgatgattat catataatttt ctgttgaatt   3180
acgttaagca tgtaataatt aacatgtaat gcatgacgtt atttatgaga tgggttttta   3240
tgattagagt cccgcaatta tacatttaat acgcgataga aaacaaaata tagcgcgcaa   3300
actatgataa attatcgcgc gcggtgtcat ctatgttact agatcgggaa ttcctcgagc   3360
aactattttt atgtatgcaa gagtcagcat atgtataatt gattcagaat cgttttgacg   3420
agttcggatg tagtagtagc cattatttaa tgtacatact aatcgtgaat agtgaatatg   3480
atgaaacatt gtatcttatt gtataaatat ccataaacac atcatgaaag cactttcttt   3540
tcacggtctg aattaattat gatacaattc taatagaaaa cgaattaaat tacgttgaat   3600
tgtatgaaat ctaattgaac aagccaacca cgacgacgac taacgttgcc tggattgact   3660
cggtttaagt taaccactaa aaaaacggag ctgtcatgta acacgcggat cgagcaggtc   3720
acagtcatga agccatcaaa gcaaagaac taatccaagg gctgagatga ttaattagtt   3780
taaaaattag ttaacacgag ggaaaaggct gtctgacagc caggtcacgt tatctttacc   3840
tgtggtcgaa atgattcgtg tctgtcgatt ttaattattt ttttgaaagg ccgaaaataa   3900
agttgtaaga gataaacccg cctatataaa ttcatatatt ttcctctccg ctttgaattg   3960
tctcgttgtc ctcctcactt tcatcagccg ttttgaatct ccggcgactt gacagagaag   4020
aacaaggaag aagactaaga gagaagtaa gagataatcc aggagattca ttctccgttt   4080
tgaatcttcc tcaatctcat cttcttccgc tcttttcttts caaggtaata ggaactttct   4140
ggatctactt tatttgctgg atctcgatct tgtttttctca atttccttga gatctggaat   4200
tcgtttaatt tggatctgtg aacctccact aaatctttg gttttactag aatcgatcta   4260
agttgaccga tcagttagct cgattatagc taccagaatt tggcttgacc ttgatggaga   4320
gatccatgtt catgttacct gggaaatgat ttgtatatgt gaattgaaat ctgaactgtt   4380
gaagttagat tgaatctgaa cactgtcaat gttagattga atctgaacac tgtttaaggt   4440
tagatgaagt ttgtgtatag attcttcgaa actttaggat ttgtagtgtc gtacgttgaa   4500
cagaaagcta tttctgattc aatcaggtt tatttgactg tattgaactc tttttgtgtg   4560
tttgcagctc ataaaaggta ccaaacaatg attgaacaag atggattgca cgcaggttct   4620
ccggccgctt gggtggagag gctattcgg tatgactggg cacaacagac aatcggctgc   4680
tctgatgccg ccgtgttccg gctgtcagcg caggggcgcc cggttctttt tgtcaagacc   4740
gacctgtccg gtgccctgaa tgaactgcag gacgaggcag cgcggctatc gtggctggcc   4800
acgacgggcg ttccttgcgc agctgtgctc gacgttgtca ctgaagcggg aagggactgg   4860
ctgctattgg gcgaagtgcc ggggcaggat ctcctgtcat ctcaccttgc tcctgccgag   4920
aaagtatcca tcatggctga tgcaatgcgg cggctgcata cgcttgatcc ggctacctgc   4980
ccattcgacc accaagcgaa acatcgcatc gagcgagcac gtactcggat ggaagccggt   5040
cttgtcgatc aggatgatct ggacgaagag catcaggggc tcgcgccagc cgaactgttc   5100
gccaggctca aggcgcgcat gcccgacggg gaggatctcg tcgtgaccca tggcgatgcc   5160
tgcttgccga atatcatggt ggaaaatggc cgcttttctg gattcatcga ctgtggccgg   5220
ctgggtgtgg cggaccgcta tcaggacata gcgttggcta cccgtgatat tgctgaagag   5280
cttggcggcg aatgggctga ccgcttcctc gtgctttacg gtatcgccgc tcccgattcg   5340
cagcgcatcg ccttctatcg ccttcttgac gagttcttt gagcgggact ctggcgatcg   5400
ccccgatcgt tcaaacattt ggcaataaag tttcttaacctg ttgaatcctg ttgccggtct   5460
tgcgatgatt atcatataat ttctgttgaa ttacgttaag catgtaataa ttaacatgta   5520
atgcatgacg ttatttatga tgggttttt tatgattaga gtcccgcaat tatacattta   5580
atacgcgata gaaaacaaaa tatagcgcgc aaactaggat aaattatcgc gcgcggtgtc   5640
atctatgtta ctagatcggg actagtttac accacaataa tcctgccac cagccagcca   5700
acagctcccc gaccggcagc tcggcacaaa atcaccactc gatacaggca gcccatcagt   5760
ccgggacggc gtcagcggga gagccgttgt aaggcgcag actttgctca tgttaccgat   5820
gctattcgga agaacggcaa ctaagctgcc gggtttgaaa cacggatgat ctcgcggagg   5880
gtagcatgtt gattgtaacg atgacagagc gttgctgcct gtgatcaaat atcatctccc   5940
tcgcagagat ccgaattatc agccttctta ttcatttctc gcttaaccgt gacaggcgtg   6000
cgatcttgag aactatgccg acataatagg aaatcgctgg ataaagccgc tgaggaagct   6060
```

```
gagtggcgct atttctttag aagtgaacgt tgacgatatc aactccccta tccattgctc  6120
accgaatggt acaggtcggg gacccgaagt tccgactgtc ggcctgatgc atccccggct  6180
gatcgacccc agatctgggg ctgagaaagc ccagtaagga aacaactgta ggttcgagtc  6240
gcgagatccc ccggaaccaa aggaagtagg ttaaacccgc tccgatcagg ccgagccacg  6300
ccaggccgag aacattggtt cctgtaggca tcgggattgg cggatcaaac actaaagcta  6360
ctggaacgag cagaagtcct ccggccgcca gttgccaggc ggtaaaggtg agcagaggca  6420
cgggaggttg ccacttgcgg gtcagcacgg ttccgaacgc catggaaacc gcccccgcca  6480
ggcccgctgc gacgccgaca ggatctagcg ctgcgtttgg tgtcaacacc aacagccgca  6540
cgcccgcagt tccgcaaata gcccccagga ccgccatcaa tcgtatcggg ctacctagca  6600
gagcggcaga gatgaacacg accatcagcg gctgcacagc gcctaccgtc gccgcgaccc  6660
cgcccggcag gcgtagacc gaaataaaca acaagctcca gaatagcgaa atattaagtg  6720
cgccgaggat gaagatgcgc atccaccaga ttcccgttgg aatctgtcgg acgatcatca  6780
cgagcaataa acccgccggc aacgcccgca gcagcatacc ggcgacccct cggccctcgct  6840
gttcgggctc cacgaaaacg ccggacagat gcgccttgtg agcgtccttg gggccgtcct  6900
cctgtttgaa gaccgacagc ccaatgatct cgccgtcgat gtaggcgccg aatgccacgg  6960
catctcgcaa ccgttcagcg aacgcctcca tgggcttttt ctcctcgtgc tcgtaaacgg  7020
acccgaacat ctctggagct ttcttcaggg ccgacaatcg gatctcgcgg aaatcctgca  7080
cgtcggccgc tccaagccgt cgaatctgac ccttaatcac aattgtcaat tttaatcctc  7140
tgtttatcgg cagttcgtag agcgcgccgt cgctcccgag cgatactgag cgaagcaagt  7200
gcgtcgagca gtgcccgctt gttcctgaaa tgccagtaaa gcgctggctg ctgaaccccc  7260
agccggaact gaccccacaa ggcccctagcg tttgcaatgc accaggtcat cattgaccca  7320
ggcgtgttcc accaggccgc tgcctcgcaa ctcttcgcag gttcgccga cctgctcgcg  7380
ccacttcttc acgcgggtgg aatccgatcc gcacatgagg cggaaggttt ccagcttgag  7440
cgggtacggc tccgggtgcg agctgaaata gtcgaacatc cgtcgggccg tcggcgacag  7500
cttgcggtac ttctccccata tgaatttcgt gtagtggtcg ccagcaaaca gcacgacgat  7560
ttcctcgtcg atcaggacct ggcaacggga cgttttcttg ccacggtcca ggacgcggaa  7620
gcggtcagc agcgacaccg attccaggtg cccaacgcgg tcggacgtga agcccatcgc  7680
cgtcgcctgt aggcgcgaca ggcattcctc ggccttcgtg taataccggc cattgatcga  7740
ccagcccagg tcctggcaaa gctcgtagaa cgtgaaggtg atcggctcgc cgatagggt  7800
gcgcttcgcg tactccaaca cctgctgcca caccagttcg tcatcgtcgg ccgcagctc  7860
gacgccggtg taggtgatct tcacgtcctt gttgacgtgg aaaatgacct tgttttgcag  7920
cgcctcgcgc gggattttct tgttgcgcgt ggtgaacagg gcagagcggg ccgtgtcgtt  7980
tggcatcgct cgcatcgtgt ccggccacgg cgcaatatcg aacaaggaaa gctgcatttc  8040
cttgatctgc tgcttcgtgt gtttcagcaa cgcggccgtc ttggcctcgc tgacctgtt  8100
tgccaggtcc tcgccgcggg ttttcgctt cttggtcgtc atagttcctc gcgtgtcgat  8160
ggtcatcgac ttcgccaaac ctgccgcctc ctgttcgaga cgacgcgaac gctccacggc  8220
ggccgatggc gcgggcaggg caggggagc cagttcacg ctgtcgcgct cgatcttggc  8280
cgtagcttgc tggaccatcg agccgacgga ctggaaggtt tcgcggggcg cacgcatgac  8340
ggtgcggctt gcgatggttt cggcatcctc ggcggaaaac cccgcgtcga tcagttcttg  8400
cctgtatgcc ttccggtcaa acgtccgatt cattcaccct ccttgcggga ttgcccgac  8460
tcacgccggg gcaatgtgcc cttattcctg atttgacccg cctggtgcct tggtgtccag  8520
ataatccacc ttatcggcaa tgaagtcggt cccgtagacc gtctggccgt ccttctcgta  8580
cttggtattc cgaatcttgc cctgcacgaa taccagcgac aatacttgcc  8640
gtgggcctcg gcctgagagc caaaacactt gatgcgaag aagtcggtgc gctcctgctt  8700
gtcgccggca tcgttgcgcc acatctaggt actaaacaa ttcatccagt aaaatataat  8760
attttatttt ctcccaatca ggcttgatcc ccagtaagtc aaaaaatagc tcgacatact  8820
gttcttcccc gatatcctcc ctgatcgacc ggacgcagaa ggcaatgtca taccacttgt  8880
ccgccctgcc gcttctccca agatcaataa agccacttac tttgccatct ttcacaaaga  8940
tgttgctgtc tcccaggtcg ccgtgggaaa agacaagttc ctcttcgggc ttttccgtct  9000
ttaaaaaatc atacagctcg cgcggatctt taaatggagt gtcttcttcc cagttttcgc  9060
aatccacatc ggccagatcg ttattcagta agtaatccaa ttcggctaag cggctgtcca  9120
agctattcgt ataggacaa tccgatatgt cgatggagtg aaagagcctg atgcactccg  9180
catacagctc gataatcttt tcagggcttt gttcatcttc atactcttcc gagcaaagga  9240
cgccatcggc ctcactcatg agcagattgc tccagccatc atgccgttca aagtgcagga  9300
cctttggaac aggcagcttt ccttccagcc atagcatcat gtccttttcc cgttccacat  9360
cataggtggt ccctttatac cggctgtccg tcattttta atataggttt tcatttctc  9420
ccaccagctt atataccta gcaggagaca ttccttccgt atcttttacg cagcggtatt  9480
tttcgatcag ttttttcaat tccgtgata ttctcatttt agccattat tatttccttc  9540
ctcttttcta cagtatttaa agataccca agaagctaat tataacaaga cgaactccaa  9600
ttcactgttc cttgcattct aaaaccttaa ataccagaaa acagctttt caaagttgtt  9660
ttcaaagttg gcgtataaca tagtatcgac ggagccgatt tgaaaccac aattatgggt  9720
gatgctgcca acttactgat ttagtgtatg atggtgtttt tgaggtgctc cagtggcttc  9780
tgtgtctatc agctgtccct cctgttcagc tactgacggg gtggtgcgta acggcaaaag  9840
caccgcggga catcagcgct atctctgctc tcactgccgt aaaacatggc aactgcagtt  9900
cacttacacc gcttctcaac ccggtacgca ccagaaaatc attgatatgg ccatgaatgg  9960
cgttggatgc cgggcaacag cccgcattat gggcgttggc ctcaacacga ttttacgtca  10020
cttaaaaaac tcaggccgca gtcggtaacc tcgcgcatac agccgggcag tgacgtcatc  10080
gtctgcgcgg aaatggacga acagtggggc tatgtcgggg ctaaatcgcg ccagcgctgg  10140
ctgttttacg cgtatgcagt tctccggaag acggttgttg cgcacgtatt cggtgaacgc  10200
actatggcga cgctggggcg tcttatgagc ctgctgtcac cctttgacgt ggtgatatgg  10260
atgacggatg gctgggccgct gtatgaatcc cgcctgaagg gaaagctgca cgtaatcagc  10320
aagcgatata cgcagcgaat tgagcggcat aacctgaatc tgaggcagca cctggcacgg  10380
ctgggacgga agtcgctgtc gttctcaaaa tcggtggagc tgcatgacaa agtcatcggg  10440
cattatctga acataaaaca ctatcaataa gttgagtca ttacccaatt atgatagaat  10500
ttacaagcta taaggttatt gtcctgggtt tcaagcatta gtccatgcaa gttttttatgc  10560
tttgcccatt ctatagatat attgataagc gcgctgccta tgccttgccc cctgaaatcc  10620
ttacatacg cgatatcttc tatataaaag atatattatc ttatcagtat tgtcaatata  10680
ttcaaggcaa tctgcctcct catcctcttc atcctcttcg tcttggtagc ttttttaaata  10740
tggcgcttca tagagtaatt ctgtaaaggt ccaattctcg ttttcatacc tcggtataat  10800
```

```
cttacctatc acctcaaatg gttcgctggg tttatcgcac ccccgaacac gagcacggca    10860
cccgcgacca ctatgccaag aatgcccaag gtaaaaattg ccggcccccgc catgaagtcc   10920
gtgaatgccc cgacggccga agtgaagggc aggccgccac ccaggccgcc gccctcactg   10980
cccggcacct ggtcgctgaa tgtcgatgcc agcacctgcg gcacgtcaat gcttccgggc   11040
gtcgcgctcg ggctgatcgc ccatcccgtt actgccccga tcccggcaat ggcaaggact   11100
gccagcgctg ccatttttgg ggtgaggccg ttcgcggccg aggggcgcag ccctcggggg   11160
gatgggaggc ccgcgttagc gggccgggag ggttcgagaa gggggggcac cccccttcgg   11220
cgtgcgcggt cacgcgcaca gggcgcagcc ctggttaaaa acaaggttta taaatattgg   11280
tttaaaagca ggttaaaaga caggttagcg gtggccgaaa aacgggcgga aaccctttgca   11340
aatgctggat tttctgcctg tggacagccc ctcaaatgtc aataggtgcg cccctccatct   11400
gtcagcactc tgcccctcaa gtgtcaagga tcgcgcccct catctgtcag tagtcgcgcc   11460
cctcaagtgt caataccgca gggcacttat ccccaggctt gtccacatca tctgtgggaa   11520
actcgcgtaa aatcaggcgt tttcgccgat ttgcgaggct ggccagctcc acgtcgccgg   11580
ccgaaatcga gcctgcccct catctgtcaa cgccgccgca ggtgagtcgg tgtgcgtgcg   11640
gtcaacgtcc gcccctcatc tgtcagtgag ggccaagttt tccgcgaggt atccacaacg   11700
ccggcggccg cggtgtctcg cacacggctt cgacggcgtt tctgcgcgcgt ttgcagggcc   11760
atagacggcg gccagcccag cggcgagggc aaccagcccg g                         11801

SEQ ID NO: 113         moltype = DNA   length = 2499
FEATURE                Location/Qualifiers
misc_feature           1..2499
                       note = Description of Artificial Sequence: Synthetic
                       polynucleotide
source                 1..2499
                       mol_type = other DNA
                       organism = synthetic construct
SEQUENCE: 113
tctaggagca aaaaaaaaaa aaaaaaaaaa aacaagtagt agtagtagta gtaaatggaa     60
aaatagagag gcaatttttt ttagtatctt actttatcca ttagcactta aaaaacatag    120
gtttacatgc tctcattgtc acgccaggcc gctaattaaa tggtacattt catcatcccc    180
atttttttggc ctcatagtta attatcacaa tttctgaaag caacatcaga acaaccccac   240
atttcttgtg gtcctataat tactgctaga tagtccaaac ccatctgcct atttagggct    300
tgtgaatgag gattgaaaat ggtagagaat atttgcaaag gcatcatgca tatatggaaa   360
agactaaaga gagagttagt gccttgcaaa gcggattctc acagttgtag aaaaggactc    420
accattttca agaatactcc cggcatgaag atggacaatt taatataaaa aacaaagaaa    480
atagtaatta agtgcgttga gatgaatgaa atttatccgc tcttaattga atatgggggaa   540
ttgaaagaaa tttctgataa taaattaatg agtcttacat gacgtggatc cgacttaatc    600
tagtctatt aaactaagaa tagataagaa tagagaatat agacaaaaga gaggctcatt      660
ggctagggtt tcaagggagt tccttgaaca taagtggcaa gtacaagcac aaagccaatt    720
tccatggact aaagatgaat aagatgtgtc gtgtggtatg gtgggaaggt gaggaggtat    780
ggggtaattg gagatgctaa acctctctaa aagctctttt gctccaaata tctaaatcca    840
tctctatcac ttttggcgac tgccccaaaa tttgcaactt atgaattaaa gttttaatat    900
ttttaagtta ataaattctg aattaataat ttaacatatt caataaactt ttaaaacaa    960
attacgtata taccatcaaa ctggctgcac catgatcact ttctaaactc acaatgacat   1020
atggatttaa tcaggcacaa agtcatgttg atagaaagag atagtacgga gaatgaagaa    1080
aaaaggtagg ggagagagat ggggtgagtg ggggaaagat agggttctct ttttagtgaa    1140
agcgacaggg tctgagaacc ctaggtcaaa agttgcaaaa acctctatac aggcttcttc   1200
actccctcac tactaatata ctctcattaa ggcttgaggt ttaattcatt aaaattgtgg    1260
tttaattatt gtatccccctc aaacgaaata attgtccttg tcgaggttag acaatgttgc   1320
gtactatttt caaacgcagt cagccattat tctcctatcc tttacagtcg agattcaaag    1380
acagaaagta gcatgcaagc tgttattaat ttactttgat taggactttg ccaagaaaat    1440
gaagaacctt ttcttttttc ttttaattta gttatcttca aacatgtaat ttttcctagc    1500
aagcaaatac ggtaactttt ttttttattc tcatttaatt tgttggagct attgctactt    1560
tgatgacttc aaccaaatcc tggttggtag gcggagggtg ctgacgatgg aaactacccc    1620
tcttgtccaa atacgataac ctaaaaaaata gaataatagc ttattgtact gtgctgcaaa    1680
aattgcattg tcagtataca taattaaaat ctattttgaa tgtgtggagg gcaaagaggg    1740
gtgactggtc tagggttgta gaaatcaggt gggagagaga atggtatttg tctctgtgtc    1800
agctgatatc acgtgaagag gcacaataag aagtccttcg tatccattca cttcccaaaa    1860
ataccggcat tactacaaat atagtactag cacttgcttt ctctatcccc atctttgcta    1920
tttcctttcc ctttccaact ttttggcttt agaattgcaa agatggaggg aattgtggtt    1980
ctttgtatct gtaaaatttt tcctccaagc tccagttgta gctagcttaa tgcgtggacg    2040
cgcgcgcaca cactagaaat ctgcaatcta tatatatatt cacaaggcac tcacatatca    2100
aaaaccacat agacattgta tagagagagc tgtcgttctc aagcagaaaa aatgatatga    2160
tttcatcagc atgtggtcaa ccaaatagtt caattctagt ctttgcttcc tcttttctaat   2220
tactgtataa atagagccac aaggacatag aattgagaaa ataaaagaca ataaaaacaa     2280
atctagctac ttaagcgaat gatgatgact ctctctcagt agtcttaact cttaatacccc   2340
ttgttttcct tcttgtgctg cagtttgatt ggttaattaa cctaatcaaa agatgtttta    2400
actgtgtttt atccgtctttt ctcaagatct atcttagtcc caccacatag ctccctcaag    2460
ctacagctgc aaaatatata ctatatatat atataacaa                             2499

SEQ ID NO: 114         moltype = DNA   length = 2500
FEATURE                Location/Qualifiers
misc_feature           1..2500
                       note = Description of Artificial Sequence: Synthetic
                       polynucleotide
source                 1..2500
                       mol_type = other DNA
                       organism = synthetic construct
SEQUENCE: 114
```

```
tgacattgct ttggtggttt aagttctcag ccagtatatg cattgtccta ataggtctca   60
catggaagca gcactgagag ttgtaagata cataaaagaa gctcctggct taggtctctt  120
cttgcctgta aaatcttcag atcaactaag tgcttttgt gactcagatt ggggagcatg  180
tatacaaatt agaaggttag ttacagggta cttggtaaag tttgaaagtg ctcttatatc  240
ctggaagtct aagaagcaga gtactgtgtc taggagctct aatgaagctg agtttataag  300
tatggcttca tgtgcagcag aagttacctg gccggtagga ctgttcagtg aacttggtgt  360
caaggttaaa cttcctataa acttggtatg tgatagtaaa gctgcaatcc aaattgcagc  420
aaatccaatc ttccatgaaa gaacaaaaca tattgatata gactgtcact ttgtaaagga  480
aaagctaagt ctaaggatgc taaaaactga gtatgtcaac atggaggatc actggcagat  540
atacttacaa aaggattgtg aagagctcaa catgtacatt tgctgaacaa gctagggttg  600
aagaatctgt atcaaccatc agcttgagag ggagtgttaa tcaacatggt taccactagt  660
ttatttataa agtgtaaatg ctaaaccata gctagtgagt tagttaatag ttagttgagt  720
ttgttataaa tattagtcag ctgtacagtt taacatagct tctctttcag aaatgaaaat  780
tgctccttctc tcatttcctc tcttctagat tcttcttctc cctccttctc ttagctcaga  840
tctctcttat gacagctaac aataaatacg aatatttctt gtaacggttg ctcattgaat  900
gttgtctttc tcaaccgata tctttctttc aagttttccc cccgattcga gtattttga   960
aactcactca gcaccggtca catattcgta atcggtgcca gctatttgct tactcatatc 1020
ttatttgact tcattgtcac gtgtcagaca gaagtatgtg cgcatatacc atcaagtctc 1080
aatttgaaat aaaatcaact taagcagtta aaagtcaaat ctcttttagt tcggtcttta 1140
aaataataat ttaaataatg aacctataaa acacgcaact cacactgaat ataggggcag 1200
acataaaagc cgaaagactg aattccgaac cggaccgaat tatttcggta tttcgatatc 1260
ggtttattca gtatttcggt actatttcgg tataggattt ttagttattc ggtatttcgg 1320
tacgatcctc ggtattgaaa tttcgatatt tcggtatacc gaaataccga ataatttaag 1380
tacaccttcc ttcactgccc agcccgttat caatttcag cccaagtttc taacttgtta 1440
tttctttccc ttagccagta gcctactaag attaagccca acgccccaac ctaacattag 1500
aaattattat aattagaaaa gtataaagaa agtactacca ttctactgct atgctcatgt 1560
agtgatttct attagaaatt attagaagtg aaggtactgc ccacattttc ttgttgctat 1620
actcattatc acgcaattag aaattttcta atgaattaga attcagtagt tcagcacaga 1680
ggcggatgta gcgtattacc tacggggttca actgaaccta taactttcga cacagagtaa 1740
aaatttatat gtaaaaattc tttaaaattg taaaaatcgt agatatgaac ccataacttt 1800
aaaaatataa tgggtaacat taaaatttgaa cccatagaat ttaaatcctg gattcgcctc 1860
tggttcagca ttgtttagtt cacaaaaata tggtacgatg ccgaaccgta tcgaaaccat 1920
accgaaccaa acaagaagat atcgaacaat accgaactac tttggtacag tatttggtat 1980
gcacacttga tatatcgaat accgaaatac cgaaccgtaa ttttcgaata ccgtaccgaa 2040
ataccgaaca ctcacccata actaaacatt aaaaagctag aactcaggtg tttaatgact 2100
aaacggaagt aagatctaga taatccgtca ctctgttgat ttgtaaggct atcgacatgc 2160
aaaagtggaa gcaaatggaa gccgaaattt taacaaaaat gctgaaccaa taccatgaaa 2220
ttgatgaatg gtgggaccct atttcactct ttttagaattt gcgtaagacc agaaaataac 2280
ttcaatcgaa atcaaaataa ataccaaccc ttttaggccc caaatcacta cgtgtgattt 2340
gcaaacgtca ttagccttat gtaaacagtg acctcatgcc aacatattat cgcagcctat 2400
aaatcttagt ttacatttca tttctttca aacacacaca cctcacaata gaactaagtt 2460
gtaagagttt cattttcttt gttctttctc acaaaccaaa                        2500
```

| SEQ ID NO: 115 | moltype = DNA length = 2500 |
|---|---|
| FEATURE | Location/Qualifiers |
| misc_feature | 1..2500 |
| | note = Description of Artificial Sequence: Synthetic polynucleotide |
| source | 1..2500 |
| | mol_type = other DNA |
| | organism = synthetic construct |

SEQUENCE: 115

```
tgccagacag tctaaaattc aaaaatagga cagcccacat cccctccacc ccactagatc   60
tcactacttc ttaattagga cttgtggggg ggagtagagg gatttgcaaa ggcggccgcg  120
gcatgcatat acggaaaaga gaagttagtg gtttgcaaag atgattgtgg aaaagggctt  180
acctaacaat gaagaagagg aagagggtag atggataata ataactcaaa aatagaaaga  240
agagggacaa gtgggggctc aatggctaag gttttaaggg aggtcttgga aacatcatta  300
gcaagtacat gcagtattac caccctacat cagactgtgg ggtctgatgg aatattcttc  360
tactatactc ttttaaatag agggaattaa tgagcctttta taatgttgaa attatataaga  420
aaatagtata acttttttaaa tctcttaatt atgtatcaaa tcaaatctca tatttaccct  480
ttagtggatc tattcactga agtctgaata aatcgtacca gtaattcata ccgaatgtgt  540
aaataatttg aaagaaagat agacaaggcc tcaatgkcta gggatttgtt agcatcaata  600
gcaagtataa gcagaaatat ataccaccaa ggagtgaggt ggaagaatta agatttactc  660
taatgaaata tatatcaa gattgagtca tgtgaatgaa gaatttctta gtaccttaaa  720
ttaagcgaat atcacataac agaggtgtaa aaaaacgaaa gatggacaag ctaagtggct  780
ctcaatggct gggtttttaa gggatcggag gtcttgttaa catcagacgg aagtacaatt  840
agagtatata tgctactcta ataatacttg gctacaaaca taaaaaaata tctctatcac  900
tatctctcaa ctcgccatat agacttaatt ggcacaaagt catgctgatg gaaagagata  960
taaggagaat gggaagacaa aaaaaaaagt gggatagaa agagtgtcca agtagctaga 1020
aggggggtggg ggtggggggt ggggggagttg ttgttttagt tgtggaagag ataggtttct 1080
cttttttagtg aaagtgacat atatagctag actgagaacc ctggtcaaaa gttgctttgc 1140
cttaacgttt ctaaatgcct gacctctgag aggctatctt ctcctctcat tctctcgacc 1200
cttactgttc atataccccc aaatttgagg tctaattttat ccacactatg gtttcttact 1260
gttgtcttct tctctgaaac aatattgctt gtcgatcttg gacttggcca cgtcaacgtg 1320
taacttcagc aactaggtg actccaagtc ataga
cagat ctaggtcgac ttctgtgaat 1380
ttaactaaac aaaattatta atttcgactc aaaatagata tgtactatat atatatatag 1440
taaacttatt gtgaacttac taacttaaaa ttttcaagtt tgcagtattt tttggaataa 1500
gaaagggaa aagaggcag aaaacccat atttcttcct ctttggagtt gacgctaaag 1560
ggataaagct aacatgcaag ctcttaacaa ataacatact cagtataatc tcacaaatgg 1620
```

```
ggtatagaga ggataaaacg tacacaaatc ttaacaatat acacagtgta attccataag    1680
tgagttctgt ggacggtagt agcttacccc ttgcctttaa catgcaagct cttaagcttt    1740
gtatttttat tttgttcttt cttttggag aggaagaagt ggtggttgaa gactagagat    1800
aaggaagaaa agagaaggat ttttgtcagt tgctatcacg tgaactgaag gggcacaatt    1860
agagagaagt ctatatgctt cacttcccat aaaatcagtt gtaactacaa caagtactaa    1920
gagtgtcccc tccatttcct ttcttccct caattcccct tcatacttt aaagcttaat     1980
tccacagcta gaaaagaag cctttctttt tctctagagg tatttagcaa agatggaagg    2040
acaatattac agctctcttt gtctctacag gtaacaaacc attgcctgtc tttctcaatc    2100
tccagtattt ccagctatct tataatgctt tgagtactcc cacaaaacac atgcattata    2160
gccactagct acatatatat atatattgt aaaaccacac attaatttag ctgtcattct     2220
caaccaaaaa gctatgttat catcaacata ttgacaaatt acctataatt ccttcccctc    2280
tagctatatg atctatctca ctttattatg cacttaaaaa gttatgttgt ccctctcaaa    2340
agtcttaatt aattaacctt gttttgcatc ttgctgcagc tagctagctt attaaattga    2400
caaactcaga agatgttgtg gttctttcaa cttcaataaa aagctaagag tagtacttgt    2460
gcttgtatat ccgtccttct caagctcaag tcccacttca                          2500

SEQ ID NO: 116        moltype = DNA  length = 3433
FEATURE               Location/Qualifiers
misc_feature          1..3433
                      note = Description of Artificial Sequence: Synthetic
                      polynucleotide
source                1..3433
                      mol_type = other DNA
                      organism = synthetic construct
SEQUENCE: 116
gttggagcta aaaataagag aaatggacaa gtgtcaaatt ctagcgtcca tggtagcgcg    60
acgcactatt gtggcgctag aaatagaaga ccaaaatttc caatgttggc gtcgaccttg    120
cgttgcggta tttttctat ttcgctaggg acaagattat ttcaacaaaa ggggttctaa     180
acctaatttg gaggatatct aacatacttt gaaggcgaat tcacgtaagg gaatacaaac    240
cacgcttgga aggggctttc aactagtttt tcttctcttc ttttctcttc ctttcatctc    300
attatgtatt agttctaggg ttgttggtac ttacattaac gttatagttt gaagcttgga    360
ttatcttatt atttatcat attggttat ttattcaatc ttgcgcttga taatttaatt     420
ttaattgatt gatcaccaat taaatactat ctacgaattt aggattgaaa tcgggagaga    480
aaattttaga ttgcatatag gattgagtag agtaagatct tgaacctgaa ttacgaggga    540
acgaatttgc gattaggata taaggatata cctaatcgtc ttgcttggtt actatacggg    600
aattattaat acgttcttat taatcctaat ccactggaat ataggcgttg agttagcttg    660
aacaggcgag tagtacttcg ggagaatact acgagtaata ttaaattgtc aatcaataaa    720
ctagataaat ttataagata gtttaagtaa aaaactcaat gagattgtta gttgacccat    780
aactctgaaa tattttctcc cattagattg tctttaagct tgccggcata gtttttctag    840
ttttctagtt tacaactcta gattagttat agttaacaat cacactttag aaaatcgctt    900
gagtagatta attgttaatt tagttgatag ttaatcataa gtcatcgagg aacgatact     960
ctacttatca ctttattact tatcgaccac gtatacttga gtgcgtttgg gagcaacaaa    1020
tttttgacgc cgttgccggg acgttagttg atgtttcaa ctagtgaaca aaatgcaaat    1080
atgttatgca attcggtgcc atttacacgt ctatgaggag ttatattaaa gaactttatg    1140
taggatgttg gttggatcct acaagctaaa attatggcta agaaaattgt gaattactaa    1200
taaacttgta ataagataaa aaataatttc ctagaacgta atagaattga agtgagatta    1260
gaccgacacc tcttcgtcgg aaaactatgt tatatatgta ggttatttta tatatatata    1320
tatatatata tataatttc ttggcgttta atttttata ttttgattct tcctactaat      1380
aattctaact ctatcactga attaaacgta caggattcat ttcttataca aaagaggttg    1440
atcattatta ggtctgggca ctgtcagagg ctgaccgata tgagtagttc ttcacatgct    1500
tggcagcaat ttgaactgtg attgcttgag gggcgaaaaa gagagtagaa tctaagttcg    1560
gtaattttta tctgaattct gtatttgtct taaaaattta ttgagtatgc ataaaattat    1620
tattttaaac tcagtaattt aaaaaattta gaattcgaac tcataaattt caaattggga    1680
ctccacctct gattgtttgt aagtggagtt tagggggcaga actagctcaa aaagttcggg    1740
ttcgattgaa ctcagtaaat ttgattcaaa gtctatatat ttattgaaaa atcaactaaa    1800
tatgtatata tacaataaat ttcaaattca taaaaattta aatcctgaat taacctaata    1860
gtaaaaccgc agactctaac tagtggtcta gtttagagag tcaaattatg gttttttaaca    1920
accttaaaca agcacaaata cttttccact attggttcaa ttttggttgt taacaacctt    1980
gattggtaat tacgtacttg catgggcatt tgaaaattaa gttacgtacg tgtaaaacgt    2040
tttagagtag tccgtactaa ttaagaacac aaacactgct tgagattttg tggcggaagt    2100
ttgtttttgac ttagcatggg taggcccacg aattccccat tttgaataaa agacaacctg    2160
tgctagtcga ttagctatta tttaattact agaatattac ttactccctc cttttaatt    2220
tagacgattt agtttgactt ggcacaaagt ttaagaaaa aaaaaagact tttgaaatat     2280
gtggtgttaa aatcttaatg ggcaaaagct aagtgggatc atgatatttg tgtgactata    2340
aaaacttctc attaagaata aagtgagtaa aataaaaaat taaagtcaaa ttatttctaa    2400
atatagaaat atatcattct tttttgaacg gactaatacg gaaagtgtgt catttaaatt    2460
aaaataaata aagtaatatt tatcatatga ttttaacatg taaatatcat acaagtaatc    2520
taatcgtcaa gcgcggatct aataaataag ggaacgggtat ttttgtttagg ctgtgtatat    2580
ataatttttt aaaatctact aaaaaagaac aaataataga tttgtaaatt agagggatat    2640
ggtagaatct aactataaac ccttaaagtt caaatcttgt atctgcttgt ggtaatagtg    2700
tatatatatt ttttacacgt ttttgttgta tagaactcaa actaaaaagg gcattccagt    2760
gcacaaagca tctcctattc acacacaatt cggtgaaggg ccgcactgta tgcaagggg     2820
gtgatatcgg cagtctatcc tgatgcaagc atcaatggtt gattccacgg ctcgaatccg    2880
ttacctatag gtcatacgga gataacttta ccgttactcc aagtcccct tctacataa     2940
acttgcatca atagctgatt tcacgactcg aacccataac ctagttgata cgaagataac    3000
tttaccgttg cttcaaggtc cgtctacaca aaactgatca aattattttc ataaataaag    3060
aagctatcat ttctctataa atagaactag agtccttgca tattccaaca taagtatcag    3120
ttccaggaaa atcaagacat aatctgttag cttttctctt tgccattctc nnnnnnnnat    3180
ggattcctta ccagtctcct ccattgaatc tctagtcatt gagatcaaga aagagatgtt    3240
```

```
ctcaaaccaa gaatttaaca cttttgtcac cccaatatct gcctatgaca ctgcttggtt    3300
ggccatgatt tcttataata atcaagaaga agccattaat ggtcattctt tttctggccc    3360
tatgtttaag agttgtttaa attggattct caacaaccaa aatgagcaag gattttgggg    3420
agaatccaat ggt                                                       3433

SEQ ID NO: 117          moltype = DNA   length = 2512
FEATURE                 Location/Qualifiers
misc_feature            1..2512
                        note = Description of Artificial Sequence: Synthetic
                          polynucleotide
source                  1..2512
                        mol_type = other DNA
                        organism = synthetic construct
SEQUENCE: 117
aagctggtac ccttatgttt agtccaagaa aaataaccat acccaaatat aagggtttgt    60
tgaagacgga aatatataaa caaataaaca aatatcatca tatctccgat agtttaaaat    120
tttagattgg atatttcaca caatttatca aaattttcaa aaaaaaattc tacttttttct   180
tgcttggaac ttggaagggg aagggggtggt ggtggagata gggcggggca tcttctatct   240
agtctatgtg attaatataa caaaacaaaa agggcgaggc aaaaacatgg atgaatggtg   300
gtccttttct atatttatat ggattgttac gatacgtcga tttcactttg caaaatacca    360
attagattca tttagttatc ttttttgatca ctctgctttt actatcatat atatatagga    420
gtccttccac gtttcgcatg tgtcattgtt tatattttcg ggtgcttcc ttccaaatgg    480
ctaaaaaaat ttgacacagt ggtcccaaaa gtttatagaa atagaattca acagtgaggc   540
atataccat gaattctatt ttacatcttc atcgtataaa atagaatgtg ttataaactt    600
tacctcgtga tgcttacaag gggtgaaaat ataaaagcac tttatagatt tacaagagtc   660
acaccttgat ttatcctaag attttatttt tttacatgcc aaacaatgaa gtatgggaga   720
tccaattgga ataacatcaa atttaataaa attcgaaata gtcagagagc tgtctactga    780
ggtatattga aacttatttt tttttaatag aaaatatcaa aacttagca atatattaaa    840
atgtttcata aattacattg tttaaaccaa gcgttgaaac atatgctgat acgaggtagg    900
cttattgatg aatttataag ggcctcattg gaaaagacga tccaaagcaa tgggctaaaa    960
aattggccca ttttctgcca cccagtgtat ggtattact agtttcaccc acacagattt    1020
gcacttcatt agaggacaat gttgctgaat ttgaaacata agtccattta tctccactgt    1080
acagtccttc ctggagtcca atcctgacca tatcttcatg atttatgta atgtggtgaa    1140
taagcaaagt ttcatgttat gctttgtctc atttatagc aaattcattt cctcataaaa    1200
tttacttcaa aaaagtttcg tttgattttc agaaatcaaa atatgctttt cggtaaccaa    1260
atggttttca attttgttta cgaagaactt aaaactttcc aacaccctac atctatgatt    1320
gcaagttaaa attgcagaaa tatgacactt tttggagtgg tctttatcgt ttaacttcac    1380
ttgcacttta agggcaaaag ttaaagtgt ttccatgaag caagcgaggg ataacattta    1440
ttaaacttga aattctactc atagaccaaa acaaggacaa aaattcaaga ctatctatgt    1500
gggtaaacgt acgaaaattg ggcttctcca gattagagcc ggaccttgtg gaaagacaga    1560
gaaattcgag gcccacttcc agtttctaag gagattaagc ctatcaaacg atggtccaga    1620
acgaaatatg tctttcttta ttctctacta tatagctgac tcagaatcgt tagaatttgc    1680
aatttcctca taataaaatg tgaggcagta tagattcgaa aaccttttgtt gaagattatt    1740
gactcagcta cgcgaaacaa actgtagtat ccaatgtacc gattaacaag cgacttggta    1800
actatgaatt tgttagctcg acaaaatcac cggttaataa tgagtttgtg agttcgataa    1860
aatctaattt tctgatagaa attttatata ttatgcagaa atttaataaa agtagactta    1920
acttatatat tttagcattg actcttttga agtaaaatcc attccatcta aattatgact    1980
tccctacatc gagtaagtaa gttgcgtctg tatcctcatt ttaccactt ttcgctatgc    2040
aattattcaa ggatctttac acaaatagca agccaatatt aatatttat ttttttttagt    2100
catatatata aattatacat atattatata cccattaatt attttttaatt taagtgatag    2160
attggacgac tatttggatt aattcttcgt tattcaagat atagatgtc gtctctaaata    2220
catgagctag aagataataa ggattactag gccgaaaggc tgatggaaat gaacaagaag    2280
ataagctcct aaatggaaac agtacggaaa aagtcaaaga gcagtgcatg ggaggaatca    2340
tcagtcagaa aaggaagcca cgtgtcaagt agaaacaagc acgtgtccat gcaaaagcca    2400
cgtaactccc ttccatcaca tcttccttct tcaaaacctc gtgttttact ctctcttttc    2460
tcactgccag tgatcgtcag gactgtgcat gtttgtttaa aaactaaagg ca             2512

SEQ ID NO: 118          moltype = DNA   length = 941
FEATURE                 Location/Qualifiers
misc_feature            1..941
                        note = Description of Artificial Sequence: Synthetic
                          polynucleotide
source                  1..941
                        mol_type = other DNA
                        organism = synthetic construct
SEQUENCE: 118
tttaaaacgc caaaaaataa gggacggcca tggcgtagca atgactattg ttccgtaggt    60
catttgtgaa ggaccgacaa aattttaggc gatccgggtc cgattttttcg gttctgctca    120
agaaaactcg atctgcacga atagcttata atcaaaccct tttttttttt tcaagaatgt    180
ctaattgatc ctaaaagac aaccttatat gttccaccat ggcaggatcg gccttattac    240
taagggtttg ccaatagaca cgttttttaac attcaagtaa aaaaaacatt tattcttaat    300
aacccaccta ctatagtacg ttatttggca gtagactacg ttgtacattt gggacctttt    360
ggaacactcg tctttcacga gtcactaatt tttgtgttga atgcataaaa tttgtttttt    420
tcttttttcga aattgaacaa ttttatcttcg gatcacacct atagtatatt attaccttat    480
tgttagaaaa tattttattt tattattgac tcctaataaa aagtggggta aatttgggtc    540
tttttttttaa agaatgtgaa ctactcattt cactttggtt agaacaaata tgagaagatt    600
tgctaatgac agcaaaatga atagaccaaa agcgtaacga atattaaaaa taaacaattc    660
cgaataactg gttactgaaa attgtggaac tctacatagc cgttgtgagt atggtattgt    720
ttgttcttgt gggcagaata actagttacg gaaaatttat gaatttgctt cacattattt    780
```

```
ttttcatttt cttttttgct tcaaaagata agtacaagtt tttatactct tatttcattg   840
cctataaata cctctattga gttactgctc attcacaact ctaaatagca atctttctta   900
ttattaaaat tcctatcctt ttttactcat tcagagaaac g                       941

SEQ ID NO: 119          moltype = DNA   length = 3013
FEATURE                 Location/Qualifiers
misc_feature            1..3013
                        note = Description of Artificial Sequence: Synthetic
                        polynucleotide
source                  1..3013
                        mol_type = other DNA
                        organism = synthetic construct
SEQUENCE: 119
tttaaaacgc caaaaaataa gggacggcca tggcgtagca atgactattg ttccgtaggt    60
catttgtgaa ggaccgacaa aattttaggc gatccgggtc cgattttcg gttctgctca    120
agaaaactcg atctgcacga atagcttata atcaaaccct ttttttttt tcaagaatgt    180
ctaattgatc ctaaaaagac aaccttatat gttccaccat ggcaggatcg gccttattac   240
taagggtttg ccaatagaca cgtttttaac attcaagtaa aaaaaacatt tattcttaat   300
aacccaccta ctatagtacg ttatttggca gtagactacg ttgtacattt gggaccattt   360
ggaacactcg tctttcacga gtcactaatt tttgtgttga atgcataaaa tttgtttttt   420
tcttttttcga aattgaacaa ttttatcttc gatcacacct atagtatatt attacccttat  480
tgttagaaaa tattttattt tattattgac tcctaataaa agtgggta aatttgggtc     540
tttttttaa agaatgtgaa ctactcattt cactttggtt agaacaaata tgagaagatt    600
tgctaatgac agcaaaatga atagaccaaa agcgtaacga atattaaaaa taaacaattc    660
cgaataactg gttactgaaa attgtggaac tctacatagc cgttgtgagt atggtattgt    720
ttgttcttgt gggcagaata actagttacg gaaaatttat gaatttgctt cacattattt    780
ttttcatttt cttttttgct tcaaaagata agtacaagtt tttatactct tatttcattg    840
cctataaata cctctattga gttactgctc attcacaact ctaaatagca atctttctta   900
ttattaaaat tcctatccta atttactcaa acagagaaac gatgtatccg ccaagcaaca    960
gctgcaacta cagccccatt tcaacatcc cttctccttg tatgcaatat ggagacgaac   1020
tattcttcca atattatcct gaccatttcc ttcaacagca acaagtgcct ttgataagg    1080
atcagagtgt tgcatctta gctgattgca ctgagaatgt tactaacgaa gaaactgtca   1140
tcaatactga tactgtaaaa gttctttatg acacaggagc tgttacaaac agtcagtgtt   1200
ggggaggaaa tgaagaagta gaagaaggcc gcgaaaacaa aagagaatgc atgagaagca   1260
ccattagtat tattcatgta cggaaaaaca agaaatgttc caataaagat cgacatagca   1320
agattaacac tgctcgtggc ctcagagacc gaaggatgag actttccctt gatgcagctc   1380
gcaagttttt cagtttacaa gacatgttgg ggttcgataa ggcaagtaaa actgtagaat   1440
ggttgcttat caaatcggag tctgaaatcg aagagctagc caaaggcaat aaaggaggag   1500
gcattcctaa acaaagctgc agtactacta atggaattgg tgcaattagt actgcaatat   1560
cctctatttc tgagtgtgag gttatatcag gaactgatga atctttctct attacttata   1620
aaaagaagct gaaaactgct aaaggagcct cgaaaaagac ggctaaaact gctcgtagag   1680
ctgcatttga tcgtcttatt acaagggaaa cgaggaatca agcaagggct agggctagag   1740
agagaacaaa aataaagaaa agcctcggta aatccaacga cagtgct gattactgta     1800
atttggtgga taattatgga gattggagtc aatttagtat cttcaactat cagaaaaatg   1860
cagttggaat ttcccatgat caggtgggtt caataattaa acaacatgat tttttaggat   1920
ttcaataggc tcgctcctg tgtaacatgg cataagcagt cttggcaatg atgctctttg   1980
ttgcctatgg tttgtctcca tttattcctc taatacccca taaaaataat aaaatataaa   2040
ttacatctac atgactggtt ttgaattatg ataatgaaca tgaagttaca cttcttatga   2100
tttttttcaag tacattgtgt tttgattacc gcataaatat ttaagcatgg tcatctttt    2160
tttgattcat ttgttgttag agtgactaat taatctgtag tatatgtctg gaggcttgag   2220
gaatctgaaa aaatgtgcgt gtttgcatag ttctttcaaa atagtatagg acaatatatt   2280
cttttaaaaa aaggagtccg gtgcacaaag catgtcgcat tgttccgagt aaaagctgca   2340
cccaaagagt gtgatgcaga caacctactc taatacaagc attaatgaac gcgttgctcc   2400
aaggctccgg ccccttcaat atatttcttt atgaaccgtg aatttattca tgtttaaaag   2460
ctttcttttca attccatctt ttctttttgtt ctaacatttg ttagtaaacg tgaatgaatg   2520
tagaggttca agctagagaa tgcaaaacag aaagcaatac attccctgga ttatgcatta   2580
ccaaaccacc atgcagaaaa gcttgtatca gtgagggatt tactgatggt cattgtagca   2640
aaatcctcag aaggtgccta tgcactaagc catgtgtgtt tgatgagaag atgatcaaaa   2700
caggagctga aacttttgct gaggaagcaa aactttggc tgcagctttg cttgaagaag   2760
agataatgga taactaatta gagattagag gaaaggatta attcagtgtc acacataata   2820
aagttgctgc ctttcttaaa aggatagcta atgtattggc ttttagtagc ctttgttacc   2880
ctaaaataag tgtgacatgt caatccttttt gatctagtac caagtttatg tatgttttaa   2940
tgaaaaatga tcttctatgg tcattgcaat cccattatat tccaagaaca aaacttcatt   3000
attttcttgg tcc                                                      3013

SEQ ID NO: 120          moltype = DNA   length = 120
FEATURE                 Location/Qualifiers
misc_feature            1..120
                        note = Description of Artificial Sequence: Synthetic
                        polynucleotide
source                  1..120
                        mol_type = other DNA
                        organism = synthetic construct
SEQUENCE: 120
tagcaatctt tcttattatt aaaattccta tcctttttta ctcattcaga gaaacgatgt    60
ctcgctcctt tgtttcatg gcatttgcag tcttggcaat gatgctcttt gttgcctatg   120

SEQ ID NO: 121          moltype = DNA   length = 5668
FEATURE                 Location/Qualifiers
```

| misc_feature | 1..5668 |
| | note = Description of Artificial Sequence: Synthetic polynucleotide |
| source | 1..5668 |
| | mol_type = other DNA |
| | organism = synthetic construct |

SEQUENCE: 121

```
tttaaaacgc caaaaaataa gggacggcca tggcgtagca atgactattg ttccgtaggt   60
catttgtgaa ggaccgacaa aattttaggc gatccgggtc cgattttcg gttctgtca   120
agaaaactcg atctgcacga atagcttata atcaaaccct tttttttttt tcaagaatgt  180
ctaattgatc ctaaaaagac aaccttatat gttccaccat ggcaggatcg gccttattac  240
taagggtttg ccaatagaca cgttttttaac attcaagtaa aaaaaacatt tattcttaat  300
aacccaccta ctatagtacg ttatttggca gtagactacg ttgtacattt gggaccattt  360
ggaacactcg tcttcacga gtcactaatt tttgtgttga atgcataaaa tttgttttt  420
tcttttcga aattgaacaa ttttatcttc gatcacacct atagtatatt attacctat   480
tgttagaaaa tattttattt tattattgac tcctaataaa aagtgggta aatttgggtc   540
ttttttttaa agaatgtgaa ctactcattt cactttggtt agaacaaata tgagaagatt   600
tgctaatgac agcaaaatga ataagaccaaa agcgtaacga atattaaaaa taaacaattc   660
cgaataactg gttactgaaa attgtggaac tctacatagc cgttgtgagt atggtattgt   720
ttgttcttgt gggcagaata actagttacg gaaaatttat gaatttgctt cacattattt   780
ttttcatttt ctttttttgct tcaaagata agtacaagtt tttatactct tatttcattg   840
cctataaata cctctattga gttactgctc attcacaact ctaaatagca atctttctta   900
ttattaaaat tcctatccta atttactcaa acagagaaac gtctaggagc aaaaaaaaaa   960
aaaaaaaaaa aaacaagtag tagtagtagt agtaaatgga aaaatagaga ggcaatttt  1020
tttagtatct tactttatcc attgcacttt aaaaaacata ggtttacatg ctctcattgt  1080
cacgccaggc cgctaattaa atggtacatt tcatccccc catttttgg cctcatagtt  1140
aattatcaca atttctgaaa gcaacatcag aacaacccca catttcttgt ggtcctaaa  1200
ttactgctag atagtccaaa cccatctgcc tatttagggc ttgtgaatga ggattgaaaa  1260
tggtagagaa tatttgcaaa ggcatcatgc atatatggaa aagactaaag agagagttag  1320
tgccttgcaa agcggattct cacagttgta gaaaaggact caccattttc aagaatactc  1380
ccggcatgaa gatggacaat ttaatataaa aaacaaagaa aatagtaatt aagtgcgttg  1440
agatgaatga aatttatccg ctcttaattg aatatgggga attgaaagaa atttctgata  1500
ataaattaat gagtcttaca tgacgtggat ccgacttaat ctagtctatt taaactaaga  1560
atagataaga atagagaata tagacaaaag agaggctcat tggctagggt ttcaagggag  1620
ttccttgaac ataagtggca agtacaagca caaagccaat ttccatggcc taaagatgaa  1680
taagatgtgt cgtgtggtat ggtgggaagg tgaggaggta tggggtaatt ggagatgcta  1740
aacctctcta aaagctcttt tgctccaaat atctaaatcc atctctatca cttttgcga   1800
ctgccccaaa atttgcaact tatgaattaa agtttttaata tttttaagtt aataaattct  1860
gaattaataa tttaacatat tcaataaact ttttaaaaca aattacgtat ataccatcaa  1920
actggctgca ccatgatcac tttctaaact cacaatgaca tatggattta atcaggcaca  1980
aagtcatgtt gatagaaaga gatagtacgg agaatgaaga aaaaggtag gggagagaga  2040
tggggtgagt ggggaaaaga tagggttctc ttttagtgaa aagcgacagg gtctgagaac  2100
cctaggtcaa aagttgcata aacctctata caggcttctt cactcccta ctactaatat  2160
actctcatta aggcttgagg tttaattcat taaaattgtg gtttaattat tgtatccct  2220
caaacgaaat aattgtcctt gtcgaggtta gacaatgttg cgtactattt tcaaacgcag  2280
tcagccatta ttctcctatc ctttacagtc gagattcaaa gacagaaagt agcatgcaag  2340
ctgttattaa tttactttga ttaggacttt gccaagaaaa tgaagaacct tttctttttt  2400
ctttttaattt agttatctta caacatgtaa tttttcctag caagcaaata cggtaacttt  2460
ttttttttatt ctcatttaat ttgttggagc tattgctact ttgatgactt caaccaaatc  2520
ctggttggta ggcggagggt gctgacgatg gaaactaccc ctcttgtcca aatacgataa  2580
cctaaaaaat agaataatag cttattgtac tgtgctgcaa aaattgcatt gtcagtatac  2640
ataattaaaa tctattttga atgtgtggag ggcaaagagg ggtgactggt ctagggttgt  2700
agaaatcagg tgggagagag aatggtattt gtctctgtgt cagctgatat cacgtgaaga  2760
ggcacaataa gaagtcctc gtatccatc acttcccaaa aataccggca ttactacaaa  2820
tatagtacta gcacttgctt tctctatccc catctttgct atttcctttc cctttccaac  2880
tttttggctt tagaattgca aagatggagg gaattgtggt tctttgtatc tgtaaaattt  2940
ttcctccaag ctccagttgt agctagctta atgcgtggac gcgcgcgcac acactagaaa  3000
tctgcaatct atatatatat tcacaaggca ctcacatatc aaaaaccaca tagacattgt  3060
atagagagag ctgtcgttct caagcagaaa aaatgatatg atttcatcag catgtggtca  3120
accaaatagt tcaattctag tctttgcttc ctctttctaa ttactgtata aatagagcca  3180
caaggacata gaattgagaa aataaaagac aataaaaaca aatctagcta cttaagcgaa  3240
tgatgatgac tctctctcag tagtcttaac tcttaatacc cttgttttcc ttcttgtgct  3300
gcagtttgat tggttaatta acctaatcaa aagatgtttt aactgtgttt tatccgtctt  3360
tctcaagatc tatcttagtc ccaccacata gctccctcaa gctacagctg caaaatatat  3420
actatatata tatataacaa atgtatccgt caagcaacag ctgtaattac agcctcaata  3480
tttcctcctc aaataactta tttcacattc catctccgaa ttctatgcaa tatgaacacg  3540
aacttttcca atattttcat gaccatcatc tccttcaacc caacaacaa caacaacaac  3600
aacaactctt gactacacct gatcattata ggcagcaga ttccaacaaa gacaccgtaa  3660
tcagtagtac taatcaagat cctgaagaag ttgaattaca aggccgctgc aagaacaaaa  3720
aaggtgacaa taagagacgt gttgcttaca agaagatag acacagcaag attaacactg  3780
ctcacggccc tagagaccga agaatgagac tttctctcga tgtagctcgc aaatttttca  3840
atttgcaaga cttgcttgga ttcgataagg ctagcaaaac tgtggagtgg ttgctaacaa  3900
agtccaaatg tgctgtcaat gagctcgtcc aaggcataaa taaagaaaat tgcgctactg  3960
ctaatattgg tgcaattagt acatgctcta ctacatcgta gtgtgaagtt gtatcaggaa  4020
ttgatgaatc tacaaccact aatgatattc agaagcagtc aaatagaggt aaagtagggg  4080
agaagaagaa ggctaataaa ctagttcgta gagctgcatt taatcctgtg gcaaaggaat  4140
caagaaagca agctagagcg agggcaaggg agagaacaaa aataaagaaa agcttttaa  4200
atattggtga tcagtctatg gcgggctgatg atttaaaacg attaggatgt tggagtcttt  4260
ttgaaacagg tgaagaatca ggtattcaag gtactaatca tcaaattgaa gaacacacca  4320
```

```
cgcaccacga ggagcctctt ttggggacta atgagaatgt tgatgattgt aatttggttg   4380
ttaccggcaa ctggaaccca tataccatct tcaattatca ccacagtact gaaatttctc   4440
acgaggtagg ttttacactt catttaaatc caagagtaat tctttagag ttcaagattc    4500
tgatatttt tttggtggcg agacccttc ttatatcaaa gcaacttca aggtacatac      4560
aagattggat aaaccaattc tgagctcgct ccttgtgtaa catggcataa gcagtcttgg   4620
caatgatgct ctttgttgcc tatggtttgt ctccatttat tcctctaata ccccataaaa   4680
ataataaaat ataaattaca tctacatgac tggttttgaa ttatgataat gaacatgaag   4740
ttacacttct tatgattttt tcaagtacat tgtgttttga ttaccgcata aatatttaag   4800
catggtcatc ttttttttga ttcatttgtt gttagagtga ctaattaatc tgtagtatat   4860
gtctggaggc ttgaggaatc tgaaaaaatg tgcgtgtttg catagttctt tcaaaatagt   4920
ataggacaat atattctttt aaaaaaagga gtccggtgca caaagcatgt cgcattgttc   4980
cgagtaaaag ctgcacccaa agagtgtgat gcagacaacc tactctaata caagcattaa   5040
tgaacgcgtt gctccaaggc tccggcccct tcaatatatt tctttatgaa ccgtgaatt   5100
attcatgttt aaaagctttc tttcaattcc atcttttctt ttgttctaac attttgttagt  5160
aaacgtgaat gaatgtagag gttcaagcta gagaatgcaa aacagaaagc aatacattcc   5220
ctggattatg cattaccaaa ccaccatgca gaaaagcttg tatcagtgag ggatttactg   5280
atggtcattg tagcaaaatc ctcagaaggt gcctatgcac taagccatgt gtgtttgatg   5340
agaagatgat caaaacagga gctgaaactt ttgctgagga agcaaaaact ttggctgcag   5400
ctttgcttga agaagagata atggataact aattagagat tagaggaaag gattaattca   5460
gtgtcacaca taatataagtt gctgccttc ttaaaaggat agctaatgta ttggcttta    5520
gtagcctttg ttaccctaaa ataagtgtga catgtcaatc cttttgatct agtaccaagt   5580
ttatgtatgt tttaatgaaa aatgatcttc tatggtcatt gcaatccat tatattccaa   5640
gaacaaaact tcattatttt cttggtcc                                      5668

SEQ ID NO: 122           moltype = DNA   length = 210
FEATURE                  Location/Qualifiers
misc_feature             1..210
                         note = Description of Artificial Sequence: Synthetic
                         polynucleotide
source                   1..210
                         mol_type = other DNA
                         organism = synthetic construct
SEQUENCE: 122
atgaattcaa agaaaaacaa ctcaccaaga aaaaggttga gaaaatatca tacaagaaaa    60
gctcctatta ttagctctta tatggacatg gctgaagcta gaagagaaat tgttcatgct  120
ttacaacttc atcgatcttc atcttcatct ccaactccgt ctattaatag cccaaagaag  180
tacacattat tgggtcaagg agttgtaagc                                    210

SEQ ID NO: 123           moltype = DNA   length = 1575
FEATURE                  Location/Qualifiers
misc_feature             1..1575
                         note = Description of Artificial Sequence: Synthetic
                         polynucleotide
source                   1..1575
                         mol_type = other DNA
                         organism = synthetic construct
SEQUENCE: 123
atgattggat acccaaaacg tttcaccttg catggccttt ggccggcaaa cagtactgga    60
tatagtctaa aatgtgctcc acctccagag ggtaccagcg tgtggacaac agacggacag  120
ttacggacag ctcttcaaaa atgttggtat agtctgatcc ggggtcgtcc caattacata  180
ctgtggaaac atgaatggaa ggattatggc tattgctcta gtcatacaat aaaagatact  240
gactacttct gggctgcagt acgaaagcat ggaagaaaca ccaagattgc gggcgatgcg  300
attgttaacg aattgagtga tgcagaaatc agtccgtcaa atgataagga aaggagatgc  360
gagactgaaa gcgatagcag ccatcactac caacattctg aacaccatca acgaagatgg  420
ctgggaagac gacgagaatg cgacaccaaa cggtactccc aggcaaagta tatcacctcc  480
cctcacgaaa gcgtgacggc ttcacgcgaa aagagagcat ccacatccac aattgaggaa  540
gcaccaccag cagtgaagaa actattatta gagtggctga caagcactat aaacaatata  600
ttcgacaaac ctgcccaaaa ggagaatggc aacaccgcac aagcagatat cgtaacaact  660
actggcgagc agcctcttcc tcggacaggt aacacttacc ccactatggc cgcagggct   720
aagaaggcgg aagccagggt gaacgacata ttcgctgtta ggcaatcgtc tggcgaggga  780
ctcagagact cctcgcccg atttaacagg gaagaaatcc acaatgccta ttgcgccaag  840
gagagagccg acgatgatga ccttaacggt ccaatccaac ggctgacatc ggttcaagaa  900
gaatcgagaa gtgatcatcg taatgatagt caaagggatc agtcgggccc ccgtctcagc  960
cgagaaagac atcaacacta cgtcagaaca accgtcctgc catctcctcg acacatggaa 1020
gggccgccca ggccgtacat agggacacag cgaaacgaaa gaggtatgcc tccactctta 1080
tccactcaca atttttgtgt ttctccttca aaaatagtgt acgcactaaa gaagctcggc 1140
acgatggtga aatgtccaca aaagatgaag tccggcccaa atactcagaa gttgaatgcc 1200
atttgtgaat ttcaccagga acgaggtcac aaaaccgagg attgcatagg tttgcgacaa 1260
gaggtagtga gaatgttaaa ccaagggaac ttgaaagaac tgatgagtga tcgcggacga 1320
gtcaactttg cccgtggacg cgaactaccc cagggacctc ctaagcctcc ctctccagct 1380
cgcactatcc aaatgatcat cggtggaggc gacgaagcta tgatcaacca tatgaagttc 1440
accaccacga taaattgaa acggtcgatg acccacgaac ggtacgacga tttcggagac 1500
agtatcatct tcgataagtc agataccgac ggtttgactt ttccttatt tgaagctatc 1560
gttattactt tatga                                                   1575

SEQ ID NO: 124           moltype = DNA   length = 1032
FEATURE                  Location/Qualifiers
misc_feature             1..1032
                         note = Description of Artificial Sequence: Synthetic
```

```
                        polynucleotide
source                  1..1032
                        mol_type = other DNA
                        organism = synthetic construct
SEQUENCE: 124
atgagttgcc agaacagtaa aacagaagaa acggccgacg agcaacacaa taccagcaaa    60
gaccctaaac acaaaccctt ctttgacgtt tacggccctc aggggagggc agatattgtt   120
ttcaatcaac cggaatccaa ttcaactttg aatcttcaag acgtgcaagg tcttgtcaca   180
tgggtgcttg ctgatgggtt catgccgtca tgggctttta tcaaaaacaa gcctttgatc   240
cctaaagtgg ttatgctgta tgttcctggc cttgatgccg ctctatattt gtcacagtct   300
aaagtgctca aaggtttcaa agaatgctgt ggtattccga ggccagtttt agctctgagc   360
tgtgtatcag atggaaatca gacaatagat gcactcctta cgtacaaatc aaagaggaaa   420
aggaaagaag ctgagcacat tcaccaata aacaccgagc cttctgaaca aggtgctgag    480
actcccacta tggagcctct atcttttgtt gacctcaaaa aggatatacc atttcccaaa   540
agttattaca cacttacgga taaggaacta gaagaaaatg gatactgtta tgaccaacca   600
gaatttcttt cgacgctccc tgctccttca ggaacatctc cacatgaaat tttggccctt   660
gactgcgaga tggttctgct ggataaattg gtcaaaccat caaacaacat tgttgactac   720
aatactaggt atagtggaat tacttgtcag atgttggagg atgtgactac cactcttaaa   780
gatatccagg aggagttctt gaaactggtt tacaaggaga ccattctggt tgggcattcc   840
ttggaaaatg atttgttagc cctgaagatc attcataatt tggtaataga tactgctgtg   900
ttgtacaaac atccaagagg atcctacaaa gctgctcttc gcgttctgag cagaaaattt   960
ctcggcaggg agatacagga ctcgggcaat gggcatgaca gcattgaaga tgcaaagcta  1020
cactggaact ag                                                      1032

SEQ ID NO: 125          moltype = DNA  length = 2172
FEATURE                 Location/Qualifiers
misc_feature            1..2172
                        note = Description of Artificial Sequence: Synthetic
                        polynucleotide
source                  1..2172
                        mol_type = other DNA
                        organism = synthetic construct
SEQUENCE: 125
atggcctcca cctcctacat caccttcaaa cccctttcaac aaactcaact caaactctat    60
tacttcactc actgcagtaa gcattcttca actctgtttc actcttcttt tcatactctc   120
cttttctgcac caacaaata cacactggaa ccaccaagaa ttttgccctc cattcaagtt   180
aaagcacatg tcactcactt ggaaacaaga ttgtcctttg aaccagagca agaaatatca   240
ggcagtagaa ctaataatga aaatagttct gggttttctt cctttagtcc caaagataag   300
atggttggca tgaaatcttc aagagaaaat ttagatggc actgtcaaac tttagatgaa   360
ttggtgcaat tgttcaagag cagtgcagaa gcttctaata caaaaagtgt gagaggcgaa   420
caggaagatc atggaattaa agtgagtgaa gaagtgaaac actatgcact taaatatggt   480
tttaagatat atgagaagat gcggtcagag aaggtacaaa tgaatgaagc aacccttaca   540
tctgttgcaa gaatggcaat ggcattggga aatggtgaca tgcatttga tgtggtaagg   600
ctaattaaag aatatggaat aaaccccgagg ctgcgatctt atggtcctgc cttatctgtt   660
ttctgcaata atggggatgt tgacaaggca tttatggttg aagaacacat gttggagcat   720
ggtgtctatc cagaggaacc cgaactggag gcacttttaa aagtaagtgt agaagctggt   780
aggagtgaga aggtgtacta tttgttgcat aagcttcgag aaggagttcg acaagtctca   840
ccttctactg cagatttgat tgagaagtgg ttcaacagca agatagcttc aagggttggg   900
aaaagaaaat gggatgaaag aaccatacgc gaagctatta aaaatggagg tggtgggtgg   960
catgacaag gctggttggg taatggtaaa tggactgtat cacacgcata tgttgactct  1020
gacggctgct gcaaatgctg tggtgagaag ctggtgaagc ttgatcttga tcctgttgaa  1080
actgaaaatt ttgccaagtc agttgcttct atagctgcgc agagagagag aaattcaagc  1140
ttccagaaat tcaaagatg gcttgactat tatggaccct tgaagctat tgttgatgga  1200
gcaaatgttg gcctttatag ccaagaaaaa tttaggccat ctagggtcaa tgctattgtc  1260
aacggaattc gccagatgct tccttgcaaa aagtggccgc tgatagtttc gcataataga  1320
cgtattactg gagataagat ggatgaacca ttcaatagag cgtactggct gtatgcagct  1380
ataaaattta agtgcttaat tgtgacgaat gatgaaatga gggaccatt gtttcaactt  1440
ctgggaaatg acttttttccc aaagtggaaa gaacggcatc aggtgcattt cagtttctct  1500
gaaacaggtc cagtacttca catgccgcct ccctgttctg ttgtaattca gtcatcggaa  1560
agatttggac cagacagaag gatatatcat ggacggagta gcagaacttt gaaagataaa  1620
gaactatcag ggtctcggga ttcaggatat cccaggttat cggattacaa tttcaatatc  1680
aatttgatga agttggtttc agttatgaga acatcaagg aagcaaggtt cccgaaacca  1740
attcgatcat actccagtca aaaggatcat tttaaaatta agcgtgtgtt ggttgatcca  1800
gtagttctg ccaatattat ccaactaagg tgcttagaac aagcaaagct aatcgaagtt  1860
ccgacaatga agcttctggc cgggttcaac ctaacaagcg taacgaccca aggagagatc  1920
gtgttgccta catatgctga aggggtacg aaatccacct tgttcaaagt gtggatggc   1980
gatatggct acaatgtaat tatcggtagg ccatggatcc acaaaataaa agttgtgcca  2040
tcaacttatg atcaatttct aaattttcct acatcagacg ggattaagca gattagaggt  2100
gatcaacctg ctgcaaggga aatgaatgtt gtcacctttt ctagcagtaa tgcggaggaa  2160
atcaacaaat ag                                                     2172

SEQ ID NO: 126          moltype = DNA  length = 468
FEATURE                 Location/Qualifiers
misc_feature            1..468
                        note = Description of Artificial Sequence: Synthetic
                        polynucleotide
source                  1..468
                        mol_type = other DNA
                        organism = synthetic construct
```

```
SEQUENCE: 126
atgcagtcgc cggaatcttg cgtcatagtg agttgcccaa ctactctaat agccgacgaa   60
gatgaagagg tggcagatat ggagacatct gttaaggcag tggaggaaat cttgaattac  120
aaattcatta aaccaaaact tcttgaagaa gcccttacgc actcttcttg cattgattct  180
gtttcttatc agcgccttga gttcgttgga gagcaggcag agttccatgg aggagcaatg  240
aaggcgccga aggttcttgc tgatattgtg gagtctgtgg cggcagctgt atatgtggat  300
tgtggctttg atctgaagaa tctctggctg cttcttctga gaacaaagaa aatgctaact  360
tcacgctgca aggctgcact ccaaaagtta gcttttaaat ctattggtaa gacggatctg  420
aagttgaacc aaatacagag attgatgggg caagcaaaag ctgcatga                468

SEQ ID NO: 127        moltype = DNA  length = 705
FEATURE               Location/Qualifiers
misc_feature          1..705
                      note = Description of Artificial Sequence: Synthetic
                      polynucleotide
source                1..705
                      mol_type = other DNA
                      organism = synthetic construct
SEQUENCE: 127
atgaaacctc aaaaatcatt gttgatcaag gttcttatta cacaatgttt gttagttctt   60
tgtgttgcac aacaggactt tgatttcttc tactttgttc aacagtggcc agcatcttat  120
tgtgataacaa gacgtagttg ttgttatccg actaccggaa aacctgatga agattttagc  180
atccatggtc tatggccaaa ctatgaaaat ggtaaatggc ctcaaaactg tgatcgtgaa  240
agctctttgg atgagtcaaa gatctcagat cttataagta caatgaaaaa gaattggcca  300
tcattggctt gcccaagtag cgatggtgta agattttgga gtcatgaatg gctaaaacat  360
ggaacctgtt ctgctcttgg tgaacgtgct tactttcaag ctgctcttgg cttcaggaaa  420
aaatcaaacc ttcttgaaaa ccttaagaat gcagggatta caccaaggaa tggagaacat  480
tacactttag aaagcattaa aaaggcaata gaagaaggag taggacacag cccttacata  540
gaatgcaatg tggatacaca aggaaatcac cagatttacc aagtttatct ctgtatggac  600
aaaactgcaa cagattttat tgattgccca gttttcccac atggccgagg atgtggttcc  660
aagattgaat tccctccttt ctcctctgac catgatgaat tttaa                   705

SEQ ID NO: 128        moltype = DNA  length = 654
FEATURE               Location/Qualifiers
misc_feature          1..654
                      note = Description of Artificial Sequence: Synthetic
                      polynucleotide
source                1..654
                      mol_type = other DNA
                      organism = synthetic construct
SEQUENCE: 128
atggcaacta gaagacgaga ggctgacttt gatttcttct actttgttca acagtggccg   60
gcatcttatt gtgacacaag gcgtagttgc tgctatccaa caacgggaaa accagatgaa  120
gattttagca tccatggtct atggccaaac tatgaaaatg gcaaatggcc tcaaaactgc  180
gatcgtgaaa gctctttgga tgaatcagag atctcagatc ttataagtac aatgaaaaag  240
aattggccat cgttggcttg cccaagtagt gatggtgtaa gattttggag tcatgaatgg  300
ctaaaacatg ggacctgttc agctcttggc gaacgtgctt actttcaagc tgctcttgac  360
ttcaggaaga aatccaacct tcttgaaaac cttaagaatg caggattaa tccaaggaat  420
ggagaacatt acactttaga aagcattaaa aaggcaatag aagaaggagt aggacacagc  480
ccttatatag aatgcaatgt ggatacacaa ggaaaccacc agatttacca gtttatctg  540
tgtgtggaca aaactgcaac agattttatt gattgcccag ttttccctcg gggccgagga  600
tgtggttcca agattgaatt ccctcctttc tcctctgacc atgatgaatt taa          654

SEQ ID NO: 129        moltype = DNA  length = 483
FEATURE               Location/Qualifiers
misc_feature          1..483
                      note = Description of Artificial Sequence: Synthetic
                      polynucleotide
source                1..483
                      mol_type = other DNA
                      organism = synthetic construct
SEQUENCE: 129
atgggtgtca ctacctataa ccaagaggtc acaacactag ttgccccaac taggttattc   60
aaagctttgg ttcttgattc tgaaaacctt gtcccaaaat tgatgccaca agttgttaag  120
aacattgaga ttgtagtggg tgatggtgat gcaggaagca tcaagaagat gaactttgtt  180
gaaggttctc ctatcaagta cttgaagcac aagatccatg ttattgatga caagaacttg  240
gtaaccaagt attcactgat cgaaggagat gtttttaggtg ataaactgga gttcgttacc  300
tatgatatca aattcgaagc ttcaggaaat ggaggatgta tttgcaagac ttcaactgag  360
taccacactg agggtgatta tgtgtttaaa gaagaagaac actatgaggg caaaaagcaa  420
gccatggaac ttttcaagac tgttgaagat tacctcctcg caaatcctcc cgtctatgtt  480
tga                                                                 483

SEQ ID NO: 130        moltype = DNA  length = 483
FEATURE               Location/Qualifiers
misc_feature          1..483
                      note = Description of Artificial Sequence: Synthetic
                      polynucleotide
source                1..483
                      mol_type = other DNA
```

```
                        organism = synthetic construct
SEQUENCE: 130
atgggtgttg caattttttac ccaagaattt acatccccta tagcaccaat tcgtttgttt     60
aaagctctaa ttgtggactc aaagtccctc atacccaaac tcttgcctca atttgttgag    120
agtgttgatt tgttacaagg agatggtgga gctggaagta tcgaacaagt gaacttcaca    180
aaaggtagtc cttttgagtt tgtgaaacat agaatagatg aactagataa agaaaatatg    240
gtgtgcaaat acactatgat tgaagggggat gcattggcag ataagtttga ctctatttct    300
tatgaagtaa aatttgaaga gtccaataat ggtggctgta tttgcaagat gacaactgag    360
tatattggaa ttggtgattt tatcgtcaaa gaagaagata tcaaggctgg aaagatagt    420
gcaattggca tatataaagc tgtggaatct cacctccttc aaaatccaaa cctttatgcg    480
taa                                                                  483

SEQ ID NO: 131              moltype = DNA  length = 483
FEATURE                     Location/Qualifiers
misc_feature                1..483
                            note = Description of Artificial Sequence: Synthetic
                             polynucleotide
source                      1..483
                            mol_type = other DNA
                            organism = synthetic construct
SEQUENCE: 131
atgggtgtca ctacctatac tcatgaggtc acaacatcag ttgccccaac taggttattc     60
aaagctattg ttcttgattc tgaaaacctt gtcccaaaat tgatgccaaa agtagttaag    120
aacattgaga ttattgaggg tgatggtggt gctggaagca tcaagaagat gaactttgtt    180
gaaggttctc ctaacaagta cttgaagcac aagatccatg ttattgacga caagaacttg    240
gtgaccaaat attcactgat cgaaggagta gttttaggag acaaaactgag gttcgttact    300
tatgagatca aattcgaagc atctggaaat ggaggatgta tttgcaaaac ttcaactgag    360
taccacacaa agggtgacta tgtatttaaa gaagaagaac acaatgaagg caaaaatcaa    420
gctatggaac ttttcaagac tgttgaagat tacctcctcg ccaatccttc ggtctatgtt    480
taa                                                                  483

SEQ ID NO: 132              moltype = DNA  length = 483
FEATURE                     Location/Qualifiers
misc_feature                1..483
                            note = Description of Artificial Sequence: Synthetic
                             polynucleotide
source                      1..483
                            mol_type = other DNA
                            organism = synthetic construct
SEQUENCE: 132
atggctatca cttccttcac tgatgagtac acttgtccta ttcctccatc aagaatcttt     60
aaagcctcca ttattgattc tcacaatttg atgccaaagc taatgccaca agctattaaa    120
agtattgaat ttgttcaggg taatggaggt gctggaagta ttaagcaaat caactttcct    180
gaaggtggca atttttaagtc cattaagtat aggattgatg agcttaatga agagaaattt    240
gtttacaaat acactttgat tgaaggtgat gccttggttg ataaactcga aaaaataact    300
tacgaggtga agtttgagca gtcagcagat ggtggttcta tctctaaggt gacaagcaca    360
tattatacgg agggcgattt caagctcaag gaagaagaaa ttaaagcagg caaagagaaa    420
gtcttaggaa tgtataaagc agtagaagtc tatctcctgc agaatcctga tgcatatgct    480
taa                                                                  483

SEQ ID NO: 133              moltype = DNA  length = 690
FEATURE                     Location/Qualifiers
misc_feature                1..690
                            note = Description of Artificial Sequence: Synthetic
                             polynucleotide
source                      1..690
                            mol_type = other DNA
                            organism = synthetic construct
SEQUENCE: 133
atggcttcaa attcggccac ttctctgttc ttgacactat ttcttattat acagtgttta     60
tcactcctta ctgctgctca agattttgac tttttctact tgttcaaca gtggccaggg    120
tcttactgtg acactaaaca aagttgttgc taccccaaaa ctggaaaacc agcatcagat    180
tttggaatcc atggactttg gcctaataac aatgatggct cttacccatc aaactgtgat    240
tctaacagtc cttatgatca atctcaggtt tctgacttaa tcagcagaat gcaacaaaat    300
tggccaactc tagcatgccc aagtggtact ggctcagcat tttggtcaca tgaatgggaa    360
aaacatggca cttgttctga atctatttt gaccaacatg gctatttcaa gaaagctctt    420
gatctcaaaa atcaaattaa tcttttggaa attcttcagg gtgctggaat taaccctgat    480
ggcggattt atagcttgaa cagcattaaa aatgcgatta acagcgcaat tgggtatact    540
cctggaatcg aatgtaatgt agacgagtcg ggtaatagcc agttatacca ggtttatatt    600
tgtgtcgatg gctcgggttc aaatctcatc gaatgccctg ttttctag gggaaaatgt    660
ggctccagca ttgagttccc aacatttaa                                      690

SEQ ID NO: 134              moltype = DNA  length = 690
FEATURE                     Location/Qualifiers
misc_feature                1..690
                            note = Description of Artificial Sequence: Synthetic
                             polynucleotide
source                      1..690
                            mol_type = other DNA
```

```
                         organism = synthetic construct
SEQUENCE: 134
atggcttcca attcagccac ttctcggttc ttgacactat ttcttattac gcagtgttta    60
tcagtcctca ctgctgctca agattttgac tttttctact ttgttcaaca gtggccagga   120
tcatactgtg atactaaaca aagttgttgt taccccaaaa ctggaaaacc agcatcagat   180
tttggaatcc atggactttg gccaaataat aatgatggct cttacccatc aaactgtgat   240
tctaacagtc cttatgatca atctcaggtt tctgacttaa ttagcagaat gcaacaaaat   300
tggccaactc tggcatgccc aagtgatact ggctcagcat tttggtcaca tgaatgggaa   360
aaacatggca cttgtgcaga aaatgttttt gaccaacagt gttatttcaa gaaagcactt   420
gatctcaaaa atcaaattaa tcttttggaa attcttcagg gtgctggaat taaccctgat   480
ggtggatttt atagcttgaa caatattaaa aatgcgatta gaagcgcggt tggttatact   540
cctgaaattg aatgtaatgt agacgagtct ggtaatagcc agttatacca ggtttatatt   600
tgtgtcgatg gctcgggttc agatctcatc gaatgccctg tttttcctag aggaaaatgt   660
ggctcgagca ttgagttccc aacattctaa                                    690

SEQ ID NO: 135            moltype = DNA   length = 723
FEATURE                   Location/Qualifiers
misc_feature              1..723
                          note = Description of Artificial Sequence: Synthetic
                          polynucleotide
source                    1..723
                          mol_type = other DNA
                          organism = synthetic construct
SEQUENCE: 135
atgaggtcca tccaacttgt tttggtcaag cttgttatct ttcaatgtat catgttatta    60
catgctcagg attttgattt cttctacttt gctcaacagt ggaatccagc atcatgtgac   120
agcaagataa aatgttgcta cccaacaaat ggaaaaccag cacaagattt tggtattcat   180
gggctctggc caaattacaa caatggctca ttttccaaaaa gctgtaacaa aaatgcccgt   240
tatgatgaaa cgcagatttc ggacttgata agtagtatgc agaagaattg ccgacacta    300
tcttgtccat caaacaatgg aacaaggttt tggtctcagta aatggaagaa acatggtact   360
tgttctcttt ctatgctaga tatgcattct tatttccaag ctgctcttgc cttgaaggaa   420
aaggtgaacc tgcttcaatt tctcaataat gcaggtatta aaccagatgg aggatttac    480
agctatgaag caatgaaaga agcaatagaa aaggcattg acatactgt tggtgtagaa    540
tgcaatatgg atttatttgg gaatcgccag cttttttgagg tttatgtgtg tgttgataaa   600
tgtggttcgg aaatcattga ctgcccaatt gtcccagaaa gtaagagatg caaagaaagt   660
attgaatttg ctgtcttcga atcagaaagt ctccttgatg agaaatctgc ctattcactc   720
tag                                                                 723

SEQ ID NO: 136            moltype = DNA   length = 798
FEATURE                   Location/Qualifiers
misc_feature              1..798
                          note = Description of Artificial Sequence: Synthetic
                          polynucleotide
source                    1..798
                          mol_type = other DNA
                          organism = synthetic construct
SEQUENCE: 136
atgagatcca tcaagtttgt cttggtcaag ctcgttatct ttcaatgtat aacgttatta    60
gtacatgcta aggacttaga tttctaccgc cttaccctac agcagtggaa tccagcagca   120
tgctacaata ggattatagg taaatgctgt aacacaacca cgggaagacc agcagaagat   180
tttggtattg ctggactatg gccatcttac aacaatctca catatccaga aaactgtaat   240
aaggcaggcc cttatgatga aacgcaagta agttttgata aaatacagat ctcggacttg   300
ctgagtagta tgcaaaagaa ttggcccaaa atatccttgtc catcaaacaa tggaactagt   360
ctgtgggcta aggaatggaa ggaacgtggt acttgttcta ggctcaacat gcattcttat   420
ttcgaaacag ctcttgatct taaggaaaag tgaacctga ttcaagatgt taagcgttac    480
ggtacagatc ttacacatgt gcatatgcat ggactcgaac caaatggaca attttaccac   540
tggcgtcaca tcaatgcagc cataaaatta gctattggac atgtgatcgc tatagaatgc   600
aatcttggtt taactgcgga cagccagttt tacagggttc acatatgtgt tgataaatct   660
ggttcggact tcattgactg cccaattaac ctcaccgaaa tctctgagac aacatgttct   720
tcatctacta aatggtctgg ctacgataca gatagtgtcc ttgaagagcg atctgcctat   780
tcttgggcaa ggaaataa                                                 798

SEQ ID NO: 137            moltype = DNA   length = 1482
FEATURE                   Location/Qualifiers
misc_feature              1..1482
                          note = Description of Artificial Sequence: Synthetic
                          polynucleotide
source                    1..1482
                          mol_type = other DNA
                          organism = synthetic construct
SEQUENCE: 137
atggggtcct ttagttttgc agtatgtgtt agcttaatgt tgctggttat ggtggttgct    60
attcctttg aacccaaaaa tggcagaagg atagggcggc tgcaccgctg gtgggacccc   120
ttaatacgat cgccggtaga tcgtgatgat gaggtggaag acagcaatag tgttcgttgg   180
gcagttcttg ttgctggttc aaatggatac ggaaattatc ggcatcaggc agatgtatgt   240
catgcttacc agatttttgaa aagaggagga ttgaaagatg agaacatagt tgtattcatg   300
tatgatgaca ttgccaaaag tgagctgaat ccaggcctg gagtcataat caatcatcca   360
aatggcagtg atgtctatgc tggtgtgcca aaggactaca ctggtgagca tgtcactgct   420
gcgaatctgt atgctgtgct tcttggtgat aagagtgctg tgaaaggtgg aagtgggaag   480
```

```
gtcatcgata gtaaaccgaa tgacagaata tttctctatt actctgatca tggtggtcca    540
ggggtcctcg ggatgccaaa catgcctttt ctttatgcca aagatttat tgaggccttg    600
aaaaagaagc atgcagcagg gacctacaaa gaaatggtcc tctacattga agcttgtgag    660
agcgggagtg tttttgaggg tatgatgcct gaagacttga acatttatgt gacaacagca    720
tcaaatgccg acgagagcag ctgggggacg tattgcccga gaatggatcc tccacctcca    780
ccagaatata tcacatgttt gggagacttg tatagtgttg catggatgga ggatagtgag    840
tctcacaacc tgaagaagga aacaataaaa caacagtacg agaaggtgaa ggaaagaact    900
tccaacttca acaactataa tgctggatct catgttatgg aatatggaag caaagaaatt    960
aagccagaga aagtatatct gtaccaagga tttgatcctg ccactgcgaa tcttcctgga   1020
aacaagattg attttgcgca cttggaggtt gtcaaccaga gggatgctga tcttctcttc   1080
ttatgggaga gatacaagaa gctagcagac aattcattgg agaaggccaa gcttcggaaa   1140
gagataacgg acacaatgct gcatagacaa catctagacg ggagcgtaga tgcaattgga   1200
gtctttctt tcggcccaac aaaggggtct tctgttctca actctgttag aaaacctggt   1260
ttacctctcg ttgatgattg ggattgccta aaatgcatgc acg ttcgcctttt cgagctacat   1320
tgtggctcgc taacacaata cgggatgaag cacatgagag catttgcaaa catttgcaac   1380
aatggagtgt ctagagatgc tatggaggaa gcttttatgg ctgcttgcaa tgagcataag   1440
atagaggagt atatcgctgc caaccggggc ttcagcgctt ga                      1482

SEQ ID NO: 138           moltype = DNA   length = 1485
FEATURE                  Location/Qualifiers
misc_feature             1..1485
                         note = Description of Artificial Sequence: Synthetic
                          polynucleotide
source                   1..1485
                         mol_type = other DNA
                         organism = synthetic construct
SEQUENCE: 138
atggggtcct ttagttttgc agtatgtgta agcttaatgt tgctggttat ggtcgttgct     60
attccttttg aattacccaa aaatggcaga aggatagggc ggctgcaccg ctggtgggac    120
cccttaatac gatcgccggt aagatcgtgat gatgagtctg aagacaagga cggtgttgtc    180
tgggcagttc tcgtggctgg ttctaatgga tacggaaatt atcggcatca ggcagatgta    240
tgtcatgctt accagatttt gaaaagagga ggattgaaag atgagaacat agttgtattc    300
atgtatgatg acattgccaa gagtgagcta atccaagac ccggagtcat aatcaaccat    360
ccaaacgta gtgatgtcta tgcctggtgtg ccgaaggatt acactggcga gcatgtcact    420
gcggcgaact tgtatgccgt gcttcttggt gataagagtg ctgtgaaagg tggaagtggg    480
aagatcgtcg atagtaaacc aaatgacaga atatttctct attactctga tcatggtggt    540
ccagggggtgc tcgggatgcc gaacatgcct tttctttatg ccaaagatt tattgaggtc    600
ttgaaaaaga aacatgcagc agggacctac aagaaatgg tcctctacat tgaagcttgt    660
gagagcggga gtgtttttga gggtatgatg cctgaacaga tgaacattta tgtgacaaca    720
gcatcaaatg ccgaagagag cagctggggg acgtattgcc caggaatgga tcctccacct    780
ccaccggaat atatcacatg tttgggagac ttatatagtg ttgcatggat ggaggatagt    840
gagtctcata acctgaagaa ggaaacaata aaacaacagt acgagaaggt gaaggaaaga    900
acttccaact tcaacaacta taatgctgga tctcatgtta tggaatatgg aagcaaagaa    960
attaagccag aaaaagttta tttgtaccaa ggatttgatc ctgccaccgc gaatcttcct   1020
gcaaacaaga ttgcttttgc gcacgtggag gttgtcaacc agagggatgc tgatcttctc   1080
ttcttatggg agagatacaa gaagctagca gacaattcat tggagaaggc caagcttcgg   1140
aaagagataa cggacacaat gctgcataga aaacatctag gagcgtcaatt              1200
ggagtctttc ttttcggccc aacaaagggt tcttctgttc tcaactctgt tagagaacct   1260
ggtttacctc tcgttgatga ttgggattgc ctaaaatcga cggttcgcct tttcgagcta   1320
cattgtggtt ctctaacaca atacgggatg aagcacatga gagcatttgc aaacatttgc   1380
aacaatggag tgtcgagaga tgctatggag gaagcttta tggctgcttg caatgagcgt   1440
aagagagagg agtataccgc tgccaaccgg ggcttcagtg cttga                   1485

SEQ ID NO: 139           moltype = DNA   length = 2307
FEATURE                  Location/Qualifiers
misc_feature             1..2307
                         note = Description of Artificial Sequence: Synthetic
                          polynucleotide
source                   1..2307
                         mol_type = other DNA
                         organism = synthetic construct
SEQUENCE: 139
atgtacgatg atattgctaa caatagcgag aaccccagac ctggagtcct catcaataac     60
ccacacggtc aagatgttta tcaaggtgtt cctaaggatt atgtgggtga agatgttaat    120
gctgacaatt ttttcaatgt tatacttgcc aacaaaagtg gtatcactag gggtagtggg    180
aaaattttgg acagtggccc aaatgacaat attttcatct attatactga tcatggtggc    240
cctgaaattg tctcaatgcc aactggaatt gtctatgcga acgatctgat taacgtgttg    300
gaaaagaagc atgcttctgg gacatatagt aaaatggtat tttacttgga agcttgtgag    360
tcgggaagca tgtttgatgg tcttcttccc gaaggtctaa atatctatgt cacgactgca    420
tcaaaaccag atgaaaacag ttggggaacg tattgtggtt gggtcgtgg tgcttgttta    480
gttgagtgtc ctcctcccga gtttgacggt gtttgcttgg gagacttgta cagtgtgct    540
tggatgaaag acagtgatgt ccaagatcga caaacttcaa cgttggataa ccagtatgac    600
aggattgcat gcagaactgc agccaaccta acatatggtt cccatgtcat gcaatatggt    660
gatatggtga taagtgttga tgctcttttc cagtatatgg gttctgtttc cacaagccat    720
agtcaagctc ccagtcccat ggcagctgct cccagtccca tggatgccgc gtcattcttg    780
acatcctcag aaaatgtgaa ccaacgtgac actgaactttt tctacttgac atccaaatac    840
caaggtgctc ctgaaggcac taacgaggaa tttgcagctg atcggaagct taatgaggtt    900
gtagcacaaa gaagtcaagt ggataacaac gtaaaacgtc ttggagagct tctgtttgga    960
gtcgaaaaag gtaatgaggc gctgcagagt gttcgacctg ctggacaacc acttgttgac   1020
```

```
gattgggatt gccttaaatc ctatgtcaag acattcgagg cacactgtgg aaaattaacc   1080
gcgtacggga agaaacatgt acgtggtatc gccaacatat gcaatgctgg aattgagagt   1140
gaggagatgg ttgatgcaac tgcacaagca tgttcagccg cctctgaaat cggccctaac   1200
tctcctactt ttactcaaac tgattttatt ttacctcctt ctcacccact ctatcttcat   1260
ccttctgaca atcctgaccc cgatatttca caaagtgtta tatactctaa gtctgctaag   1320
agactatggg ataaaattga accaaaggta tgggcaagca aatggtgcta agatgtatga   1380
gttcaaaaag acctaagcac tatatttcaa ggttcttctg atgtaggaag ttatttcact   1440
agggttaaaa gactccagga tgaaatggag tcacttgatg ctgattcctt ttgtgtttgc   1500
gaatgcaaat gtggaggtaa acacaaaatg atcaaaagga tggaaaatca gaaattgatg   1560
cagttttttga tgggtttgaa tgaggagaga ggatatgatc caaaaatgcc atattgtaga   1620
tattgtaaaa agccaggaca tgtaattgag aagtgctata agttacatgg atttccacga   1680
ccttcaaaat cagggaacaa gaatatccga gttgctgcac atgtccattc atcttctgat   1740
gctaagccta acaggtctta tgacaataac atcaatattg ccaacaccat catacctgat   1800
caatacaagc agcacatgac tatccttcaa catattcaag ttggttctaa tgattctcaa   1860
agccaatttg ccacagctaa ttttgcaggt attttttgctt catctgccca tctgatgagt   1920
tgtggtaatt gtacttgttt aagtagtgtt ctaacttctg aaacctggat actagattct   1980
ggaacatcag ttcacatgac atttaacaaa tattcgctta caaatataac aactttatat   2040
gttccctacc tcatcacatt acccaatggg tataaagtca aagtgaccac aattggttct   2100
gtcaaattaa actcttcagt cattttgtcc aaggtgctat atgtgcctac ttttaaatac   2160
aatctcattt tagtccataa gttattagtt gatactttat cattgctatg tttttctcaa   2220
catgcatgtt ttctactaca tggcccttct ctgaggatgc cattgatact tggtaagtgt   2280
cacaacccaa aatctcaccc atcgtga                                       2307

SEQ ID NO: 140          moltype = DNA  length = 1374
FEATURE                 Location/Qualifiers
misc_feature            1..1374
                        note = Description of Artificial Sequence: Synthetic
                        polynucleotide
source                  1..1374
                        mol_type = other DNA
                        organism = synthetic construct
SEQUENCE: 140
atggttcaaa aaaatggtgt tgtttcattc ctagttgtac ttttttgtcat agtttgtact   60
gctgagggtc gtaacttgtt ggagagtatt gttgaagatg ataatgcgac tggaactaaa   120
tgggctgtgt tggtagctgg atcaaatgag tgggataatt acagacacca ggcggatgta   180
tgccatgcat atcaactact gaagaaagga ggtctaaaag atgaaaacat catcgtattc   240
atgtacgacg atattgctta taataaaaac aaccctagac ctggagtcat catcaatagc   300
ccccacggcc atgatgttta taaggagtcc ccaaggatt acacaggaaa agattgtaat   360
gctgataact ttttcgctgt tatcctggga aacaagagtg ctctaactgg gggcagtgga   420
aaagttgtgg aaaatggtcc aaatgattat atatttatct actacgctga ccacggtgct   480
cctgccctta ttggtatgcc tagtggagat gatgtctatg ccgacgatct gatcaaagtc   540
ctgattaaaa acacactttt gggatatat tccaaattgg tatttacat ggaagcttgt   600
gagtctgaaa gtatgtttga tggtcttctc ccaaaaggtt tgaacatttca cgtaacaaca   660
gcatcaaagc ctgatgaggg cagttgggct acatactgta tttctttagg tgatgaagat   720
gtagtctgct taggagactt gtacagtgtt gcttggttgg aggatagtga tttgcacgat   780
cggcaagttg aaactttgga gaacagtat cagctggttc gtaagagaac tctaaataat   840
ggtacagtcg aaggctccca tgtcatgcaa tatggtgatt tacatataag tgaggatcct   900
cttttcagat atatgggttc taattctgca aaaaatagtt actatagtac ttctaccaac   960
gatgagtcat ggctaccctc aaggactgtt aatcagcgcg atgttcatct catgcactta   1020
tggtctaagt tccggtctgc tcctgaaggc tctgctagaa aaactgaagc tcaaaggcaa   1080
ttaagggaag ctatatcaca aagagaacac gtagacacac ggtgagaca tattggagaa   1140
gttttgtttg gagttgagaa aggtcccgag gtgctgcaga ctgttcgacc tgctggacaa   1200
cccctcgttg atgattggga ctgccttaaa tcctttgtca agatatttga gtcacaatgt   1260
ggaaagctaa ctccctacgg aaggaaacac gttcgtggct ttgctaacct gtgcaatgct   1320
ggaattcgaa gggagcaaat ggctgcagca gctaaacaag catgtccttc ttaa        1374

SEQ ID NO: 141          moltype = DNA  length = 1080
FEATURE                 Location/Qualifiers
misc_feature            1..1080
                        note = Description of Artificial Sequence: Synthetic
                        polynucleotide
source                  1..1080
                        mol_type = other DNA
                        organism = synthetic construct
SEQUENCE: 141
atgattcgaa aaaatggtgt tgtgccattc ctagttgcac ttttttgtcct agtttgtact   60
gctgagggtc gtaacttgct ggagagtatt gttgaagatg ataatccgac tggaactaaa   120
tgggctgtgt tggtagctgg atcaaatgag tgggataatt acagacacca ggcggatgta   180
tgtcatgcat atcaactact gaagaaagga ggtctaaaag atgaaaacat catcgtattc   240
atgtacgacg atattgctta taataaaaac aaccccagac ctggaattat catcaatagc   300
ccccacggcc atgatgttta taggagtac ccaagtggga aggttgtgga aaatggtcca   360
aatgattata tctttatcta ctacgctgat catggtgctc ctggccttat tggtatgcct   420
agtggagatg ttgtctatgc cgacgatctg aacagagtcc tgattaaaaa acacactttt   480
ggaacatatt caaaattggt attttacatg aagcttgat atctggaag tatgtttgat   540
ggtttactcc cgaaaggttt aaacatatac gtaacagcag catcaaagcc tgatgagagc   600
agttgggcta cctactgtat tcgtttaggt gatgaagatc aatgcttagg agacttgtac   660
agtgtttctt ggtggagga tagtgatttg cacgatcggc aagttgaaac tttggagaag   720
cagtatcagc tggttcgtaa gagaactcta aacaatggta cagaagaagg ctcccatgtc   780
atgcaatatg tgatttaca tattagtgag gatcctcttt tcagaatatg ggttctaatt   840
```

```
ctgcaaaaaa tagttataat acttcataac aacgacgagt catggctacc ctcaaggact  900
gttaaccagc gcgatgttca tctcatgcat ttatggtcta aggtcaagat atttgagtca  960
caatgtggaa cgttaactcc ctacggaagg aaacacgttc gtggctttgc taacttgtgc 1020
aatgctggaa ttcgaaggga gcaaatggct gcagcagcta acaagcatg tcctccttaa 1080

SEQ ID NO: 142         moltype = DNA   length = 1062
FEATURE                Location/Qualifiers
misc_feature           1..1062
                       note = Description of Artificial Sequence: Synthetic
                         polynucleotide
source                 1..1062
                       mol_type = other DNA
                       organism = synthetic construct
SEQUENCE: 142
atgataccgg caagaatggc tgatgtatgt cacgcttacc aattactaaa ggatggaggt   60
ctaaaagatg aaaacatcat cgtattcatg tacgatgata ttgctaataa tagggagaac  120
cccagacctg gagtcattat caataaccca catggccatg atgtttacaa aggtgtcccc  180
aaggattatg tgcttgaaga tgttaatgct aacaacttt acaatgttat ccttggaaac  240
aaaagcgctg tagttggggg cagtgggaaa gtagtgaaca gtggtccaaa tgaccatatc  300
ttcatctatt atactgatca tggtggcccct ggtgtggttt cgatgccaag tggagaagat  360
gtttacgcta atgatctgat tgatatgttg aaaaagaagc atgcttcagg gacatatgac  420
agactgttgt tttacttaga agctctgtgag tccggaagca tgtttgatgg tcttcttcct  480
gaaggtctag acatatatgt catgactgca tcagaaccta atgaagatag ttgggcgacg  540
tattgtggtg agggtactcc tgatgatccc tgcttggttg agtgtccccc tcccgagttt  600
cagggtgtgt gcttgggaga tttgtacagt gttgcttgga tggaagatag cacaattgat  660
agacttctt tcttacacc acacgatttc tattcatttt ttctgaatg tttgcagcac  720
caaaatgccc ctgaaggctc tgatgagaaa ttcaaagctc atgcgagact tactgaagct  780
atatcacaga gaactcaagt ggacaacaat gtaaaacatc ttgggagct tctttttggt  840
gttgaaaaag gtaatgagat actacacagt gttcgacctg ctggacaacc acttgttgac  900
agctgggatt gccttaagtc ctacgtcaag atatttgagg cacattgtgg aagattaacc  960
tcgtatggaa agaaacacat acgtggtata gccaacatct gcaacgctgg aattgcgagt 1020
gaacaaatgg ctgctacatc tgcacaagca tgttcaagtt ag                    1062

SEQ ID NO: 143         moltype = DNA   length = 1452
FEATURE                Location/Qualifiers
misc_feature           1..1452
                       note = Description of Artificial Sequence: Synthetic
                         polynucleotide
source                 1..1452
                       mol_type = other DNA
                       organism = synthetic construct
SEQUENCE: 143
atgattgttc gctacgttgt gagtgctgtc ttgatcattg gactgtcaat tctcgccgcc   60
gttgagcagg gatgtgctga aattaccgtc ggaagcatta aagttttcag tggtgagtac  120
gatgatgatt caattggtac taaatgggct gtgctggttg ctggatcaag aggttgctgg  180
aattacaggc accaggcaga tgtttgtcac gcatatcagc tgttgaagaa aggtggcctc  240
aaggattatg atattattgt gtttatgtat gatgacattg ctcaaacttc tgagaatcct  300
aggccaggag tcatcataaa tagccctaat ggtcatgatg tctataaagg agttccaaag  360
gattatacag ggcatcatgt tacagccaac aacgttcttg ctgttatcct tgggaacaaa  420
agcgctctta gtggaggcag tgggaaggtg gtggaaagtg gtccgaatga tcatatcttc  480
atcttctaca gtgatcatgg tggtcctgga gtgcttggga tgcctagtgg ccccttatcc  540
tatgctgatg atttaattga tgccttgaaa aggaagcatg cttcagggac atacaaacgc  600
ttagtctttt acattgaggc ttgtgaatct gggagtatat tgagggcct tctacctgaa  660
ggtcttaata tctgtgcaac aacagcatca aatgctgaag aggacagttg gggaacctac  720
tgtccaggag actatccagg tcctcctcca gaataccaga cctgcttggg tgacttgtac  780
gctgtgtctt ggatggaaga tagtgaaaaa cacaatctcc aaagagaaac tttaggaatg  840
caatatgagc tggttaaaag gagaactgcc aactcgtttc cctatgcaag ttcccatgta  900
atgcaatatg gtgatctgaa gctaatggat gatcctcttt ccctttatat ggggaccaat  960
cccgcaaatg ataattacac ttttctggac gagaattcct cactgctctc tgcaaagcct 1020
gttaaccaac gtgatgcaga tctttttgcat ttctgggaca gttcctcaa ggctcctcaa 1080
ggttctatta ggaaaattga agccagaag cagctgactg aagctatgtc acacagaatg 1140
cacatagacg acagcattgc acttgttggg aagcttctat tcggaattga gaaggtcct 1200
gaggtgctga ttagagtcag acctactggc gagcctcttg ttgatgattg ggattgtctt 1260
aaatcctttg taagaacatt tgagacacat tgtggatcat tatcccagta tggaatgaaa 1320
catatgcgtg ctgttgctaa catatgcaac tctggtataa aaatgagca gatagccaaa 1380
gcatcagcac aagcttgtgt gagtattcct tccaactctt ggagttcgct cgacgaggga 1440
tttagtgcat ag                                                     1452

SEQ ID NO: 144         moltype = DNA   length = 474
FEATURE                Location/Qualifiers
misc_feature           1..474
                       note = Description of Artificial Sequence: Synthetic
                         polynucleotide
source                 1..474
                       mol_type = other DNA
                       organism = synthetic construct
SEQUENCE: 144
atgagctatg tgaccaatc acaaactatt ggtgaccttg cttttgagaa attcacattt   60
ccttctattt ttggaaataa tgttaacatt cttgatgttg tctttggctg cggtcatgac  120
```

```
aatagtggca cgttcaacaa ctatacttct gttattattg gcttaggtgg tggtgaagtt    180
tcaattgtca accaattgga taaagaaatc aatggaaaat tctcttattg tttaatcaca    240
attccattac aatcatcaat ttctaatgcc accagtcaca taaattttga tgcagattta    300
gagttgtcgc cttcgagcac gtttgcagaa gtggaggaag atttggtttc tcttacaata    360
gtgccagcag aggaagttgc cattttttgga aacttggagc aggcaaattt cctaattgga    420
tatgatcttg ttgccaacaa aatctcctcc ttgccaacag actgcactag ctaa           474

SEQ ID NO: 145          moltype = DNA   length = 867
FEATURE                 Location/Qualifiers
misc_feature            1..867
                        note = Description of Artificial Sequence: Synthetic
                        polynucleotide
source                  1..867
                        mol_type = other DNA
                        organism = synthetic construct
SEQUENCE: 145
atgattaata gtcgacaccg tcgaaaatat ggaagtaaag atgaatggaa tatgcgattt     60
gggatttatc aatccaatgt tcaattatc gacttcttca attccctcaa cctttcttac    120
aacctcactg acaatgcttt tgcagatatg acaaacctcg agtttaattc taaatattta    180
ggttataaga aacgtaaaca ttcaaagcaa ttagcagcac caaatatcac gtgtgacagc    240
tctaaattgc ctatcagtgt cgattggaga aagagtggag ttgtaacacg agtcaaggat    300
caagaaaatt gtgaagctg ttgggcattc tctgcagtag cagcagttga aggcataaac    360
aagatcaaaa cagggaaatt agtgtcacta tcagaacaac aactagtgga ctgtgatgtt    420
ttctcagaca accaaggatg taacggagga ttcatggaaa aagcttttgc tttcattaat    480
aaaaacggtg gcattacaac tgaaaaaaat tatcattacg taggaaaaga ccagaaatgt    540
aacactacca aagcaaaaca acatgcagtt acaataagtg gctatgaaat ggtagccaaa    600
aatgaggaat ctcttcaagc tgcatttacc aaacaaccta tatcagtggc cattgatgca    660
agtggctatg attttcagct ttgcgctggt ggggtttact ctgttttttt cggaaatagc    720
ctaaatcatg gagtgccatt aattggctat ggtgtagatg atggtgagaa atattggcta    780
gttaagaatt catggggtac tatgtggggt gaagatggtt atatcaaaat taagaggtgg    840
tcaaatgaca aaaaaggaa cgtgtag                                         867

SEQ ID NO: 146          moltype = DNA   length = 2121
FEATURE                 Location/Qualifiers
misc_feature            1..2121
                        note = Description of Artificial Sequence: Synthetic
                        polynucleotide
source                  1..2121
                        mol_type = other DNA
                        organism = synthetic construct
SEQUENCE: 146
atggccaatt ctctcctctc ttccaacttc atgggttctc aaatctttgt ctctcctccc     60
accctaaaa caacaaagta tttccatttt cactccaaaa gaaagtcttt aatccctcaa    120
tcaattctca acaaaaaacc caattcagat aattcaaaga atattccttc aaaagctgct    180
ttagctgctt tactcttttc ttcaatcact ccacatgcct atgctcttga taatactacc    240
cctacagtac caaccctca agtgattcaa gctgaagcag ccaatccac cacttcaaat    300
ccattctctc aaaatataat cttgaatgct ccaaagcctc aagcacagac caatcctgaa    360
cttccagaag tttctcaatg gagatacagt gagttcttga atgctgtaaa gaagggtaaa    420
gttgaaagag tcagattcag taaagacgga actacccttc agcttaatgc tgttgatggc    480
cgtagagcta gtgtaattgt gcctaatgac ccggatttaa ttgacatttt ggctatgaat    540
ggtgttgata tatcagtttc tgaaggtgat tctggtggta atgggttgtt taattttaatt    600
ggaagtttat tccctttat tgcttttgct ggattgttct atcttttcca gagatctcaa    660
ggtgggcctg gtgggcctgg tgggcttggt gggcccatgg attttggtag atcaaagtcc    720
aagtttcaag aagttcctga aactggagtg tcttttgctg atgttgctgg tgctgatcaa    780
gctaaattgg agttacaaga agtagttgat ttttttaaaga atcctgataa gtatacagct    840
ttaggtgcta aaataccaaa agggtgtctt ttggtggacc acctggtaca ggaaagacac    900
tttttggctag agcagttgct ggtgaagctg gtgtaccatt tttctatgtg cagcatcaga    960
gttgttgagt tgtttgttgg tgttggagct tctagagtga gggatttgtt cgagaaggcg   1020
aagtcgaaag cgccttgcat tgtgtttatt gatgagattg atgctgtggg aaggcagaga   1080
ggtgcaggaa tgggaggtgg gaatgatgag agagagcaga ctattaatca actcttgact   1140
gaaatggatg gttttctgg aaatagtgga gtaattgttt tggctgcaac caataggcct   1200
gatgttcttg attctgcatt gttgagacct gggaggttcg atcgacaagt gactgtcgac   1260
aggcctgatg ttgctggtag aatcaagatt cttcaggtgc attctagagg aaaggccctt   1320
gcaaaggatg tggactttga gaagattgcc aggagaacac cgggtttcac tggtgcagat   1380
ttgcaaaact tgatgaatga agcagcgatc cttgcagcta ggcgtgaact aaaggaaata   1440
agtaaagatg agatatctga tgctttggag aggataattg ctggaccgga gaagaaaaat   1500
gctgttgtct cagaggagaa gaagaagctg gtagcttatc atgaggccgg ccatgccttg   1560
gttggtgcac ttatgcccga gtatgatcct gttgccaaga tatctattat tcctcggggc   1620
caagctggtg gtcttacctt ctttgccct agcgaagaaga gacttgagtc gggcttgaa   1680
agcaggagct acctagagaa tcaaatggca gttgcacttg gtggaagggt tgctgaggag   1740
gttattttttg acaagacaa cgtaacaact ggggcatcta acgatttcat gcaagtttca   1800
cgagtggcaa ggcagatggt tgagagatta gggttcagca aaaagatcgg acaggttgcc   1860
attggaggag gtggaggaaa tccttcccta ggtcaacaga tgtcaaccca gaaagactac   1920
tccatgcaa cagccgatgt ggttgatgct gaagtaaggg aattggttga aagagcatat   1980
gaaagggcaa cacagattat cacaacacac attgacatcc tacacaagct tgctcagctg   2040
ttgatagaga aagaaactgt tgatggtgaa gagttcatga gcctttttcat cgatggcaag   2100
gccgagctat acatttcatg a                                              2121

SEQ ID NO: 147          moltype = DNA   length = 2238
```

```
FEATURE              Location/Qualifiers
misc_feature         1..2238
                     note = Description of Artificial Sequence: Synthetic
                     polynucleotide
source               1..2238
                     mol_type = other DNA
                     organism = synthetic construct
SEQUENCE: 147
atgattatag aggtgctcat attgtggcat gcagatgtta ggcataatat atctctaact   60
gcactcagct ctactcagtc cttttacaaa gatgaccttt acattgtttt cttgaaagat  120
catccggtga acgaagaatc gctatttcag agacatatta ttgtcctatc atctttaaag  180
ggaagtgatg gggctgcaac agaatctcat gtttatagct atacaaaaat cttcaatgca  240
tttgcagcaa agctatctca acatgaagtt cacatgttat ccagcatgga tgaagtggtt  300
tctgtcatac caaacagata caggaagcta catactacaa gatcatggga atttattggt  360
ttgcctgcaa ctgcaaaaag aagattgaaa agggagagca acattatcgt gggtgttttc  420
gatacaggga taactcctca atcaaaaagc tttaaggatg atggtcttgg tcctcctcca  480
gtaaaatgga aggaagttg tggccatttt gcaaattttt ctggatgcaa caacaagctt  540
ataggagcaa gatacttcaa gctggacaaa gttcctgatc caaatgacat attgtcacca  600
attgatgtgc acgccacgg aacacataca tcatccaccc tagcgggaag tatggtgcct  660
gatgcaagct tgtttggtct tgcccgaggg actgcacgtg gagcggttcc ttctgctaga  720
gtggctatgt acaaagtctg ttgggtgacc tcaggttgtg cagatattga cattctagct  780
gcatttgaag ctgcaattag tgatggtgtg gacttaatat ccatctcaat tggtggtctc  840
agtggtagtt atacaactga tgtgatagcc attggatcat ttcatgccat gagaaaaggg  900
attcttactg tggcttctgc tggaaatgat ggacctaacc tcaacaccgt cgcgaaccat  960
gcaccatgga tgctaactgt agcggctagt ggcattgata gggagttcag gagtaaggtg 1020
gcgttgggaa atgggagaat agtctcaggg attggagtta gcgcgtttga tccaaagaaa 1080
aaattgtatc ctcttacggc gggagtggat atggccaaga gctctgacac tcgagacagt 1140
tcaaggtact gtggtgaagg atcaatggat cctagaaagg taagggaaa gcttgtttat 1200
tgccagttgg gtacttgggg tgctgattct gttataaaag aacttggagg atcggcact 1260
atcattgaaa gcgatcagtt tcttgattct gccccaattt tcatgctct tgcaacaata 1320
gttaattcca gcatagggaa aaacattaat aactatatgc attcagagag attaccttca 1380
gcagtaatat acaaatcaca ggaagttaag atcaaagctc catttattgc atcatttca 1440
tcaagaggtc caaatccagg aacaatacgc cttctgaagc ctgatattgc agctccagga 1500
attgacattc tggcttctta cacccccctg aaatcactca ctggtttgaa aggcgatact 1560
caatattcag aattcacct catgtctgge acttccatgt catgccctca cgttggcggt 1620
gcagctgctt atgtaaagtc ataccatcca gattggtctc cttctgctat taagtctgcc 1680
ctcgtgacta ctgcaagacc tatgagctca aggtggaca gggaagcaga gttcgcgtat 1740
ggtgctggac aagttaatcc gacgaaagca agaagtcctg gattaattta tgcatggat 1800
gatatgtcat atatccagtt cttatgccat gaaggttaca attcatcatc agtatccagt 1860
ttacttcgac aacgggtaaa ttgctccaca ttgattcctg caaatggtga agatgctatc 1920
aactatccca caatgcagct tggcctaaag agtaatcaag aaccaccat ggcattttc 1980
aggaggaaag ttaccaatgt tggacaagct atatctgttt ataatgccac tatcagagct 2040
cctaagggag tggatatcac agtaaaacca acgactcctc cattcaacg tgcaatgcag 2100
acaagaagtt tcaaggttgt tgtgaaggca aaaccaatgt caaatgctgc aatattgtca 2160
ggttcactca tttggaagag ctcccgccat cttgtaagaa gtcctattgt catatatgat 2220
ccaaaggttt ttgattaa                                               2238

SEQ ID NO: 148       moltype = DNA  length = 5000
FEATURE              Location/Qualifiers
misc_feature         1..5000
                     note = Description of Artificial Sequence: Synthetic
                     polynucleotide
source               1..5000
                     mol_type = other DNA
                     organism = synthetic construct
SEQUENCE: 148
aaaaatatga gaatcgtgcg gaatttcagt tttatggaac taaacgccaa aaatggagg    60
aacggtcatg gagaggcgat aactaatgtt ccttaggttt tttagatgg gccgaaaaaa  120
ttttaggcga tacgggtaag gcgtccgaaa cacacgaaa tttgaaaatc gggcgaattc  180
ttgttttatg acactacaac accaaaaagt atggaagatt atggcgatgc gatgcgatga  240
ataatgttcc ttaggttatt tttgatgggt gacaacattt taggttatac gagaccgggt  300
tcccgggccc acaccagtgg cgtgggctat attgcacacg aaaatatggg aatcgagcga  360
atttctacat ttatggcact aaaatgcaaa acaaaaagga acagtcatgg cgaggcaatg  420
actaatgttc ctaggggttat ttagatgggc ggaaaagtt ttaggtgatc ctggtcgtga  480
cgctcgagcc cacgatggta gtgtgggcac acgaaaatc gggaaccgtg ctgaattcta  540
gttttatggc cttaaaacac caaaccaac aagaggaat tctcatggag gggcgatgaa  600
taatgttcct taggttgttt tagatattcc agaaagattt taggtgatcc gggttgcggt  660
gcctgggccc acaccagtg gggtgggcta tagcgcatgc aaatgtggga atcgagcga  720
attctaattt tatagcccta aaacaccaaa taatgttgaa cggtcatgac acgatgatga  780
ctaatgttcc ttaggttatt tttgatgggc tagcaaaatg ttagaagatt cgggtccggc  840
tgcccgggcc catgccagca caagaaaatc tgggaatcag gcaaattcca tattatggcg  900
attatgggcga ggcgatgaat aatattactt agattgtttt ttacaggctg gcagaatttt  960
aggttatcca ggtgcgggcg tctgggcctc tgccggtgge gtgggctgta gtacacaaaa 1020
attagggaat caggtagaat tttagttttta tggccctaaa atacaaaaaa aggagaaaa 1080
gtcatggcga ggtgatgact aatgtgcctt aggtaatatt ttatgttccg aaaaaaattt 1140
atgtgattca ggtccgggag ctcgtgccca tgcagatggc gtgggctata gcacccgaaa 1200
atctcaaaat catgtggaat tccatttta tggccataaa atgctaaaca taggaaacgg 1260
tcatggagag gcgatggcta atgttcattg ggtcgtattt gataggacgg caaaattata 1320
ggcgattcag gtccggcgcc gggcccatgc agatggcgtg ggctaataat agcacacgaa 1380
```

```
aatctgagaa tcgggtggaa ttcatgtttt atggccctaa aacgcaaaaa acaaatgaga    1440
aacggtcatg gcgaggcgat gacaaatgtt ccatgagtca tttttgatgg gccagcaaaa    1500
gtttaggcga ttcggtttcg ggggcccggg cccatgcaga tggcctgggc tattgcacac    1560
gaacaactag gaatctggtg gaattccact tttacagcaa taaaatacca aacaatgaga    1620
aacggttatg gcgaggcgac gactagtgtt ccttaggtcg gtttagatgt ccggaaaaat    1680
aataggcgat cgggtccagg cgtccgggcc tgcgccaatt gcgtgggcca tagcatatga    1740
aaatatggga atcgggtgaa attcgagttt tatggcccta aaatactaaa aaggaggacg    1800
gtcatggcga ggcgatgatt aatgttcctt aggtcacttt ttatgggcag acataatttt    1860
tggcgatctg tgtctgggag accgaggcca tgtaggtagc gtaagctata gcacacgaca    1920
taattccagg tttatggacc taaaacatca aaaatggagg aacggtcatg gtgagcgat     1980
tactaatatt ccttaggtcg ttttggatgg gccgaaaaaa tttagggcga ttcgggtgcg    2040
gacgcccgag cacatacaaa tggtgtgggc tataccacac gaaaatctga ttacctgaca    2100
gaattccagt tttatggccc taaaatgcca aaatcgaaga acggtcatgg tgaggcgatg    2160
actaatgttc ctaaggtcgt tcttgatggg ccgacaaatt tttaggcgat tcgggtgcgg    2220
acgcccaagc acatgtagat ggcgtgggct ataccacacg taaagcaggg aatcgggcgg    2280
aattcaagtt ttatggccct aaaacgccat aaacgaagaa cggttatggc gaggcgatga    2340
ctaatgttcc ttaaatcatt tttgatgggc cgtcaaaatt ttaagcgatt cgggtcaggg    2400
cgccctggtc catgcagatg gcgtagcaca cgaaaatctg agaattgagc agaattctag    2460
ttttatggcc ttaaaacgcc aaggaacgag gaacggtcat gtgaaggcta tgattaatgt    2520
tccttaggtc gtttttaagg gcaggcaaaa ctttaggcta ttcagttctg gacgcccaga    2580
cccatgtaga tggcgtggct atagaacacg aaaatctagg aatcaggcgg aattccagtt    2640
ttatggtcat aaaaatgctaa aaatgaggaa ctgtcatgga gaggcgacaa ctaatattcg    2700
ttgggtcatt tttgatggtc cagcaatatt ttagatgatt cgggtttggg cgcccgggcc    2760
catgcagatg gcatgtgcta ttgcatacac aaatctgtga accgggtgga attcaagttt    2820
tatggcccta aaatacaaaa aaatagagaa acggtcatgg cgatgcgatg gatatgttcc    2880
ataaggcatt tttgatggga tagcaaactt ttaggtgatt ctggtccggg agctagggtc    2940
tatgcagatg gcgtgggcta ttgcacacga aaatttaggt atcggtggaa tttcagtttt    3000
atggccataa aatgcataaa atgagaaacg gttatagcga ggctatgacc agtgtgtcct    3060
taggtcgttt tagatgggct ggcaaaatgt taggcgattt gagtccgggt gcccgggcct    3120
gcgccaattg cgtgggtcat agcatacgaa aatataggaa tcggacgaaa ttctagtttt    3180
atggccctaa aatactaaaa aggaggaact gtcatgacga ggcgatgact aatgtttctt    3240
aggtcgtgtt tgttaggccg gcataatttt aggcgatctg ggtctggacg cccaggtca     3300
tgcaggtagc ataggctgta gcacacgaaa attttgaaat cgggcgaaat tctagttta     3360
tggccttaaa acgcgaaaaa caaaatgaat ggtcatggga atgcgatgac taatgttcct    3420
taggtcgttc ttgatgggac ggcaaaatgt taggcgattc gggtgtgggc gcctgggcac    3480
atgcatatgg cgtgggccat catagcatat gaaaatatgg gaatcgggca gaatttcagt    3540
tttatggccc taaaacgcca aaaacgaaaa acggccatgg cgaggtgatg actaatattc    3600
cttaggtcat ttctgatagg ccggcaaaat tttagacgat tcgggtaagg acgccctggc    3660
ccatgcagat ggcgtagcac acgaaaatct gggaatcgaa aagaattcca gttttatggc    3720
cctaaaatgc gaaataacat ggaacggtca tgtcaaggcg atgattaatt tttcttaggt    3780
ttttttgat gggcaggaaa aatattaggt tatgcccatg cagatggcgt ggctatagca    3840
cacgaaaatc tgggaatcgg gcggaattct agttttatgg ccctaaaacg ccaaaatgtg    3900
aggaacggtc atgtcaaagc aatgattatt attccttagt tcattttga ttgtcggaca    3960
aaatgttagg caattcgggt ccgttcaccc ggatggatgc atatggtgtg gctagtaca     4020
cgaaaatctt ggaatcggac ggaattccag ttttatggct ttaaaacgcc aaaaaataag    4080
ggacggccat ggcgtagcaa tgactattgt tccgtaggtc atttgtgaag gaccgacaaa    4140
attttaggcg atccgggtcc gatttttcgg ttctgctcaa gaaaactcga tctgcacgaa    4200
tagcttataa tcaaacccct tttttttttt caagaatgtc taattgatcc taaaaagaca    4260
accttatatg ttccaccatg gcaggatcgg ccttattact aagggtttgc aatagacac     4320
gttttttaaca ttcaagtaaa aaaaacattt attcttaata acccacctac tatagtacgt    4380
tatttggcag tagactacgt tgtacatttg ggaccatttg gaacactcgt cttttcacgag    4440
tcactaattt ttgtgttgaa tgcataaaat ttgttttttt cttttcgaa attgaacaat     4500
tttatcttcg atcacaccta tagtatatta ttaccttatt gttagaaaat attttatttt    4560
attattgact cctaataaaa agtggggtaa atttgggtct ttttttttaaa gaatgtgaac    4620
tactcatttc acttttggtta gaacaaatat gagaagattt gctaatgaca gcaaaatgaa    4680
tagaccaaaa gcgtaacgaa tattaaaaat aaacaattcc gaataactgg ttactgaaaa    4740
ttgtggaact ctacatagcc gttgtgagta tggtattgtt tgttcttgtg ggcagaataa    4800
ctagttacgg aaaatttatg aatttgcttc acattatttt tttcatttc ttttttgctt     4860
caaaagataa gtacaagttt ttatactctt atttcattgc ctataaatac ctctattgag    4920
ttactgctca ttcacaactc taaatagcaa tctttcttat tattaaaatt cctatccttt    4980
tttactcatt cagagaaacg                                                5000
```

SEQ ID NO: 149        moltype = DNA  length = 5000
FEATURE               Location/Qualifiers
misc_feature          1..5000
                      note = Description of Artificial Sequence: Synthetic
                      polynucleotide
source                1..5000
                      mol_type = other DNA
                      organism = synthetic construct
SEQUENCE: 149

```
gctgatctac aaagggctta gaaagaagta agaaagaaa tggataaagg aaagggaaag       60
attgcagaat cctcagagct gttgaggaag aggagatgga actggtccat caagaaaggg     120
gtacatcagt ggaggttcct accccaagcc aaaaagccca agacttcctc caagaagtct    180
tcctctgtgt ctgaggctgt tgaacctaca ctagccaaga ggacaagatc tgcagtgaaa    240
acaacaatca aaaatttctg aagatgatga ctggagtgga gaagaagaag aaaatgattc    300
tgagaaggaa caggatagct tgccagtttg gcaaagaaa gattttaaag ggtagactgc    360
tgaaagacct ggtggaacca ggaatgatga gatgtggatg cttagctgc tcaggatgga      420
aggacatggt ccttcagatg gatggtaggc tagccagaaa tgagctaatt gaatttatgg    480
```

```
caatgtctgg ttaaggatgg catgttagta gcctggtgaa aggagttcaa gtgcagtttg    540
atgcaaagaa actgggagag atcctggaca taccctctga aggtttgat gactatacaa    600
ggcaaaggtg gccctgcctg gactccctcc ctactgctct tgtaattacc aggaggtttt    660
gtgattctga agatgtgaat gaagccaggg ctgtgcagaa aagtgaaatg aggcctgagc    720
acaaggactt gtttgaattt gtcaacaagt gtttattgcc cagacaggag agaagtcaca    780
ttgccaatta catggatcta gttcttatag agtgcctgga gagaggaaag caaatcaatt    840
gtctgccttc attatcaagc tgctcgacag ggttataaat ggctccaagg ctcatgctac    900
tctttatggc tttattctaa ccacagttct ggatagtctc aatgtgcctc taaagaaatg    960
ggaaatgatc tcgagaaagg atcactttgg catcaatact cttcttgctt gtgactatgc   1020
agtcaatgac atcccaaatg aacctggtac atcctagaag acacccatca acagcaaagt   1080
caggactctg gttcaggaat atgtagccaa ggatgctgaa atagctaggc ttttggctcg   1140
tgtgattgaa gtgaaatttg agagggatgg tctcagaact gagcttgaca agaaaaagga   1200
gaaaaatgat ggaattcttc ataacatgct gaaccttcc caagcccaaa cccaaccata   1260
tagttcttcc aagccttagg actcctagct tttgtctcct gaacttgttt agtacctcag   1320
tgacccagat tagggatttt tctatctttt atttttgctc atgatttgga tgttttttctt   1380
tcttttttgtg gattgttggt ggcaacatat ctctgtcaat gataactact attttgctct   1440
tgtttaatgt taatttgtcc ttgatatttt aaatatattt tcttgattac tgatgattac   1500
tccatgatta catttgcagt tgccgcagtg gccatgggta cttattaaaa tctgggaatc   1560
acactttgta tgtaacattt cgatgatgcc aaaagggaga agagagttgt gctttacaca   1620
cattctgaaa taagtaatat ttataaccta attaacctgg tccttgatgt taagtgaatt   1680
ttctaagttt agtattgatg gttaagctga gttcttacag gtcccaaata agtaaaaagc   1740
acagagtttg tcatcatcaa aaagggggaat tgttggccc aagaacaggt gaagttttga   1800
agatgacaaa agaactcaga catgaccag gtccatcttg tgaagcacag tcatgatcaa   1860
cctatacatg tgagatgcac gtgaaagaga taagtcttac tgattaagca acaatatctc   1920
ttgatctgat cgaaaggat gaagatagtg ttagagtttg agatcatcat gaactcttcc   1980
acgatagaag agcagcaatt gagtcacaat caaactctga ttactaacct attaaatgtc   2040
agtttgttct cttttacagg aaatacacat acgcaaagt taaactaaat tgagagcaaa   2100
agagcaaggc gatttgcaa gcaatttatg tggatttgag tgtgcactcc tgaagctact   2160
tgaacgagat agaagaacca gttccatcgt gtctatcttt ttctagttca attgtagtag   2220
gtggttttaaa ttatacctttt cagctttcat agaagcaatt attattagata cctagagtgt   2280
tcaagttata gctaacttga agttgtcgca acagttgagg ttgtgtgcca caacgggatt   2340
agagttaatc cttaggttta taaagagttt ttgtaaaagc tattttggct cagtgatttt   2400
agtggaagtt tgggaaaatc ctactgagtt gtaggtcatg gtttttttcac cttttgagcc   2460
aggtgttttc cacgtaaaaa tctccgtgtt cttttatttct tgtatttatta ttccgcaatt   2520
agtagtagtt ggaacaccta gaaaaccaag ttcttctata gagtagttaa gcgaaaattg   2580
ggtgccacac aaaacacccct ctagtgtggg attgacgctt aaacatcaat tagttaattt   2640
ctggagcaac tagctactag ttgttattaa aatagttagt ttctttgtta gctaaatatgt   2700
tgtttttggtt gtaaattagt tccggtgtgt agtttggact ttggaagaag acttgtacca   2760
attgtgtttg ttatttttctt tggtcttatg aatgctcaca ctaaacatca agttggtatt   2820
tgattttgca tttgaattag aagtagtatt gagacgtgtt gttgctatgc ataagtagta   2880
aaagattggt ttgagcttag ttggtttcgt gataagattg gaaataaaag aaatgtgtca   2940
aagttatgta aaaatcagta aaataggctg ctaccttttta atattaccac aagtccacat   3000
ttattttagt tttaaacaat ataaatttgt taaggtaatc ttctacaat agtctcaact   3060
tttaattttag taacagataa ttgcaaagtc aatccaacta atcatacact acccatatgt   3120
aaaaaaaaaa aaaaaaaaaa aaaaaaaaa aagtgaacaa tcaatgcaca aaaagaaaaa   3180
aaaatatttt tcttctttaa ttaattccat aacatagtcc ttaaaattag ttaattcttg   3240
ttttagaaaa attgtaacag tctagttaat tctccaaaat gaagcaaaag atttttttc   3300
ttaagtatta cgtcactttt tttattaatc caccaaataa attaaattag atttagttca   3360
ctaaataaac tcaataagat cagatgtttt atttattta aaaataactc aattacttaa   3420
tcacaaatga tcatgactaa ctcaaaagta atttgtttta acaaaaataa ttaatttcgt   3480
cttaaccgat gtcgggacga ctcatttttgg aataaataca taaataaaat ggccaggtcg   3540
cgaggacacg tcatattcca attctttcaa ataagcttgt tatttattaa cttgagtagg   3600
ctccaatttt aggtgcggcg cacgaactaa ggtcggagat attcatcttg ttagcgtaa   3660
gctagggttg gggatattcg tcctagtttg agattaatta agtcatcaac agtaaaagtg   3720
gacataggca aaacatgaaa accgaataaa gcacaattta tccataatta attcatgcca   3780
aatttaagtt aataaagcaa ctgtgctaga accacggact cggagaatgc tttacacttc   3840
tccccgatca acaaaaatct ttattcggac tttattttttg cagaccgata ataatagagt   3900
caaatcttcc tttgactagg gattcaaata aaaagtgact tggaacatgc aaaaatcaat   3960
tccaagcggg cgaatctgta aacaaaaaat ccttattcaa atttgtcact ttaattgaaa   4020
aactctttaa cccactattc ataacatata tattttgggg gtagaaaagg ggttgacagt   4080
tatgacctac tttatgcatc agtgttcgaa tttattttga tcaacaccct tttgaagag   4140
cgtttgatag aaatggttgg cttaataaac aatcatatta tcatcacctg cggaatcata   4200
tcattaactt ttgaaaatta aaatggtttt caaagacgtt ttgataaaag aattcctatt   4260
gtcgcagttg gaatctacaa gaccaagatg ttgatctagt gctatatttg gagaaagtgc   4320
cttaattaaa aaaattgtt cattagttgt cttaagattt tttattattt aaaaaaaaat   4380
taagacacaa agaaacacat ttacgagtat atgtcggccg actaatgtga agttcccacg   4440
gacaacccac acatattgtg gtcaagatgg attctatcat aatcaaaagt catcatcaat   4500
tcaattctca tatttggcat ctcaagtaca tgcacaaaag caacttagga tgtaagttta   4560
tatgcacatt cttgaaatag aacctattta tacgtagtac ttaattagtt acagtagtat   4620
tatttattct ctgctacaga gctatgtttt atcaaatata tcagattatc atttgttgtg   4680
taggccatttt ccttatttgt acttggtatt aattctggca aaagcacaaa actgggaaat   4740
gaggttcttc ttccttaata tgagtcacag attagtacca ctactatagc caagaaaatg   4800
tgaaatcata tagtactaaa tattaatttc agatgccaaa accataaatt tcccctcctc   4860
catcattgaa aaccccctctg tccttttcccc tagagagacc cctttttcct ctctctctcc   4920
ttctcttttt attagacgca tatattctct cttctttctc tttctagggt tttcacctga   4980
aatagtttta tttcggtgat                                              5000

SEQ ID NO: 150      moltype = DNA   length = 5000
FEATURE             Location/Qualifiers
```

| misc_feature | 1..5000 |
| | note = Description of Artificial Sequence: Synthetic polynucleotide |
| source | 1..5000 |
| | mol_type = other DNA |
| | organism = synthetic construct |

SEQUENCE: 150

```
atttaaaacc ctaaaaaaca agattttat ctatctgcat ggtgaaggac aaagaggtct    60
tcaatctcag gttctttttt ttttttttt ttatatatat atcttgtttg ggtttaaggt   120
tattgggctg atgaatgttt taattttaac ataggtctac ttacgtagta gttataggtt   180
gataatgaga tataattaac taagtctttg tataatgcag atcctgaact taatctttat   240
ttgtattatt tttttttgtt actgaaagat tctgttacca aatttatca gtctatttaa   300
ttagaggcca acgattgtta ggtatgtggc acttcgagtg ggaaatgata tattcccatt   360
aaaggtgtta attaaccacc aaattgttct ttaggtctgt ttgtcatttt gtattaagt   420
ggatggttta ttatatatat cttctcttta atgctaatca tgcttaactt tttcatttag   480
taccagcaag catatttgtt tacttttattg gttattcctt atcaaagtct tcatcttgtt   540
gcttttttt attgtacttt acaaaagatt tctagtatta atggaaagtg ctcatatttg   600
gaaaaagaca tggccaacaa gaaatgtcta tacccccat ttcttcttct tcttctttt   660
ttccgaaaat ttcttatttt tgtttttatt tctgtttctt gttgagtgct ttcatggtag   720
aagaagaagt aggagattct tggacatggc tgcatgagaa ttgttaaata accccgtata   780
catacacaag tagtgttggc tgtctttgat atcaaaccat ttattgccct aatttctgcc   840
tttgtcccc tcaacaaaac catcaaagtt ctcaaagagg gtttattctt gtttcccact   900
ttgccccca cctattaggg ccaccccacc aaagggatct ctctcgtgtc tagtgttttt   960
tcccaaggac caccactcct tttttttct ctaccataac ttcgtccaca ccatcttatt  1020
gtgatatttt cgtttaatga atttgcagcc atgcctcat tcatcatcag aactcagtca  1080
taagcacaga ttctgagaga gtaattaatg aatgaactga tggtgatttg acgtaaagta  1140
tacatgatta tggttttag ctgaataagc agagggagaa aatatataca tatataaaca  1200
agtagagtaa aagaatgacg caagattagt accaaaagag tgaaggaaga gatttaatat  1260
tatagggaaa agggaagtag taggtgatac ttgacaggtt gataagatgg ttattactac  1320
aagttgatgt attgacgcta actcacgcaa gagagccta ctcactgtac aatatttta  1380
caagaataag cgattctttc tctctttact tgcaagaatt gtgtgttgtg tgagttgtat  1440
ggcgcatttt ctaggagcct gtggtagtga tggatgtatt catataatac aatacaatac  1500
atatggaata gatagataga taagatggtg cacgcatgag aggcaattat gcaacttacg  1560
tcaactactt ccatccatcc atcttttctt ccttctgttt ctgtctgata tagtgagtat  1620
atgcttgtgc tggtgttgtg tgctttctg gcctgggatt ttcctaacac tttagataat  1680
ttaggttccc atcaataata atgtcttttt agaggagcat catcgataga tattcaaata  1740
ttaaacctgg cctagctact atctagggcg tctgctaggt ttttccatta cccttttgtat  1800
atctcttatg tgggacctt tgtttatgga agaatatgga gtactttat tcatctcgta  1860
gggtcttgaa tacaagattt tatatatatc actctttaaa aatgaccatc ctaaaattct  1920
tcctctttca tttgcattta ccagaattga tattagtacc taaactagta ctcttcactg  1980
aggccttttg tatttagtcc tattatattt gaatttggca ctatttaaat taaaaaaata  2040
atctacaata aaaaattctt ccctaaacat taccccatcaa atactcacca cctaaggtaa  2100
ctctaccatg tttaattt ttggatcaaa tctagtagag ttaattctc cacttatgtt  2160
ctttcggaac tggctaagta atcttcaaaa gctagggcat ctccgcagtc atatcgtgcc  2220
ctcccaagta tagcgaccgc ttctatattt tccctgaatt tcatctgtgc tagggcttgt  2280
tttcacgttg atttcaaaca aaggctaaca atttcattga gtaacttttt ctcatttcag  2340
gactcgaacc ttaaacctct gttcaaataa ctttcaagaa gtatatatgt atacaatgtt  2400
tgtattcatt gtgacaaagt attatgagtt gtacaacttt cttgtgaaga tagagcataa  2460
tgttaaacaa ggatctatat agagcataat gtcaacaaaa caacaacatc aacccagtaa  2520
tcatcctact aataggattt ggggagggta gagtgtacgt aaaccttacc catacagggg  2580
aggggtaaa gaggttattt tcgggagacc ctcggctcag agacaaaaaa atctataata  2640
acaacagaaa ccagacaaat aatatcagca tcataagaga caacaaataa gtggaatgac  2700
aataattatg ccaataataa cattgaaaaa aataaaatta aaaattaaaa ataaaaatag  2760
tgtgatgaac aaaaatcgct agcagtctta gacaaaacac tatcagacta gctggaacaa  2820
cgaggaaaaa cgctgaagta ccccctaacc tacaaccccta atgctcgaca tccacaccctc  2880
cctatccagg gtcatgtcct cggaaatctc aaatcgcgtc atgtcctgcc tgatcaccctc  2940
gccccattac ttcttaggtc gccctctacc tcttctcata cctgtcaaag ccaaccgtca  3000
cacctcctaa ctgggggcatc taggcttctc ggggccggcc agcccgtaga tctaaaagga  3060
tccatcccata gcgcccgaac catccacgcc tcgctttccg catcttgtcg tccatgggag  3120
ccacgcccac cttatccagc cttatccagc ctagtgtgcc cccacatcat ctcaacatcc  3180
tcatttcgac tactttccatc ttctggatac aagaattctt gactggccaa cattcagctc  3240
catacaacat ggtcgatcta accaccactc tataaaactt gcctttaaat ttcagtggca  3300
tgttagtatg tttactttag atacaatgtt ttttagagtc ttatagtctt gttagaatac  3360
tatatattat aaaatatgga gacttctggg cactttttgt tatttttata taagatagga  3420
ttggaatgaa ttcaattgga gggacatgca tgataaatga atattcatgt agccgatata  3480
tgtttgggac tgaaacgaca ttattattgt gaaatatttt acaattgcat ttcacactca  3540
ctgaagtgaa actttgattc cacgtcggtc aatacttagg tgttacggtt tggctgcgag  3600
gggaatcgaa gagagcaaat taattaaagt atttaatgag gaatcatgag ttagttggtg  3660
gaattataat agtcaaatga atgagttatt cgcctgataa tatagttgat agtagtatat  3720
actatatatg ttgatactag ttattggtgg tgacctaatt aagtaaagag aagagaagag  3780
tggttatgta aaggaatcta ggtatagtgg gggatggggg gaggcaaggt taaagaaag  3840
gtggaaaatc caagaatcct gcttcctcta gtaacatagc atatcctgca attcgtgctt  3900
ttgtttcctc tcacaagata actactttt tgattaatta ttcatttga cacatacata  3960
caaacctata aaattagaca tccttatgga atcttacgac tccgaacttg tcatatatcc  4020
tttaattatg cttagctttt tgctaaaaac aaaaaggata tccttattcc aaaatgcaac  4080
taggagcatc ttcccacatt tcttttttat gcctctgcat catcaaatcc cataatgccg  4140
cacaacaatt tcttttttact taagtatatt ctagcttagc tatttcatac gaataatggg  4200
tatacaaatt tgcttatttt aggttttaaa taccgattta aatatattgg atgggttcaa  4260
cttttaaaat tcttacactg atatacatgc atagaatatg tggaaaactt taatattaat  4320
```

```
tacaactgct aaacatttga atggattctt catgccgtgt gctcctttgt tgaagaacac   4380
gtactccctc cgttcgcatt tatttggcac gttttgactt ttcacgcccc ttaagaaata   4440
ataaataaaa tgcataattt atcatgataa acatatcaat ttatgcatat tttattagat   4500
ttgagaaaat aatttgaaat gagtaataaa tactgtgagt ataacaggaa attttttttt   4560
gtcttctctt gatatgcata aaatagcaag taaaaataaa aatctattt taatataaat    4620
gtcaagtaaa agtgaatgga ggaagtattt ggaagggcga tatcgaataa aaaagttata   4680
ctaataacaa acagcaacaa ttacaagaaa ctgtagagtt ggccagtacc aggtatatat   4740
gtagaatttt tttatgagg aatttagtga aacgctagct atttcaacac ttcagacata    4800
tcaataccaa ttttatggtt tctcttaggt gttgatagat tctcttttgt cagcaaacat   4860
tatttatgaa atttataata aaatgctgct cttttcgagt ttacattctc cgtcccaata   4920
caatatatac ttgatttgac gaaagaaatg taacaataga atcttaagtc ggaaaagtc    4980
aaatcaaatt tgaaaaaaat                                               5000
```

SEQ ID NO: 151        moltype = DNA  length = 5000
FEATURE             Location/Qualifiers
misc_feature       1..5000
                      note = Description of Artificial Sequence: Synthetic
                      polynucleotide
source              1..5000
                      mol_type = other DNA
                      organism = synthetic construct
SEQUENCE: 151
```
gaaaactaaa aaaagaacta aggcatttac actaggtctt caccggggct cgtcccatca    60
ccagaacccg ttggcctcag gtctcttggc ttctttaatc ttggccgaca ggtcaaaacc   120
tcgggaatgg atatcctcga gggtctctct ctggtatagc cgctttacgt actcggtctt   180
catctttaag cgggccttcag ctatctccac atcagcctta ctgggcca gcatttcctc    240
gacgtcggag gaatcaatag aagttgcctc caacttggat ctcagcgcgt tatattcttg   300
gtcgagggca tcccattccg tgacggctga gttcagctgt gctcggagtt catcatttag   360
ccgagatcac ttgtcggcct tgtccttgc cacccggagt tggtccttta tcgatgtcaa    420
ctcctctttt gcagcctctt tttccgaagc cagtaggtcc atcctgccct tctacgcctc   480
ggtcgtggcc ttgacctcat ccatctcagc ccgaagccgg tcgatcaggt ctaccttctc   540
ttggacctgg gaagttgcgt tgttagtcac cacgagtagc ttctcatttt tagcctcaaa   600
gatccttacc ttctcgacca agtcagcgtg ctcccacttc atggacaagg cctccttctg   660
agcctttcc agctcggctc agagaattgg gaggtacttg agggcctcgt cttattgttc    720
gctgagagac ctgtaaatgt cctttctccg gatcagttct ttaagtcgaa actcaagctg   780
actgatttgc aagagagacc gaaggaagct ttcatgatga agcattcaaa tctgaaaatat 840
aataaggtca ttagaaatatg cggagcaaat attcgcaaag gatacaaagg atagacgtct   900
tacccggttc aatgcctatt gcacctcgtt gaagaggctc tacgtgccta cttcattcat   960
ctttgcctaa tccttatcgg tcaccaggca acgaaggtag ctggctatgc cgaccggagc  1020
ggacagggct cgggcgtcca tcgggatagt aagaatgacc attctcttac ggtcgggtc    1080
aacacccggg gggagggaac ttcttcacta gtttcgggct caagctcgag ctcggcttgc  1140
tcgctcccga tgacacatcc ttttttggga cctccaggtg accaagcctg gagaagtcct  1200
ccaatgcgac catgtccatg ccatcaaaga acgtgttgag tgcattatct ggacccgacg  1260
ctatctcatt taatttctct ttattagctt gaacctcttc gagcatggac tcagtatagg  1320
acggcgtctc tgcgatgtca atgatactag ctacatcctt cgggacagga gcggcttctc  1380
gataggccat ggactccgtc tctccctctg gttctcgagc tagaggggga tcgacctctt  1440
ggtcacctttt cctggttgcc accttctccc tctcgttgag gtcgactca tgagcaatga   1500
actcaaggtc gtcatcctca ggataatccc taagccggta gagggaatca gatttcggta  1560
ccctcgactt ggtgctcttt ttgttttttct ggacctggac gaccaccctc ttcttcttca  1620
cctcgacatc cggggagcct gtggatttcc tttattcttt ctttttctct tcccttacgg  1680
cggcctcggg ctgtcccgaa gcggagggtt cagcgagcga ggacggatcc tcgtcctcat  1740
ccaatggctt gagctcggtg gtcatgggtg aacctgtgag aagaaagaag acttagcgat  1800
atattcatca agtatatgaa tgtaatcatt cgggagagag actcactatg gaacgagcc    1860
tcccatttgc cctcgagag cttgcgccat acgctcgaag taggacatct atttgcacat    1920
cccctcgatt cactccttga agcagggggaa tgtattagga acctgggcaa ctgctacata  1980
atggcaaata caggcaatta gaaaaaagaa taaaaggaaa tgccagatac tcgagaggga  2040
aaagacttac gggatgcgtt tcacttttttg aggaatggta gaaattcgga gaggatgagg  2100
tcttcggttt tcacccgaac gaacctcccc taccaacctc gatctcggtc ctcgtcgatg  2160
ctcgagaacg gagcctgct tgctcggcga acgatcttaa tcaaccctc tcggaagatt    2220
cgaggactgt atagatgaag tagatgttcg agggtgaact gaggtgcttc agttttgttt  2280
acaaagtgtt ggaggaggat tacgatcctc caaaaggaca ggtgaaggca gaccttgcac  2340
cttttatga tgtcgaggac tatggggtcc accgggacga gcgtgaagga gtaagtgtaa  2400
acacttaggt acccctccac gtgagtggtg atgtcttgt tgggccgggg gacgaccacc    2460
tcctttcccct cccagttaca ctctacccga actatggcgta gtgtctcctc agtaacagag  2520
catatgtacc tccatgctcc ctcgtctcgg tcctgttgac tggaggcttt ctcgacgttg  2580
aagtcattct cgatagagca gcccccgagt acgaagctct tcagggagg ctcatgggct    2640
acctcaggaa tggccacctc ggcatttatg gccagattgg aaaataaagg agcggtttgt  2700
tgaggaacga atttgaaagt ttttgctatc gggttctgaa aaaatgaag gttgaagaa     2760
aaaatatgaa gatttgaaga tagaatgaa atatgaagt ctgggttgaa gattgaaaga    2820
gaatgtatga agattgagga tgaaggtatg aaaatctaag gagcaatcta tgaagatttg  2880
aaggagttaa aggtatgtaa agaattcaag ggtaaatcaa ggagctctag aatcgaaaag  2940
tggagaagtg aaaaaggggt cggagctttt atagaggaag gacaatcaat gcatgacgtt  3000
tcacattcga ggacagtcaa tcaacggccg atacgtgtcc gatgttagaa cgatgcgact  3060
aatgggacgt ttcattgatc cgtcatctcg gttgtaacgt acgaagaaag gaatcgggt    3120
tcatttatcg cttcccgtcg tttcgataaa tctatcctcc gaaaacaag gggactatct   3180
gtatacgggt aaaatcaggc aatgtctacc ctgattctcc tataagagaa taagggggaa  3240
gcgcggatcc gcgagattgt aatcgaggac agagacccat cgtatcaaga tccaagaaga  3300
gtgaacgata tatctaacat cagacacggc aaagcgatgt accccggacc gaatataact  3360
cctagaccctc gggagaagcg ggggacggtt atgcatgaca gatagggagac tgtatactcg  3420
```

```
ccctcaatcg gatattacga cgcgaatctc gtcagtaaca attatggatc aataattact    3480
ggaaaaagaa gatttttacc tttttttagac ttatactagg actgaaattc tcgtactata   3540
taaaggtaaa gttttttcttt gatctgacac attgtaacac gcaattcaaa gaaataaaaa   3600
tttgttttttg ccttctaact aatgttaaaa attttgctca cttgttctgt tcttcattca   3660
cgactggact cgaaccgagg gtccaatcga gtacgaggtc actgttcaat ctaagatcat    3720
gcttggtcat aacattgcga ttggtttgat catttatttc gtctttaatt catttatctg   3780
ttatttttaa ttattcgtgt tgaattaaat cacgtatcat ttaaaccgcg tacaaattta   3840
attgttaccc atttttaagg taaacaacta tagacgaaaa aaaaaatata aatattaaat   3900
attatgtttc gaaagataca caatagacaa gaaaagaaaa gaaaaatccc ttataaaatt   3960
tggatttagc ccaccagttt tattgagacg tctttgtgtg ttagttaccc ggcaaaggtt   4020
atgaacctac tttatgcgtc aatgtccgaa tttattttta tcaacatcct tttggaagag   4080
cttttgatag aaatggttgg cttaattagc aatcatatta tcatcacctg cgctttggtg   4140
ttatatcatt cggaatcata tcattacctt tgaaattta aatggtttt caaagacgtt     4200
tcgataaaaa aattcctatt gtcgcagttg gaatctacaa gacgaagatg ttgatctagt   4260
gctatatttg gagaaagtgc cttaattaaa aataaaaaat tgttgatcag ttgtcttaag   4320
atttttttatt attaaaaaaa aaaaattaag atacaaagaa acacatttac gagtatatgt   4380
cggccgacta attaatgtga agttccacac ggtcaaccca cacatattgt ggtcaagata   4440
gattctatca taatcaaaag tcattatcga ctcaatttttc atatttggca tcttaagtac   4500
atgcacaaaa gctacttagg atgtaagttt ataatcattc attcttgaaa tagaacctat   4560
ttaatagtac ttaattagtt acagtagtat aatttattct ctgctaaaga gctattgttc   4620
atcaaatata tcagattatc ctttgtggtg tagaccattt ccttatttgt acttagtatt   4680
aattctggca aaagcacaaa actgggaaat gaggttcctc ttcattaatg ttgagtcaag   4740
attagtacta ctactatagc caagaaaatg tgaaatcata tagtactaac tttcccttct   4800
ccctagctac tgataaactct aattaattg agatgccaaa accataaatt tccccctcctc   4860
catcattgaa aacccctttg tccttctcccc ccagaccccc ttttcctctc tctctctctc   4920
cttttctcttt ttattagacg catattctct cttctttctc tttctagggt tttcacctga   4980
aatagtttta tttcgttgat                                                5000

SEQ ID NO: 152         moltype = DNA  length = 5000
FEATURE                Location/Qualifiers
misc_feature           1..5000
                       note = Description of Artificial Sequence: Synthetic
                       polynucleotide
source                 1..5000
                       mol_type = other DNA
                       organism = synthetic construct
SEQUENCE: 152
attataaggg aaattaaaac cctaaaaaca agattttatc tatctgcatg gtgaaggaca     60
aagaggtctt caatctcagg ttctttttgt tttttaact tgtttggata tgaggttatt    120
gagctgatga atgttttaat tttaacatag gcctacttac gtagtagtta taggttgata   180
atgatatata tttaactaag tctttgtata atgcagatcc tgaacttaat ttttattttt   240
attattttgt tgttaatgaa agattctgtt accaaatttt atcagtctat ttaattagag   300
gccaaagatt gttaggtatg tggcacttgg agtgggaaat agatattcc cattaaagt    360
gttaattaac caccaaattg ttctttaggg ctgtttgtca ttttgtatta aggtggatgg   420
ttcattatct tctctctttaat gctaatcatg cttcaccttt tcatttagta ctagcaagca   480
tatttgttta cttttattggt tattccttat caaagtcttt atcttgttgc tttttttttt   540
attgtacttt acaaaagatt tctggtatta atggaaagtg ctcatatttg gaaaaagaca   600
tggccaacaa gaaaggtgta taccccattt ctttttcttt ttctccaaat ttttttttt    660
tttttttctg tttcttgttg agttctttca tggaagaaga agaagagtag gagattcttg   720
gacatggctg catgagaatt gttattgttt tgtgcactta aataaacccg tatacataca   780
caagtagtgt tggctgtctt tgatattgca ccattttatt cccttaatttc tgccttttgt   840
ccccctcaaca aaaccatcaa agttctcaaa tagggtttat tcttgttttcc cactttgccc   900
cccacccatt agggccaccc caccaaaggg atctctctcg tgtctagtgt ttttttccaa    960
ggaccaccac tactttttttt tttttctcta ccataacttc cacaccatct tgtgatcttt   1020
cgtttaataa tgatttttgca gccatgcctt cgttcatcga aactcggtca taagcacaga   1080
ttctgagaga gtaattaatg aatgaatcag tggtgatttg acttatacat gattatggtt   1140
tttagctcaa taagcagagg gagaaaatat atataaacaa gtaaatctag tagaagaagt   1200
agaagtttta tagctagagt agtgggaaag aatgacgcaa gattagtacc aaaagagtga   1260
aggaagagct ttaatatagg gaaaagggaa gtagtaggtg atactgaca ggttgataag   1320
atggttacta ctacaagttg atgtattgac gctaactaac gcaagagacc tactcactgt   1380
gcaatatttta caagaagcga ttcttttctct ctttacttgc aagagttgtg tgttccgagt   1440
tgtatgcgc atatgaacct tttttcatac aatacaatac atatggaata gatagataag   1500
acggtgcacg catgaggcaa ttatgcaact taacatcaac tacttccatc atctttttctt   1560
ccctctgttt ctgttttctgt ttctgttttct gtctgatata ctatatgctt ctctgcctg    1620
gattttccta actctttttga taatttaggt tcccatcaat aatgtctttt tagaggagca   1680
tcatatcgat agatattcaa atattaaaacc tggcctaggg ctaggcgtc tgctaggttt   1740
ttgcattact ctttgtatat ctcatctgtg ggaccttttg tttatggaag aatatacttt   1800
tattcatctt gttgggtctt aaattcaaga tttaatatta tctcttaaaa attaatgact   1860
atcctaaaat tcttcctctt ttatttgcat ttacaagaat tgatattagt acctaaaact   1920
cttctctggg gccttttgta tttagtcctt ttatgtttga aattgacact atttaaataa   1980
aacataatct acaataagat gttcttcacc cttcgggttg cccggttggt ttggatggga   2040
tcgattcccc cgatatcttc tgggttgagc atatcgcaca gggcttgtct agtgcggttt   2100
gcattcccta tgtggtttgc attccctatg tggtttcat gctattatac atgggtttac   2160
ccagtggaca caaagtattc aatacagagt gttcacccga gaacagaagg ctgtggcaaa   2220
gattgtaacg gccgcgggtt tccccctctta caaaaaaaaa aatgttcttc cttaaacatt   2280
acccatcaaa gactcaccaa agatagctct accaagtatt attttttgat caaatggcat   2340
ttccacggtc atatctcctc ccccccccct caccccccccc ccaaagcta gtgatcactt   2400
ccatattttt tcctgatttc atcggtgctc aaatacttgt tcattcatct tcattccaaa   2460
caaaggcgaa aaacttcact attgagtgct tttttcctat tccaagtgtc aaaccctaaa   2520
```

```
cttctagtca aataatatct aagatgtata ctcttatact atgtttgtat tcattatgac   2580
aaagtatgat gagttgtaca attttcttgc ggacttagtg aaaatagagc ataatgttaa   2640
aaaaatattt acatgatatt aattagccgg attaagttta taacgttagt atatatgtct   2700
actttaggta caatacaagt cttatactct tgtcagaatt tatatgtcac aaaatataga   2760
aacttctagc tactttttt taatttttata taatataata ttggaatgaa tttaagtgga   2820
gcaaaagtga atattcatgt agtcgatata ttctaatctg tttggggctg agatgacatg   2880
attgtagtga aatattgtac cattgcattt cacactcact gaactgaaac tttggttcca   2940
cgtcggtgat catttgcatg tttcattagt caatactgtg gctgttatga tttggctgcg   3000
aggggatcg aagagagcac attaaagtat ttaatcagga tttatgagtt gaatgctgtt   3060
agttggcgga attaatagtc aaataatgaa tgagttactc gctgatatag ttaatagtac   3120
tccgtatata tgttgattct agttattggt ggtgacctaa gtaaagaaa tagatgagag   3180
gagtggtggt atgtaaagga atctaggtaa aggggtgggg gtgggggggag gcaaagttga   3240
aaagaaaggt ggaaaatcca agaatcctgc ttcctctagt aacatagcat atcctgctat   3300
tcgtgctttt gtttcctctc acaagataac tacttttga ttaattatta catttgacgc   3360
atacaaacct ataaaattaa actaatcaac gacatcctta tggaatctta cgagtccgaa   3420
cttgtcatat ataaacttttt aaagtactttt gtcacttctt aatatgctcc tttaattgtg   3480
cttagctttt tgctaaaaaa caaaaggat atccttattc caaaatgcaa ctgggagcat   3540
cttctcactt ttctttttta tgcctctgca tcatcaaatc ccacaatgcc gcacaacaaa   3600
ctcttgttac ttaagtatat attctacttc ataagaataa tgggtataaa aatttgctta   3660
ttttatgttt taaataccac cgaaaattca taagcaaatt caggatttaa atatattaaa   3720
tgaattcaac ttttaaaatt gttgcactta tatatatata tatatatata tatgcatatc   3780
caagttgagg gatacgggtt cacatgaact catattactt tctctaaacc atgtataaca   3840
atgttatatt ttttcaaaat tatttaaata tatgtgtgtg aacccattct caaaatctct   3900
tatggtgcaa ttattattgg gtgcacatct acaagtgaaa tttgcagctc aaaacctcat   3960
ctgggcggtc ttgttttccg catggagtat aactatatat gtgaaaatta ctagaatttc   4020
aaaatgaata taattttgaa atgttgtggg ttcctggtaa gagactaaag ttaaactgtt   4080
caaatataaa ttctagatcc acctcttcac aatagtgcac ccattctttt gaaattctga   4140
atctgcctct gttaataata tatatatata tatatatata tatatatata tatatatata   4200
tatatatata taaacacaaa aaaatatgtg gaaaacttta ctattaatta ccactgctaa   4260
acattttgaat ggattcttca tgccgtgtgc tcctttgttg aagaacacgt acttgggagg   4320
gcgagatttc gaataaaaaa gttactactaa taacaaacag caacaattat aagaaaatga   4380
aaataaaagg gaaagagcac tcacataaac tagaaactgt agagttggca agtaccaggt   4440
atatatgtcc ttgaatgttt tttacgagga attgagtaaa acgctagcta tttcaacaca   4500
tatataaaaa gcatcaatac caatttttatg gtttctcttt ggtgttgata gattctcttt   4560
tgtcagcaaa gttcttgcat taactatata aaatttataa taaaaatgct gctcttttaa   4620
ttgagtatac atgcagtctc ctaacatata cattctccgt cccgatatat acttgatttg   4680
atgcatttca aaaattaaat gtttgagtgt tttggtgaat tgtgcttgat atagaagtat   4740
ttaaaataag aaagaaatgt aacggcagaa tcttaagtcg aaagtcaaat taaatttgaa   4800
aaataaaaaa taatactctt gatacttact agtactagtc aatgggcagc tctttcggga   4860
ctaaccaaaa gcattattct tattgtttcc ggcatagtat taaaatgtaa caatgcttaa   4920
ttatgttaca aaattaatgt ttttgtggac ttcggaataa tttatttctg aattcgccgg   4980
tgttatcgaa aacatgggga                                               5000
```

```
SEQ ID NO: 153         moltype = DNA   length = 5007
FEATURE                Location/Qualifiers
misc_feature           1..5007
                       note = Description of Artificial Sequence: Synthetic
                       polynucleotide
source                 1..5007
                       mol_type = other DNA
                       organism = synthetic construct
SEQUENCE: 153
tgggggccct ccgcacaagg gaggagctag gggaggcaag aaaattacat gtgtatataa    60
gattaaattt tcttcttctt ttttgtgtat aggataaata tttaattttc ttaatttttt   120
tgcgtagtta ctcttttaat tatttttaac tcctctgaac gcaagtctta cctccgccgc   180
tgactcctct agagaggagg ggtcaaatg catgcaactc aaacgacgaa agggtctttg   240
cctaactaaa ggttccttat tctaatatat ccttctagaa aaggtaatag aagttgattc   300
gaatatcaaa gagagataca tgtcggttac aaaaataatt ctcaagataa tcaatagaca   360
tctctagatt ctcggactta aaagatccat ttagacacat aatcatattt tttttccaaa   420
caatcgtcga aggcagcttg ttgcacaaaa tatttcgtat ttacataagg tttaaggaaa   480
aatcgtactt caaagagtat gatgtagata atacattcta attagggtcg gctctatagg   540
tgtaaggcaa gtgtcttagg ccccaatttt gggaggcccc attttttagt aatactatat   600
atttagagg tttataattt ttttttaaat aattaaataa tatatatagt atttttttac   660
ttttcatata taaaaaagaa aaactttaa tatattaata aagtaaagat taaatagta   720
ctaaaaaata gttgtcactt tgatttgatt tgacaacttt actttttgct cttcttccca   780
aataattcct agaccccaatc caacatttca attttcatt agaaggatga gacatagtaa   840
catacccttc tcctttctt tgattcgtgc tcatttgtt tctactagat ttctttcttt   900
ctccaaaact ccaacaagcc aacaactaca tattttgaaa tcaaagtctt caaattttt   960
gaatcagtta gtcgggtaat atcattctaa cttttttagta ttattttat ttattattta  1020
ttattttatt aattttacca tgtacatatt gtttaatttt ttagaatat aaatatgtct  1080
acaagaaaat atgcatccgg atattcaaaa atccaaaga aagaaaagt tgaaaattta  1140
ataaaatctc aaaaggagt tctcgagaat ttttgacaaa taataaaaa actaaatcgc  1200
aaaatgtagg agaatattct gtagatgaac aagtcactaa ctttgagtca gatgataaca  1260
aaattcaaat tgaagaagat gtttatgaga aatctgacga agaacaaac tttagcctta  1320
ggccctatat taaactttgg ccctaggcct catatgagct tgagtcgccc taattctaa  1380
tacaagtatt agtggctact ttcacggctt gtgacttatg gattacaaac aactttcag  1440
ttacgtcaag gctccacgta gttctcaatt tatggagcat atattagatg attaacgcag  1500
ggaaagattc tgctctcctc tgatacatgg ctattattcc tcgtttagtt caaaaggaa  1560
aaagagggta gtcttgttat attattggg aatgaattat ggtttcaaac ttttcaaact  1620
```

```
taaaggattt tgtacatggt aaaacctaaa ttgacacgta acttggtact ttcaaagaca    1680
cgatctttta cgcgtatttt taaataaaga aaagatcaag tcaaaacatg ggccaaaaag    1740
aaaaacccca tgattttttc tgataaaaag ctgctaactt ttagtttgtt ttatccaata    1800
aaacatcttt aacggtctgc ctgctttagt ttaatcctct ttttaagatg taattaagca    1860
taaaatagaa aagggaaaaa aaaggtccat tggattttgg aagaaatttt aagaaagtac    1920
aagaactagt aaagtcattt tgtatagagt atgttaaaaa ggtgagtgac aattcgaaaa    1980
agaaagcatt gataagtcaa tcactaaata aaaaagcaca cctaataatc attcattcaa    2040
aaaaacaaat ttctatgaaa gataatcatt atcataagtc actgcagaaa tcccatatac    2100
agtagagtac caggatttta cgataaggtg ttagcaaact atctattcat ttttttgacaa    2160
gcattttatg tttggtcatt tgttgggaaa aattagggag aaatttaaaa atagttagat    2220
ttacaactgg tcattaaaaa tagcccaatt tcaaagtaa tcgaaattta gccacttttc    2280
atgtaaagat aaatctgagc gaaaatattg ttcaaaccc ggaaaatacg cccgtatatt    2340
atactggagt tccagcataa gtatgcttga actccagcat attatacggg agttctagga    2400
taactatgtt ggaactccag cataaatatg tggagttcca gcataagtac actagaactc    2460
cagcatatta tacgggagtt ccaacaagta taactgtccc gtaatatata ttggagtttg    2520
gagcaccggt gctccagtct cccgtatatt atacaggagt cagcaaagta taccggtcca    2580
gcataaatatg ctggagttcg tacacagatg caccgaactc acgtatatta tgcggaaccg    2640
gtctctgttg cagcaaaata gtggctattt ttcattgact tcgtaaacgg tggctatttt    2700
tgaatgacca gtccgaaaac tggctatacc gtgctatttt gacgaaaaat tatcccccca    2760
cccacccacc cacccaaacg caccttacac acattagtgc acatctttta actagttttt    2820
ggttatttt ttatttgatg cccgatattc gtatatggat ttcgattaat tagaattcac    2880
accgaaacat tcttcttag gattttgtac atacttaata gtcgaataca aaacctatgc    2940
ggaaaggtaa gggaacctat tcatccctct acagtacttg tgataatgtt atactttttt    3000
gaatttaatt tgggagacat gtcaatcttt attttgaaaa aaaaatagaa taaaaccata    3060
gggaaatgaa caatttatct ttcactccta tctcatttta tttgtcttga attttcaaa    3120
attttgaatt atatttgaa acttcttcaa tttatttct tggaatcttc agaattcaat    3180
ttaaaattcc aaaattccaa ggatttagct cccgtttggc cacagatttt ggcttcattt    3240
ttttaaaaaa aattttgaaa acattctttg tttatgcaat atgatcatgt tttaggggaa    3300
aaaaattaaa aaaaataaaa aaaaatcaaa ttcccaaaaa ctggttaggc aattttttgga    3360
tgatattttt tcttccactc acaaaacttt aacatgtcca aacacaactt caacttcaaa    3420
aattattttc aacacaattt taaaaactct tttttcaagt ttcaatcaaa tctatatccaa    3480
aatgttagct tagtatcaaa taagtgattg aaatcaaatt aaaatcgagt ggtaaataaa    3540
atagaggaga gctcggtaaa ttacaagagt gcggtaaatc tttctccctt tactctcact    3600
gtagcctatt ctatctgttg taactaataa gtaactgagc tacggaaaaa gtgcctagac    3660
ttttaacttc acaagtataa taaatagaag tcaattctt cataatattg tttccatcct    3720
atcaaacaga ctttgtctca ctgaccttcc ttctgagtgt gtctttata tgtcattttt    3780
agtgaatcca tatgatttag agactctaat attccacatg cgggtcttaa tttggtgtat    3840
atgtatatgg taataatttt tgttaggtag ctgtagtatt ctattattgt tatgtattga    3900
ctcatcatgt aaataaagcc ggttagataa ggctagaaaa atatgagtat acctagaaat    3960
tattagcata ttgtttggaa catgtcaaaa atttcaatga cctagctaga gctgtcaatt    4020
agtcaaataa ctttattaat atttacttat gaaaacactt tgaaattctt ggagtttaag    4080
ggaaagacta ctgactaaaa aacaaagcaa aagtctatgc attactatac tatacacagc    4140
acagcatttt ccaatagtat ttgagatgaa tctccaatca gctactgttg ttctttttctt    4200
ttctttattt agtttaagtt ttatgtgttg atggtataca aattatttgc acaatcaaat    4260
ggcttatctg gataatatag gtaaacctct tgtaatcact aattggtaat ctggtaaaaa    4320
taacactatt tctattccaa tttatgtgat caatttcact agacaaaaat ttaagaaga    4380
aataaattt ttagaacttg tagtcataaa caagttgtaa catttgtatg gctataattt    4440
ttttaacttg tgatgttaaa catgtcagat tgtttgtgta gctataaaag tttttcatta    4500
ggcgtaaaat taaaaattta gattaaatta ttattaaatt tagaaagagg tcattttttt    4560
tagcgaagta aaaaagaaat cggttcacat aaaccgaaac atagagtaag taatctgtta    4620
tgacaaatta aaaattactt gtagtgtaaa aaaatcttta caacattcgt gtatatactt    4680
aaatcttttt tatttttggg caagagatag ttgttcagca aaagtaagtt agaaatggt    4740
ctgtccttct gactttgtaa ctctgaaatg aaaattcaa aatcccttct attttctttt    4800
tccccccccc cccccctcac aaaccccaac tcactcttat ttaataaaaa gctctactta    4860
gaaaagacac ccttgtccat ctgtctatat aggtagaatg agagtaaagg agaaaacata    4920
tcctcctctc catttctgta gacaaagatt ctcaaagaga aacaaattaa acactagaga    4980
gtgagagagt gctataagaa aaagaat                                       5007

SEQ ID NO: 154        moltype = DNA  length = 5000
FEATURE               Location/Qualifiers
misc_feature          1..5000
                      note = Description of Artificial Sequence: Synthetic
                      polynucleotide
source                1..5000
                      mol_type = other DNA
                      organism = synthetic construct
SEQUENCE: 154
agaagaaatg actgttgaaa agaaaacaaa tgcaagtacc attaggaaga tttgaaaggg     60
cgtttgggta tgggggttgc caagaagatt cagactttt ttggggtttt gtgtagttgt    120
ggtagaatta ttattgaatg aaaaaaaaaa acttcctgta ctttaattcg tcagtacata    180
ctacatacta ctacaaagta gttaaaagcc tattctattt gtgctttttt tttcactcga    240
tgttcaataa ttatattggt ttttgattaa atttgaatttt gagcaaggaa gatcaacatt    300
ggagggataa attgtttcct aacgaaggcg attacatact tagaacttga actcaatatc    360
tctaattaaa atgaagtaa tacttataat aactccaaca caattcttat tgttgtgcat    420
ttctttataa aatatgtaaa taatgggtca tatatattgt ttacctttc tattcatata    480
catagatttt aaattaatta tacacatata tataatacat taattattca tatattatat    540
ttttgctagc tattttagt ttaagcgatt tggtaggcga ctacttgggt taattcttt    600
ttttttaatat atatatcaaa ataatgaagc tgtataaac acttaaaaat catatttgaa    660
aggtattaaa tacgacttag gagagttctt aaaccatttt ggaaccttgt ctacgtactt    720
```

```
ttatgcaata gctgtttttg tttgtctctg ctaaaaccta tgctcccaa ccgtgcacca   780
atcaacttag aagttagaac tcagaaataa atgtaactat actccacaga aagttaaaaa   840
gttttactgt taccattcac tcaaggatca gaaactgaaa gacaaatgaa tcagtgcttc   900
actgttcttc actaaaagaa atactgttta cattagtttc aaaagagttt aatcataaaa   960
acaaatgtac cataaaaagg ggagattatc aacctgaaca tgaaacagaa catacgttat  1020
atatcaatct atatacggtc gagatcggac tcgtctatta cacgacagat cgggattgaa  1080
acgtaacagt tttgaagatc aaccccgggt tccgtcggac cgaggtacaa ggtcagaatg  1140
cccgttctcg agaacatcga gtccatgacc ccagaatcaa ccctgacccc aaatgagctc  1200
gaggaaacat ccggataacg gaaggcgaaa tatccgtaac cggtcgggta tcacggccatg 1260
aatttcggca cgtaacaatg agaaaccggc taattagcaa atcatggaat tttttacctt  1320
ttatagaatt gtaactaaag tgggattccc ctactatgta aaggggtct gactatttgt   1380
acgggacatt cattaaacgc atcccaaagt aatataatat tattttcttt ttgtaagcta  1440
ttgttctcct gtatctgata ctatttgaat tgcatcaagt tcaagtgaga ctcattttt   1500
caaggctata attgttcaag tcgcacggtt tgaatttatt cgatcattgt tcgctttaat  1560
tacaattcaa ttcatcgctt tatgtcaaat taatccacat atccttaaaa ccacttacaa  1620
atttaattgt tatcaaattt taagggtaaa cagtttggcg ctcaccgtgg agctaaggat  1680
aatagtggtt gtttgatata gattttcata acacacacta ttttacaatt gttcttcgaa  1740
gtgtctctca tttcaggttt aagctcaaaa tgtcaaactc acaattggca cccctacctg  1800
cacacaatga gtctggtcac catggtgaaa ataacaacat agcacctggt aacgaggtac  1860
cgcccgctga tccatcagaa atttcaatcg cggaccgtt ggacgctaac tcgcatgtgg   1920
ctatcgacat gttacagtct caacaggcga cgatagctca gttacaaaac caaagccgca  1980
caccgagcag agttgaactc gatccgtccc ggaaaatcac ctgcagggaa gaaccgtccg  2040
cggagaggtc aaatggagat gagtcgggga ctaaccccga gatcataaaa atgcttgagg  2100
aaccgatgat acggattgaa tcaggggaaa agaaaatcga ggcaaatgac aagaaggtaa  2160
aaacttacaa tttcacggtc aaccaaatcc cgggagcacc gccggtactg aaaagcttgg  2220
attccaagaa gttcgtgcaa aaacatttcc ctccgagtgt ggccccgaaa tcgatcccaa  2280
aaacatttat atgcccgaga ttcttaagta taatggacaa accgaccaaa acgagtatgt  2340
cacttcttac acatgcccta tcaaaggaa caacttagag gttgatgaga tcgagtctgt  2400
tttgttgaag aaattcggag agaccctgtc aaatggagct atgatatggt atcacttacc  2460
tcctaattct attgactcat ttgcaatgct tgcaaactct ttcgtgaaag cacacgcag   2520
ggctatcaag gtcgagaccc agaagtcgga cctcttcaaa gtaagacaga aggataatga  2580
gatgctcaaa gagtccgtgt cctagtttca aatgaaacag aaggacctac caccggtcgc  2640
tgatgattgg gccgttcaag cttttcaccca aggactcaat gttcgaagct cggtggcttc  2700
acagcagttg aagcaaaatc tgataaagta cccaactgtt atttgggcca atgtgcataa  2760
ccgctatcaa tcaaaaatca aagtcgaaga tgatcaactt gaggctcttt ccgggtcggt  2820
ttaccctgtc agactcgtcg acagaatcaa gagagatatc gaccgtgaac caaggtcaaa  2880
cgtagatcat tactagccat atgatggaga ttggaaaagc aataggtctg ggtgaagttc  2940
tacacagaat gaaaagagaa atgatccagg tcagagcact cgaggactcg caagcaagaa  3000
cgacttcgac aggcctatca ggcctaaaga agcaccaagg ttatcgaaat aaactttaa   3060
tattgatgcg gctgccatcg tatcagctat cagacgcatc aaagatacca aatggcctcg  3120
acctttacaa tccgatccag cccaaaggga tcctaaccaa atgtgcaaat atcatggcac  3180
ttctggccac agaataaagg attgtcgacg gttaagagag gaagtagccc ggttgttcaa  3240
taacggacac cttcaagaat ttctgagcga ccgagccaaa aatcatttta gaataaggga  3300
ttctaacaaa tagaccgaac cagaagaacc tcaacacgtc attaacatga tcatcggtgg  3360
agtcgatgcc cctcaagtgc tgatgttgaa gcgcaccaaa gtgtccatta caagggaaaa  3420
acggactcga gattacatat tagaaggaac cttgtctttc aacgacgagg atgcagaagg  3480
gatcgtgcag cctcacaatg atgcattggt aatatctgta ctcataaata aatctcgagt  3540
taagcgtgtg ttaattgatc caggtagctc aaccaacatc atccgattga gggtcctaga  3600
atggcttggc ctacaagatc aaatcatgcc tgcagtccga gttctaaatg gattcaacat  3660
agcatgcaaa accactaagg gagaaataac attgccggtg aataccacca gaaccatcca  3720
ggaaaccaag ttttatgtga tcgaaggaga catgaggtac aacgctctgt tcgggaggct  3780
aaggatctac agcatgaggg cagcacccct cgactcttca caagtgttaa agttcccaac  3840
gtcgggaggg atcaaaacaa tctacgggga gcaaccggcc gcaaaagaaa tatttgcagt  3900
cgaagaagag atcccggtat agacactagc aacatcaaag gaaccgagtt cggataagaa  3960
ataataggct aaaatagcaat tatcgacacc agccacgacc caatcggata aaaaggggac  4020
tgatgaagat gatgattatg gggttcccag atctttata gtccctgatg attctgacgc  4080
caccaaatca atggtcgagg agctggaaca ggtcacatta atcgaacgtc tacccaatca  4140
gaaggtatac ctgggcacga ggttaacccc cgagcttagg aaaaactcat tcaatttctt  4200
atagctaaca tagactattt tgcttggtcc catattgata tgacagggat cccaccggag  4260
ataatcattc aaaagctgag cctgacttg aaattctacc cagtcaagca gaaaaggaga   4320
ccccagtcaa aaatcaaaca tgctttcatc aaggacgagt atttgcacaa aactttcaac  4380
atattgaaga agtacaatat gaagctaaac ccggagaaat gtgcattcag agtcggatca  4440
ggtaaattcc tcggattcat ggtatccaat cggggaattg agatcaaccc cgacaagatc  4500
aaatccatca aagatatcac gatcgtggac aacgtgaagg ccgtcaaag attaatcggc   4560
cgcatagccg ccttgggca atttatctcg agattctcag ataaaagtca ccggttcatt   4620
tcgctactaa agaagaagca caacttttcg tggaccccgg agtgtcaccg ggacttggag  4680
gaactcaagc ggagatagct gcttcacaca acaaaggcaa acgaacaact ataccctatc  4740
ttggcagtat cggagatagc ggtaagtgga gtcttggtcc gggaagaaca aggtacacaa  4800
tttccaattt actatgttag caggaccata gtgaggccta cccttcaccta  4860
gaaatattgg cattcacttt gctaagcgcg tctaggaaac tgaaaccata tttctagtga  4920
catcccatat gtgttgtgat taccaaccaa ttgtggaata taatgtataa acggctactc  4980
tcgggatgat tggccaaatg                                             5000
```

SEQ ID NO: 155        moltype = DNA   length = 5002
FEATURE               Location/Qualifiers
misc_feature          1..5002
                      note = Description of Artificial Sequence: Synthetic
                      polynucleotide
source                1..5002 mol_type = other DNA
organism = synthetic construct

SEQUENCE: 155

```
aatgcagcct cagtcttcaa cataaaaaat cacatgagta tataagatta attttttttt    60
ttttgtatat atgttagatg ttgaatttct tagttgtttt gcgtgtgttt tttttttttt   120
ttttttgacct ccctcggtaa aagtcttacc tccggcaact gtctccgcga gagagaggg   180
gtctaaacgc atgtaattat tcaatgattg aaggatggtc tttgcctaaa tactaaaggt   240
tccttattgt ataggtcata ggtgttgatt cgaatatcaa agagagattc ctgtgggtta   300
taaaagtaat tctaagataa taaatactct ttttagaggt gttgttttac tgtaaaatac   360
gtatttggtt aaagtgatag acatatctag attctcagac ataaaagatc catttagaca   420
cataatcata tttttgccag atagttgttg cagctgaaaa ttggagcata tacttaga    480
agtagcataa cactttactt ccatatagtc ggatggaaaa ttggagtatc atatcttctt   540
ttaattcaca gttaaatctt taaacatatt taataaattt tttaatacaa atataaagtc   600
tatgcaaaag ttattgggtt ggtccaagcc cttaatttcg atctctagct ccgtccccgc   660
atataattct aaaacttctg cttctcctat gatacatggc taatgtttat cgtttagttc   720
aacaagaaaa agagggtagt cttattatat tatgaacggc aaaggtccaa atatgccctt   780
gtactatacg aaattgagta catttgccat ttgttaatac tttagctcaa atataccctt   840
accgtcacgt agttggtcca tatacactac tagaaatccg gtaaaaccga ccaaaaaaac   900
cgaccaactt tggtcggtaa tggccaataa ccgtccaaaa cacgaccatt acgtgtggac   960
ggtattttag gggtcggaaa ggcataccga ccaaagttgg tgtaaattac cgaccaattt  1020
tggtcggtca attaaattaa aaaaaaaccg accaaagttg atcggtattt taattatgta  1080
atcaaaagat tgaccatctg ggaatcgaac cggggtttgt attgtggcag gatactattc  1140
taccactagg ccattagtgc attttgtttt aagactgttt tttatttgat ttatactctt  1200
taattgtatt ttcgcacgaa aataaccgat caaagttagt cgattttatt aaaaaataaa  1260
attaccgacc aaagttggtc ggttttttaa aatgaccggc cgaattaacc gaccaatttt  1320
ggtcggtttt ttaatattaa tttttatta ttttaattaa aactgaccaa aattggtcgg  1380
tttcttgaaa aaaatttccg ggactcgaaa atagttttt gcattttct ccaaagaaaa    1440
ccgaccaaag ttggtcgatt tcgtaaaaaa aaattaaaaa taaatatttt taaaaaaccg  1500
accaactttt gtcggttttt tggtcggtgt tttgaccgac caaagttggt cggtcgacct  1560
tggtcggttt ttgccgaatt tctagtagtg atataccctt agagttacac aattggcaca  1620
tatatgccct tctcaaaacg aaattcaccc aaaaattatg gtttaaactt taaaataata  1680
aaaacatctc aaactttaac aatactcaaa agaccaaaat atttaaatta tttctaaaaa  1740
gataaatttaa tgattaaaag cctagagttc aagttgtagt gttataaatt tgagttgtta  1800
gtcttttttca tcttttttcag ctggacattt tctattttt ttattaacta tgtaaattag  1860
gggtgtacat ggaacgggtt ggatcgattt ttatcaaaac taaaccaaac cgattatatc  1920
ggtttgaatt gttcggtttt attggttttt tcagattttt tgttacataa atattatttc  1980
aatcttgctt tgttaaattt tttagaacta aatatatgtt cagtaaaact taaaaaattg  2040
acaaacatat gatctatctt gattaccttga tgggagaatt ttcttagtaa ttggaattca  2100
tgagttttgt caagtgaaat tggtgacgaa aatagagaag acatcagtaa ttgaggaaat  2160
cggataaggg agaagaaaa agaaaaaag aaaaaagaa gaaagaaaag agaaggtaa   2220
agaaaaaagc actaataaaa aggaaatagt atttgtaata tactttaata caattaacgt  2280
aagagctaat tagtttgagt ggattccgtt ttgaaaaggg catacatgtg ccaattatat  2340
aactctaagg gcatatatgg accaactatc tgacggtaag ggcatatttg agttaatata  2400
ttaacgaatg acaaatgtgc tcaatttcgt ataatacaag gacatattac attttcccta  2460
ttatgaaatg gttcaaactt aaggattttg tacatggtaa aacctaaatt gacatgtaac  2520
ttggtacttt ccattgggca aagacacgat cttttacgtg atattttaaa tcaagtaaag  2580
atcaagtcgg gccaaaaaga aaaaaaccca tgatttttta agataaaaag ctgctaactt  2640
ttagtttgtt tcatccaata aaacatcttt aacgatctgt ctgctttagt ttaatcctct  2700
ttttaagatg taactaagca tgaaatagaa aaggggaaaa aaaaggacca ttggattttg  2760
gaagaagttt taagaaagta caagaactag taaagtcatt ttgtatagag tatgttaaaa  2820
aggtagtgaa caattcgaaa aagagagagc attgataagt caatcaataa aataaaagca  2880
cacctgataa tcattcattc agaaaacaaa tttctatgaa tgataatcat tatcataagt  2940
cactgcagaa atcccatata cagtagagta ccaggatttt acgataaggt gttagcagac  3000
tatctattca tttttttgaca accattttac gtttggtcat ttttttgggaa acgaactctc  3060
ccaacattct tccaaattac cccacgcacc ttactgtgca catcttttaa ccaacttctg  3120
gttattttt cttttgatgt ccgatattcg tatatgaatt cccattaatt ctaagttgca  3180
ccgaaatggt ttttatcaag attttgtata tatttaatat tcgaattcaa aactaatggt  3240
cgaaggtgga agatcgtatc catcccatca taatatttgg ttgtaatat cacacccttt  3300
tgaatttggg agacttgtca atttttattt tgaaaaaaga aaaaaaaaag aaatagaaac  3360
taaaaccata gggaaatgaa caatttattt ttcactccta cctcattta tttgtcttga  3420
attttcaat tttgttttga aacttcttca gtttatttc ttggaatctt cagaatttaa  3480
tttgaaattc caaaattcca aggatttagt gtcaaatcag tgcttgaaat taaatttaaa  3540
acgagtggta aataaaatag aggagaactc ggtaaattac aggagtgcgg taaatctttt  3600
ctccttttct ctctttggag cctactctat tctattgta ctaagtaact taactacgaa  3660
aaacgtgcct agactttaa cttcacaagt ataataaata gaagtcaaat tctttcataa  3720
tattgtttcc atcctatcaa acagactttg cctcactgac tctccttctg agtgtgtctt  3780
ttttatgtca ttttagtga atccaattga tttagagact caaatattcc acatgcgtgt  3840
cttaatttgg tgtatataatg gtaataattt tgttaggta gctgtagtat tctattattg  3900
ttatgtatta actcatgtaa ataaaagccg gttagataag actagaaaaa atagagtcta  3960
cttagaaatt attagcctat tgtttggaac atgtcaaaaa ttcagtgact cagctagagc  4020
tgtcaattag tcaaataact ttattaatat taacttatga aaacacttgg ggattcttgt  4080
agtttaaggg aaagactact gactgaaaaa caaagcaaaa gtctatgcat tactatatta  4140
tacacaatac agcattttcc aatagtattt tagataaatc tccaatcagc tactgttgtt  4200
cttttcttt ctttttttagt ttaagttgta tgtgttgacg gtatacaaat tatttgcaca  4260
attagatgc ttatctagat aatacgtgta aatctattga taatcattaa ttagtaatct  4320
ggtaaaaata atattgcttt tgttctaata taatgtgata tatttgactg ggtacgaaat  4380
ttaaaaaaaa ataagacata tagaacttgt tgtcttaaac aattcataac atttgtgtgg  4440
ctataattct tttgaaactt atggtgttaa acatgtctaa ttgtttgtgt atgtataaaa  4500
gattctcatt aagcgtagga aaatttgaat taaattattt ttttaattta aaagagatc  4560
```

```
actcctttta gagctgactt aaaaagaaat tgattcacat aaactcgcac ggagggaata   4620
agtaatatac tatcaaaaat taaaaatcac ttgtagtgta aaaaaatctt tacaccaatc   4680
gtgtatattc tcaattttt ttttttttt ggcgagaggt agttgttcag caaaagtaag    4740
ttagaaatag gtctgtactt ttgactttgt aactctgaaa tgaaaaattc aaaatctctt   4800
cttttttact gttttaaaaa ctccaactca ctcttattaa tataaagctc tagttagcaa   4860
agacacccctt gtccacttgt ctatatagca agaaagagag taaaggagaa aacatattcc  4920
cctctccatt tctgtagaca agattctcaa aaagaaacaa attaaacact agagagtgag  4980
agagaactat aagaaaaaga at                                           5002

SEQ ID NO: 156          moltype = DNA    length = 5000
FEATURE                 Location/Qualifiers
misc_feature            1..5000
                        note = Description of Artificial Sequence: Synthetic
                        polynucleotide
source                  1..5000
                        mol_type = other DNA
                        organism = synthetic construct
SEQUENCE: 156
agaagaaatg actagctgtt gaaaagagaa acaaatgta agtacaccat taggaagatt    60
tgaaagggcg tttgggtatg ggggttggca agaagattca aacttttct ggggttttgt   120
gtaattgtgg tggaattatt attattgaaa cttctttact tcaatttaaa tcgtcggtac   180
atattacgta gttgtagtaa aagcctttc cttttttgtc ttttttttt ttttcgtgtt    240
cgtattaaga cttcattaaa tccaaatttg cataggacg gtcaacatta gaggaataaa   300
ttgcttccta acaaagacga ttttatactc aagagttcga gcccgaaaaa cgacctctgg   360
ttaagggtaa aaatagtaat tacaataact ccaccacaat cctattggt gtgcatttct    420
tcattaaata ctccctccaa tccacttaa ttgatttgtt tttggctatt tttatatata    480
ttaaggaatt atcttttagc attaatcaat aatgaaattg accatattaa ccttttagtt   540
cattggaaat ataacaaata ctcctaggct ttttaattca agagcaactt ttaaatccga   600
atttgggcta agaatacaag cttgttcttt tttatctgtt tttcactcgg tgtacgagga   660
ctcaattaaa tccgaatttg agctaagaat acagacatta gaggtaatat gcttttctaac  720
aaatgtgact caatgttcag actcagaact cgatatctct ggtaaggatg acatagtact   780
tacaataact ccatcataat ctttataggg atgtatttct ttataaaata tgtaaatagt   840
gttatgattt tttgtatcaa aaatgatgaa gtataatact cttaaaaatc atactccatc   900
cgtttcaatt tatgtgaacg tatttcttt ttagtctgtg ccaaaaagaa tgacctattt   960
ccttatttgg aaataattta cctttatgca atgatttata gtcacacaaa atatatgtgt  1020
ctcatttta accacaagtt caaaagtctt ctatctttt ttaaactctg tgcccagtca   1080
aatgagttca cataaattaa aacggaggga ataaaaaaa tgtattaaag actcttagg    1140
agagttcatta aaaaaccatt ttggaaccat gtctacgtac tttatgcaa taactgctta  1200
agtttgtctc tgctaaaacc tatgctcccc aaccgtgcac caatcagctt agaaatttga  1260
actcaggaat aaaatgtaact acactccaca gaaacttaaa aagttttact gttaccattc  1320
actcaaggat cagaactgaa aaacaaaaga atcagtgctt cactaaaaga aatactgttt  1380
acattattt caaaagagtt taatcattaa aatagatgta ccatcagatt agctaaaaga  1440
taaataatcg ttaaaaaaag gagattatca acttgaaaat gaaacaaatt atatgttata  1500
atatgtcaaa atatactgac agtataaaaa ctcgttaaat gtgttaaatc ctatgaaaaa  1560
actgcccaaa taaatatttg agcttaggtg tcaaatgttg tactcaacaa caataacaac  1620
aacgcattag gatcctacta gtggggtgtc caatgttgta ctattgaaca ttattcaact  1680
aactttttgtt aggtgttcct gtagtttagt gaaattaaag tccactgttc ccctatatat  1740
taatcccaaa ttaattaatc aagtgcagat aaaaatttct catttctat taattttatta  1800
agtgtaacaa actaaagaaa ttcaagaatc ttgaatgatg agaaagagtc atgcatgtag  1860
aaaaatagat aataatacat ggaaatatat atgtatttgg ggatttgcat ggtagctcaa  1920
agattattgg aaagtgacag gaagataaat caaaatctca gtgttatttc aaaaaataaa  1980
ggcacagatt atttaaataa ttgcagccaa gtttttataat actatgtggg aggggacaga  2040
gatcaatcca tgtacgtgca tggcaatat taaagtaagg gagaaaaaaa tattaagtta  2100
attgatgatt aaaaatagta aaatttcaga cgtatatcac ggcaatgaag agtttgatct  2160
ttaatatctg tataatggtc cataatatga tggataggcg ttgtttatga tatgattgat  2220
tgatcattga tcattgacta ttgtttcttg aataattaat cagtatggga aagggtccca  2280
ttaaagttga ccatttgctt agcaatatta tcttaggtaa gctccatatt agttaatcc    2340
acttgcgaat atattccgtc ctcgcaaatc aatatttaca attctttttt ttcagttttc  2400
tatccggtat ctgatacttg cattggtgtt cgacaaaatc tgtattcgcg tcaaaaaatt  2460
tcatattatg gggcaaaatg ctccataata aaagcgactc aatattaggg ctcgaaccaa  2520
tggcggaaac aagatttta ctaagggaat tcaaaaaata aaaacgaaaa cacatgaaga  2580
accctcaggga attcaacatc taatataaat atatgaaata aaaatttgat tctattgtaa  2640
tttgatatac agtgtaattt acaccgtagg ggatttggct aaacctcctt ccgcgtacct  2700
agctccgtcc ctgactcgaa tccgaggtat ttggttaaaa atgaaagagt acttcctaaa  2760
acctcgtcgg ttttttgttc taatcaatct ttatattgtt aaaacataaa acgttactt   2820
ccttttcttct tctttttaagt tttgaaaatg ataactactt ttgtttgact aatattttgt  2880
agttttttgat gctaatcaat tttgtaaaaa ttactgtact tcaactagcg tttactaccc  2940
cacctcactt taaaaaaattc cctaaagaga taacttttttg attaattcat aaactaaatt  3000
gaagaactttt tcaaatgaga gtaagttgaa aatgcatatt attattgagt atataattgc  3060
aattttgcat aacttaccgt aaaatgttct tccttttaat gatttgttaa tatgggaaat  3120
ttgaactttt cttctcttga aattgtattc ttgtcccatg gtttctatgc aatctcaatc  3180
atcaaattgc aattattttt ttttgttttt tgttggcaaa ttcaggagag cttaggtcag  3240
tgatatatga aaaactattt tttactctta tttattttac ccttacttta ttaaagaata  3300
aagtccaaga cgaatagacg atgtacaacg caaatgtaaa aatacaaaaa aatgtttacg  3360
acttcttctc tatttatttt ctacttaatt tacttattaa acaagtactt acttgttaaa  3420
ctagctaatc tgaccaacaa tgtgaaatg tttgacatta tacatcttga cttttttattt  3480
ctctattatt ttctcgatgg ttacttcaaa tcatagattt gctaatctga ccaatatcgt  3540
ttaacttcaa gtagaacgaa atgaacattt caaggttta gaaaacagtt gaaattggac  3600
cctaaaaataa ataaaatgaa gttattaata ggtttacacc ccaatcttat ctaatgctta  3660
```

```
aaacacatag tgtggagcgg aattcattgt cttcacatta ttgtacatta atcatatttt  3720
cttaactaat tctgacgatt atttgtgttc atcctaataga aaatgcaaaa gtcattttcc  3780
ttaatacttg gcatctttat agtcaaaata taactcatat ccaatgcaaa agtacagtca  3840
tgcacaacaa tttaaagtat taggagcatt tattagtttc acttgtttat taatgtaaaa  3900
gtacgtagta aaatgaaagg taaactcaaa aatatcacat acatatttta atttgatcga  3960
tcaagtcagc ttgagttctt gaactttgtg aaagcaatat atataatatg aatgaaacac  4020
ttatgcattg cgacattgag agttaattta agaaaatttt accccacaag ttctagcttt  4080
gattgacagg cctagccaca aagtaagata tgcacaattt atcttagtgc ttctatgttg  4140
tgtatcaaaa ctcaacaagt tatgtttagt actcctatga tgtttatcct aatttaaaag  4200
tcaatattaa gtaaataaaa ataaaaataa attaaagtct atgtatgtat tctcttacca  4260
atgcctatag tttaggccca gaacctacca tctccctgcc aacccactac tcttactggt  4320
tttgcagaaa tagttgctga tcaaatcatt tatccaaaga tctagtttca accttaaaga  4380
tggaaggttc gagtcacttg attttgaagt attgacttaa tgatgtactt tctttaacat  4440
aaggtgaaat tagttgtgga cttcatcgat aatctgtcgt taaatcgttt gtagctaact  4500
aaaaatctat cgcgaaatag gattaacgac gaatttttct gtttaactag agaatttttt  4560
cgtcgctaat taattttttt ttttttgtagt gagtacatat tagaaagaaa aaaaaaaaaa  4620
aaaaggaaag tgttgaagtc gtaatgtgta caacatatga agtccataac ctgccaggta  4680
caattccttta aagaattaaa atggaagaag aaaggtaaaa gcaaagattg acaacaattt  4740
ttttgtggct cgatgaaaat tattagtgtc aaagaaagaa ataaaggtaa aaaatggcag  4800
aggaaagaat caccctttggg aaatagcccc ttcacaaaga ctagagtcca aaattacaaa  4860
catcaaaaga tctttggtcg gttctactgt ttgcatctct tgttgttgct ttcgtcttgt  4920
gaaaaatcat tgaggtacta tgtaaattta taatcagttt tttaatctta ttgaaagttt  4980
catagtgaga aggaatttat                                              5000

SEQ ID NO: 157          moltype = DNA  length = 5000
FEATURE                 Location/Qualifiers
misc_feature            1..5000
                        note = Description of Artificial Sequence: Synthetic
                        polynucleotide
source                  1..5000
                        mol_type = other DNA
                        organism = synthetic construct
SEQUENCE: 157
gtactatcag aaaagattta aatctaacct tcgttataat ttgagtccaa atataccct   60
gatgctatac tattggttca aatatattct tttccattaa gtttgtccaa agtggacatc  120
caatcctacg ttgcactgac atttgatgat gtgggtgtca catggcttgc cacctcagcg  180
ccccaaatcc atatattaga gactaaaatt tgaaatacaa taattttttcg taatggtggc  240
aatagtgatg gaagggaaga aaattttagt ggtggaaaaa aaaaatagaa ggaagggta   300
aaataggtta tgagcgctga ggtggcatgt cacctcagtc ctgcactgag tttcgtagga  360
ttggatgtcc accttggaca aacttaacag aagatgggta tatttaaacc aatagtatta  420
cggcaatgat atattttgac ccaaagtata acgaaagata tttactcata gtacaacgat  480
acatttcgtc atttaccgaa tttcgaattt acattctcaa agaactcata actttgatgt  540
taactaatta agtttaaact ttagatcacc ctacaattgt tgggagacat atcaaaccca  600
taccattgat atatataaga actttgtaaa actctttttt atatgttagg gtatgtacta  660
gctagcacca tggatagtgc gtgtcaccat tttacagcaa ataatatgcc tcatgaattg  720
gtagggaaag ggtctttaaa gttgaagtgt ttttttcttt ttcttggtag gtagtggggg  780
aggggaaaaat aagggggacaa aacacaaaat caatttgaat gcaatttaca caagtctcca  840
tatattgata tagtgctgaa aagaaatata atgttctaag gcaaagggga taacacttag  900
aaattagcca acctcatgtt tcttacaagt ggatgagggt tcgactttgc atttagcatc  960
accttattct ctctaatttt caacaggaca tgttaataaa aggatgacaa tccagattga  1020
caaagttatg aaagtgaaag cactgtaaca tttcattcaa tcatgcaagc atctcccgtt  1080
aattttctta tcttttggaa tattacgaaa atcaaaccaa cctttttacg tataagtttc  1140
taatgacatc agggggactc ctgagaaata ttctcactca aggtcgaaaa ggacccttta  1200
ataatgatca atataaattt ttttttataat ggtcctttaa tattcgaatc agctcgtaca  1260
catctcaatt tttgtaatga gtacatgtta tccccgacta tatatata agataacttt  1320
gccctcaaga atttatatcg acagataaga gatcacataa tatttttgtc tttgttggaa  1380
tgtaaactct acttttatga aattttatta actggtaggt cacatcctac agagcttta   1440
gtcaatgtta ctattattaa gaaggaaaaa aagaagaagc aaaaggaaga tattaacaat  1500
agtataacaa cattcataaa cgtgatttag gaaataaagt atggaaaaat gaatagtgaa  1560
aaaaagtcaa gtacttagga gttaaggttc gtaagttgat gggacagatc gcggtggaaa  1620
aggaagataa gcttcaaaga tacaaaagca aagggggtt gggttgagat tctgagttgt  1680
gattaatacc actcatgaac aaaaagttat gtcatgcac cattcatgag attaagacaa  1740
cggtggaatt aagaattta ttaaagggag tcaattttta aaaaaataaa ttcatcaaaa  1800
agttaaagag tatcaatata tatcaatata tatatatata tatatatata tatatatata  1860
tatatattta tattaaatta tctaattaca cagtataatt tttaacgaaa gggtgtcgat  1920
cgacaccctt gaatgcatgt ggccccgcca ctgcattcag agccaactct cccccaaaag  1980
aaaaggcgca aacaaaagg atttgaaaca gtagttgtgg aggtgattca gccatgcttt  2040
catgactcat caataccctac tttttatgtt tttctttttc cttttttattt tcaggatata  2100
aattttgttg taaactgata taaagaaata aatttactct cttcaaccta ttaagctttt  2160
aggtgaaatt agtaagtcgt acaatttaac atggtgtaga attgataaa gtcgtagaca  2220
ctcataggtg cactttgtag tgaaaattag gagaaattag ggtcaaaat ccaactaaga  2280
taaagatgc ttggtaattt cttcacatct gcttagaaat aatctgctta aatttggatg  2340
agcaaagtta tccaatacaa gtgttgctga gaaataatcg gtatcaata gaatagtcga  2400
gatgcacgca aataagtttt gactctactt taacaaaaaa acaataggc agatgtatcc  2460
aaaattcata tcttatggtc actcgtcaac aaaaatattc cttatgttta gtccaagaaa  2520
aataaccata cccaaatata agggtttgtt gaagacggaa atatataaac aaataaacaa  2580
atatcatcat atctccgata gtttaaaatt ttagattgga tatttcacac aatttatcaa  2640
aattttcaaa aaaaaattct acttttttctt gcttggaact tggaagggga aggggtggtg  2700
gtggagatag ggcggggcat cttctatcta gtctatgtga ttaatataac aaaacaaaaa  2760
```

```
gggcgaggca aaaacatgga tgaatggtgg tccttttcta tatttatatg gattgttacg 2820
atacgtcgat ttcactttgc aaaataccaa ttagattcat ttagttatct ttttgatcac 2880
tctgctttta ctatcatata tatataggag tccttccacg tttcgcatgt gtcattgttt 2940
atattttcca tggtcttcct tccaaatggc taaaaaaatt tgacacagtg gtcccaaaag 3000
tttatagaaa tagaattcaa cagtgaggca tacctacgta aattctattt tacatcttca 3060
tcgtataaaa tagaatgtgt tataaacttt acctcgtgat gcttacaagg ggtgaaaata 3120
taaaagcact ttatagattt acaagagtca caccttgatt tatcctaaga ttttattttt 3180
ttacatgcca aacaatgaag tatgggagat ccaattggaa taacatcaaa tttaataaaa 3240
ttcgaaatag tcagagagct gtctactgag gtatattgaa acttattttt ttttaataga 3300
aaatatcaaa tacttagcaa tatattaaaa tgtttcataa attacattgt ttaaaccaag 3360
cgttgaaaca tatgctgata cgaggtaggc ttattgatga atttataagg gcctcattgg 3420
aaaagacgat ccaaagcaat gggctaaaaa ttggcccatt ttctgccacc cagtgtatgg 3480
ttattactag tttcacccac acagatttgc acttcattag aggacaatgt tgctgaattt 3540
gaaacataag tccatttctc tccactgtac agtccttcct ggagtccaat cctgaccata 3600
tcttcatgat tttatgtaat gtggtgaata agcaaagttt catgttatgc tttgtctcat 3660
tttatagcaa attcatttcc tcataaaatt tacttcaaaa aagtttcgtt tgattttcag 3720
aaatcaaaat atgcttttcg gtaaccaaat ggttttcaat tttgtttacg aagaacttaa 3780
aactttccaa caccctacat ctatgattgc aagttaaaat tgcagaaata tgacacttt 3840
tggagtggtc tttatcgttt aacttcactt gcacttttaag ggcaaaagtt aaaagtgttt 3900
ccatgaagca agcgagggat aacacttatt aaacttgaaa ttctactcat agaccaaaac 3960
aaggacaaaa attcaagact atctatgtgg gtaaacgtac gaaaattggg cttctccaga 4020
ttagagccgg acccttgtgga aagacagaga aattcgaacg ccacttccag tttctaagga 4080
gattaagcct atcaaacgat ggtccagaac gaaatatgtc tttctttatt ctctactata 4140
tagctgactc agaatcgtta gaatttgcaa tttcctcata ataaaatgtg aggcagtata 4200
gattcgaaaa cctttgttga agattattga ctcagctacg cgaaacaaac tgtagtatcc 4260
aatgtaccga ttaacaagcg actggttaac tatgaatttg ttagctcgac aaaatcaccg 4320
gttaataatg agtttgtgag ttcgataaaa tctaattttc tgatagaaat tttatatatt 4380
atgcagaaat ttaataaaag tagacttaac ttatatattt tagcattgac tcttttgaag 4440
taaaatccat tccatctaaa ttatgacttc cctacatcga gtaagtaagt tgcgtctgta 4500
tcctcatttt acccacttt cgctatgcaa ttattcaagg atctttacac aaatagcaag 4560
ccaatattaa ttatttattt tttttagtca tatatataaa ttatacatat attatatacc 4620
cattaattat ttttaattta agtgatagat tggacgacta tttggattaa ttcttcgtta 4680
ttcaagataa tagatgtcgt ctctaataca tgagctagaa gataataagg attactaggc 4740
cgaaaggctg atggaaatga acaagaagat aagctcctaa ggaaaacag tacggaaaaa 4800
gtcaaagagc agtgcatggg aggaatcatc agtcagaaaa ggaagccacg tgtcaagtag 4860
aaacaagcac gtgtccatgc aaaagccacg taactcccct ccatcacatc ttccttcttc 4920
aaaacctcgt gttttactct ctcttttctc actgccagtg atcgtcagga ctgtgcatgt 4980
ttgtttaaaa actaaaggca                                              5000

SEQ ID NO: 158          moltype = DNA   length = 5000
FEATURE                 Location/Qualifiers
misc_feature            1..5000
                        note = Description of Artificial Sequence: Synthetic
                        polynucleotide
source                  1..5000
                        mol_type = other DNA
                        organism = synthetic construct
SEQUENCE: 158
acatgacccg gttgtctcct tgtggtgtc tttcagaaca tcgccagtag ttcgttgatg  60
tggtgttgag tgaatacttt ttcaatatat aagcaatttc gtgccttttt tggttcatttt 120
tgaggcttat gtaatatatt tgatcatgta atcgtagaca cttcaataaa aggtaactct 180
tcctcagata atgtaaccaa gaataatttc attgaaggga agcggtataa gcataaaggt 240
aactttccct gtgatgaaga atgatgatat caagtaggcg ttgttgatca actttccaaa 300
tgggtggagg gtaagctact tcactgcctt acttcctcta agttcaagtt gggggaggta 360
tgatcgggga ttctctatct tcttgttgaa caagaaaaca gtactactac ttagcatata 420
tagtttcaat caataaaatag gaactgtact aacaatcaga gcccttattt tcacttagca 480
tagttgtata ccagttagaa ctcatactgt ggaaacagag actcgtggac tagcaatgcc 540
cttattaaaa actatcatgg atgctctact cattgtctct ccaaacaaca gcactctttc 600
ataaaaaggt acttcatgcg acatccatta atacaagaag ttcaagatac ataacatgca 660
gtaacagaac tcgactcaac ttagacttat cccacatcga gcttgatttt ccatcaaacc 720
agtgtgcgta aaagtaaaac ataacttatag aattgatccc atggtaaatc acattcacat 780
aacaagcggt tgggataaaa agatggtcag ttctaaggct tcaaaattaa tatagccaat 840
tagtcgaacg gacggtgtgc aatcctagat gacttctatg aaagtgagac gaatcaatct 900
cccaaaagtt tagtacaaag aaataacagc aaccgttcaa caatctaat acggctacac 960
atattaatct tcacaaatta aacattacaa caaaagcata ctaaattctg aactcagtaa 1020
agattcaaat caacagcacc atattataga cataacaaca ctagtgaatt ggtcatcaaa 1080
gcaacgaaga gcacagaaaa gttcgaaatt taaccaatca cgaacctgat cgaagctctt 1140
gtggaacatc tacacgcttc ctgacttgtg gagacaagag tctcgagtag attcggaaac 1200
tgcccagtct aattttgata cgtattctac aatttccta ctaaagagaa aaagagaaag 1260
tgtgtgagaa tataaaattg gcgccttctt tctttttggcg ctatttatct agttttagcg 1320
accagttatc atgattttta aagatatttt tagattgcca attttcgctg agaaaaaaag 1380
gaggtaaaag gggtggtagt taaaagtgat aatcaacttt ataatagact agtcttaata 1440
tacgtgcgtt gcgcgtgtca taaaaaatat tttaaaaaat atatttgtgt tataatataa 1500
aaattaatac aaatttgcaa gcttcaaaat aatgaattaa tcatatttag gagtttgatc 1560
cactctagtg gttttttggtt catcttgctt cattgtacaa aaaatttgag tatacttcca 1620
attctaagtc gttctattgt tcaaaggaaa aaaagtgtcc taattgctct tcaacttcta 1680
aaatattgcc tatctcttac cttaaaatatg aattatcatt tctgcgtcca tattttttt 1740
ttaaatcaaa attgtctttt tcgttttttt tttttagaa aactatactc tatagcccac 1800
aaaattttaa tagctcatgt cttttctcac ttacacgaaa tggcccttt gcccaaacat 1860
```

```
aatagaccga aatgtctatt ttgtatattt tttgtatagt gacagtctat tttgaatatt  1920
tttttatata atgacagtct attttgtata tatattgtat agtgacggtg gggagtgggt  1980
tgctctagtg gtaagcaccc tccacttcca accaagaggt tgtgagttcg agtcacccca  2040
agagcaaggt ggggagttct tggagggagg gagccgaggg tctatcagaa aagcctctct  2100
accccagggt agaggtaagg tctgcgtaca cactaccctc cacataccct actagtggga  2160
ttatactgga tcgttgttgt tgttgttgtt gtattgtata gtgacggtct atttagtata  2220
taattgtata gtgtttgtat attttttgta tagtgacagt ctattgtata taaattgtac  2280
agtgacagac tattttatat attttttgta tactgacagt ctattttgta tatatgttgt  2340
atagtgacaa tctatttatt actccctccg ttccaattta tgtgaacatg tttgactggg  2400
catgaaattt aagaaaaaat aaagactttt ggaatttgtg gtcctaaaca agtcaaaagg  2460
aggtccagag tatttgtggg gttataaaag cttctcatta agggtacaat tgtaagttta  2520
agctaaatta ttatcaaatt tagaaaaggg tcattctttt tggaacagac caaaaaggaa  2580
ataggttcac ataaactgga acaaatggag tatatttttt gtatagtgag agtctatttt  2640
tcatacttct atgctaagta ttgactttaa acactgttca aacttaaacg tgtctctttc  2700
gcgtgaaatt actctatatt gaactactac aactatttgt gccggatttt gtcaaaaaat  2760
tcaatttttcc ggccaagttc gttctgcttc ctcctcccat ccttccaatc ttattctttc  2820
tgccactttt cagcaatagt gatacaacta agatatgttt taaggttttg aactatttgt  2880
gtggaagagt tttatggcat atacttttttc tttggtcgtt gagaagagag gtcgacgtcg  2940
ctcatgaaga cattctgccg ccgacgaaac agatcttata gctagccgct agaattattt  3000
taggctataa aatgtatatt ataatttttgg actactggat gatatatgtt ttgggccgat  3060
gggctataaa tgaattttgc tcatttttttt aacgtgttct ttattagcat aaaaattgca  3120
ggatgagttt gttactttaa tttcattaat ttactctttt tttgcagaat atacatacat  3180
gaaaagtaac atgtagtaaa tattattatg ttacatatat agtttaaata aaggaaaaag  3240
ttaatgtaag gtagaatttt aattgacttt aaattcctaa attttaggac ttctcaccta  3300
gttcaaaataa gtaaatattt aataatcagc atcttagtta atttcaaagt actaaatatt  3360
atgataataa ttaaatgact atttttgtcta gtcgaaatct attttttaag ggtaaaaaaa  3420
gcgaacgata tttcgctaag aaccttcgtg cttttaat aatactagtt tctatgtacg  3480
tgcgttgcac gtaaatcttt agtttatcat ttatatgaaa aaacaataca ttaaatttac  3540
tggaaaatca tatacaaaaa gaccgaataa agccattaat gtgggaacaa tgcaatagta  3600
tcgtcaatgg gaacatgcat tgcacatata ttccgtgtca atagttatct ttgtgaaata  3660
aaaaatgata catgtaattt tatactatca ttctattat gaataaactt gtttgatttt  3720
taaaatagaa aataataaag agcacgaaaa gttactgcta gtcattaaaa tttgttatga  3780
acattgactc tattatagaa taactcatca agaagaattt taagtgcaat attgaaggat  3840
ttgctttagt ttctaaatagt ataaatcgat gtctcttatc ggatcataaa accaaaagaa  3900
ctataatgtc catacaactc cctatgtatg tttacaattt gctttgtgtg tgtaaacatt  3960
agaacttttc acctaaatat ctcataccte ttaagaaaga atccttgctg gatacttttc  4020
ttttggagct tcacaattat aagttaccaa ttaactaatc tctccaagcc tctatttaac  4080
atatacacgt ttatctctgg acgaaacaaac aatagatggc gtcgaagatc cactcttcat  4140
cttcctgatt ttcatcaact tccttatgcc tatttattctc ttgttttcag ttaattcgac  4200
aaattaaatt agaacaaaat ccattactgc tggttatcag acaaagaaaa actaaagtaa  4260
ctccttttgc caacaccaat gtagaacata aataagctta aagtaattt cttttaaatt  4320
ttaggcaaaa cctttatgta aacgaacatt taagccgtgg ctttgccatt ggagttctaa  4380
tacaaatagg acctttagtt ttcaatgact tgaattctac aactaatgaa ctgtttttac  4440
gttttttggat attaatgttg aagacatgat ttaaatatga agggtaaaaa agtcggtcaa  4500
tatttcaggg acatttttgt cgttcaatat ttagcgtgta acattcgtgt ttttataata  4560
atatagatat agatatagat ttctctcccc aaccccgaga ttttttaaaa gtatttttaaa  4620
ataggggttac tgtgcacata taagaatcag aaattccag gaccatagca atgagcatta  4680
ttgaacagta gtagtacgta tgtccttttct ggtataggat atgtagcttc attaaaagat  4740
agaaaatgaa aagcgtataa agttttgtgat acatttacta ataaatccaa cgaataaaag  4800
aaatactcgt atataaaagt agaaaagtaa gtgtttgtac ttttttataaa aacacaatag  4860
gtggagttga gagggatatg gaaattgcct tggatattat gtaggcatca tgaaccaatt  4920
aatgggacct acaagattaa tgttttggct atccttatct tttattgaca ggcccttcaa  4980
tttaaatcgt tgctgcccaa                                              5000

SEQ ID NO: 159        moltype = DNA  length = 5000
FEATURE               Location/Qualifiers
misc_feature          1..5000
                      note = Description of Artificial Sequence: Synthetic
                      polynucleotide
source                1..5000
                      mol_type = other DNA
                      organism = synthetic construct
SEQUENCE: 159
ccgactaaca aaggagtcaa acaatggcga aactagaaat ttacccaagg gtattcaaat    60
ttaaaaaaag tgaaaacaaa ttcctacaaa gggtgtttaa tatgtgttat atacttctaa   120
aacgtaatat ttatctataa acacaatgca attttttcaac gaagagtgat caactgacca   180
ccttataacc gccactggag tcaaacccta gttttctttt ttagcttctt tgtattattg   240
gtagaggtga accattttat acaaacatac atacatatat gtgtgtgtga gagagaaact   300
ttataaaaat agtactatga atattgaata tcgaatttcc attctcaaat aactcataac   360
tttaatgtta actcattgta aaaccttttt tttacatgtt agggtctgta ctagctagca   420
ccatggatag tgcgtgtcac cattttacag caaataatat gcctcatgaa ttggtagggg   480
aagggtcttt aaagttagtg tgttttttttt tctttttctt ggtaggtggt ggggagggg    540
aaaatgaggg gacaaaaaaa atcaattgga gtacaattta cacaagactc cattgtatag    600
aaaagtttaga aaatatatg ttgtaaggca aagaggataa cactttagaa attatagcca   660
acctcatgtt tcttacaagt ggatgagggt tcgactttgc atttagcatc accttattcc    720
ctctaatttt caacaggaca tgttaataaa aggatgacaa tccagattga caagttatg    780
aaagtgaaag cactgtaaca tttcattcaa tcatgaaaag catctcccat taatttttct   840
atctttttgga atattacgaa aatcaaacca acttttttac gtaaaatttt ctaatgatgt   900
cagggggaact cctgagaaat attctcactc aagttcgaaa aggacccttt aataatgatc   960
```

```
aataattttt ttttaatggtc gtgtaatatt cgaatcagct cgtacacatt tcaattattg  1020
taacaagtac cttttatccc ccaacaatac atatataagg taacttatca cgtaatattt  1080
ttgtctttgt tggaatgtaa atcctgtttt tataatttttt atccacttta ttgaccgcta  1140
ggtcacatct tatggagctt ttttagtcat gataaatatt actattatta agaagggaga  1200
aaaaagcaaa aggaagatat taacattagt ataacaccat tcataaacgt gatttaggaa  1260
ataaagtatg aagaaatgaa tagtgaaaaa agtcaagtac ttaggagtta aggttcgtaa  1320
gtagatggga cagatcgcgg tggaaaagga agagaagctt gaaagataca aaagcaaagg  1380
ggggttgggt tgagattctg agttgtgatt aataccactc atgaagaaaa agatatgtca  1440
tggcaccatt caggacatac agagccaact ctcccccccaa aagaaaaggc gcaaaacaaa  1500
aggtttgaaa cagtacttgt ggaggtgatt cagccatgct ttcatgactc atcaatgcct  1560
acttttttttt ctgttttttgt ttttcctttt tattttcagg atataaagtt tgttgttaac  1620
ttaaataaag aaataaaatt actctcttca acctattaag ctttaggtga aattagtaac  1680
tcataaaatt taacatggta tgaattgata gaagtcgtag acacccatag gtgcgctttg  1740
tagtgaaaat tagggttcaa ataagataaa acatgcttga tgatttcttc tcatcggttt  1800
aagtttggat gagcaaagtt atccaataca agtattgccg gtacctaata aaatactcga  1860
gatgcacgca aacaaatttt gacactactg ttaacaataa acaatatgca gctgtccaaa  1920
attaatacta tatcttattg tcactcagtc aacaaaaata ttccttatgt ttagtccaag  1980
aaaaataacc atacccaatt ataagggttt gttgaagaca gaaatatata aataaatgaa  2040
tcatcatatc tccaatagtt taaaatttca aatgggggta tttcacacaa tttatcaaaa  2100
ttttaaataa ttttttatact ttttcttgct tggaagggga aggggtggtg gtggagatag  2160
ggcgggcat cttctatcta gtctatgtga ttaatataac taaacaaaaa gggcaaggca  2220
aaaacatgga tgaatggtgg tccttttcta tatttatatg gattgttacg atacgtcgat  2280
ttcactttgc aaaatacccca ctagattcat ttagttttct ttttgatcac tctgcttttt  2340
ctatcatata tataggaagt ccttccacgt ttcgcatgtg tcattgttta tattttccat  2400
ggtcttcctt ccaaatggct aaataatttt gacacagtgg tcccgaaagt ttatagaaat  2460
agaattcaac agtgaggcat atacgtatga attatattt acatcttcat cgtataaaat  2520
agaatgtgct ataaacttta cctcgtgatg cttacaaggg gtgaaaatat aaaagcactt  2580
tatagattta caagagtcac accttcttga tttatcctaa gattgtattt tttacatgc  2640
caagcaatga agtatgggag atccaattgg aataacatca aaattaataa gattcgaaat  2700
tgtcagagag ctgtctactg agatacattg aaacttattt ctttttgtaca acagaaaata  2760
tcaaatattt agcaacatat taaaatcttc ataaattaca ttgttttaaat cttacgctgt  2820
aacatatgtt gataggaggt aggcctattg atgaatttat aaggtgaaaa tacatggact  2880
agccagtttt cgaactagta attgaaaaaa ggtatattat cacttttagc ccgcgccaga  2940
aattatttat atttggtagt tgaaaaagtg tataaatttg taattttttg tatataacac  3000
acataatgtg tgtgtgagtg tatatatata cacacacaaa aactatatat attttttcta  3060
ttatttttgag agtggttata cagtgtcatc tttctaatcg aaaatagcca gcgtttgcaa  3120
tgttattaaa aaaaaatagc cactatttta gctgaaacac ggaaagttcc agcataaat  3180
atcggatttc agagctcctg catataaact tccagcacat tatgaaattc catcacatta  3240
tgctgaaatt tttccggatt cttaaggtgt tttcattcag attttatctt tacataaaaa  3300
aatggctaaa tttcgattac ttttgaaatt atagctctt ttcaattact aatttataaat  3360
ctgactattt ctgatttttt gcctctggtc aaaatggcat ggcatagtca ttttttagggg  3420
tggttattga aaaatagcta gtattcacaa agttattgaa aatagtcatt atttacggcg  3480
aagattaaat cttaacaaat gtacctgagt taaaacaaa aagttacaa cataatatgt  3540
tggatcatgg aactccttca tgtatgcttc tagcatatta tgttgaaact ccagcacatt  3600
atgaattcca acacattatg tcgaaatctc atatgtaaaa aattcgaact ctggcatatt  3660
atgctggaat ttttcgtat ttttatcag atttttatttt cacataacaa agtgactaga  3720
tttcaataac ttttgaaact atgaccaatt ttcaattaat tgtaaatcaa attatttctg  3780
atttttttcc tccagggcaa taatgggact caacttagg caacaaaaaa ctgtttatgt  3840
aggtaaacgc acgaaaattg ggcttctcca gattagagcc gggccttgtg gaaagacaag  3900
aaattcgagg cccacttcta gtttctaagg agattaagcg taaaaatagc actggctagc  3960
cagtttttcgg actgatcatt caaaaatagc cagtatttgc aaagtcattg aaaaatagcc  4020
attagtattt tgctgcaaca cgaaaagttc caacataata tattggagat cagtgcacct  4080
atgtatgaac ttccagcata ttatgctgga actccaacac gcggaaagtt ccactataat  4140
atactggaga ttggagcacc ggtgtcaaca aatctatcat ttaataggat ttatggctat  4200
ttttaaatga ccacttgtaa atctgattat tttttaattt ctcccgctta agcctaacca  4260
acgatggtca tgaacgaaat gtctgttttt actctctact atatagctga cccagaatca  4320
ttacaatttg caatttcctc ataataaat gtgatgtagt atagatttga aaacccttga  4380
agattattaa tttatctttc gcgaaacaaa ctgtagtatc caaggtaccg aatagtaagc  4440
gattggctca caatgagtct gtttgttcga taaaatcatt ggttaataat gagtctctga  4500
gttccataca atctaatgct ctgatagaaa tttttatatat atgcagaaag taataaaaat  4560
agactatgac ttactatatt ttaacattca ctcttttgaa gtaaaatccc ttccgtcaaa  4620
attatgactt cattacacca aattgcgcct gtatactcat tttaccttct cttcactatg  4680
caattattga gataaaaat ttcgtctcta agacatagct agaggataag gatcttaggc  4740
cgaaacactg atgaactga acaagaagat aatcacctaa atgggaacag tacggaaaaa  4800
gtcaaagagc agtgcatggg aggaatcatc agtcagagaa ggtagccacg tgtcaagtag  4860
aaacaagcac gtgtccatgc aaaagccacg taactccact ccctcatatc ttccttcttc  4920
aaaacctcgt gttttactcc ccctttcctc actgccggtg atcgtcagga ctgtgcatgt  4980
ttgtttaaaa attaaaggcg                                              5000
```

SEQ ID NO: 160 moltype = DNA length = 5000
FEATURE Location/Qualifiers
misc_feature 1..5000
  note = Description of Artificial Sequence: Synthetic polynucleotide
source 1..5000
  mol_type = other DNA
  organism = synthetic construct
SEQUENCE: 160
acatgacccg gttgtctcct tggtggtgtc attcaaaaaa tcgccagtag ttcgttgatg  60

```
tggtgttgag tgcatacttt ttcaatataa gcaatttcgt gccttttgtt tttccatttt    120
gaggcttatg tagtatattt gatcatgtaa tcgtgaatat ttcaataaaa ggtaactttt    180
ccttagataa tgtgaccaat gatgatctca ttgaagggta acttttcct gtgaagaaga    240
atgatgatac tcctatcatg taggcgttgt tgatcaactt tcccaatggg tgaagggtaa    300
gctacttcac tgccttactt tttctaagtt caagttggtg gaggtgtgat tggggatcct    360
ttatcttctt gttgaacaag aaaacgctac taattagcaa tgaataggaa ctgtactaac    420
aatcagagcc cttattttca cttagtatag ttgtatgtat accagttaga acctatactc    480
tggaaacagg gactcgtcaa caataaccag aagggtggat tagaaactat catgaattcc    540
ctactcattg tctctccaaa caacaacact cttttataaa aagtgtactg caagaatcat    600
gttatgcttt taaggaatgt gcatcaagat tgaagtatca tgcgacatcc attaacacga    660
gaagttcaag atgcacaacg tgcactaact gaagtcgact caacgtagac ttattccaca    720
tctaacttga tctttcataa accggtgtg cgtaaaacat tactatagaa ttgatcccac    780
ggttactcat attcacacaa caagcaattg ggacaaaaag atggtcagtt ctaaggcttc    840
aaaattcata cagccaatta gtcgaacatg cggtgtgaa tcctagatga cttctatgaa    900
aatgagacca atcaatcttc caaaagttca gtacaaagaa ataacagcaa cccttcaaac    960
aatctaatac aacgacacat attaatcttc acaaattaaa cacaacatca aaagcgtact   1020
agattttgaa ctcggtaaag aatccaaatc aacagcaccg aattatcgac ataataccac   1080
tagtgaatta gtcatcaaag caacgaagag cacagaaaaa gttaagaaat ttaaccaata   1140
acaaacctga tcgaagatct cttagaacat ctacacgctt cccgacttgt ggcgacaaga   1200
gtctcaagta gactcggaag ctgctccagtc taatttttaaa tatatattct acactttcct   1260
cgcaaaagag aaaaagagag tgtatgagaa tattaaaattg gcgccttttt cttttggcgg   1320
aattgttcta gttttagcga ccagttatca tgattttact actatgtaaa tcgcaagcat   1380
taaagttata gcaagaaatg agaccgagtg acctaaaaac aatcacattt gtatgtttcg   1440
gttccacgag cagctctggg cggacctagt aggagctcct ttgcactgtt gcaggagtgc   1500
tcaagtacct ttactctctt ggtgactcag acactactgc catatcaatg agaaaaaagg   1560
aggtaaagtg gtagttaaaa gtgataatcc atttatata aaatccctcc cccgccccc     1620
ataccccgg aattgtaaaa atattttaa atagtgttac tatgcgcata tactagtcag    1680
aaatttgtag gattacggga ggtagtacgt gcgggtgtac aaaccaaatc ggaaaatcgc   1740
accaaaccga aaagtcaaat caaaaccgat taaaagattc gactagattt ggtttggtat   1800
tgagtaaaac aacccgaatt aaaccgacat ataaaataaa attttatgt atactttaa    1860
gatttttata tagaattttc tttaagaaaa tatctaaaaa tatttgggat tctcttacgg   1920
gatataaat ttaataaaat atgaagtgct ccatatttat taaccttaaa caatgggtcg    1980
tatgatcact ttcttatcaa gtgttactga aatgcgtcaa tctctttgtt cttccatagt   2040
caagatctat taaattctta tatcttttc gaattgaaag tggttattat tatttaagta   2100
tcatattgac ttttacgttt aattactaaa ttcggttaac cttgaaagtg tatatcaaca   2160
aaaattattg tcggacgact aaaagactaa ctatcatgtg ttattaagta aattcacgca   2220
taagaatatt taatagataa tatattttc taattttaa aatttttact aaatatattt     2280
acttataaaa aattaacaa agtaagattg aaataatatt taagtaacga aaaaccagcc   2340
aaaaccgata tagttttgtgt agtttgattt aaataaaagt cgaacccaac ccgatccatg   2400
tacacccctta atagtacgta tgtccttct ggcatactgg taggatttgt agctgcatta   2460
aagatagaaa gcgaaaatcg tacaaagttt gtaatactag tacattacta ataaatccaa   2520
cggataaaag aaatatataa aagtagaaaa gtaattggtc tagattttat gaaacacaat   2580
aggtggagtt gagagggta tggaaattgg cttggatatt atgtaggcat catgaaccat   2640
taatgggacc tacaagatta atgttttgga tatccatatc ttttgttgac aggccttca    2700
attgaaatct ttgttgccca aaatgattcc actgtcaacc aattataagt tttttgttaa    2760
aaggtttatt gcaccattgc tccactaact tcatgtgcat ttgcaactta ccacacaaga    2820
gagaagaaaa agtttccagta cacaggatta acatttgcta agttgattcg gagttttagt    2880
tagcaaagtt gaaattatca aagacagatt ttgaaactat aagccagtgg atcgctaagg    2940
ggttcctcgt tgataaatac ttattttcat ctggtgttta tactaatcca ataaatatat    3000
aatatatgtc tttacaaata tggttataat taaatcataa ttaattagta cacattgtta   3060
cctcacgtta tcactttacc atgataagag tttggtataa atcttggtgg gactaagttt    3120
tttaccttcc tcgtttagtg tctacaagcc taattaggtg aagatggtgc tggattttt    3180
tttttttttg ttacaagtgt agactacaga aattaaatta ctggtcctat tgtgcaaaat   3240
ttgaattcaa atcttcgtgc atttcagtat gttatttggt acaaaaaaca tggcatttat    3300
ggcttcgcat tgaggaagaa ctttctatata gcttgaatgc tcttgttaca tccaccctcc   3360
ttaaataccc ctagttgatc aacaggcacc aaaaatgtct agacacaaac atgaaccagt    3420
tttatttcta ttctctttat tgtaggtaat tgtttgctgt catcatataa tataagctag    3480
gaagaaaata agtaaaaatc atcagatgtg ataggtcttg aatagagaag caaacctaat    3540
gtagcataat aagaaaggaa gattaggtgg gagaccatta tttatgacct catcccaatt    3600
ttaatcatat ttcattattc caggttacta ctaccaaaca aaaataaacg acaagaataa    3660
tgcataaact tccacaatag ctcattattt atttatcagc cggagtgtat taagtaatg    3720
atataattag aagacaattg agttgctact taaactgatg ctaacctgac gcgttttcgt    3780
tttccaggta cagtcttcca acatcagatg tcccaattgg agttccaagt caaagtggaa    3840
ttggaaaatg gtaagaaaac tctcagcctt agctgtgaca tagacatcaa taaagtagaa    3900
aaaaatcata agatttcaat gtttgaatgc taagcgacac aaaaatcact aataattttt   3960
tttcatttct gactaagtct ttatgagcaa aactatttat tacttacaat tttgtgatga    4020
taggagatat caaatactcg tggaatactt gaggtaccca caagtgatt gagaagttgc     4080
tgttaattaa aaaatccttg catcagatcc cttcagtttg aggtcaaaag cacaatcgtg    4140
aaaagccctc tcacagcaca ttcacttgat ccattctatt ttacgtcttt tctctaacta    4200
cgacttaagt tcttctaact tttaatcatt accaccctat taaaacttat ctaaagactg    4260
tttttctctg cttttctcca tatttacctc aacgtctcct tccatatcca agctttggta    4320
cttttttcccc ttgtggtatt gattcaggca tggtccttc tccaatcatta tcaatcaaac    4380
atatactaat aaagtataat ataccaccga ctttggtgtc aaccacgagt tcgggagctt    4440
aataaatatg gtggtattta gccaattttt ttctttttaa aaatttagga aattaggaac    4500
caacttgccg gcttcataat aaagtatata gttgaaatgg ttcagaaata ttaaatttcaa    4560
ttctataaat tacttggatt cggtccatcc taaaggtggt cacttctagg atcaagccc    4620
attgttggct aaattttggt tttaaataga ttaattagct tggagtcgaa cagcaagcat    4680
taagtttacc aggtctatga tttagttagg catgaattgt aatacaaaga tgatttatgc    4740
agtgattaat gatatcagga tatatatata taagtattgt tatactataa ataacaacaa    4800
```

```
caacaacgac ccagtaaagt cccactaagt ggggtttggg gaaggtagtg tgtacgcaga    4860
ccttatcctt accctgatag ggcagagagg ttgtttccga tagatcctca gctcaggaag    4920
atgaaaataa aacaagaaaa caagaaaaga cagtaaccat agaaataatg acagcatcct    4980
aaaaaccata aaatagatga                                                5000
```

SEQ ID NO: 161           moltype = AA    length = 524
FEATURE                  Location/Qualifiers
REGION                   1..524
                         note = Description of Artificial Sequence: Synthetic
                          polypeptide
source                   1..524
                         mol_type = protein
                         organism = synthetic construct
SEQUENCE: 161
```
MIGYPKRFTL HGLWPANSTG YSLKCAPPPE GTSVWTTDGQ LRTALQKCWY SLIRGRPNYI    60
LWKHEWKDYG YCSSHTIKDT DYFWAAVRKH GRNTKIAGDA IVNELSDAEI SPSNDKERRC    120
ETESDSSHHY QHSEHHQRRW LGRRRECDTK RYSQAKYITS PHESVTASRE KRASTSTIEE    180
APPAVKKLLL EWLTSTINNI FDKPAQKENG NTAQADIVTT TGEQPLPRTG NTYPTMDAGA    240
KKAEARVNDI FAVRQSSGEG LRDFLARFNR EEIHNAYCAK ERADDDDLNG PIQRLTSVQE    300
ESRSDHRNDS QRDQSGPRLS RERHQHYVRT TVLPSPRHME GPPRPYIGTQ RNERGMPPLL    360
STHNFCVSPS KIVYALKKLG TMVKCPQKMK SGPNTQKLNA ICEFHQERGH KTEDCIGLRQ    420
EVVRMLNQGN LKELMSDRGR VNFARGRELP QGPPKPPSPA RTIQMIIGGG DEAMINHMKF    480
TTTHKLKRSM THERYDDFGD SIIFDKSDTD GLTFPYFEAI VITL                     524
```

SEQ ID NO: 162           moltype = AA    length = 343
FEATURE                  Location/Qualifiers
REGION                   1..343
                         note = Description of Artificial Sequence: Synthetic
                          polypeptide
source                   1..343
                         mol_type = protein
                         organism = synthetic construct
SEQUENCE: 162
```
MSCQNSKTEE TADEQHNTSK DPKHKPFFDV YGPQGRADIV FNQPESNSTL NLQDVQGLVT    60
WVLADGFMPS WAFIKNKPLI PKVVMLYVPG LDAALYLSQS KVLKGFKECC GIPRPVLALS    120
CVSDGNQTID ALLTYKSKRK RKEAEHISPI NTEPSEQGAE TPTMEPLSFV DLKKDIPFPI    180
SYYTLTDKEL EENGYCYDQP EFLSTLPAPS GTSPHEILAL DCEMVLLDKL VKPSNNIVDY    240
NTRYSGITCQ MLEDVTTTLK DIQEEFLKLV YKETILVGHS LENDLLALKI IHNLVIDTAV    300
LYKHPRGSYK AALRVLSRKF LGREIQDSGN GHDSIEDAKL HWN                      343
```

SEQ ID NO: 163           moltype = AA    length = 723
FEATURE                  Location/Qualifiers
REGION                   1..723
                         note = Description of Artificial Sequence: Synthetic
                          polypeptide
source                   1..723
                         mol_type = protein
                         organism = synthetic construct
SEQUENCE: 163
```
MASTSYITFK PLQQTQLKLY YFTHCSKHSS TLFHSSFHTL LSAPTKYTLE PPRILPSIQV    60
KAHVTHLETR LSFEPEQEIS GSRTNNENSS GFSSFSPKDK MVGMKSSREN LDRHCQTLDE    120
LVQLFKSSAE ASNTKSVRGE QEDHGIKVSE EVKHYALKYG FKIYEKMRSE KVQMNEATLT    180
SVARMAMALG NGDMAFDVVR LIKEYGINPR LRSYGPALSV FCNNGDVDKA FMVEEHMLEH    240
GVYPEEPELE ALLKVSVEAG RSEKVYYLLH KLREGVRQVS PSTADLIEKW FNSKIASRVG    300
KRKWDERTIR EAIKNGGGGW HGQGWLGNGK WTVSHAYVDS DGCCKCCGEK LVTIDLDPVE    360
TENFAKSVAS IAAQRERNSS FQKFQRWLDY YGPFEAIVDG ANVGLYSQRK FRPSRVNAIV    420
NGIRQMLPSK KWPLIVLHNR RITGDKMDEP FNRAYWLYAA IKFKCLIVTN DEMRDHLFQL    480
LGNDFFPKWK ERHQVHFSFS ETGPVLHMPP PCSVVIQSSE RFGPDRRIYH GRSSRTLKDK    540
ELSGSRDSGY PRLSDYNFNI NLIELVSVMR NIKEARFPKP IRSYSSQKDH FKIKRVLVDP    600
GSSANIIQLR VLEQAKLIEV PTMKLLAGFN LTSVTTQGEI VLPTYAEGVT KSTLFKVVDG    660
DMGYNVIIGR PWIHKIKVVP STYDQFLNFP TSDGIKQIRG DQPAAREMNV VTLSSSNAEE    720
INK                                                                  723
```

SEQ ID NO: 164           moltype = AA    length = 155
FEATURE                  Location/Qualifiers
REGION                   1..155
                         note = Description of Artificial Sequence: Synthetic
                          polypeptide
source                   1..155
                         mol_type = protein
                         organism = synthetic construct
SEQUENCE: 164
```
MQSPESCVIV SCPTTLIADE DEEVADMETS VKAVEEILNY KFIKPKLLEE ALTHSSCIDS    60
VSYQRLEFVG EQAEFHGGAM KAPKVLADIV ESVAAAVYVD CGFDLKNLWL LLLRTKKMLT    120
SRCKAALQKL AFKSIGKTDL KLNQIQRLMG QAKAA                               155
```

SEQ ID NO: 165           moltype = AA    length = 234
FEATURE                  Location/Qualifiers
REGION                   1..234

```
                       note = Description of Artificial Sequence: Synthetic
                         polypeptide
source                 1..234
                       mol_type = protein
                       organism = synthetic construct
SEQUENCE: 165
MKPQKSLLIK VLITQCLLVL CVAQQDFDFF YFVQQWPASY CDTRRSCCYP TTGKPDEDFS    60
IHGLWPNYEN GKWPQNCDRE SSLDESKISD LISTMEKNWP SLACPSSDGV RFWSHEWLKH   120
GTCSALGERA YFQAALDFRK KSNLLENLKN AGITPRNGEH YTLESIKKAI EEGVGHSPYI   180
ECNVDTQGNH QIYQVYLCMD KTATDFIDCP VFPHGRGCGS KIEFPPFSSD HDEF         234

SEQ ID NO: 166         moltype = AA   length = 217
FEATURE                Location/Qualifiers
REGION                 1..217
                       note = Description of Artificial Sequence: Synthetic
                         polypeptide
source                 1..217
                       mol_type = protein
                       organism = synthetic construct
SEQUENCE: 166
MATRRREADF DFFYFVQQWP ASYCDTRRSC CYPTTGKPDE DFSIHGLWPN YENGKWPQNC    60
DRESSLDESE ISDLISTMEK NWPSLACPSS DGVRFWSHEW LKHGTCSALG ERAYFQAALD   120
FRKKSNLLEN LKNAGINPRN GEHYTLESIK KAIEEGVGHS PYIECNVDTQ GNHQIYQVYL   180
CVDKTATDFI DCPVFPRGRG CGSKIEFPPF SSDHDEF                            217

SEQ ID NO: 167         moltype = AA   length = 160
FEATURE                Location/Qualifiers
REGION                 1..160
                       note = Description of Artificial Sequence: Synthetic
                         polypeptide
source                 1..160
                       mol_type = protein
                       organism = synthetic construct
SEQUENCE: 167
MGVTTYNQEV TTLVAPTRLF KALVLDSENL VPKLMPQVVK NIEIVVGDGD AGSIKKMNFV    60
EGSPIKYLKH KIHVIDDKNL VTKYSLIEGD VLGDKLEFVT YDIKFEASGN GGCICKTSTE   120
YHTKGDYVFK EEEHYEGKKQ AMELFKTVED YLLANPSVYV                         160

SEQ ID NO: 168         moltype = AA   length = 160
FEATURE                Location/Qualifiers
REGION                 1..160
                       note = Description of Artificial Sequence: Synthetic
                         polypeptide
source                 1..160
                       mol_type = protein
                       organism = synthetic construct
SEQUENCE: 168
MGVAIFTQEF TSPIAPIRLF KALIVDSKSL IPKLLPQFVE SVDLLQGDGG AGSIEQVNFT    60
KGSPFEFVKH RIDELDKENM VCKYTMIEGD ALADKFDSIS YEVKFEESNN GGCICKMTTE   120
YIGIGDFIVK EEDIKAGKDS AIGIYKAVES HLLQNPNLYA                         160

SEQ ID NO: 169         moltype = AA   length = 160
FEATURE                Location/Qualifiers
REGION                 1..160
                       note = Description of Artificial Sequence: Synthetic
                         polypeptide
source                 1..160
                       mol_type = protein
                       organism = synthetic construct
SEQUENCE: 169
MGVTTYTHEV TTSVAPTRLF KAIVLDSENL VPKLMPKVVK NIEIIEGDGG AGSIKKMNFV    60
EGSPNKYLKH KIHVIDDKNL VTKYSLIEGD VLGDKLEFVT YEIKFEASGN GGCICKTSTE   120
YHTKGDYVFK EEEHNEGKNQ AMELFKTVED YLLANPSVYV                         160

SEQ ID NO: 170         moltype = AA   length = 160
FEATURE                Location/Qualifiers
REGION                 1..160
                       note = Description of Artificial Sequence: Synthetic
                         polypeptide
source                 1..160
                       mol_type = protein
                       organism = synthetic construct
SEQUENCE: 170
MAITSFTDEY TCPIPPSRIF KASIIDSHNL MPKLMPQAIK SIEFVQGNGG AGSIKQINFP    60
EGGNFKSIKY RIDELNEEKF VYKYTLIEGD ALVDKLEKIT YEVKFEQSAD GGSISKVTST   120
YYTEGDFKLK EEEIKAGKEK VLGMYKAVEV YLLQNPDAYA                         160

SEQ ID NO: 171         moltype = AA   length = 229
FEATURE                Location/Qualifiers
```

```
REGION                      1..229
                            note = Description of Artificial Sequence: Synthetic
                              polypeptide
source                      1..229
                            mol_type = protein
                            organism = synthetic construct
SEQUENCE: 171
MASNSATSLF LTLFLIIQCL SLLTAAQDFD FFYFVQQWPG SYCDTKQSCC YPKTGKPASD   60
FGIHGLWPNN NDGSYPSNCD SNSPYDQSQV SDLISRMQQN WPTLACPSGT GSAFWSHEWE  120
KHGTCSESIF DQHGYFKKAL DLKNQINLLE ILQGAGINPD GGFYSLNSIK NAINSAIGYT  180
PGIECNVDES GNSQLYQVYI CVDGSGSNLI ECPVFPRGKC GSSIEFPTF             229

SEQ ID NO: 172              moltype = AA  length = 229
FEATURE                     Location/Qualifiers
REGION                      1..229
                            note = Description of Artificial Sequence: Synthetic
                              polypeptide
source                      1..229
                            mol_type = protein
                            organism = synthetic construct
SEQUENCE: 172
MASNSATSRF LTLFLITQCL SVLTAAQDFD FFYFVQQWPG SYCDTKQSCC YPKTGKPASD   60
FGIHGLWPNN NDGSYPSNCD SNSPYDQSQV SDLISRMQQN WPTLACPSDT GSAFWSHEWE  120
KHGTCAENVF DQHGYFKKAL DLKNQINLLE ILQGAGINPD GGFYSLNNIK NAIRSAVGYT  180
PGIECNVDES GNSQLYQVYI CVDGSGSDLI ECPVFPRGKC GSSIEFPTF             229

SEQ ID NO: 173              moltype = AA  length = 240
FEATURE                     Location/Qualifiers
REGION                      1..240
                            note = Description of Artificial Sequence: Synthetic
                              polypeptide
source                      1..240
                            mol_type = protein
                            organism = synthetic construct
SEQUENCE: 173
MRSIQLVLVK LVIFQCIMLL HAQDFDFFYF AQQWNPASCD SKIKCCYPTN GKPAQDFGIH   60
GLWPNYNNGS FPKSCNKNAR YDETQISDLI SSMQKNWPTL SCPSNNGTRF WSHEWKKHGT  120
CSLSMLDMHS YFQAALALKE KVNLLQFLNN AGIKPDGGFY SYEAMKEAIE KGIGHTVGVE  180
CNIDLFGNRQ LFEVYVCVDK CGSEIIDCPI VPESKRCKES IEFAVFESES LLDEKSAYSL  240

SEQ ID NO: 174              moltype = AA  length = 265
FEATURE                     Location/Qualifiers
REGION                      1..265
                            note = Description of Artificial Sequence: Synthetic
                              polypeptide
source                      1..265
                            mol_type = protein
                            organism = synthetic construct
SEQUENCE: 174
MRSIKFVLVK LVIFQCITLL VHAKDLDFYR LTLQQWNPAA CYNRIIGKCC NTTTGRPAED   60
FGIAGLWPSY NNLTYPENCN KAGPYDETQV SFDKIQISDL LSSMQKNWPK ISCPSNNGTS  120
LWAKEWKERG TCSRLNMHSY FETALDLKEK LNLIQDVKRY GTDLTHVHMH GLEPNGQFYH  180
WRHINAAIKL AIGHVIAIEC NLGLTADSQF YRVHICVDKS GSDFIDCPIN LTEISETTCS  240
SSTKWSGYDT DSVLEERSAY SWARK                                      265

SEQ ID NO: 175              moltype = AA  length = 493
FEATURE                     Location/Qualifiers
REGION                      1..493
                            note = Description of Artificial Sequence: Synthetic
                              polypeptide
source                      1..493
                            mol_type = protein
                            organism = synthetic construct
SEQUENCE: 175
MGSFSFAVCV SLMLLVMVVA IPFEPKNGRR IGRLHRWWDP LIRSPVDRDD EVEDSNSVRW   60
AVLVAGSNGY GNYRHQADVC HAYQILKRGG LKDENIVVFM YDDIAKSELN PRPGVIINHP  120
NGSDVYAGVP KDYTGEHVTA ANLYAVLLGD KSAVKGGSGK VIDSKPNDRI FLYYSDHGGP  180
GVLGMPNMPF LYAKDPIEAL KKKHAAGTYK EMVLYIEACE SGSVFEGMMP EDLNIYVTTA  240
SNADESSWGT YCPGMDPPPP PEYITCLGDL YSVAWMEDSE SHNLKKETIK QQYEKVKERT  300
SNFNNYNAGS HVMEYGSKEI KPEKVYLYQG FDPATANLPA NKIDFAHLEV VNQRDADLLF  360
LWERYKKLAD NSLEKAKLRK EITDTMLHRQ HLDGSVDAIG VFLFGPTKGS SVLNSVRKPG  420
LPLVDDWDCL KSTVRLFELH CGSLTQYGMK HMRAFANICN NGVSRDAMEE AFMAACNEHK  480
IEEYIAANRG FSA                                                   493

SEQ ID NO: 176              moltype = AA  length = 494
FEATURE                     Location/Qualifiers
REGION                      1..494
                            note = Description of Artificial Sequence: Synthetic
                              polypeptide
```

```
                        source          1..494
                                        mol_type = protein
                                        organism = synthetic construct
SEQUENCE: 176
MGSFSFAVCV SLMLLVMVVA IPFELPKNGR RIGRLHRWWD PLIRSPVDRD DESEDKDGVR    60
WAVLVAGSNG YGNYRHQADV CHAYQILKRG GLKDENIVVF MYDDIAKSEL NPRPGVIINH   120
PNGSDVYAGV PKDYTGEHVT AANLYAVLLG DKSAVKGGSG KIVDKSPNDR IFLYYSDHGG   180
PGVLGMPNMP FLYAKDFIEV LKKKHAAGTY KEMVLYIEAC ESGSVFEGMM PEDLNIYVTT   240
ASNAEESSWG TYCPGMDPPP PPEYITCLGD LYSVAWMEDS ESHNLKKETI KQQYEKVKER   300
TSNFNNYNAG SHVMEYGSKE IKPEKVYLYQ GFDPATANLP ANKIAFAHVE VVNQRDADLL   360
FLWERYKKLA DNSLEKAKLR KEITDTMLHR KHLDGSVDAI GVFLFGPTKG SSVLNSVREP   420
GLPLVDDWDC LKSTVRLFEL HCGSLTQYGM KHMRAFANIC NNGVSRDAME EAFMAACNER   480
KREEYTAANR GFSA                                                    494

SEQ ID NO: 177          moltype = AA   length = 768
FEATURE                 Location/Qualifiers
REGION                  1..768
                        note = Description of Artificial Sequence: Synthetic
                         polypeptide
source                  1..768
                        mol_type = protein
                        organism = synthetic construct
SEQUENCE: 177
MYDDIANNSE NPRPGVLINN PHGQDVYQGV PKDYVGEDVN ADNFFNVILA NKSGITRGSG    60
KILDSGPNDN IFIYYTDHGG PGIVSMPTGI VYANDLINVL EKKHASGTYS KMVFYLEACE   120
SGSMFDGLLP EGLNIYVTTA SKPDENSWGT YCGLGRGACL VECPPPEFDG VCLGDLYSVA   180
WMEDSDVQDR QTSTLDNQYD RIACRTAANL TYGSHVMQYG DMELSVDALF QYMGSVSTSH   240
SQAPSPMAAA PSPMDAASFL TSSENVNQRD TELFYLTSKY QGAPEGTNEE FAADRKLNEV   300
VAQRSQVDNN VKRLGELLFG VEKGNEVLQS VRPAGQPLVD DWDCLKSYVK TFEAHCGKLT   360
AYGKKHVRGI ANICNAGIES EEMVDATAQA CSAASEIGPN SPTFTQTDFI LPPSHPLYLH   420
PSDNPDPDIS QSVIYSKSAK RLWDKLNQRY GQANGAKMYE VQKDLSTIFQ GSSDVGSYFT   480
RVKRLQDEME SLDADSFCVC ECKCGGHKKM IKRMENQKLM QFLMGLNEER GYDPKMPYCR   540
YCKKPGHVIE KCYKLHGFPR PSKSGNKNIR VAAHVHSSSD AKPNRSYDNN INIANTIIPD   600
QYKQHMTILQ HIQVGSNDSQ SQFATANFAG IFASSAHLMS CGNCTCLSSV LTSETWILDS   660
GTSVHMTFNK YSLTNITTLY VPYLITLPNG YKVKVTTIGS VKLNSSVILS KVLYVPTFKY   720
NLILVHKLLV DTLSLLCFSQ HACFLLHGPS LRMPLILGKC HNPKSHPS               768

SEQ ID NO: 178          moltype = AA   length = 457
FEATURE                 Location/Qualifiers
REGION                  1..457
                        note = Description of Artificial Sequence: Synthetic
                         polypeptide
source                  1..457
                        mol_type = protein
                        organism = synthetic construct
SEQUENCE: 178
MVQKNGVVSF LVVLFVIVCT AEGRNLLESI VEDDNATGTK WAVLVAGSNE WDNYRHQADV    60
CHAYQLLKKG GLKDENIIVF MYDDIAYNKN NPRPGVIINS PHGHDVYKGV PKDYTGKDCN   120
ADNFFAVILG NKSALTGGSG KVVENGPNDY IFIYYADHGA PGLIGMPSGD DVYADDLIKV   180
LIKKHTFGIY SKLVFYMEAC ESGSMFDGLL PKGLNIYVTT ASKPDEGSWA TYCISLGDED   240
VVCLGDLYSV AWLEDSDLHD RQVETLEKQY QLVRKRTLNN GTVEGSHVMQ YGDLHISEDP   300
LFRYMGSNSA KNSYYSTSTN DESWLPSRTV NQRDVHLMHL WSKFRSAPEG SARKTEAQRQ   360
LREAISQREH VDNSVRHIGE VLFGVEKGPE VLQTVRPAGQ PLVDDWDCLK SFVKIFESQC   420
GKLTPYGRKH VRGFANLCNA GIRREQMAAA AKQACPS                           457

SEQ ID NO: 179          moltype = AA   length = 359
FEATURE                 Location/Qualifiers
REGION                  1..359
                        note = Description of Artificial Sequence: Synthetic
                         polypeptide
source                  1..359
                        mol_type = protein
                        organism = synthetic construct
SEQUENCE: 179
MIRKNGVVPF LVALFVLVCT AEGRNLLESI VEDDNPTGTK WAVLVAGSNE WDNYRHQADV    60
CHAYQLLKKG GLKDENIIVF MYDDIAYNKN NPRPGIIINS PHGHDVYKEY PSGKVVENGP   120
NDYIFIYYAD HGAPGLIGMP SGDVVYADDL NRVLIKKHTF GTYSKLVFYM EACESGSMFD   180
GLLPKGLNIY VTAASKPDES SWATYCIRLG DEDQCLGLSV SVSWLEDSDL HDRQVETLEK   240
QYQLVRKRTL NNGTEEGSHV MQYGDLHISE DPLFRIWVLI LQKIVIILHN NDESWLPSRT   300
VNQRDVHLMH LWSKVKIFES QCGTLTPYGR KHVRGFANLC NAGIRREQMA AAAKQACPP   359

SEQ ID NO: 180          moltype = AA   length = 301
FEATURE                 Location/Qualifiers
REGION                  1..301
                        note = Description of Artificial Sequence: Synthetic
                         polypeptide
source                  1..301
                        mol_type = protein
                        organism = synthetic construct
```

```
SEQUENCE: 180
MIPARMADVC HAYQLLKDGG LKDENIIVFM YDDIANNREN PRPGVIINNP HGHDVYKGVP      60
KDYVLEDVNA NNFYNVILGN KSAVVGGSGK VVNSGPNDHI FIYYTDHGGP GVVSMPSGED     120
VYANDLIDML KKKHASGTYD RLVFYLEACE SGSMFDGLLP EGLDIYVMTA SEPNEDSWAT    180
YCGEGTPDDP CLVECPPPEF QGVCLGDLYS VAWMEDSTID RLLFLTPHDF YSFFSECLQH    240
QNAPEGSDEK FKAHARLTEA ISQRTQVDNN VKHLGELLFG VEKGNEILHS VRPAGQPLVD    300
S                                                                    301

SEQ ID NO: 181         moltype = AA  length = 483
FEATURE                Location/Qualifiers
REGION                 1..483
                       note = Description of Artificial Sequence: Synthetic
                        polypeptide
source                 1..483
                       mol_type = protein
                       organism = synthetic construct
SEQUENCE: 181
MIVRYVVSAV LIIGLSILAA VEQGCAEITV GSIKVFSGEY DDDSIGTKWA VLVAGSRGCW     60
NYRHQADVCH AYQLLKKGGL KDENIIVFMY DDIAHNPENP RPGVIINSPN GHDVYKGVPK    120
DYTGHHVTAN NVLAVILGNK SALSGGSGKV VESGPNDHIF IFYSDHGGPG VLGMPSGPYL    180
YADDLIDALK RKHASGTYKR LVFYIEACES GSIFEGLLPE GLNICATTAS NAEEDSWGTY    240
CPGDYPGPPP EYQTCLGDLY AVSWMEDSEK HNLQRETLGM QYELVKRRTA NSFPYASSHV    300
MQYGDLKLMD DPLSLYMGTN PANDNYTFLD ENSSLLSAKP VNQRDADLLH FWDKFLKAPQ    360
GSIRKIEAQK QLTEAMSHRM HIDDSIALVG KLLFGIEKGP EVLIRVRPTG EPLVDDWDCL    420
KSFVRTFETH CGSLSQYGMK HMRAVANICN SGIKMEQIAK ASAQACVSIP SNSWSSLDEG    480
FSA                                                                  483

SEQ ID NO: 182         moltype = AA  length = 157
FEATURE                Location/Qualifiers
REGION                 1..157
                       note = Description of Artificial Sequence: Synthetic
                        polypeptide
source                 1..157
                       mol_type = protein
                       organism = synthetic construct
SEQUENCE: 182
MSYGDQSQTI GDLAFEKFTF PSIFGNNVNI LDVVFGCGHD NSGTFNNYTS VIIGLGGGEV     60
SIVNQLDKEI NGKFSYCLIT IPLQSSISNA TSHINFDADL ELSPSSTFAE VEEDLVSLTI    120
VPAEEVAIFG NLEQANFLIG YDLVANKISS LPTDCTS                             157

SEQ ID NO: 183         moltype = AA  length = 288
FEATURE                Location/Qualifiers
REGION                 1..288
                       note = Description of Artificial Sequence: Synthetic
                        polypeptide
source                 1..288
                       mol_type = protein
                       organism = synthetic construct
SEQUENCE: 183
MINSRHRRKY GSKDEWNMRF GIYQSNVQFI DFFNSLNLSY NLTDNAFADM TNLEFNSKYL     60
GYKKRKHSKQ LAAPNITCDS SKLPISVDWR KSGVVTRVKD QENCGSCWAF SAVAAVEGIN    120
KIKTGKLVSL SEQQLVDCDV FSDNQGCNGG FMEKAFAFIN KNGGITTEKN YHYVGKDQKC    180
NTTKAKQHAV TISGYEMVAK NEESLQAAFT KQPISVAIDA SGYDFQLCAG GVYSVFFGNS    240
LNHGVPLIGY GVDDGEKYWL VKNSWGTMWG EDGYIKIKRW SNDKKRNV                 288

SEQ ID NO: 184         moltype = AA  length = 706
FEATURE                Location/Qualifiers
REGION                 1..706
                       note = Description of Artificial Sequence: Synthetic
                        polypeptide
source                 1..706
                       mol_type = protein
                       organism = synthetic construct
SEQUENCE: 184
MANSLLSSNF MGSQIFVSPP TPKTTKYFHF HSKRKSLIPQ SILNKKPNSD NSKNIPSKAA     60
LAALLFSSIT PHAYALDNTT PTVPTPQVIQ AEAANPTTSN PFSQNIILNA PKPQAQTNPE    120
LPEVSQWRYS EFLNAVKKGK VERVRFSKDG TTLQLNAVDG RRASVIVPND PDLIDILAMN    180
GVDISVSEGD SGGNGLFNLI GSLFPFIAFA GLFYLFQRSQ GGPGGPGGLG GPMDFGRSKS    240
KFQEVPETGV SFADVAGADQ AKLELQEVVD FLKNPDKYTA LGAKIPKGCL LVDHLVQERH    300
FWLEQLLVKL VYHFSMCSIR VVELFVGVGA SRVRDLFEKA KSKAPCIVFI DEIDAVGRQR    360
GAGMGGGNDE REQTINQLLT EMDGFSGNSG VIVLAATNRP DVLDSALLRP GRFDRQVTVD    420
RPDVAGRIKI LQVHSRGKAL AKDVDFEKIA RRTPGFTGAD LQNLMNEAAI LAARRELKEI    480
SKDEISDALE RIIAGPEKKN AVVSEEKKKL VAYHEAGHAL VGALMPEYDP VAKISIIPRG    540
QAGGLTFFAP SEERLESGLY SRSYLENQMA VALGGRVAEE VIFGQDNVTT GASNDFMQVS    600
RVARQMVERL GFSKKIGQVA IGGGGGNPFL GQQMSTQKDY SMATADVVDA EVRELVERAY    660
ERATQIITTH IDILHKLAQL LIEKETVDGE EFMSLFIDGK AELYIS                   706

SEQ ID NO: 185         moltype = AA  length = 745
FEATURE                Location/Qualifiers
```

|  |  |
|---|---|
| REGION | 1..745 |
|  | note = Description of Artificial Sequence: Synthetic polypeptide |
| source | 1..745 |
|  | mol_type = protein |
|  | organism = synthetic construct |

SEQUENCE: 185

```
MIIEVLILWH ADVRHNISLT ALSSTQSFYK DDLYIVFLKD HPVNEESLFQ RHIIVLSSLK   60
GSDGAATESH VYSYTKIFNA FAAKLSQHEV HMLSSMDEVV SVIPNRYRKL HTTRSWEFIG  120
LPATAKRRLK RESNIIVGVF DTGITPQSKS FKDDGLGPPP VKWKGSCGHF ANFSGCNNKL  180
IGARYFKLDK VPDPNDILSP IDVHGHGTHT SSTLAGSMVP DASLFGLARG TARGAVPSAR  240
VAMYKVCWVT SGCADIDILA AFEAAISDGV DLISISIGGL SGSYTTDVIA IGSFHAMRKG  300
ILTVASAGND GPNLNTVANH APWMLTVAAS GIDREFRSKV ALGNGRIVSG IGVSAFDPKK  360
KLYPLTAGVD MAKSSDTRDS SRYCGEGSMD PRKVKGKLVY CQLGTWGADS VIKELGGIGT  420
IIESDQFLDS APIFMALATI VNSSIGKNIN NYMHSERLPS AVIYKSQEVK IKAPFIASFS  480
SRGPNPGTIR LLKPDIAAPG IDILASYTPL KSLTGLKGDT QYSEFTLMSG TSMSCPHVGG  540
AAAYVKSYHP DWSPSAIKSA LVTTARPMSS KVDREAEFAY GAGQVNPTKA RSPGLIYDMD  600
DMSYIQPLCH EGYNSSSVSS LLRQRVNCST LIPANGEDAI NYPTMQLGLK SNQEPTIGIF  660
RRKVTNVGQA ISVYNATIRA PKGVDITVKP TTLSFTRAMQ TRSFKVVVKA KPMSNAVILS  720
GSLIWKSSRH LVRSPIVIYD PKVFD                                       745
```

|  |  |
|---|---|
| SEQ ID NO: 186 | moltype = DNA length = 2372 |
| FEATURE | Location/Qualifiers |
| misc_feature | 1..2372 |
|  | note = Description of Artificial Sequence: Synthetic polynucleotide |
| source | 1..2372 |
|  | mol_type = other DNA |
|  | organism = synthetic construct |

SEQUENCE: 186

```
atggattcct taccagtctc ctccattgaa tctctagtca ttgagatcaa gaaagagatg   60
ttctcaaacc aagaatttaa cacttttgtc accccaatat ctgcctatga cactgcttgg  120
ttggccatga tttcttataa taatcaagaa gaagccatta atggtcattc tttttctggc  180
cctatgttta gagttgttt aaattggatt ctcaacaacc aaaatgagca aggattttgg  240
ggagaatcca atggtgtttg aaattyattc atgctaatac ggaaatactt ctgaaagaa  300
attctcaaca atttccacgt tggttcatca ttgttttccc tgcaatggtt caactttcta  360
aatcagtagg cctggagatt attttgtga atggatcaga aagattactt tcggacgttg  420
caatgaaaag gaaagtaatt cttgaaagtg aaaagctaat ggacgtgaca gcagggcatg  480
atcaacctct attggcatat ttagagagct tgccaaatta tgttttgaat caaaaagacc  540
aaatcctaaa acatttaagt gaagatggtt ctttgtttca atctccctct gctacagcac  600
aagcattcat ggccacagga aaccaaaaat ctcttgaata tctcatgtcc attgttcata  660
agtgtccaaa tggagtgcag taccttcaat gttttccagtg gatgaagagc taacaaagct  720
ttgcatagtt gaccacattc aaagaatgga tgtttatct gagagattat acaaggacct  780
attggctttt cgacttctcc gtttgcaagg ctataaaata aatgaaggga agttttgttt  840
ggtttgttca tcaaccgcag ataagggcct acatagaaaa gaatcaagaa cgttttacgt  900
atgtgatgta caatgtgtac agagctacag atctcatgtt taaggagaa tctgaaatgg  960
aggaagtacg atctttgcc agatatttc ttgaacgttc aatgaagctc gtgaacaatg 1020
agggcagctt attacttctt cctacacttc aaaaagtgat taagcatgag ttgaatgttc 1080
catgggttgc tcgactagaa catcttgatc acagattatg gattgaatta agtcaatctc 1140
tccctctttc aattggaaaa tccgcagatt attggttgtc ttgtctgcac aatgacaaat 1200
tgctgaaatt agcagtgcaa aattacgaat tccggcagtc agtttacgag acggaattga 1260
aagaactaaa gagagttggt cgaaagagaa aggccttgtg gacattggat tgggcgagaa 1320
gaaaactaca tattcctatt ttgcaagtgc agctagcagc agcagttttc taccttttga 1380
ttcttattat gatgaggaag cttctttaag tgacttgcaa atcttaaccg acgctgtaca 1440
aaggttacat aggtgggatg gaagtaacct tgatggccat agtaagatca tatttgatgc 1500
acttgatgat cttgtgtgtg atgttgctaa gttataccac cttcgacacg caattgacat 1560
caccccagaa cttcgacatg tggcaggaga catttcttgc atggatgatg gaagtacgt 1620
ggagtaataa tgtagccatg ccatctagga atcaatacct agaaattggc atgatatcaa 1680
tcggtgcaca tattttggtt cttcacgctc ttctcttgaa aaatccaagc ttgccaaggg 1740
aaaaacttag gccaattaat ggcaatatg aaaatattac aaagttgcta atggccacca 1800
ctcgtttgtt gaatgacatc cagagctatc aacagaaaga atgtgaagta gggaaaatga 1860
actacacatt acttcacatg aatgaaaatc caggggcaca acttgatggt tcaattgaat 1920
ttgtgaaaga gatttttggcc aacaagaaga aagaatttct tgaaaatgtt ctaatggatg 1980
gattcaatga tatgccaaag aaatgcaaac ttcttcatct ttcttgccta aatgtatttc 2040
acatgttctt caattcttgc aatttatttg ataccaaagc agcaattctt gaagatataa 2100
tgagagctat ttacgttcct cttcaagaac aaacctcagt tccacccttta aaacttctc 2160
caattttaac acctcaagaa aagaagaaga agaagaagaa gaagattgag aatattccaa 2220
ctaaagtttc tgcttgtctc aatgggaaaa acttcaaaca ccaagttggc attggcataa 2280
gtttgttgg aagtaaagct cctaagaata atcctttgg ttggtataca aaaggatttg 2340
cttcacaaaa gttaagttca tgtttcatat ga                              2372
```

|  |  |
|---|---|
| SEQ ID NO: 187 | moltype = AA length = 86 |
| FEATURE | Location/Qualifiers |
| REGION | 1..86 |
|  | note = Description of Artificial Sequence: Synthetic polypeptide |
| source | 1..86 |
|  | mol_type = protein |
|  | organism = synthetic construct |

```
SEQUENCE: 187
MDSLPVSSIE SLVIEIKKEM FSNQEFNTFV TPISAYDTAW LAMISYNNQE EAINGHSFSG    60
PMFKSCLNWI LNNQNEQGFW GESNGV                                        86

SEQ ID NO: 188          moltype = DNA   length = 1029
FEATURE                 Location/Qualifiers
misc_feature            1..1029
                        note = Description of Artificial Sequence: Synthetic
                        polynucleotide
source                  1..1029
                        mol_type = other DNA
                        organism = synthetic construct
SEQUENCE: 188
atgggggggg gtggttctag tggaaatact tcttcatgtt taatgggtta tggagatgac    60
aacaacaaca ataacagtgg aaatgcagcc ctatgtcctc ctcctatgat gatgcctcct   120
cctcctatta ataataacaa tggagaaagc agcaataata ttggtggcaa caacaacaac   180
aatatcctgt ttctcccttt tatggccaac aacaacaata atccacatga agacgcaaac   240
tgttcttctt ctagttccat caagtctaag attatggctc atcctcacta ccctcgtctc   300
ttgtctgctt atgtcaattg tcaaaagata ggagctccgc cggaagtggt ggcaaggcta   360
gaggaagtat gtgccacgtc agcaacaata ggccgtaaca gtggcggcat tatcggagaa   420
gatccagcgc tagatcagtt catggaagct tactgtgaaa tgctgacaaa atatgagcaa   480
gaactttcaa aacccttaa ggaagccatg gttttcctct caagaattga gtgccagttt   540
aaagctctca ctcttacttc ctcctctgaa tctgttgcag ctctaggtga ggcaatcgat   600
agaaatggat cgtctgaaga ggaggttgat gtgaataacg tttcatcga ccctcaggct   660
gaagatcaag aactgaaagg tcaattgctg cgcaaataca gtggttactt gggtagcctt   720
aagcaggagt tcatgaagaa gaggaagaaa ggcaagctgc ctaaggaagc aaggcaacaa   780
ctactggact ggtggaccag acattacaaa tggccatatc catcggaatc ccagaagctg   840
gcactggctg aatctacagg attggaccaa aaacaaataa caactggtt tatcaaccaa   900
aggaaaaggc actggaaacc ttcagaggat atgcagtttg tggtaatgga tgctgctcat   960
ccacattact atatggacaa tgttctcggt aatcctttc caatggatat tacaccaact  1020
ctcctctaa                                                          1029

SEQ ID NO: 189          moltype = AA   length = 342
FEATURE                 Location/Qualifiers
REGION                  1..342
                        note = Description of Artificial Sequence: Synthetic
                        polypeptide
source                  1..342
                        mol_type = protein
                        organism = synthetic construct
SEQUENCE: 189
MGGGGSSGNT SSCLMGYGDD NNNNNSGNAA LCPPPMMMPP PPINNNNGES SNNIGGNNNN    60
NILFLPFMAN NNNNPHEDAN CSSSSSIKSK IMAHPHYPRL LSAYVNCQKI GAPPEVVARL   120
EEVCATSATI GRNSGGIIGE DPALDQFMEA YCEMLTKYEQ ELSKPFKEAM VFLSRIECQF   180
KALTLTSSSE SVAALGEAID RNGSSEEEVD VNNGFIDPQA EDQELKGQLL RKYSGYLGSL   240
KQEFMKKRKK GKLPKEARQQ LLDWWTRHYK WPYPSESQKL ALAESTGLDQ KQINNWFINQ   300
RKRHWKPSED MQFVVMDAAH PHYYMDNVLG NPFPMDITPT LL                      342

SEQ ID NO: 190          moltype = DNA   length = 738
FEATURE                 Location/Qualifiers
misc_feature            1..738
                        note = Description of Artificial Sequence: Synthetic
                        polynucleotide
source                  1..738
                        mol_type = other DNA
                        organism = synthetic construct
SEQUENCE: 190
atgtataccc cagacactcc ggcgcaagaa ctatatgacg aggaatatta cgacgagcag    60
tcgccggaga agaagcgccg tctcactccc gagcaggtgc acttgctgga gaagagcttt   120
gaggcggaga acaagctgga gccagagcgt aagactcaag aagcttggcc tg           180
cagcccaggc aagtggctgt gtggttccaa aaccgccgcg cccggtggaa gaccaagacg   240
ctcgaaaggg attatgatca gctcaaatcc tcttatgact ctcttctctc tgattttgac   300
tccattcgca aagataatga aagctcaaa gctgaggtgg tttcattgat ggagaagttg   360
caggggaaag tggttggtga agcagggta ataaatgaa aatgtgaagt tttgaggta    420
gatgcgctga cccttcaagt gaaggtgaag gcgaggaca ggctgagcag tggcagcggc    480
ggaagtgcgg tggtagatga gcacagtcca cagctggtgg acagtgggga ctcctatttt   540
cacactggtc atatgaaga gtatccacta ggggctggag gatgtaataa tattcctccg   600
cctatggatg gtttgcagtc ggaggaagat gatggtagta atgacggcgg cggccatggc   660
tacttctgta acgtctttgt ggcggcagag gagcagcaac atgaagaagg agagcctatt   720
gggtggttct ggtcttga                                                738

SEQ ID NO: 191          moltype = AA   length = 245
FEATURE                 Location/Qualifiers
REGION                  1..245
                        note = Description of Artificial Sequence: Synthetic
                        polypeptide
source                  1..245
                        mol_type = protein
                        organism = synthetic construct
```

```
SEQUENCE: 191
MYTPDTPAQE LYDEEYYDEQ SPEKKRRLTP EQVHLLEKSF EAENKLEPER KTQLAKKLGL     60
QPRQVAVWFQ NRRARWKTKT LERDYDQLKS SYDSLLSDFD SIRKDNEKLK AEVVSLMEKL    120
QGKVVGEAGV INEKCEVLEV DALTLQVKVK AEDRLSSGSG GSAVVDEHSP QLVDSGDSYF    180
HTGHMEEYPL GAGGCNNIPP PMDGLQSEED DGSDDGGHG YFCNVFVAAE EQQHEEGEPI     240
GWFWS                                                               245

SEQ ID NO: 192          moltype = DNA  length = 1641
FEATURE                 Location/Qualifiers
misc_feature            1..1641
                        note = Description of Artificial Sequence: Synthetic
                        polynucleotide
source                  1..1641
                        mol_type = other DNA
                        organism = synthetic construct
SEQUENCE: 192
acacattaaa ctaaagaaga gagaacttta gaggttagag agatgaagac gcaacatcaa    60
tggtgggaag ttcttgatcc attcttgaca caacacgaag ctcttattgc attcttgact   120
tttgcagcgg ttgtaattgt gatttacttg taccgaccct cctggtccgt atgcaatgtt   180
cccggtccaa ccgctatgcc tctagttggt cacttgccct tgatggctaa gtatggtcct   240
gatgtcttct ccgttcttgc taagcaatat ggccctattt tcagatttca gatggggagg   300
caaccactga taataatagc agaagcagag ctttgcagag aagttgggat aaagaagttc   360
aaagatcttc caaacagaag cattccttcc ccaatctcag cttctcctct tcacaagaaa   420
ggcctcttct tcaccaggga caagagatgg tctaaaatga aaacaccat cctatctctc    480
tatcagcctt cacatttaac aagtcttatc cctacaatgc atagtttcat cacttctgct   540
actcataatc ttgattctaa accgcgagat atcgttttct ccaacctctt cctcaaactt   600
accactgata tcatcggaca agcggctttt ggagtcgact tcggtctttc cgggaagaaa   660
ccaatcaaag atgtggaggt gactgatttc ataaaccagc atgtactc tacaacacaa     720
ctcaagatgg atttatcagg atcactctct atcatcttag cttactgat tccgattctt    780
caagagccgt ttaggcaggt gttgaagagg ataccgactg caatgactg gagagtcgag    840
aagactaatg caagactgag tggacaactt aatgagattg tgtcaaagcg agccaaggag   900
gctgagactg actcaaaaga cttcttgtca ttgattttga aagctcgaga gtccgatcct   960
ttcgccaaaa acatcttcac atcggattat attagtgctg tgacttatga gcatcttctt  1020
cttgatgttg agaaacgtct gcttcaagaa attgacgggt ttgggaaccg tgatctgatc  1080
ccgactgctc atgacttaca acacaagttt ccatacctcg atcaggtcat taaagaggct  1140
atgagattct acatggtttc tcctttggtt gcaaggaaa ctgctaaaga agtggagata    1200
ggaggttatt tactcccaaa ggggacatgg gtttggttag cactaggagt tctagcaaag  1260
gaccctaaaa actttccaga accggagaag ttcaagccgg aaagatttga tccgaacgga  1320
gaagaggaga aacatagaca tccatacgct ttcatcccat tcggtatcgg tccacgagcc  1380
tgtgttggac agagatttgc cctgcaagag atcaaactca cattactgca tctctaccgt  1440
aattacattt tcagacattc cctagaaatg gagataccac tgcagcttga ttatggtata  1500
attctcagct tcaagaacgg ggttaagctc agaaccatca aagattctg attcttgaaa   1560
caagtgaaat aaaagcaaga ctgaaattta tatttaaatt caaaactcca atgtagttcc  1620
aaaggaaaaa gaacaattaa c                                            1641

SEQ ID NO: 193          moltype = AA  length = 522
FEATURE                 Location/Qualifiers
REGION                  1..522
                        note = Description of Artificial Sequence: Synthetic
                        polypeptide
source                  1..522
                        mol_type = protein
                        organism = synthetic construct
SEQUENCE: 193
MKTQHQWWEV LDPFLTQHEA LIAFLTFAAV VIVIYLYRPS WSVCNVPGPT AMPLVGHLPL     60
MAKYGPDVFS VLAKQYGPIF RFQMGRQPLI IIAEAELCRE VGIKKFKDLP NRSIPSPISA   120
SPLHKKGLFF TRDKRWSKMR NTILSLYQPS HLTSLIPTMH SFITSATHNL DSKPRDIVFS   180
NLFLKLTTDI IGQAAFGVDF GLSGKKPIKD VEVTDFINQH VYSTTQLKMD LSGSLSIILG   240
LLIPILQEPF RQVLKRIPGT MDWRVEKTNA RLSGQLNEIV SKRAKEAETD SKDFLSLILK   300
ARESDPFAKN IFTSDYISAV TYEHLLAGSA TTAFTLSSVL YLVSGHLDVE KRLLQEIDGF   360
GNRDLIPTAH DLQHKFPYLD QVIKEAMRFY MVSPLVARET AKEVEIGGYL LPKGTWVWLA   420
LGVLAKDPKN FPEPEKFKPE RFDPNGEEEK HRHPYAFIPF GIGPRACVGQ RFALQEIKLT   480
LLHLYRNYIF RHSLEMEIPL QLDYGIILSF KNGVKLRTIK RF                      522

SEQ ID NO: 194          moltype = DNA  length = 2329
FEATURE                 Location/Qualifiers
misc_feature            1..2329
                        note = Description of Artificial Sequence: Synthetic
                        polynucleotide
source                  1..2329
                        mol_type = other DNA
                        organism = synthetic construct
SEQUENCE: 194
atctcctctc ttgtagattt gccgcttctc atggcttcca ctactctctc cgacctccct    60
gacgtcatct tatccaccat ttcctctctc gtatccgatt cccgagctcg caactctctc   120
tccctcgtct ctcacaaatt cctcgctctc gaacgatcca ctcgctctca cctcactatc   180
cgtggcaacg ctcgtgatct ctccctcgtc ccgactgtt ccgatcaat ctcacatctc     240
gatctctctt tcctctcccc atggggtcac actcttctcg cttctctccc aatcgatcac   300
cagaaccttc tcgctctccg tctcaaattc tgtttcccctt cgtcgagtc tctaaacgtc  360
```

```
tacacacgat ctccgagctc tctcgagctt ctacttcctc aatggccgag aattcgccac   420
atcaagctcc tccgatggca tcaacgagct tctcagatcc ctaccggtgg cgattttgtt   480
cctattttg aacactgtgg tggtttcctt gagtctttag atctctccaa cttctatcac    540
tggactgaag acttacctcc tgtgcttctc cgctatgctg acgtggcggc gaggcttaca   600
cggttagatc tcttgacggc gtcgttcacc gagggataca aatcaagcga aatcgttagt   660
atcaccaaat cttgccctaa tttgaagact tttcgtgtag cttgtacgtt tgatccgaga   720
tactttgaat tcgtcggaga cgagactctc tccgccgtag ctaccagttc ccctaagtta   780
acgcttctac acatggtgga cacagcttcg ttggcgaatc ctagagctat tccaggtacg   840
gaagctggag attcagctgt cacggcgggg acgctaattg aagttttctc aggtttaccg   900
aatctagagg agctggttct tgacgtagga aaggatgtga agcatagtgg tgtagcttta   960
gaggcattga attctaaatg caagaagtta agagtattga agctaggaca gttccaaggt  1020
gtttgctctg ctacagaatg gaggaggctc gacggtgtgg ctttatgtgg aggattgcag  1080
tcgttgtcga ttaagaattc cggcgatttg actgatatgg gtttggtggc tataggggaga 1140
ggatgttgta agttgactac gtttgagatt caagggtgta agaatgtaac agtggatgga  1200
ctaagaacaa tggttagtct tcggagtaag actttgactg atgtgagaat ctcttgctgc  1260
aagaatcttg acacagctgc ttctttaaag gcaattgagc cgatttgtga tcggatcaag  1320
agactgcata tagactgtgt gtggtctggt tcagaggacg aggaggtaga aggaagagtg  1380
gaaactagtg aggctgacca cgaagaggag gatgatggtt acgagaggag ccagaagagg  1440
tgcaagtatt cattcgagga agaacactgc tcaactagtg atgtgaatgg attctgttct  1500
gaagatagag tatgggagaa actgaagtat ctatctttat ggatcaatgt tggagaattt  1560
ttgacgccat tacctatgac aggactagat gactgtccga atttggaaga gattaggatc  1620
aagatagaag gagattgcag aggtaaacgc aggccagcgg acgcagagtt tgggttaagt  1680
tgtctcgctc tctacccaaa gctctcaaag atgcagttag attgcgggga cacaatcggt  1740
ttcgcactga ccgcaccgcc aatgcagatg gatttgagtt tatgggaaag attcttcttg  1800
accggaattg gaagcttgag cttgagcgag cttgattatt ggccaccaca ggatagagat  1860
gttaaccaga ggagtctctc gcttcctgga gcaggtctgt tacaagagtg cctgactttg  1920
aggaagctgt tcatccatgg aacagctcat gagcattcaa tgaacttttt gttgagaatc  1980
ccaaacttaa gggatgtaca gcttagagca gactattatc cggcgccgga gaacgatatg  2040
agcacagaga tgagagttgg ttcgtgtagc cgattcgagg accaattgaa cagccgcaac  2100
atcattgact gaaacttgaa gagtgagtta cctacactat tatatctgta ttgacttcag  2160
aaactggtcc attttatttg tatggtcaag agtgtttgt atatgtttgt aagaggaaag   2220
gacaaagact ataatttgcg atgattaatg atatcataaa acaataatcc attttataa   2280
atgataaaac tcaaatgaag aagccggaga gatctggagt acaaactca              2329

SEQ ID NO: 195          moltype = AA  length = 693
FEATURE                 Location/Qualifiers
REGION                  1..693
                        note = Description of Artificial Sequence: Synthetic
                         polypeptide
source                  1..693
                        mol_type = protein
                        organism = synthetic construct
SEQUENCE: 195
MASTTLSDLP DVILSTISSL VSDSRARNSL SLVSHKFLAL ERSTRSHLTI RGNARDLSLV    60
PDCFRSISHL DLSFLSPWGH TLLASLPIDH QNLLALRLKF CFPPFVESLNV YTRSPSSLEL  120
LLPQWPRIRH IKLLRWHQRA SQIPTGGDFV PIFEHCGGFL ESLDLSNFYH WTEDLPPVLL  180
RYADVAARLT RLDLLTASFT EGYKSSEIVS ITKSCPNLKF FRVACTFDPR YFEFVGDETL  240
SAVATSSPKL TLLHMVDTAS LANPRAIPGT EAGDSAVTAG TLIEVFSGLP NLEELVLDVG  300
KDVKHSGVAL EALNSKCKKL RVLKLGQFQG VCSATEWRRL DGVALCGGLQ SLSIKNSGDL  360
TDMGLVAIGR GCCKLTTFEI QGCENVTVDG LRTMVSLRSK TLTDVRISCC KNLDTAASLK  420
AIEPICDRIK RLHIDCVWSG SEDEEVEGRV ETSEADHEEE DDGYERSQKR CKYSFEEEHC  480
STSDVNGFCS EDRVWEKLEY LSLWINVGEF LTPLPMTGLD DCPNLEEIRI KIEGDCRGKR  540
RPAEPEFGLS CLALYPKLSK MQLDCGDTIG FALTAPPMQM DLSLWERFFL TGIGSLSLSE  600
LDYWPPQDRD VNQRSLSLPG AGLLQECLTL RKLFIHGTAH EHFMNFLLRI PNLRDVQLRA  660
DYYPAPENDM STEMRVGSCS RFEDQLNSRN IID                               693

SEQ ID NO: 196          moltype = DNA  length = 1110
FEATURE                 Location/Qualifiers
misc_feature            1..1110
                        note = Description of Artificial Sequence: Synthetic
                         polynucleotide
source                  1..1110
                        mol_type = other DNA
                        organism = synthetic construct
SEQUENCE: 196
atgggcagac agccactagt tatagtagca gatgcagagc tatgcagaga agttggaata    60
aagaaattca aggacatacc aaatagaagc atcccatctc ccattgcagc atccctctct   120
catcagaaag gcctattttt tactagggac tccagatggt caacaatgag aaacactatt   180
ctatcagtct accagccatc ttaccttgtt aagttagtgc caatcatgca atcgtttatc   240
gagtcttcaa ctaaaaatct tgattctgag ggagatctca cattctctga tctctcccctc  300
aagttagcta ctgatgtaat tggacaagct gcttttgaaa gaacaaacaa gaatttaagc   360
aggaggttag atgagatagt ggcaaagagg atggaggaaa aagatcgcag ttcaaaggac   420
ttcttatcgc ttatactgca ggcaagggag tcagagaagt tagctaagaa tgttttcacc   480
tcagattata tcagtgctgt aacttatgag cacttactgg ctggttctgc aacaacttcc   540
tttacattgt cttctattat ctatttggtt gctggccatc cagaggttga gcagaagtta   600
ctcacggaga tagatgcttt tgggcctaat gatcacatac tcactgccat tgagcttcag   660
cagaaattcc catccttga tcaggtaatc aaagaagcaa tgaggtgtta tgtcgtctca    720
cccttagttg ccagagaaac atcagctgag gtggagatcg gaggctataa acttcctaag   780
ggcacatggg tttggttggc tcttggagtt cttgctaagg attcaaagaa cttccccgaa   840
```

```
ccagagaagt ttagaccaga gaggtttgat ccaagctgtg aagaggaaaa acaaaggcat   900
ccttatgcaa atattccatt tggaataggg ccgcgagcat gcataggaca gaagttctcc   960
atacaagaac ttaaactctc actgattcac ttatatcgca agtacatttt tcgacactct  1020
cccccttatgg aaaagccact ggaacttgag tatggtatag tacttaacta taagcatgga  1080
gtcaaggttt gtgccatcaa gcgtaaatga                                    1110

SEQ ID NO: 197          moltype = AA  length = 369
FEATURE                 Location/Qualifiers
REGION                  1..369
                        note = Description of Artificial Sequence: Synthetic
                        polypeptide
source                  1..369
                        mol_type = protein
                        organism = synthetic construct
SEQUENCE: 197
MGRQPLVIVA DAELCREVGI KKFKDIPNRS IPSPIAASPL HQKGLFFTRD SRWSTMRNTI    60
LSVYQPSYLV KLVPIMQSFI ESSTKNLDSE GDLTFSDLSL KLATDVIGQA AFERTNKNLS   120
RRLDEIVAKR MEEKDRSSKD FLSLILQARE SEKLAKNVFT SDYISAVTYE HLLAGSATTS   180
FTLSSIIYLV AGHPEVEQKL LTEIDAFGPN DHILTAIELQ QKFPYLDQVI KEAMRCYVVS   240
PLVARETSAE VEIGGYKLPK GTWVWLALGV LAKDSKNFPE PEKFRPERFD PSCEEEKQRH   300
PYANIPFGIG PRACIGQKFS IQELKLSLIH LYRKYIFRHS PLMEKPLELE YGIVLNYKHG   360
VKVCAIKRK                                                          369

SEQ ID NO: 198          moltype = DNA  length = 2175
FEATURE                 Location/Qualifiers
misc_feature            1..2175
                        note = Description of Artificial Sequence: Synthetic
                        polynucleotide
source                  1..2175
                        mol_type = other DNA
                        organism = synthetic construct
SEQUENCE: 198
atggctacag ctacacaact tacttgttct accattatta cgacctacc tgatgtgatc     60
cttttctaaca tcatcgccgc aatctccgac gtccgcagcc gcaactccgc cgccctcgtc   120
tgccggaaat gcctcgtcct cgaacgttcc acgcgcgtct ccctcacgct ccgtgccaac   180
gtccgtgacc tcttcatgtt acccacttgc ttcagatccg taactcacct tgacctctcc   240
cttatctctc cttggggtca cccactcctc tctccggtcg acggcgccgg cgcagaagct   300
gacccttccc tcatcgccca ccttctccgc cacgcgtttc cttccgtcac ttccctcgtt   360
gtctacacgc gccacccatt cacctccag cttttgcctc cctctatgcc ccacctaaag   420
gaaatcaagc ttgtgcgtg gcaccagcgt cccaattag ctactggtga tgaatttaat    480
atgctatttg agaattgccc acagcttaaa tctctagatt tgtcgacttt ttactgctgg   540
acggatgata ttcctacagc acttgaatct catcctatgg ttgcttctaa tctcactagc   600
tttaatctct tgaattccag ttttcctgaa gggtttaagt ctgatgagat taaggtaatt   660
acacaagctt gtcctaattt gaaagagttt aaggttgctt gtatgtttga tcctaggtac   720
attggtttt tggtgatga aggtttggtt tctatagcta caaactgtac caaattatca   780
gtgcttcatt tggcggacac atcagctttg tccaactcta ggggtgatcc aaatgatgag   840
gggttcaccg aagaggatgc gaagattagt gttggaactt tgattgaggt atttctcggtt  900
cttccattac ttgaagagct tgtttagat gtttgtaata atgttagaga cacgggtcct   960
gccttggaga ttttgaatag aaaatgtccc aaattgagat cgttgaagtt ggggcaattc  1020
cacggtattt ctgtgccaat tgaatcgaag ttggatgggg ttgctctttg tcaagggctt  1080
caatctctgt cgataagtaa tgtggggac ttgaatgata tgggttttgat agctattggt  1140
agagggtgtt cgaggttagc caagtttgag attcgaggtt gtaagaagat aactatgagg  1200
ggaatgagga cactagcttc tttgcttagc agaactttgg ttgatgtcaa gatatcttgc  1260
tgcaagaatc ttgagccttc ttcttcattg aaagcattgg aaccgataca agacgatta  1320
caaaagcttc acattgactg tgtgtgggac agcgttgaaa aatttgaaa tcttgatggt  1380
aatggatacg ggtttgatct taacaggaat gatggaggg aggcatcaag caactttgct  1440
tgttccgggg acacatttgg atgcgaggaa gatgcttaca tgtttagaca gaagaaaaga  1500
tgcaagttct cctatgatat taatagttg tatgaggatg tcaatggcca tggcaatgga  1560
tatagtggac gatcatggga taagctgcaa tgcctctctc tttggattgg tgttggtgag  1620
ctttgactc ctttaacaac tgcaggtctt gaagactgtc ctaacttaga ggagatcaag  1680
attagggtgg aaggagattg caggctttgg tcaaaacctt cggagcgggc atttggactg  1740
agcaccctac tactctatcc taagctttcc aagatgcatt ggattgtgg agataccata  1800
ggttatgcac acactgcgcc atcagggcag atggatttga gcttgtggga gaggttttat  1860
ctgtttggga ttgaaatttt gagccttgcc gaactagatt actggccacc tcaagataggg  1920
gacgttaacc aaaggtgtct atccctacca gcagctgggc tgctacaaga atgcatcaca  1980
ctcagaaaac tgttcatcca tggaacagcg catgaacatt tcatgatgtt ccttcttaga  2040
atcccaaaca taagagatgt acaactgaga gaggattact atccagcacc agagaatgac  2100
atgagtacag agatgagagc agactccttg agccgcttg aagctgccct aaacaggcgc  2160
ccaatatccg attga                                                   2175

SEQ ID NO: 199          moltype = AA  length = 724
FEATURE                 Location/Qualifiers
REGION                  1..724
                        note = Description of Artificial Sequence: Synthetic
                        polypeptide
source                  1..724
                        mol_type = protein
                        organism = synthetic construct
SEQUENCE: 199
```

```
MATATQLTCS TIINDLPDVI LSNIIAAISD VRSRNSAALV CRKCLVLERS TRVSLTLRGN   60
VRDLFMLPTC FRSVTHLDLS LISPWGHPLL SPVDGAGAEA DPSLIAHLLR HAFPSVTSLV  120
VYTRHPFTLQ LLPPLWPHLK EIKLVRWHQR PQLATGDEFN MLFENCPQLK SLDLSTFYCW  180
TDDIPTALES HPMVASNLTS FNLLNSSFPE GFKSDEIKVI TQACPNLKEF KVACMFDPRY  240
IGFVGDEGLV SIATNCTKLS VLHLADTSAL SNSRGDPNDE GFTEEDAKIS VGTLIEVFSG  300
LPLLEELVLD VCNNVRDTGP ALEILNRKCP KLRSLKLGQF HGISVPIESK LDGVALCQGL  360
QSLSISNVGD LNDMGLIAIG RGCSRLAKFE IRGCKKITMR GMRTLASLLS RTLVDVKISC  420
CKNLGASSSL KALEPIQRRI QKLHIDCVWD SVEEFENLDG NGYGFDLRN  DGGEASSNFA  480
CSGDTFGCEE DAYMFRQKKR CKFSYDINSL YEDVNGHGNG YSGRSWDKLQ CLSLWIGVGE  540
LLTPLTTAGL EDCPNLEEIK IRVEGDCRLW SKPSERAFGL STLLLYPKLS KMHLDCGDTI  600
GYAHTAPSGQ MDLSLWERFY LFGIGNLSLA ELDYWPPQDR DVNQRCLSLP AAGLLQECIT  660
LRKLFIHGTA HEHFMMFLLR IPNIRDVQLR EDYYPAPEND MSTEMRADSL SRFEAALNRR  720
PISD                                                              724

SEQ ID NO: 200          moltype = DNA   length = 1338
FEATURE                 Location/Qualifiers
misc_feature            1..1338
                        note = Description of Artificial Sequence: Synthetic
                        polynucleotide
source                  1..1338
                        mol_type = other DNA
                        organism = synthetic construct
SEQUENCE: 200
atgcttactt ccttcaaatc ctctagctcc tcctccgaag atgccaccgc taccaccacc    60
gagaatcctc ctcctttgtg catcgcctcc tcctcggccg caacctccgc tcacatcac   120
ctccgtcgtc ttcttttcac cgctgcgaat ttcgtctccc agtcaaactt caccgccgct   180
caaaacttac tctcaatcct ctcccttaac tcttctcctc acggcgactc caccgagcga   240
cttgtacacc tcttcactaa agccttgtcc gtacgaatca accgtcagca acaagatcag   300
acggctgaaa cggttgccac gtggacgacg aacgaaatga cgatgagtaa ctccacggtg   360
ttcacgagca gtgtatgcaa agaacagttc ttgtttcgaa ccaagaacaa caattctgac   420
ttcgagtctt gttactatct ttggctaaac caactaacgc cgtttattcg gttcggtcat   480
ttaacggcga accaagctat cctcgacgcg acggagacaa acgataacgg agctctacat   540
atacttgatt tagatatatc acaaggactt caatggcctc cattgatgca agccctagca   600
gagaggtcat caaaccctag cagtccacct ccatctctcc gcataaccgg atgcggtcga   660
gatgtaaccg gattaaaccg aactggagac cggttaaccc ggttcgctga ctcttttaggt  720
ctccaattcc agtttcacac gctagtgatc gtagaagaag atctcgccgg acttttgcta   780
cagatccgat tgttagctct ctcagccgta caaggagaga ccattgccgt caattgtgtt   840
cacttcctcc acaaaatatt taacgacgat ggagatatga tcggtcactt cttgtcagcg   900
atcaagagct taaactctag aatcgttaca atggcagaga gagaagctaa tcatggagat   960
cactcgttct tgaatagatt ctctgaggca gtggatcatt acatggcgat cttttgattcg 1020
ttggaagcga cgttgccgcc aaatagccga gagagactaa ccctagagca acggtggttc  1080
ggtaaggaga tttttggatgt tgtggcggcg aagagacgg agagaaagca aagacatcgg   1140
agggtttgaga tttgggaaga gatgatgaag aggtttggtt tcgttaacgt tcctattgga  1200
agctttgctt tgtctcaagc taagcttctt cttagacttc attatccttc agaaggttat  1260
aatcttcagt tccttaacaa ttctttgttt cttggctggc aaaatcgtcc cctcttctcc  1320
gtttcgtcgt ggaaatga                                                1338

SEQ ID NO: 201          moltype = AA   length = 445
FEATURE                 Location/Qualifiers
REGION                  1..445
                        note = Description of Artificial Sequence: Synthetic
                        polypeptide
source                  1..445
                        mol_type = protein
                        organism = synthetic construct
SEQUENCE: 201
MLTSFKSSSS SSEDATATTT ENPPPLCIAS SSAATSASHH LRRLLFTAAN FVSQSNFTAA   60
QNLLSILSLN SSPHGDSTER LVHLFTKALS VRINRQQQDQ TAETVATWTT NEMTMSNSTV  120
FTSSVCKEQF LFRTKNNNSD FESCYYLWLN QLTPFIRFGH LTANQAILDA TETNDNGALH  180
ILDLDISQGL QWPPLMQALA ERSSNPSSPP PSLRITGCGR DVTGLNRTGD RLTRFADSLG  240
LQFQFHTLVI VEEDLAGLLL QIRLLALSAV QGETIAVNCV HPLHKIFNDD GDMIGHFLSA  300
IKSLNSRIVT MAEREANHGD HSFLNRFSEA VDHYMAIFDS LEATLPPNSR ERLTLEQRWF  360
GKEILDVVAA EETERKQRHR RFEIWEEMMK RGFVNVPIG SFALSQAKLL LRLHYPSEGY   420
NLQFLNNSLF LGWQNRPLFS VSSWK                                        445

SEQ ID NO: 202          moltype = DNA   length = 990
FEATURE                 Location/Qualifiers
misc_feature            1..990
                        note = Description of Artificial Sequence: Synthetic
                        polynucleotide
source                  1..990
                        mol_type = other DNA
                        organism = synthetic construct
SEQUENCE: 202
atgggaagag ctccgtgttg cgacaagaca aaagtgaagc gagggccttg gtcgcctgaa    60
gaagactcta aacttagaga ttacattgaa agtatggta  atggtggaaa ttggatctct   120
ttccccctca aagccggttt gaggagatgt gggaagagtt gtagactgag gtggctaaac   180
tatttgagac caaacataaa gcatggtgac ttctctgagg aagaagacag gatcatttt    240
agtctcttcg ctgccatagg aagcaggtgg tcaataaatg cagctcatct accgggacga   300
```

```
acagacaacg acataaaaaa ctattggaac acaaagctaa ggaagaaact cttgtcttct    360
tcctctgatt catcatcatc agccatggct tctccttatc taaacccta t ttctcaggat    420
gtgaaaagac caacctcacc aacaacaatc ccatcttctt cttacaatcc gtatgctgaa    480
aaccctaatc aatacccaac aaaatccctc atctccagca tcaatggctt cgaagctggt    540
gacaaacaga taatttccta tattaaccct aattatcctc aagatctcta tctctcggac    600
agcaacaaca acacctcgaa cgcaaatggt tccttgctca accacaatat gtgtgatcag    660
tacaagaacc acaccagttt ttcttcagac gtcaatggga taagatcaga gattatgatg    720
aagcaagaag agataatgat gatgatgatg atagaccacc acattgacca gaggacaaaa    780
gggtacaatg gggaattcac acaagggtat tataattact acaatgggca tggggatttg    840
aagcaaatga ttagtggaac aggcactaat tctaacataa acatgggtgg ttcaggttca    900
tcttctagtt cgataagcaa cctagctgag aacaaaagca gtggtagcct cctactagaa    960
tacaaatgct tgcccta ttt ctactcctag                                     990

SEQ ID NO: 203            moltype = AA   length = 329
FEATURE                   Location/Qualifiers
REGION                    1..329
                          note = Description of Artificial Sequence: Synthetic
                          polypeptide
source                    1..329
                          mol_type = protein
                          organism = synthetic construct
SEQUENCE: 203
MGRAPCCDKT KVKRGPWSPE EDSKLRDYIE KYGNGGNWIS FPLKAGLRRC GKSCRLRWLN     60
YLRPNIKHGD FSEEEDRIIF SLFAAIGSRW SIIAAHLPGR TDNDIKNYWN TKLRKKLLSS    120
SSDSSSSAMA SPYLNPISQD VKRPTSPTTI PSSSYNPYAE NPNQYPTKSL ISSINGFEAG    180
DKQIISYINP NYPQDLYLSD SNNNTSNANG FLLNHNMCDQ YKNHTSFSSD VNGIRSEIMM    240
KQEEIMMMMM IDHHIDQRTK GYNGEFTQGY YNYYNGHGDL KQMISGTGTN SNINMGGSGS    300
SSSSISNLAE NKSSGSLLLE YKCLPYFYS                                     329

SEQ ID NO: 204            moltype = DNA   length = 5000
FEATURE                   Location/Qualifiers
misc_feature              1..5000
                          note = Description of Artificial Sequence: Synthetic
                          polynucleotide
source                    1..5000
                          mol_type = other DNA
                          organism = synthetic construct
SEQUENCE: 204
aagctagcac catagatagt gggtgtgcacc attttacagc aaataatatg cctcaattgg     60
tggagaaagg gtctttaaag ttgaagtgtt tttcttttt t tctctttctt tttcttggta    120
ggtggtgggg aaggggaaaa tgaggggaca aaacacgaaa aatcaatttt gatgtataat    180
ttacacaaga ctcaagctaa gtgatagagt tgataaaagg ataacaataa tatgggacac    240
ataaattcat gacgtctccg tttatcggat attttctcaa attgatgtaa catatgtttt    300
aagaagttca ataatgtgt atatagattt atttctataa aatattttt cgaattataa    360
atcttcgact caagaaaaaa taaaaatgtt agatatggca aaggggatag cacttagaca    420
attaggcaac ctcatatttg ttacaagtgg gggtgagggt tcaactttgc attatttagc    480
atcactttgt tatttatttt tttta tataa aatttataga acaggagatg ttaatataag    540
gatgacaatc cagattgaca aagttgtgat agtgatacta ctgtaacatc ttattcaatc    600
atgcaaagca tctcccatta atttgtccat ctttt cgaat attacgaaaa tcagacctac    660
tttttttaca tataattttc tctaatgaca tcacaggaac tactcctgag agaaatattc    720
tcactcaagt ttgaaaacga ctcttaaatt atgataaagt gataactaca atgaccggct    780
aactcttgcg tgcattatga gtgtatatag ttatatgtta tttactctcg tcgtaaatat    840
caagtgcgaa taatatgtat gaaatttaga gaaatgagag taaattagtc gatgttttta    900
atttacgttg tgatttattc gttactttt t gctttctcta aagtcaattt cagtagttcg    960
tggagataca ttagattaaa ttaatctaat ctgttaaata ctacacggta aaaaataaaa   1020
aatatttaaa acgacataaa attttattat caaaataagt aaatcacaaa ttggggggg   1080
gtttggcttt tttttttttt gtccgaaaat tattatcatc ggtatatata actatgcttc   1140
ttatattata ttttttt agt gaaaattcta attttcgtag gcatacattt aattaagata   1200
agtaaatatg atgaataaga acagattgat aaacgtgatt taagaaaaat aagaaaagga   1260
gaaatgaata gtagttccaa tttataaaaa aaagtcaagt acttaggagt taaggttcgt   1320
gagtagatgg gacatatcac ggtggaaaag gtagaagaag cttcaaagat acaaaagaaa   1380
aagagggggtt gagattctgt gttgtgatta atacaattca atcaaagaaa aagatgtgtc   1440
attttggaca tacaactctc cctaaaataa aatgccaata aacacagtac ttgtggacat   1500
catccaccca tccttttatg actcatcaca caaaaaaac acttttttcc ttctttttt t   1560
tgaagatatt ctatgaagtt tgttgtaaac ttaaacaaaa taaatcaaca aaattgtcct   1620
atctctaaat agaggagttt ttaaaagtta aaaatcaata gaatagatac atgaagtagt   1680
cgaaggagat ttgacatttt attatgtata tatataaaat tattt taatc atatataaaa   1740
aatataattt tctatcaaaa agtgaatcct ttcatatttg tatctccgcc ctatctccaa   1800
atattaagct cacacatgaa aagagcgaga gacgaatgta gcctattggc tatgggttcc   1860
ctcactttcg atatgatgtg tataaaaaaa ttaattgaaa tctcaataaa tattagattt   1920
taacaataag ttaaaaattc aaatcattaa gtggggtctt gatttatttt ctttt gtttt   1980
ctttctcaaa ctgatgtttt tattaaggat ttattgaaaa aatatttcta tctctcgggg   2040
taggaattaa atttgctatg tgtatatcct accttttgtt aaatttagtt tacagaatta   2100
tcggttaaat atgttagata tgttattatt gttgttacgt ccgaatagac acccataggt   2160
gtagtgtagt caaattaata aaaccatgga atacgatggg atatcaaagt tgataatttt   2220
taactaaaaa aaaatgtcac tagatgattt tttttctct caattgtcta atcttgacag   2280
aaagatgtac ctaatgaaat aataaaagtg caacaaaaaa gaatagacaa atttccaaaa   2340
attgaatctt ttgttggtac tcgtcaacaa gttattcttc atgtctaaat cctaaaaaaa   2400
atatctcctc gtgtaaagac tggtatattg aaaatttaaa ataaattaat acatctaaac   2460
```

```
gtatcatatc ttctatataa tataaaattt ttagtgactc gtttcttaca attcaataat  2520
ttagtataaa taatttgtcg attgcgcgga tgaaagaaag gggtggtggt ggagatataa  2580
agtgtgatcg atagggtatc ttgtatgtga ttaatatagc taaacaaaaa ggtgaaaggc  2640
aaaaacatat atgaatggtg gtcctattcc atatttaaat ggattattag gatacgtcga  2700
tttcactttg caaaatacoc tctatagatt catatatttt cttttctcat caactttttt  2760
ttctatcata taactagcct tactctggct tctcacgttt cacatgtctc aatgtttatt  2820
tgttttttt ccactcttgg gcgtctaaag ggtttagaaa aatttgacaa tgtggaccac  2880
ccaaagttta taaaattaga attaaacagt catgaaggca tatacctagg agttccattt  2940
acatcttcac gtataaaatg tgtactttat attaattta tttatctcat gattcttatt  3000
agagatgata aatgtaacat tttttttttg tttttattaa attttagaag agataaacctt  3060
cttgattaat tctatgattt tccttttta ttacgaaact gaaacttaac aattaactga  3120
gacataacaa acatgaatgt agttcatatc taaattaaca tcaaagccat catatctaac  3180
tcaactaagt tagtcatggt actcttgtga ttgacataaa ttttacaata aactttctta  3240
gctagaacgg actcaccaac aaatataaaa ccacagaaaa aattatatcg aactcaatac  3300
taaacaaaga agtatggaag actaaatatg ttgatacgag gtaggcttat tggtgatttt  3360
acaagggctt atatagcaaa agttgataca aacaaatggg ctaaaaagta aatggcccat  3420
ttattttatt tattttttcc attatcaata cacagatttg cacttcgtta gcggacaatt  3480
ttgggtaaat tatgaaaatt gggcctcttc acaatttaga tcccgaccgt gtggatggat  3540
ggacaaggaa atttttaggtc cagttccagt tatattgggg agataaaagg aaaaattacg  3600
tggttaagta atatatatat tagttaatta gttattataa taattatttt agttaattat  3660
tattcgcgat taacattagt gataattatg taggctgaga ttttgagttt gtataatttg  3720
aaattttaag atataaatttc tataacttt atatagtaca attttataaa atattatttg  3780
tataattgat aaaatttaga tgtttgtgtt tgtataaatt tatattttag atttatcaaa  3840
atataactca attattcaaa ctaaccataa tacgtacgaa ttcactcaca aattatacaa  3900
acaatacaat ttgaaccata gctgcaaccc ctaataatgc gagctacgac tataaagtat  3960
aattaaattt atttactata acggatattt gcaaaaattc tccttaggca taaccaataa  4020
tggcccctga acgagttgct cgaaaaagct aattaaagat cattcatttt tggaaaacta  4080
tataaatcag aagactaaaa tatagctttt agcttttcac ttgaaataag ttattttta  4140
tttaaataaa ttatttttgat aattattaaa cactctaata aattaaaaag atgatttta  4200
agtcagattg atcagctttt aagtccatct aaagatgctt tattacatc ttattttta  4260
aaaaaaatta attattaaaa tttcaaagtt ttcattgctc tcgaagacat tttttttaat  4320
gtccggtaca ttgtaataat atattattta atggaaggaa agtatagaag gatttttaa  4380
aaaaaataat taagtgataa acttttttag aaattataat atgttgtata tttacgttaa  4440
atttcttaat tttttaattt aacatttccc aaaaattttg tgttatccaa atgtccgaat  4500
aacaaccaat taactgacac tgaatttgtg aattttacga gacaaatgtt cttgttaaaa  4560
tttcatatta ggtttcaact gtgagttatt tttggaaatt taaattatgt gtgttgatca  4620
aaatacttta aatattttt tttcattata tcatgaattt taaatagata tcatatattt  4680
ttaaaagatt tagatttaaa ttttactatt aatatatgcaa accgacatag cctaaagttg  4740
aaaaaatatc aaattcatcg agggaaaacg aaaattgcaa gtatatttgg ccaaacgaag  4800
cacctgtcca tgaaatgcca cgtaaaaatt ctaagcaaaa atactacaat aagtgcatgg  4860
aatgagacga gcacgtgtca agttgaaaga agcacctgtc catgaaatgc cacgtaactc  4920
acaccttcaa aacctctcca ttgctacaaa tctccatatt tttgtttttt tttttaaga  4980
aaagataaa agtactagca                                               5000
SEQ ID NO: 205          moltype = DNA  length = 2058
FEATURE                 Location/Qualifiers
misc_feature            1..2058
                        note = Description of Artificial Sequence: Synthetic
                        polynucleotide
source                  1..2058
                        mol_type = other DNA
                        organism = synthetic construct
SEQUENCE: 205
atgtcggtga aaaattgtat gtcgattcaa tgttgcaaaa tcttgttcaa gtttctactg   60
tttatgatta ttatcatcag tagcgtgttt atcgatgtaa gagctaaaag agaaaatgaa  120
ggttgggaat ggggtttagg tcctctgatt aaaagagcag aaagaaaaac agttatttca  180
actgaaaatg gtgaagtctc atcagtcaca gtagctgatg aacaaccta tcatcttcaa  240
ttcatcacat tggaacccaa ctccctcttc cttcccgttg ttctacatac agatatggtt  300
ttttatgttc acactgggtc ggggaagcta acttggatga atgaaaatga agagaaatca  360
gtggatttaa gaataggaga tgtattcagg ctgcctttg gatctatttt cttcttagag  420
agtgacttag accctatcag acacaaactt agacttatt ccatttttcc caattcaggc  480
cgagaatcac tgagtgagcc ctactccagc atccgtaaaa tggttcttgg attcgacaag  540
aaagtcctcc aagcggcatt tcatgtacca gaggatgtga tagaagaagt gttggctgga  600
acagaagtac cagccatagt gcacggtgtg ccaaagtcaa ctaagaagaa gagaaactta  660
tgggagatgg aggctcagtt catgaagact gttttaggaa ggggtagtta tagtttcttt  720
gacaaccgaa ggaataaaaa gaagagttct caattgttca atgtattcca agagaaacca  780
gattttgaga attgcaacgg gtggagcacg gtaataaaca ggaagaaatt gccggcgtta  840
aagggctcgc aaaattggtat ttacgtagtg aacttaacga aaggatcaat gatggggcga  900
cattggaatc caatggctac tgaaattgga atagcaattc aaggagaagg aatggtgagg  960
gtagtttgct caaagagtgg aacagggtgt aaaaacatga ggtttaaagt ggaagaaggg 1020
gatgtatttg ttgtgccaag gtttgatcct atggctcaaa tggcattcaa taacaattca 1080
tttgtgtttg tggggtttag cacaactaca agaaacatc atcctcagta cttaacgggg 1140
aaggcatcgg tcctccgaac attggatagg cagatattgg aagcatcttt caatgtgggc 1200
aacacaacaa tgcatcagat tcttgaagca caggtgatt cagttatact ggagtgtaca 1260
tcttgtgctg aggaagagaa gaggttgatg gaggaagaa tgaggaagga ggaggaggaa 1320
gcgaagaaga aagaggaggc aagaaggct gaagaagaga gaagagaaa agaagcgag 1380
gaagaaagga agagacaaga ggaagaagca aggaaagggg aggaagagga aataaggagg 1440
agacaggaag agaggaagc taggagaaga caagaggaag aggaagagga aagagagaga 1500
caggaagcta gaaagaaaca agaagaggaa gaagcagcac aaagagaggc agagcaagca 1560
```

```
aggagagaag aggaagaagc agaaaaaaga aggcaggagg aggaagaatc aaggagagag    1620
gagaaagcaa gaagaaggca acaggaggaa gcaaggagga gagaggagga agaagcagca    1680
aaaaggcaac atgaggaaga agcagagaga gaggcagagg aagcaagaag gatagaggag    1740
gaagaagcac aaagagaggc agaagaagca aggagaatac aacaggagga agaagcagag    1800
agagcaagga gaaggaagca agaagcagaa acaagaagga agaaggagga ggaggaagaa    1860
tcaaggagac aagaggagga atcaaggagg agtgaagaag aggcagcaag agaggcagag    1920
agggaaaggc aagaggaagc tgaaagacaa gaagaagcta ggagacggga ggaagaaaca    1980
gaagagaggc atcaacaaga agaaaccgag gaagaggagc caggccaacc tgaaatgaac    2040
ggatattcct caaactag                                                  2058

SEQ ID NO: 206              moltype = AA   length = 685
FEATURE                     Location/Qualifiers
REGION                      1..685
                            note = Description of Artificial Sequence: Synthetic
                             polypeptide
source                      1..685
                            mol_type = protein
                            organism = synthetic construct
SEQUENCE: 206
MSVKNCMSIQ CCKILFKFLL FMIIIISSVF IDVRAKRENE GWEWGLGPLI KRAERKTVIS     60
TENGEVSSVT VADGTTYHLQ FITLEPNSLF LPVVLHTDMV FYVHTGSGKL TWMNENEEKS    120
VDLRIGDVFR LPFGSIFFLE SDLDPIRHKL RLYSIFPNSG RESLSEPYSS IRKMVLGFDK    180
KVLQAAFHVP EDVIEEVLAG TEVPAIVHGV PKSTKKKKNL WEMEAQFMKT VLGRGSYSFF    240
DNRRNKKKSS QLFNVFQEKP DFENCNGWST VINRKKLPAL KGSQIGIYVV NLTKGSMMGP    300
HWNPMATEIG IAIQGEGMVR VVCSKSGTGC KNMRFKVEEG DVFVVPRFDP MAQMAFNNNS    360
FVFVGFSTTT KKHHPQYLTG KASVLRTLDR QILEASFNVG NTTMHQILEA QGDSVILECT    420
SCAEEEKRLM EEEMRKEEEE AKKKEEARKA EEERREKEAE EERKRQEEEA RKREEEEIRR    480
RQEEEEARRR QEEEEEERER QEARKKQEEE EAAQREAEQA RREEEEAEKR RQEEEESRRE    540
EKARRRQQEE ARRREEEEAA KRQHEEEAER EAEEARRIEE EEAQREAEEA RRIQQEEEAE    600
RARRREEEAE TRRKEEEEEE SRRQEESSRR SEEEAAREAE RERQEEAERQ EEARRREEET    660
EERHQQEETE EEEPGQPEMN GYSSN                                         685

SEQ ID NO: 207              moltype = DNA   length = 633
FEATURE                     Location/Qualifiers
misc_feature                1..633
                            note = Description of Artificial Sequence: Synthetic
                             polynucleotide
source                      1..633
                            mol_type = other DNA
                            organism = synthetic construct
SEQUENCE: 207
atgggtgatt ctgacgtcgg tgatcgtctt ccccctccat cttcttccga cgaactctcg     60
agcttctcc gacagattct ttcccgtact cctacagtc aaccttcttc accaccgaag     120
agtactaatg tttcctccgc tgagaccttc ttcccttccg tttccggcgg agctgttcct    180
tccgtcggtt atggagtctc tgaaactggc aagacaaat atgctttcga acacaagaga    240
agtggagcta aacagagaaa ttcgttgaag agaaacattg atgctcaatt ccacaacttg    300
tctgaaaaga agaggaggag caagatcaac gagaaaatga aagctttgca gaaactcatt    360
cccaattcca acaagactga taaagcctca atgcttgatg aagctataga atatctgaag    420
cagcttcaac ttcaagtcca gactttagcc gttatgaatg gttaggctt aaaccccatg    480
cgattaccac aggttccacc tccaactcat acaaggatca atgagacctt agagcaagac    540
ctgaacctag agactcttct cgctgctcct cactcgctgg aaccagctaa acaagtcaa    600
ggaatgtgct tttccacagc cactctgctt tga                                633

SEQ ID NO: 208              moltype = AA   length = 210
FEATURE                     Location/Qualifiers
REGION                      1..210
                            note = Description of Artificial Sequence: Synthetic
                             polypeptide
source                      1..210
                            mol_type = protein
                            organism = synthetic construct
SEQUENCE: 208
MGDSDVGDRL PPPSSSDELS SFLRQILSRT PTAQPSSPPK STNVSSAETF FPSVSGGAVS     60
SVGYGVSETG QDKYAFEHKR SGAKQRNSLK RNIDAQFHNL SEKKRRSKIN EKMKALQKLI    120
PNSNKTDKAS MLDEAIEYLK QLQLQVQTLA VMNGLGLNPM RLPQVPPPTH TRINETLEQD    180
LNLETLLAAP HSLEPAKTSQ GMCFSTATLL                                     210

SEQ ID NO: 209              moltype = DNA   length = 1047
FEATURE                     Location/Qualifiers
misc_feature                1..1047
                            note = Description of Artificial Sequence: Synthetic
                             polynucleotide
source                      1..1047
                            mol_type = other DNA
                            organism = synthetic construct
SEQUENCE: 209
atggaaagtc tcgcacacat tcctcccggt tatcgattcc atccgaccga tgaagaactc     60
gttgactatt atctcaagaa caagttgca ttcccgggaa tgcaagttga tgttatcaaa    120
gatgttgatc tctacaaaat cgagccatgg gacatccaag agttatgtgg aagagggaca    180
```

```
ggagaagaga gggaatggta tttctttagc cacaaggaca agaaatatcc aactgggaca    240
cgaaccaata gagcaacggg ctccggattt tggaaagcaa cgggtcgaga caaggccatt    300
tactcaaagc aagagcttgt tgggatgagg aagactcttg tcttttacaa aggtagggcc    360
ccaaatggtc agaaatctga ttggataatg cacgaatacc gtcttgagac cgatgaaaat    420
ggaccgcctc atgaggaagg atgggtggtt tgtcgcgctt tcaagaagaa gctaaccacg    480
atgaactaca acaatccaag aacaatgatg ggatcatcat caggccaaga atctaactgg    540
ttcacgcagc aaatggatgt ggggaatggt aattactatc atcttcctga tctagagagt    600
ccgagaatgt ttcaaggctc atcatcatca tcactatcat cattacatca gaatgatcaa    660
gacccttatg gtgtcgtact cagcactatt aacgcaaccc caactacaat aatgcaacga    720
gatgatggtc atgtgattac caatgatgat gatcatatga tcatgatgaa cacaagtact    780
ggtgatcatc atcaatcagg attactagtc aatgatgatc ataatgatca agtaatggat    840
tggcaaacgc ttgacaagtt tgttgcttct cagctaatca tgagccaaga agaggaagaa    900
gttaacaaag atccatcaga taattcttcg aatgaaacat tcatcatct ctctgaagag     960
caagctgcaa caatggtttc gatgaatgct tcttcctctt cttctccatg ttccttctac   1020
tcttgggctc aaaatacaca cacgtaa                                        1047

SEQ ID NO: 210          moltype = AA  length = 348
FEATURE                 Location/Qualifiers
REGION                  1..348
                        note = Description of Artificial Sequence: Synthetic
                        polypeptide
source                  1..348
                        mol_type = protein
                        organism = synthetic construct
SEQUENCE: 210
MESLAHIPPG YRFHPTDEEL VDYYLKNKVA FPGMQVDVIK DVDLYKIEPW DIQELCGRGT     60
GEEREWYFFS HKDKKYPTGT RTNRATGSGF WKATGRDKAI YSKQELVGMR KTLVFYKGRA    120
PNGQKSDWIM HEYRLETDEN GPPHEEGWVV CRAFKKKLTT MNYNNPRTMM GSSSGQESNW    180
FTQQMDVGNG NYYHLPDLES PRMFQGSSSS SLSSLHQNDQ DPYGVVLSTI NATPTTIMQR    240
DDGHVITNDD DHMIMMNTST GDHHQSGLLV NDDHNDQVMD WQTLDKFVAS QLIMSQEEEE    300
VNKDPSDNSS NETFHHLSEE QAATMVSMNA SSSSSPCSFY SWAQNTHT                 348

SEQ ID NO: 211          moltype = DNA  length = 975
FEATURE                 Location/Qualifiers
misc_feature            1..975
                        note = Description of Artificial Sequence: Synthetic
                        polynucleotide
source                  1..975
                        mol_type = other DNA
                        organism = synthetic construct
SEQUENCE: 211
atggataata taatgcaatc gtcaatgcca ccgggattcc gatttcatcc gacagaggaa     60
gagctggtgg gttattacct agataggaag atcaattcaa tgaagagtgc tttagatgtc    120
attgtagaga ttgatctcta caaaatggag ccatgggata tacaagcgag tgtaaaacta    180
gggtatgaag agcaaaacga gtggtacttc tttagtcata aggacaggaa gtaccctacc    240
gggactagga ccaaccgagc cactgcggct gggttctgga agccacggg tagagacaag     300
gcggtactat caaaaacag tgtcatcgga atgcggaaga cacttgtcta ctacaagggt    360
cgagctccta atggaagaaa gtccgattgg atcatgcacg aataccgtct ccaaaactcc    420
gagcttgccc cggttcagga ggaaggctgg gtggtgtgtc gagcatttag gaagccaatt    480
ccaaaccaga ggccattagg gtacgagcca tgcagaacc agctctacca cgtcgaaagt     540
agtaacaact actcatcttc agtgacaatg aacacgatc atcatatcgg tgcatcttca    600
tcaagtcata accttaatca aatgctcatg agcaataacc actacaatcc taataataca    660
tcctcatcga tgcatcaata tggcaacatt gagctcccgc agttggacag cccgagcttg    720
tcgcctagtt tagggacgaa taaagatcag aacgagagtt tcgagcaaga agaagagaag    780
agctttaact gtgtggattg gagaaacacta gatacctttgc ttgagacaca agtcatacat    840
ccgcataacc ctaatattct tatgttcgaa acgcagtcgt ataatccggc gccaagcttc    900
ccttccatgc atcaaagcta taatgaggtc gaagctaata ttcatcattc tcttggatgc    960
ttccctgact cgtaa                                                     975

SEQ ID NO: 212          moltype = AA  length = 324
FEATURE                 Location/Qualifiers
REGION                  1..324
                        note = Description of Artificial Sequence: Synthetic
                        polypeptide
source                  1..324
                        mol_type = protein
                        organism = synthetic construct
SEQUENCE: 212
MDNIMQSSMP PGFRFHPTEE ELVGYYLDRK INSMKSALDV IVEIDLYKME PWDIQARCKL     60
GYEEQNEWYF FSHKDRKYPT GTRTNRATAA GFWKATGRDK AVLSKNSVIG MRKTLVYYKG    120
RAPNGRKSDW IMHEYRLQNS ELAPVQEEGW VVCRAFRKPI PNQRPLGYEP WQNQLYHVES    180
SNNYSSSVTM NTSHHIGASS SSHNLNQMLM SNNHYNPNNT SSSMHQYGNI ELPQLDSPSL    240
SPSLGTNKDQ NESFEQEEEK SFNCVDWRTL DTLLETQVIH PHNPNILMFE TQSYNPAPSF    300
PSMHQSYNEV EANIHHSLGC FPDS                                           324

SEQ ID NO: 213          moltype = DNA  length = 2103
FEATURE                 Location/Qualifiers
misc_feature            1..2103
                        note = Description of Artificial Sequence: Synthetic
```

```
                          polynucleotide
source                    1..2103
                          mol_type = other DNA
                          organism = synthetic construct
SEQUENCE: 213
atggaaagga tacctgaagt tagagaatca actaggcagt ttcctatagg ggctaaggtg    60
gctcatactt tctcaacctc caagaaggag gtcggtatta gaggctttcg agattttgac   120
ttggctattc caatacaaac atggaaagga agacctcct atcaggagga agaagacctg   180
atggtcgatg ctggtacaat caagcgtagt gatgattcac ttgaagatag tggtctcaca   240
tcatttcatg gggcgagtca ccctccggaa cctgttgata cagacctaat gagaccagtg   300
tatgtaccaa ttggtcaaaa caaagcagat gggaaatgtc tggtgaaaaa cgtatctttg   360
aagggtcctt tcttggacga tctttcaatc cggatgccaa atgtgaaacc aagcccatcc   420
cttctttcac cggcagagag cttggttgaa gagccaaatg atctaggtgt aatctcctct   480
ccatttacag ttcctcgtcc ttctcaaaac acagaaacca gtctgcctcc tgattccgaa   540
gagaaagaat gtatttggga tgcatcactg cctccaagcg gaaatgtgag tccacttagt   600
agcattgata gtactggtgt tgtgagatct atgagtattg tcaacagttg cacaagcacg   660
tacaggagtg atgtgcttat gagtgatggc atgcttagtg tggacagaaa ctatgagagc   720
acgaaaggga gcattcgagg ggattcactc gaaagtagta aaactagctc tagcagagca   780
agtgacagta gtggacttag tgatgatagt aattggagta acatcactgg cagtgccaat   840
aagcctcaca aaggaaatga tcctagatgg aaggctattc tcgcaattcg ggcacgtgat   900
ggtatattag gcatgagcca ctttaagtta ctcaaaagac ttggttgtgg agacattgga   960
agtgtttatc tttctgagct tagcgggact cgctgctatt ttgcaatgaa agtgatggat  1020
aaggcatcac ttgcaagcag gaagaaattg acgcgtgctc agacagaaag agaaatccta  1080
cagtgtattag accatccatt cttgccaaca ttgtacactc attttgagac cgatcgcttc  1140
tcatgtttgg tcatggaata ttgtcctgga ggagatctgc atactctacg acagcgacaa  1200
cctgggaagc attttttcaga atatgctgca aggttttatg cagcagaagt tctattggcg  1260
cttgaatatc tacatatgct tggtgtagtg tacagggatt taaaacctga aaatgttctt  1320
gtgcgtgacg atggccacat tatgcttta gattttgacc tctccttgag atgtgcagtt  1380
tcacctacgc tcataaggat ctcatctgat gatccttcta aacgaggagc tgcatttgt  1440
gtgcagccag cctgtattga gcccacaact gtatgcatgc agcagcctgc ttttcttcca  1500
cgtttatttc ctcaaaagag caagaaaaaa acacctaagc ctcgagctga ttctgggttt  1560
caagctaatt caatgcctga gctagttgcg gaacctactt cagcacggtc aatgtcattt  1620
gttgggactc atgaatattt ggcccccgag attatcaagg gagaaggcca tggcagtgca  1680
gttgactggt ggacatttgg tattttcctt catgaactac tctatggaaa gacccctcca  1740
aagggatcag gaaacagggc aactcttttc aatgtagttg gccaacaact taaatttcca  1800
gattctcctg caaccagtta tgccagccgt gatctgatac gtggcttgct tgttaaagag  1860
cctcaaaacc ggcttgggt gaaacgagga gcaactgaga tcaagcaaca tcctttcttt  1920
gaaggtgtta ttgggctct aatacgttgc agtacaccac ctgaagtgcc aagacccgtg  1980
gagccagact accctgcgaa gtacgggcaa gtgaaccctg ttggggttgg caataccagt  2040
aaaagagtgg tagggcaga tgcaaagtct gggggtaaat atcttgactt tgagttcttt  2100
tag                                                               2103

SEQ ID NO: 214           moltype = AA   length = 700
FEATURE                  Location/Qualifiers
REGION                   1..700
                         note = Description of Artificial Sequence: Synthetic
                         polypeptide
source                   1..700
                         mol_type = protein
                         organism = synthetic construct
SEQUENCE: 214
MERIPEVRES TRQFPIGAKV AHTFSTSKKE VGIRGFRDFD LAIPIQTWKG KTSYQEEEDL    60
MVDAGTIKRS DDSLEDSGST SFHGASHPPE PVDTDLMRPV YVPIGQNKAD GKCLVKNVSL   120
KGPFLDDLSI RMPNVKPSPS LLSPAESLVE EPNDLGVISS PFTVPRPSQN TETSLPPDSE   180
EKECIWDASL PPSGNVSPLS SIDSTGVVRS MSIVNSCTST YRSDVLMSDG MLSVDRNYES   240
TKGSIRGDSL ESGKTSLSRA SDSSGLSDDS NWSNITGSAN KPHKGNDPRW KAILAIRARD   300
GILGMSHFKL LKRLGCGDIG SVYLSELSGT RCYFAMKVMD KASLASRKKL TRAQTEREIL   360
QLLDHPFLPT LYTHFETDRF SCLVMEYCPG GDLHTLRQRQ PGKHFSEYAA RFYAAEVLLA   420
LEYLHMLGVV YRDLKPENVL VRDDGHIMLS DFDLSLRCAV SPTLIRISSD DPSKRGAAFC   480
VQPACIEPTT VCMQPACFLP RLFPQKSKKK TPKPRADSGF QANSMPELVA EPTSARSMSF   540
VGTHEYLAPE IIKGEGHGSA VDWWTFGIFL HELLYGKTPF KGSGNRATLF NVVGQQLKFP   600
DSPATSYASR DLIRGLLVKE PQNRLGVKRG ATEIKQHPFF EGVNWALIRC STPPEVPRPV   660
EPDYPAKYGQ VNPVGVGNTS KRVVGADAKS GGKYLDFEFF                         700

SEQ ID NO: 215           moltype = DNA   length = 1068
FEATURE                  Location/Qualifiers
misc_feature             1..1068
                         note = Description of Artificial Sequence: Synthetic
                         polynucleotide
source                   1..1068
                         mol_type = other DNA
                         organism = synthetic construct
SEQUENCE: 215
atggcttttt ctgccaccatc actttccaaa ttctctcttt tggttgccat ttcagcatca    60
gctctcctct gttgtgctttt tgcccgtgat ttctccattg ttggatacac gccggagcat   120
ttgacaaaca ctgacaagct tctagagctc ttcgagtcat ggatgtcaga acacagcaag   180
gcttacaaaa gcgtggagga gaaggtgcac aggtttgagg ttttcagaga gaatctgatg   240
catatagacc agaggaacaa tgagatcaac agttactggc tcggtttgaa cgagtttgcg   300
gatttgaccc atgaagagtt caaaggaaga tatctaggac ttgcaaagcc acaattctct   360
```

```
agaaagagac agccctcagc taacttcagg tacagagata tcacggactt gcctaaatcc    420
gtagactgga gaaagaaagg cgctgtggct cctgtcaagg accagggtca atgtggtagc    480
tgttgggcat tttcaacagt tgcagctgtc gaggggatca accagatcac aacagggaat    540
ctgagttcgc tttcagagca agaactcata gactgtgaca caactttcaa cagtggctgc    600
aatggaggtc tcatggacta cgcattccag tacataattt cgaccggtgg tctccacaaa    660
gaagatgatt acccttatct catggaggaa ggaatttgtc aagagcagaa agaggatgtg    720
gaacgtgtga caatcagcgg ctacgaagat gtccctgaaa atgatgacga aagcctggtg    780
aaggctttag ctcatcagcc agtcagtgtg gctattgagg cttcaggaag agacttccag    840
ttctacaaag ggggagtgtt taatggtaaa tgtggaacag acctagacca cggtgtggca    900
gcggttggat atggttcatc aaagggatct gactatgtta ttgtcaagaa ctcatgggga    960
ccaagatggg gagagaaagg gtttattagg atgaagagaa acactggtaa accagaggga   1020
ctctgtggaa tcaacaagat ggcctcatat cctaccaaga ccaagtga                1068

SEQ ID NO: 216         moltype = AA  length = 355
FEATURE                Location/Qualifiers
REGION                 1..355
                       note = Description of Artificial Sequence: Synthetic
                       polypeptide
source                 1..355
                       mol_type = protein
                       organism = synthetic construct
SEQUENCE: 216
MAFSAPSLSK FSLLVAISAS ALLCCAFARD FSIVGYTPEH LTNTDKLLEL FESWMSEHSK    60
AYKSVEEKVH RFEVFRENLM HIDQRNNEIN SYWLGLNEFA DLTHEEFKGR YLGLAKPQFS   120
RKRQPSANFR YRDITDLPKS VDWRKKGAVA PVKDQGQCGS CWAFSTVAAV EGINQITTGN   180
LSSLSEQELI DCDTTFNSGC NGGLMDYAFQ YIISTGGLSH KEDDYPYLMEE GICQEQKEDV   240
ERVTISGYED VPENDDESLV KALAHQPVSV AIEASGRDFQ FYKGGVFNGK CGTDLDHGVA   300
AVGYGSSKGS DYVIVKNSWG PRWGEKGFIR MKRNTGKPEG LCGINKMASY PTKTK        355

SEQ ID NO: 217         moltype = DNA  length = 1071
FEATURE                Location/Qualifiers
misc_feature           1..1071
                       note = Description of Artificial Sequence: Synthetic
                       polynucleotide
source                 1..1071
                       mol_type = other DNA
                       organism = synthetic construct
SEQUENCE: 217
atggctcttt cttcaccttc aagaatcctc tgttttgctc ttgccttatc cgctgcttct     60
ctctccctct ctttcgcttc ttcccacgat tactccatcg ttggatactc ccccgaggat   120
ttggaatctc atgacaaact catagaactc ttcgaaaact ggatctcaaa tttttgagaaa   180
gcttatgaaa ccgttgaaga gaagtttctt aggttcgaag ttttcaagga taatctaaag   240
cacatcgatg agactaacaa gaaagggaaa agctactgtc tcgggctcaa cgagtttgga   300
gatttgagcc atgaggagtt caagaaaatg tatttagggc tcaagactga tatagtgaga   360
cgcgatgaag aaagatctta cgcagagtgc gcttacaggg acgtcgaagc tgttcctaag   420
tctgttgact ggagaaagaa aggagctgtg gcggaagtta agaaccaggg ctcttgtgga   480
agttgttggg cgttttcgac agtagcagct gtcgaagtta taaacaagat tgtgacagga   540
aacttgacaa cattgtcaga acaagaactc atagactgtg acacgaccta caacaatggc   600
tgcaacggtg gtctcatgga ctatgccttt gagtacattg ttaagaacgg aggtctacgc   660
aaggaagaag attatcctta ctctatggaa gaaggaactt gcgagatgca aaaggatgaa   720
tctgaaacag taaccattaa tggacaccaa gacgtaccta ctaatgatga gaagagtctc   780
ttgaaggcat tggctcatca gcctctcagt gtcgccattg atgcatctgg tagagagttc   840
cagttctata cgcggcggcgt gtttgatggg cggtgcgggg ttgatcttga ccacggtgtg   900
gctgcggttg gtatggatc aagcaagggt tcagattaca tcattgtgaa gaattcttgg   960
ggaccaaaat ggggagaaaa aggttacatc aggctgaaga gaacactgg gaaaccagag   1020
ggtctctgtg gaatcaacaa gatggcttct ttccccacca aactaagtg a             1071

SEQ ID NO: 218         moltype = AA  length = 356
FEATURE                Location/Qualifiers
REGION                 1..356
                       note = Description of Artificial Sequence: Synthetic
                       polypeptide
source                 1..356
                       mol_type = protein
                       organism = synthetic construct
SEQUENCE: 218
MALSSPSRIL CFALALSAAS LSLSFASSHD YSIVGYSPED LESHDKLIEL FENWISNFEK    60
AYETVEEKFL RFEVFKDNLK HIDETNKKGK SYWLGLNEFA DLSHEEFKKM YLGLKTDIVR   120
RDEERSYAEF AYRDVEAVPK SVDWRKKGAV AEVKNQGSCG SCWAFSTVAA VEGINKIVTG   180
NLTTLSEQEL IDCDTTYNNG CNGGLMDYAF EYIVKNGGLR KEEDYPYSME EGTCEMQKDE   240
SETVTINGHQ DVPTNDEKSL LKALAHQPLS VAIDASGREF QFYSGGVFDG RCGVDLDHGV   300
AAVGYGSSKG SDYIIVKNSW GPKWGEKGYI RLKRNTGKPE GLCGINKMAS FPTKTK       356

SEQ ID NO: 219         moltype = DNA  length = 1257
FEATURE                Location/Qualifiers
misc_feature           1..1257
                       note = Description of Artificial Sequence: Synthetic
                       polynucleotide
source                 1..1257
```

```
                        mol_type = other DNA
                        organism = synthetic construct
SEQUENCE: 219
atgacgaaaa aggcggtgct tattgggatc aattacccag gaaccaaggc ggagttacgg    60
ggatgcgtca acgatgttcg tcgtatgtac aaatgtctcg ttgaacggta cggcttctcc   120
gaggagaaca tcaccgttct catcgacacc gatgaatcct ctactcagcc tactggcaag   180
aacatccgcc gcgcgcttgc tgatctcgtc gaatctgccg attccggcga cgttcttgtc   240
gttcattaca gtggacacgg tacgaggttg ccggctgaga ctggtgaaga cgatgacact   300
ggtttcgacg agtgtattgt tccttgcgac atgaatctga ttactgatga tgattttaga   360
gatcttgtgg acaaggttcc tccaggttgc agaatgacaa tcatttcaga ctcttgtcac   420
agtggtggcc taatcgacga agccaaggag cagattggag agagcactaa gaaagaagcc   480
gaggacgaag atgaatctga agaatcttct tcaagattcg ggtttaggaa gttcttgcgc   540
agcaaagtgg aaggcgccat cgagtctcga gggtttcaca ttggagggaa caagaaggat   600
gaagatgagg cggaagaaat cgagactaag gagattgagc ttgaagacgg agaaaacgatc   660
catgccaaag acaaatctct tcctctgcag accttgattg atattctcaa gcagcaaaca   720
gggaatgata atatcgaagt tgggaaaatc aggccaagcc ttttttgatgc gtttggtgat   780
gattcgagcc cgaaagtgaa gaagtttatg aaagtgatct taggtaagct tcaggctgga   840
aatggagaag aaggtggatt aatgggaatg gtttggcaaat tggctcaggg gtttcttgag   900
ggtaaactaa acgatgaaga ctatgtgaaa cccgctatgc agacacacgt tgggagtaaa   960
gaagaggttt atgctggtgg atcaagaggt tcggttccgc ttccagacag cgggatactg   1020
atcagcggtt gccaaaccga tcagacctct gctgatgcga ctccagcggg gaaaccaact   1080
gaggcttatg gagcgatgag caattcgata cagacgatcc tggaggagac agacggtgag   1140
atatcaaaca gagaaatggt tacaaggggc aggaaggcat tgaagaagca agggtttact   1200
cagcagccag gtttgtattg ccatgatggt tatgccaacg ctcctttcat ctgttga      1257

SEQ ID NO: 220     moltype = AA    length = 418
FEATURE            Location/Qualifiers
REGION             1..418
                   note = Description of Artificial Sequence: Synthetic
                       polypeptide
source             1..418
                   mol_type = protein
                   organism = synthetic construct
SEQUENCE: 220
MTKKAVLIGI NYPGTKAELR GCVNDVRRMY KCLVERYGFS EENITVLIDT DESSTQPTGK    60
NIRRALADLV ESADSGDVLV VHYSGHGTRL PAETGEDDDT GFDECIVPCD MNLITDDDFR   120
DLVDKVPPGC RMTIISDSCH SGGLIDEAKE QIGESTKKEA EDEDESEESS SRFGFRKFLR   180
SKVEGAIESR GFHIGGNKKD EDEAEEIETK EIELEDGETI HAKDKSLPLQ TLIDILKQQT   240
GNDNIEVGKI RPSLFDAFGD DSSPKVKKFM KVILGKLQAG NGEEGGLMGM LGKLASGFLE   300
GKLNDEDYVK PAMQTHVGSK EEVYAGGSRG SVPLPDSGIL ISGCQTDQTS ADATPAGKPT   360
EAYGAMSNSI QTILEETDGE ISNREMVTRA RKALKKQGFT QQPGLYCHDG YANAPFIC    418

SEQ ID NO: 221     moltype = DNA   length = 2965
FEATURE            Location/Qualifiers
misc_feature       1..2965
                   note = Description of Artificial Sequence: Synthetic
                       polynucleotide
source             1..2965
                   mol_type = other DNA
                   organism = synthetic construct
SEQUENCE: 221
gtgatcaatt ccagtgtgca caccacttgt ttgatgaatt gtctctgtgg agatttttt    60
ttagatggga ggttgtttct ctgtttcatt gccatgtgat caagtagtga gtcagttctc   120
tcagttgtta tgtgtcaggg gaagttatat tcacaatctc tccaagaatc tggcttctct   180
gcagaaggcc atgcgaatgc tcaaggctcg gcaaatatgt gtgataagaa ggttggaaac   240
agaagagttt acagggcgtc aacaaaggct ttcccaagtt caggtatggc ttactagtgt   300
cctaatcatt caaaccagtt taatgatct gcttcgtagt aatgaagttg agcttcaaag   360
gttgtgtctt tgtggtttct gctccaaaga tttgaaattg agctatcgtt atgggaaaag   420
agttatcatg atgttgaagg aagttgagag tctcagttct caaggattct ttgatggtt   480
ttctgaggca actccgtttg ctgatgtgga tgagatccct tttcaaccca caattgttgg   540
tcaggagata atgcttgaaa aggcatggaa ccgtctcatg gaagatggat ccgggatttt   600
gggtctgtac ggtatggggg gagtaggcaa aacgacacta ctcacgaaga tcaacaataa   660
gttttctaaa atagatgaca gatttgatgt tgtgatatgg gttgttgtgt ctagaagttc   720
aacagtccgt aagatacaaa gagacatagc agaaaaggta ggccttgggg gaatggagtg   780
gagcgagaaa aacgataacc agatagccgt tgacatccac aatgtcctta ggagacgaaa   840
gtttgtttta ttgttggatg acatatggga gaagtgaat ttaaaagcgg ttggagtccc   900
gtatccaagc aaagataacg gatgcaaggt agcattcact actcgttctc gagatgtgtg   960
tgggcgcatg ggggttgatg atccgatgga agttagctgt ctacaacccg aagaatcttg  1020
gatttgtttt caaatgaagg ttgggaaaaa tacactggga agtcacccag acattcccgg  1080
acttgctaga aaagtcgcta ggaaatgtcg tggcctacca ttagcactca atgttatcgg  1140
tgaagctatg catgcaaaaa gaacagtaca tgaatggtgt catgccattg acgttttaac  1200
atcatctgcc atagatttt caggtatgga agatgaaatt ctccatgttt tgaagtatag  1260
ctatgataat ttaaatgggg agctgatgaa atcctgcttc ctctattgct ctctgtttcc  1320
tgaagactat cttattgata aagagggggt ggtagactaa ttgataagtg agggattcat  1380
aaatgaaaaa gaaggcagag agaggaatat taaccaaggt tatgagataa ttggtaccct  1440
tgtccgtgca tgtttgttgt tggaggaaga aggaacaaaa tcaaacgtga aatgcatga   1500
tgtggttcgt gagatggctc tatggatatc atccgatctt gggaagcaaa aggagaaatg  1560
tattgtgcga gctggtgttg ggttacgtga agtaccaaaa gtcaaggatt ggaacactgt  1620
gagaaagatt tctttgatga ataatgagat tgaagagata tttgacagtc acgagtgtgc  1680
```

-continued

```
tgcacttaca actctatttc tccaaaagaa cgacgtggta aagatctcgg ctgaattctt   1740
tcgatgtatg cctcatctgg tggttttaga tctatcagag aatcagagtc ttaatgaatt   1800
accagaagaa atatcagagc tggcctcttt gagatatttc aacttgtcat atacatgtat   1860
acatcaacta cccgttggtt tatggacatt gaaaaagcta atacatctga atctcgaaca   1920
catgagcagt cttgggagta tattagggat atcaaatttg tggaatttga ggacattggg   1980
actacgagat tccagactgt tgctagatat gagtttagtg aaggagctgc agctcttaga   2040
acatctagaa gttataaccc tagatatatc atcaagtttg gttgcagagc cattgttatg   2100
ctctcaaagg ttggtggaat gtataaaaga ggtagatttt aagtaccttaa aggaagaatc   2160
agtgagagta ttgactttgc caaccatggg taatctccgc aagctcggga taaaaagatg   2220
tggaatgagg gagataaaga tagagaggac aacttcatca tcgtctcgga acaaaagtcc   2280
cacaactcca tgcttctcaa acctctccag agtctttata gctaaatgcc atggtcttaa   2340
ggatttgacg tggcttttgt ttgctcctaa tcttactttt cttgaagttg ggttctcaaa   2400
ggaagtagag gatataatta gtgaagagaa agctgaggag cattcagcta cgattgttcc   2460
ttttaggaaa ttggagacac tacacctgtt tgaattacgc ggctcaaga gaatctatgc   2520
aaaggctctg cattttccgt gtctgaaagt tatccacgta gaaaaatgtg aaaagctgag   2580
aaagcttcca ttggattcta aaagtgggat cgcgggtgaa gaacttgtca tatattatgg   2640
agagagagaa tggatagaaa gggttgaatg ggaggaccaa gcaactcaac tccgtttctt   2700
accttcatcc aggtggcggt ggagagaaac ataatgaact tcactttctt ctacaaactt   2760
ttgttgtcat ggtctaaaga catttgccgg tgtgtaaatc tcttccttgt ctcttccttgt   2820
ttgcataacc gttctcatcg ttcttttggt tagtgatcat tggatttgta cttatctctt   2880
tctctaaacg atgagtgttt gtttcggctt catagaaaca ttacacagag actcatgaga   2940
aaatgaataa aaacttgcaa gttcc                                         2965

SEQ ID NO: 222      moltype = AA   length = 889
FEATURE             Location/Qualifiers
REGION              1..889
                    note = Description of Artificial Sequence: Synthetic
                    polypeptide
source              1..889
                    mol_type = protein
                    organism = synthetic construct
SEQUENCE: 222
MGGCFSVSLP CDQVVSQFSQ LLCVRGSYIH NLSKNLASLQ KAMRMLKARQ YDVIRRLETE    60
EFTGRQQRLS QVQVWLTSVL IIQNQFNDLL RSNEVELQRL CLCGFCSKDL KLSYRYGKRV   120
IMMLKEVESL SSQGFFDVVS EATPFADVDE IPFQPTIVGQ EIMLEKAWNR LMEDGSILG    180
LYGMGGVGKT TLLTKINNKF SKIDDRFDVV IWVVVSRSST VRKIQRDIAE KVGLGGMEWS   240
EKNDNQIAVD IHNVLRRRKF VLLLDDIWEK VNLKAVGVPY PSKDNGCKVA FTTRSRDVCG   300
RMGVDDPMEV SCLQPEESWD LFQMKVGKNT LGSHPDIPGL ARKVARKCRG LPLALNVIGE   360
AMACKRTVHE WCHAIDVLTS SAIDFSGMED EILHVLKYSY DNLNGELMKS CFLYCSLFPE   420
DYLIDKEGLV DYWISEGFIN EKEGRERNIN QGYEIIGTLV RACLLLEEER NKSNVKMHDV   480
VREMALWISS DLGKQKEKCI VRAGVGLREV PKVKDWNTVR KISLMNNEIE EIFDSHECAA   540
LTTLFLQKND VVKISAEFFR CMPHLVVLDL SENQSLNELP EEISELASLR YFNLSYTCIH   600
QLPVGLWTLK KLIHLNLEHM SSLGSILGIS NLWNLRTLGL RDSRLLLDMS LVKELQLLEH   660
LEVITLDISS SLVAEPLLCS QRLVECIKEV DFKYLKEESV RVLTLPTMGN LRKLGIKRCG   720
MREIKIERTT SSSSRNKSPT TPCFSNLSRV FIAKCHGLKD LTWLLFAPNL TFLEVGFSKE   780
VEDIISEEKA EEHSATIVPF RKLETLHLFE LRGLKRIYAK ALHFPCLKVI HVEKCEKLRK   840
LPLDSKSGIA GEELVIYYGE REWIERVEWE DQATQLRFLP SSRWRWRET              889

SEQ ID NO: 223      moltype = DNA   length = 3435
FEATURE             Location/Qualifiers
misc_feature        1..3435
                    note = Description of Artificial Sequence: Synthetic
                    polynucleotide
source              1..3435
                    mol_type = other DNA
                    organism = synthetic construct
SEQUENCE: 223
atggcatctt cttcttcttc ttctagatgg agctatgatg ttttcttaag ttttagaggc    60
gaagatactc gaaaaacgtt tacaagtcac ttatacgaag tcttgaatga taagggaata   120
aaaacctttc aagatgataa aaggctagag tacggcgcaa ccatcccagg tgaactctgt   180
aaagctatag aagagtctca atttgccatt gttgtttttct cagagaatta tgcaacatca   240
aggtggtgtt tgaatgaact agtgaagatc atggaatgca aaactcgatt taagcaaact   300
gttataccga tattctatga tgtggatcca tcacatgttc ggaaccaaaa ggagagcttt   360
gcaaaagcct ttgaagacta tgaaacaaag tataaggatg atgttgaggg aatacaaaga   420
tggaggattg ctttaaatga agcggccaat ctcaaaggcc cctgtgataa tcgtgacaag   480
actgatgcag actgtattcg acagattgtt gaccaaatct catccaaatt atgcaagatt   540
tcttttatctt atttgcaaaa cattgttgga atagatactc atttagagaa aatagaatcc   600
ttactagaga taggaatcaa tggtgttcgg attatgggaa tctggggaat ggggggagtc   660
ggtaaaacaa caatagcaag tcatatattt gatactcttt taggaagaat ggatagttcc   720
tatcaatttg atggtgcttg tttccttaag gatattaaag aaaacaaacg tggaatgcat   780
tctttgcaaa atgcccttct ctctgaactt ttaaggaaaa agtcaattaa caataatgag   840
gaggatggaa agcaccaaat ggctagtaga cttcgttcga gaaggtcct aattgtgctt   900
gatgtatagat ataataaaga tcattatttg gagtatttag caggtgatct tgattggttt   960
ggtaatgtga ttataatatt tataacaact agagacaagt atttgataga gaagaatgat  1020
ataatatatg aggtgactgc actacccgat catgaatcca ttcaattgtt caaacacaat  1080
gctttcggaa aagaagttcc aaatgagaat tttgagaagc tttcattaga ggtagtaaat  1140
tatgctaaag gccttccttt agccctcaaa gtgtggggtt ctttgctgca taacctacga  1200
ttaactgaat ggaaaagtgc tatagagcac atgaaaaata actcttattc tggaattatt  1260
gataagctca aaataagtta tgatggatta gagcccaaac aacaagagat gttttagat  1320
```

-continued

```
atagcatgct tcttgcgagg ggaagaaaaa gattacatcc tacaaatcct tgagagttgt 1380
catattggag ctgaatacgg gttacgtatt ttaattgaca aatctcttgt gttcatctct 1440
gaatataatc aggttcaaat gcatgactta atacaggata tgggtaaata tatagtgaat 1500
tttcaaaaag atcccggaga acgtagcaga ttatggctcg ccaaggaagt cgaagaagtg 1560
atgagcaaca acacagggac catggcaatg gaagcaattt gggtttcttc ttattctagt 1620
actctacgct ttagcaatca ggccgtgaaa aatatgaaaa ggcttagggt atttaacatg 1680
gggaggtcgt cgacacatta tgccatcgat tatctgccca caaacttgcg ttgttttgtt 1740
tgcactaact atccttggga gtcatttcca tctacatttg aactcaaaat gcttgttcac 1800
ctccaactcc gacacaattc tctgcgtcat ttatgacgag aaacaaagca tttgccgtct 1860
ctacggagga tagatctcag ctggtctaaa agattgacgc gaacaccaga tttcacgggg 1920
atgccaaatt tggagtatgt gaatttgtat caatgtagta atcttgaaga agttcaccat 1980
tccctgggat gttgcagcaa agtcattggt ttatatttga atgattgtaa aagccttaag 2040
aggtttccat gtgttaacgt ggaatctctt gaatatctgg gtcaagaag ttgcgatagt 2100
ttagagaaat tgccagaaat ctacgaggga atgaagccga agatacagat tcacatgcaa 2160
ggctctggga taagggaact accatcatct atttttcagt acaaaactca tgttaccaag 2220
ctattgttgt ggaatatgaa aaccttgta gctcttccaa gcagcatatg taggttgaaa 2280
agtttggtta gtctgagtgt gtcgggttgc tcaaaacttg aaagcttgcc agaagagata 2340
ggggatttag acaacttacg ggtgtttgat gccagtgata ctctaatttt acgacctccg 2400
tcttccatca tacgcttgaa caaacttata atcttgatgt ttcgaggctt caaagatgga 2460
gtgcactttg agttccctcc tgtggctgaa ggattacact cattggaata tctgaatctc 2520
agttactgca atctaatgga tggaggactt ccggaagaga ttggatcctt atcctctttg 2580
aaaaagttgg atctcagtag aaataatttt gagcatttgc cttcaagtat agcccaactt 2640
ggtgctcttc aatccttaga cttaaaagat tgccagaggc ttacacagct accagaactt 2700
cccccagaat taaatgaatt gcatgtagat tgtcatatgg ctctgaaatt tatccattat 2760
ttagtaacaa agagaaagaa actacataga gtgaaacttg atgatgcaca caatgatact 2820
atgtacaatt tgttttgcata taccatgttt cagaatatct cttccatgag gcatgacatc 2880
tctgcttcag attccttgtc actaacagta tttaccggtc aaccgtatcc tgaaaagatc 2940
ccgagttggt tccaccatca gggttgggat agtagtgtat cagtcaattt gcctgaaaat 3000
tggtatatac ctgataaatt cttgggattt gctgtatgtt actctcgtag cttaattgac 3060
acaacgctc acttgattcc cgtatgtgat gacaagatgt cgcgcatgac ccagaaactt 3120
gccttatcag aatgtgatac agaatcatcc aactattcag aatgggatat acatttttc 3180
tttgtacctt ttgctggctt atgggataca tctaaggcaa atggaaaaac accaaatgat 3240
tatgggatta ttaggctatc tttttctgga gaagagaaga tgtatggact tcgtttgttg 3300
tataaagaag gaccagaggt taatgccttg ttacaaatga gggaaaatag caatgaacca 3360
acagaacatt ccactgggat aaggaggact caatataaca acagaacttc ctttttatgag 3420
ctcatcaatg ggtga 3435
```

```
SEQ ID NO: 224        moltype = AA   length = 1144
FEATURE               Location/Qualifiers
REGION                1..1144
                      note = Description of Artificial Sequence: Synthetic
                      polypeptide
source                1..1144
                      mol_type = protein
                      organism = synthetic construct
SEQUENCE: 224
MASSSSSSRW SYDVFLSFRG EDTRKTFTSH LYEVLNDKGI KTFQDDKRLE YGATIPGELC   60
KAIEESQFAI VVFSENYATS RWCLNELVKI MECKTRFKQT VIPIFYDVDP SHVRNQKESF  120
AKAFEEHETK YKDDVEGIQR WRIALNEAAN LKGSCDNRDK TDADCIRQIV DQISSKLCKI  180
SLSYLQNIVG IDTHLEKIES LLEIGINGVR IMGIWGMGGV GKTTIARAIF DTLLGRMDSS  240
YQFDGACFLK DIKENKRGMH SLQNALLSEL LREKANYNNE EDGKHQMASR LRSKKVLIVL  300
DDIDNKDHYL EYLAGDLDWF GNGSRIIITT RDKHLIEKND IIYEVTALPD HESIQLFKQH  360
AFGKEVPNEN FEKLSEVVN YAKGLPLALK VWGSLLHNLR LTEWKSAIEH MKNNSYSGII   420
DKLKISYDGL EPKQQEMFLD IACFLRGEEK DYILQILESC HIGAEYGLRI LIDKSLVFIS  480
EYNQVQMHDL IQDMGKYIVN FQKDPGERSR LWLAKEVEEV MSNNTGTMAM EAIWVSSYSS  540
TLRFSNQAVK NMKRLRVFNM GRSSTHYAID YLPNNLRCFV CTNYPWESFP STFELKMLVH  600
LQLRHNSLRH LWTETKHLPS LRRIDLSWSK RLTRTPDFTG MPNLEYVNLY QCSNLEEVHH  660
SLGCCSKVIG LYLNDCKSLK RFPCVNVESL EYLGLRSCDS LEKLPEIYGR MKPEIQIHMQ  720
GSGIRELPSS IFQYKTHVTK LLLWNMKNLV ALPSSICRLK SLVSLSVSGC SKLESLPEEI  780
GDLDNLRVFD ASDTLILRPP SSIIRLNKLI ILMFRGFKDG VHFEFPPVAE GLHSLEYLNL  840
SYCNLIDGGL PEEIGSLSSL KKLDLSRNNF EHLPSSIAQL GALQSLDLKD CQRLTQLPEL  900
PPELNELHVD CHMALKFIHY LVTKRKKLHR VKLDDAHNDT MYNLFAYTMF QNISSMRHDI  960
SASDSLSLTV FTGQPYPEKI PSWFHHQGWD SSVSVNLPEN WYIPDKFLGF AVCYSRSLID 1020
TTAHLIPVCD DKMSRMTQKL ALSECDTESS NYSEWDIHFF FVPFAGLWDT SKANGKTPND 1080
YGIIRLSFSG EEKMYGLRLL YKEGPEVNAL LQMRENSNEP TEHSTGIRRT QYNNRTSFYE 1140
LING                                                             1144
```

```
SEQ ID NO: 225        moltype = RNA   length = 20
FEATURE               Location/Qualifiers
misc_feature          1..20
                      note = Description of Artificial Sequence: Synthetic
                      oligonucleotide
source                1..20
                      mol_type = other RNA
                      organism = synthetic construct
SEQUENCE: 225
ttggattgaa gggagctctg                                             20

SEQ ID NO: 226        moltype = DNA   length = 188
```

```
FEATURE                 Location/Qualifiers
misc_feature            1..188
                        note = Description of Artificial Sequence: Synthetic
                           polynucleotide
source                  1..188
                        mol_type = other DNA
                        organism = synthetic construct
SEQUENCE: 226
gttttgagag tggagctcct tgaagtccaa cagaggatct aacaggtaag attgagctgc    60
tgacctatgg attcctcagc cctatctatt atttgattgg ataggtttgt gggttgcata   120
tgtcaggagc ttcattgccc taagttggat cccttttttgg attgaaggga gctctacatt  180
catttgac                                                            188

SEQ ID NO: 227          moltype = RNA  length = 20
FEATURE                 Location/Qualifiers
misc_feature            1..20
                        note = Description of Artificial Sequence: Synthetic
                           oligonucleotide
source                  1..20
                        mol_type = other RNA
                        organism = synthetic construct
SEQUENCE: 227
tttggattga agggagctct                                                20

SEQ ID NO: 228          moltype = DNA  length = 1107
FEATURE                 Location/Qualifiers
misc_feature            1..1107
                        note = Description of Artificial Sequence: Synthetic
                           polynucleotide
source                  1..1107
                        mol_type = other DNA
                        organism = synthetic construct
SEQUENCE: 228
atggtggatg ggcatgtatc agctggttca agaaatgaga acggtacaac acccagaaat    60
aataatgtgg aaatttcaat agcaacagcg tcatcaatgt ttcctggttt caggtttttca  120
ccaacggacg aagaactcat atcatattac ttgaaaaaga aacttgaggg gtctgataag   180
tgtgttgaag ttatttctga ggttgagatt tggaaacatg aaccttggga tttaccagca   240
aaatccgtca ttcaatcaga taatgaatgg ttcttctttt ctcctcgtgg aaggaagtat   300
ccaaacgggt cgcaaagtaa aagggcaact gaatctggtt actggaaggc cacaggaaaa   360
gaacgtaatg tgaaatctgg ttcgaatctc attggcacaa agagaactct ggtgttccac   420
actggtcgag cacctaaagg acagaggaca cattggataa tgcatgaata ttgcatgagc   480
ggaaacacta attatcagga ttctatggtt gtctgccgcc tccggaagaa tagtgagttt   540
catttgaatg acaccccaag aaatcaaagg aatcaactgg ctgctaccgc tactgcaacc   600
gctcagtctg gagcaggaca attgggcagc ttggaattgg tcactgtagg ggattgctgt   660
tgttcaaagg aagggagtag cagttttat tcccattcgg ttgagcagat tgactctgga   720
tcagaatctg ataaaccaac taagagttc tctcagcacg attcctctgg ccacttcaag   780
gactgtgatg gcgaggagga ctggtttgct gatataatga aagatgatat cattaagcta   840
gacgaatctt cgttgaatgc ccaacctatt tccatggttc ccagtaggcc tgaatcctcg   900
atatcaactc atgaagctcg agctgcgatg tccggtgtgg ctccttttcca gggcaccgct   960
aatcgaagac tcgactagt aagggaaaaa gtagtggtgt gtccagtaga gggatccaga  1020
atgtatgaag ctaccaaaaa gaataaaatc ggagtgagca taactagttc aggaagatgg  1080
ctgagaaaca tgttttcagt taaatga                                      1107

SEQ ID NO: 229          moltype = AA  length = 368
FEATURE                 Location/Qualifiers
REGION                  1..368
                        note = Description of Artificial Sequence: Synthetic
                           polypeptide
source                  1..368
                        mol_type = protein
                        organism = synthetic construct
SEQUENCE: 229
MVDGHVSAGS RNENGTTPRN NNVEISIATA SSMFPGFRFS PTDEELISYY LKKKLEGSDK    60
CVEVISEVEI WKHEPWDLPA KSVIQSDNEW FFFSPRGRKY PNGSQSKRAT ESGYWKATGK   120
ERNVKSGSNL IGTKRTLVFH TGRAPKGQRT HWIMHEYCMS GNTNYQDSMV VCRLRKNSEF   180
HLNDTPRNQR NQLAATATAT AQSGAGQLGS LELVTVGDCC CSKEGSSSFY SHSVEQIDSG   240
SESDKPTKEF SQHDSSGHFK DCDGEEDWFA DIMKDDIIKL DESSLNAQPI SMVPSRPESS   300
ISTHEARAAM SGVAPFQGTA NRRLRLVREK VVVCPVEGSR MYEATKKNKI GVSITSSGRW   360
LRNMFSVK                                                            368

SEQ ID NO: 230          moltype = DNA  length = 3822
FEATURE                 Location/Qualifiers
misc_feature            1..3822
                        note = Description of Artificial Sequence: Synthetic
                           polynucleotide
source                  1..3822
                        mol_type = other DNA
                        organism = synthetic construct
SEQUENCE: 230
```

```
atgtatccca tgtatgggtt catggacaca catccttacc aaagaaaccg agtacctcac    60
aaccctcctt attatcccca gtttgaaccg aatcatcatc atctgaacat tgatccagct   120
agatctcctg tagcttatga atcctggcct tgtggtggta actatgggca tccttatcca   180
ccgcagtgtc acagttgctg tatccataac aattccccga gccagtgtgc attcggtcct   240
ccttatccct accttccact gcctccctac aacaactgta gcaatccagc atatccggtg   300
atgtatgctg ctaattatgt ttctccccat tttactatgg agcagcctcg gtacgaatat   360
gataagaata tgggaagtgg tcatcacttc tgtggctgtc caaatcatcc atgttatacg   420
aaaggaggga gcaacattaa aatagaagaa caggaccagg ataagaaaaa tgaaagcaat   480
gagtccttgg ttccttttgg gttcaagaat tgtccttatc ctgttctgtg gatgccacct   540
gattatatga tgaatagcgc acacgtgaag cctaatggaa ttgaaggtaa acgggatgag   600
gtgaaagatg tgaaaccgta tggtgattgc agatctttcg aacaaccaaa tatctggaat   660
gtatggtctc cttatcaagg gaacaactcg gaattaccaa agcaaggggg agatccaccc   720
agaaaacaac accacgatga tatgaacaag aaacagtttc catttccaat aatctggatg   780
ccttacaaac ctgaggaaat agacggcaaa gttagcaagg agactggtgt tgatcaggag   840
cagacctccc ccttaaaatc taccatacca aagttacatg atgttgaaga ggatagaagc   900
gattctagag aaaatgtagt gaatagagga agtgaaatcc acggaaaggg actgaataaa   960
gattctgtta cgaaaatcat tccagtaagg caaatggagc aaattgagga tgtcttggat  1020
ggaaaaccgg aagtgcttc caaacagcat gatgttgatg ctaaagagaa gaaaaccact  1080
gaagacggtg caagaagca gtcgtcttct cctacaaagt catccaagct gccccctgtt  1140
tgtctaagag ttgatcccct gcctaggaaa aaaagcagta acggcagttc taggtcccct  1200
agtcctcctg gtgggaaacg gaaattagta gattcgccaa gtgacagctc caaacctccc  1260
atcttatcaa atgagaagga gaatgttcat cttgacaaat catccacaac agctacgccg  1320
gagaaaagca tagaagtgga tccaagtgaa ggaaaaagaa aagttgttaa ggttgcccaa  1380
gggactagca aagaagataa acttcaagat caatatacgg ttttccctga tctgaaaggg  1440
aaggcaaggg gccaaagcag tgagggtgat actagtaaag caaccaatga gctcaagcat  1500
caacctgatg gagtagcagc agaacctcag tccaacaatc aaggacatca gattggtgag  1560
gccagagaag cagcgaaggg aaatgcgggt ttagttgtgt acatgaaacc agataggagt  1620
aagctgtctg atgataacgc ggctactgtg attcagtcgg cataccgagg gttcaacgtg  1680
cggagatggg agcctctgaa gaaattaaag cagataacta aaataaagga gcagatggct  1740
gagcttaaaa actgtattca ggcttttgag agctcagctg acaacaaaca gatgactatt  1800
ctcacagaag ccataatggg tcttctgctg aagcttgacg ctattcaggg gttacatcca  1860
accgttaggg aatatagaaa atctgtagca aaggagcttg ttagcctgca ggagaagctg  1920
gatcttctga actgtaagaa gcaactggca gaaagtgaac aggcttttaac tgctcaatcc  1980
agcggggatg catgcaggac ggtggaagac aacatttcca tgcagggagg ccgagaggtg  2040
ccaaagttg aacaggatga tgatttagcg cggggagatg aagaaataaa ggtacatgca  2100
aaggagccct gtcaagagca gcctctttgt gcggcagaga cactcccaa ctctcatcac  2160
gtaggcaatg cagaggaagt ggtcggtaaa aagaaaagtg agaacgttga ggaggtggtg  2220
gagaacttt caagtggtgg tgcagtggtg gatgaggcaa cagaatcact ttctgaatct  2280
aaagaaatt tgaatgataa gtcacctgat gagaatacgg tagtagtga gaatcagaa   2340
gagcatgaca aagctgaaca atctttgcca aatcctattc catttctgt agatctgaca  2400
gaaaacttgg gcttagaggt cagaggttgt ggtttgaagg ggaagggtgg aggtgttgat  2460
gaattggaag agctcccgca aggagtcctt gatgaagaga ctagtgttca agggtctact  2520
gagatcagaa aagacgaggt cctccaacat gacaatggaa accttactgc tcatattcct  2580
gaagaaaaag tctctgatac agagaggcga gagcaccacc acttggaagc attaggtgaa  2640
acactagttg ttttggggcc aatgaacatc cacagcagca atggacaaaa agaaaattca  2700
gaagttctgt aaacagataa aacagtacga gttgatgctc cagaacagga gaagaagat  2760
ctcagaccat taaatgaaga tgggaagatc tctgatgttg atgctcaagt tggtatggaa  2820
gaggatggcg aggaacgtgg acaatgcagc actgggtcag acgcgtttcc aatatactca  2880
caggaagaag caatcaccat gaagcagtct acagatgcca ccaacatgga ggaattggaa  2940
acaactggag ttctgcagga gaaaatgcaa aatgcagtag agagagacat tgaaatcctt  3000
aattcaaaaa aaaccattga agtgtcagca gaacctcaac tatttactgc taccattgaa  3060
gaggccaaag aatattatgc tcaggataag cagaatgttg gggaggaaaa tatggaggtg  3120
caaggtgagg aattgcctgc tcgcagtgat gctttggtct ctgtactcaa gagtgaacac  3180
aaagagaata atgtggaggt tgagcagagg catctggagg aaaactttga gatgcaagag  3240
gaagaaccag tggctgctga taaccctgca cctatgaccg aggaaccagt ggatgaaagt  3300
atagtgatga ctgctccaaa atcagaagct gtaactactg agacgcagct gttaggggag  3360
aaaagagcttg gtgtagcaga ggaccgcagc acatatccat cgacatgtga tactgtggaa  3420
ggtaattcag ctgatgctgt ctgctctttt ggttctacgc ctaatgaagc acaagtaatg  3480
gatgcaaagg agcttaaaga atggaagaga gtggaaatgt caccatcatc acctactgct  3540
agccaagtat cctttgatag tgatgcattc tcagagagcg gtcaaaagct tatagaagag  3600
aatgaaaaat taagggagat gatggagaaa ctaataaaag cagggaaaga acaactcact  3660
gttgtatcca gtctttctgg aagagttaag gacctggaga agagattgtc caggaagaag  3720
aagctgagat tgagacgata tagggtacca agagcaggtt cagtctgtat gaagccattg  3780
aatgactcac tgaaagacag agctgcgggg ttggcaatgt ga                      3822
```

SEQ ID NO: 231         moltype = AA  length = 1273
FEATURE                 Location/Qualifiers
REGION                  1..1273
                         note = Description of Artificial Sequence: Synthetic
                         polypeptide
source                  1..1273
                         mol_type = protein
                         organism = synthetic construct
SEQUENCE: 231
MYPMYGFMDT HPYQRNRVPH NPPYYPQFEP NHHHLNIDPA RSPVAYESWP CGGNYGHPYP    60
PQCHSCCIHN NSPSQCAFGP PYPYLPLPPY NNCSNPAYPV MYAANYVSPH FTMEQPRYEY   120
DKNMGSGHHF CGCPNHPCYT KGGSNIKIEE QDQDKKNESN ESLVPFGFKN CPYPVLWMPP   180
DYMMNSAHVK PNGFEGKRDE VKDVKPYGDC RSFEQPNIWN VWSPYQGNNS ELPKQRGDPP   240
RKQHHDDMNK KQFPFPIIWM PYKPEEIDGK VSKETGVDQE QTSPLKSTIP KLHDVEEDRS   300

```
DSRENVVNRG SEIHGKGLNK DSVTKIIPVR QMEQIEDVLD GKPEDASKQH DVDAKEKKTT    360
EDGGKKQSSS PTKSSKLPPV CLRVDPLPRK KSSNGSSRSP SPPGGKRKLV DSPSDSSKPP    420
ILSNEKENVH LDKSSTTATP EKSIEVDPSE GKRKVVKVAQ GTSKEDKLQD QYTVFPDLKG    480
KARGQSSEGD TSKATNELKH QPDGVAAEPQ SNNQGHQIGE AREAAKGNAG LVVYMKPDRS    540
KLSDDNAATV IQSAYRGFNV RRWEPLKKLK QITKIKEQMA ELKNCIQALE SSADNKQMTI    600
LTEAIMGLLL KLDAIQGLHP TVREYRKSVA KELVSLQEKL DLLNCKKQLA ESEQALTAQS    660
SGDACRTVED NISMQGGREV PKFEQDDDLA RGDEEIKVHA KEPCQEQPLC AAETLPNSHH    720
VGNAEEVVGK EESENVEEVV ENFSSGGAVV DEATESLSES KENLNDKSPD ENTVVVEKSE    780
EHDKAEQSLP NPIPFSVDLT ENLGLEVRGC GLKGKGGGVD ELEELPQGVL DEETSVQGST    840
EIRKDEVLQH DNGNLTAHIP EEKVSDTERR EHHHLEALGE TLVVLGPMNI HSSNGQKENS    900
EVLETDKTVR VDAPEQEKED LRPLNEDGKI SDVDAKVGME EDGEERGQCS TGSDAFPIYS    960
QEEAITMKQS TDATNMEELE TTGVLQEKMQ NAVERDIEIL NSKKTIEVSA EPQLFTATID   1020
EAKEYYAQDK QNVGEENMEV QGEELPARSD ALVSVLKSEH KENNVEVEQR HLEENFEMQE   1080
EEPVAADNPA PMTEEPVDES IVMTAPKSEA VTTETQLLGE KELGVAEDRS TYPSTCDTVE   1140
GNSADAVCSF GSTPNEAQVM DAKELKEWKR VEMSPSSPTA SQVSFDSDAF SESSQKLIEE   1200
NEKLREMMEK LIKAGKEQLT VVSSLSGRVK DLEKRLSRKK KLRLRRYRVP RAGSVCMKPL   1260
NDSLKDRAAG LAM                                                     1273

SEQ ID NO: 232            moltype = DNA  length = 1122
FEATURE                   Location/Qualifiers
misc_feature              1..1122
                          note = Description of Artificial Sequence: Synthetic
                           polynucleotide
source                    1..1122
                          mol_type = other DNA
                          organism = synthetic construct
SEQUENCE: 232
atgcgacctc ttcaaccacc cccaccagcc gccgccgcca ccacctcctc ctccaccacc    60
gcatcaccta tgccccctcc tccttcacgc aaccgtcccc gtcgtcgcac cgatttaact   120
ctccccttc cccaacgtga cccagctctc gccgtacccc tcccccctcc ccctacttcc   180
gcccttctt cctcgtcgtc ttcctcttcc tccccactcc ccaccccctt aaacttctcc   240
gaacttgagc gtatcaatcg catcggcagc ggcgctggcg gtacggttta caaagtccta   300
catcgcccca ccggaagact ctacgctctc aaagtcatct acggtaacca cgaggactcc   360
gttcgccttc agatgtgccg tgagatcgag attctccgtg acgtcgacaa ccctaacgtc   420
gttagatgtc acgatatgtt cgatcacaac ggtgaaatcc aagtcctcct tgaattcatg   480
gataaaggct ctctcgaagg gatccacatc cctaaagagt cagctctttc ggatctaacc   540
cgacaagtcc tctcgggtct ctattatctc cacaggcgta agattgtgca cagagatatc   600
aagcccctcga atttactaat caactcgagg cgcgaggtga aaattgctga ctttggggtg   660
tcgagatgc tggcacaaga tatggatcct tgtaatgatt cagttgggac aaattgcctat   720
atgagtccag agagaatcaa cacagatctg aatcatggac agtacgatgg gtatgctgga   780
gatatatgga gtcttggtgt tagcatattg gagttttatt tgggaaggtt tccgttttct   840
gttggagggt caggtgattg ggctagtctt atgtgcgcca tttgtatgtc gcagccgccg   900
gaggccccgg cgaatgcttc tagagagttc agggacttta ttgcttgctg tttgcagagg   960
gatcctgcac gacggtggac ggcggtgcag ctgttgcgtc atccatttat tacccagaat  1020
agcccagccg ccaccaccac cggtaatatg atgccactc ctaatcaggt tcatcagcca  1080
gcacatcaat tgttacctcc acctcctcat ttttcttctt aa                    1122

SEQ ID NO: 233            moltype = AA  length = 373
FEATURE                   Location/Qualifiers
REGION                    1..373
                          note = Description of Artificial Sequence: Synthetic
                           polypeptide
source                    1..373
                          mol_type = protein
                          organism = synthetic construct
SEQUENCE: 233
MRPLQPPPPA AAATTSSSTT ASPMPPPPSR NRPRRRTDLT LPLPQRDPAL AVPLPLPPTS    60
APSSSSSSS SPLPTPLNFS ELERINRIGS GAGGTVYKVL HRPTGRLYAL KVIYGNHEDS   120
VRLQMCREIE ILRDVDNPNV VRCHDMFDHN GEIQVLLEFM DKGSLEGIHI PKESALSDLT   180
RQVLSGLYYL HRRKIVHRDI KPSNLLINSR REVKIADFGV SRVLAQDMDP CNDSVGTIAY   240
MSPERINTDL NHGQYDGYAG DIWSLGVSIL EFYLGRFPFS VGRSGDWASL MCAICMSQPP   300
EAPANASREF RDFIACCLQR DPARRWTAVQ LLRHPFITQN SPAATTTGNM MPLPNQVHQP   360
AHQLLPPPPH FSS                                                     373

SEQ ID NO: 234            moltype = DNA  length = 1245
FEATURE                   Location/Qualifiers
misc_feature              1..1245
                          note = Description of Artificial Sequence: Synthetic
                           polynucleotide
source                    1..1245
                          mol_type = other DNA
                          organism = synthetic construct
SEQUENCE: 234
atggagtctc atcctcacaa caaaactgac cagacccagc atatcatcct cgtacacggt    60
cccatcatca tcggagctgg cccttctggt cttgccactt cagcatgtct ctcgagccgt   120
ggagtcccctt ctttgatcct agaacggtcg gattcaatag catctctatg gaaatctaaa   180
acctacgacc gactcagact ccatctccca aaacactttt gccggttacc ctcctggac   240
ttccctgaat attacccaaa ataccccttcc aaaaacgagt tcttggccta ccttgagtcc   300
tacgcttccc acttccgcat cgctccaagg ttcaacaaga acgtacaaaa cgcagcttac   360
```

```
gattcttcct ccggtttctg gagagtaaag actcatgata acacagagta cctctccaaa   420
tggcttatcg tagccaccgg tgagaacgca gatccatact tccccgagat tccaggagaa   480
aagaagtttt ccggcggaaa aatcgttcac gcgagtgagt acaaaagcgg cgaagagttc   540
cggcggcaga aagttttggt tgtcggatgt ggaaattccg gcatgaaat tagcttagac   600
ctcgtccgac ataacgcatc tcctcatctt gttgtccgga acaccgttca tgtgttgcca   660
agggagatac ttggggtatc aacatttgga gttggaatga cacttctcaa atgcttaccc   720
ttaaggctcg ttgacaagtt cttgttattg atgccaatc tttcgtttgg aaataccgac   780
cggttgggcc ttcgccgacc aaaaacgggt ccgcttgagc tgaaaaatgt caccggcaaa   840
agtccggttc tcgatgtcgg agctatgtct ctcatcgat ccggcatgat tcagataatg   900
gaaggtgtaa aggaaataac aagaaagga gcaagtttta tggatggtca agaaaaggac   960
tttgactcta tcatatttgc cactggttac aaaagcaacg tgcctacttg gcttcaggga  1020
ggtgattttt tcacggacga tgggatgccg aaaacgccgt ttcctaacgg ctggagagga  1080
gggaaaggat tgtacacagt tggttttacg agaagaggac tccttggaac ggcgtctgac  1140
gccgttaaga tcgctggcga aattggtgac cagtggagaa acgaaatcaa ggggtccacc  1200
aggaatatgt gcagttctcg ttttgtcttt acctctaaat cctaa                  1245

SEQ ID NO: 235         moltype = AA    length = 414
FEATURE                Location/Qualifiers
REGION                 1..414
                       note = Description of Artificial Sequence: Synthetic
                       polypeptide
source                 1..414
                       mol_type = protein
                       organism = synthetic construct
SEQUENCE: 235
MESHPHNKTD QTQHIILVHG PIIIGAGPSG LATSACLSSR GVPSLILERS DSIASLWKSK    60
TYDRLRLHLP KHFCRLPLLD FPEYYPKYPS KNEFLAYLES YASHFRIAPR FNKNVQNAAY   120
DSSSGFWRVK THDNTEYLSK WLIVATGENA DPYFPEIPGR KKFSGGKIVH ASEYKSGEEF   180
RRQKVLVVGC GNSGMEISLD LVRHNASPHL VVRNTVHVLP REILGVSTFG VGMTLLKCLP   240
LRLVDKFLLL MANLSFGNTD RLGLRRPKTG PLELKNVTGK SPVLDVGAMS LIRSGMIQIM   300
EGVKEITKKG AKFMDGQEKD FDSIIFATGY KSNVPTWLQG GDFFTDDGMP KTPFPNGWRG   360
GKGLYTVGFT RRGLLGTASD AVKIAGEIGD QWRDEIKGST RNMCSSRFVF TSKS         414

SEQ ID NO: 236         moltype = DNA    length = 1869
FEATURE                Location/Qualifiers
misc_feature           1..1869
                       note = Description of Artificial Sequence: Synthetic
                       polynucleotide
source                 1..1869
                       mol_type = other DNA
                       organism = synthetic construct
SEQUENCE: 236
atgattacgg cggcggactt ctaccacgtt atgacggcta tggttccgtt atacgtagct    60
atgatcctcg cttacggctc tgtcaaatgg tggaaaatct tcacaccaga ccaatgctcc   120
ggcataaacc gtttcgtcgc tctcttcgcc gttcctctcc tctctttcca cttcatcgcc   180
gctaacaacc cttacgccat gaacctccgt ttcctcgccg cagattctct ccagaaagtc   240
attgtcctct ctctcctctt cctctggtgc aaactcagcc gcaacggttc tttagattgg   300
accataactc tcttctctct ctcgacactc cccaacactc tagtcatggg gatacctctt   360
ctcaaaggca tgtatggtaa tttctccggc gacctcatgg ttcaaatcgt tgttcttcag   420
tgtatcattt ggtacacact catgctcttt ctctttgagt accgtggagc taagcttttg   480
atctccgaca gtttccagac acagcagga tctattgttt cgattcatgt tgattccgac   540
attatgtctt tagatggaag acaacccttg gaaactgaag ctgagattaa agaagatggg   600
aagcttcatg ttactgttcg tcgttctaat gcttcaaggt ctgatattta ctcgagaagg   660
tctcaaggct tatctgcgac acctagacct tcgaatctaa ccaacgctga gatatattcg   720
cttcagagtt caagaaaccc aacgccacgt ggctctagtt ttaatcatac tgattttac   780
tcgatgatgg cttctggtgg tggtcggaac tctaactttg gtcctggaga agctgtgttt   840
ggttctaaag gtcctactcc gagaccttcc aactacgaag aagacggtgg tcctgctaaa   900
ccgacgcgct ctggaactgc tgctggagct gggaggtttc attatcaatc tggaggaagt   960
ggtggcggtg gaggagcgca ttatccggcg ccgaacccag ggatgttttc gcccaacact  1020
ggcggtggtg gaggcacggc ggcgaaagga aacgctccgg tggttggtgg gaaaagacaa  1080
gacgaaacg gaagagatct tcacatgttt gtgtggagct caagtgcttc gccggtctca  1140
gatgtgttcg gcggtggagg aggaaaccac cacgccgatt actccaccgc tacgaacgat  1200
catcaaaagg acgttaagat ctctgtacct caggggaata gtaacgacaa ccagtacgtg  1260
gagagggaag agtttagttt cggtaacaaa gacgatgata gcaagtattt ggcaacggac  1320
ggtgggaaca acataagcaa caaaacgacg caggctaagg tgatgccacc aacaagtgtg  1380
atgacaagac tcattctcat tatggtttgg aggaaactta ttcgtaatcc caactcttac  1440
tccagtttat tcggcatcac ctggtccctc atttccttca gtggaacat gaaatgcca  1500
gctcttatag caaagtctat ctccatactc tcagatgcag gtctaggcat ggctatgttc  1560
agtcttggt tgttcatggc gttaaaccca agaataatag cttgtggaaa cagaagagca  1620
gcttttgcgg cggctatgag atttgtcgtt ggacctgccg tcatgctcgt tgcttcttat  1680
gccgttggcc tccgtggcgt cctcctccat gttgccatta tccaggcagc tttgccgcaa  1740
ggaatagtac cgtttgtgtt tgccaaagag tataatgtgc atcctgacat tcttagcact  1800
gcggtgatat ttgggatgtt gatcgcgttg cccataactc ttctctacta cattctcttg  1860
ggtctatga                                                          1869

SEQ ID NO: 237         moltype = AA    length = 622
FEATURE                Location/Qualifiers
REGION                 1..622
                       note = Description of Artificial Sequence: Synthetic
```

```
                        polypeptide
source                  1..622
                        mol_type = protein
                        organism = synthetic construct
SEQUENCE: 237
MITAADFYHV MTAMVPLYVA MILAYGSVKW WKIFTPDQCS GINRFVALFA VPLLSFHFIA    60
ANNPYAMNLR FLAADSLQKV IVLSLLFLWC KLSRNGSLDW TITLFSLSTL PNTLVMGIPL   120
LKGMYGNFSG DLMVQIVVLQ CIIWYTLMLF LFEYRGAKLL ISEQFPDTAG SIVSIHVDSD   180
IMSLDGRQPL ETEAEIKEDG KLHVTVRRSN ASRSDIYSRR SQGLSATPRP SNLTNAEIYS   240
LQSSRNPTPR GSSFNHTDFY SMMASGGGRN SNFGPGEAVF GSKGPTPRPS NYEEDGGPAK   300
PTAAGTAAGA GRFHYQSGGS GGGGGAHYPA PNPGMFSPNT GGGGGTAAKG NAPVVGGKRQ   360
DGNGRDLHMF VWSSSASPVS DVFGGGGGNH HADYSTATND HQKDVKISVP QGNSNDNQYV   420
EREEFSFGNK DDDSKVLATD GGNNISNKTT QAKVMPPTSV MTRLILIMVW RKLIRNPNSY   480
SSLFGITWSL ISFKWNIEMP ALIAKSISIL SDAGLGMAMF SLGLFMALNP RIIACGNRRA   540
AFAAAMRFVV GPAVMLVASY AVGLRGVLLH VAIIQAALPQ GIVPFVFAKE YNVHPDILST   600
AVIFGMLIAL PITLLYYILL GL                                            622

SEQ ID NO: 238          moltype = DNA   length = 1176
FEATURE                 Location/Qualifiers
misc_feature            1..1176
                        note = Description of Artificial Sequence: Synthetic
                         polynucleotide
source                  1..1176
                        mol_type = other DNA
                        organism = synthetic construct
SEQUENCE: 238
atggtgaaac tggagaactc gaggaaaccc gaaaaatttc gaacaagaa catccccatg     60
tccgatttcg tggtcaatct ggatcatggt gatccaacgg cgtacgaaga atactggagg   120
aagatgggtg acaggtgtac ggtgacgata cgtggttgtg atctcatgag ttacttcagc   180
gacatgacga acttgtgttg gttccttgag ccagagcttg aagatgcgat caaggacttg   240
cacggtgttg ttggtaacgc tgccgacgag gatcggtaca tagtggttgg gaccggttcg   300
acgcagcttt gtcaagccgc cgtccacgca ctctcttcac tagccaggag tcaacctgtc   360
agcgtcgtcg ccgccgctcc tttttactcc acatatgtgg aggagacgac atatgttcgg   420
tcgggtatgt acaagtggga aggagacgca tgggggtttcg acaaaaaggg tccgtacatc   480
gagctagtga cgtcacctaa taaccctgac ggaaccatca gagagacggt ggtgaaccgt   540
ccagacgacg acgaagccaa agtgatccat gactttgctt attactggcc ccactacact   600
cccatcactc gccgtcaaga ccatgacatc atgctcttca ctttctccaa gatcacaggc   660
cacgctgggt cccgtattgg gtgggcattg gtgaaggaca aggaggtagc taagaagatg   720
gttgagtata ttattgtgaa ctcgattggt gtgtctaagg agtcacaggt tcgaacagct   780
aagatactca acgttctaaa ggagacttgt aagagcgagt ccgagtctga gaatttcttc   840
aagtatggtc gtgagatgat gaagaatcgt gggagaagc tacgtgaagt tgtgaaagag   900
agcgatgctt tcactcttcc caagtaccct gaagcatttt gcaactactt tggaaaatca   960
ctcgaatctt accctgcgtt tgcgtggcta gggacgaagg aagaacgtga tctggtaagt  1020
gaattgagga gacacaaggt aatgagcaga gctggagagg gttgtggatc tgacaagaag  1080
catgtccgag tcagcatgct tagtcgtgaa gacgttttca atgtctttct cgagagactc  1140
gccaacatga agctcattaa aagcattgac ctttag                            1176

SEQ ID NO: 239          moltype = AA   length = 391
FEATURE                 Location/Qualifiers
REGION                  1..391
                        note = Description of Artificial Sequence: Synthetic
                         polypeptide
source                  1..391
                        mol_type = protein
                        organism = synthetic construct
SEQUENCE: 239
MVKLENSRKP EKISNKNIPM SDFVVNLDHG DPTAYEEYWR KMGDRCTVTI RGCDLMSYFS    60
DMTNLCWFLE PELEDAIKDL HGVVGNAATE DRYIVVGTGS TQLCQAAVHA LSSLARSQPV   120
SVVAAPFYS TYVEETTYVR SGMYKWEGDA WGFDKKGPYI ELVTSPNNPD GTIRETVVNR   180
PDDDEAKVIH DFAYYWPHYT PITRRQDHDI MLFTFSKITG HAGSRIGWAL VKDKEVAKKM   240
VEYIIVNSIG VSKESQVRTA KILNVLKETC KSESESENFF KYGREMMKNR WEKLREVVKE   300
SDAFTLPKYP EAFCNYFGKS LESYPAFAWL GTKEETDLVS ELRRHKVMSR AGERCGSDKK   360
HVRVSMLSRE DVFNVFLERL ANMKLIKSID L                                  391

SEQ ID NO: 240          moltype = DNA   length = 4107
FEATURE                 Location/Qualifiers
misc_feature            1..4107
                        note = Description of Artificial Sequence: Synthetic
                         polynucleotide
source                  1..4107
                        mol_type = other DNA
                        organism = synthetic construct
SEQUENCE: 240
atgggtgaga aagcgattga cgaagacaaa gtagaagcga tgaagagcag caagacctct     60
cttgttttcg ccattaacgg acaaagattc gagctcgagc tctcttctat tgatccttcc    120
accacactcg tcgatttctt gcgcaacaag actcctttca agagcgtcaa gcttggttgt    180
ggcgaaggtg gttgtggcgc ttgtgttgtt cttcttcaa agtatgatcc attgctcgaa    240
aaagtcgatg aattcacaat tagctcgtgt ctcacgcttc tctgtagcat tgatggctgt    300
tccatcacta ccctcagacgg gctcggcaac agcgagtcg gttccatgc cgtccacgag    360
```

```
cgtatcgccg gttttcatgc cacacaatgc ggtttctgta ctcctggaat gagcgtttcg    420
atgttttctg ctctcttgaa cgctgataag tctcatccac ctcctcgcag cggtttctca    480
aatctcacgg ctgtagaagc tgagaaggct gtgtcaggga atctttgccg gtgtactgga    540
tatagaccgc ttgtggatgc ttgtaagagt tttgcagcgg atgtggatat cgaagatctc    600
ggattcaatg ccttttgcaa gaagggagaa aacagagatg aggttttaag aaggttgcca    660
tgttatgatc atacatcatc tcatgtctgt acatttccgg agttcttgaa gaaggaaatc    720
aagaacgata tgagtcttca ttcaagaaag tatcgatggt caagcccggt tagtgtctca    780
gagcttcaag ggttattaga agtcgagaat ggtttgtcgg ttaagttagt tgcgggtaac    840
acgagcaccg ggtattacaa agaagaaaaa gagaggaagt acgaaagatt tatcgatatc    900
aggaagattc cggagtttac tatggtgaga agtgatgaga aaggagttga attaggagct    960
tgtgtcacta tatcgaaagc tattgaggtt ctaagagagg aaaaaaatgt ttctgtgttg   1020
gcgaaaatcg ctactcatat ggagaaaatt gcaaacagat cgtgaggaa cacgggaacg   1080
ataggtggaa acattatgat ggctcagaga aaacagtttc cttcggatct tgcaaccata   1140
cttgttgctc ctcaagcaac ggtgagatc atgactagca gctcgagtca agaacagttc   1200
acattggagg agtttctaca caacctcct cttgatgcaa aatctcttct tttgagcctc   1260
gagattccat cttggcactc cgcgaagaag aacggttctt cagaagatag tatttttgcta   1320
tttgaaactt acagagcagc gcctcgtcct ctaggaaacg cattggcatt tctgaatgcg   1380
gctttctcag ctgaagttac tgaagcactt gatggcattt tgtaaatga ttgccaatta   1440
gtttttggag cttatgggac caaacatgca cacagggcaa agaaagtaga agagtttctt   1500
acaggaaaag tgatatctga tgaagttttg atggaagcta ttagcttact taaagatgag   1560
atagtacctg ataagggtac ttcgaatccc gggtatagat caagcttggc tgttactttt   1620
ctcttcgagt tcttcggatc tttaactaaa aaaaacgtcaa aaacgacaaa cggttggctc   1680
aatgaggat gcaaagagat tggttttgat cagaatgttg aatctttgaa acctgaagct   1740
atgctgtcat ctgcacaaca aatagttgaa aatcaagagc atagtccggt cgggaaaggc   1800
attacaaagg ctggagcttg tctccaagca tctggtgagg ctgtttatgt agacgacatt   1860
cctgctccgg aaaattgtct atacggcgca tttattttaca gtacaatgcc gctagcgcga   1920
attaagggta taaggttcaa gcaaaacaga gttccagaag gagttcttgg cattattact   1980
tacaaagata ttcccaaagg cgggcaaaat atcggtacca acggtttctt tacctcggat   2040
cttttgttcg cagaagaagt cactcattgt gcgggtcaga taatcgcctt tttggttgca   2100
gatgtcaaa agcatgcaga tattgcagca aatcttgttg tgatagatta cgacaccaaa   2160
gatttaaaac cacctatact gtccttagaa gaagctgtcg aaaactttag ccttttcgag   2220
gtccctccac ctctgcgtgg ttaccccggtt ggtgatatca ccaagggaat ggatgaagct   2280
gaacataaga ttcttggatc aaagataagt ttcgggtcac agtacttctt ctatatggag   2340
acacaaacag ctcttgcagt gccggatgaa gacaactgta tggtggttta tagctcgact   2400
caaacccctg agtttgtaca tcaaaccatc gctggatgtc ttggagttcc tgagaacaat   2460
gtgcgtgtca tcactagaag agttggaggc ggattcggtg ggaaagccgt gaaatcaatg   2520
cctgttgctg cagcttgtgc acttgcagca tccaaaatgc agcgtcctgt gaggacatat   2580
gtgaaccgaa aaacggatat gataactacc ggaggaagac atcgatgaa agtcacatat   2640
agtgttggat tcaaatccaa tggaaagatt actgctttag atgtagaggt gttacttgat   2700
gcagggttaa ccgaagatat aagcccgctt atgccgaagg gaatacaagg agcactaatg   2760
aagtatgatt gggtgtctct gtcttcaat gtgaaagtat gcaaacaaa cactgtgagc   2820
agaaccgcgc tgagagctcc tggggatgta caaggatcat atataggaga agccatcatt   2880
gaaaaagtag cttcatatct ttcagttgat gttgatgaaa tcaggaaggt taatcttcat   2940
acatatgaga gcttaaggtt gtttcacagt gccaaagctg gtgaattttc tgagtatacg   3000
ttaccattgc tttgggacag aatcgatgag ttctcgggat ttaacaagcg gaggaaggtg   3060
gttgaggagt ttaatgcatc aaacaagtgg agaaagagag ggatttcacg tgtgcctgcg   3120
gtttatgcag tgaacatgcg atcaacaccg ggaagagtaa gcgttttggg agatgggtca   3180
atagttgtgg aggttcaagg gattgagata ggacaagggc tttggacaaa ggtgaaacag   3240
atggctgcat attcccttgg tttgatccag tgccgtacta caagtgatga actgcttaaa   3300
aaaatcaggg tcattcaatc cgacacacta agtatggtgc aaggctcaat gactgctggt   3360
agtacaacct ctgaagcgag tagtgaagcg gtaaggattt gctgtgatcg cttagttgaa   3420
aggcttttac cagtcaagac cgctttggtg gagcaaacag gaggacctgt gacttgggat   3480
agtctcatca gtcaggctta tcagcaatcg ataaacatgt ccgttagtag caaatacatg   3540
cctgactcca ctggcaaata cctgaactat ggaattgcag cgagcgaggt tgaagtaaac   3600
gttttgacgg gagaaaacaa gatcctgcgt acagatatta tctatgattg tgggaagagt   3660
ctcaatcccg ctgttgattt aggacagatt gaaggagcct ttgttcaagg acttggtttc   3720
ttcatgcttg aagagttcct aatgaactca gacggtctcg tggtaacaga cagcacatgg   3780
acttacaaga tcccaacggt tgacacaatc caagacagt ttaatgtgga gattctcaac   3840
agtggacaac acaagaatcg tgttctttca tccaaagctt cgggtgaacc gccattgctt   3900
ttagcggctt ctgttcactg cgcggtacga gcagctgtta aagaagctag gaaacagatc   3960
ctgtcatgga atagtaataa acaagggact gatatgtact cgaattgcc tgttccagca   4020
acaatgccta ttgtgaagga gttttgtgga cttgatgttg tcgagaaata cttggaatgg   4080
aaaatccagc aaaggaaaaa tgtttga                                      4107

SEQ ID NO: 241       moltype = AA   length = 1368
FEATURE              Location/Qualifiers
REGION               1..1368
                     note = Description of Artificial Sequence: Synthetic
                     polypeptide
source               1..1368
                     mol_type = protein
                     organism = synthetic construct
SEQUENCE: 241
MGEKAIDEDK VEAMKSSKTS LVFAINGQRF ELELSSIDPS TTLVDFLRNK TPFKSVKLGC    60
GEGGCGACVV LLSKYDPLLE KVDEFTISSC LTLLCSIDGC SITTSDGLGN SRVGFHAVHE   120
RIAGFHATQC GFCTPGMSVS MFSALLNADK SHPPPRSGFS NLTAVEAEKA VSGNLCRCTG   180
YRPLVDACKS FAADVDIEDL GFNAFCKKGE NRDEVLRRLP CYDHTSSHVC TFPEFLKKEI   240
KNDMSLHSRK YRWSSPVSVS ELQGLLEVEN GLSVKLVAGN TSTGYYKEEK ERKYERFIDI   300
RKIPEFTMVR SDEKGVELGA CVTISKAIEV LREEKNVSVL AKIATHMEKI ANRFVRNTGT   360
```

```
IGGNIMMAQR  KQFPSDLATI  LVAAQATVKI  MTSSSSQEQF  TLEEFLQQPP  LDAKSLLLSL   420
EIPSWHSAKK  NGSSEDSILL  FETYRAAPRP  LGNALAFLNA  AFSAEVTEAL  DGIVVNDCQL   480
VFGAYGTKHA  HRAKKVEEFL  TGKVISDEVL  MEAISLLKDE  IVPDKGTSNP  GYRSSLAVTF   540
LFEFFGSLTK  KNAKTTNGWL  NGGCKEIGFD  QNVESLKPEA  MLSSAQQIVE  NQEHSPVGKG   600
ITKAGACLQA  SGEAVYVDDI  PAPENCLYGA  FIYSTMPLAR  IKGIRFKQNR  VPEGVLGIIT   660
YKDIPKGGQN  IGTNGFFTSD  LLFAEEVTHC  AGQIIAFLVA  DSQKHADIAA  NLVVIDYDTK   720
DLKPPILSLE  EAVENFSLFE  VPPPLRGYPV  GDITKGMDEA  EHKILGSKIS  FGSQYFFYME   780
TQTALAVPDE  DNCMVVYSST  QTPEFVHQTI  AGCLGVPENN  VRVITRRVGG  GFGGKAVKSM   840
PVAAACALAA  SKMQRPVRTY  VNRKTDMITT  GGRHPMKVTY  SVGFKSNGKI  TALDVEVLLD   900
AGLTEDISPL  MPKGIQGALM  KYDWGALSFN  VKVCKTNTVS  RTALRAPGDV  QGSYIGEAII   960
EKVASYLSVD  VDEIRKVNLH  TYESLRLFHS  AKAGEFSEYT  LPLLWDRIDE  FSGFNKRRKV  1020
VEEFNASNKW  RKRGISRVPA  VYAVNMRSTP  GRVSVLGDGS  IVVEVQGIEI  GQGLWTKVKQ  1080
MAAYSLGLIQ  CGTTSDELLK  KIRVIQSDTL  SMVQGSMTAG  STTSEASSEA  VRICCDGLVE  1140
RLLPVKTALV  EQTGGPVTWD  SLISQAYQQS  INMSVSSKYM  PDSTGEYLNY  GIAASEVEVN  1200
VLTGETTILR  TDIIYDCGKS  LNPAVDLGQI  EGAFVQGLGF  FMLEEFLMNS  DGLVVTDSTW  1260
TYKIPTVDTI  PRQFNVEILN  SGQHKNRVLS  SKASGEPPLL  LAASVHCAVR  AAVKEARKQI  1320
LSWNSNKQGT  DMYFELPVPA  TMPIVKEFCG  LDVVEKYLEW  KIQQRKNV               1368

SEQ ID NO: 242        moltype = DNA  length = 1278
FEATURE               Location/Qualifiers
misc_feature          1..1278
                      note = Description of Artificial Sequence: Synthetic
                      polynucleotide
source                1..1278
                      mol_type = other DNA
                      organism = synthetic construct
SEQUENCE: 242
atggcgacca ataatgattt tggagctttc attgagaaag ttacaatctc tccaacttct   60
acttcctcgt cgcctccttc tctacagggt cttactttcg ccattaaaga cattttkgat  120
gtggaaggac gcgttaccgg ttttggtaac ccggattggt taaggacaca ctcggcagct  180
acttctacag ctccagtagt ttcatctctc ttagaagctg gtgccacagc tttgggtatt  240
accattatgg atgaaatggc ttacagtata aacggagaaa atgcgcatta tgggactccg  300
agaaacccga ttgctttcga tagagtgcct gggggatcat cgagtggctc agccgtagct  360
gtagctgctc gtcttgtgga tttttctatt ggaactgata ccggagggag tgtacgagtt  420
ccagcatctt actgtgggat tttcggtttc cggccatccc acggtgcagt ttccactgtc  480
ggacttactc caatggctca gagcttcgac acagttggat ggtttgctcg ggacacagcc  540
actttgaaaac gtgtaggttg cgttctcctg cagcagcatc acttgaaccc catcgaacca  600
tctcaactga ttatcgcgga tgactgcttc aagctgtgta gtgtaccgca tgatctcttg  660
gtgcagcctc tggttggatc cgtggaaaaa tcgtttggag gcaacactgt agtaaagagg  720
gtgaatcttg gagagtacat tggacagaat gttccaagcc ttaaacattt catgacaagt  780
gacgatgtca ctacacaaca agagttctgc attccgtctc tcatggccct atcgagttca  840
atgagattgt tacaaagaca tgaattcaag ataaaccacg tgcatggat ctcgtcggtc  900
aagccagagt ttggtcctgg aatatcagaa cgaattgagg aagctatcga aacatccgac  960
gagaagatcg accattgccg gtccgtgaaa tctgaactga taacggctct ttcaactttg 1020
ctcgggagaa agggtgtgtt ggtgattcca acggtaccag tcctccacc gcatctccaa 1080
gctaatgtgg ctgcacttga atctttccgc agcagagcct tcagcttgtt gtcgatcgca 1140
ggcgtttctg gattctgtca ggtgagcata ccattgggc tacacgaaaa tcttccggtt 1200
tcggtatcat tggtagctaa gtatggctca gacgttttc ttctgagtct tgtggattcc 1260
cttgctgcat ttatttga                                                1278

SEQ ID NO: 243        moltype = AA   length = 425
FEATURE               Location/Qualifiers
REGION                1..425
                      note = Description of Artificial Sequence: Synthetic
                      polypeptide
source                1..425
                      mol_type = protein
                      organism = synthetic construct
SEQUENCE: 243
MATNNDFGAF  IEKVTISPTS  TSSSPPSLQG  LTFAIKDIFD  VEGRVTGFGN  PDWLRTHSAA   60
TSTAPVVSSL  LEAGATALGI  TIMDEMAYSI  NGENAHYGTP  RNPIAFDRVP  GGSSSGSAVA  120
VAARLVDFSI  GTDTGGSVRV  PASYCGIFGF  RPSHGAVSTV  GLTPMAQSFD  TVGWFARDTA  180
TLKRVGCVLL  QQHHLNPIEP  SQLIIADDCF  KLCSVPHDLL  VQPLVGSVEK  SFGGNTVVKK  240
VNLGEYIGQN  VPSLKHFMTS  DDVTTQQEFC  IPSLMALSSS  MRLLQRHEFK  INHGAWISSV  300
KPEFGPGISE  RIEEAIRTSD  EKIDHCRSVK  SELITALSTL  LGEKGVLVIP  TVPGPPPHLQ  360
ANVAALESFR  SRAFSLLSIA  GVSGFCQVSI  PLGLHENLPV  SVSLVAKYGS  DGFLLSLVDS  420
LAAFI                                                                  425

SEQ ID NO: 244        moltype = DNA  length = 1248
FEATURE               Location/Qualifiers
misc_feature          1..1248
                      note = Description of Artificial Sequence: Synthetic
                      polynucleotide
source                1..1248
                      mol_type = other DNA
                      organism = synthetic construct
SEQUENCE: 244
atgggttctt gtaaagaaga agaaaaaact gatcaacaac caaaatggtt atgggttaat   60
ggacctataa tagtaggtgc tggaccttct ggtttagcag tttcagcttc tcttaaagaa  120
```

```
aatggagtcc cttcacttat tcttgaaaga agtgattgta ttgcttcttt atggcaacaa    180
aaaacctatg atcgtttaaa acttcatctc cctaaacagt tttgtcaact cccattattt    240
ggttttcctg aaaatttccc taaataccct tcaaaaaaac agttcatttc ttacttagag    300
gattatgcta aacactttgg tataattccc aagtttaaac agtctgtaaa agttgcagaa    360
tttgatcatg ttagtggatt ttggaaggtg gaaactcaag attttttgta tctttcaaag    420
tggttgattg tggctacagg ggaaaatgca gagccagtta taccagaaat tcaagggatt    480
ggtaagttta aaggaacagt aatgcatact agtctttata agtctggtac tgagtttaat    540
aatcaaaggg ttttggtaat tggctgtgga aattctggta tggaagttag cttggacctt    600
tgtagacata atgccatccc tcacatggtc gtcagaaatt ccgtgcatat tttaccaagg    660
gaaatgttag ggatatcaac attttcaata gcaatggcac ttctcaaatg gttgcctata    720
agagttgttg acaagttgct attactagta gccaatttga ccttaggtag cacagataag    780
ttaggtctcc ggcgaccaaa aaccggtcca cttgaactga aaaatgccac cggaaaaact    840
ccggtactcg acgttggtgc attgtcacaa ataagaaatg gaaaaattca gattatgcac    900
ggtgtgaagg agataactaa aataggagca aagtctatga tggaaaaga aggagaattt    960
gattcaataa tcctagcaac tggatacaaa agcaatgttc cttcttggct taagggaact   1020
gacttcttca cagaacaagg gatgccaaaa acaccatttc ctaatggctg aaagggaa    1080
aatgattat acacggtggg gtttacaaga gagggcttt agggactgc aaatgatgca    1140
aaaaacattg ccagggatat tagtgatcaa tggaggaat acaagggctt ctgcaaaat    1200
ttttgtactt caagaaatct atcagatagc cagggtatat gtttttag               1248

SEQ ID NO: 245          moltype = AA  length = 415
FEATURE                 Location/Qualifiers
REGION                  1..415
                        note = Description of Artificial Sequence: Synthetic
                        polypeptide
source                  1..415
                        mol_type = protein
                        organism = synthetic construct
SEQUENCE: 245
MGSCKEEEKT DQQPKWLWVN GPIIVGAGPS GLAVSASLKE NGVPSLILER SDCIASLWQQ    60
KTYDRLKLHL PKQFCQLPLF GFPENFPKYP SKKQFISYLE DYAKHFGIIP KFKQSVKVAE   120
FDHVSGFWKV ETQDFYLSK WLIVATGENA EPVIPEIQGI GKFKGTVMHT SLYKSGTEFN   180
NQRVLVIGCG NSGMEVSLDL CRHNAIPHMV VRNSVHILPR EMLGISTFSI AMALLKWLPI   240
RVVDKLLLLV ANLTLGSTDK LGLRRPKTGP LELKNATGKT PVLDVGALSQ IRNGKIQIMH   300
GVKEITKIGA KSIDGKEGEF DSIILATGYK SNVPSWLKGT DFFTEQGMPK TPFPNGWKGE   360
NGLYTVGFTR RGLLGTANDA KNIARDISDQ WRKYKGFCKN FCTSRNLSDS QGICF         415

SEQ ID NO: 246          moltype = DNA  length = 1167
FEATURE                 Location/Qualifiers
misc_feature            1..1167
                        note = Description of Artificial Sequence: Synthetic
                        polynucleotide
source                  1..1167
                        mol_type = other DNA
                        organism = synthetic construct
SEQUENCE: 246
atgggttctt ataaagaaga agaaaaaacc gatcaacaac caaaatggtt atgggttaat    60
ggacctataa tagtaggtgc tggaccttc ggtttagcag tttcagcttg tcttaaagaa   120
aatggagtcc cttcacttat tcttgaaaga agtgattgta ttgcttcttt atggcaacaa   180
aaaacttatg atcgtttaaa acttcatctc cctaaacagt tttgtcaact cccattattt   240
ggttttcctg aaaatttccc taaataccct tcaaaaaaac tgttcatttc ttacttagag   300
gattatgcta aacactttgg tatagttcct aagtttaaac agtctgttaa agttgcagaa   360
tttgatcatg ttagtggatt ttggaaggta gaaactcaag attttttgta tctttcaaaa   420
tggttgattg tggctacagg agaaaatgca gagccagtaa taccagaaat tcaagggatt   480
gataagttta aaggagcggt gttgcatact agtgtttata agtcaggtac tgagtttaat   540
aatcaaaggg ttttggtaat tggttgtgga aattctggta tggaagttag cttggacctt   600
tgtagacata atgccatccc tcacatggtc gtcagaaatt ctgtgcatat tttaccaagg   660
gaaatgttag ggatatcaac attttcaata gcaatggcac ttctcaaatg gttgcctata   720
agagtagttg acaagttgct gttactagta gcaaatttga cctlaggtag cacagataag   780
ttaggtctcc ggcgaccaaa aaccggtcca cttgaactga aaaatgccac cggaaaaactc   840
gtctcgacgt tgattatgca cggtgtgaag gagataacta aaataggagc aaagtttata   900
gatgaaaaag aaggagaata tgattcaata atccttagca actggataca aagcaatgtt   960
ccttcttggc ttaagggaac tgacttcttc acagaacaag gatgccaaa gacaccttt   1020
ccaaatggtt ggaaggga aatggatta tacacagtgg gtttacaag aagggctt   1080
ttagggactg caaatgatgc aaaaaaaatt gccagggaca taagtgatca atggaggaaa   1140
tacaagggct tctgcaaaaa cttttga                                       1167

SEQ ID NO: 247          moltype = AA  length = 388
FEATURE                 Location/Qualifiers
REGION                  1..388
                        note = Description of Artificial Sequence: Synthetic
                        polypeptide
source                  1..388
                        mol_type = protein
                        organism = synthetic construct
SEQUENCE: 247
MGSYKEEEKT DQQPKWLWVN GPIIVGAGPS GLAVSACLKE NGVPSLILER SDCIASLWQQ    60
KTYDRLKLHL PKQFCQLPLF GFPENFPKYP SKKLFISYLE DYAKHFGIVP KFKQSVKVAE   120
FDHVSGFWKV ETQDFYLSK WLIVATGENA EPVIPEIQGI DKFKGAVLHT SVYKSGTEFN   180
```

```
NQRVLVIGCG NSGMEVSLDL CRHNAIPHMV VRNSVHILPR EMLGISTFSI AMALLKWLPI   240
RVVDKLLLLV ANLTLGSTDK LGLRRPKTGP LELKNATEKL VSTLIMHGVK EITKIGAKFI   300
DGKEGEYDSI ILATGYKSNV PSWLKGTDFF TEQGMPKTPF PNGWKGENGL YTVGFTRRGL   360
LGTANDAKKI ARDISDQWRK YKGFCKNF                                     388

SEQ ID NO: 248          moltype = DNA   length = 1833
FEATURE                 Location/Qualifiers
misc_feature            1..1833
                        note = Description of Artificial Sequence: Synthetic
                         polynucleotide
source                  1..1833
                        mol_type = other DNA
                        organism = synthetic construct
SEQUENCE: 248
atgataactt tatctgattt ctaccatgtt atgactgctg ttgtgccact ttatgtggct   60
atgatattag cttatggttc tgttaaatgg tggaagattt tttcacctga ccagtgttct   120
ggtattaaca gatttgttgc acttttcgca gttccacttc tctctttcca ctttatagct   180
gctaataatc cttacactat gaacatacgg ttcattgctg ctgacactct tcagaaactt   240
attgttcttg gagctcttgc tatttgggct aattttagca aaaggggtag tttagaatgg   300
agtataacac tcttttcttt atcaactctt ccaaatactt tagttatggg tattcctttg   360
ttaaaaggaa tgtatggtga ttttttcaggg agtttaatgg ttcaaatagt tgtactacag   420
tgtattattt ggtacacttt gatgcttttt atgtttgagt tcagaggtgc aaggatgctg   480
atctctgagc aatttcctga tactgctggc tcaattgtct caatccatgt tgattctgat   540
gtcatgtcat tagatggtag acaagttttg gaaactgaag ctgaagtgaa agaagatgga   600
aaacttcatg ttactgtgag aaaatcaaat gcctcaaggt ctgatatatt ttcaagaagg   660
tcgcagggat tttcttctac aactccaaga ccatcaaatt taacaaatgc agagatttac   720
tctctacaat cttcaagaaa tccaactcca agagggtcaa gttttaacca tactgatttt   780
tactcaatgg ttgctggtgg gagaaactca aactttggtg caaatgatgt ttatgggatg   840
tcagcttcaa gaggaccaac tcctagacct tcaaattatg aggaagaaag tggaaaatca   900
agatttaatt acaaccatgg agctgcagca caacaaagta atactaataa taatactact   960
cattatccag ctccaaatcc tggtatgttt tcacctagta atggtgcaaa agcagtgggt   1020
tctaacacta taacaagaa aggtaacaaa ggagaggaag tggtaaagga tcttcatatg   1080
tttgtttgga gttcaagtgc ttctcctgtt tctgatgtat tggtggtca tgattatgga   1140
gctaatttag accagaatac agctaaggat gtaaagagtt ctatctctcc tggaaaagtt   1200
gaggtgcaaa gaaacaatca agaaaactac atggagagag atgactttag ctttgcaaat   1260
agagatgcag aaatgaatat tcacaaccaa gaaggtgaaa aaggtggaga aaataaagca   1320
aaggttatgc caccaacaag tgtaatgact aggcttatac taattatggt ttggaggaaa   1380
cttattagaa atccaaacac ttattcaagc ttgtttggtc tcacttggtc tctagtttca   1440
ttcaggtgga atttgaagat gcctgctata attgcacagt ccatatctat attgtcagat   1500
gcaggacttg gcatggcaat gttcagtcta ggtctgttta tggctttgca accaaggata   1560
atagcatgtg ggaattctac agcagctttt gctatggctg tgagattcct tacaggtcca   1620
gctgtcatgg cagctgcttc cattgctgtt ggccttcgtg gagttctctt acacgtagcc   1680
attgtacagg cagctctacc ccaaggaatt gtcccctttg tcttcgccaa ggaatacaac   1740
gttcaccctg acattcttag cacgggtgtc attttgggga tgttgattgc cttgccgatt   1800
acactggtct actacatttt gatgggactt taa                               1833

SEQ ID NO: 249          moltype = AA   length = 610
FEATURE                 Location/Qualifiers
REGION                  1..610
                        note = Description of Artificial Sequence: Synthetic
                         polypeptide
source                  1..610
                        mol_type = protein
                        organism = synthetic construct
SEQUENCE: 249
MITLSDFYHV MTAVVPLYVA MILAYGSVKW WKIFSPDQCS GINRFVALFA VPLLSFHFIA   60
ANNPYTMNIR FIAADTLQKL IVLGALAIWA NFSKRGSLEW SITLFSLSTL PNTLVMGIPL   120
LKGMYGDFSG SLMVQIVVLQ CIIWYTLMLF MFEFRGARML ISEQFPDTAG SIVSIHVDSD   180
VMSLDGRQVL ETEAEVKEDG KLHVTVRKSN ASRSDIFSRR SQGFSSTTPR PSNLTNAEIY   240
SLQSSRNPTP RGSSFNHTDF YSMVAGGRNS NFGANDVYGM SASRGPTPRP SNYEEESGKS   300
RFNYNHGAAA QQSNTNNNTT HYPAPNPGMF SPSNGAKAVG SNTNNKKGNK GEEGGKDLHM   360
FVWSSSASPV SDVFGGHDYG ANLDQNTAKD VRVPISPGKV EVQRNNQENY MERDDFSFAN   420
RDAEMNIHNQ EGEKGGENKA KVMPPTSVMT RLILIMVWRK LIRNPNTYSS LFGLTWSLVS   480
FRWNLKMPAI IAQSISILSD AGLGMAMFSL GLFMALQPRI IACGNSTAAF AMAVRFLTGP   540
AVMAAASIAV GLRGVLLHVA IVQAALPQGI VPFVFAKEYN VHPDILSTGV IFGMLIALPI   600
TLVYYILMGL                                                         610

SEQ ID NO: 250          moltype = DNA   length = 1191
FEATURE                 Location/Qualifiers
misc_feature            1..1191
                        note = Description of Artificial Sequence: Synthetic
                         polynucleotide
source                  1..1191
                        mol_type = other DNA
                        organism = synthetic construct
SEQUENCE: 250
atgtgtggca cagaggcttg tcttatcaag tgttctccag tcccttgtgt gactcctgaa   60
acaagagaaa atgcactct catcaagtgg gatactctta tcaatcttga tcatggtgat   120
ccagtaatgt atgaatcata ctggcgaaag atgggaaaca ggtgtgacat tacattcagt   180
```

```
ggttatcagt cattgagtta ttttgctaac gccaagaact tgtgctggtt ccttgagcca    240
aaactagaag aagagatcaa gaggctgcac aatgtggttg gaaatgcaat tgtggatgat    300
cattatatcg tcgttgggac aggatcaagc cagcttatac aggctgcact ctatgctctt    360
tctcctacag atgaacctga accaatcagt gtagtttcag ctgcaccttt ctattcgtca    420
tatccagaag tgactgattt tgtgcgttca gggctgtaca aatgggcagg agatgcaaga    480
aattttgaga aagatggacc atatattgag ttcattacat ctccaaataa cccagatggg    540
gttactcgag agcctgtagt taatggaatt caagggatat taattcatga tttagcttat    600
tactggccac agtacactgc tattacctct cctgccaaat atgatgttat gctctttaca    660
gtttccaaat gcactggcca tgctggatcc agaattggtt gggctcttgt tagggacaaa    720
gaggtggcta ggaagatgac aaaattcatg gaaattgcaa caatagggat atcaaaggaa    780
gctcaattga gagctgcaaa gattcttgga ctgatttctg atagctgttt agatcccaca    840
ttggaaaact tctttgagta tagtcaatct cacatgacta aagatggcga gggttaaga    900
gaagttgtta agagcagtga cctttcact ctccagaaat atccacttca gtattgccac    960
ttcacaagag acttctatga atcacaccct gcttttgcat ggctaatgtg caaggaagt   1020
gaagatgacc ttgagaagct tcttaaagga tacaagattc aaacaaggag tggaagaaaa   1080
tttgggagtg atccaaaatg tgttaggata agtatgctga gtagggatga agacttcaac   1140
atttttttgc agaggcttat gtctattcaa ggagttacaa atggaaatta a            1191

SEQ ID NO: 251         moltype = AA  length = 396
FEATURE                Location/Qualifiers
REGION                 1..396
                       note = Description of Artificial Sequence: Synthetic
                       polypeptide
source                 1..396
                       mol_type = protein
                       organism = synthetic construct
SEQUENCE: 251
MCGTEACLIK CSPVPCVTPE TRENGTLIKW DTLINLDHGD PVMYESYWRK MGNRCDITFS    60
GYQSLSYFAN AKNLCWFLEP KLEEEIKRLH NVVGNAIVDD HYIVVGTSS QLIQAALYAL    120
SPTDEPEPIS VVSAAPFYSS YPEVTDFVRS GLYKWAGDAR NFEKDGPYIE FITSPNNPDG    180
VTREPVVNGI QGILIHDLAY YWPQYTAITS PAKYDVMLFT VSKCTGHAGS RIGWALVRDK    240
EVARKMTKFM EISTIGVSKE AQLRAAKILG LISDSCLDPT LENFFEYSQS HMTKRWQRLR    300
EVVKSSDLFT LQKYPLQYCH FTRDFYESHP AFAWLMCKGS EDDLEKLLKG YKIQTRSGRK    360
FGSDPKCVRI SMLSRDEDFN IFLQRLMSIQ GVTNGN                              396

SEQ ID NO: 252         moltype = DNA  length = 4062
FEATURE                Location/Qualifiers
misc_feature           1..4062
                       note = Description of Artificial Sequence: Synthetic
                       polynucleotide
source                 1..4062
                       mol_type = other DNA
                       organism = synthetic construct
SEQUENCE: 252
atggaacaga aaaagggaa tttagttttt gcagtaaatg agagaggtt tgagttgcca    60
aatattgacc cctctactac tttacttcag ttcttgcgtt ctgagacttg tttcaagagt   120
cctaaacttg gttgtggtga aggtggttgt ggggcttgtta ttgttctggt ctcaaagtat   180
gatcctaagc ttaaaaaggt cgaagatttt agcgcgagtt catgccttac acttctttgt   240
agtttaaatg gttactcaat tactacaagt gaaggccttg gaacaccag atggttttt    300
cactctattc atgaaagatt tgctggtttc catgcttctc aatgtggctt ttgcactcct   360
ggaatgtgta tgtcatttt ctcagctctt gtcaatgcac ataaaggaaa caagccgat   420
cctccaccag gattttctaa gcttacttca tctgaagctg aaaaagccat agcagggaac   480
ctctgtcggt gcactggata ccggcctatt gctgatgcct gcaagacttt tgctgctgat   540
attgatatag aggatttggg gttcaattct ttttggaaaa agggagattc caaggaattg   600
aaaataagta aattacctcc ttatgatcca accaagaatt ttagtacata tccggagttc   660
ttgaaaagtg aatgcgccac aaatttggac tccacaaggt acccttggta cagtcctact   720
tccattgaag agctgcagag cttgttgaac tccagtgtgg cggataatgg tgcgagcttt   780
aaactggtcg ttggtaatac aggcacaggt tattataagg aaactcagcg atatgatcat   840
tacgttgatc tcaggtatat tcctgaactc tcaatcatca aaagagatca gacaggcatt   900
gaagtgggag caactgtgac tatctctaaa cttatagcat tcttgaaaga ggaaacaaa   960
gtcaatttgg gtccatatgg gaagctggtg tccgaaaagc tggttaacca catggagaag  1020
attgcttcac catttgttag gaactctgct agtgtgggag gaaatttggt tatggcacaa  1080
aagaatggtt ttccttcaga tattgctaca ttatttcttg gtgtgggtgc taccgttagc  1140
ttgatgaccg gtcatggact tgaaaaactc acatgggaga aattattatc gagaccgcca  1200
atagactcaa ggaccgtgct tctaagtgtt tggatcccat ttaaagaaga gagttctctc  1260
aaaaccttta ctaagttttt gtttgagacc tatcgagctg ctccccgacc tcatgggaat  1320
gcaatagcat atgtaaacgc tgcttttggg gttgatgttt ctctctgcca gaacggcatc  1380
ctgataaacg atatccggct ggcgtttggt gcttatggta caaaacatgc aacaagggct  1440
aaaatggtag aggaaatctct aacagggaaa atattaagtg cacatgtttt aagtgaagca  1500
cttaaaattag tcaaactagc tgtggtaccg gaagatggga cttttacccc agagtataga  1560
tcaagcttgg ccgtcagtta tgtttttcag tttctttatc ccttagttga tgttcattct  1620
gctattgtca atgaatcaa tgacatctca ctcgaggaag tttcaaaaag tagtaatgat  1680
agtcagggga gaaacaaac actactgtct tcttctaagc aggttgtgga atcaagtagc  1740
gagcactca cagtgggtga accaatgaag aaggttgatc catgcagtca agtgctagtt  1800
gaagctgttt atgtagatga cattccgtca ccaccaaact gcctgcacgg agcatttatc  1860
tacagcacaa aaccattagc aggtgtaaaa ggaatccatc ttgagtctaa ttcattaaca  1920
gatggattca ccgacattat tactttcaag gatatcccaa gtgaggggtc aaatgtagga  1980
tctattacaa tgtttggtcc tgagccttta ttcgcagacg atctcgcccg atgtgctggc  2040
gacagaattg cagttgcggt tgctgacact cagaggtctg ctgatgtggc tgccacaaca  2100
```

```
gcccttgttg aatatgacac tgtaaatgta aattcaccga ttttaactgt cgaggaagct  2160
gttgagaaat ctagctttt  ccaaatcccg ccatttctat atccaaaaca ggttggcgat  2220
ttctcaaaag gaatggctga agctgatcac aagattctct ctgctgaggt aagacttggt  2280
tccgagtact atttttatat ggagacacag actgcccttg caattccaga tgaagacaac  2340
tgtatggttg tttatacttc aagccagtgc cctgagtatg cgcaaaatgt gattgccagt  2400
tgtcttggtg ttcctgaaca caatatccgt gttattacaa gaagggttgg aggtggcttt  2460
gggggcaagg cagtcagagc aatgcctgtt tcgacagcct gtgcacttgc agcatacaag  2520
ttaaggcggc ctgtgaggat aaatgtcaac cggaacagcg acatgataat gacaggagga  2580
agacacccaa tgaaagtaac atacagtgta ggattcaagt caagcggaaa gatcacagca  2640
ttacatcttg atatattgat aaatgctggg atttcgaag  atataagccc cctcctacca  2700
tcaaatgtga ttaaagcatt aaagaaatat gattggggtg ccttatcttt tgatgtaaaa  2760
gtatgcaaga cgaatcttac cagcaaatca gctatgcggg cccctgggga ggtgcaagga  2820
tcttatattg ccgaagctat aatggagcat gtagcgagtt tactgtcaaa ggaggtggat  2880
tctgtcagaa ataataatgt tcatacattg gaaagcatta attattcta tgataacatc  2940
gtaactgaag taggagaata tacgttgcct agtatcatgg ataagttggc cgtgtcctcg  3000
agctttttcc aacgtagcaa gatggtggaa cagtttaacc agaaaaacac atggaagaaa  3060
aagggtattt ctcgactgcc aataatgttt gaagctatgc aacgaccgac cccaggaaaa  3120
gtcagtatcc tgtcggatgg atcaattgtt gtagaggttg gagggattga aatcggccaa  3180
gggctatgga caaaggttag acagatgact gcatatgctc ttggtttaat tgaaagtagt  3240
tggagtgaag aacttgtagg gaaagtacga gtcatacaag cagacagctt aagcttagtg  3300
caaggtgggt atacggctgg aagcactaca tcggaatcaa gctgtgaagc agttagacgt  3360
tgctgtagtg tcttggttga aacagttgac tcctctgaaga aacagttgca ggaacaaaat  3420
ggctctcttg attggccaac gctcattcgc caggcacaaa tgcaagcagt aaacttagca  3480
gcaaattctt attatgtacc agaatccagt tccatgagtt atttgaactt tggtgccgct  3540
gtcagtgagg tggatataga tattcttact ggagagactg ccatttttgca gtcggatatt  3600
atttacgact gtgggcagag cttgaatcca gctgtcgata tgggacagat tgaaggacgt  3660
tatgtacaag gaattggatt ttttatgcat gaagaatatc ttacaaacga cgatgggttg  3720
atggtctcaa atagcacttg gacatacaag atcccaacaa tcgacaccat accccagaat  3780
ttcaacgttc atttggtaaa cagtggacat cacgaaaaac gtgttctctc ttccaaagca  3840
tctggtgaac cgccactgct acttgcagct tcagtccatt gtgcaacaag aggctgtt   3900
aaagcagcaa gagaacaact caaagtttgg ggcaagctcg acgagtctgc ttcagaattc  3960
tatctgggatg ttcctgccat attacctgtt gtgaagacgc agtgtggtct agattatgtg  4020
gagaaatact tagaaagttt actgactcag aaatctaact aa                    4062

SEQ ID NO: 253         moltype = AA  length = 1353
FEATURE                Location/Qualifiers
REGION                 1..1353
                       note = Description of Artificial Sequence: Synthetic
                        polypeptide
source                 1..1353
                       mol_type = protein
                       organism = synthetic construct
SEQUENCE: 253
MEQKKGNLVF AVNGERFELP NIDPSTTLLQ FLRSETCFKS PKLGCGEGGC GACVVLVSKY   60
DPKLKKVEDF SASSCLTLLC SLNGYSITTS EGLGNTRDGF HSIHERFAGF HASQCGFCTP  120
GMCMSFFSAL VNADKGNKPD PPPGFSKLTS SEAEKAIAGN LCRCTGYRPI ADACKTFAAD  180
IDIEDLGFNS FWKKGDSKEL KISKLPPYDP TKNFSTYPEF LKSECATNLD STRYPWYSPT  240
SIEELQSLLN SSVADNGASF KLVVGNTGTG YYKETQRYDH YVDLRYIPEL SIIKRDQTGI  300
EVGATVTISK LIAFLKEENK VNLGPYGKLV SEKLVNHMEK IASPFVRNSA SVGGNLVMAQ  360
KNGFPSDIAT LFLGVGATVS LMTGHGLEKL TWEELLSRPP IDSRTVLLSV WIPFKEESSL  420
KTFTKFLFET YRAAPRPHGN AIAYVNAAFG VDVSLCQNGI LINDIRLAFG AYGTKHATRA  480
KMVEEYLTGK ILNAHVLSEA LKLVKLAVVP EDGTLHPEYR SSLAVSYVFQ FLYPLVDVHS  540
AIVNGINDIS LEEVSKSSND SQGRKQTLLS SSKQVVESSS EHYPVGEPMK KVGAAMQAAG  600
EAVYVDDIPS PPNCLHGAFI YSTKPLAGVK GIHLESNSLT DGFTDIITFK DIPSGGSNVG  660
SITMFGPEPL FADDLARCAG DRIAVAVADT QRSADVAATT KQSADVTDVNV NSPILTVEEA  720
VEKSSFFQIP PFLYPKQVGD FSKGMAEADH KILSAEVRLG SEYYFYMETQ TALAIPDEDN  780
CMVVYTSSQC PEYAQNVIAS CLGVPEHNIR VITRRVGGGF GGKAVRAMPV STACALAAYK  840
LRRPVRINVN RNSDMIMTGG RHPMKVTYSV GFKSSGKITA LHLDILINAG ISEDISPLLP  900
SNVIKALKKY DWGALSFDVK VCKTNLTSKS AMRAPGEVQG SYIAEAIMEH VASLLSKEVD  960
SVRNNNVHTL ESINLFYDNI VTEVGEYTLP SIMDKLAVSS SFFQRSKMVE QFNQKNTWKK 1020
KGISRLPIMF EAMQRPTPGK VSILSDGSIV VEVGGIEIGQ GLWTKVRQMT AYALGLIESS 1080
WSEELVGKVR VIQADSLSLV QGGYTAGSTT SESSCEAVRR CCSVLVERLT PLKKQLQEQN 1140
GSLDWPTLIR QAQMQAVNLA ANSYYVPESS SMSYLNFGAA VSEVDIDILT GETAILQSDI 1200
IYDCGQSLNP AVDMGQIEGA YVQGIGFFMH EEYLTNDDGL MVSNSTWTYK IPTIDTIPQN 1260
FNVHLVNSGH HEKRVLSSKA SGEPPLLLAA SVHCATRAAV KAAREQLKVW GKLDESASEF 1320
YLDVPAILPV VKTQCGLDYV EKYLESLLTQ KSN                              1353

SEQ ID NO: 254         moltype = DNA  length = 1278
FEATURE                Location/Qualifiers
misc_feature           1..1278
                       note = Description of Artificial Sequence: Synthetic
                        polynucleotide
source                 1..1278
                       mol_type = other DNA
                       organism = synthetic construct
SEQUENCE: 254
atggagacat gtaatatgg  agctctcatt gagaaattca cactgcaacc aatttgctct   60
tcttcagagc aagtcccctt gaatggctta acctttgccg tgaaagacat atttgatgtg  120
gaaggacata tcactggttt tggaaatcca gactgggcca gacccattc  tgcggcaaca  180
```

```
tctactgcaa caactgtgct cactcttttg aaggctggtg ctacttgtat tggtaaaact  240
gtcatggatg aaatggctta cagcataaat ggtgaaaatg ttcattatgg cacgcctttg  300
aatcctgttt caccagatcg ggtacctgga gggtcttcaa gtggatctgc agttgcagtc  360
ggtgcaaagc ttgtagattt ctccttaggg actgacactg gaggaagtgt tagagttcct  420
gcatcatatt gtggaattta tggtattcga ccttctcatg gagttgtttc aactgccgga  480
gtcacaccta tggcacaaag ctttgataca gtggggtggt ttgcaaggga tcctctgatc  540
ttaaagcaag ttggaagagt cctacttcaa tctcccaaa tgaaatccgt gcgtccaact   600
aacagtatca ttgcagaaga ctgttttaag ctcctggatt ccaagagtaa ccaattgatt  660
gaagtacttg ttaactcagt ggagaagcta tatggaagtc atatgattaa atacgtgagt  720
gtaggggatt atattgaggg aaatgttcca agtttgaaga aattcatgac gcttggaact  780
ggcaatgatg aatcttacat tccatccttg ctagctctct cagctgccat gcggttgctt  840
caaaggtatg aattcaagga gaatcatgga gaatgggtta gtacagtcaa acctagttta  900
ggtccgggaa tagcagaacg cgtatgggaa gcgctgaagg ccacagatga aaatattgat  960
gtgtgccact ctgtgaaggc tgagcttcga gcagctctca ctgctctcct tggggattct 1020
ggtatacttg caatcccaac tgttcctgga cctccaccaa aactaagaag cgagacaagt 1080
gcattggaag gatttcgtgt taaggctttt agtctgttat caattgctgg agtatctgga 1140
ttttgccagg tcagcatacc tctggggatg caagacaatc ttcctatatc agtttcttta 1200
ctggtaaaac atggttcaga ctggttgctg cttgatgctg ttgaagctat tcacaaagtt 1260
ctcaaggggc aaatctga                                               1278

SEQ ID NO: 255         moltype = AA  length = 425
FEATURE                Location/Qualifiers
REGION                 1..425
                       note = Description of Artificial Sequence: Synthetic
                       polypeptide
source                 1..425
                       mol_type = protein
                       organism = synthetic construct
SEQUENCE: 255
METCEYGALI EKFTLQPICS SSEQVPLNGL TFAVKDIFDV EGHITGFGNP DWAKTHSAAT   60
STATTVLTLL KAGATCIGKT VMDEMAYSIN GENVHYGTPL NPVSPDRVPG GSSSGSAVAV  120
GAKLVDFSLG TDTGGSVRVP ASYCGIYGIR PSHGVVSTAG VTPMAQSFDT VGWFARDPLI  180
LKQVGRVLLQ SPQMKSVRPT NSIIAEDCFK LLDSKSNQLI EVLVNSVEKL YGSHMIKYVS  240
VGDYIEGNVP SLKKFMTLGT GNDESYIPSL LALSAAMRLL QRYEFKENHG EWVSTVKPSL  300
GPGIAERVWE ALKATDENID VCHSVKAELR AALTALLGDS GILAIPTVPG PPPKLRSETS  360
ALEGFRVKAF SLLSIAGVSG FCQVSIPLGM QDNLPISVSL LVKHGSDWLL LDAVEAIHKV  420
LKGQI                                                             425

SEQ ID NO: 256         moltype = AA  length = 6
FEATURE                Location/Qualifiers
REGION                 1..6
                       note = Description of Artificial Sequence: Synthetic 6xHis
                       tag
source                 1..6
                       mol_type = protein
                       organism = synthetic construct
SEQUENCE: 256
HHHHHH                                                              6
```

What is claimed is:

1. A modified tobacco plant comprising reduced suckers compared to a control tobacco plant of the same variety when grown under comparable conditions, wherein the modified tobacco plant comprises a transgene encoding a polypeptide comprising an amino acid sequence at least 90% identical or similar to the amino acid sequence of SEQ ID NO: 80 operably linked to a promoter comprising a nucleic acid sequence at least 90% identical to a sequence selected from the group consisting of SEQ ID NOs: 148 and 157.

2. The modified tobacco plant of claim 1, wherein nucleic acid sequence is at least 95% identical to a sequence selected from the group consisting of SEQ ID NOs: 148 and 157.

3. The modified tobacco plant of claim 1, wherein nucleic acid sequence is 100% identical to a sequence selected from the group consisting of SEQ ID NOs: 148 and 157.

4. The modified tobacco plant of claim 1, wherein the reduced suckers comprises at least 10% fewer suckers.

5. The modified tobacco plant of claim 1, wherein the reduced suckers comprises reduced mass, reduced length, or both.

6. The modified tobacco plant of claim 1, wherein the modified tobacco plant requires reduced management for controlling suckers compared to a control tobacco plant when grown under comparable conditions.

7. The modified tobacco plant of claim 6, wherein the reduced management comprises reduced manual removal frequency to control suckers, reduced chemical application frequency to control suckers, reduced quantities of chemical application to control suckers, or any combination thereof.

8. The modified tobacco plant of claim 1, wherein the suckers are topping-induced suckers.

9. The modified tobacco plant of claim 8, wherein the reduced topping-induced suckers comprises fewer total suckers, smaller suckers, or both when compared to topping-induced suckers of a control tobacco plant when grown under comparable conditions.

10. A tobacco leaf of the modified tobacco plant of claim 1.

11. A tobacco product comprising cured tobacco material from the modified tobacco plant of claim 1.

12. The tobacco product of claim 11, wherein the tobacco product is selected from the group consisting of a cigarette, a kretek, a bidi cigarette, a cigar, a cigarillo, a non-ventilated cigarette, a vented recess filter cigarette, pipe tobacco, snuff, chewing tobacco, moist smokeless tobacco, fine cut chewing tobacco, long cut chewing tobacco, pouched chewing tobacco product, gum, a tablet, a lozenge, and a dissolving strip.

13. The tobacco product of claim 11, wherein the tobacco product is a smokeless tobacco product.

14. Cured tobacco material comprising a plant component from the modified tobacco plant of claim 1.

15. The cured tobacco material of claim 14, wherein the plant component is selected from the group consisting of a stem and a leaf.

16. The cured tobacco material of claim 14, wherein the cured tobacco material is cured by a method selected from the group consisting of flue-cured, sun-cured, air-cured, and fire-cured.

17. The modified tobacco plant of claim 1, wherein the polypeptide comprises an amino acid sequence at least 95% identical or similar to SEQ ID NO: 80.

18. The modified tobacco plant of claim 1, wherein the polypeptide comprises an amino acid sequence 100% identical or similar to SEQ ID NO: 80.

19. The modified tobacco plant of claim 1, wherein the modified tobacco plant is of a tobacco variety selected from the group consisting of a Burley tobacco variety, a Maryland tobacco variety, a bright tobacco variety, a Virginia tobacco variety, an Oriental tobacco variety, and a Turkish tobacco variety.

20. The modified tobacco plant of claim 1, wherein the modified tobacco plant is of a tobacco variety selected from the group consisting of BU 64, CC 101, CC 200, CC 13, CC 27, CC 33, CC 35, CC 37, CC 65, CC 67, CC 301, CC 400, CC 500, CC 600, CC 700, CC 800, CC 900, CC 1063, Coker 176, Coker 319, Coker 371 Gold, Coker 48, CU 263, DF911, Galpão, GL 26H, GL 338, GL 350, GL 395, GL 600, GL 737, GL 939, GL 973, GF 157, GF 318, RJR 901, HB 04P, K 149, K 326, K 346, K 358, K394, K 399, K 730, NC 196, NC 37NF, NC 471, NC 55, NC 92, NC2326, NC 95, NC 925, PVH 1118, PVH 1452, PVH 2110, PVH 2254, PVH 2275, VA 116, VA 119, KDH 959, KT 200, KT204LC, KY 10, KY 14, KY 160, KY 17, KY 171, KY 907, KY 907LC, KTY14×L8 LC, Little Crittenden, McNair 373, McNair 944, male sterile KY 14×L8, Narrow Leaf Madole, MS KY171, Narrow Leaf Madole (phph), MS Narrow Leaf Madole, MS TND950, PD 7302LC, PD 7305LC, PD 7309LC, PD 7312LC, PD 7318LC, PD 7319LC, MSTKS 2002, TKF 2002, TKF 6400, TKF 4028, TKF 4024, KT206LC, KT209LC, KT210LC, KT212LC, NC 100, NC 102, NC 2000, NC 291, NC 297, NC 299, NC 3, NC 4, NC 5, NC 6, NC7, NC 606, NC 71, NC 72, NC 810, NC BH 129, NC 2002, Neal Smith Madole, OXFORD 207, 'Perique', PVH03, PVH09, PVH19, PVH50, PVH51, R 610, R 630, R 7-11, R 7-12, RG 17, RG 81, RG H51, RGH 4, RGH 51, RS 1410, Speight 168, Speight 172, Speight 179, Speight 210, Speight 220, Speight 225, Speight 227, Speight 234, Speight G-28, Speight G-70, Speight H-6, Speight H20, Speight NF3, TI 1406, TI 1269, TN 86, TN86LC, TN 90, TN90LC, TN 97, TN97LC, TN D94, TN D950, a Tom Rosson (TR) Madole, VA 309, and VA 359.

* * * * *